United States Patent
Arnold et al.

(10) Patent No.: US 11,472,793 B2
(45) Date of Patent: Oct. 18, 2022

(54) INHIBITORS OF CYSTEINE PROTEASES AND METHODS OF USE THEREOF

(71) Applicant: Pardes Biosciences, Inc., Carlsbad, CA (US)

(72) Inventors: Lee D. Arnold, Rancho Santa Fe, CA (US); Andy Jennings, San Diego, CA (US); Walter Keung, Encinitas, CA (US)

(73) Assignee: Pardes Biosciences, Inc., Carlsbad, CA (US)

( * ) Notice: Subject to any disclaimer, the term of this patent is extended or adjusted under 35 U.S.C. 154(b) by 0 days.

(21) Appl. No.: 17/665,204

(22) Filed: Feb. 4, 2022

(65) Prior Publication Data

US 2022/0162194 A1 May 26, 2022

Related U.S. Application Data

(63) Continuation of application No. 17/384,369, filed on Jul. 23, 2021, now Pat. No. 11,312,704, which is a continuation of application No. 17/230,727, filed on Apr. 14, 2021, now Pat. No. 11,124,497.

(60) Provisional application No. 63/173,146, filed on Apr. 9, 2021, provisional application No. 63/172,478, filed on Apr. 8, 2021, provisional application No. 63/171,675, filed on Apr. 7, 2021, provisional application No. 63/129,018, filed on Dec. 22, 2020, provisional application No. 63/091,630, filed on Oct. 14, 2020, provisional application No. 63/067,669, filed on Aug. 19, 2020, provisional application No. 63/039,297, filed on Jun. 15, 2020, provisional application No. 63/036,866, filed on Jun. 9, 2020, provisional application No. 63/031,357, filed on May 28, 2020, provisional application No. 63/012,039, filed on Apr. 17, 2020.

(51) Int. Cl.
| | |
|---|---|
| C07D 403/12 | (2006.01) |
| C07D 207/26 | (2006.01) |
| C07D 401/12 | (2006.01) |
| C07D 471/04 | (2006.01) |
| C07D 403/14 | (2006.01) |
| C07D 417/14 | (2006.01) |
| C07D 401/14 | (2006.01) |

(52) U.S. Cl.
CPC ......... *C07D 403/12* (2013.01); *C07D 207/26* (2013.01); *C07D 401/12* (2013.01); *C07D 401/14* (2013.01); *C07D 403/14* (2013.01); *C07D 417/14* (2013.01); *C07D 471/04* (2013.01)

(58) Field of Classification Search
CPC .................................................. C07D 403/12
See application file for complete search history.

(56) References Cited

U.S. PATENT DOCUMENTS

| | | | |
|---|---|---|---|
| 6,514,997 | B2 | 2/2003 | Dragovich et al. |
| 7,504,382 | B2 | 3/2009 | Cai et al. |
| 7,504,392 | B2 | 3/2009 | Forbes et al. |
| 9,309,284 | B2 | 4/2016 | Chang et al. |
| 9,474,759 | B2 | 10/2016 | Chang et al. |
| 9,975,885 | B2 | 5/2018 | St. John et al. |
| 2004/0235952 | A1 | 11/2004 | Fuhrman et al. |
| 2005/0143319 | A1 | 6/2005 | Yang et al. |
| 2005/0143320 | A1 | 6/2005 | Yang et al. |
| 2006/0014821 | A1 | 1/2006 | He et al. |
| 2014/0243341 | A1 | 8/2014 | Chang et al. |
| 2019/0151400 | A1 | 5/2019 | Chang et al. |
| 2021/0008150 | A1 | 1/2021 | Schinazi et al. |

FOREIGN PATENT DOCUMENTS

| | | |
|---|---|---|
| CN | 102838523 A | 12/2012 |
| CN | 103130710 A | 6/2013 |
| CN | 103145608 B | 9/2015 |
| CN | 110105348 A | 8/2019 |
| CN | 110818691 A | 2/2020 |
| CN | 107459511 B | 5/2020 |
| CN | 111135167 A | 5/2020 |
| CN | 113444144 A | 9/2021 |
| CN | 114057702 A | 2/2022 |
| JP | 2006169176 A | 6/2006 |
| WO | WO-97/31939 A1 | 9/1997 |

(Continued)

OTHER PUBLICATIONS

Abranyi-Balogh, et al. "A road map for prioritizing warheads for cysteine targeting covalent inhibitors," European Journal of Medicinal Chemistry, vol. 160, 2018, pp. 94-107.

Adedeji, et al. "Antiviral drugs specific for coronaviruses in preclinical development," Curr Opin Virol. Oct. 2014;8:45-53.

Albuquerque, et al. "MurineHepatitis Virus Strain 1 Produces a Clinically Relevant Model of Severe Acute Respiratory Syndrome in A/J Mice," Journal of Virology Oct. 2006, 80 (21) 10382-10394.

(Continued)

*Primary Examiner* — Brian E McDowell
(74) *Attorney, Agent, or Firm* — Goodwin Procter LLP

(57) ABSTRACT

The disclosure provides compounds, such as compounds of Formula II, with warheads and their use in treating medical diseases or disorders, such as viral infections. Pharmaceutical compositions and methods of making various compounds with warheads are provided. The compounds are contemplated to inhibit proteases, such as the 3C, CL- or 3CL-like protease.

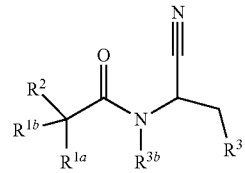

Formula II

4 Claims, No Drawings

(56) References Cited

FOREIGN PATENT DOCUMENTS

| WO | WO-99/24460 A2 | 5/1999 |
|---|---|---|
| WO | WO-2001/010894 A2 | 2/2001 |
| WO | WO-01/19816 A1 | 3/2001 |
| WO | WO-2001/40189 A1 | 6/2001 |
| WO | WO-01/49288 A1 | 7/2001 |
| WO | WO-2004/020441 A1 | 3/2004 |
| WO | WO-2004092360 A2 | 10/2004 |
| WO | WO-2004/093860 A1 | 11/2004 |
| WO | WO-2005058821 A1 | 6/2005 |
| WO | WO-2005/113580 A1 | 12/2005 |
| WO | WO-2006/061714 A2 | 6/2006 |
| WO | WO-2007/120160 A2 | 10/2007 |
| WO | WO-2013/049382 A2 | 4/2013 |
| WO | WO-2017/114509 A1 | 7/2017 |
| WO | WO-2017/197377 A1 | 11/2017 |
| WO | WO-2017/222935 A1 | 12/2017 |
| WO | WO-2018/042343 A2 | 3/2018 |
| WO | WO-2020/030143 A1 | 2/2020 |
| WO | WO-2020/247665 A1 | 12/2020 |
| WO | WO-2021/191827 A1 | 9/2021 |
| WO | WO-2021/206876 A1 | 10/2021 |
| WO | WO-2021/216195 A1 | 10/2021 |
| WO | WO-2021205298 A1 | 10/2021 |
| WO | WO-2021226546 A1 | 11/2021 |
| WO | WO-2021250648 A1 | 12/2021 |
| WO | WO-2022020242 A1 | 1/2022 |

OTHER PUBLICATIONS

Altmann, et al "Dipeptide nitrile inhibitors of cathepsin K." Bioorg Med Chem Lett. May 1, 2006;16(9):2549-54. doi: 10.1016/j.bmcl.2006.01.104. Epub Feb. 9, 2006.
Amblard, et al., "Synthesis and antiviral evaluation of novel peptidomimetics as norovirus protease inhibitors," Bioorganic & Medicinal Chemistry Letters, vol. 28, Issue 12, 2018, pp. 2165-2170.
Amin, Sk Abdul et al. "Protease targeted COVID-19 drug discovery and its challenges: Insight into viral main protease (Mpro) and papain-like protease (PLpro) inhibitors." *Bioorganic & medicinal chemistry* vol. 29 (2021): 115860. doi:10.1016/j.bmc.2020.115860.
Bai et al: "Peptidomimetic nitrile warheads as SARS-CoV-2 3CL protease inhibitors," RSC Med. Chem., 2021, 12, 1722-1730 DOI:10.1039/D1MD00247C.
Bandyopadhyay, et al. "Targeting biomolecules with reversible covalent chemistry," Current Opinion in Chemical Biology, vol. 34, 2016, pp. 110-116.
Bernassola, et al. "HECT-Type E3 Ubiquitin Ligases in Cancer," Trends Biochem Sci. Dec. 2019;44(12):1057-1075.
Berteottti, et al. "Predicting the Reactivity of Nitrile-Carrying Compounds with Cysteine: A Combined Computational and Experimental Study," ACS Med. Chem. Lett. 2014, 5, 5, 501-505.
Boras, et al "Discovery of a Novel Inhibitor of Coronavirus 3CL Protease as a Clinical Candidate for the Potential Treatment of COVID-19" bioRxiv 2020.09.12.293498; doi: https://doi.org/10.1101/2020.09.12.293498.
Boras, et al., "Discovery of a Novel Inhibitor of Coronavirus 3CL Protease for the Potential Treatment of COVID-19," bioRxiv 2020.09.12.293498; doi: https://doi.org/10.1101/2020.09.12.293498.
Cai, et al. "4-(3-Trifluoromethylphenyl)-pyrimidine-2-carbonitrile as cathepsin S inhibitors: N3, not N1 is critically important," Bioorg Med Chem Lett . Aug. 1, 2010;20(15):4507-10.
Casimiro-Garcia, et al. "Identification of Cyanamide-Based Janus Kinase 3 (JAK3) Covalent Inhibitors," J. Med. Chem. 2018, 61, 23, 10665-10699.
Chang, Kyeong-Ok et al. "Antiviral Drug Discovery: Norovirus Proteases and Development of Inhibitors." *Viruses* vol. 11,2 197. Feb. 25, 2019, doi:10.3390/v11020197.
Chatterjee, et al. "Can Relative Binding Free Energy Predict Selectivity of Reversible Covalent Inhibitors?," J. Am. Chem. Soc. 2017, 139, 49, 17945-17952.
Chuck, et al., "Design, synthesis and crystallographic analysis of nitrile-based broad-spectrum peptidomimetic inhibitors for coronavirus 3C-like proteases," Eur J Med Chem. Jan. 2013;59:1-6.
Chuck, et al., "Supplementary Material: Design, synthesis and crystallographic analysis of nitrile-based broad-spectrum peptidomimetic inhibitors for coronavirus 3C-like proteases," Eur J Med Chem. Jan. 2013;59:1-6.
Cianni, et al. "Optimization strategy of single-digit nanomolar cross-class inhibitors of mammalian and protozoa cysteine proteases," Bioorganic Chemistry 101. Jun. 2020; 1-20.
Coteron, et al. "Falcipain Inhibitors: Optimization Studies of the 2-Pyrimidinecarbonitrile Lead Series," J. Med. Chem. 2010, 53, 16, 6129-6152.
Dai, et al. "Design, Synthesis, and Biological Evaluation of Peptidomimetic Aldehydes as Broad-Spectrum Inhibitors against Enterovirus and SARS-CoV-2," Journal of Medicinal Chemistry, (Ahead of Print), 2021 (available online on Apr. 19, 2021), pages A-O, Issn: 0022-2623.
Dai, et al., "Structure-based design of antiviral drug candidates targeting the SARS-CoV-2 main protease," Science Jun. 19, 2020: vol. 368, Issue 6497, pp. 1331-1335.
Dai, Rongchen et al. "Cathepsin K: The Action in and Beyond Bone." *Frontiers in cell and developmental biology* vol. 8 433. Jun. 4, 2020, doi:10.3389/fcell.2020.00433.
Dai, Wenhao et al. "Supplementary Materials for: Structure-based design of antiviral drug candidates targeting the SARS-CoV-2 main protease." *Science (New York, N.Y.)* vol. 368,6497 (2020): 1331-1335. doi:10.1126/science.abb4489.
Damalanka, et al., "Structure-guided design, synthesis and evaluation of oxazolidinone-based inhibitors of norovirus 3CL protease," European Journal of Medicinal Chemistry, vol. 143, 2018, pp. 881-890.
De Cesco, et al. "Covalent inhibitors design and discovery," Eur J Med Chem . Sep. 29, 2017;138:96-114.
De Vries, et al: "Comparative study of a 3CLpro inhibitor and remdesivir against both major SARS-CoV-2 clades in human airway models" bioRxiv 2020.08.28.272880.
Doheny, et al. "Are Human Challenge Trials for COVID-19 Vaccine Worth the Risk?" Medscape, Medscape, Oct. 7, 2020, www.medscape.com/viewarticle/935377#:~:text=The%20trials%20could%20effectively%20deliver,or%20potentially%20the%20life%2C%20of.
Dong, et al. "Discovering drugs to treat coronavirus disease 2019 (COVID-19)," Drug Discov Ther. 2020;14(1):58-60.
Douangamath, Alice et al. "Crystallographic and electrophilic fragment screening of the SARS-CoV-2 main protease." *Nature communications* vol. 11,1 5047. Oct. 7, 2020, doi:10.1038/s41467-020-18709-w.
Dragovich et al "Structure-based design, synthesis, and biological evaluation of irreversible human rhinovirus 3C protease inhibitors. 2. Peptide structure-activity studies." J Med Chem. Jul. 16, 1998;41(15):2819-34. doi: 10.1021/jm9800696. PMID: 9667971.
Dragovich, et al. "Structure-Based Design, Synthesis, and Biological Evaluation of Irreversible Human Rhinovirus 3C Protease Inhibitors. 4. Incorporation of P1 Lactam Moieties as I-Glutamine Replacements," J. Med. Chem. 1999, 42, 7, 1213-1224.
Dragovich, P S et al. "Structure-based design, synthesis, and biological evaluation of irreversible human rhinovirus 3C protease inhibitors. 3. Structure-activity studies of ketomethylene-containing peptidomimetics." *Journal of medicinal chemistry* vol. 42,7 (1999): 1203-12. doi:10.1021/jm980537b.
Dragovich, Peter S et al. "Structure-based design, synthesis, and biological evaluation of irreversible human rhinovirus 3C protease inhibitors. 6. Structure-activity studies of orally bioavailable, 2-pyridone-containing peptidomimetics." Journal of medicinal chemistry vol. 45,8 (2002): 1607-23. doi:10.1021/jm010469k.
Dragovich, Peter S et al. "Structure-based design, synthesis, and biological evaluation of irreversible human rhinovirus 3C protease inhibitors. Part 7: structure-activity studies of bicyclic 2-pyridone-containing peptidomimetics." Bioorganic & medicinal chemistry letters vol. 12,5 (2002): 733-8. doi:10.1016/s0960-894x(02)00008-2.

(56) References Cited

OTHER PUBLICATIONS

Dragovich, Peter S. et al. "Structure-based design, synthesis, and biological evaluation of irreversible human rhinovirus 3C protease inhibitors. 1. Michael acceptor structure-activity studies." Journal of medicinal chemistry 41 15 (1998): 2806-18.
Dragovich, Peter S. et al. "Structure-Based Design, Synthesis, and Biological Evaluation of Irreversible Human Rhinovirus 3C Protease Inhibitors. 8. Pharmacological Optimization ofOrally Bioavailable 2-Pyridone-Containing Peptidomimetics." Journal of medicinal chemistry 46 21 (2003): 4572-85.
Eaton, et al. "Selective covalent targeting of GPX4 using masked nitrile-oxide electrophiles," Nature Chemical Biology vol. 16, pp. 497-506(2020).
Ehmke, et al., "Tuning and predicting biological affinity: arylnitriles as cysteine protease inhibitors," Org. Biomol. Chem., 2012,10, 5764-5768.
Fischer, et al. "Inhibitors for Novel Coronavirus Protease Identified by Virtual Screening of 687 Million Compounds," Mar. 2020; Preprint. https://doi.org/10.26434/chemrxiv.11923239.v1.
Flanagan, et al., "Chemical and Computational Methods for the Characterization of Covalent Reactive Groups for the Prospective Design of Irreversible Inhibitors," Journal of Medicinal Chemistry, 2014, 57, 23, 10072-10079.
Fleming, et al. "Nitrile-Containing Pharmaceuticals: Efficacious Roles of the Nitrile Pharmacophore," J. Med. Chem. 2010, 53, 22, 7902-7917.
Frizler, et al "Development of nitrile-based peptidic inhibitors of cysteine cathepsins." Curr Top Med Chem. 2010;10(3):294-322. doi: 10.2174/156802610790725452.
Gehringer, et al., "Emerging and Re-Emerging Warheads for Targeted Covalent Inhibitors: Applications in Medicinal Chemistry and Chemical Biology," J. Med. Chem. Jun. 27, 2019;62(12):5673-5724.
Ghosh, Arun K., and Sandra Gemma. "Design of Cysteine Protease Inhibitors." Structure-Based Design of Drugs and Other Bioactive Molecules, May 29, 2015, pp. 131-142, 10.1002/9783527665211.ch5. Accessed Feb. 14, 2022.
Gurard-Levin, Zachary A et al. "Evaluation of SARS-CoV-2 3C-like protease inhibitors using self-assembled monolayer desorption ionization mass spectrometry." Antiviral research vol. 182 (2020): 104924. doi:10.1016/j.antiviral.2020.104924.
Günther, Sebastian et al. "X-ray screening identifies active site and allosteric inhibitors of SARS-CoV-2 main protease." *Science (New York, N.Y.)* vol. 372,6542 (2021): 642-646. doi:10.1126/science.abf7945.
He, Jun et al. "Potential of coronavirus 3C-like protease inhibitors for the development of new anti-SARS-CoV-2 drugs: Insights from structures of protease and inhibitors." *International journal of antimicrobial agents* vol. 56,2 (2020): 106055. doi:10.1016/j.ijantimicag.2020.106055.
Hoffman, et al. "Discovery of Ketone-Based Covalent Inhibitors of Coronavirus 3CL Proteases for the Ptential Therapeutic Treatment of COVID-19," Journal of Medicinal Chemistry, vol. 63(21), 2020 (published on Oct. 15, 2020), pp. 12725-12747.
Hoffman, Robert L et al. "Discovery of Ketone-Based Covalent Inhibitors of Coronavirus 3CL Proteases for the Potential Therapeutic Treatment of COVID-19." Journal of medicinal chemistry vol. 63,21 (2020): 12725-12747. doi:10.1021/acs.jmedchem.0c01063.
Hou, et al. "SARS-CoV-2 Reverse Genetics Reveals a Variable Infection Gradient in the Respiratory Tract," Cell . Jul. 23, 2020;182(2):429-446.e14.
Iketani, et al: "Lead compounds for the development of SARS-CoV-2 3CL protease inhibitors." Nat Commun. Apr. 1, 2021;12(1):2016. doi: 10.1038/s41467-021-22362-2. Erratum in: Nat Commun. May 5, 2021;12(1):2708.
Jacobs, et al. "Discovery, synthesis, and structure-based optimization of a Series of N-(tert-butyl)-2-(N-arylamido)-2-(pyridine-3-yl) acetamides (ML188) as potent noncovalent small molecule inhibitors of the severe acute respiratory syndrome coronavirus (SARS-CoV) 3CL protease," Journal of Medicinal Chemistry, 2013, vol. 56, No. 2, 534-546.
Jeon, et al. "Identification of Antiviral Drug Candidates against SARS-CoV-2 from FDA-Approved Drugs," Antimicrobial Agents and Chemotherapy Jun. 2020, 64 (7) e00819-20.
Jeong, Gi Uk et al. "Therapeutic Strategies Against COVID-19 and Structural Characterization of SARS-CoV-2: A Review." *Frontiers in microbiology* vol. 11 1723. Jul. 14, 2020, doi:10.3389/fmicb.2020.01723.
Johnson, et al. "Structure-based design of a parallel synthetic array directed toward the discovery of irreversible inhibitors of human rhinovirus 3C protease," J Med Chem. May 9, 2002;45(10):2016-23.
Keyser, et al. "Computation-Guided Rational Design of a Peptide Motif That Reacts with Cyanobenzothiazoles via Internal Cysteine-Lysine Relay," J. Org. Chem. 2018, 83, 14, 7467-7479.
Kim, et al., "Broad-spectrum antivirals against 3C or 3C-like proteases of picornaviruses, noroviruses, and coronaviruses," J Virol . Nov. 2012;86(21):11754-62.
Kim, et al., "Broad-spectrum inhibitors against 3C-like proteases of feline coronaviruses and feline caliciviruses," J Virol . May 2015;89(9):4942-50.
Kim, et al., "Reversal of the Progression of Fatal Coronavirus Infection in Cats by a Broad-Spectrum Coronavirus Protease Inhibitor," PLoS Pathog . Mar. 30, 2016;12(3):e1005531.
Kitamura, et al., "Expedited Approach toward the Rational Design of Noncovalent SARS-CoV-2 Main Protease Inhibitors," J. Med. Chem., 2021, Publication Date:Apr. 23, 2021; https://doi.org/10.1021/acs.jmedchem.1c00509.
Kneller, et al "Direct Observation of Protonation State Modulation in SARS-CoV-2 Main Protease upon Inhibitor Binding with Neutron Crystallography." J Med Chem. Apr. 22, 2021;64(8):4991-5000. doi: 10.1021/acs.jmedchem.1c00058.
Konno, et al., "Design and synthesis of new tripeptide-type SARS-CoV 3CL protease inhibitors containing an electrophilic arylketone moiety," Bioorg Med Chem, Jan. 15, 2013;21(2):412-24.
Korkmaz, et al: "Lung Protection by Cathepsin C Inhibition: A New Hope for COVID-19 and ARDS?" J Med Chem. Nov. 25, 2020;63(22):13258-13265. doi: 10.1021/acs.jmedchem.0c00776. Epub Aug. 7, 2020.
Kruse, et al., "Therapeutic strategies in an outbreak scenario to treat the novel coronavirus originating in Wuhan, China," F1000Res. Jan. 31, 2020;9:72.
Kuhn, et al. "Prospective Evaluation of Free Energy Calculations for the Prioritization of Cathepsin L Inhibitors," J. Med. Chem. 2017, 60, 6, 2485-2497.
Lagoutte, et al. "Covalent inhibitors: an opportunity for rational target selectivity," Curr Opin Chem Biol . Aug. 2017;39:54-63.
Laine, et al. "Discovery of Novel Cyanamide-Based Inhibitors of Cathepsin C," ACS Med. Chem. Lett. 2011, 2, 2, 142-147.
Liu, et al. "Research and Development on Therapeutic Agents and Vaccines for COVID-19 and Related Human Coronavirus Diseases," ACS Cent. Sci. 2020, 6, 3, 315-331.
Liu, et al: "The development of Coronavirus 3C-Like protease (3CLpro) inhibitors from 2010 to 2020." Eur J Med Chem. Nov. 15, 2020;206:112711. doi: 10.1016/j.ejmech.2020.112711. Epub Aug. 6, 2020.
Lockbaum, et al "Pan-3C Protease Inhibitor Rupintrivir Binds SARS-CoV-2 Main Protease in a Unique Binding Mode. Biochemistry." Oct. 5, 2021;60(39):2925-2931. doi: 10.1021/acs.biochem.1c00414. Epub Sep. 10, 2021.
Lonsdale, et al. "Structure-based design of targeted covalent inhibitors," Chem. Soc. Rev., 2018, 47, 3816-3830.
Ma, et al., "Boceprevir, GC-376, and calpain inhibitors II, XII inhibit SARS-CoV-2 viral replication by targeting the viral main protease," Cell Res. Aug. 2020; 30(8): 678-692.
MacFaul, et al. "A simple in vitro assay for assessing the reactivity of nitrile containing compounds," Bioorganic & Medicinal Chemistry Letters, vol. 19, Issue 4, 2009, pp. 1136-1138.
Martin, et al., "Characterising covalent warhead reactivity," Bioorganic & Medicinal Chemistry, May 15, 2019;27(10):2066-2074.

(56) References Cited

OTHER PUBLICATIONS

Masand, et al. "Structure features of peptide-type SARS-CoV main protease inhibitors: Quantitative structure activity relationship study," Chemometrics and Intelligent Laboratory Systems, vol. 206, 104172, 2020 (available online on Oct. 3, 2020).
Montagutelli, et al. "The B1.351 and P.1 variants extend SARS-CoV-2 host range to mice," bioRxiv 2021.03.18.436013.
Mott, et al., "Identification and optimization of inhibitors of Trypanosomal cysteine proteases: cruzain, rhodesain, and TbCatB," Journal of Medicinal Chemistry, Jan. 14, 2010;53(1):52-60.
Namoto, et al. "Structure-based design and synthesis of macrocyclic human rhinovirus 3C protease inhibitors," Bioorg Med Chem Lett. Mar. 1, 2018;28(5):906-909.
Oballa, et al., "A generally applicable method for assessing the electrophilicity and reactivity of diverse nitrile-containing compounds," Bioorganic & Medicinal Chemistry Letters, vol. 17, Issue 4, 2007, pp. 998-1002.
Ono, Yasuko et al. "Calpain research for drug discovery: challenges and potential." *Nature reviews. Drug discovery* vol. 15,12 (2016): 854-876. doi:10.1038/nrd.2016.212.
Owen et al: "An Oral SARS-CoV-2 Mpro Inhibitor Clinical Candidate for the Treatment of COVID-19," medRxiv 2021.07.28. 21261232; DOI: https://doi.org/10.1101/2021.07.28.21261232.
Paasche, et al. "Mechanistic Insights into SARS Coronavirus Main Protease by Computational Chemistry Methods," 2012: n. pag. Print. Doctoral Thesis, University of Würzburg. https://d-nb.info/1037687825/34.
Patick, et al. "Protease Inhibitors as Antiviral Agents," Clin Microbiol Rev. Oct. 1998; 11(4): 614-627.
Pillaiyar, et al., "An Overview of Severe Acute Respiratory Syndrome-Coronavirus (SARS-CoV) 3CL Protease Inhibitors: Peptidomimetics and Small Molecule Chemotherapy," J. Med. Chem. 2016, 59, 14, 6595-6628.
Prior, et al., "Design, synthesis, and bioevaluation of viral 3C and 3C-like protease inhibitors," Bioorganic & Medicinal Chemistry Letters, vol. 23, Issue 23, 2013, pp. 6317-6320.
Qiao et al: "SARS-CoV-2 M pro inhibitors with antiviral activity in a transgenic mouse model," Science. Mar. 26, 2021;371(6536):1374-1378. DOI: 10.1126/science.abf1611. Epub Feb. 18, 2021.
Qin, et al "Acrylamide Fragment Inhibitors that Induce Unprecedented Conformational Distortions in Enterovirus 71 3C and SARS-CoV-2 Main Protease" bioRxiv 2020.11.06.370916; doi: <https://doi.org/10.1101/2020.11.06.370916>.
Rathnayake, et al "Structure-Guided Optimization of Dipeptidyl Inhibitors of Norovirus 3CL Protease." J Med Chem. Oct. 22, 2020;63(20):11945-11963. doi: 10.1021/acs.jmedchem.0c01252.
Rathnayake, et al., "3C-like protease inhibitors block coronavirus replication in vitro and improve survival in MERS-CoV-infected mice," Science Translational Medicine, Aug. 19, 2020: vol. 12, Issue 557, eabc5332.
Ray, et al. "New Electrophiles and Strategies for Mechanism-Based and Targeted Covalent Inhibitor Design," Biochemistry 2019, 58, 52, 5234-5244.
Rut Wioletta et al "Substrate specificity profiling of SARS-CoV-2 Mpro protease provides basis for anti-COVID-19 drug design" Marcin Drag bioRxiv 2020.03.07.981928; doi: https://doi.org/10.1101/2020.03.07.981928.
Sacco, Michael Dominic et al. "Structure and inhibition of the SARS-CoV-2 main protease reveals strategy for developing dual inhibitors against Mpro and cathepsin L." *bioRxiv : the preprint server for biology* 2020.07.27.223727. Jul. 27, 2020, doi:10.1101/2020.07.27.223727.
Santos, et al., "Experimental study and computational modelling of cruzain cysteine protease inhibition by dipeptidyl nitriles," Phys. Chem. Chem. Phys., 2018, 20, 24317-24328.
Santos, et al., "Michael acceptors as cysteine protease inhibitors," Mini Rev Med Chem . Oct. 2007;7(10):1040-50.
Schade, et al. "Highly Selective Sub-Nanomolar Cathepsin S Inhibitors by Merging Fragment Binders with Nitrile Inhibitors," J. Med. Chem. 2020, 63, 20, 11801-11808.
Schnute, et al. "Aminopyrazole Carboxamide Bruton's Tyrosine Kinase Inhibitors. Irreversible to Reversible Covalent Reactive Group Tuning," ACS Med. Chem. Lett. 2019, 10, 1, 80-85.
Schuller, Marion et al. "Fragment binding to the Nsp3 macrodomain of SARS-CoV-2 identified through crystallographic screening and computational docking." *Science advances* vol. 7,16 eabf8711. Apr. 14, 2021, doi:10.1126/sciadv.abf8711.
Serafimova, et al. (2013). Reversible targeting of noncatalytic cysteines with chemically tuned electrophiles. UCSF. ProQuest ID: Serafimova_ucsf_0034D_10695.REDACTED. Merritt ID: ark:/13030/m5x36bhx. Retrieved from https://escholarship.org/uc/item/0cj6m628.
Silva, et al. "A comparative study of warheads for design of cysteine protease inhibitors," Bioorg Med Chem Lett. Nov. 15, 2017;27(22):5031-5035.
Sinha, et al. "Electrophilicity of pyridazine-3-carbonitrile, pyrimidine-2-carbonitrile, and pyridine-carbonitrile derivatives: a chemical model to describe the formation of thiazoline derivatives in human liver microsomes," Chem Res Toxicol. Dec. 15, 2014;27(12):2052-61.
Steinhauer, et al., "Rapid evolution of RNA viruses," Annu Rev Microbiol. 1987;41:409-33.
Steuten, et al. "Challenges for Targeting SARS-CoV-2 Proteases as a Therapeutic Strategy for COVID-19," ACS Infect. Dis. 2021, Publication date: Feb. 11, 2021; https://doi.org/10.1021/acsinfecdis.0c00815.
STN Registry Database Entry for 1831065-26-9 entered STN Dec. 16, 2015.
STN Registry Database Entry for 2248095-92-1 entered STN Nov. 13, 2018.
STN Registry Database Entry for 2628280-40-8 entered STN Apr. 7, 2021.
Thanigaimalai Pillaiyar et al: "Design, synthesis, and biological evaluation of novel dipeptide-type SARS-CoV 3CL protease inhibitors: Structure-activity relationships," European Journal of Medicinal Chemistry, Elsevier, Amsterdam, NL, vol. 65, May 20, 2013 (May 20, 2013), pp. 436-447, DOI: 10.1016/J.EJMECH.2013.05.005.
Thanigaimalai, et al. "Development of potent dipeptide-type SARS-CoV 3CL protease inhibitors with novel P3 scaffolds: Design, synthesis, biological evaluation, and docking studies," European Journal of Medicinal Chemistry, vol. 68, 2013, pp. 372-384, ISSN: 0223-5234.
Tomar, et al. "Understanding the determinants for substrate recognition, regulation of enzymatic activity and the development of broad-spectrum inhibitors of coronavirus 3-chymotrypsin-like proteases," (2015). Open Access Dissertations. 1322. https://docs.lib.purdue.edu/open_access_dissertations/1322.
Totura, et al. "Broad-spectrum coronavirus antiviral drug discovery," Expert Opin Drug Discov. Apr. 2019;14(4):397-412.
Vandyck, et al: "ALG-097111, a potent and selective SARS-CoV-2 3-chymotrypsin-like cysteine protease inhibitor exhibits in vivo efficacy in a Syrian Hamster model." Biochem Biophys Res Commun. May 28, 2021;555:134-139. doi: 10.1016/j.bbrc.2021.03.096. Epub Mar. 26, 2021.
Verma, Sonia et al. "Cysteine Proteases: Modes of Activation and Future Prospects as Pharmacological Targets." *Frontiers in pharmacology* vol. 7 107. Apr. 25, 2016, doi:10.3389/fphar.2016.00107.
Vuong et al: "Improved Synthesis of a Cyclic Glutamine Analogue Used in Antiviral Agents Targeting 3C and 3CL Proteases Including SARS-CoV-2 MPRO," The Journal of Organic Chemistry 2021 86 (18), 13104-13110 DOI: 10.1021/acs.joc.1c01299.
Vuong, et al., "Feline coronavirus drug inhibits the main protease of SARS-CoV-2 and blocks virus replication," Nat Commun . Aug. 27, 2020;11(1):4282.
Wang, et al "Comprehensive Insights into the Catalytic Mechanism of Middle East Respiratory Syndrome 3C-Like Protease and Severe Acute Respiratory Syndrome 3C-Like Protease." ACS Catal. 2020;10:5871-5890. doi: 10.1021/acscatal.0c00110. Epub Apr. 28, 2020.
Wang, et al., "Covalent binding design strategy: A prospective method for discovery of potent targeted anticancer agents," European Journal of Medicinal Chemistry, vol. 142, 2017, pp. 493-505.

(56) References Cited

OTHER PUBLICATIONS

Wang, et al., "Inhibition of enterovirus 71 replication by an ?-hydroxy-nitrile derivative NK-1.9k," Antiviral Res . May 2017;141:91-100.

Westberg et al: "Rational design of a new class of protease inhibitors for the potential treatment of coronavirus diseases," bioRxiv 2020.09.15.275891; DOI: https://doi.org/10.1101/2020.09.15.275891.

White, et al., "Plitidepsin has potent preclinical efficacy against SARS-CoV-2 by targeting the host protein eEF1A," Science Feb. 26, 2021: vol. 371, Issue 6532, pp. 926-931.

Yang, Syaulan et al. "Synthesis, crystal structure, structure-activity relationships, and antiviral activity of a potent SARS coronavirus 3CL protease inhibitor." *Journal of medicinal chemistry* vol. 49,16 (2006): 4971-80. doi:10.1021/jm0603926.

Ye, et al., "Structural Basis for Inhibiting Porcine Epidemic Diarrhea Virus Replication with the 3C-Like Protease Inhibitor GC376," Viruses. Feb. 21, 2020;12(2):240.

Yuto Unoh et al "Discovery of S-217622, a Non-Covalent Oral SARS-CoV-2 3CL Protease Inhibitor Clinical Candidate for Treating COVID-19", bioRxiv 2022.01.26.477782; doi: https://doi.org/10.1101/2022.01.26.477782.

Zaidman, et al. "An automatic pipeline for the design of irreversible derivatives identifies a potent SARS-CoV-2 Mpro inhibitor," bioRxiv 2020.09.21.299776.

Zhai, et al., "Cyanohydrin as an Anchoring Group for Potent and Selective Inhibitors of Enterovirus 71 3C Protease," J. Med. Chem. 2015, 58, 23, 9414-9420.

Zhang, Chun-Hui et al. "Potent Noncovalent Inhibitors of the Main Protease of SARS-CoV-2 from Molecular Sculpting of the Drug Perampanel Guided by Free Energy Perturbation Calculations." ACS central science vol. 7,3 (2021): 467-475. doi:10.1021/acscentsci.1c00039.

Zhang, et al Supplementary Materials for: Crystal structure of SARS-CoV-2 main protease provides a basis for design of improved ?-ketoamide inhibitors. Science. 2020;368(6489):409-412. doi:10.1126/science.abb3405.

Zhang, Linlin et al. "Crystal structure of SARS-CoV-2 main protease provides a basis for design of improved ?-ketoamide inhibitors." Science (New York, N.Y.) vol. 368,6489 (2020): 409-412. doi:10.1126/science.abb3405.

Zhao, et al. "Progress with covalent small-molecule kinase inhibitors," vol. 23, Issue 3, 2018, pp. 727-735, ISSN 1359-6446.

INHIBITORS OF CYSTEINE PROTEASES AND METHODS OF USE THEREOF

CROSS REFERENCE TO RELATED APPLICATIONS

This application is a continuation of Ser. No. 17/384,369 filed Jul. 23, 2021, which is a continuation of U.S. Ser. No. 17/230,727, filed Apr. 14, 2021, which claims the benefit of, and priority to, U.S. Ser. No. 63/012,039 filed Apr. 17, 2020; U.S. Ser. No. 63/031,357 filed May 28, 2020; U.S. Ser. No. 63/036,866 filed Jun. 9, 2020; U.S. Ser. No. 63/039,297 filed Jun. 15, 2020; U.S. Ser. No. 63/067,669 filed Aug. 19, 2020; U.S. Ser. No. 63/091,630 filed Oct. 14, 2020; U.S. Ser. No. 63/129,018 filed Dec. 22, 2020; U.S. Ser. No. 63/171,675 filed Apr. 7, 2021; U.S. Ser. No. 63/172,478 filed Apr. 8, 2021; and U.S. Ser. No. 63/173,146 filed Apr. 9, 2021, the contents of each of which are incorporated herein by reference in their entirety.

BACKGROUND

The Coronaviridae family of viruses are enveloped, single-stranded, positive-sense RNA viruses and include 141 species that are classified into four genera according to their phylogenetic relationships: α-, β-, γ-, and δ-coronavirus. Coronaviruses (CoVs) are zoonotic viruses that infect a variety of animals from whales to birds, bats, cats, and humans. Typically, CoV infection results in mild to moderate respiratory tract infections; however, some CoV species are extremely virulent and can result in widespread fatality. Severe acute respiratory syndrome coronavirus (SARS-CoV) is a human CoV that was responsible for the first pandemic of the 21$^{st}$ century, infecting over 8,000 people with a 10% mortality rate. Middle East respiratory syndrome coronavirus (MERS-CoV) was identified in November 2012 and had since infected over 1,600 people in 26 countries with 36% mortality rate. More recently, COVID-19 (SARS CoV2) coronaviruses have raised a global pandemic since they had been first identified in China in late 2019. Therefore, it is important to identify coronavirus drug targets that can be utilized for the development of broad-spectrum anti-coronaviral therapeutics to combat infections of existing and emerging coronaviruses.

All CoVs express a >800 kDa replicase polyprotein that contains either two or three cysteine proteases, the papain-like protease(s) (PLPpro, or PLP1 and PLP2) and the 3C-like protease (3CLpro, nsp5, or Mpro). These proteases process the CoV replicase polyprotein by cleaving it into 16 non-structural proteins, which are responsible for a variety of aspects of CoV replication. The CoV 3CLpro is responsible for processing 11 cleavage sites of within the replicase polyprotein and is essential for CoV replication, making it a highly valuable target for therapeutic development. The overall active site architecture and substrate recognition pockets are structurally conserved across CoV 3CLpros, increasing its attractiveness as a target for the development of broad-spectrum anti-CoV therapeutics. Moreover, high sequence conservation in the vicinity of active site among CoV 3CLpros from different coronavirus subclasses make them an excellent target for the development of broad-spectrum therapeutics for coronavirus infections. Accordingly, the development of CoV 3CLpro inhibitors is a promising path for the treatment of respiratory tract infections and related diseases.

Numerous studies on targeting the immediate zoonotic reservoirs of coronaviruses with small molecule inhibitors have helped inform structure-based design strategies aimed at creating molecular scaffolds that may aid in the development of therapeutic against coronaviral infection; however, small molecule antiviral agents nor effective commercially available broad-spectrum therapeutics have not yet been identified. There is a critical need for the development of broad-spectrum CoV therapeutics to overcome the challenges of traditional anti-CoV therapeutic development, as broad-spectrum therapeutics can be rapidly implemented upon zoonotic disease outbreak.

SUMMARY

The disclosure is directed to, in part, viral protease inhibitors. Also provided are pharmaceutical compositions comprising at least one disclosed compound and a pharmaceutically acceptable carrier.

In an embodiment, provided herein is a viral protease inhibitor, comprising a warhead covalently bound to a 3C or 3CL protease inhibitor, wherein the antiviral compound covalently binds to Cys on the protease, and wherein the antiviral compound is active against one or more viruses.

Also provided herein are compounds represented by Formula II.

Formula II $$\text{structure with } R^2, R^{1b}, R^{1a}, R^{3b}, R^{3a}$$

wherein: $R^{3a}$ is selected from $$\text{structure with } A, X, R^3$$

and 4-10 membered heterocycle, wherein the heterocycle may optionally be substituted by one, two or three substituents each selected from the group consisting of hydroxyl, $C_1$-$C_8$alkoxy, oxo and a warhead A; $R^{3b}$ is selected from hydrogen and $C_1$-$C_8$alkyl; wherein $R^{3a}$ and $R^{3b}$ may be joined together to form, together with the carbon to which they are attached, a 4-10 membered heterocycle, wherein the heterocycle may optionally be substituted by one, two or three substituents each selected from $C_6$-$C_{14}$aryl and a warhead A; $R^{1a}$ is selected from the group consisting of hydrogen, $C_1$-$C_8$alkyl, $C_1$-$C_8$heteroalkyl, —($C_1$-$C_8$alkyl)-$R^1$, —($C_1$-$C_8$alkyl)-CN, $C_3$-$C_{10}$cycloalkyl, $C_6$-$C_{14}$aryl, 4-10 membered heterocycle and 5-10 membered heteroaryl; $R^{1b}$ is selected from hydrogen and $C_1$-$C_8$alkyl; or $R^1$ and $R^{1b}$ may be joined together to form, together with the carbon to which they are attached, a 4-10 membered mono or bicyclic heterocycle having a ring nitrogen, $NR^G$, or a $C_3$-$C_{10}$cycloalkyl; $R^1$ is selected from the group consisting of $C_1$-$C_8$alkyl, $C_2$-$C_{10}$alkenyl, $C_2$-$C_{10}$alkynyl, $C_3$-$C_{10}$cycloalkyl, $C_6$-$C_{14}$aryl, 5-10 membered heteroaryl and 4-10 membered heterocycle, wherein $R^1$ may optionally be substituted on a free carbon by one, two, or three substituents each selected from $R^A$; $R^A$ is independently selected, for each occurrence, halogen, cyano, hydroxyl, oxo, SF$_5$, CF$_3$, —O—CF$_3$, —O—CHF$_2$, —S—CH$_3$, —S(O)$_2$—CH$_3$, —NH$_2$, —O-phenyl, —O—(C$_1$-C$_8$alkyl)-phenyl, —NHC(O)R$^B$, —NHC(O)OR$^B$, —NHC(O)O—(C$_1$-C$_8$alkyl)-R$^B$, —N(R$^y$)$_2$, —N(R$^y$)(C$_1$-C$_8$alkyl)C(O)O-phenyl, —N(R$^y$)(C$_1$-C$_8$alkyl)C(O)N(R$^y$)$_2$, —NHC(O)O(C$_1$-C$_8$alkyl)R$^B$, —C(O)-(5-10 membered heteroaryl), —C(O)-(4-10 membered heterocycle), —C(O)—O-(4-10 membered heterocycle), —C(O)—OC(CH$_3$)$_3$, —C(O)—(C$_1$-C$_6$alkyl), —C(O)—(C$_2$-C$_{10}$alkenyl)-(C$_6$-C$_{14}$aryl), C(O)—(C$_{1-6}$alkyl)-NHC(O)R$^B$, —C$_1$-C$_8$alkyl, C$_2$-C$_{10}$alkenyl, C$_2$-C$_{10}$alkynyl, C$_1$-C$_8$heteroalkyl, C$_1$-C$_8$alkoxy, C$_3$-C$_{10}$cycloalkyl, —(C$_1$-C$_8$alkyl)-(C$_3$-C$_{10}$cycloalkyl), —(C$_1$-C$_8$alkyl)-(C$_6$-C$_{14}$aryl), —(C$_1$-C$_8$alkyl)-(5-10 membered heteroaryl), C$_6$-C$_{14}$aryl, 5-10 membered heteroaryl and 4-10 membered heterocycle, wherein the R$^B$, heterocycle, heteroaryl, or aryl may optionally be substituted by one, two or three substituents of halogen, C$_1$-C$_8$alkyl, C$_1$-C$_8$alkoxy, SF$_5$, —NH$_2$, hydroxyl or oxo; R$^2$ is selected from the group consisting of —NHC(O)R$^B$, —NHC(O)N(R$^B$)$_2$, —NHC(O)C(R$^C$)$_2$R$^B$, —NHS(O)$_2$R$^B$, —O—(C$_1$-C$_8$alkyl)-(C$_3$-C$_{10}$cycloalkyl), 4-10 membered heterocycle, C$_6$-C$_{14}$aryl and 5-10 membered heteroaryl bound through the carbon or nitrogen atom, wherein R$^2$ may optionally be substituted by one, two, or three substituents each selected from R$^x$; or R$^{1a}$ and R$^2$ may be joined together to form, together with the carbon to which they are attached, a 4-10 membered mono or bicyclic heterocycle having a ring nitrogen NR$^G$, or a C$_3$-C$_{10}$cycloalkyl, wherein the cycloalkyl or heterocycle may optionally be substituted by one, two or three substituents on a free carbon each selected from R$^A$; R$^3$ is selected from 5-10 membered heteroaryl and 4-10 membered heterocycle, wherein R$^3$ may optionally be substituted by one, two, or three substituents each selected from R$^A$; R$^B$ is independently selected, for each occurrence, from the group consisting of C$_1$-C$_8$alkyl (optionally substituted by one, two or three halo), C$_2$-C$_{10}$alkenyl, C$_2$-C$_{10}$alkynyl, C$_6$-C$_{14}$aryl, 5-10 membered heteroaryl and 4-10 membered heterocycle; R$^C$ is independently selected, for each occurrence, from hydrogen, halogen and C$_1$-C$_8$alkyl; R$^x$ is independently selected, for each occurrence, from the group consisting of halogen, hydroxyl, oxo, CF$_3$, SF$_5$, cyano, —OCHF$_2$, —OCF$_3$, —O—(C$_1$-C$_8$alkyl), —C(O)O(CH$_3$), —N(R$^y$)$_2$, —N(R$^y$)C(O)R$^y$, —N(R$^y$)(C$_1$-C$_8$alkyl)C(O)N(R$^y$)$_2$, —N(R$^y$)(C$_1$-C$_8$alkyl)C(O)OH, —(C$_1$-C$_8$alkyl)-(C$_3$-C$_{10}$cycloalkyl), C$_1$-C$_8$alkyl, C$_1$-C$_8$alkoxy, C$_3$-C$_{10}$cycloalkyl, C$_6$-C$_{14}$aryl, 5-10 membered heteroaryl and 4-10 membered heterocycle, wherein the aryl, heterocycle or heteroaryl may optionally be substituted by one or more substituents each selected from oxo, halogen and C$_1$-C$_8$alkyl; R$^G$ is selected from the group consisting of H, C$_{1-6}$alkyl (optionally substituted by one, two or three substituents each independently selected from the group consisting of —C(=O), halo, cyano, —NR$^m$R$^m$, and —NH(C=O)R$^m$), and C(=O)—C$_{1-6}$alkyl (optionally substituted by one, two or three substituents each independently selected from the group consisting of halo, cyano, —NR$^m$R$^m$, —NR$^m$(C=O)R$^m$, phenyl, cycloalkyl, heterocycle, C$_1$-C$_6$alkoxy, wherein R$^m$ is selected for each occurrence by H, C$_{1-3}$alkyl (optionally substituted by one, two or three substituents each independently selected from the group consisting of halo), phenyl (optionally substituted by halo), —S(O)$_2$—CH$_3$, C$_{3-6}$cycloalkyl, and 5-6 membered heteroaryl), —C(=O)—C$_{1-6}$alkyl (optionally substituted by one, two or three substituents each independently selected from the group consisting of halo, cyano and C$_1$-C$_6$alkoxy), C(=O)—C$_{3-6}$cycloalkyl, and C(=O)-(5-6 membered heteroaryl) (optionally substituted by halo, cyano, hydroxyl, NH$_2$, C$_{1-6}$alkyl, C$_{3-6}$cycloalkyl, C$_1$-C$_6$alkoxy, and C$_{1-6}$haloalkyl)); R is independently selected, for each occurrence, from the group consisting of hydrogen, C$_1$-C$_8$alkyl, C$_1$-C$_8$heteroalkyl, —CH$_2$CF$_3$, C$_1$-C$_8$alkoxy, —(C$_1$-C$_8$alkoxy)-(5-10 membered aryl), C$_3$-C$_6$cycloalkyl and —(C$_1$-C$_8$alkyl)COOH; A is a warhead; X is selected from the group consisting of C(R$^{xy}$) and N, wherein R$^{xy}$ is selected from the group consisting of H, D, —OH, —NH$_2$, halogen, C$_1$-C$_8$alkyl, C$_1$-C$_8$ haloalkyl, and C$_1$-C$_8$alkoxy; and pharmaceutically acceptable salts, stereoisomers, esters, and prodrugs thereof.

In some embodiments, provided herein are compounds represented by Formula II-A:

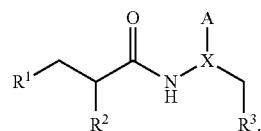

Formula II-A

In some embodiments, provided herein are compounds represented by Formula II-B:

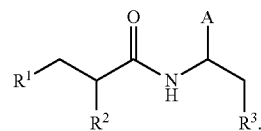

Formula II-B

In some embodiments, provided herein are compounds represented by Formula II-I:

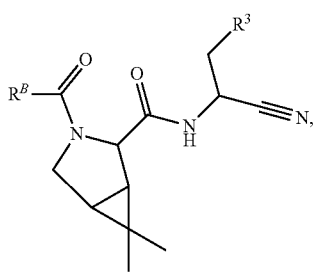

Formula II-I wherein: R$^3$ is

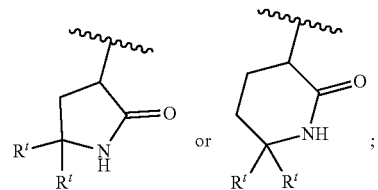

R$^t$ is independently, for each occurrence, H or methyl; or each R$^t$ may be taken, together with the carbon to which they are attached, to form a cyclopropyl; R$^B$ is selected from the group consisting of: a 9-10 membered bicyclic heteroaryl having one ring nitrogen, C$_1$-C$_6$alkyl, and C$_2$-C$_3$alkenyl; wherein R$^B$ is optionally substituted by one, two or three substituents each independently selected from the group consisting of halogen, $C_1$-$C_3$alkoxy, $NHR^m$, and phenyl (optionally substituted by one or two halogens); $R^m$ is $C_{1-3}$alkyl or —C(O)—$C_{1-3}$alkyl, wherein each $C_{1-3}$alkyl is independently optionally substituted by one, two or three halogens; or a pharmaceutically acceptable salt thereof.

In certain embodiments, provided herein are conjugates represented by Formula III:

Formula III wherein $Cys_{145}$ is cysteine at position 145 or equivalent active site cysteine on a CL or 3CL protease; IR is a viral protease inhibitor; and wherein the compound that forms the conjugate comprises a —CN warhead.

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The term "treating" includes any effect, e.g., lessening, reducing, modulating, or eliminating, that results in the improvement of the condition, disease, disorder and the like, including a reduction of viral shedding in asymptomatic individuals and prophylaxis of exposed individuals, independent of symptoms.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_1$. 3alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_1$-$C_5$alkenyl, $C_2$-$C_6$alkenyl, and $C_3$-$C_4$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_1$-$C_6$alkoxy, $C_1$-$C_6$alkoxy, and $C_2$-$C_6$alkoxy, respectively. Exemplary alkoxy groups include, but are not limited to methoxy, ethoxy, isopropoxy, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_1$-$C_5$alkoxy, $C_1$-$C_6$alkoxy, and $C_2$-$C_6$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

Examples of representative substituted aryls include the following

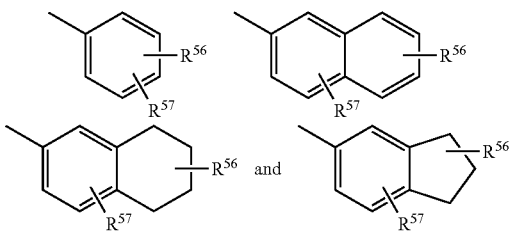

wherein one of $R^{56}$ and $R^{57}$ may be hydrogen and at least one of $R^{56}$ and $R^{57}$ is each independently selected from halogen, $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^8COR^{59}$, $NR^{58}SOR^{59}$ $NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group consisting of N, O, and S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc.

The terms "cycloalkyl" or a "carbocyclic group" as used herein refers to a saturated or partially unsaturated hydrocarbon group of, for example, 3-6, or 4-6 carbons, referred to herein as $C_3$-$C_{10}$cycloalkyl, $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The term "hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g, heteroaryl, cycloalkenyl, e.g, cycloheteroalkenyl, and the like having from 1 to 5, and particularly from 1 to 3 heteroatoms.

The terms "heteroaryl" or "heteroaromatic group" as used herein refers to a monocyclic aromatic 5-10 membered ring system containing one or more heteroatoms, for example one to three heteroatoms, such as nitrogen, oxygen, and sulfur. The term may also be used to refer to an 8-10 membered bicyclic heteroaryl. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl," "heterocycle," or "heterocyclic group" are art-recognized and refer to saturated or partially unsaturated 4-10 membered ring structures, whose ring structures include one to three heteroatoms, such as nitrogen, oxygen, and sulfur. Where possible, heterocyclyl rings may be linked to the adjacent radical through carbon or nitrogen. The term may also be used to refer to 4-10 membered saturated or partially unsaturated ring structures that are bridged, fused or spirocyclic ring structures, whose ring structures include one to three heteroatoms, such as nitrogen, oxygen, and sulfur. Examples of heterocyclyl groups include, but are not limited to, pyrrolidine, piperidine, morpholine, thiomorpholine, piperazine, oxetane, azetidine, tetrahydrofuran or dihydrofuran etc. In some embodiments, the heterocycle is a spiro heterocycle (e.g. 2,8-diazaspiro[4.5]decane). In some embodiments, the heterocycle is a bridged heterocycle (e.g. octahydro-1H-4, 7-methanoisoindole). "Spiro heterocyclyl," or "spiro heterocycle" refers to a polycyclic heterocyclyl with rings connected through one common atom (called a spiro atom), wherein the rings have one or more heteroatoms selected from the group consisting of N, O, and S(O)m (wherein m is an integer of 0 to 2) as ring atoms. Representative examples of heterocyclyl include, for example:

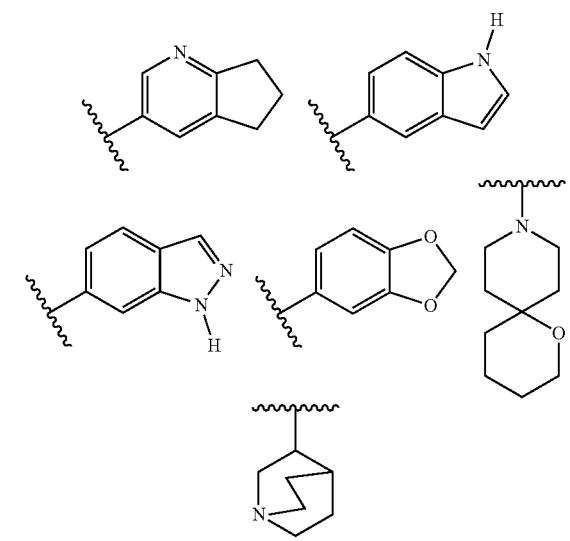

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well-known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the disclosure are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol $=\!=\!=$ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present disclosure can be prepared synthetically from commercially available starting materials that contain asymmetric or stereogenic centers, or by preparation of racemic mixtures followed by resolution methods well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well-known in the art. Stereoselective syntheses encompass both enantio- and diastereoselective transformations, and may involve the use of chiral auxiliaries. For examples, see Carreira and Kvaerno, Classics in Stereoselective Synthesis, Wiley-VCH: Weinheim, 2009.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the disclosure may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well-known in the art (for example, see Rautio, Kumpulainen, et al, Nature Reviews Drug Discovery 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as (3-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-($(C_{1-6})$alkylcarbonyloxy)ethyl, 1-methyl-1-($(C_{1-6})$alkylcarbonyloxy)ethyl $(C_{1-6})$alkoxycarbonyloxymethyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O$(C_{1-6})$alkyl)$_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

The term "warhead" or "warhead group" as used herein refers to a functional group present on a compound wherein that functional group is capable of reversibly or irreversibly participating in a reaction with a protein, e.g., 3C or 3CL protease (e.g., with a cysteine on the protease such as Cys 145). Warheads may, for example, form covalent bonds with the protein, or may create stable transition states, or be a reversible or an irreversible alkylating agent. For example, the warhead moiety can be a functional group on an inhibitor that can participate in a bond-forming reaction, wherein a new covalent bond is formed between a portion of the warhead and a donor, for example an amino acid residue of a protein. In embodiments, the warhead is an electrophile and the "donor" is a nucleophile such as the side chain of a cysteine residue. As provided herein, a warhead may include a nitrile or halo group. As also provided herein, a warhead may include an aldehyde, ketoamides, hydroxybisulfite salts, heterocyclic moieties, aziridine, oxirane, epoxy ketones, halomethyl ketones, hydroxymethyl ketones, electrophilic ketones (e.g. trifluoromethyl ketones), acyloxymethyl ketones, benzothiazolyl ketones and a Michael acceptor. For example, nitriles may be reversible covalent warheads for cysteine protease inhibition, for example, where the mechanism of action may involve a formation of reversible covalent bond between the nitrile and the active cysteine to form a thioimidate adduct. Reaction of cysteine of glutathione or other proteins is generally reversible, while the reaction with cysteine or aminoethylthiols generally irreversibly forms a thiazolidine adduct. It can be appreciated that contemplated compounds herein may be a reversible or an irreversible inhibitor.

Examples of exemplary warheads include, but not limited to, a moiety with a cyano, halomethyl, an aldehyde, ketoamide, hydroxybisulfite salt, heterocycle, epoxy ketone, halomethyl ketone, hydroxymethyl ketone, electrophilic ketone, acyloxymethyl ketone, benzothiazolyl ketone or a Michael acceptor, for example:

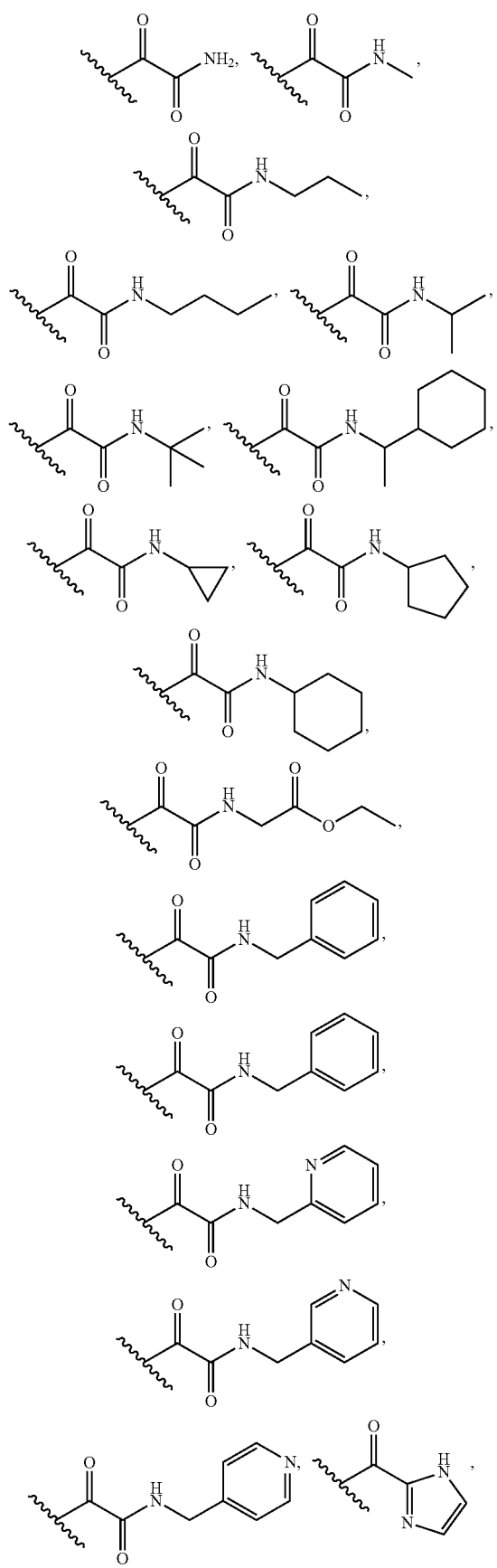
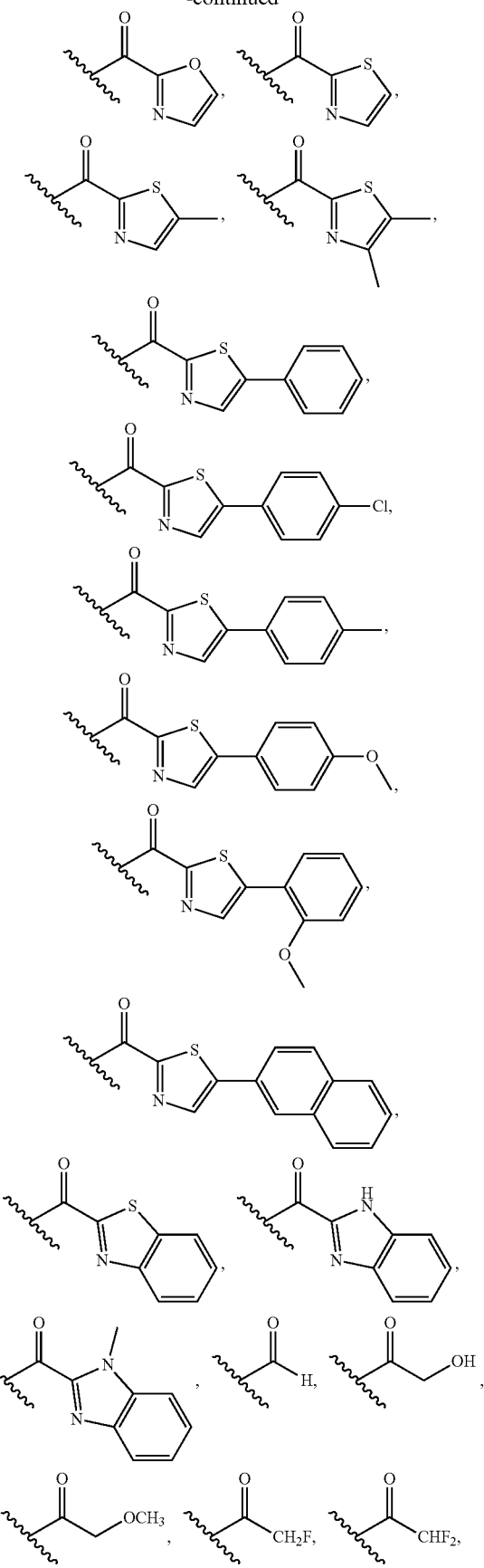

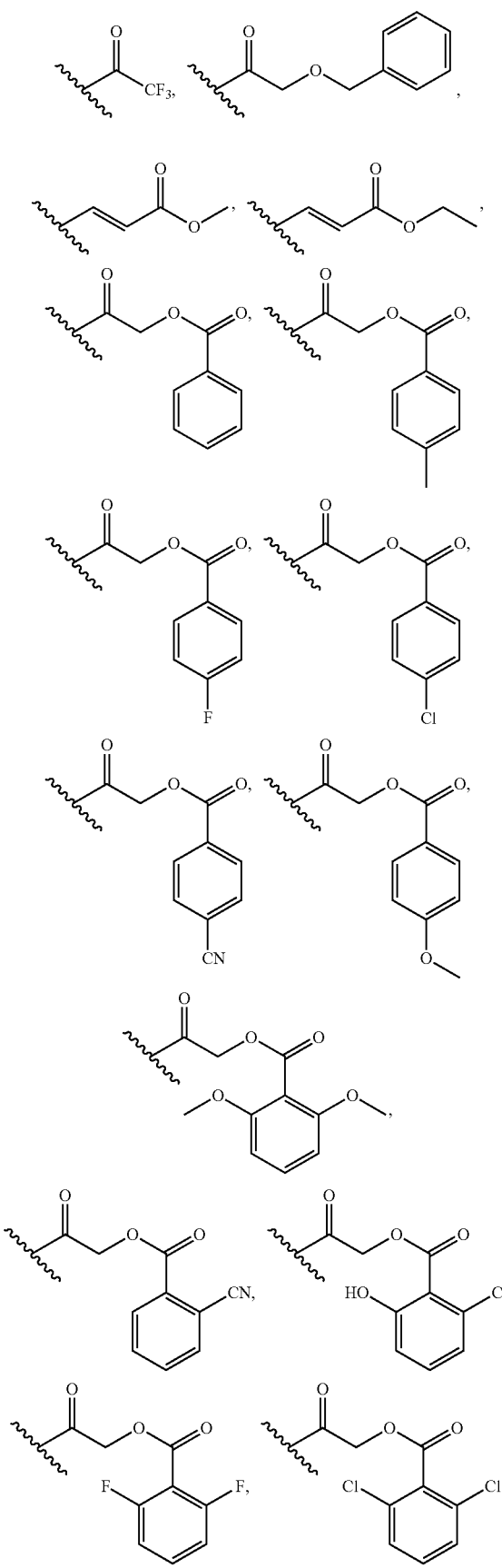
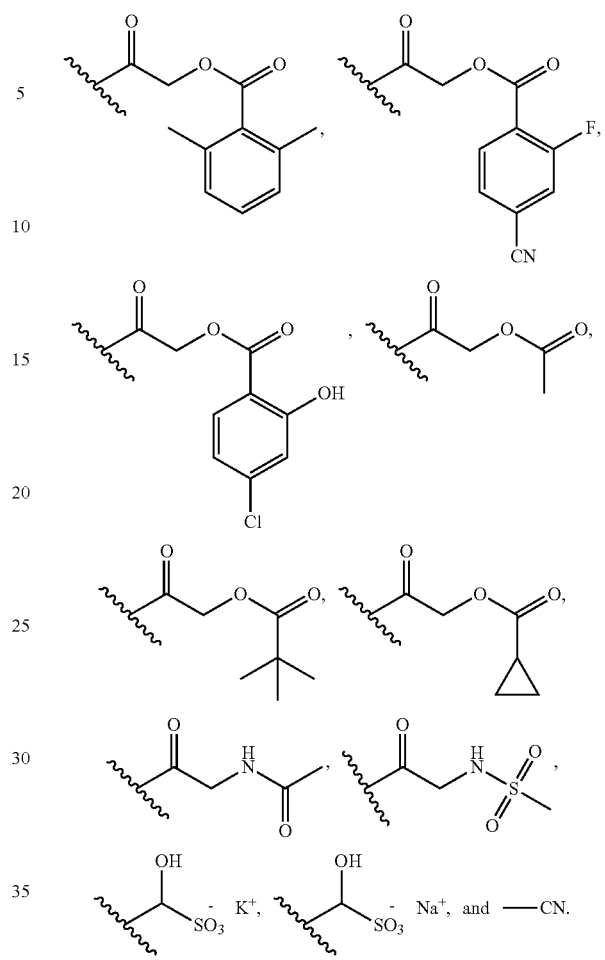
In some embodiments, the warhead is a moiety with a cyanohydrin or cyanoacrylate moiety. Examples of exemplary cyanohydrin and cyanoacrylate warheads include, but not limited to:
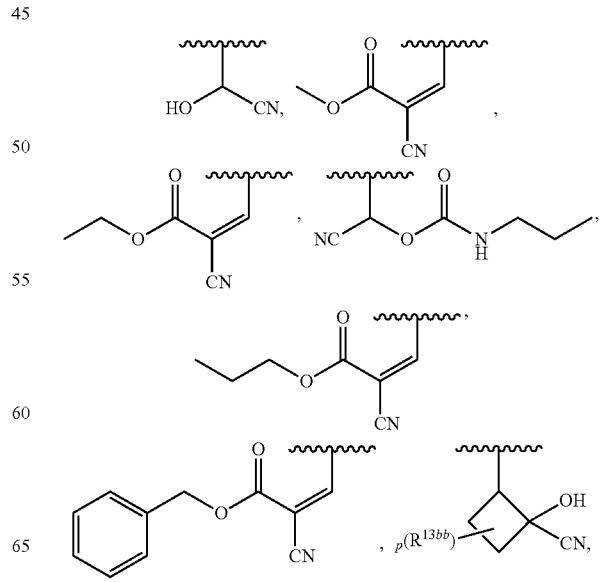

-continued

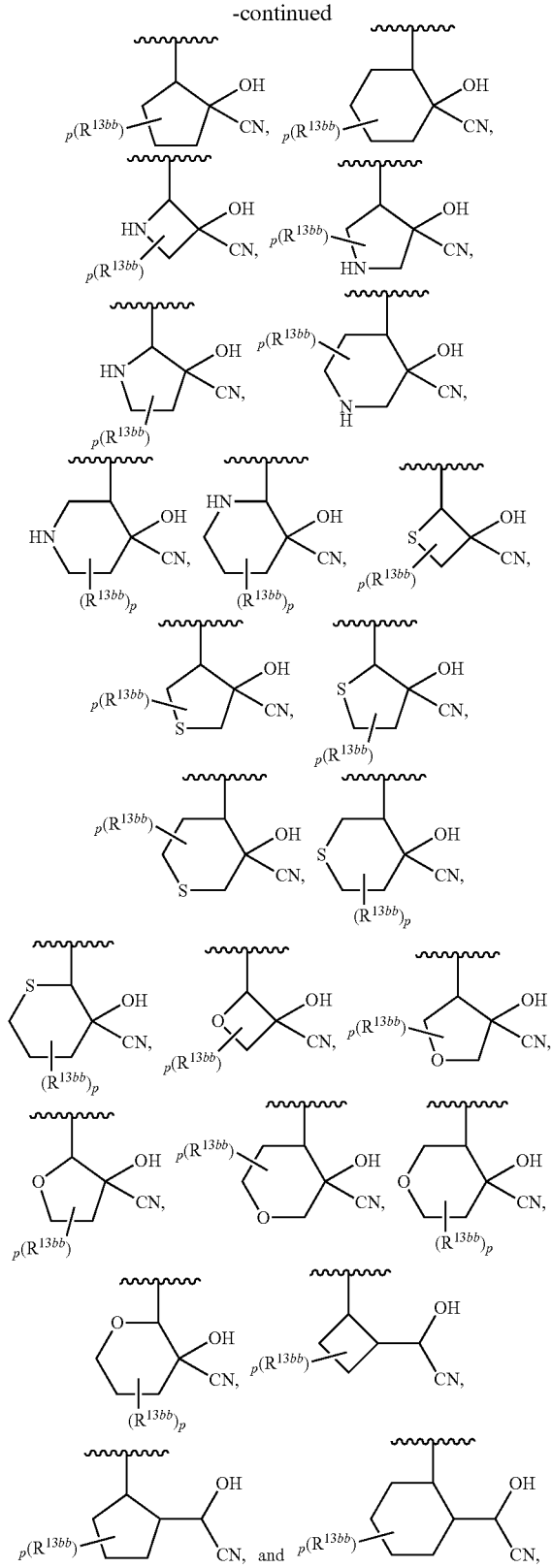

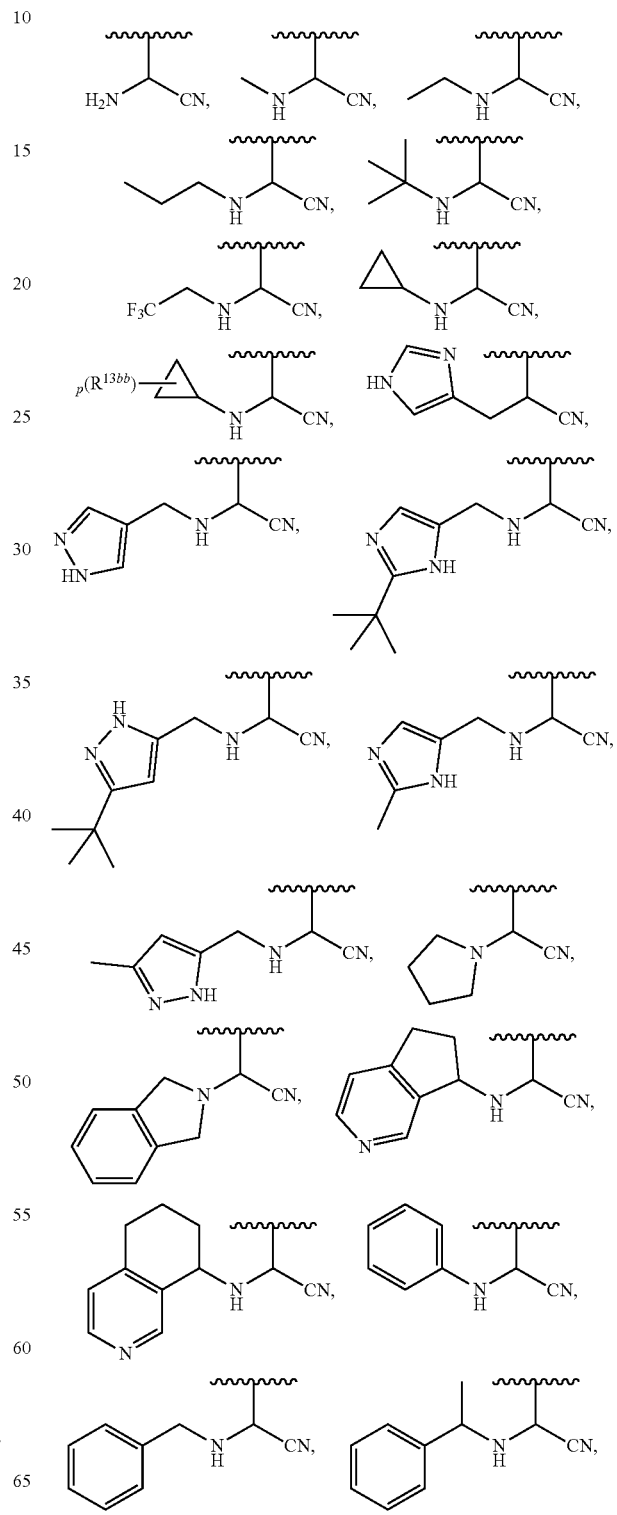

wherein $R^{13bb}$ is selected from the group consisting of halogen, $C_1$-$C_6$alkyl, $C_1$-$C_6$haloalkyl, $C_1$-$C_6$alkoxy, $C_3$-$C_{10}$cycloalkyl, —N($R^e R^f$), and —C(O)—N($R^e R^f$); $R^e$ and $R^f$ are each selected from the group consisting of hydrogen and $C_1$-$C_6$alkyl; or $R^e$ and $R^f$ may form, together with the nitrogen to which they are attached, a 4-6 membered heterocycle; and p is 0, 1, 2, 3, or 4, as valency permits.

In some embodiments, the warhead is a moiety with a cyano amine or cyano amide moiety. Examples of exemplary cyanoamine warheads include, but not limited to:

-continued

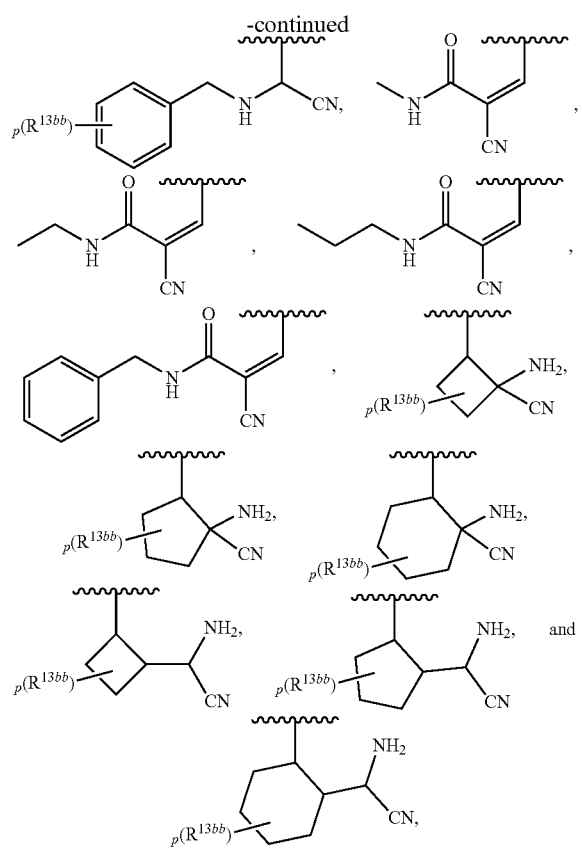

wherein $R^{13bb}$ is selected from the group consisting of halogen, $C_1$-$C_6$alkyl, $C_1$-$C_6$haloalkyl, $C_1$-$C_6$alkoxy, $C_3$-$C_{10}$cycloalkyl, —N($R^eR^f$), and —C(O)—N($R^eR^f$); $R^e$ and $R^f$ are each selected from the group consisting of hydrogen and $C_1$-$C_6$alkyl; or $R^e$ and $R^f$ may form, together with the nitrogen to which they are attached, a 4-6 membered heterocycle; and p is 0, 1, 2, 3, or 4, as valency permits.

In some embodiments, the warhead is a moiety with an imino-oxazolidinone moiety. Examples of exemplary imino-oxazolidinone warheads include, but not limited to:

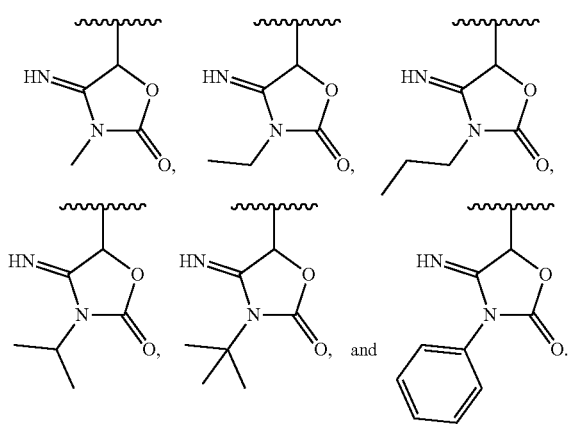

In some embodiments, the warhead is a moiety with an iminoimidazolidinone. Examples of exemplary iminoimidazolidinone warheads include, but not limited to:

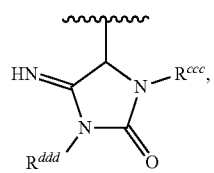

wherein each $R^{ccc}$ and $R^{ddd}$ is selected from the group consisting of hydrogen, $C_1$-$C_8$alkyl, $C_3$-$C_6$cycloalkyl, —($C_1$-$C_8$alkyl)-($C_6$-$C_{14}$aryl), and $C_6$-$C_{14}$aryl. In some embodiments, the warhead is selected from the group consisting of

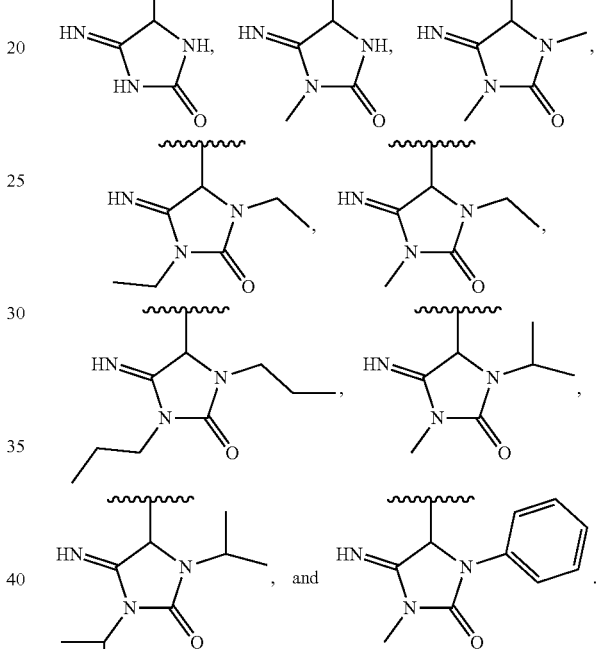

Other examples of exemplary warheads include, but not limited to:

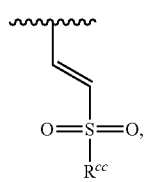

wherein $R^{cc}$ is selected from the group consisting of hydrogen, $C_1$-$C_8$alkyl, $C_3$-$C_6$cycloalkyl, —($C_1$-$C_8$alkyl)-($C_6$-$C_{14}$aryl), $C_6$-$C_{14}$aryl, 5-10 membered heteroaryl, —($C_1$-$C_8$alkyl)-(5-10 membered heteroaryl), 5-10 membered heterocycle and —N($R^bR^c$), wherein $R^b$ and $R^c$ are each selected from the group consisting of hydrogen, $C_1$-$C_8$alkyl, and $C_3$-$C_6$cycloalkyl, or $R^b$ and $R^c$ may be joined together to form, together with the nitrogen to which they are attached, a 5-10 membered heterocycle.

Some other examples of exemplary warheads include, but not limited to:

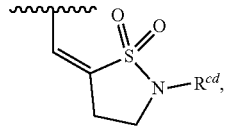

wherein $R^{cd}$ is selected from the group consisting of hydrogen, $C_1$-$C_8$alkyl, and $C_3$-$C_6$cycloalkyl.

Other examples of exemplary warheads include, but not limited to:

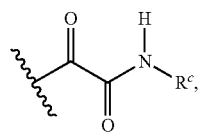

wherein $R^c$ is selected from the group consisting of hydrogen, —$CH_2C(O)O(C_1$-$C_8$alkyl), $C_1$-$C_8$alkyl, and $C_3$-$C_6$cycloalkyl, wherein the $C_1$-$C_8$alkyl may optionally be substituted by one or more substituents each selected from the group consisting of halogen, $C_3$-$C_6$cycloalkyl, 5-10 membered aryl and 5-10 membered heteroaryl;

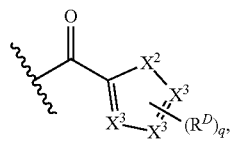

wherein $X^2$ is selected from the group consisting of NH, O and S; $X^3$ is independently selected, for each occurrence, from N and CH; $R^D$ is independently selected, for each occurrence, from the group consisting of $C_1$-$C_8$alkyl,

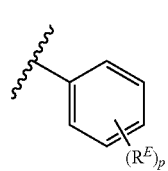 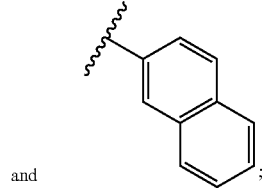

$R^E$ is independently selected, for each occurrence, from the group consisting of halogen, hydroxyl, $C_1$-$C_8$alkyl and $C_1$-$C_8$alkoxy; p is selected from 0, 1 and 2; and q is selected from 0, 1 and 2;

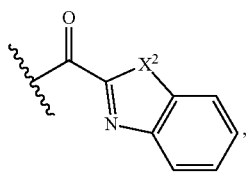

wherein $X^2$ is selected from the group consisting of NH, $NR^P$, O and S, wherein $R^P$ is $C_1$-$C_8$alkyl; and

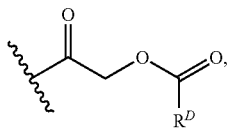

wherein $R^D$ is selected from the group consisting of $C_3$-$C_6$cycloalkyl, $C_1$-$C_8$alkyl, and

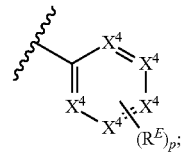

$X^4$ is independently selected, for each occurrence, from CH and N; $R^E$ is independently selected, for each occurrence, from the group consisting of halogen, —$CH_3$, —$OCH_3$, —$OCH_2CH_3$, —$OCH(CH_3)_2$, —CN, —$CF_3$, —$OCF_3$ and —$SCF_3$; and p is selected from 0, 1 and 2; —$C(O)R^D$, wherein $R^D$ is selected from the group consisting of hydrogen, —$CH_2OH$, —$CH_2OR'$ and —$CH_xF_y$, wherein x is 0, 1 or 2; y is 1, 2 or 3; and the sum of x and y is 3, wherein R' is selected from the group consisting of $C_1$-$C_8$alkyl, —($C_1$-$C_8$alkyl)-(5-10 membered aryl), $C_1$-$C_8$heteroalkyl, $C_3$-$C_6$cycloalkyl and 5-10 membered aryl; and —(CH=CH)C(O)$OR^D$, wherein $R^D$ is $C_1$-$C_8$alkyl.

It will be appreciated to one of skilled in the art that the compounds disclosed herein that include the warheads above also contemplate the precursors to those compounds, for example, where a cyano moiety involved in a warheads may be replaced with e.g., a halo moiety.

It will be appreciated to one of skilled in the art that the compounds disclosed herein can also irreversibly bind, or may otherwise inhibit e.g., a virus protein via any other mechanism of action.

The term "inhibitor" as used herein refers to a compound that binds to and/or inhibits a target protease with measurable affinity.

The term "reversible" or "reversible inhibitor" as used herein refers to a protease inhibitor that associates with a protease in such a way as to inhibit the activity of the protease while the protease and inhibitor are bound, but does not associate with a protease in such a way as to inhibit the activity of the protease when the protease and inhibitor are no longer bound. Reversible inhibitors can effect inhibition by competing with substrate for binding to the active site of the protease (competitive reversible inhibitor), or by associating with the protease bound to its substrate in a way to make the complex inactive (uncompetitive reversible inhibitor), or by associating with the protease and/or protease-substrate complex in a way that inhibits the activity of either and/or both.

As used herein, the term "irreversible" or "irreversible inhibitor" refers to an inhibitor (i.e. a compound) that is able to be covalently bonded to a target protease in a substantially non-reversible manner. An irreversible inhibitor will remain substantially bound to the target protease once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to target protease once covalent bond formation has occurred and will remain bound for a time period that is longer than the life of the protein.

I. Reversible or Irreversible Viral Protease Inhibitor Compounds

Also provided herein are compounds represented by

Formula II

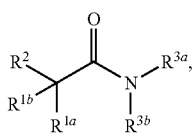

wherein: $R^{3a}$ is selected from

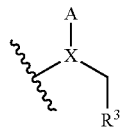

and 4-10 membered heterocycle, wherein the heterocycle may optionally be substituted by one, two or three substituents each selected from the group consisting of hydroxyl, $C_1$-$C_8$alkoxy, oxo and a warhead A; $R^{3b}$ is selected from hydrogen and $C_1$-$C_8$alkyl; wherein $R^{3a}$ and $R^{3b}$ may be joined together to form, together with the carbon to which they are attached, a 4-10 membered heterocycle, wherein the heterocycle may optionally be substituted by one, two or three substituents each selected from $C_6$-$C_{14}$aryl and a warhead A; $R^{1a}$ is selected from the group consisting of hydrogen, $C_1$-$C_8$alkyl, $C_1$-$C_8$heteroalkyl, —($C_1$-$C_8$alkyl)-$R^1$, —($C_1$-$C_8$alkyl)-CN, $C_3$-$C_{10}$cycloalkyl, $C_6$-$C_{14}$aryl, 4-10 membered heterocycle and 5-10 membered heteroaryl; $R^{1b}$ is selected from hydrogen and $C_1$-$C_8$alkyl; or $R^1$ and $R^{1b}$ may be joined together to form, together with the carbon to which they are attached, a 4-10 membered mono or bicyclic heterocycle having a ring nitrogen, $NR^G$, or a $C_3$-$C_{10}$cycloalkyl; $R^1$ is selected from the group consisting of $C_1$-$C_8$alkyl, $C_2$-$C_{10}$alkenyl, $C_2$-$C_{10}$alkynyl, $C_3$-$C_{10}$cycloalkyl, $C_6$-$C_{14}$aryl, 5-10 membered heteroaryl and 4-10 membered heterocycle, wherein $R^1$ may optionally be substituted on a free carbon by one, two, or three substituents each selected from $R^A$; $R^A$ is independently selected, for each occurrence, halogen, cyano, hydroxyl, oxo, $SF_5$, $CF_3$, —O—$CF_3$, —O—$CHF_2$, —S—$CH_3$, —S(O)$_2$—$CH_3$, —$NH_2$, —O-phenyl, —O—($C_1$-$C_8$alkyl)-phenyl, —NHC(O)$R^B$, —NHC(O)O$R^B$, —NHC(O)O—($C_1$-$C_8$alkyl)-$R^B$, —N($R^y$)$_2$, —N($R^y$)($C_1$-$C_8$alkyl)C(O)O-phenyl, —N($R^y$)($C_1$-$C_8$alkyl)C(O)N($R^y$)$_2$, —NHC(O)O($C_1$-$C_8$alkyl)$R^B$, —C(O)-(5-10 membered heteroaryl), —C(O)-(4-10 membered heterocycle), —C(O)—O-(4-10 membered heterocycle), —C(O)—OC(CH$_3$)$_3$, —C(O)—($C_1$-$C_6$alkyl), —C(O)—($C_2$-$C_{10}$alkenyl)-($C_6$-$C_{14}$aryl), C(O)—($C_1$-6alkyl)-NHC(O)$R^B$, —$C_1$-$C_8$alkyl, $C_2$-$C_{10}$alkenyl, $C_2$-$C_{10}$alkynyl, $C_1$-$C_8$heteroalkyl, $C_1$-$C_8$alkoxy, $C_3$-$C_{10}$cycloalkyl, —($C_1$-$C_8$alkyl)-($C_3$-$C_{10}$cycloalkyl), —($C_1$-$C_8$alkyl)-($C_6$-$C_{14}$aryl), —($C_1$-$C_8$alkyl)-(5-10 membered heteroaryl), $C_6$-$C_{14}$aryl, 5-10 membered heteroaryl and 4-10 membered heterocycle, wherein the $R^B$, heterocycle, heteroaryl, or aryl may optionally be substituted by one, two or three substituents of halogen, $C_1$-$C_8$alkyl, $C_1$-$C_8$alkoxy, $SF_5$, —$NH_2$, hydroxyl or oxo; $R^2$ is selected from the group consisting of —NHC(O)$R^B$, —NHC(O)N($R^B$)$_2$, —NHC(O)C($R^C$)$_2R^B$, —NHS(O)$_2R^B$, —O—($C_1$-$C_8$alkyl)-($C_3$-$C_{10}$cycloalkyl), 4-10 membered heterocycle, $C_6$-$C_{14}$aryl and 5-10 membered heteroaryl bound through the carbon or nitrogen atom, wherein $R^2$ may optionally be substituted by one, two, or three substituents each selected from $R^x$; or $R^1$ and $R^2$ may be joined together to form, together with the carbon to which they are attached, a 4-10 membered mono or bicyclic heterocycle having a ring nitrogen $NR^G$, or a $C_3$-$C_{10}$cycloalkyl, wherein the cycloalkyl or heterocycle may optionally be substituted by one, two or three substituents on a free carbon each selected from $R^A$; $R^3$ is selected from 5-10 membered heteroaryl and 4-10 membered heterocycle, wherein $R^3$ may optionally be substituted by one, two, or three substituents each selected from $R^A$; $R^B$ is independently selected, for each occurrence, from the group consisting of $C_1$-$C_8$alkyl (optionally substituted by one, two or three halo), $C_2$-$C_{10}$alkenyl, $C_2$-$C_{10}$alkynyl, $C_6$-$C_{14}$aryl, 5-10 membered heteroaryl and 4-10 membered heterocycle; $R^C$ is independently selected, for each occurrence, from hydrogen, halogen and $C_1$-$C_8$alkyl; $R^x$ is independently selected, for each occurrence, from the group consisting of halogen, hydroxyl, oxo, $CF_3$, $SF_5$, cyano, —OCHF$_2$, —OCF$_3$, —O—($C_1$-$C_8$alkyl), —C(O)O(CH$_3$), —N($R^y$)$_2$, —N($R^y$)C(O)$R^y$, —N($R^y$)($C_1$-$C_8$alkyl)C(O)N($R^y$)$_2$, —N($R^y$)($C_1$-$C_8$alkyl)C(O)OH, —($C_1$-$C_8$alkyl)-($C_3$-$C_{10}$cycloalkyl), $C_1$-$C_8$alkyl, $C_1$-$C_8$alkoxy, $C_3$-$C_{10}$cycloalkyl, $C_6$-$C_{14}$aryl, 5-10 membered heteroaryl and 4-10 membered heterocycle, wherein the aryl, heterocycle or heteroaryl may optionally be substituted by one or more substituents each selected from oxo, halogen and $C_1$-$C_8$alkyl; $R^G$ is selected from the group consisting of H, $C_{1-6}$alkyl (optionally substituted by one, two or three substituents each independently selected from the group consisting of —C(=O), halo, cyano, —NR'''R''', and —NH(C=O)R'''), and C(=O)—$C_{1-6}$alkyl (optionally substituted by one, two or three substituents each independently selected from the group consisting of halo, cyano, —NR'''R''', —NR'''(C=O)R''', phenyl, cycloalkyl, heterocycle, $C_1$-$C_6$alkoxy, wherein R''' is selected for each occurrence by H, $C_{1-3}$alkyl (optionally substituted by one, two or three substituents each independently selected from the group consisting of halo), phenyl (optionally substituted by halo), —S(O)$_2$—CH$_3$, $C_{3-6}$ cycloalkyl, and 5-6 membered heteroaryl), —C(=O)—$C_{1-6}$alkyl (optionally substituted by one, two or three substituents each independently selected from the group consisting of halo, cyano and $C_1$-$C_6$alkoxy), C(=O)—$C_{3-6}$cycloalkyl, and C(=O)-(5-6 membered heteroaryl) (optionally substituted by halo, cyano, hydroxyl, NH$_2$, $C_{1-6}$alkyl, $C_{3-6}$cycloalkyl, $C_1$-$C_6$alkoxy, and $C_{1-6}$haloalkyl)); R is independently selected, for each occurrence, from the group consisting of hydrogen, $C_1$-$C_8$alkyl, $C_1$-$C_8$heteroalkyl, —CH$_2$CF$_3$, $C_1$-$C_8$alkoxy, —($C_1$-$C_8$alkoxy)-(5-10 membered aryl), $C_3$-$C_6$cycloalkyl and —($C_1$-$C_8$alkyl)COOH; A is a warhead; X is selected from the group consisting of C($R^{xy}$) and N, wherein $R^{xy}$ is selected from the group consisting of H, D, —OH, —NH$_2$, halogen, $C_1$-$C_8$alkyl, $C_1$-$C_8$ haloalkyl, and $C_1$-$C_8$alkoxy; and pharmaceutically acceptable salts, stereoisomers, esters, and prodrugs thereof.

Also provided herein are compounds represented by

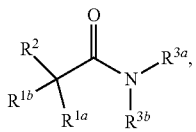

Formula II wherein $R^{3a}$ is selected from

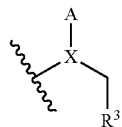

$R^3$ and 4-10 membered heterocycle, wherein the heterocycle may optionally be substituted by one, two or three substituents each selected from the group consisting of hydroxyl, $C_1$-$C_8$alkoxy, oxo and a warhead A; $R^{3b}$ is selected from hydrogen and $C_1$-$C_8$alkyl; wherein $R^{3a}$ and $R^{3b}$ may be joined together to form, together with the carbon to which they are attached, a 4-10 membered heterocycle, wherein the heterocycle may optionally be substituted by one, two or three substituents each selected from $C_6$-$C_{14}$aryl and a warhead A; $R^{1a}$ is selected from the group consisting of $C_1$-$C_8$alkyl, —($C_1$-$C_8$alkyl)-$R^1$, —($C_1$-$C_8$alkyl)-CN, $C_3$-$C_{10}$cycloalkyl, $C_6$-$C_{14}$aryl, 4-10 membered heterocycle and 5-10 membered heteroaryl; $R^{1b}$ is selected from hydrogen and $C_1$-$C_8$alkyl; $R^{1a}$ and $R^{1b}$ may be joined together to form, together with the carbon to which they are attached, a 4-10 membered heterocycle or a $C_3$-$C_{10}$cycloalkyl; $R^1$ is selected from the group consisting of $C_1$-$C_8$alkyl, $C_2$-$C_{10}$alkenyl, $C_2$-$C_{10}$alkynyl, $C_3$-$C_{10}$cycloalkyl, $C_6$-$C_{14}$aryl, 5-10 membered heteroaryl and 4-10 membered heterocycle, wherein $R^1$ may optionally be substituted by one, two, or three substituents each selected from $R^A$; $R^A$ is independently selected, for each occurrence, halogen, cyano, hydroxyl, oxo, $SF_5$, —$NH_2$, —O-phenyl, —O—($C_1$-$C_8$alkyl)-phenyl, —C(O)-(5-10 membered heteroaryl), —C(O)-(4-10 membered heterocycle), —C(O)—OC(CH$_3$)$_3$, —C(O)—($C_2$-$C_{10}$alkenyl)-($C_6$-$C_{14}$aryl) $C_1$-$C_8$alkyl, $C_2$-$C_{10}$alkenyl, $C_2$-$C_{10}$alkynyl, $C_1$-$C_8$heteroalkyl, $C_1$-$C_8$alkoxy, $C_3$-$C_{10}$cycloalkyl, —($C_1$-$C_8$alkyl)-($C_6$-$C_{14}$aryl), —($C_1$-$C_8$alkyl)-(5-10 membered heteroaryl), $C_6$-$C_{14}$aryl, 5-10 membered heteroaryl and 4-10 membered heterocycle, wherein the heterocycle, heteroaryl, or aryl may optionally be substituted by one, two or three substituents of halogen, $C_1$-$C_8$alkyl, $C_1$-$C_8$alkoxy, $SF_5$, —$NH_2$, hydroxyl or oxo; $R^2$ is selected from the group consisting of —NHC(O)$R^B$, —NHC(O)N($R^B$)$_2$, —NHC(O)C($R^C$)$_2$$R^B$, —NHS(O)$_2$$R^B$, 4-10 membered heterocycle, $C_6$-$C_{14}$aryl and 5-10 membered heteroaryl bound through the carbon or nitrogen atom, wherein $R^2$ may optionally be substituted by one, two, or three substituents each selected from $R^x$; $R^{1a}$ and $R^2$ may be joined together to form, together with the carbon to which they are attached, a 4-10 membered heterocycle or a $C_3$-$C_{10}$cycloalkyl, wherein the cycloalkyl or heterocycle may optionally be substituted by one, two or three substituents each selected from $R^A$; $R^3$ is selected from 5-10 membered heteroaryl and 4-10 membered heterocycle, wherein $R^3$ may optionally be substituted by one, two or three substituents each selected from $R^A$; $R^B$ is independently selected, for each occurrence, from the group consisting of $C_1$-$C_8$alkyl, $C_2$-$C_{10}$alkenyl, $C_2$-$C_{10}$alkynyl, $C_6$-$C_{14}$aryl, 5-10 membered heteroaryl and 4-10 membered heterocycle; $R^C$ is independently selected, for each occurrence, from hydrogen and $C_1$-$C_8$alkyl; $R^x$ is independently selected, for each occurrence, from the group consisting of halogen, hydroxyl, oxo, $SF_5$, cyano, —C(O)O(CH$_3$), —N($R^y$)$_2$, —N($R^y$)C(O)$R^y$, $C_1$-$C_8$alkyl, $C_1$-$C_8$alkoxy, $C_3$-$C_{10}$cycloalkyl, $C_6$-$C_{14}$aryl, 5-10 membered heteroaryl and 4-10 membered heterocycle, wherein the aryl, heterocycle or heteroaryl may optionally be substituted by one or more substituents each selected from oxo and $C_1$-$C_8$alkyl; $R^y$ is independently selected, for each occurrence, from the group consisting of hydrogen, $C_1$-$C_8$alkyl, $C_1$-$C_8$alkoxy, —($C_1$-$C_8$alkoxy)-(5-10 membered aryl) and $C_3$-$C_6$cycloalkyl; A is a warhead; X is selected from CH, C(CH$_3$) and N; and pharmaceutically acceptable salts, stereoisomers, esters, and prodrugs thereof.

In certain embodiments, the present disclosure provides compounds of Formula II-A:

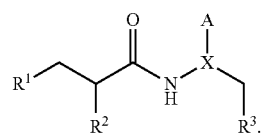

Formula II-A

In certain embodiments, the present disclosure provides compounds of Formula II-B:

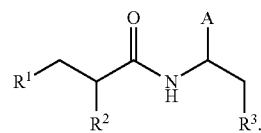

Formula II-B

In various embodiments, the present disclosure provides compounds of Formula II-C:

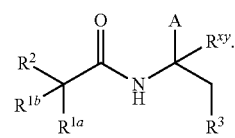

Formula II-C

In various embodiments, the present disclosure provides compounds of Formula II-D-I or Formula II-D-II:

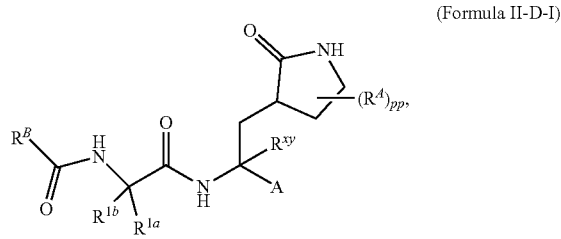

(Formula II-D-I)

27

-continued (Formula II-D-I)

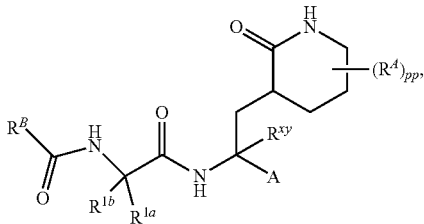

wherein pp is selected from 0, 1, 2, and 3.

In various embodiments, the present disclosure provides compounds of Formula II-E:

Formula II-E

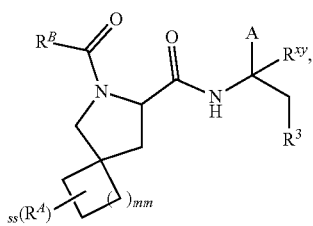

wherein ss is selected from 0, 1, 2, and 3, and mm is selected from 1, 2, and 3.

In some embodiments, provided herein are compounds represented by Formula II-I:

Formula II-I

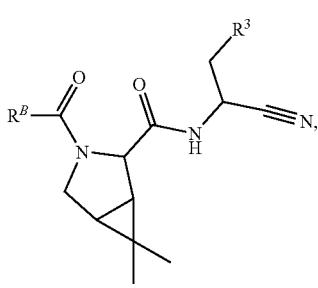

wherein: $R^3$ is

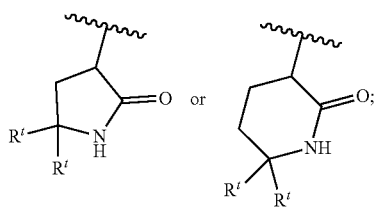

$R^t$ is independently, for each occurrence, H or methyl; or each $R^t$ may be taken, together with the carbon to which they are attached, to form a cyclopropyl; $R^B$ is selected from the group consisting of: a 9-10 membered bicyclic heteroaryl having one ring nitrogen, $C_1$-$C_6$alkyl, and $C_2$-$C_3$alkenyl; wherein $R^B$ is optionally substituted by one, two or three substituents each independently selected from the group consisting of halogen, $C_1$-$C_3$alkoxy, NHR$^m$, and phenyl

28

(optionally substituted by one or two halogens); $R^m$ is $C_{1-3}$alkyl or —C(O)—$C_{1-3}$alkyl, wherein each $C_{1-3}$alkyl is independently optionally substituted by one, two or three halogens; or a pharmaceutically acceptable salt thereof.

In certain embodiments, $R^{3a}$ is

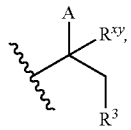

wherein $R^{xy}$ is selected from the group consisting of H, D, OH, NH$_2$, halogen, $C_1$-$C_8$alkyl, $C_1$-$C_8$ haloalkyl, and $C_1$-$C_8$alkoxy. In embodiments, $R^{xy}$ is selected from the group consisting of H, D, CH$_3$, CH$_2$CH$_3$, F, and CF$_3$. In some embodiments, $R^{xy}$ is F. In some embodiments, $R^{xy}$ is CF$_3$. In some embodiments, CH$_3$. In some embodiments, $R^{xy}$ is H.

In various embodiments, X is selected from the group consisting of CH, CD, C(CH$_3$), C(CH$_2$CH$_3$), N, CF, CCl, CBr, C(CHF$_2$), C(CH$_2$F), and C(CF$_3$). In some embodiments, X is CH. In some embodiments, X is CD. In some embodiments, X is C(CH$_3$). In some embodiments, X is C(CF$_3$). In some embodiments, X is CF. In some embodiments, X is N.

In some embodiments, A is selected from the group consisting of cyano, —C(O)R$^D$, —C(O)CH$_2$N(R$^b$R$^c$), —C(O)CH$_2$OC(O)R$^D$, —C(O)C(O)R$^D$, —(CH=CH)C(O)OR$^D$, —(CH=CCN)C(O)OR$^D$, —(CH=CCN)C(O)(NH)R$^D$, —CH(CN)(OH), —CH(CN)(NR$^b$R$^c$),

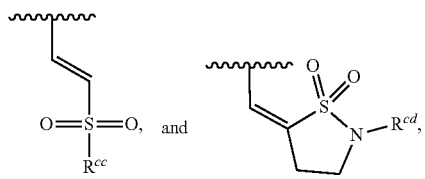

wherein $R^D$ is selected from the group consisting of hydrogen, hydroxyl, —OR$^{bb}$, —N(R$^b$R$^c$), $C_1$-$C_8$alkyl, $C_1$-$C_8$alkoxy, $C_3$-$C_6$cycloalkyl, $C_6$-$C_{14}$aryl, 5-10 membered heteroaryl, and 4-10 membered heterocycle; wherein $R^D$ may optionally be substituted by one, two, or three substituents each selected from the group consisting of halogen, hydroxyl, and $R^E$; $R^E$ is selected from the group consisting of $C_1$-$C_8$alkyl, $C_1$-$C_8$alkoxy, $C_6$-$C_{14}$aryl, 4-10 membered heterocycle, and 5-10 membered heteroaryl, wherein $R^E$ may optionally be substituted by one, two, or three substituents each selected from halogen, cyano, $C_1$-$C_8$alkyl and $C_1$-$C_8$alkoxy; $R^{bb}$ is selected from the group consisting of $C_3$-$C_6$cycloalkyl, $C_6$-$C_{14}$aryl, —($C_1$-$C_8$alkyl)-$C_6$-$C_{14}$aryl, 5-10 membered heteroaryl, and 4-10 membered heterocycle; $R^{cc}$ is selected from the group consisting of hydrogen, $C_1$-$C_8$alkyl, $C_3$-$C_6$cycloalkyl, —($C_1$-$C_8$alkyl)-($C_6$-$C_{14}$aryl), $C_6$-$C_{14}$aryl, 5-10 membered heteroaryl, —($C_1$-$C_8$alkyl)-(5-10 membered heteroaryl), 5-10 membered heterocycle and —N(R$^b$R$^c$), wherein R$^b$ and R$^c$ are each selected from the group consisting of hydrogen, $C_1$-$C_8$alkyl, and $C_3$-$C_6$cycloalkyl, or R$^b$ and R$^c$ may be joined together to form, together with the nitrogen to which they are attached, a 5-10 membered heterocycle; $R^{cd}$ is selected from the group consisting of hydrogen, $C_1$-$C_8$alkyl, and $C_3$-$C_6$cycloalkyl; and R$^b$ and R$^c$ are each selected from the group consisting of hydrogen, —CH₂C(O)O(C₁-C₈alkyl), —C(O)—(C₁-C₈alkyl), —S(O)₂—(C₁-C₈alkyl), C₁-C₈alkyl, C₃-C₆cycloalkyl and —(C₁-C₈alkyl)-C₆-C₁₄aryl, wherein the C₁-C₈alkyl may optionally be substituted by one or more substituents each selected from the group consisting of halogen, C₃-C₆cycloalkyl, C₆-C₁₄aryl, 4-10 membered heterocycle, and 5-10 membered heteroaryl.

In embodiments, A is selected from the group consisting of —CN,

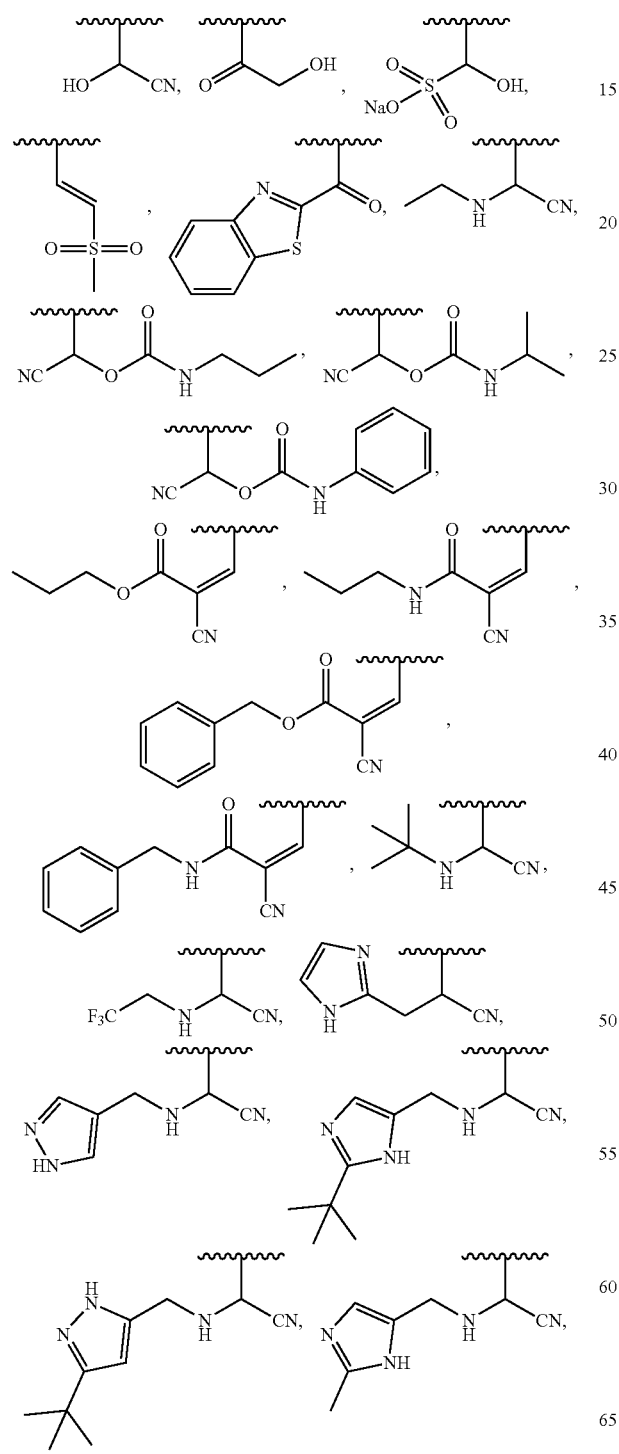

In embodiments, $R^{1a}$ is selected from the group consisting of

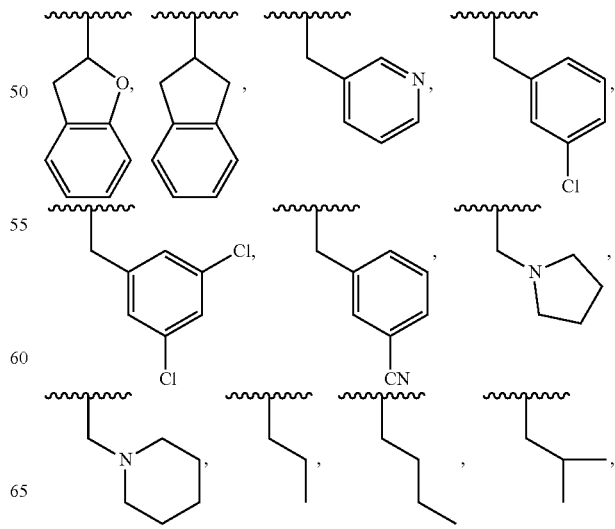

-continued

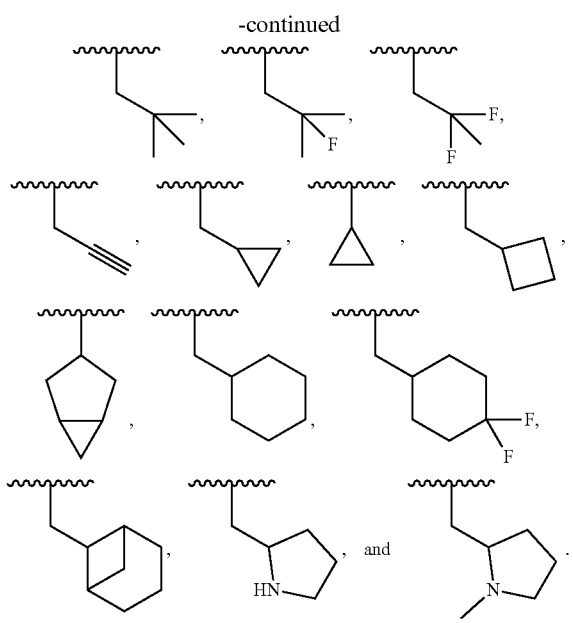

In embodiments, $R^{1a}$ is —($C_1$-$C_8$alkyl)-$R^1$.

In embodiments, $R^{1b}$ is hydrogen.

In certain embodiments, $R^{1a}$ and $R^{1b}$ are joined to together to form

In certain embodiments, $R^{3a}$ is a 4-10 membered heterocycle.

In some embodiments, $R^{3a}$ is selected from the group consisting of

In some embodiments, $R^3$ is a 4-10 membered heterocycle.

In some embodiments, $R^3$ is selected from

In some embodiments, $R^3$ is (for example, wherein $R^{x3}$ are independently for each occurrence selected from the group consisting of hydrogen, halogen, $C_1$-$C_8$alkyl, $C_1$-$C_8$ haloalkyl, $C_3$-$C_6$cycloalkyl, and $C_1$-$C_8$alkoxy; and pp is selected from 0, 1, 2, and 3. In some embodiments, $R^3$ is In some embodiments, R³ is
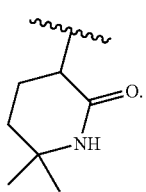 [SMILES: *C1CCC(C)(C)NC1=O]
In some embodiments, R³ is
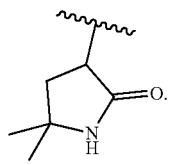 [SMILES: *C1CC(C)(C)NC1=O]
In some embodiments, R³ is
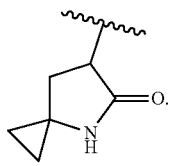 [SMILES: *C1CC2(CC2)NC1=O]
In some embodiments, R³ is
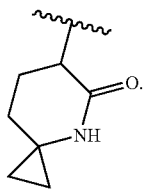 [SMILES: *C1CCC2(CC2)NC1=O]
In some embodiments, R³ is
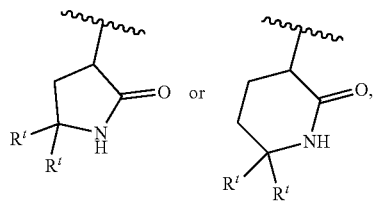
and R^t is independently, for each occurrence, H or methyl; or each R^t may be taken, together with the carbon to which they are attached, to form a cyclopropyl.
In some embodiments, R³ is selected from the group consisting of
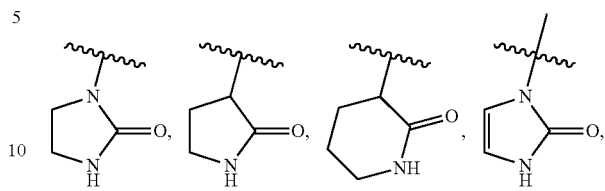
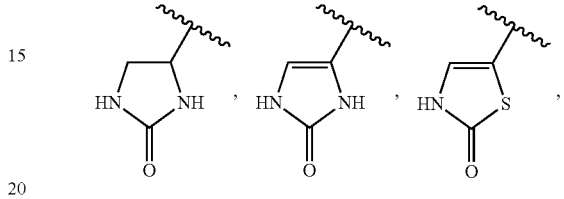
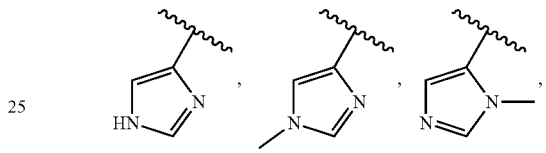
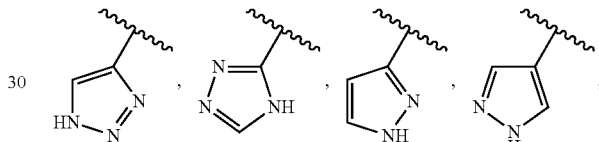
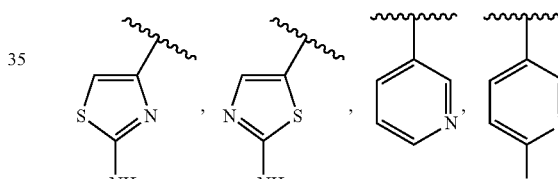
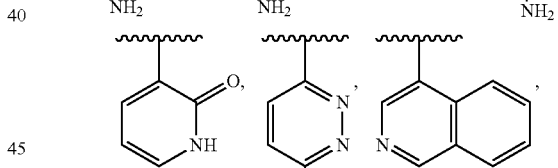
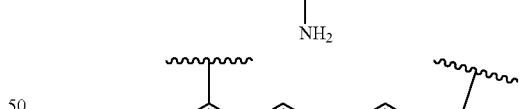
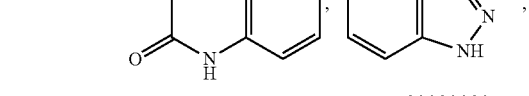
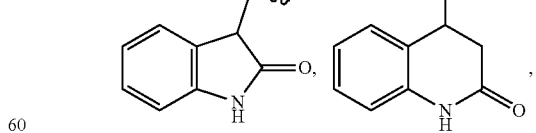
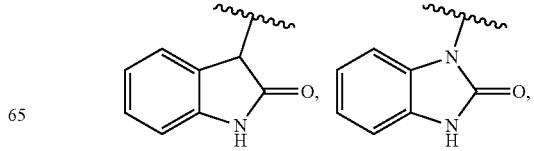

-continued
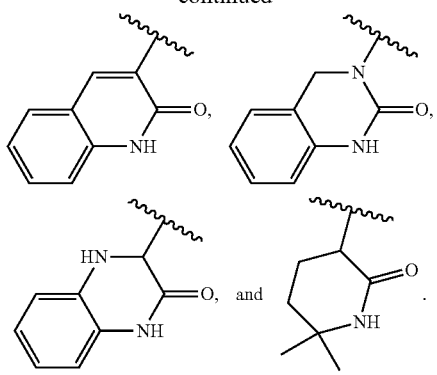
In some embodiments, wherein R³ is selected from the group consisting of
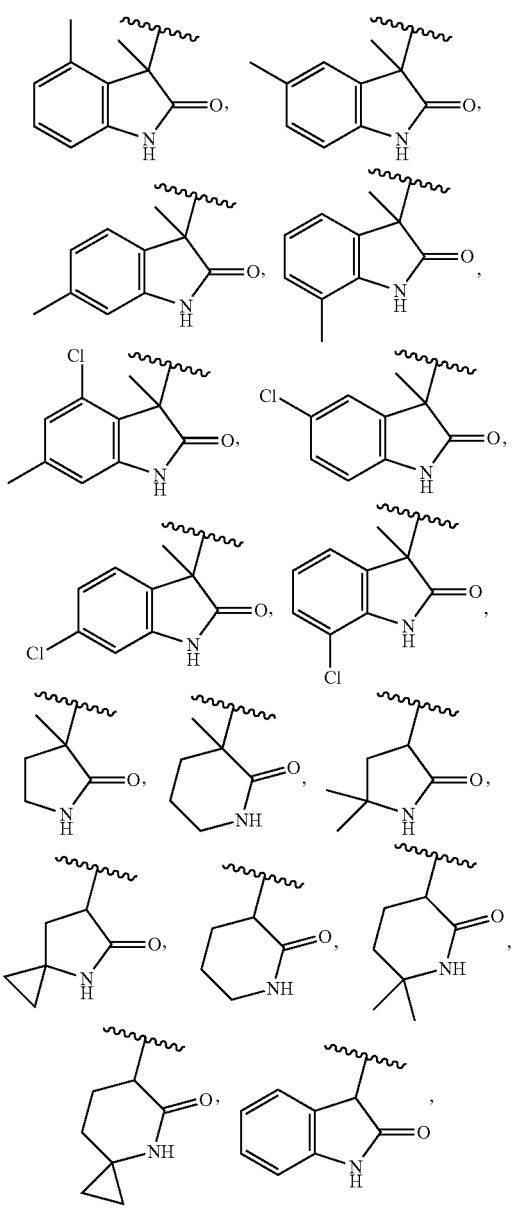
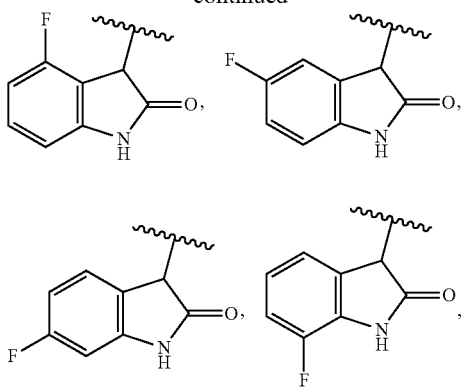

In some embodiments, wherein R³ is selected from the group consisting of
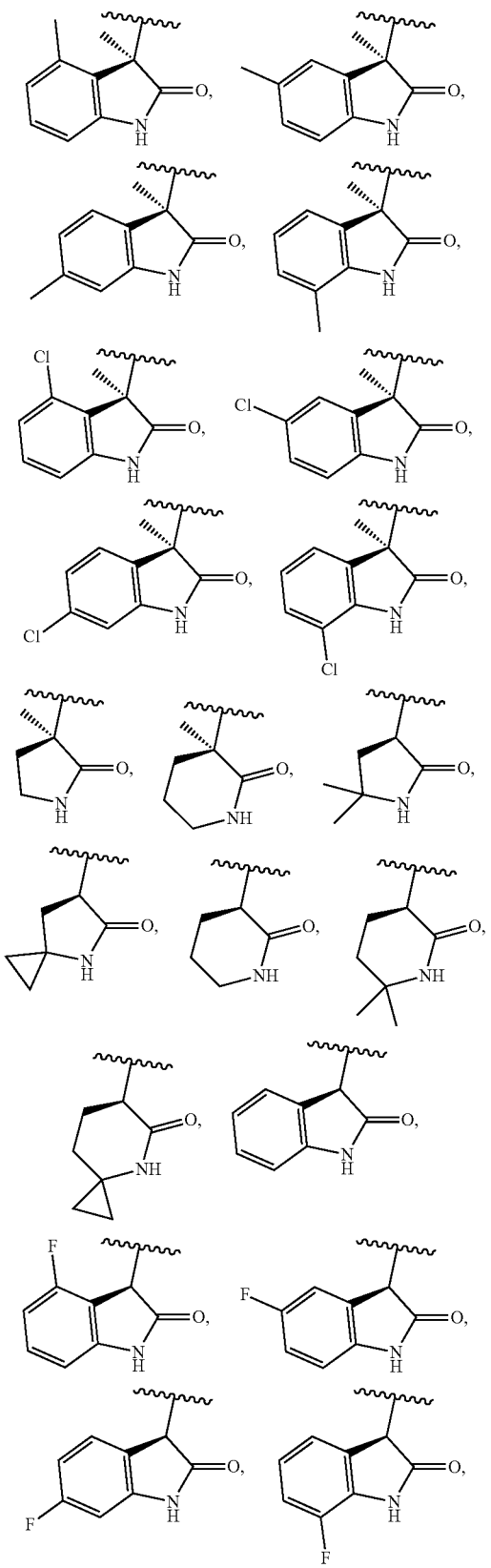
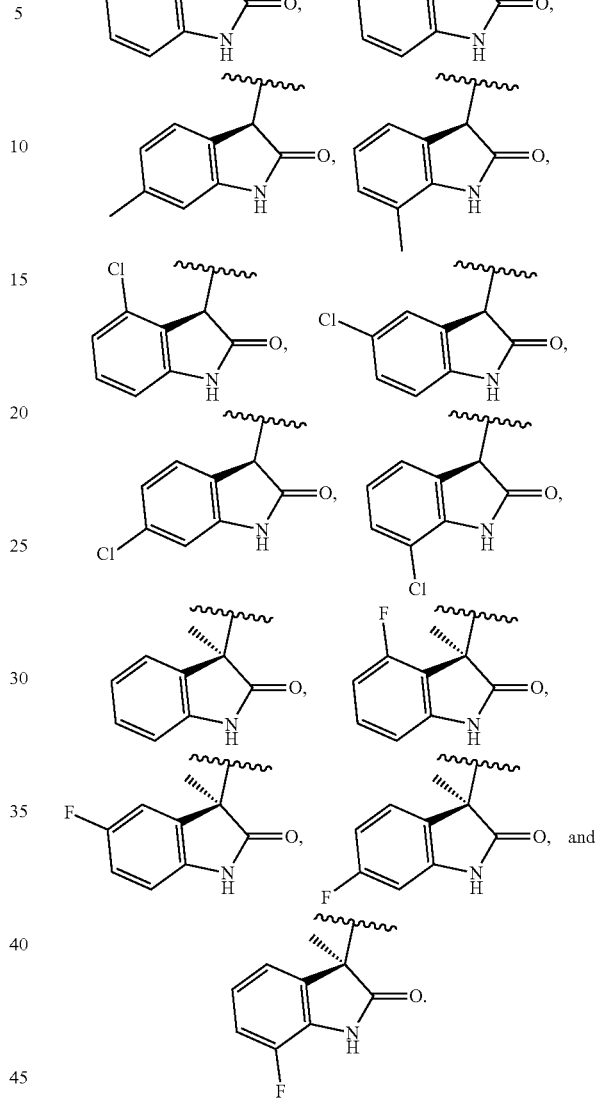
In some embodiments, R² is selected from the group consisting of
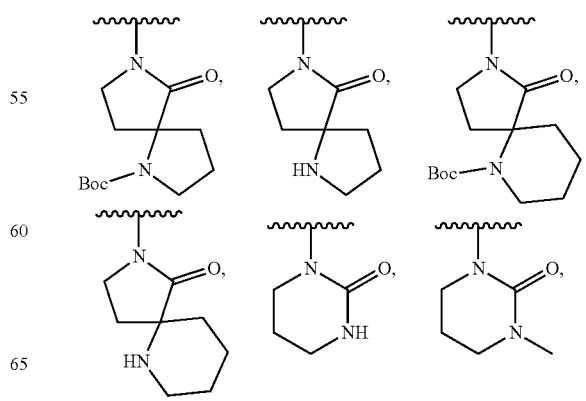

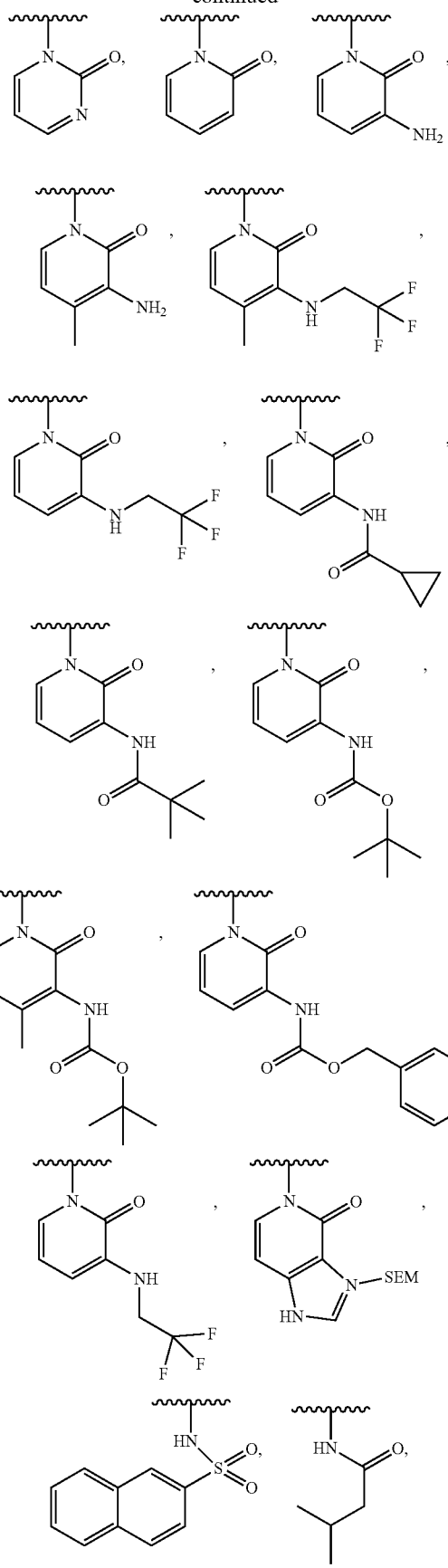
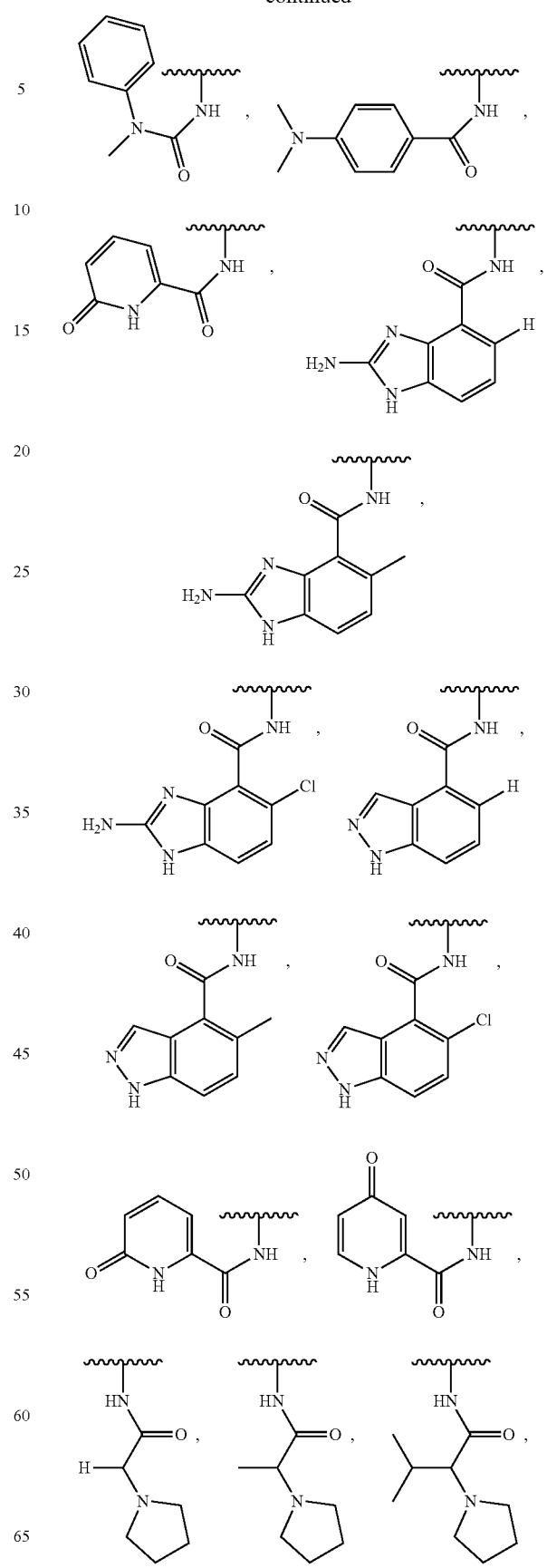

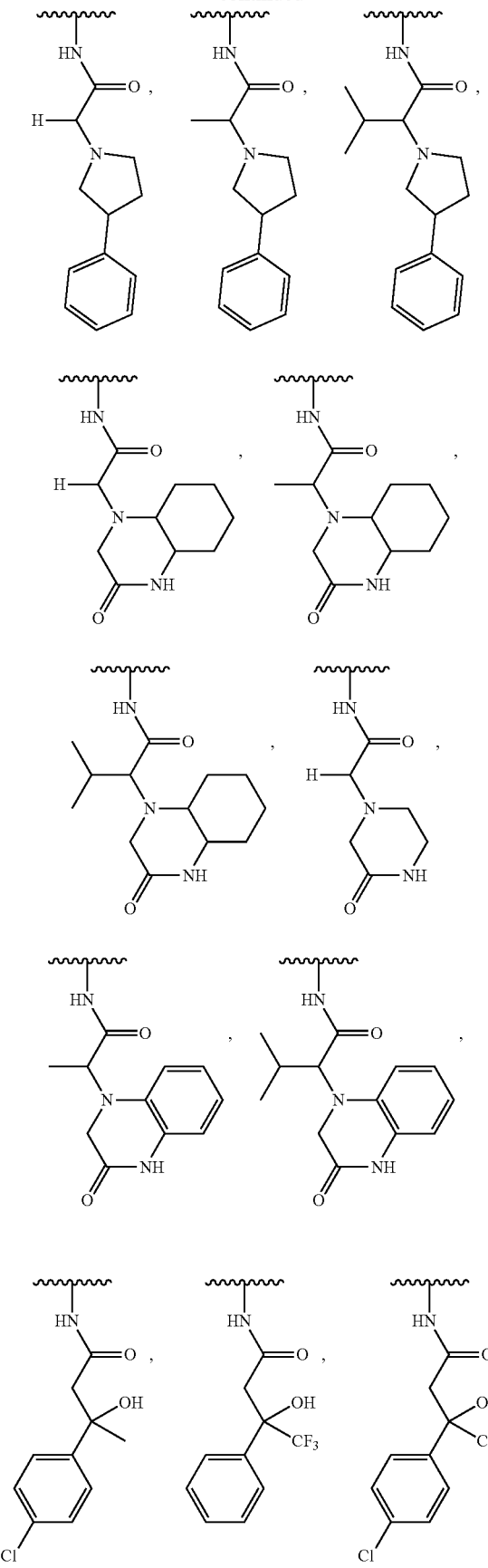
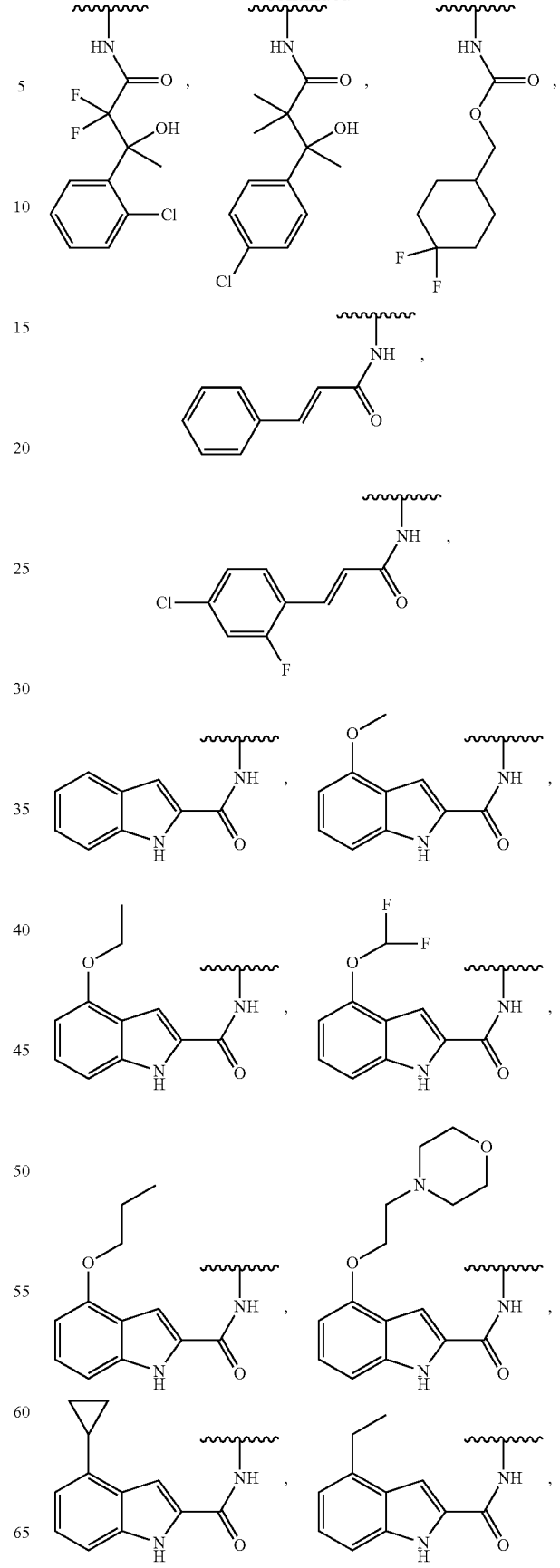

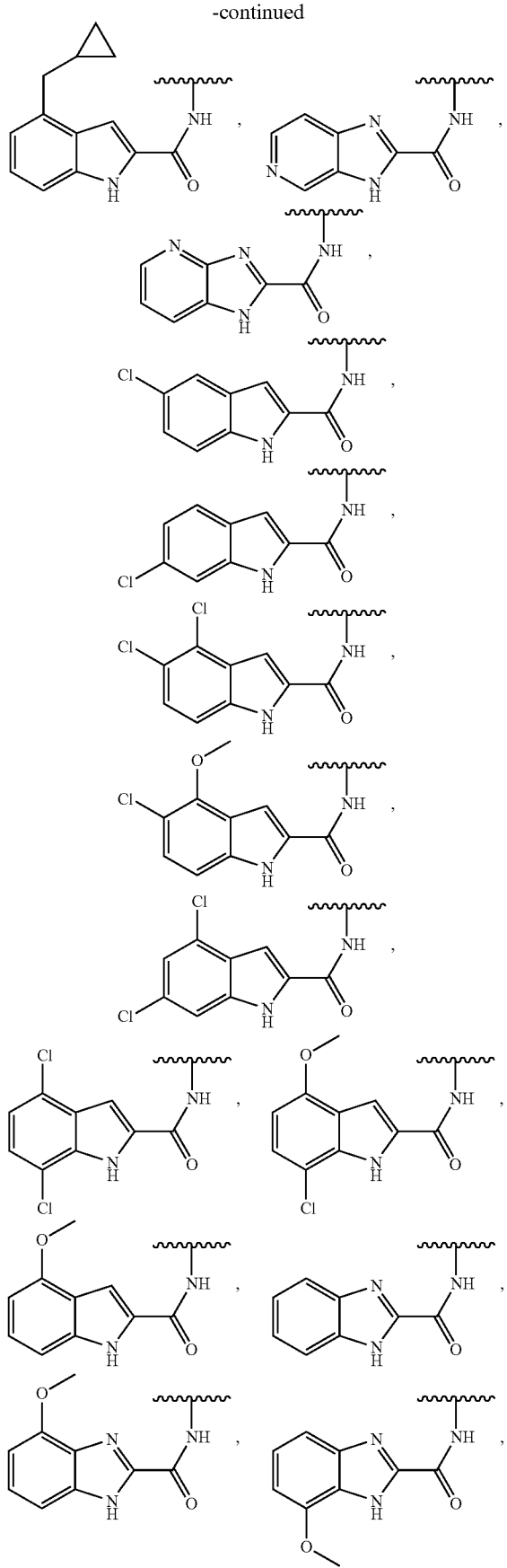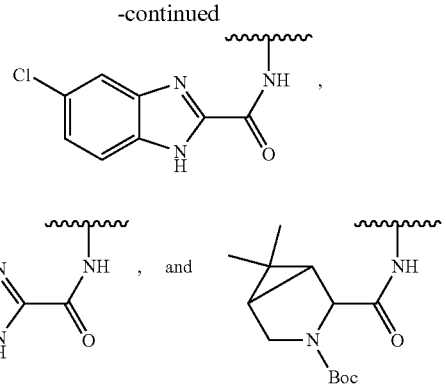
In some embodiments, $R^{1a}$ and $R^2$ are joined to together to form the heterocycle selected from the group consisting of:
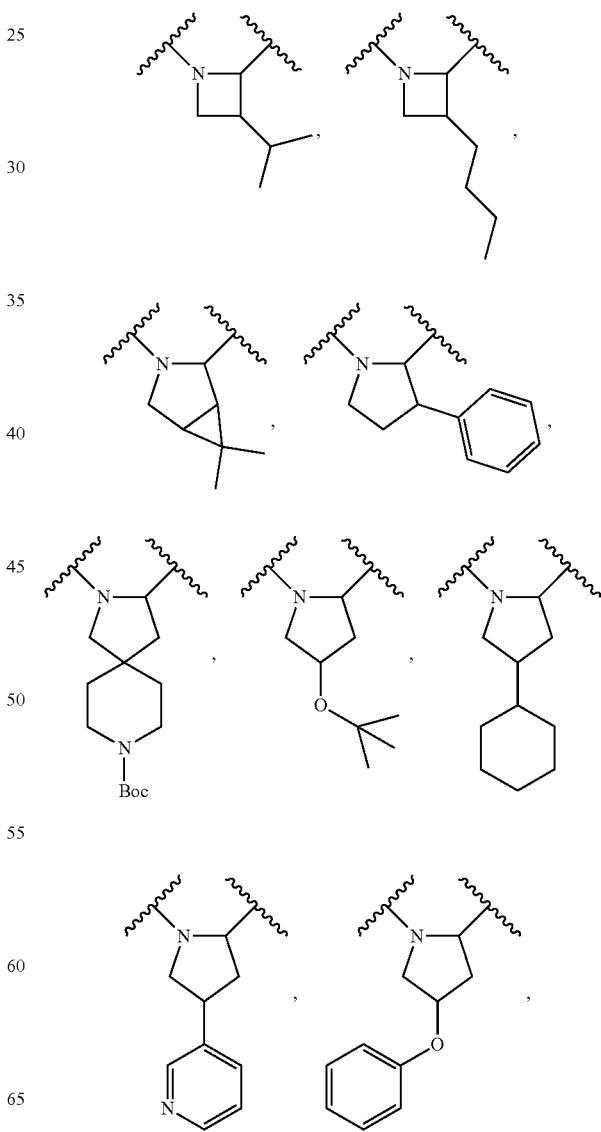

-continued
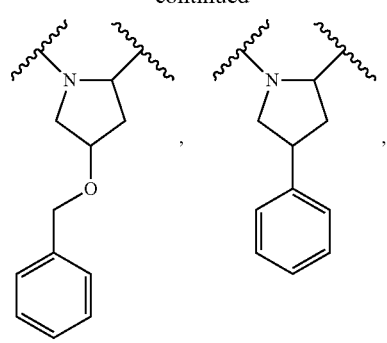
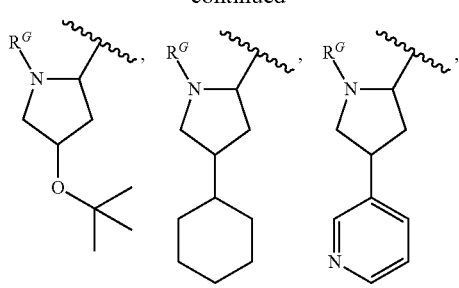
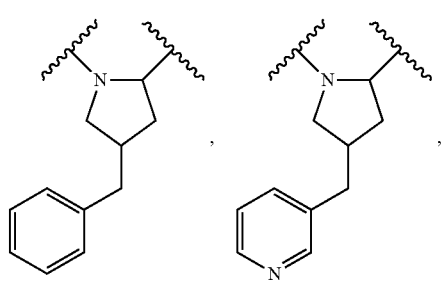
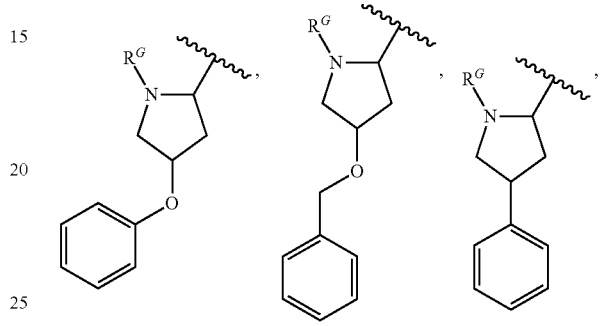
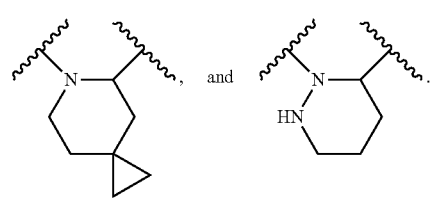
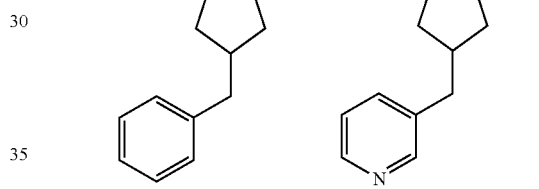
In some embodiments, $R^{1a}$ and $R^2$ are joined to together to form the heterocycle selected from the group consisting of:
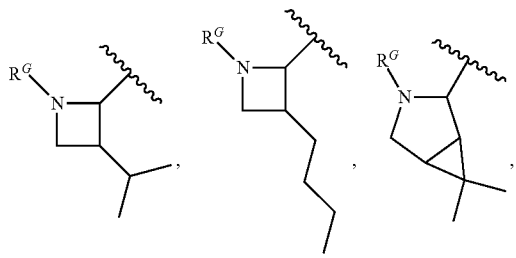
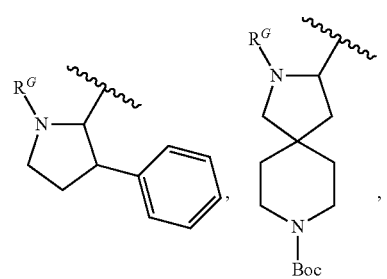
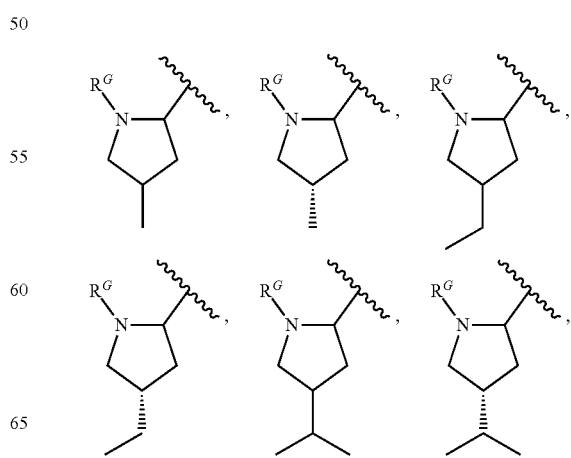
and $R^{1b}$ is H.
In some embodiments, $R^1$ and $R^2$ are joined to together to form the heterocycle selected from the group consisting of:

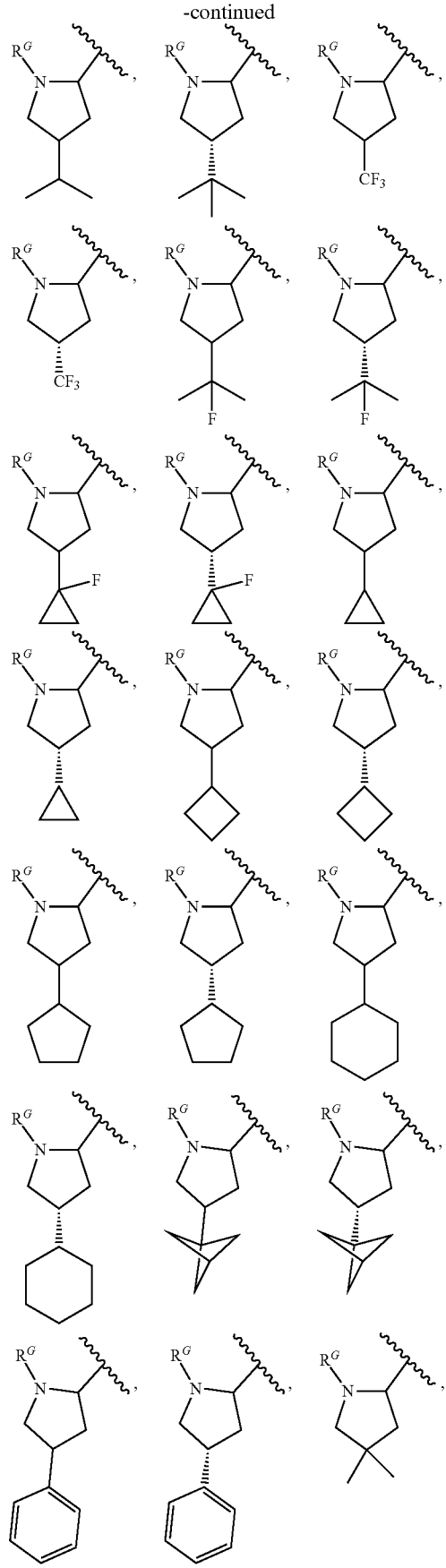
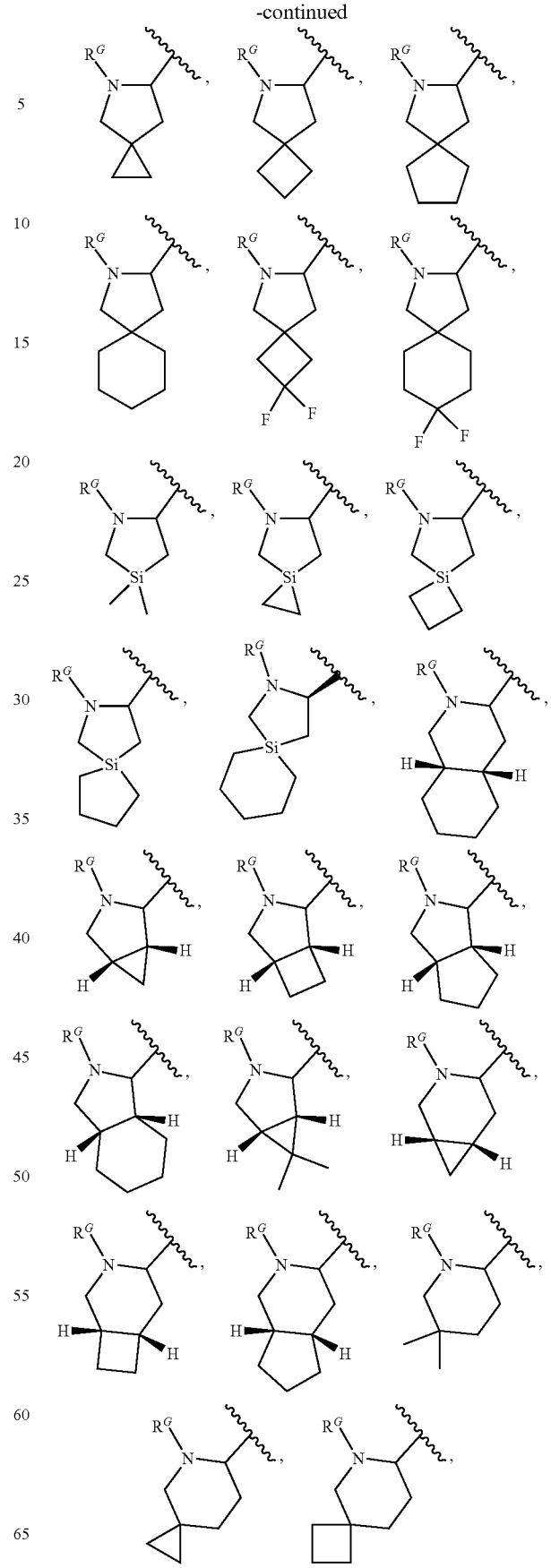

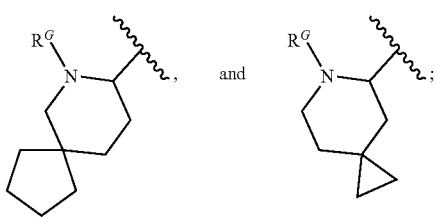
and
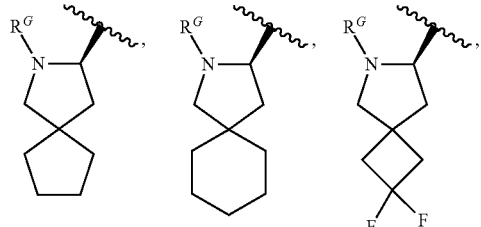
and $R^{1b}$ is H.
In some embodiments, $R^{1a}$ and $R^2$ are joined to together to form the heterocycle selected from the group consisting of:
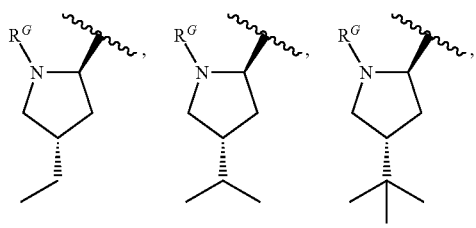
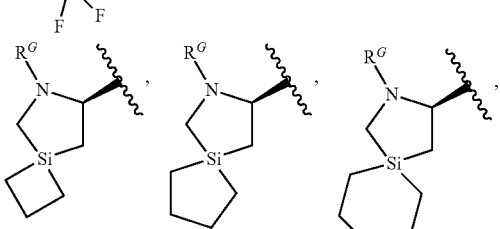
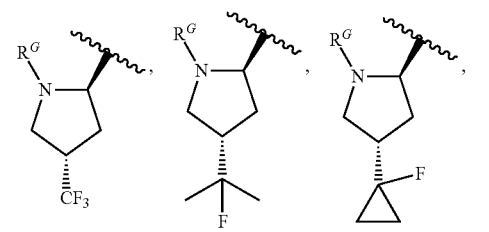
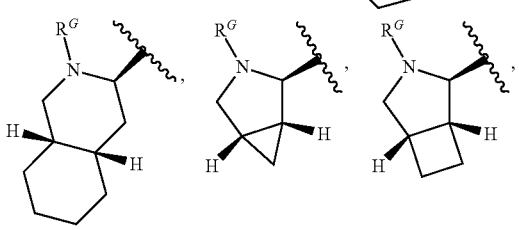
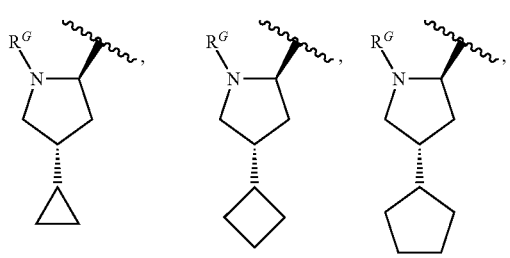
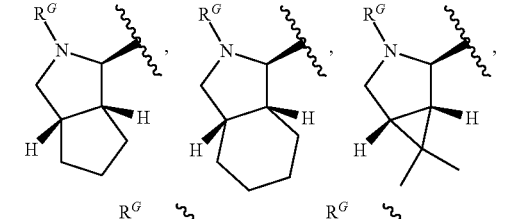
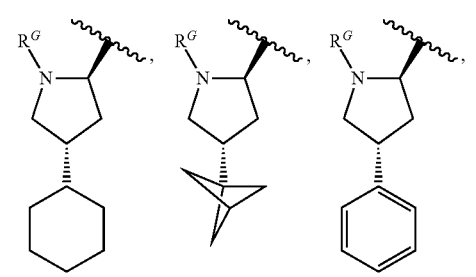
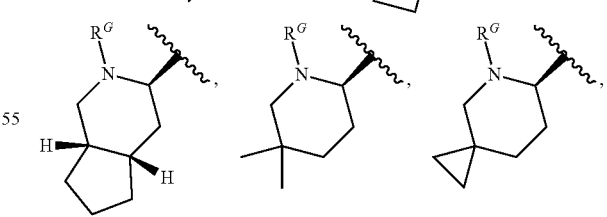
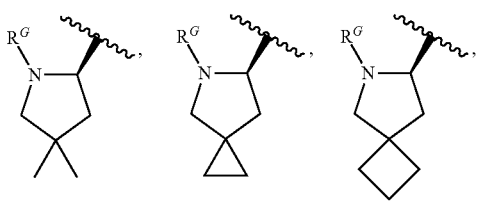
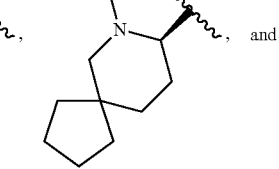

-continued

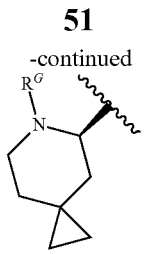

and $R^{1b}$ is H.

In some embodiments, $R^G$ is selected from the group consisting of H, $C_{1-6}$alkyl (optionally substituted by one, two or three substituents each independently selected from the group consisting of —C(=O), halo, cyano, —NR'''R''', and —NH(C=O)R''') and C(=O)—$C_{1-6}$alkyl (optionally substituted by one, two or three substituents each independently selected from the group consisting of halo, cyano, —NR'''R''', —NR'''(C=O)R''', phenyl, cycloalkyl and heterocycle, wherein R''' is selected for each occurrence by H or $C_{1-3}$alkyl (optionally substituted by one, two or three halogens, e.g., F), or $C_3$-$C_6$cycloalkyl (optionally substituted by one, two, or three F).

In some embodiments, $R^G$ is selected from the group consisting of

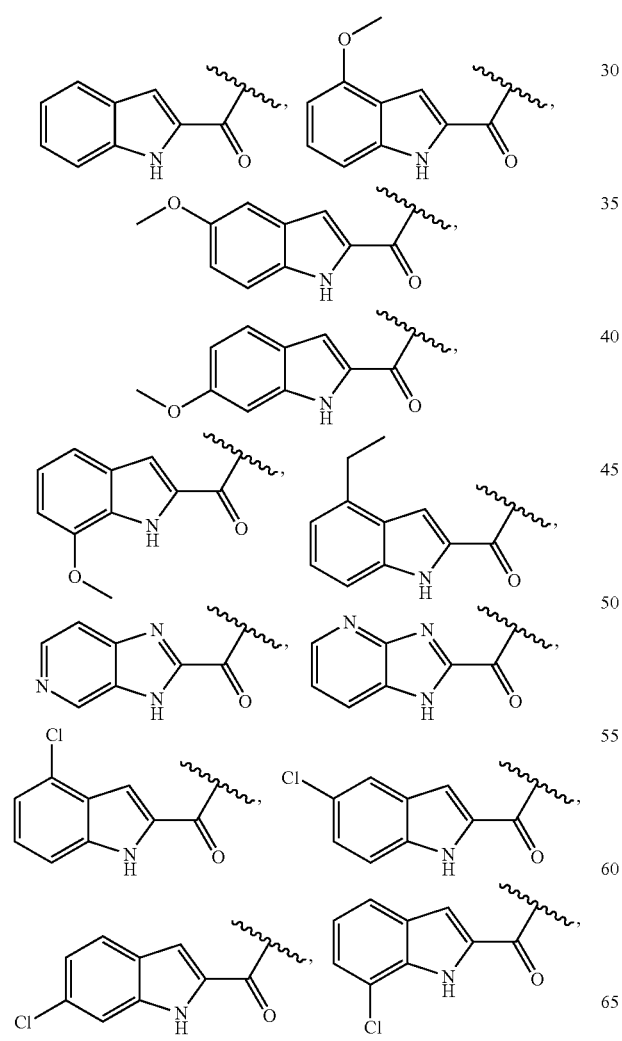

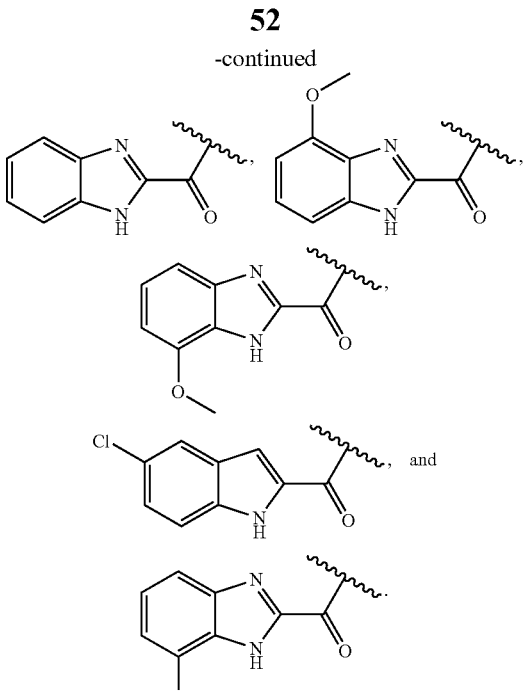

In some embodiments, $R^G$ is

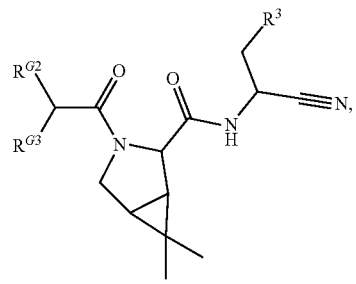

In some embodiments, the compound is represented by

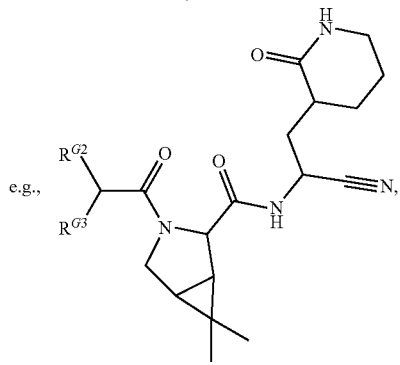

wherein $R^{G3}$ is selected from the group consisting of H, $C_{1-6}$alkyl, $C_{3-6}$cycloalkyl (e.g., t-butyl, propyl, cyclopropyl), phenyl and heterocycle; and $R^{G2}$ is —NH(C=O)$R^m$, wherein $R^m$ is selected for each occurrence by H, methyl or CF$_3$.

In some embodiments, the compound is represented by or

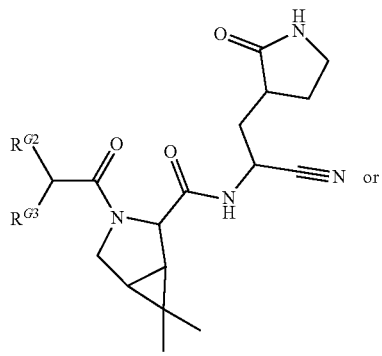

wherein $R^{G3}$ is selected from the group consisting of H, C$_{1-6}$alkyl, C$_{3-6}$cycloalkyl, phenyl and heterocycle; and $R^{G2}$ is —NH(C=O)$R^m$, wherein $R^m$ is selected for each occurrence by H, methyl or CF$_3$.

In some embodiments, the compound is represented by

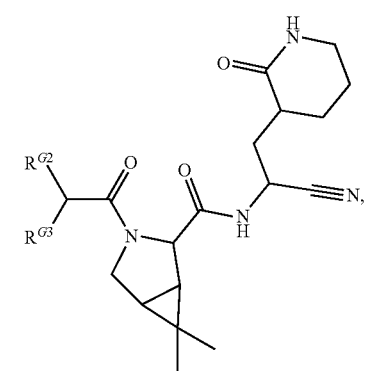

wherein $R^{G3}$ is selected from the group consisting of H, C$_{1-6}$alkyl, C$_{3-6}$cycloalkyl, phenyl and heterocycle; and $R^{G2}$ is —NH(C=O)$R^m$, wherein $R^m$ is selected for each occurrence by H, methyl or CF$_3$.

In some embodiments, the compound is represented by

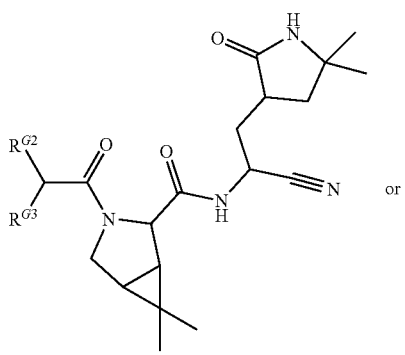

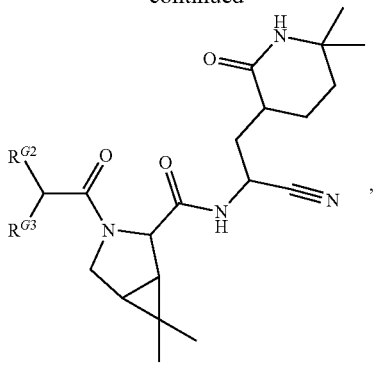

wherein $R^{G3}$ is selected from the group consisting of H, C$_{1-6}$alkyl, C$_{3-6}$cycloalkyl, phenyl and heterocycle; and $R^{G2}$ is —NH(C=O)$R^m$, wherein $R^m$ is selected for each occurrence by H, methyl or CF$_3$.

In some embodiments, the compound is represented by

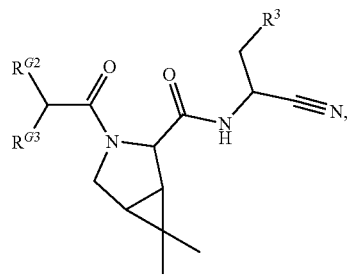

wherein $R^{G3}$ is selected from the group consisting of H, C$_{1-6}$alkyl (optionally substituted by one, two or three C$_1$-C$_6$alkoxy), C$_{3-6}$cycloalkyl, phenyl and heterocycle; and $R^{G2}$ is selected from the group consisting of —NH(C$_{1-3}$alkyl) (optionally substituted by one, two or three substituents each independently selected from the group consisting of halo, optionally substituted phenyl, —S(O)$_2$—CH$_3$, C$_{3-6}$cycloalkyl, and 5-6 membered heteroaryl) and —NH(C=O)$R^m$, wherein $R^m$ is selected for each occurrence by H, C$_{1-6}$alkyl (optionally substituted by one, two or three substituents each independently selected from the group consisting of halo, cyano and C$_1$-C$_6$alkoxy), CHF$_2$, CF$_3$, or 5-6 membered heteroaryl (optionally substituted by halo, cyano, hydroxyl, NH$_2$, C$_{1-6}$alkyl, C$_{3-6}$cycloalkyl, C$_1$-C$_6$alkoxy, CHF$_2$, and CF$_3$).

In some embodiments, the compound is represented by

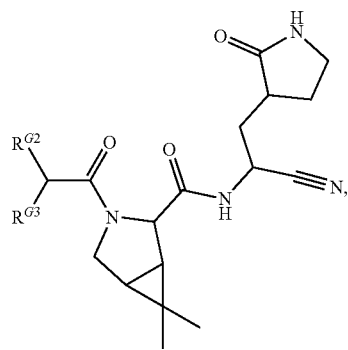

wherein $R^{G3}$ is selected from the group consisting of H, $C_{1-6}$alkyl (optionally substituted by one, two or three $C_1$-$C_6$alkoxy), $C_{3-6}$cycloalkyl, phenyl and heterocycle; and $R^{G2}$ is selected from the group consisting of —NH($C_{1-3}$alkyl) (optionally substituted by one, two or three substituents each independently selected from the group consisting of halo, optionally substituted phenyl, —S(O)$_2$—CH$_3$, $C_{3-6}$cycloalkyl, and 5-6 membered heteroaryl) and —NH (C=O)R$^m$, wherein R$^m$ is selected for each occurrence by H, $C_{1-6}$alkyl (optionally substituted by one, two or three substituents each independently selected from the group consisting of halo, cyano and $C_1$-$C_6$alkoxy), CHF$_2$, CF$_3$, or 5-6 membered heteroaryl (optionally substituted by halo, cyano, hydroxyl, NH$_2$, $C_{1-6}$alkyl, $C_{3-6}$cycloalkyl, $C_1$-$C_6$alkoxy, CHF$_2$, and CF$_3$).

In some embodiments, $R^{G3}$ is selected from the group consisting of

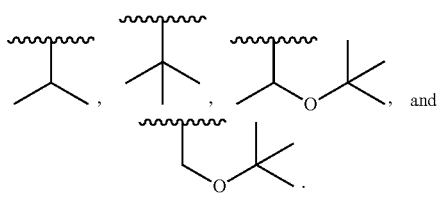
and

In some embodiments, $R^{G2}$ is selected from the group consisting of

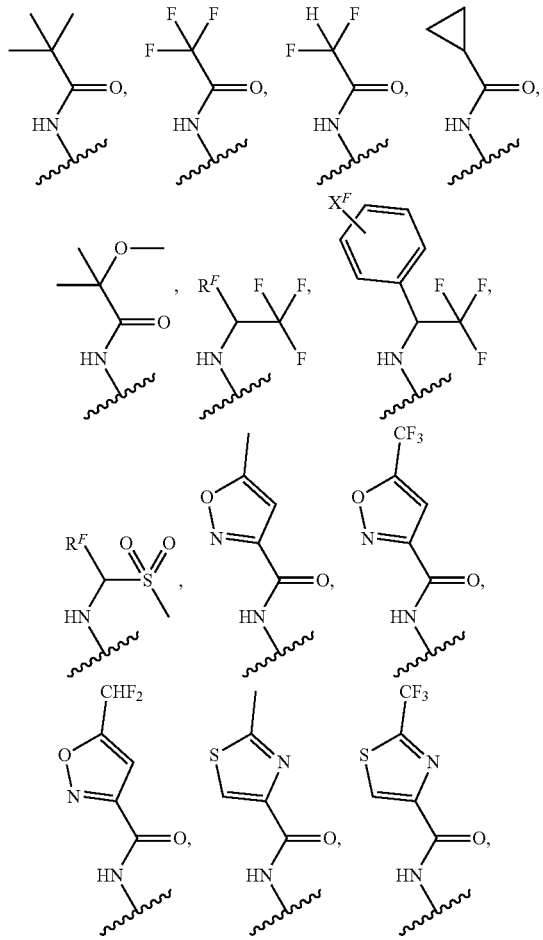

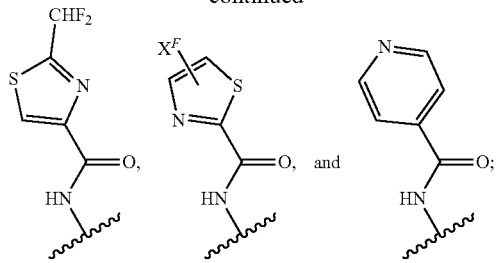

wherein $R^F$ is selected from the group consisting of $C_{1-6}$alkyl, $C_{3-6}$cycloalkyl, phenyl and 5-6 membered heteroaryl, wherein $R^F$ may optionally be substituted by one, two or three substituents selected from the group consisting of halo, cyano, hydroxyl and $C_1$-$C_6$alkoxy; and $X^F$ is selected from the group consisting of H, halo, cyano, hydroxyl, NH$_2$, $C_{1-6}$alkyl, $C_{3-6}$cycloalkyl, $C_1$-$C_6$alkoxy, and $C_{1-6}$haloalkyl.

In some embodiments, $R^{1a}$ and $R^2$ are joined to together to form the heterocycle selected from the group consisting of:

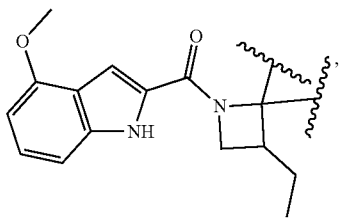

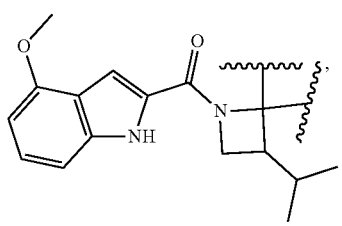

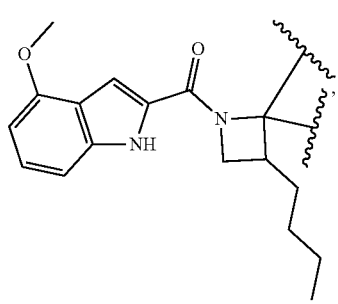

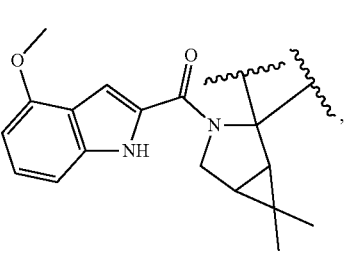

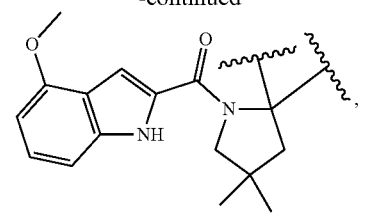
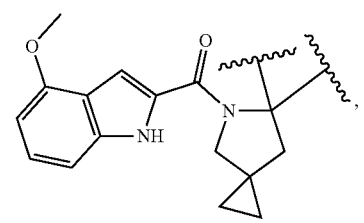
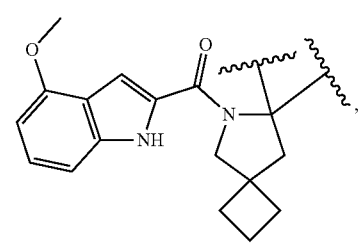
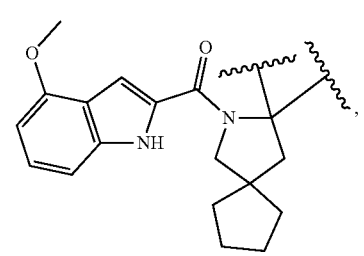
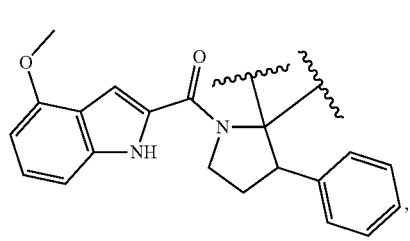
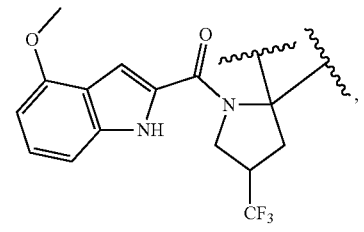
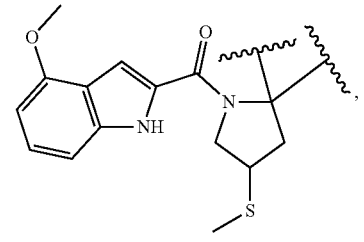
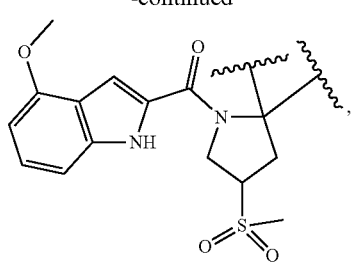
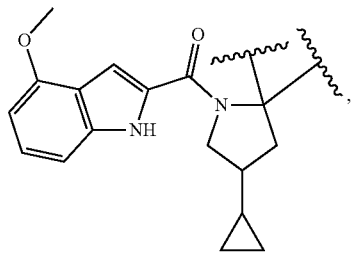
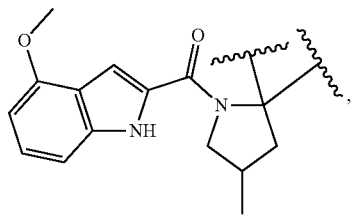
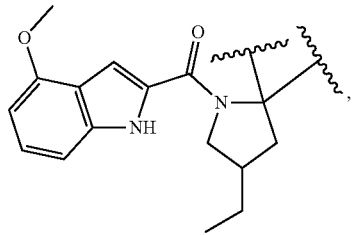
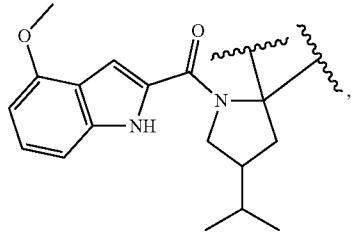
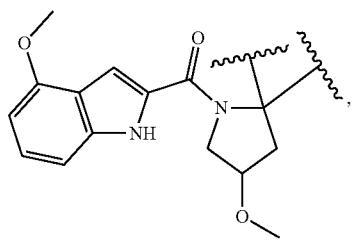
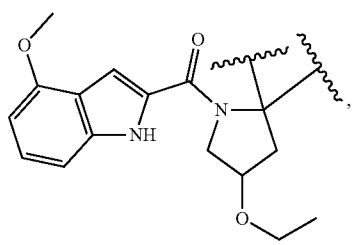

-continued
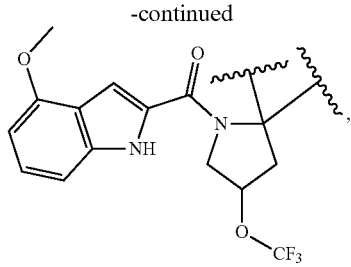
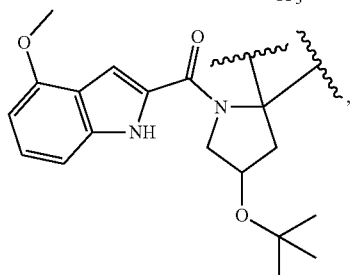
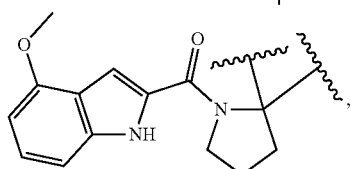
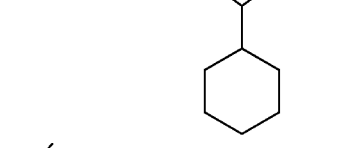
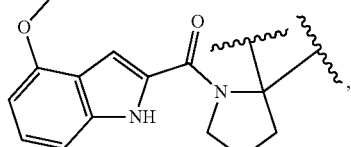
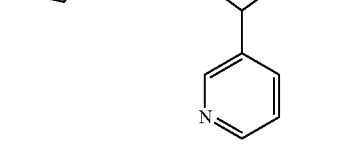
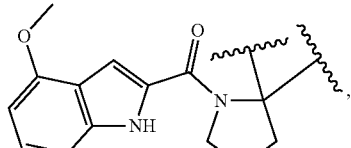
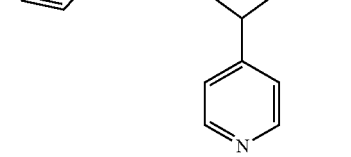
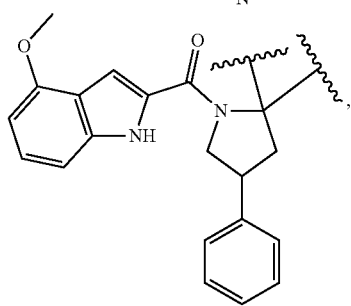
-continued
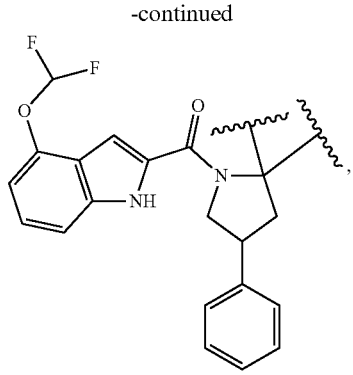
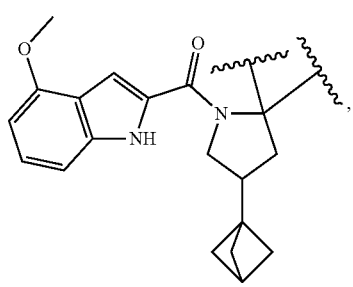
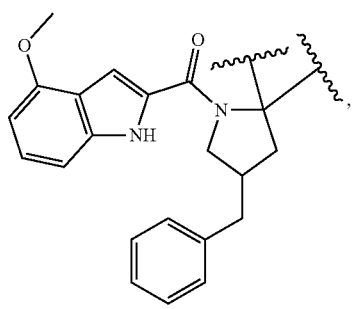
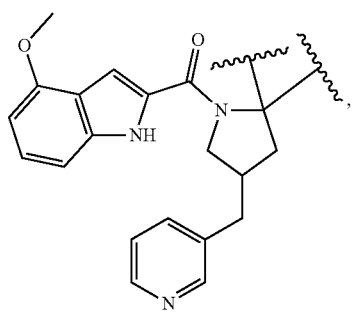
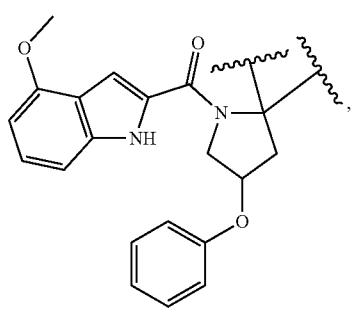

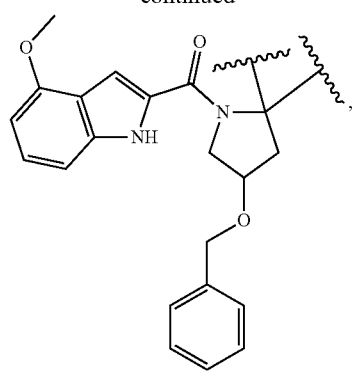
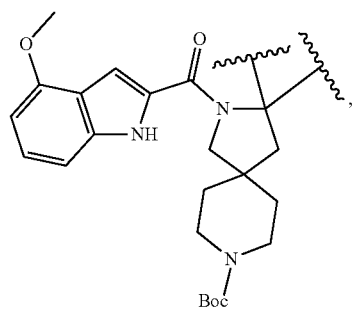
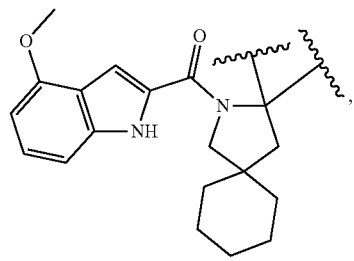
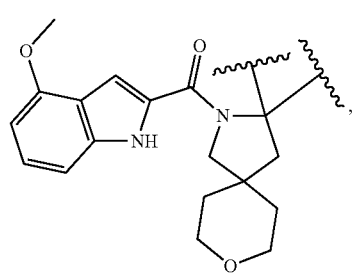
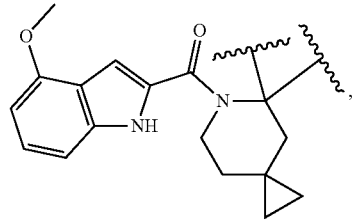
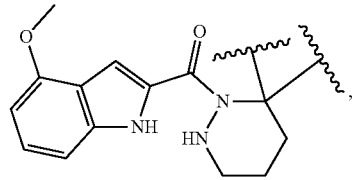
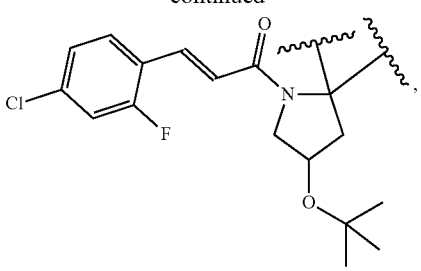
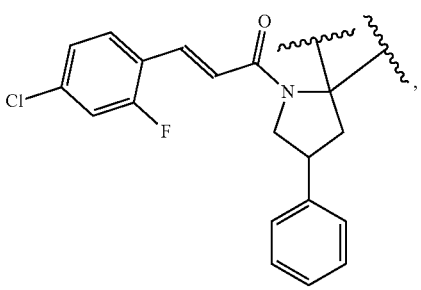
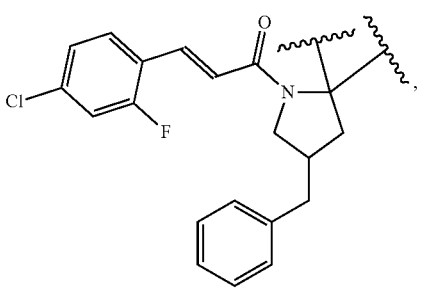
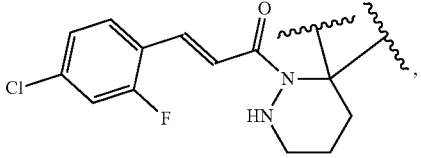
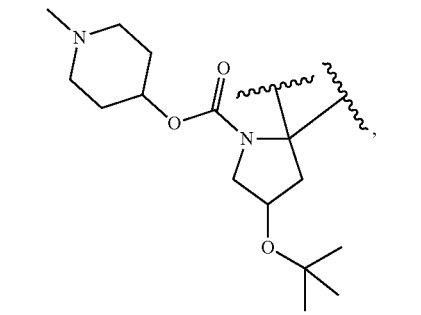
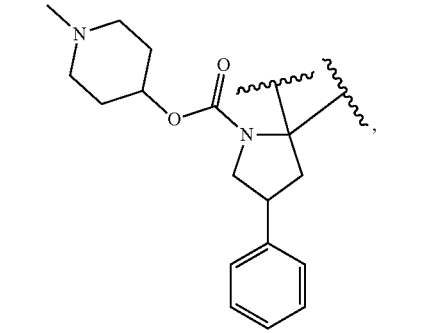

-continued
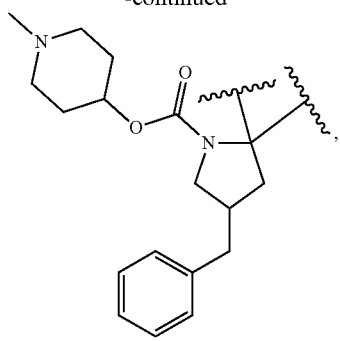
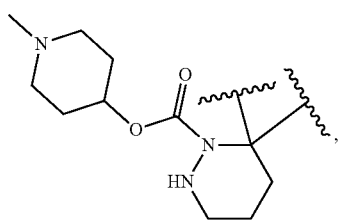
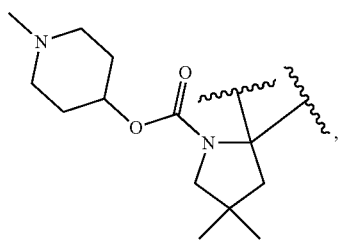
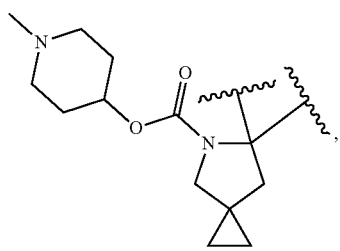
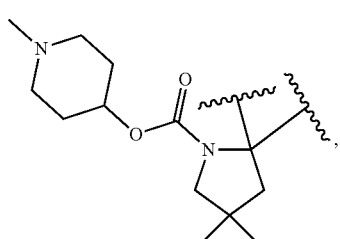
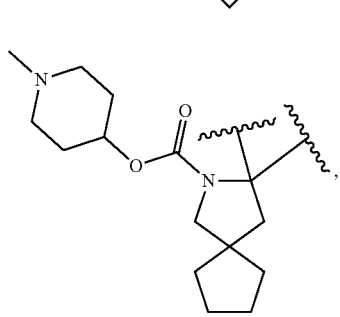
-continued
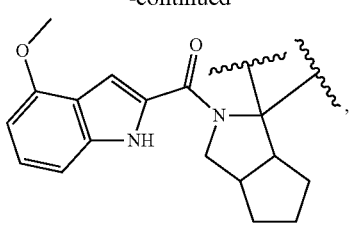
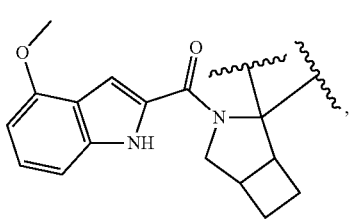
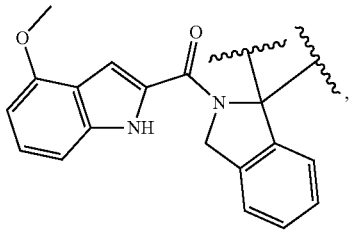
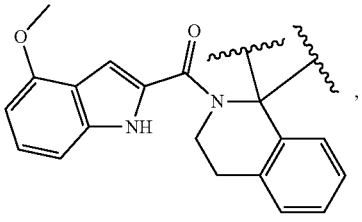
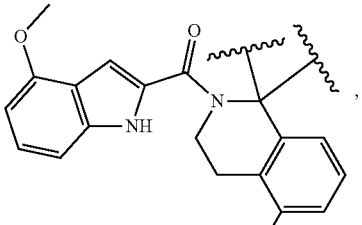
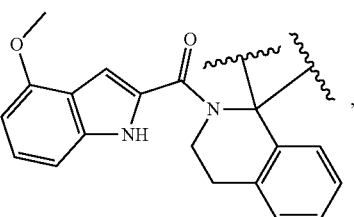
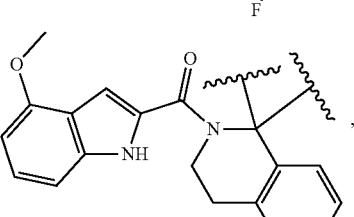

65
-continued
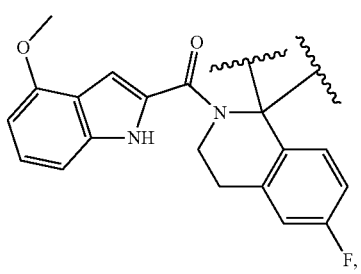
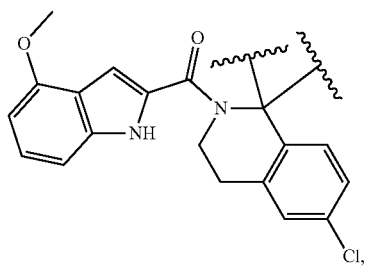
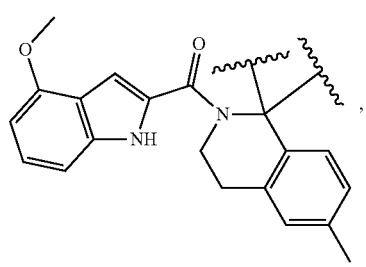
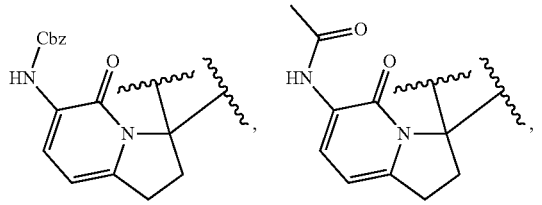
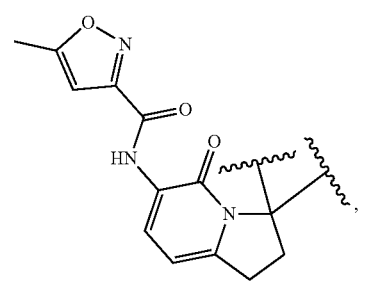
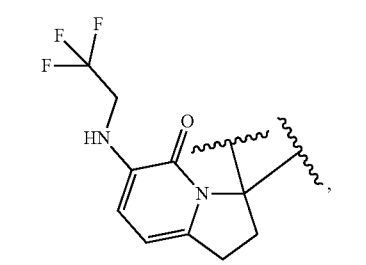
66
-continued
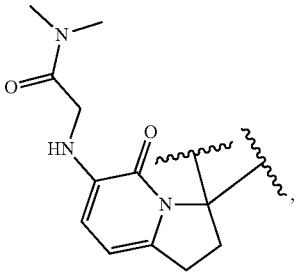
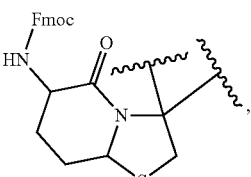
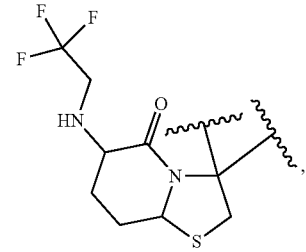
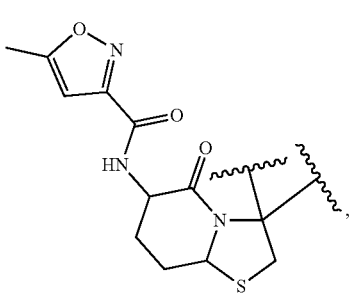
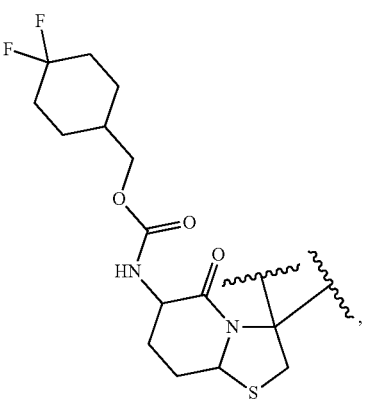

67
-continued
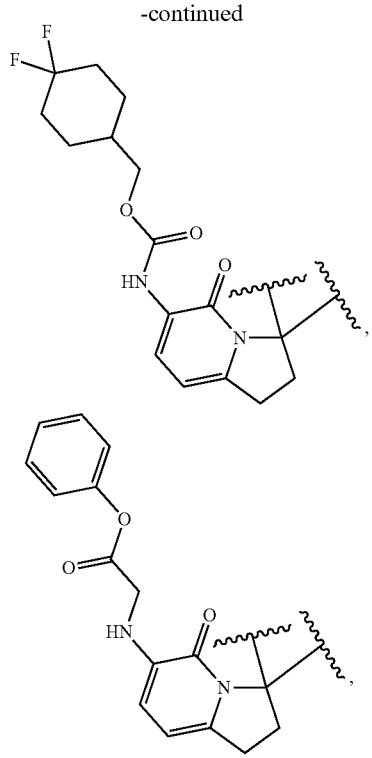
68
-continued
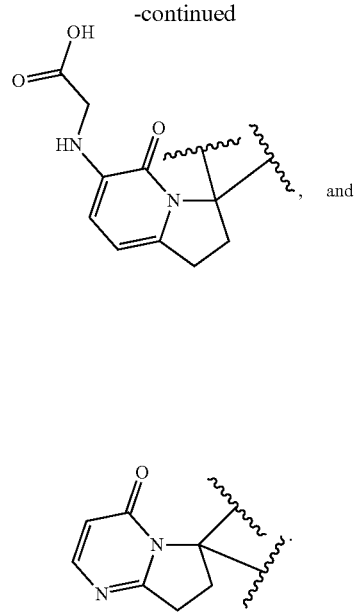
In some embodiments, the compound is selected from the group consisting of the compounds identified in Table 1 below:
TABLE 1
| Exemplary compounds. | |
| --- | --- |
| Compound No. | Structure |
| 100 | |
| 101 | |

TABLE 1-continued

Exemplary compounds.

| Compound No. | Structure |
|---|---|
| 102 | 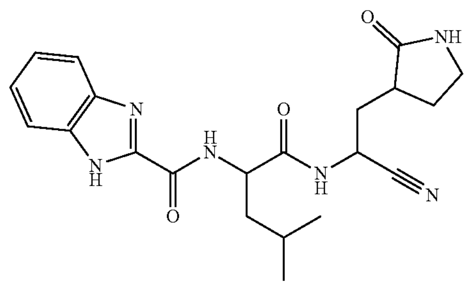 [SMILES: CC(C)CC(NC(=O)c1nc2ccccc2[nH]1)C(=O)NC(C#N)CC1CCNC1=O] |
| 103 | 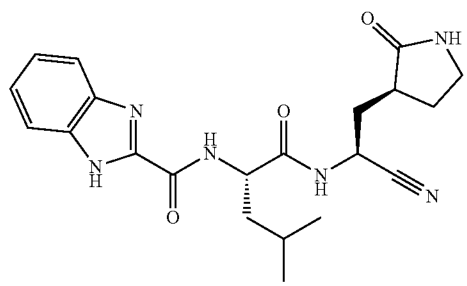 [SMILES: CC(C)C[C@H](NC(=O)c1nc2ccccc2[nH]1)C(=O)N[C@H](C#N)C[C@@H]1CCNC1=O] |
| 104 | 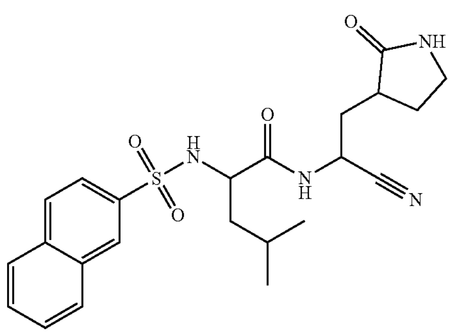 [SMILES: CC(C)CC(NS(=O)(=O)c1ccc2ccccc2c1)C(=O)NC(C#N)CC1CCNC1=O] |
| 105 | 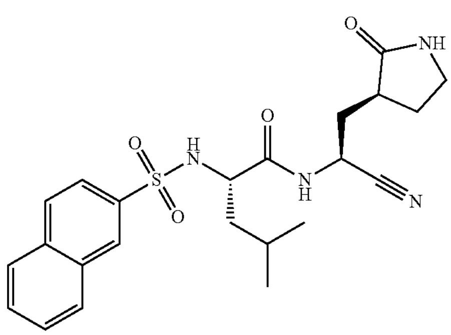 [SMILES: CC(C)C[C@H](NS(=O)(=O)c1ccc2ccccc2c1)C(=O)N[C@H](C#N)C[C@@H]1CCNC1=O] |
| 106 | 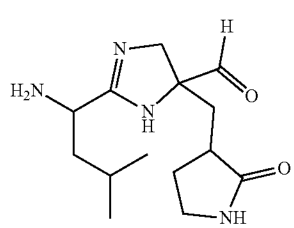 [SMILES: CC(C)CC(N)C1=NCC(C=O)(CC2CCNC2=O)N1] |

TABLE 1-continued

Exemplary compounds.

| Compound No. | Structure |
|---|---|
| 107 | 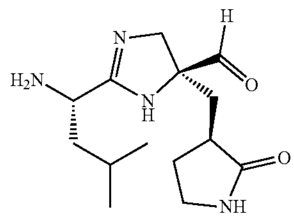 [SMILES: CC(C)C[C@H](N)C1=NC[C@](C=O)(C[C@@H]2CCNC2=O)N1] |
| 108 | 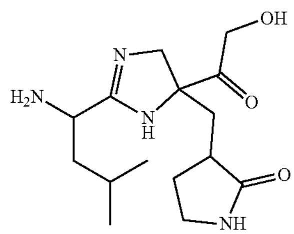 [SMILES: CC(C)CC(N)C1=NCC(CC2CCNC2=O)(C(=O)CO)N1] |
| 109 | 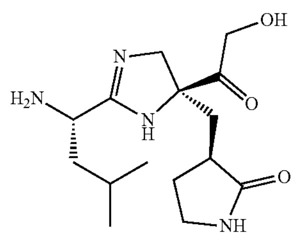 [SMILES: CC(C)C[C@H](N)C1=NC[C@@](C[C@@H]2CCNC2=O)(C(=O)CO)N1] |
| 110 | 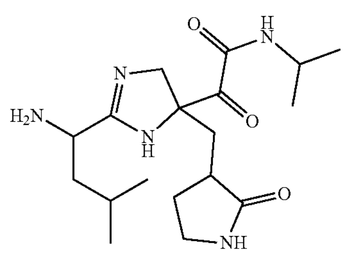 [SMILES: CC(C)CC(N)C1=NCC(CC2CCNC2=O)(C(=O)C(=O)NC(C)C)N1] |
| 111 | 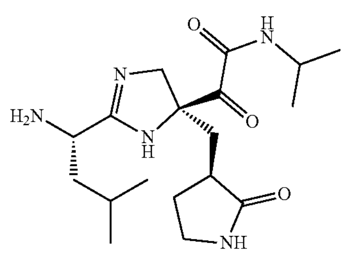 [SMILES: CC(C)C[C@H](N)C1=NC[C@@](C[C@@H]2CCNC2=O)(C(=O)C(=O)NC(C)C)N1] |
| 112 | 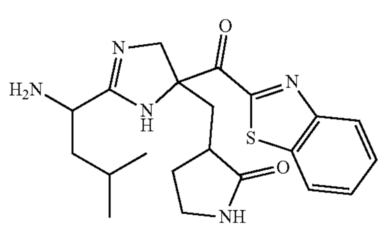 [SMILES: CC(C)CC(N)C1=NCC(CC2CCNC2=O)(C(=O)c2nc3ccccc3s2)N1] |

TABLE 1-continued

Exemplary compounds.

| Compound No. | Structure |
|---|---|
| 113 | 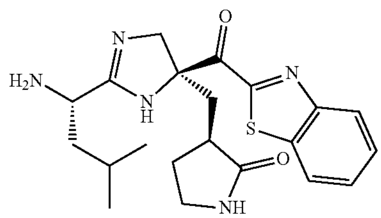 [SMILES: CC(C)C[C@H](N)C1=NC[C@@](C[C@@H]2CCNC2=O)(C(=O)c2nc3ccccc3s2)N1] |
| 114 | 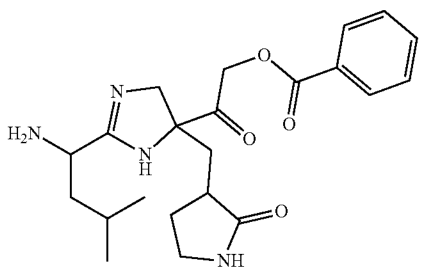 [SMILES: CC(C)CC(N)C1=NCC(CC2CCNC2=O)(C(=O)COC(=O)c2ccccc2)N1] |
| 115 | 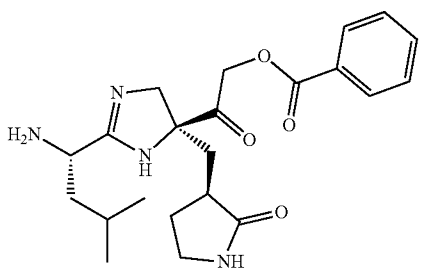 [SMILES: CC(C)C[C@H](N)C1=NC[C@@](C[C@@H]2CCNC2=O)(C(=O)COC(=O)c2ccccc2)N1] |
| 116 | 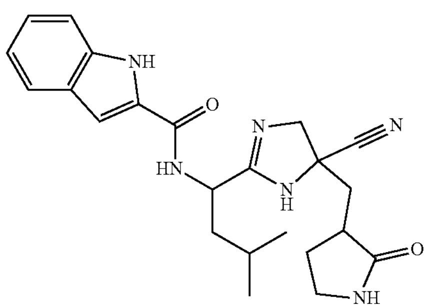 [SMILES: CC(C)CC(NC(=O)c1cc2ccccc2[nH]1)C1=NCC(C#N)(CC2CCNC2=O)N1] |
| 117 | 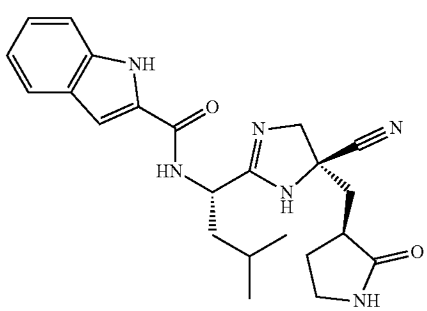 [SMILES: CC(C)C[C@H](NC(=O)c1cc2ccccc2[nH]1)C1=NC[C@](C#N)(C[C@@H]2CCNC2=O)N1] |

TABLE 1-continued

Exemplary compounds.

| Compound No. | Structure |
|---|---|
| 118 | 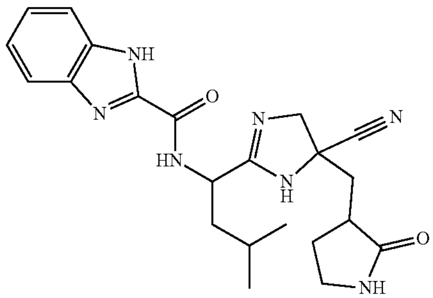 [SMILES: CC(C)CC(NC(=O)c1nc2ccccc2[nH]1)C1=NCC(C#N)(CC2CCNC2=O)N1] |
| 119 | 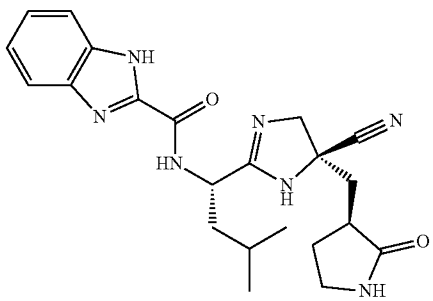 [SMILES: CC(C)C[C@H](NC(=O)c1nc2ccccc2[nH]1)C1=NC[C@](C#N)(C[C@@H]2CCNC2=O)N1] |
| 120 | 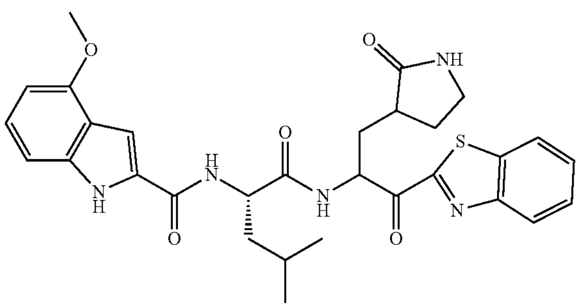 [SMILES: COc1cccc2[nH]c(C(=O)N[C@@H](CC(C)C)C(=O)NC(CC3CCNC3=O)C(=O)c3nc4ccccc4s3)cc12] |
| 121 | 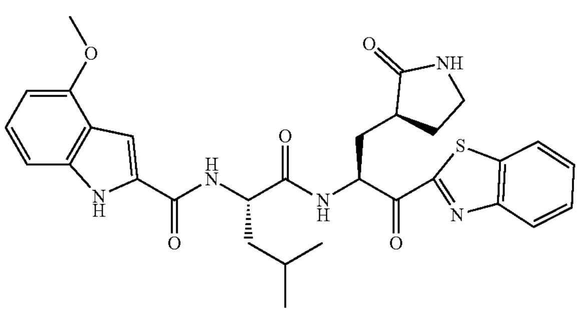 [SMILES: COc1cccc2[nH]c(C(=O)N[C@@H](CC(C)C)C(=O)N[C@@H](C[C@@H]3CCNC3=O)C(=O)c3nc4ccccc4s3)cc12] |
| 122 | 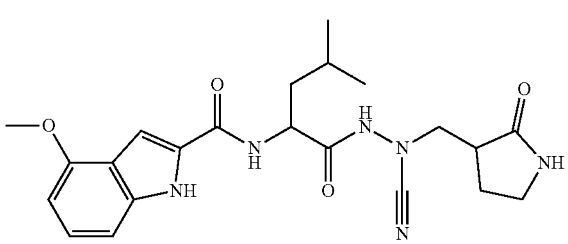 [SMILES: COc1cccc2[nH]c(C(=O)NC(CC(C)C)C(=O)NN(C#N)CC3CCNC3=O)cc12] |

TABLE 1-continued

Exemplary compounds.

| Compound No. | Structure |
|---|---|
| 123 | 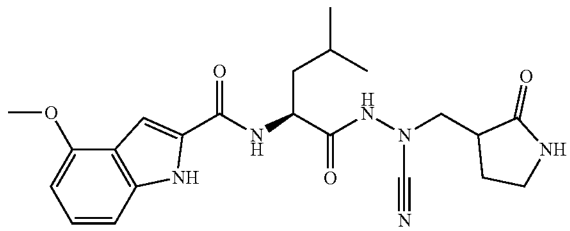 [SMILES: COc1cccc2[nH]c(C(=O)N[C@@H](CC(C)C)C(=O)NN(C#N)CC3CCNC3=O)cc12] |
| 124 | 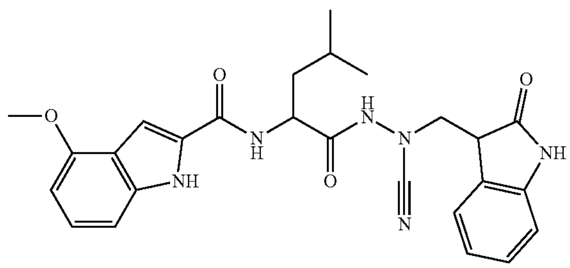 [SMILES: COc1cccc2[nH]c(C(=O)NC(CC(C)C)C(=O)NN(C#N)CC3C(=O)Nc4ccccc43)cc12] |
| 125 | 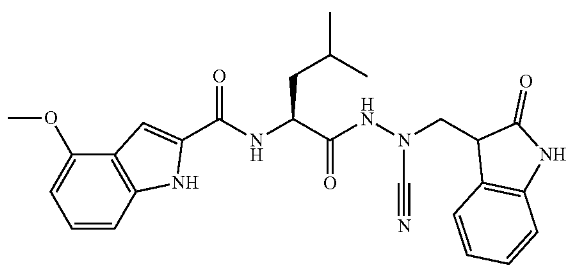 [SMILES: COc1cccc2[nH]c(C(=O)N[C@@H](CC(C)C)C(=O)NN(C#N)CC3C(=O)Nc4ccccc43)cc12] |
| 126 | 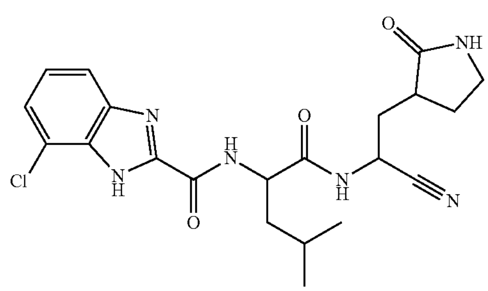 [SMILES: CC(C)CC(NC(=O)c1nc2cccc(Cl)c2[nH]1)C(=O)NC(C#N)CC1CCNC1=O] |
| 127 | 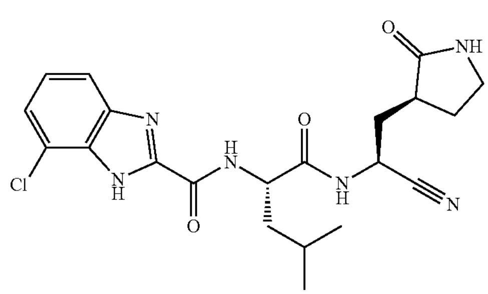 [SMILES: CC(C)C[C@H](NC(=O)c1nc2cccc(Cl)c2[nH]1)C(=O)N[C@H](C#N)C[C@@H]1CCNC1=O] |

TABLE 1-continued

Exemplary compounds.

| Compound No. | Structure |
|---|---|
| 128 | 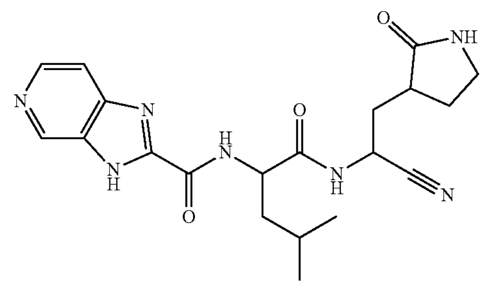 [SMILES: CC(C)CC(NC(=O)c1nc2ccncc2[nH]1)C(=O)NC(C#N)CC1CCNC1=O] |
| 129 | 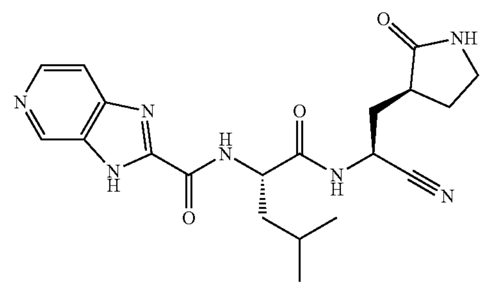 [SMILES: CC(C)C[C@H](NC(=O)c1nc2ccncc2[nH]1)C(=O)N[C@H](C#N)C[C@@H]1CCNC1=O] |
| 130 | 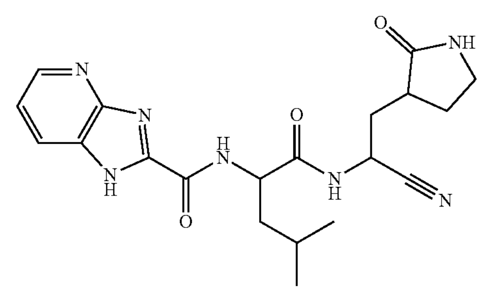 [SMILES: CC(C)CC(NC(=O)c1nc2ncccc2[nH]1)C(=O)NC(C#N)CC1CCNC1=O] |
| 131 | 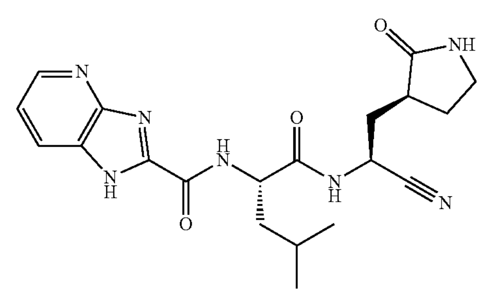 [SMILES: CC(C)C[C@H](NC(=O)c1nc2ncccc2[nH]1)C(=O)N[C@H](C#N)C[C@@H]1CCNC1=O] |
| 132 | 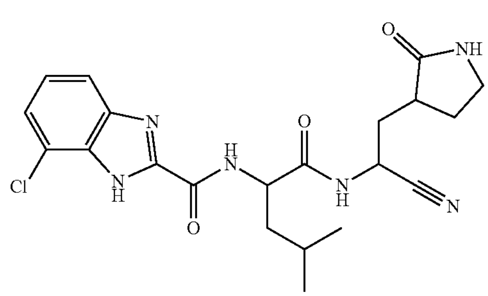 [SMILES: CC(C)CC(NC(=O)c1nc2cccc(Cl)c2[nH]1)C(=O)NC(C#N)CC1CCNC1=O] |

TABLE 1-continued

Exemplary compounds.

| Compound No. | Structure |
|---|---|
| 133 | 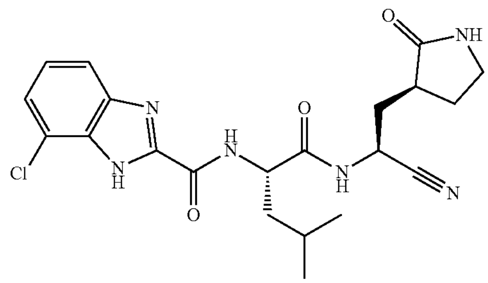 [SMILES: CC(C)C[C@H](NC(=O)c1nc2cccc(Cl)c2[nH]1)C(=O)N[C@H](C#N)C[C@@H]1CCNC1=O] |
| 134 | 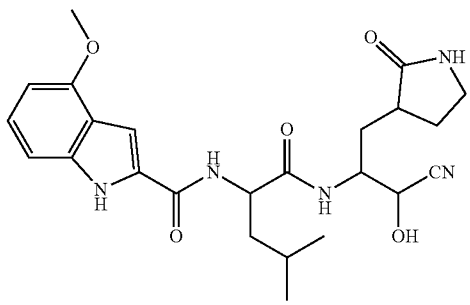 [SMILES: COc1cccc2[nH]c(C(=O)NC(CC(C)C)C(=O)NC(CC3CCNC3=O)C(O)C#N)cc12] |
| 135 | 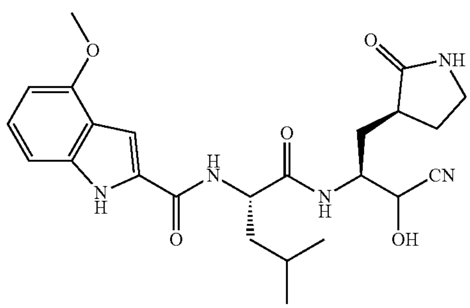 [SMILES: COc1cccc2[nH]c(C(=O)N[C@@H](CC(C)C)C(=O)N[C@@H](C[C@@H]3CCNC3=O)C(O)C#N)cc12] |
| 136 | 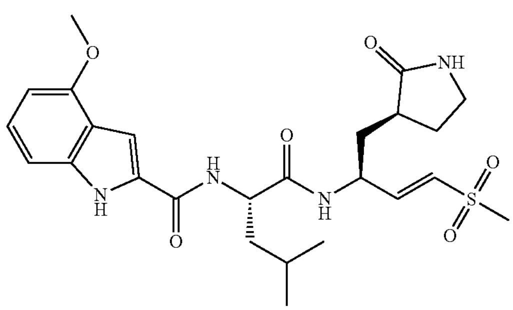 [SMILES: COc1cccc2[nH]c(C(=O)N[C@@H](CC(C)C)C(=O)N[C@H](/C=C/S(C)(=O)=O)C[C@@H]3CCNC3=O)cc12] |
| 137 | 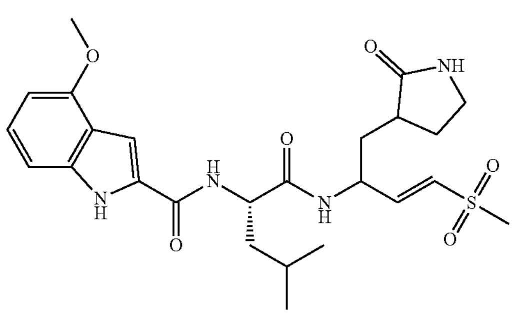 [SMILES: COc1cccc2[nH]c(C(=O)N[C@@H](CC(C)C)C(=O)NC(/C=C/S(C)(=O)=O)CC3CCNC3=O)cc12] |

TABLE 1-continued
Exemplary compounds.
| Compound No. | Structure |
|---|---|
| 138 | 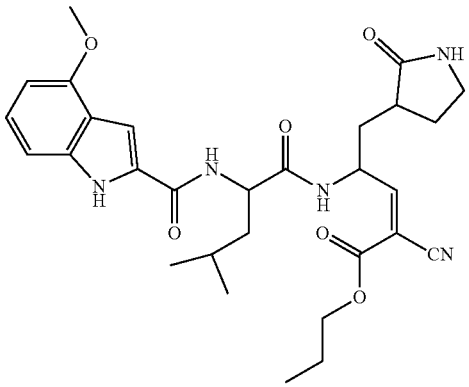 [SMILES: CCCOC(=O)/C(C#N)=C\C(CC1CCNC1=O)NC(=O)C(CC(C)C)NC(=O)c1cc2c(OC)cccc2[nH]1] |
| 139 | 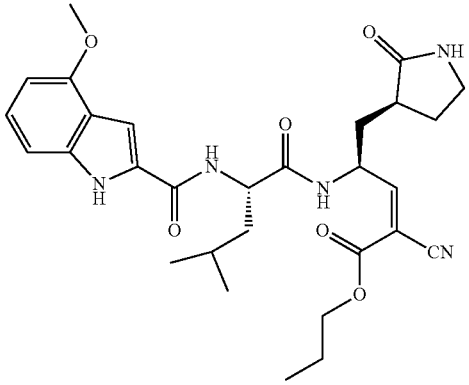 [SMILES: CCCOC(=O)/C(C#N)=C\[C@H](C[C@@H]1CCNC1=O)NC(=O)[C@H](CC(C)C)NC(=O)c1cc2c(OC)cccc2[nH]1] |
| 140 | 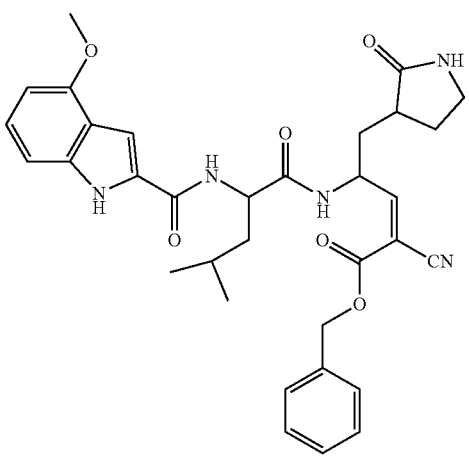 [SMILES: COc1cccc2[nH]c(C(=O)NC(CC(C)C)C(=O)NC(/C=C(/C#N)C(=O)OCc3ccccc3)CC3CCNC3=O)cc12] |

TABLE 1-continued
Exemplary compounds.
| Compound No. | Structure |
|---|---|
| 141 | 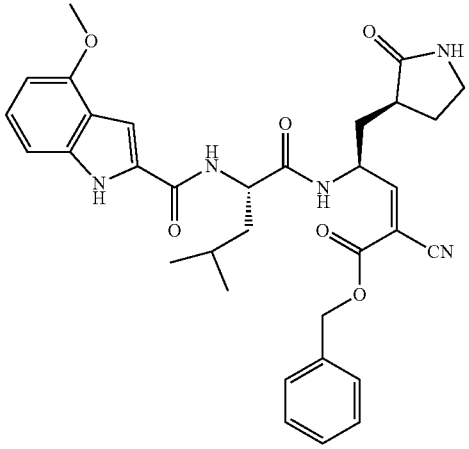 [SMILES: COc1cccc2[nH]c(C(=O)N[C@@H](CC(C)C)C(=O)N[C@H](/C=C(/C#N)C(=O)OCc3ccccc3)C[C@@H]3CCNC3=O)cc12] |
| 142 | 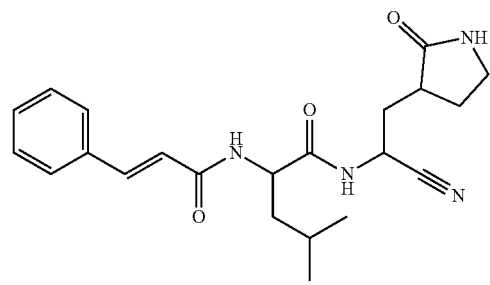 [SMILES: CC(C)CC(NC(=O)/C=C/c1ccccc1)C(=O)NC(C#N)CC1CCNC1=O] |
| 143 | 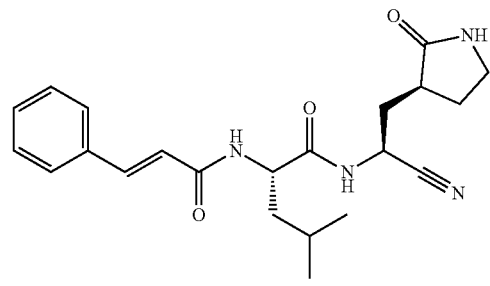 [SMILES: CC(C)C[C@H](NC(=O)/C=C/c1ccccc1)C(=O)N[C@H](C#N)C[C@@H]1CCNC1=O] |
| 144 | 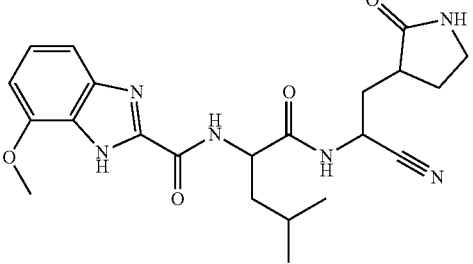 |

TABLE 1-continued
Exemplary compounds.
| Compound No. | Structure |
|---|---|
| 145 | 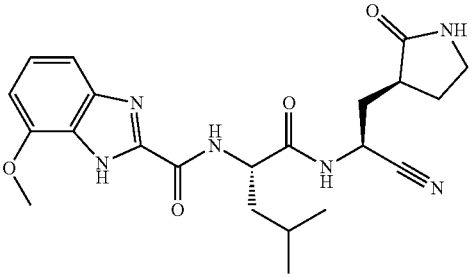 [SMILES: COc1cccc2nc(C(=O)N[C@@H](CC(C)C)C(=O)N[C@H](C#N)C[C@@H]3CCNC3=O)[nH]c12] |
| 146 | 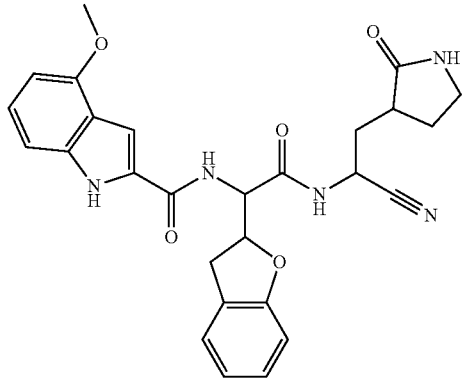 [SMILES: COc1cccc2[nH]c(C(=O)NC(C(=O)NC(C#N)CC3CCNC3=O)C3Cc4ccccc4O3)cc12] |
| 147 | 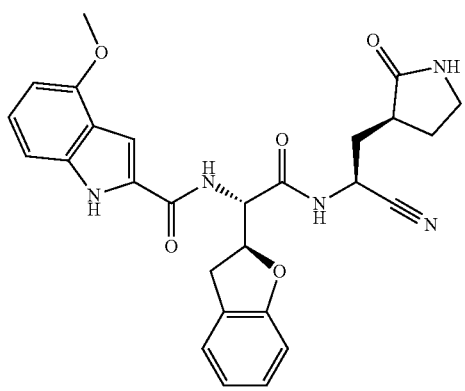 [SMILES: COc1cccc2[nH]c(C(=O)N[C@H](C(=O)N[C@H](C#N)C[C@@H]3CCNC3=O)[C@@H]3Cc4ccccc4O3)cc12] |
| 148 | 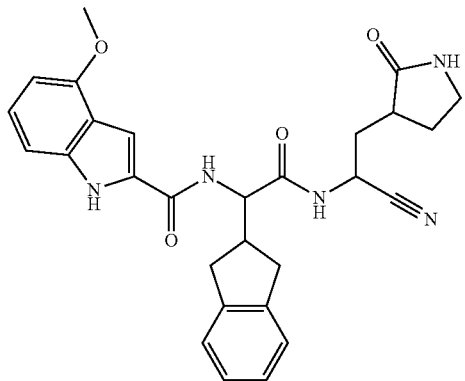 [SMILES: COc1cccc2[nH]c(C(=O)NC(C(=O)NC(C#N)CC3CCNC3=O)C3Cc4ccccc4C3)cc12] |

TABLE 1-continued

Exemplary compounds.

| Compound No. | Structure |
|---|---|
| 149 | 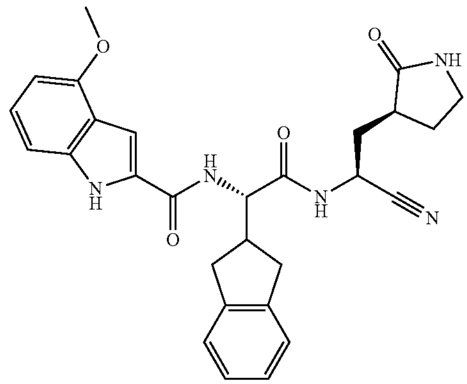 [SMILES: COc1cccc2[nH]c(C(=O)N[C@H](C(=O)N[C@H](C#N)C[C@@H]3CCNC3=O)C3Cc4ccccc4C3)cc12] |
| 150 | 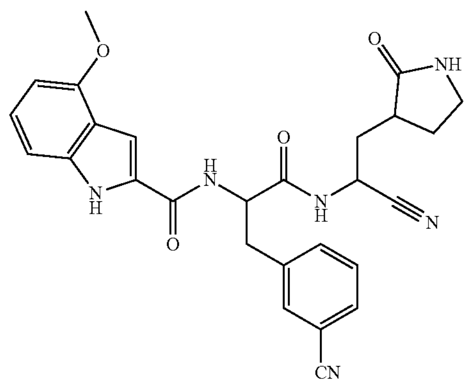 [SMILES: COc1cccc2[nH]c(C(=O)NC(Cc3cccc(C#N)c3)C(=O)NC(C#N)CC3CCNC3=O)cc12] |
| 151 | 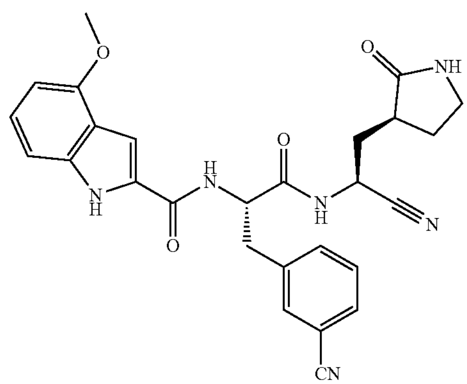 [SMILES: COc1cccc2[nH]c(C(=O)N[C@@H](Cc3cccc(C#N)c3)C(=O)N[C@H](C#N)C[C@@H]3CCNC3=O)cc12] |
| 152 | 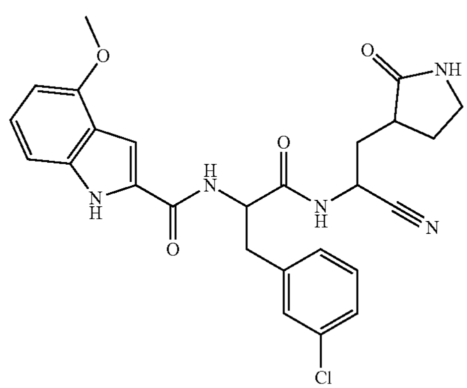 [SMILES: COc1cccc2[nH]c(C(=O)NC(Cc3cccc(Cl)c3)C(=O)NC(C#N)CC3CCNC3=O)cc12] |

TABLE 1-continued

Exemplary compounds.

| Compound No. | Structure |
|---|---|
| 153 | 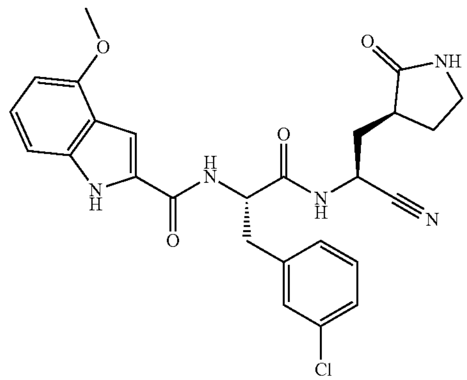 [SMILES: COc1cccc2[nH]c(C(=O)N[C@@H](Cc3cccc(Cl)c3)C(=O)N[C@H](C#N)C[C@@H]3CCNC3=O)cc12] |
| 154 | 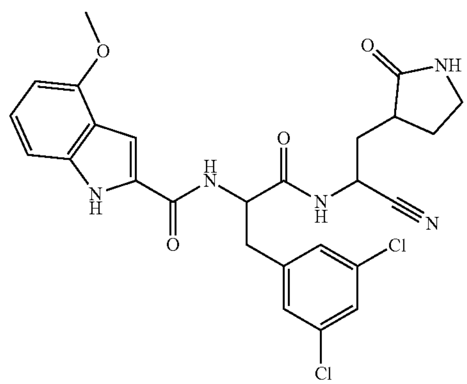 [SMILES: COc1cccc2[nH]c(C(=O)NC(Cc3cc(Cl)cc(Cl)c3)C(=O)NC(C#N)CC3CCNC3=O)cc12] |
| 155 | 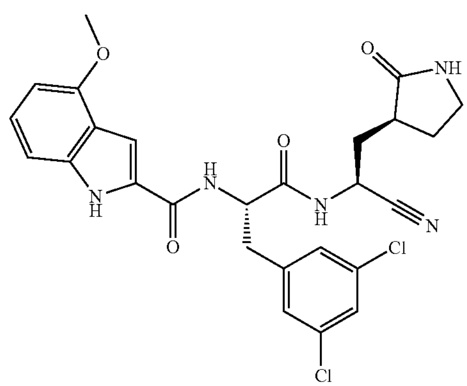 [SMILES: COc1cccc2[nH]c(C(=O)N[C@@H](Cc3cc(Cl)cc(Cl)c3)C(=O)N[C@H](C#N)C[C@@H]3CCNC3=O)cc12] |
| 156 | 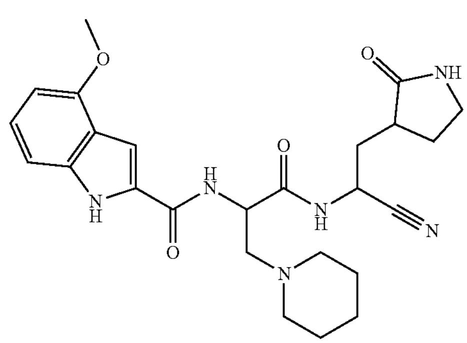 [SMILES: COc1cccc2[nH]c(C(=O)NC(CN3CCCCC3)C(=O)NC(C#N)CC3CCNC3=O)cc12] |

TABLE 1-continued

Exemplary compounds.

| Compound No. | Structure |
|---|---|
| 157 | 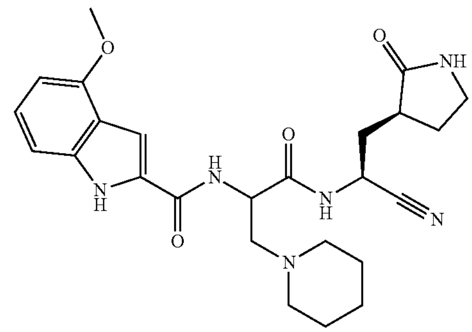 [SMILES: COc1cccc2[nH]c(C(=O)NC(CN3CCCCC3)C(=O)N[C@H](C#N)C[C@@H]3CCNC3=O)cc12] |
| 158 | 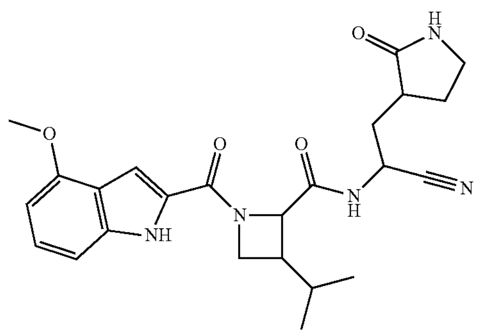 [SMILES: COc1cccc2[nH]c(C(=O)N3CC(C(C)C)C3C(=O)NC(C#N)CC3CCNC3=O)cc12] |
| 159 | 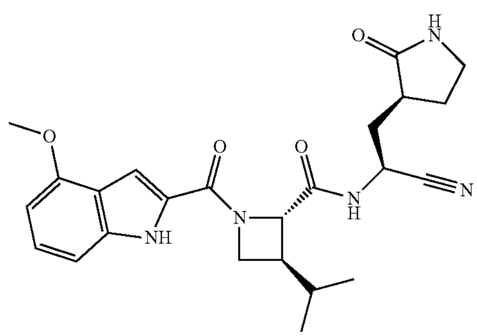 [SMILES: COc1cccc2[nH]c(C(=O)N3C[C@H](C(C)C)[C@H]3C(=O)N[C@H](C#N)C[C@@H]3CCNC3=O)cc12] |
| 160 | 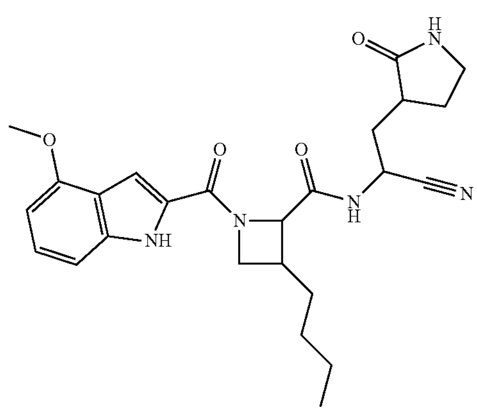 [SMILES: CCCCC1CN(C(=O)c2cc3c(OC)cccc3[nH]2)C1C(=O)NC(C#N)CC1CCNC1=O] |

TABLE 1-continued
Exemplary compounds.
| Compound No. | Structure |
|---|---|
| 161 | 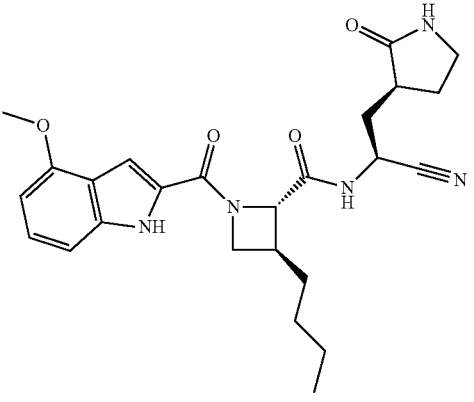 [SMILES: CCCC[C@H]1CN(C(=O)c2cc3c(OC)cccc3[nH]2)[C@@H]1C(=O)N[C@H](C#N)C[C@@H]1CCNC1=O] |
| 162 | 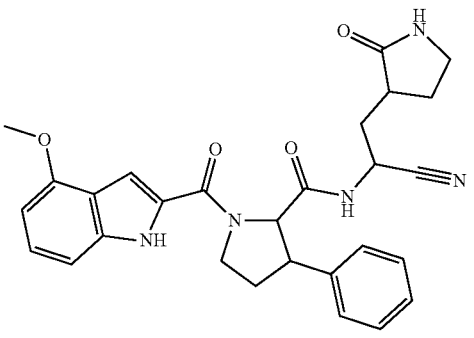 [SMILES: COc1cccc2[nH]c(C(=O)N3CCC(c4ccccc4)C3C(=O)NC(C#N)CC3CCNC3=O)cc12] |
| 163 | 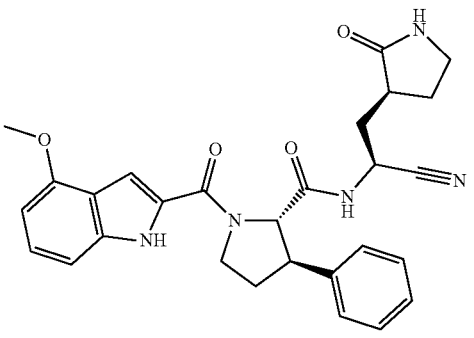 [SMILES: COc1cccc2[nH]c(C(=O)N3CC[C@H](c4ccccc4)[C@H]3C(=O)N[C@H](C#N)C[C@@H]3CCNC3=O)cc12] |
| 164 | 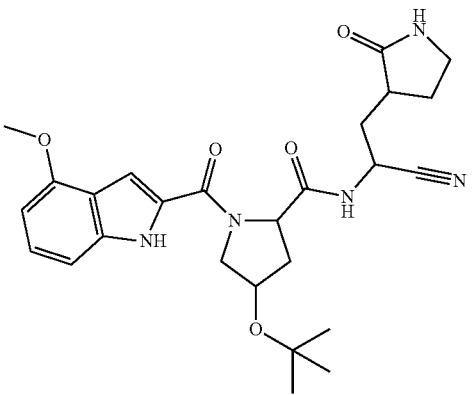 [SMILES: COc1cccc2[nH]c(C(=O)N3CC(OC(C)(C)C)CC3C(=O)NC(C#N)CC3CCNC3=O)cc12] |

TABLE 1-continued
Exemplary compounds.
| Compound No. | Structure |
|---|---|
| 165 | 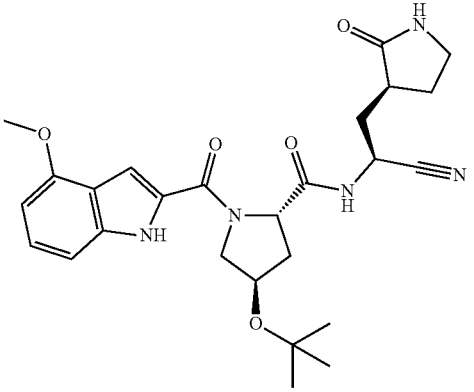 [SMILES: COc1cccc2[nH]c(C(=O)N3C[C@H](OC(C)(C)C)C[C@H]3C(=O)N[C@H](C#N)C[C@@H]3CCNC3=O)cc12] |
| 166 | 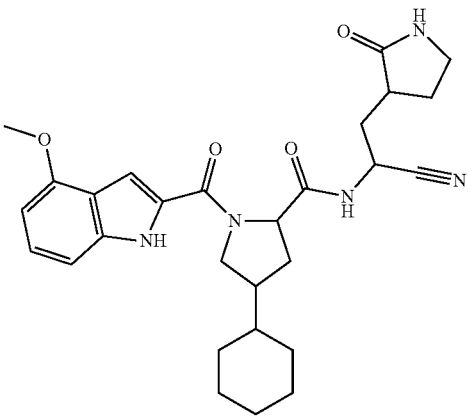 [SMILES: COc1cccc2[nH]c(C(=O)N3CC(C4CCCCC4)CC3C(=O)NC(C#N)CC3CCNC3=O)cc12] |
| 167 | 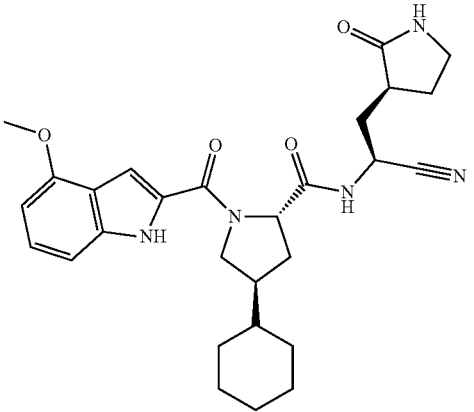 [SMILES: COc1cccc2[nH]c(C(=O)N3C[C@H](C4CCCCC4)C[C@H]3C(=O)N[C@H](C#N)C[C@@H]3CCNC3=O)cc12] |

TABLE 1-continued

Exemplary compounds.

| Compound No. | Structure |
|---|---|
| 168 | 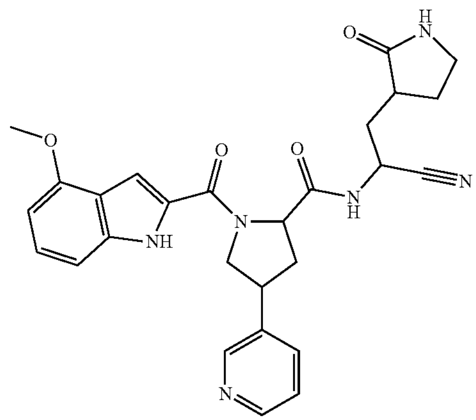 [SMILES: COc1cccc2[nH]c(C(=O)N3CC(c4cccnc4)CC3C(=O)NC(C#N)CC3CCNC3=O)cc12] |
| 169 | 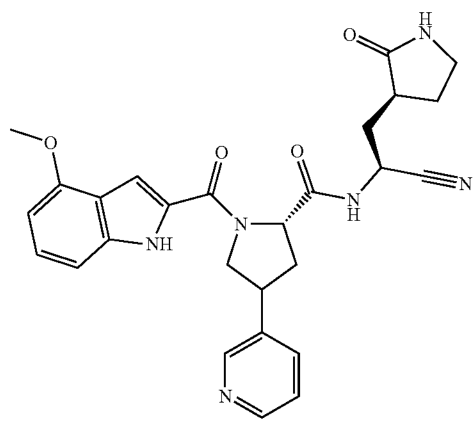 [SMILES: COc1cccc2[nH]c(C(=O)N3CC(c4cccnc4)C[C@H]3C(=O)N[C@H](C#N)C[C@@H]3CCNC3=O)cc12] |
| 170 | 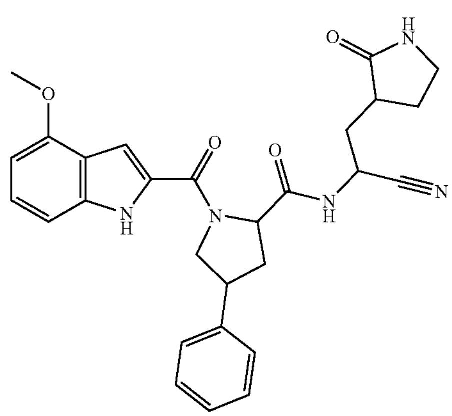 [SMILES: COc1cccc2[nH]c(C(=O)N3CC(c4ccccc4)CC3C(=O)NC(C#N)CC3CCNC3=O)cc12] |

TABLE 1-continued
Exemplary compounds.
| Compound No. | Structure |
|---|---|
| 171 | 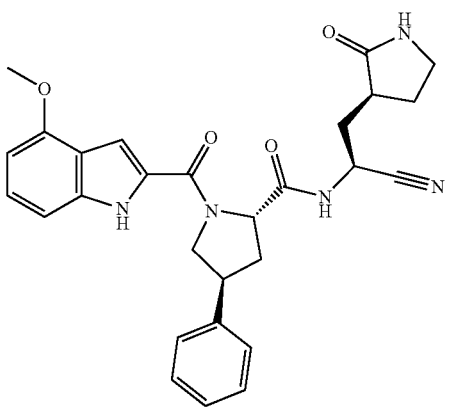 [SMILES: COc1cccc2[nH]c(C(=O)N3C[C@H](c4ccccc4)C[C@H]3C(=O)N[C@H](C#N)C[C@@H]3CCNC3=O)cc12] |
| 172 | 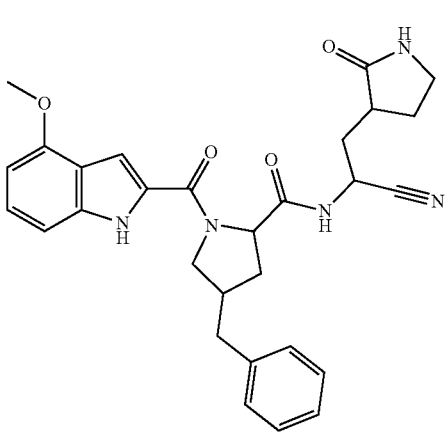 [SMILES: COc1cccc2[nH]c(C(=O)N3CC(Cc4ccccc4)CC3C(=O)NC(C#N)CC3CCNC3=O)cc12] |
| 173 | 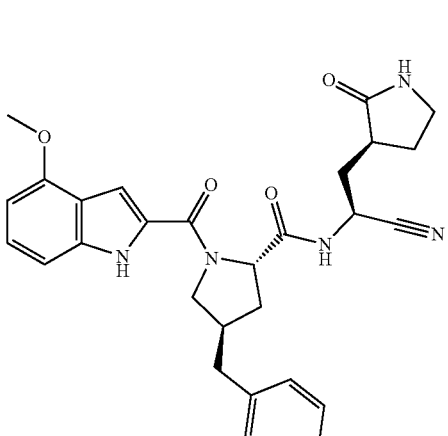 |

TABLE 1-continued

Exemplary compounds.

| Compound No. | Structure |
|---|---|
| 174 | 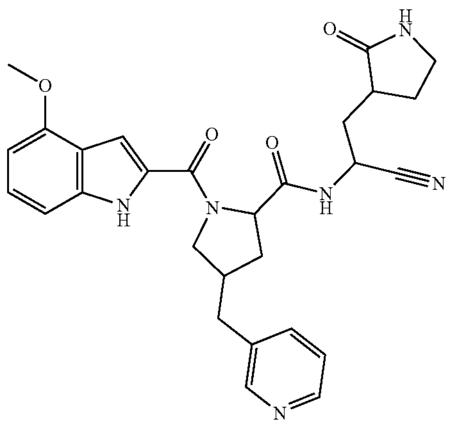 [SMILES: COc1cccc2[nH]c(C(=O)N3CC(Cc4cccnc4)CC3C(=O)NC(C#N)CC3CCNC3=O)cc12] |
| 175 | 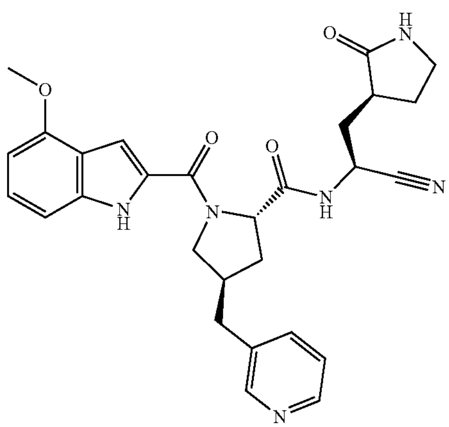 [SMILES: COc1cccc2[nH]c(C(=O)N3C[C@H](Cc4cccnc4)C[C@H]3C(=O)N[C@H](C#N)C[C@@H]3CCNC3=O)cc12] |
| 176 | 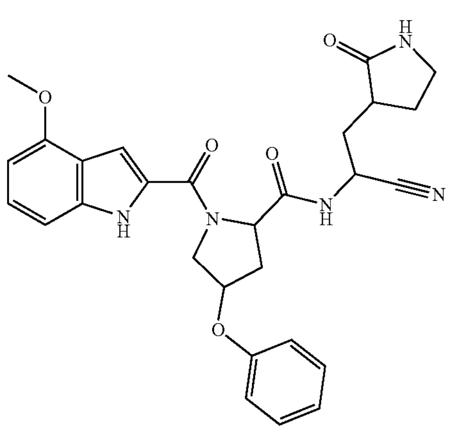 [SMILES: COc1cccc2[nH]c(C(=O)N3CC(Oc4ccccc4)CC3C(=O)NC(C#N)CC3CCNC3=O)cc12] |

TABLE 1-continued

Exemplary compounds.

| Compound No. | Structure |
|---|---|
| 177 | 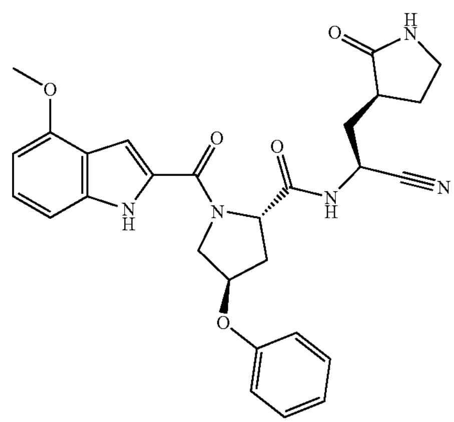 [SMILES: COc1cccc2[nH]c(C(=O)N3C[C@H](Oc4ccccc4)C[C@H]3C(=O)N[C@H](C#N)C[C@@H]3CCNC3=O)cc12] |
| 178 | 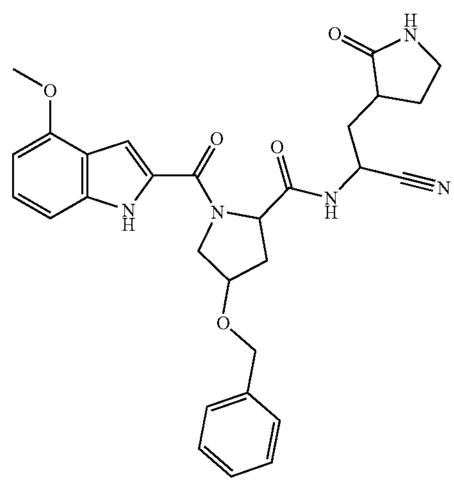 [SMILES: COc1cccc2[nH]c(C(=O)N3CC(OCc4ccccc4)CC3C(=O)NC(C#N)CC3CCNC3=O)cc12] |
| 179 | 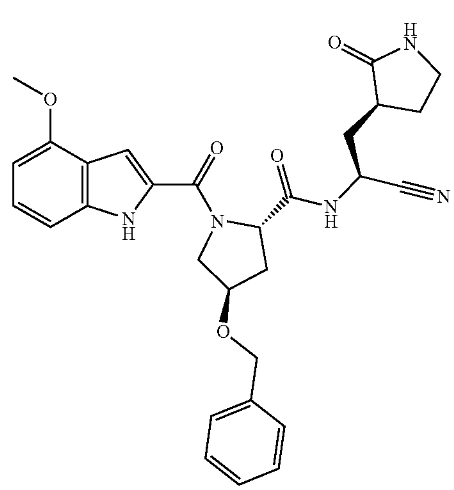 [SMILES: COc1cccc2[nH]c(C(=O)N3C[C@H](OCc4ccccc4)C[C@H]3C(=O)N[C@H](C#N)C[C@@H]3CCNC3=O)cc12] |

TABLE 1-continued

Exemplary compounds.

| Compound No. | Structure |
|---|---|
| 180 | 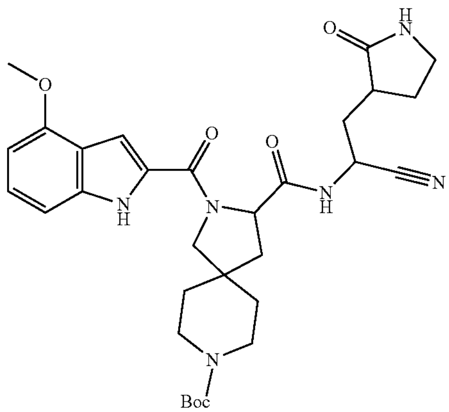 [SMILES: COc1cccc2[nH]c(C(=O)N3CC4(CCN(C(=O)OC(C)(C)C)CC4)CC3C(=O)NC(C#N)CC3CCNC3=O)cc12] |
| 181 | 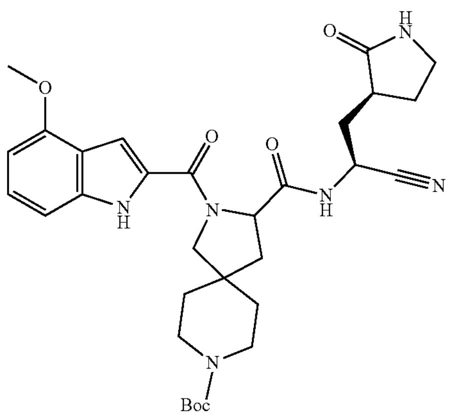 [SMILES: COc1cccc2[nH]c(C(=O)N3CC4(CCN(C(=O)OC(C)(C)C)CC4)CC3C(=O)N[C@H](C#N)C[C@@H]3CCNC3=O)cc12] |
| 182 | 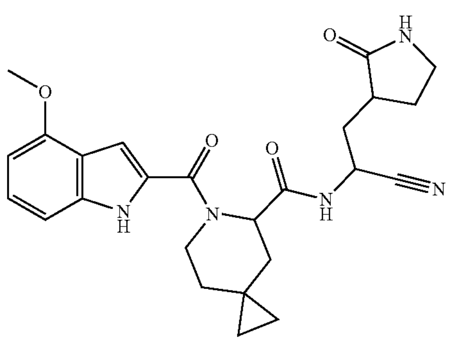 [SMILES: COc1cccc2[nH]c(C(=O)N3CCC4(CC4)CC3C(=O)NC(C#N)CC3CCNC3=O)cc12] |
| 183 | 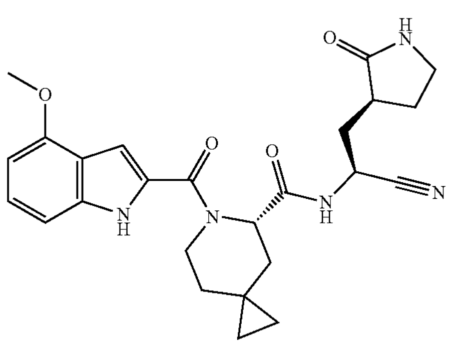 [SMILES: COc1cccc2[nH]c(C(=O)N3CCC4(CC4)C[C@H]3C(=O)N[C@H](C#N)C[C@@H]3CCNC3=O)cc12] |

TABLE 1-continued

Exemplary compounds.

| Compound No. | Structure |
|---|---|
| 184 | 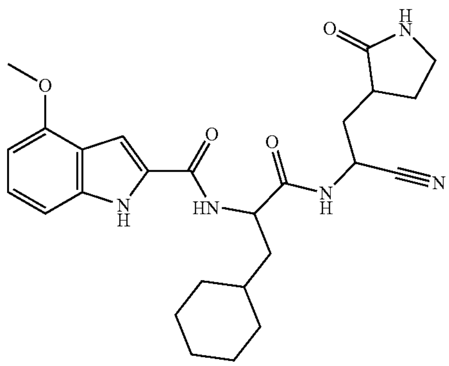 [SMILES: COc1cccc2[nH]c(C(=O)NC(CC3CCCCC3)C(=O)NC(C#N)CC3CCNC3=O)cc12] |
| 185 | 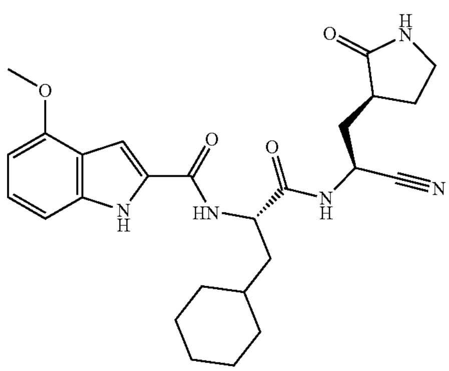 [SMILES: COc1cccc2[nH]c(C(=O)N[C@@H](CC3CCCCC3)C(=O)N[C@H](C#N)C[C@@H]3CCNC3=O)cc12] |
| 186 | 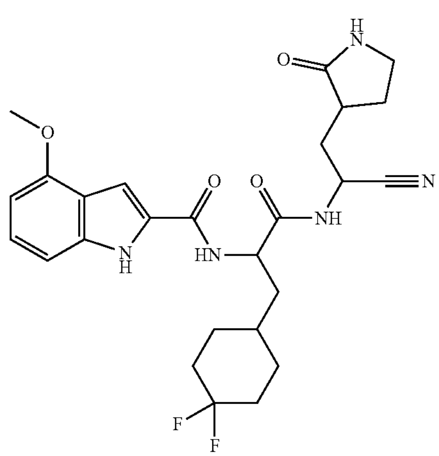 [SMILES: COc1cccc2[nH]c(C(=O)NC(CC3CCC(F)(F)CC3)C(=O)NC(C#N)CC3CCNC3=O)cc12] |

TABLE 1-continued

Exemplary compounds.

| Compound No. | Structure |
|---|---|
| 187 | 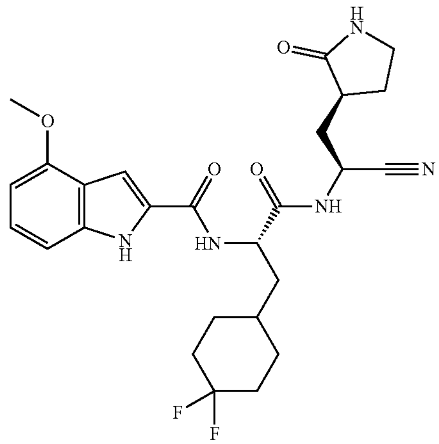 [SMILES: COc1cccc2[nH]c(C(=O)N[C@@H](CC3CCC(F)(F)CC3)C(=O)N[C@H](C#N)C[C@@H]3CCNC3=O)cc12] |
| 188 | 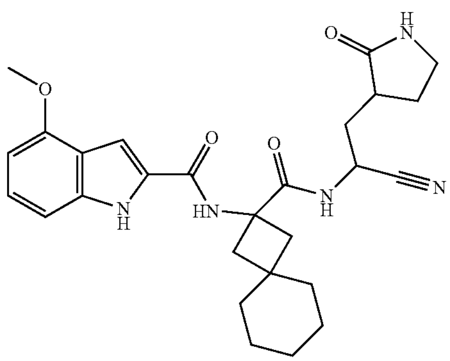 [SMILES: COc1cccc2[nH]c(C(=O)NC3(C(=O)NC(C#N)CC4CCNC4=O)CC4(CCCCC4)C3)cc12] |
| 189 | 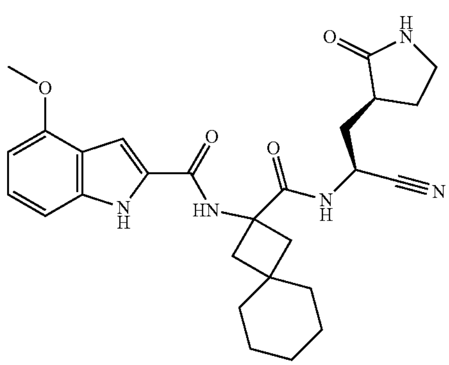 [SMILES: COc1cccc2[nH]c(C(=O)NC3(C(=O)N[C@H](C#N)C[C@@H]4CCNC4=O)CC4(CCCCC4)C3)cc12] |
| 190 | 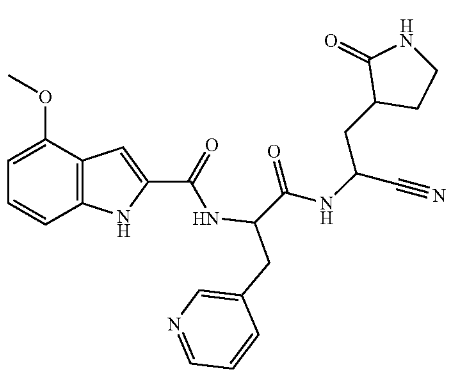 [SMILES: COc1cccc2[nH]c(C(=O)NC(Cc3cccnc3)C(=O)NC(C#N)CC3CCNC3=O)cc12] |

TABLE 1-continued

Exemplary compounds.

| Compound No. | Structure |
|---|---|
| 191 | 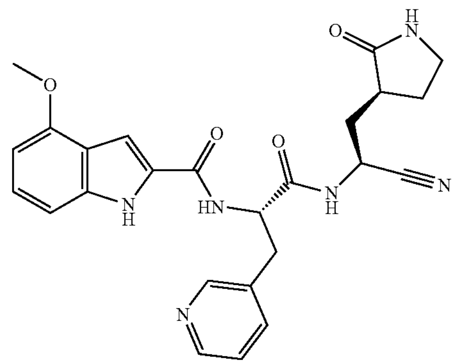 [SMILES: COc1cccc2[nH]c(C(=O)N[C@@H](Cc3cccnc3)C(=O)N[C@H](C#N)C[C@@H]3CCNC3=O)cc12] |
| 196 | 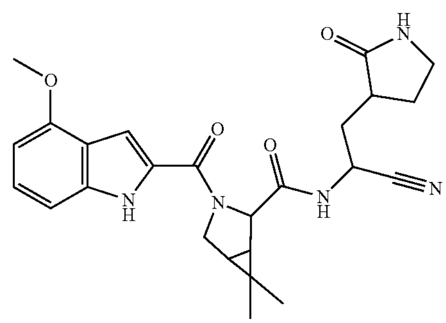 [SMILES: COc1cccc2[nH]c(C(=O)N3CC4C(C3C(=O)NC(C#N)CC3CCNC3=O)C4(C)C)cc12] |
| 197 | 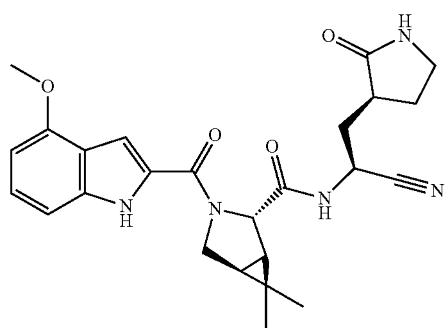 |
| 198 | 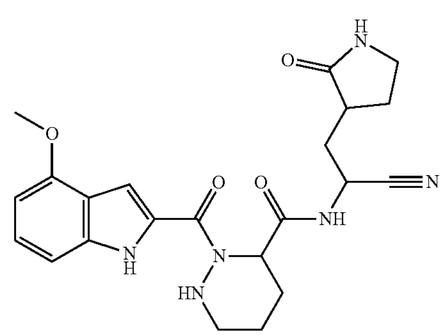 [SMILES: COc1cccc2[nH]c(C(=O)N3NCCCC3C(=O)NC(C#N)CC3CCNC3=O)cc12] |

TABLE 1-continued

Exemplary compounds.

| Compound No. | Structure |
|---|---|
| 199 | 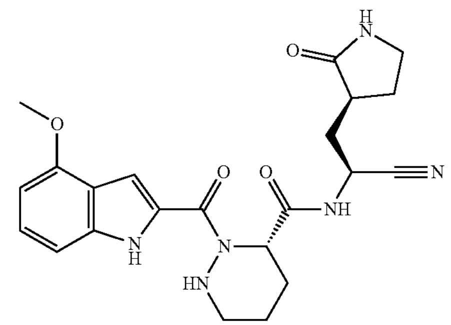 [SMILES: COc1cccc2[nH]c(C(=O)N3NCCC[C@H]3C(=O)N[C@H](C#N)C[C@@H]3CCNC3=O)cc12] |
| 200 | 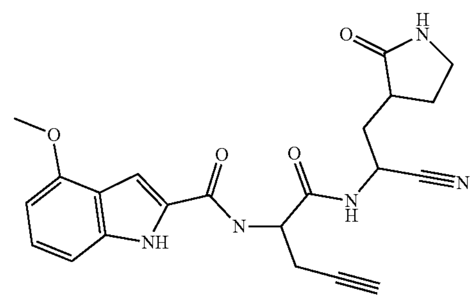 [SMILES: C#CCC(NC(=O)c1cc2c(OC)cccc2[nH]1)C(=O)NC(C#N)CC1CCNC1=O] |
| 201 | 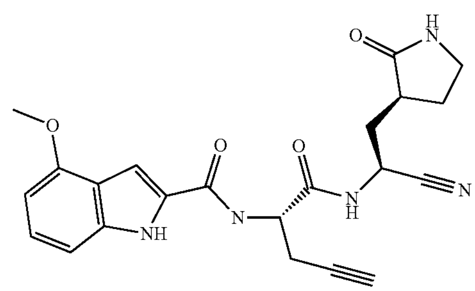 [SMILES: C#CC[C@H](NC(=O)c1cc2c(OC)cccc2[nH]1)C(=O)N[C@H](C#N)C[C@@H]1CCNC1=O] |
| 202 | 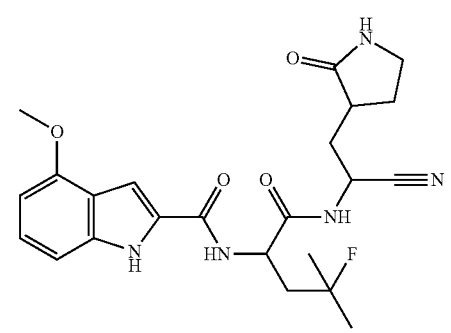 [SMILES: COc1cccc2[nH]c(C(=O)NC(CC(C)(C)F)C(=O)NC(C#N)CC3CCNC3=O)cc12] |

TABLE 1-continued

Exemplary compounds.

| Compound No. | Structure |
|---|---|
| 203 | 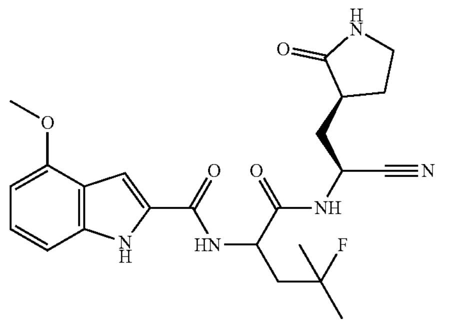 [SMILES: COc1cccc2[nH]c(C(=O)NC(CC(C)(C)F)C(=O)N[C@H](C#N)C[C@@H]3CCNC3=O)cc12] |
| 204 | 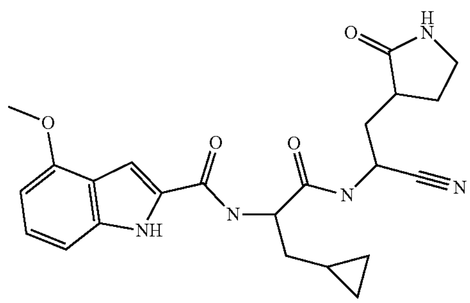 [SMILES: COc1cccc2[nH]c(C(=O)NC(CC3CC3)C(=O)NC(C#N)CC3CCNC3=O)cc12] |
| 205 | 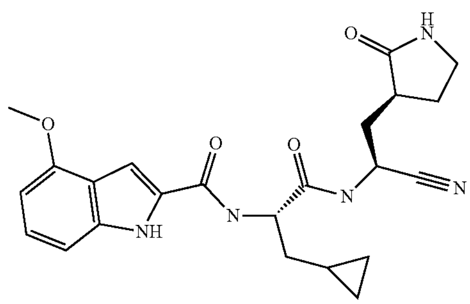 [SMILES: COc1cccc2[nH]c(C(=O)N[C@@H](CC3CC3)C(=O)N[C@H](C#N)C[C@@H]3CCNC3=O)cc12] |
| 206 | 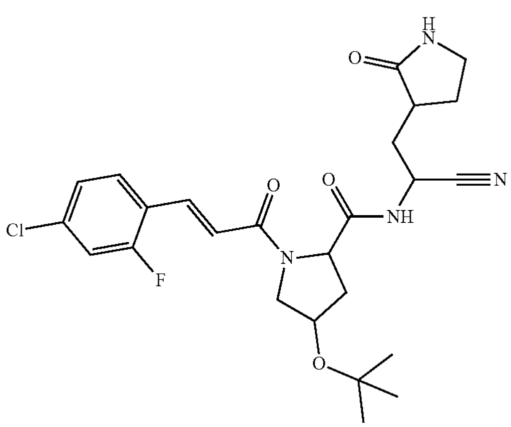 [SMILES: CC(C)(C)OC1CC(C(=O)NC(C#N)CC2CCNC2=O)N(C(=O)/C=C/c2ccc(Cl)cc2F)C1] |

TABLE 1-continued
Exemplary compounds.
| Compound No. | Structure |
|---|---|
| 207 | 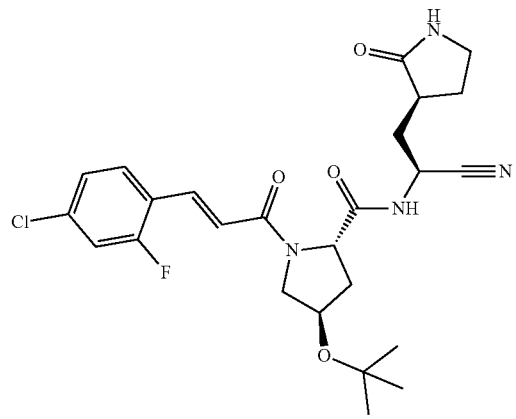 [SMILES: CC(C)(C)O[C@@H]1C[C@@H](C(=O)N[C@H](C#N)C[C@@H]2CCNC2=O)N(C(=O)/C=C/c2ccc(Cl)cc2F)C1] |
| 208 | 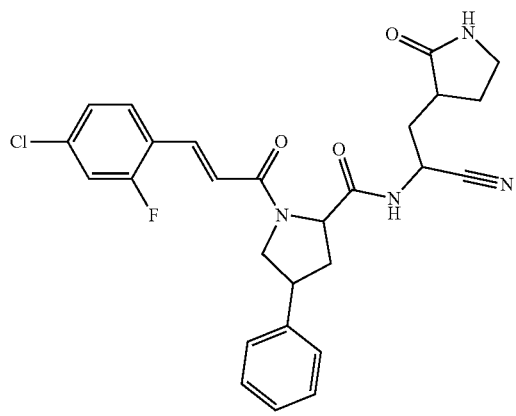 [SMILES: N#CC(CC1CCNC1=O)NC(=O)C1CC(c2ccccc2)CN1C(=O)/C=C/c1ccc(Cl)cc1F] |
| 209 | 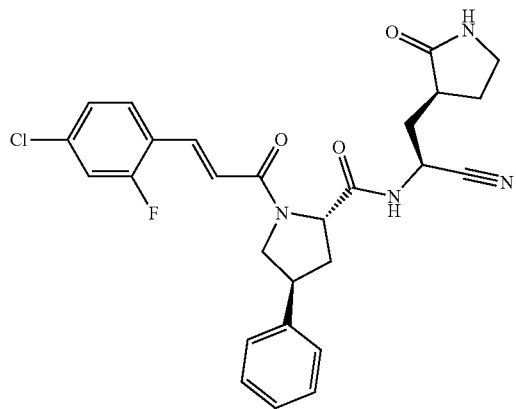 [SMILES: N#C[C@H](C[C@@H]1CCNC1=O)NC(=O)[C@@H]1C[C@@H](c2ccccc2)CN1C(=O)/C=C/c1ccc(Cl)cc1F] |

TABLE 1-continued
Exemplary compounds.
| Compound No. | Structure |
|---|---|
| 210 | 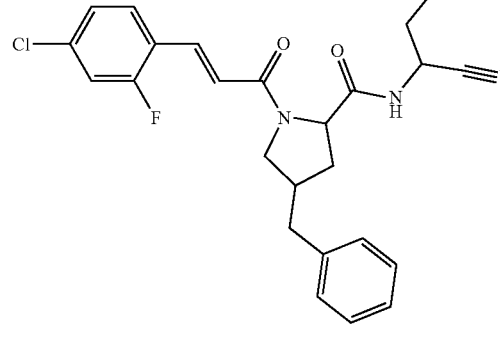 |
| 211 | 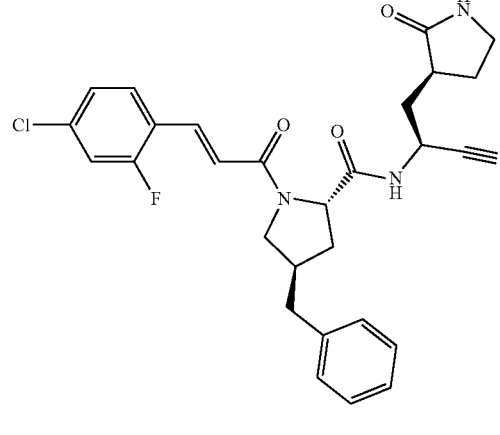 |
| 212 | 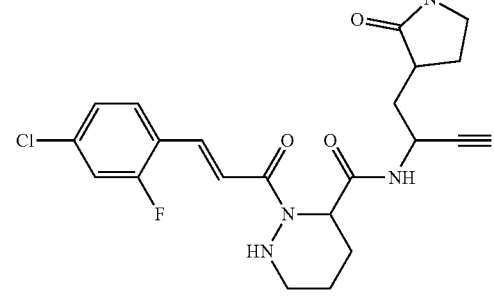 |
| 213 | 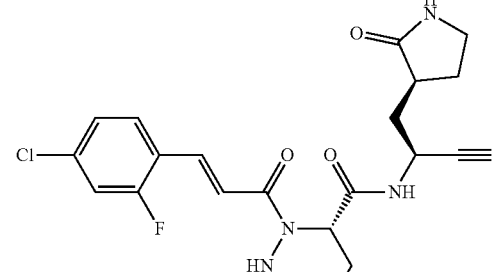 |

TABLE 1-continued
Exemplary compounds.
| Compound No. | Structure |
|---|---|
| 214 | 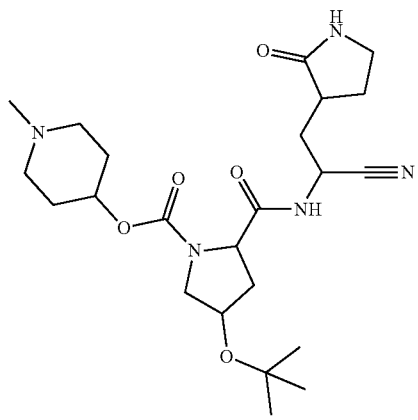 [SMILES: CN1CCC(OC(=O)N2CC(OC(C)(C)C)CC2C(=O)NC(C#N)CC2CCNC2=O)CC1] |
| 215 | 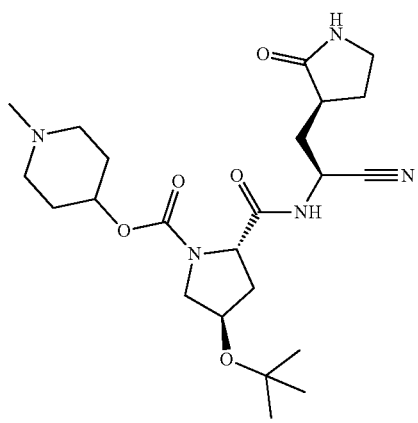 [SMILES: CN1CCC(OC(=O)N2C[C@H](OC(C)(C)C)C[C@H]2C(=O)N[C@H](C#N)C[C@@H]2CCNC2=O)CC1] |
| 216 | 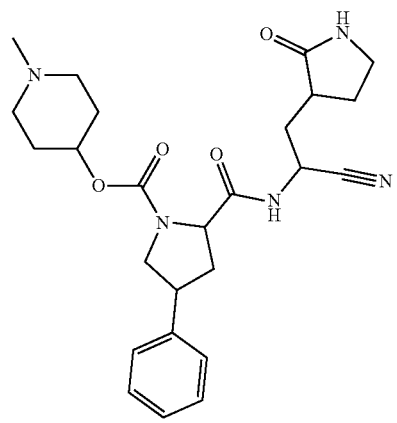 [SMILES: CN1CCC(OC(=O)N2CC(c3ccccc3)CC2C(=O)NC(C#N)CC2CCNC2=O)CC1] |

TABLE 1-continued

Exemplary compounds.

| Compound No. | Structure |
|---|---|
| 217 | 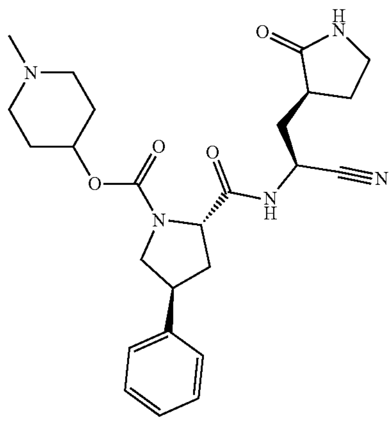 [SMILES: CN1CCC(OC(=O)N2C[C@H](c3ccccc3)C[C@H]2C(=O)N[C@H](C#N)C[C@@H]2CCNC2=O)CC1] |
| 218 | 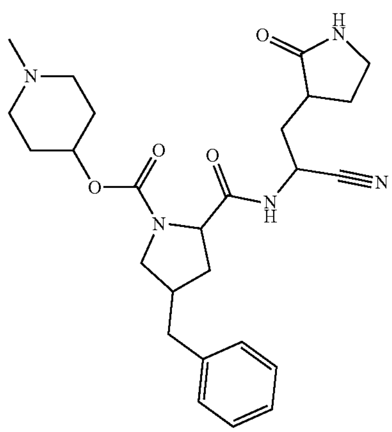 [SMILES: CN1CCC(OC(=O)N2CC(Cc3ccccc3)CC2C(=O)NC(C#N)CC2CCNC2=O)CC1] |
| 219 | 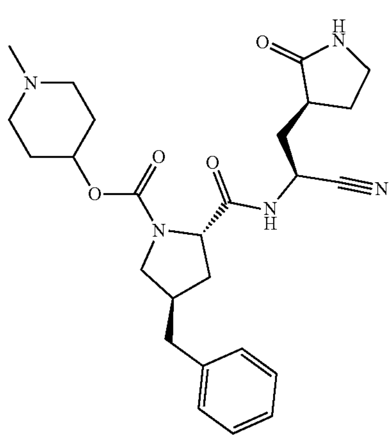 [SMILES: CN1CCC(OC(=O)N2C[C@H](Cc3ccccc3)C[C@H]2C(=O)N[C@H](C#N)C[C@@H]2CCNC2=O)CC1] |

TABLE 1-continued

Exemplary compounds.

| Compound No. | Structure |
|---|---|
| 220 | 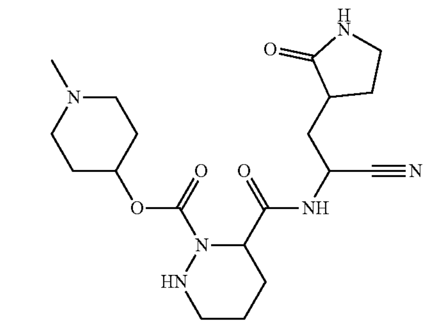 [SMILES: CN1CCC(OC(=O)N2NCCCC2C(=O)NC(C#N)CC2CCNC2=O)CC1] |
| 221 | 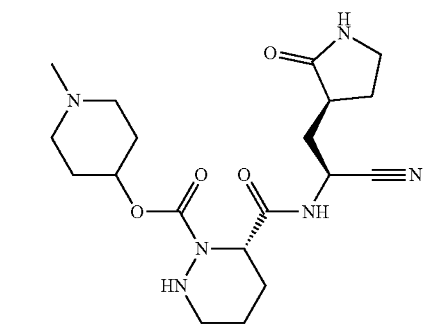 [SMILES: CN1CCC(OC(=O)N2NCCC[C@H]2C(=O)N[C@H](C#N)C[C@@H]2CCNC2=O)CC1] |
| 222 | 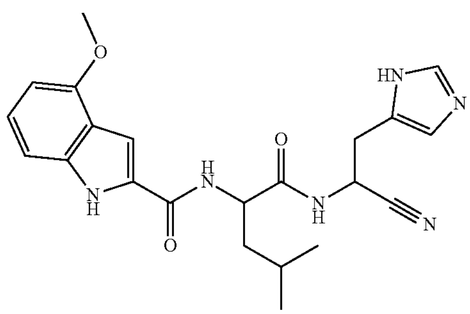 [SMILES: COc1cccc2[nH]c(C(=O)NC(CC(C)C)C(=O)NC(C#N)Cc3cnc[nH]3)cc12] |
| 223 | 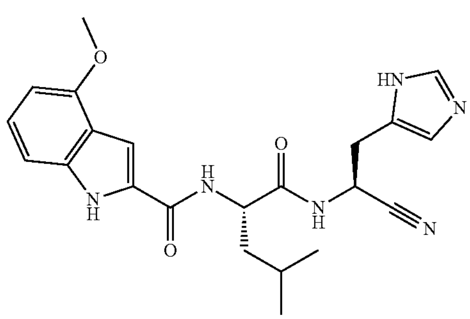 [SMILES: COc1cccc2[nH]c(C(=O)N[C@@H](CC(C)C)C(=O)N[C@H](C#N)Cc3cnc[nH]3)cc12] |

TABLE 1-continued

Exemplary compounds.

| Compound No. | Structure |
|---|---|
| 224 | 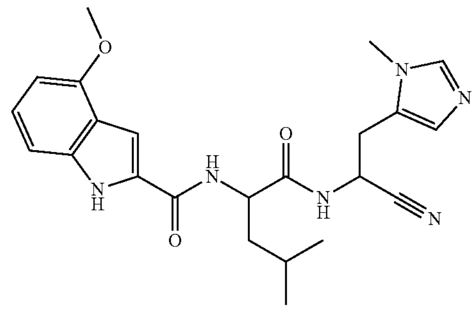 [SMILES: COc1cccc2[nH]c(C(=O)NC(CC(C)C)C(=O)NC(C#N)Cc3cncn3C)cc12] |
| 225 | 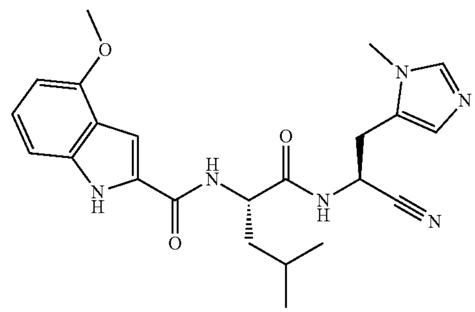 [SMILES: COc1cccc2[nH]c(C(=O)N[C@@H](CC(C)C)C(=O)N[C@H](C#N)Cc3cncn3C)cc12] |
| 226 | 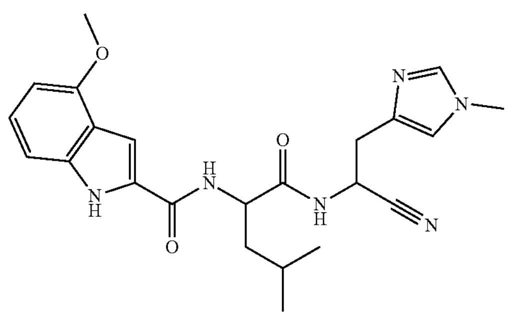 [SMILES: COc1cccc2[nH]c(C(=O)NC(CC(C)C)C(=O)NC(C#N)Cc3cn(C)cn3)cc12] |
| 227 | 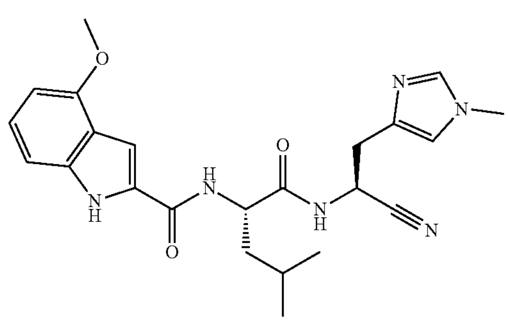 [SMILES: COc1cccc2[nH]c(C(=O)N[C@@H](CC(C)C)C(=O)N[C@H](C#N)Cc3cn(C)cn3)cc12] |

TABLE 1-continued

Exemplary compounds.

| Compound No. | Structure |
|---|---|
| 230 | 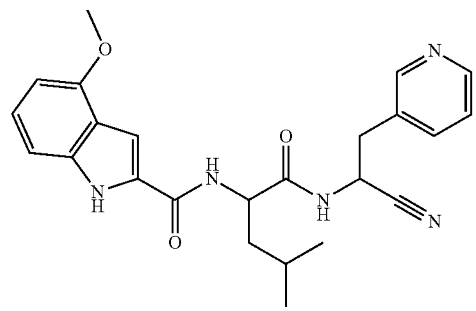 [SMILES: COc1cccc2[nH]c(C(=O)NC(CC(C)C)C(=O)NC(C#N)Cc3cccnc3)cc12] |
| 231 | 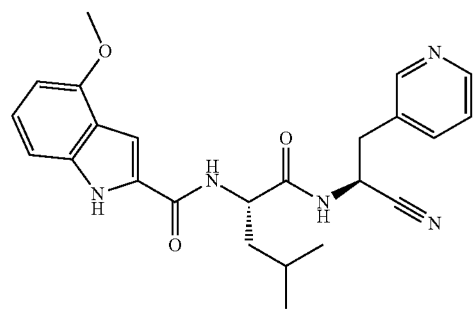 [SMILES: COc1cccc2[nH]c(C(=O)N[C@@H](CC(C)C)C(=O)N[C@H](C#N)Cc3cccnc3)cc12] |
| 232 | 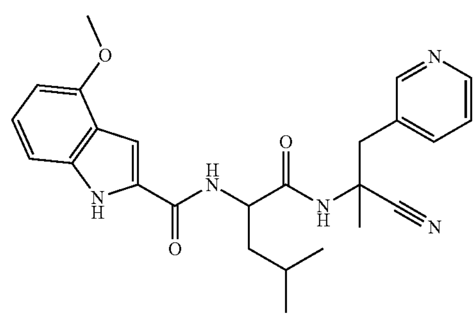 [SMILES: COc1cccc2[nH]c(C(=O)NC(CC(C)C)C(=O)NC(C)(C#N)Cc3cccnc3)cc12] |
| 233 | 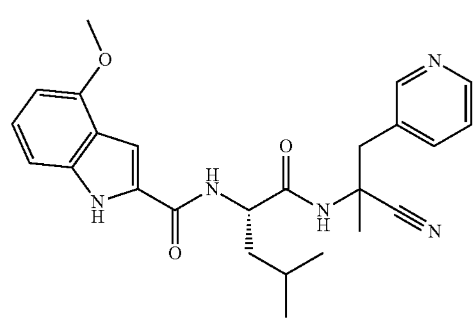 [SMILES: COc1cccc2[nH]c(C(=O)N[C@@H](CC(C)C)C(=O)NC(C)(C#N)Cc3cccnc3)cc12] |

TABLE 1-continued

Exemplary compounds.

| Compound No. | Structure |
|---|---|
| 234 | 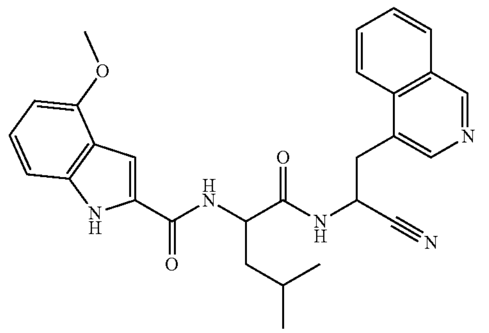 [SMILES: COc1cccc2[nH]c(C(=O)NC(CC(C)C)C(=O)NC(C#N)Cc3cncc4ccccc34)cc12] |
| 235 | 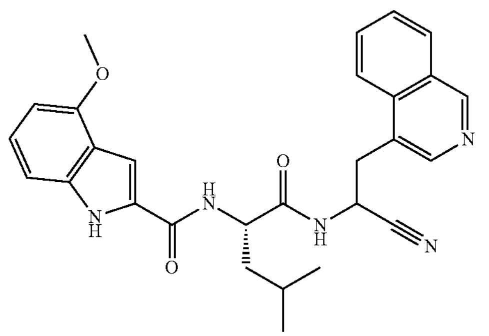 [SMILES: COc1cccc2[nH]c(C(=O)N[C@@H](CC(C)C)C(=O)NC(C#N)Cc3cncc4ccccc34)cc12] |
| 236 | 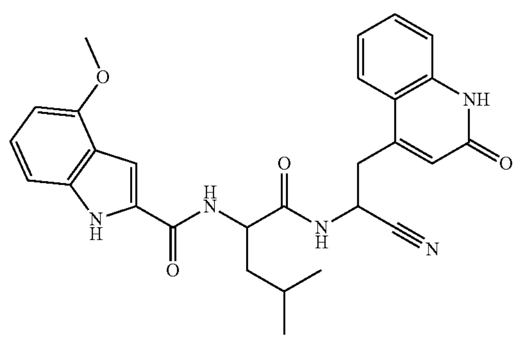 [SMILES: COc1cccc2[nH]c(C(=O)NC(CC(C)C)C(=O)NC(C#N)Cc3cc(=O)[nH]c4ccccc34)cc12] |
| 237 | 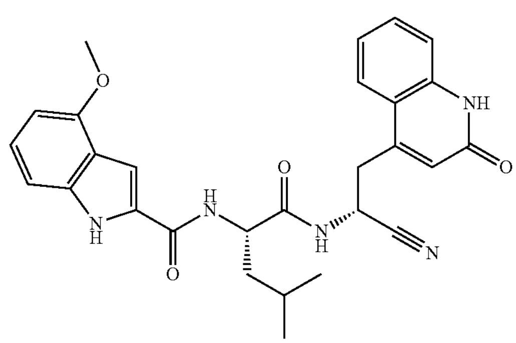 [SMILES: COc1cccc2[nH]c(C(=O)N[C@@H](CC(C)C)C(=O)N[C@@H](C#N)Cc3cc(=O)[nH]c4ccccc34)cc12] |

TABLE 1-continued
Exemplary compounds.
| Compound No. | Structure |
|---|---|
| 238 | 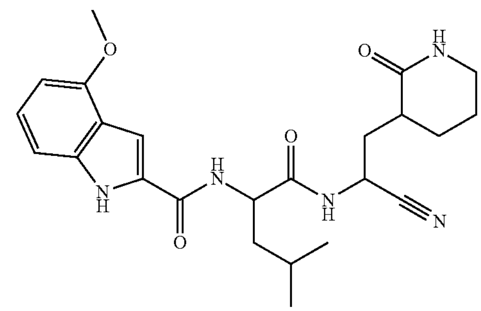 [SMILES: COc1cccc2[nH]c(C(=O)NC(CC(C)C)C(=O)NC(C#N)CC3CCCNC3=O)cc12] |
| 239 | 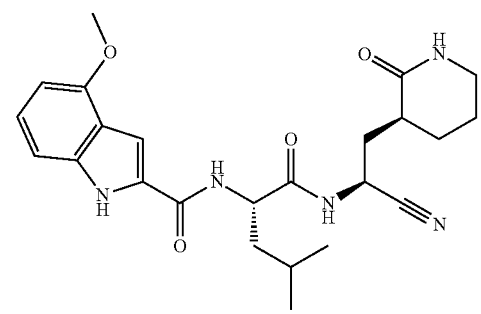 [SMILES: COc1cccc2[nH]c(C(=O)N[C@@H](CC(C)C)C(=O)N[C@H](C#N)C[C@@H]3CCCNC3=O)cc12] |
| 240 | 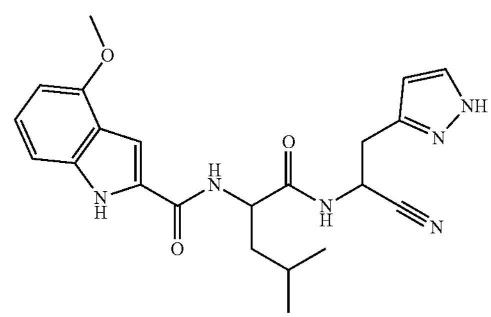 [SMILES: COc1cccc2[nH]c(C(=O)NC(CC(C)C)C(=O)NC(C#N)Cc3cc[nH]n3)cc12] |
| 241 | 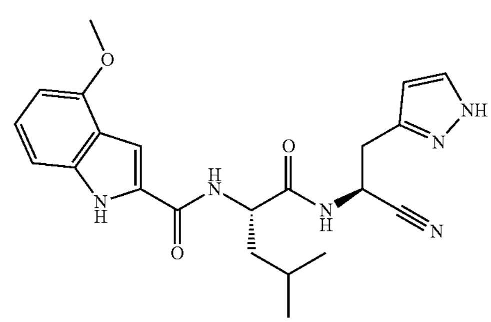 [SMILES: COc1cccc2[nH]c(C(=O)N[C@@H](CC(C)C)C(=O)N[C@H](C#N)Cc3cc[nH]n3)cc12] |

TABLE 1-continued
Exemplary compounds.
| Compound No. | Structure |
|---|---|
| 242 | 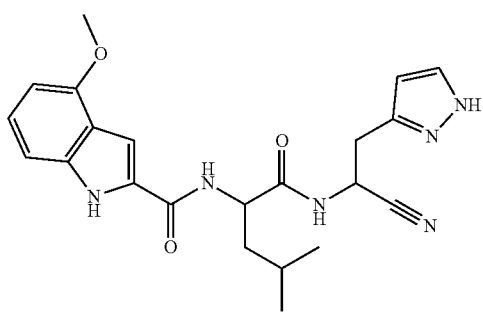 [SMILES: COc1cccc2[nH]c(C(=O)NC(CC(C)C)C(=O)NC(C#N)Cc3cc[nH]n3)cc12] |
| 243 | 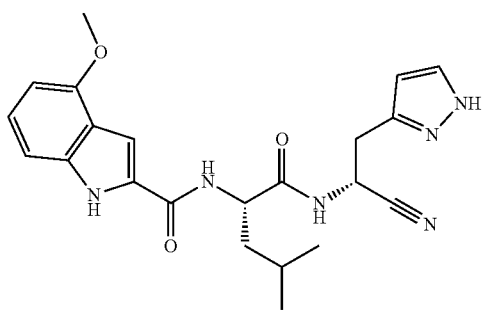 [SMILES: COc1cccc2[nH]c(C(=O)N[C@@H](CC(C)C)C(=O)N[C@@H](C#N)Cc3cc[nH]n3)cc12] |
| 244 | 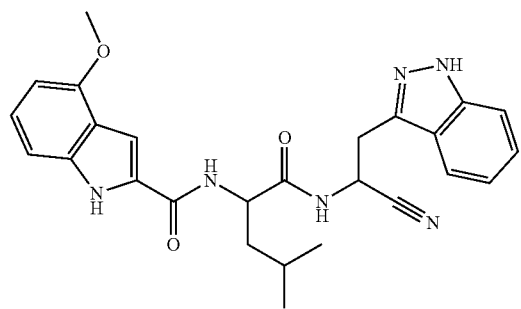 [SMILES: COc1cccc2[nH]c(C(=O)NC(CC(C)C)C(=O)NC(C#N)Cc3n[nH]c4ccccc34)cc12] |
| 245 | 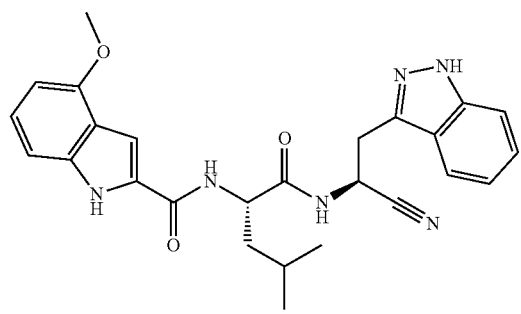 [SMILES: COc1cccc2[nH]c(C(=O)N[C@@H](CC(C)C)C(=O)N[C@H](C#N)Cc3n[nH]c4ccccc34)cc12] |

TABLE 1-continued
Exemplary compounds.
| Compound No. | Structure |
|---|---|
| 246 | 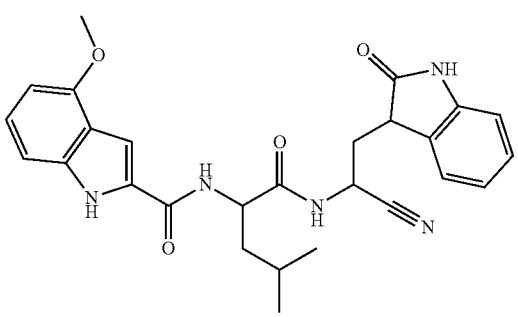 |
| 247 | 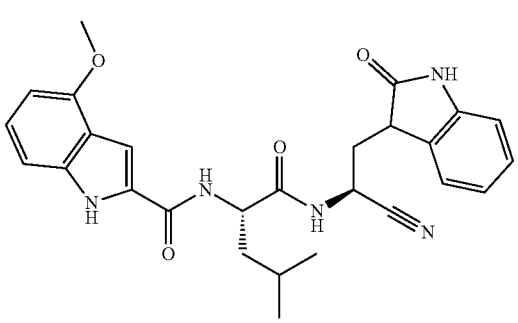 |
| 248 | 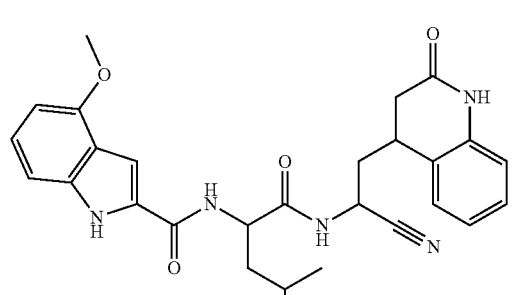 |
| 249 | 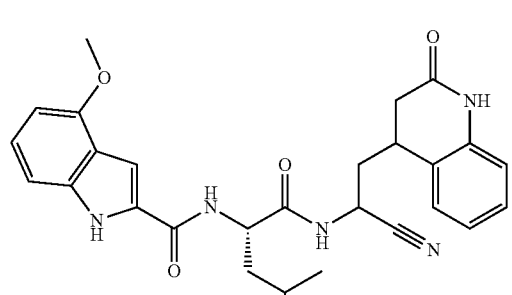 |

TABLE 1-continued

Exemplary compounds.

| Compound No. | Structure |
|---|---|
| 250 | 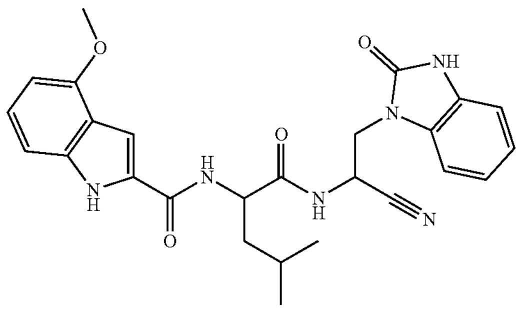 [SMILES: COc1cccc2[nH]c(C(=O)NC(CC(C)C)C(=O)NC(C#N)CC3C(=O)Nc4ccccc43)cc12] |
| 251 | 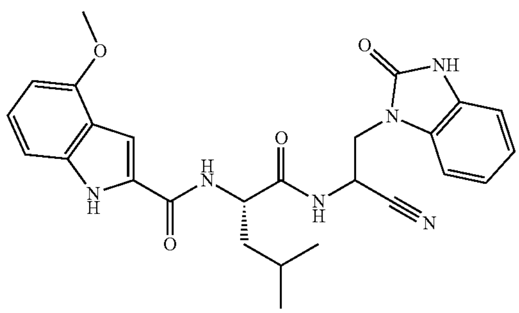 |
| 252 | 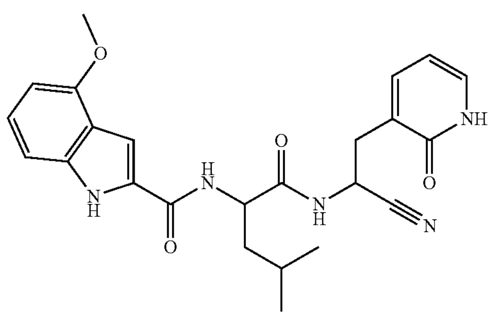 [SMILES: COc1cccc2[nH]c(C(=O)NC(CC(C)C)C(=O)NC(C#N)Cc3ccc[nH]c3=O)cc12] |
| 253 | 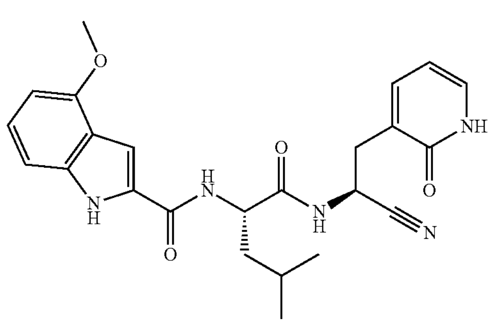 [SMILES: COc1cccc2[nH]c(C(=O)N[C@@H](CC(C)C)C(=O)N[C@H](C#N)Cc3ccc[nH]c3=O)cc12] |

TABLE 1-continued
Exemplary compounds.
| Compound No. | Structure |
|---|---|
| 254 | 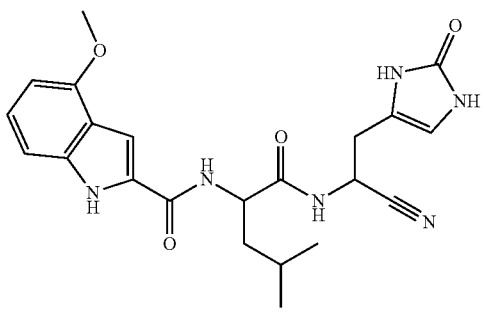 [SMILES: COc1cccc2[nH]c(C(=O)NC(CC(C)C)C(=O)NC(C#N)Cc3c[nH]c(=O)[nH]3)cc12] |
| 255 | 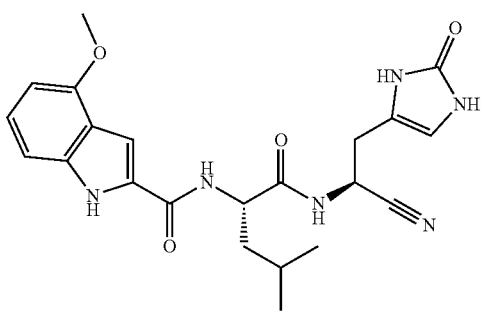 [SMILES: COc1cccc2[nH]c(C(=O)N[C@@H](CC(C)C)C(=O)N[C@H](C#N)Cc3c[nH]c(=O)[nH]3)cc12] |
| 256 | 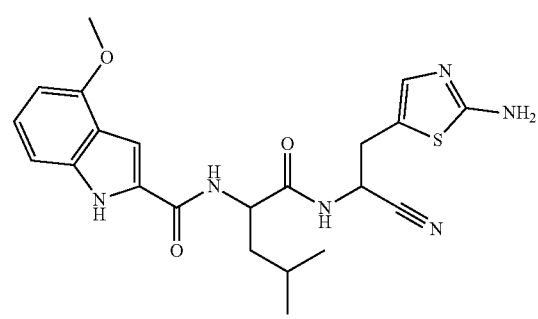 [SMILES: COc1cccc2[nH]c(C(=O)NC(CC(C)C)C(=O)NC(C#N)Cc3cnc(N)s3)cc12] |
| 257 | 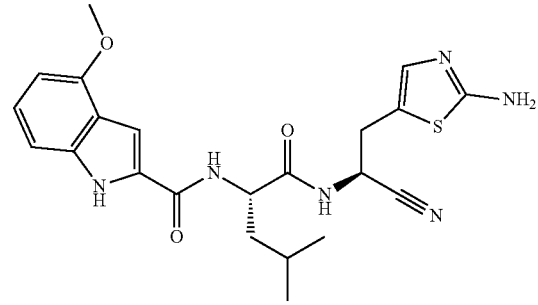 [SMILES: COc1cccc2[nH]c(C(=O)N[C@@H](CC(C)C)C(=O)N[C@H](C#N)Cc3cnc(N)s3)cc12] |

TABLE 1-continued
Exemplary compounds.
| Compound No. | Structure |
|---|---|
| 258 | 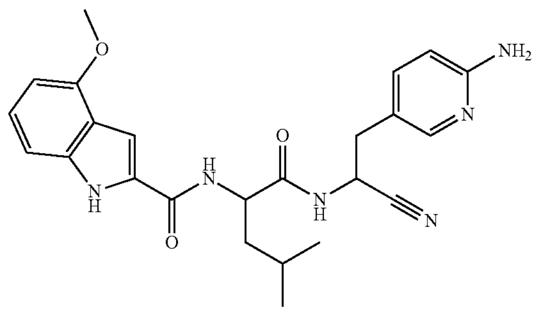 [SMILES: COc1cccc2[nH]c(C(=O)NC(CC(C)C)C(=O)NC(C#N)Cc3ccc(N)nc3)cc12] |
| 259 | 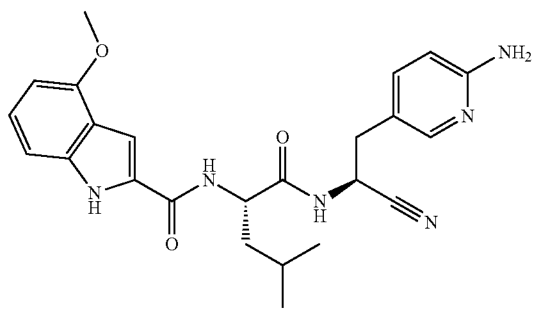 [SMILES: COc1cccc2[nH]c(C(=O)N[C@@H](CC(C)C)C(=O)N[C@H](C#N)Cc3ccc(N)nc3)cc12] |
| 260 | 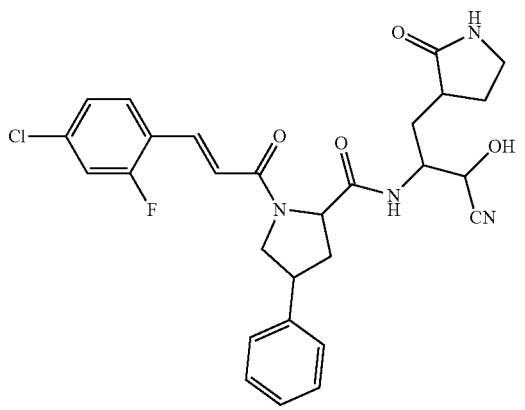 [SMILES: N#CC(O)C(CC1CCNC1=O)NC(=O)C1CC(c2ccccc2)CN1C(=O)/C=C/c1ccc(Cl)cc1F] |
| 261 | 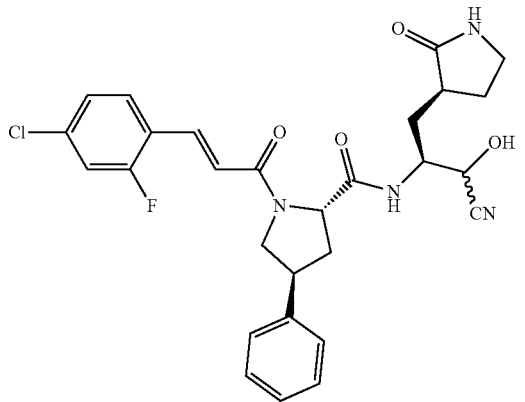 [SMILES: N#CC(O)[C@H](C[C@@H]1CCNC1=O)NC(=O)[C@@H]1C[C@@H](c2ccccc2)CN1C(=O)/C=C/c1ccc(Cl)cc1F] |

TABLE 1-continued

Exemplary compounds.

| Compound No. | Structure |
|---|---|
| 262 | (structure) |
| 263 | (structure) |
| 264 | (structure) |
| 265 | (structure) |
| 266 | (structure) |

TABLE 1-continued

Exemplary compounds.

| Compound No. | Structure |
|---|---|
| 267 | 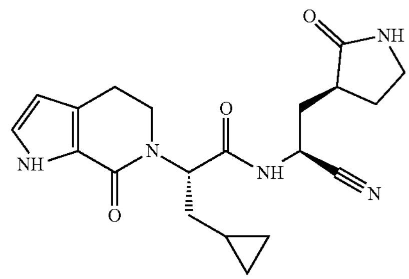 [SMILES: N#C[C@H](C[C@@H]1CCNC1=O)NC(=O)[C@H](CC1CC1)N1CCc2cc[nH]c2C1=O] |
| 268 | 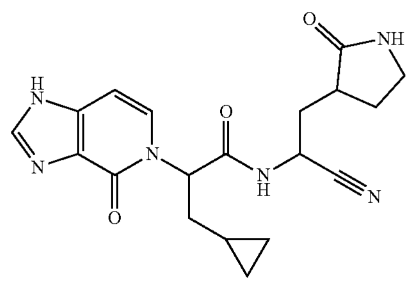 [SMILES: N#CC(CC1CCNC1=O)NC(=O)C(CC1CC1)n1ccc2[nH]cnc2c1=O] |
| 269 | 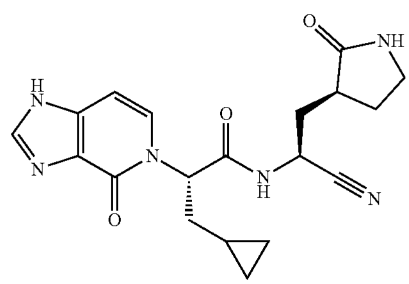 [SMILES: N#C[C@H](C[C@@H]1CCNC1=O)NC(=O)[C@H](CC1CC1)n1ccc2[nH]cnc2c1=O] |
| 270 | 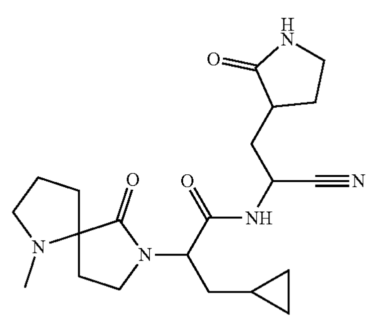 [SMILES: CN1CCCC12CCN(C(CC1CC1)C(=O)NC(C#N)CC1CCNC1=O)C2=O] |
| 271 | 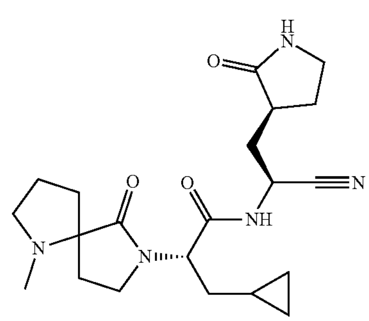 [SMILES: CN1CCCC12CCN([C@@H](CC1CC1)C(=O)N[C@H](C#N)C[C@@H]1CCNC1=O)C2=O] |

TABLE 1-continued

Exemplary compounds.

| Compound No. | Structure |
|---|---|
| 272 | 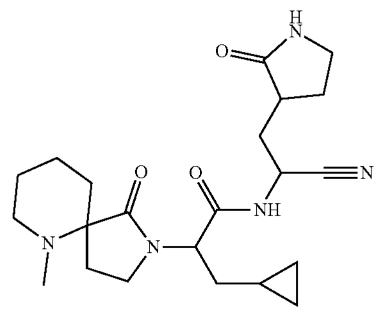 [SMILES: CN1CCCCC12CCN(C(CC1CC1)C(=O)NC(C#N)CC1CCNC1=O)C2=O] |
| 273 | 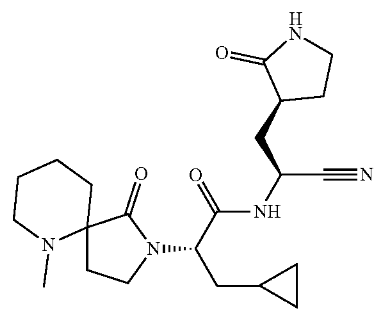 [SMILES: CN1CCCCC12CCN([C@@H](CC1CC1)C(=O)N[C@H](C#N)C[C@@H]1CCNC1=O)C2=O] |
| 274 | 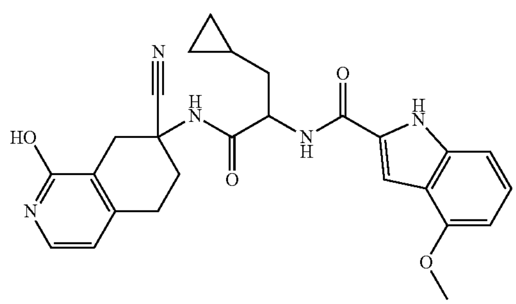 [SMILES: COc1cccc2[nH]c(C(=O)NC(CC3CC3)C(=O)NC3(C#N)CCc4ccnc(O)c4C3)cc12] |
| 275 | 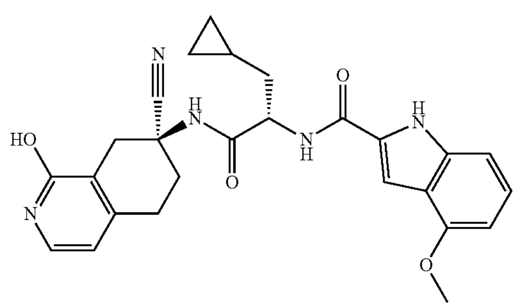 [SMILES: COc1cccc2[nH]c(C(=O)N[C@@H](CC3CC3)C(=O)N[C@@]3(C#N)CCc4ccnc(O)c4C3)cc12] |
| 276 | 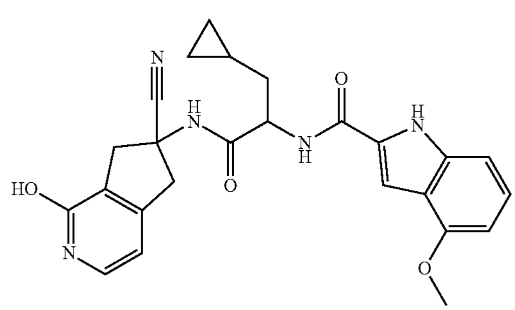 [SMILES: COc1cccc2[nH]c(C(=O)NC(CC3CC3)C(=O)NC3(C#N)Cc4ccnc(O)c4C3)cc12] |

153 154

TABLE 1-continued

Exemplary compounds.

| Compound No. | Structure |
|---|---|
| 277 | 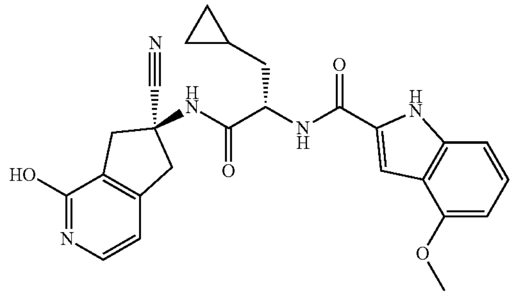 [SMILES: COc1cccc2[nH]c(C(=O)N[C@@H](CC3CC3)C(=O)N[C@@]3(C#N)Cc4ccnc(O)c4C3)cc12] |
| 278 | 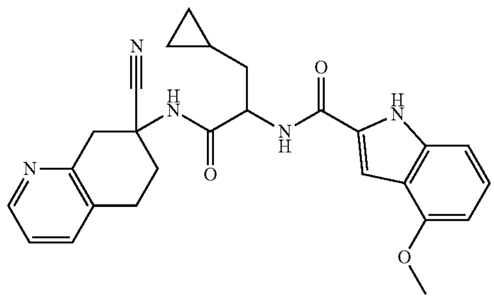 [SMILES: COc1cccc2[nH]c(C(=O)NC(CC3CC3)C(=O)NC3(C#N)CCc4cccnc4C3)cc12] |
| 279 | 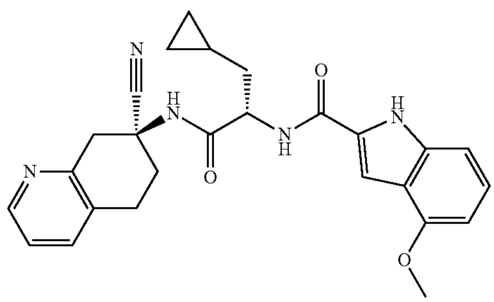 [SMILES: COc1cccc2[nH]c(C(=O)N[C@@H](CC3CC3)C(=O)N[C@@]3(C#N)CCc4cccnc4C3)cc12] |
| 280 | 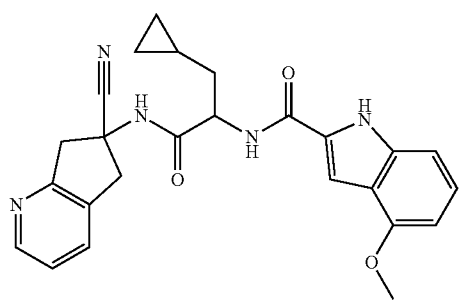 [SMILES: COc1cccc2[nH]c(C(=O)NC(CC3CC3)C(=O)NC3(C#N)Cc4cccnc4C3)cc12] |
| 281 | 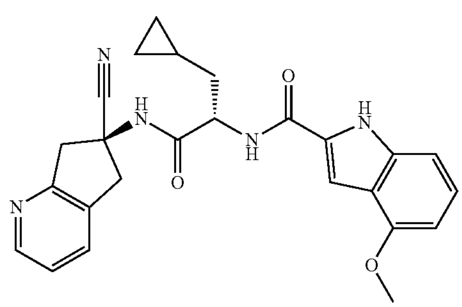 [SMILES: COc1cccc2[nH]c(C(=O)N[C@@H](CC3CC3)C(=O)N[C@@]3(C#N)Cc4cccnc4C3)cc12] |

TABLE 1-continued

Exemplary compounds.

| Compound No. | Structure |
|---|---|
| 282 | 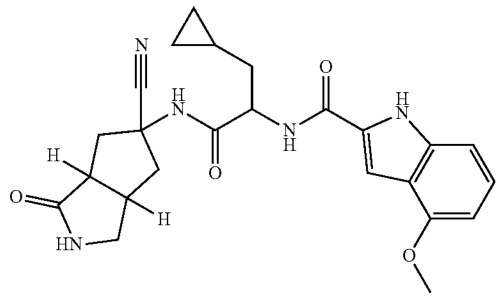 [SMILES: COc1cccc2[nH]c(C(=O)NC(CC3CC3)C(=O)NC3(C#N)CC4CNC(=O)C4C3)cc12] |
| 283 | 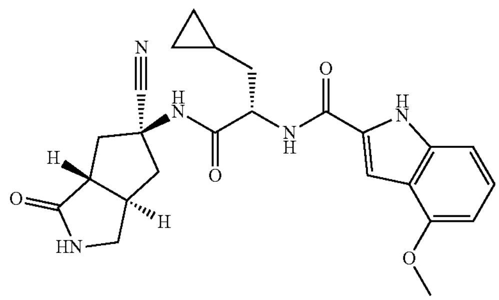 [SMILES: COc1cccc2[nH]c(C(=O)N[C@@H](CC3CC3)C(=O)N[C@@]3(C#N)C[C@H]4CNC(=O)[C@@H]4C3)cc12] |
| 284 | 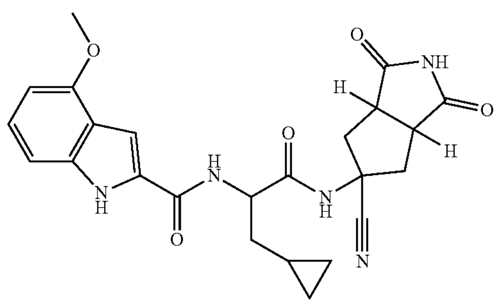 [SMILES: COc1cccc2[nH]c(C(=O)NC(CC3CC3)C(=O)NC3(C#N)CC4C(=O)NC(=O)C4C3)cc12] |
| 285 | 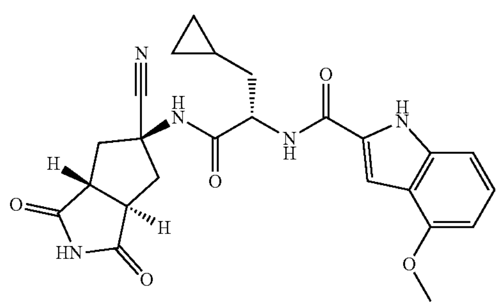 |
| 286 | 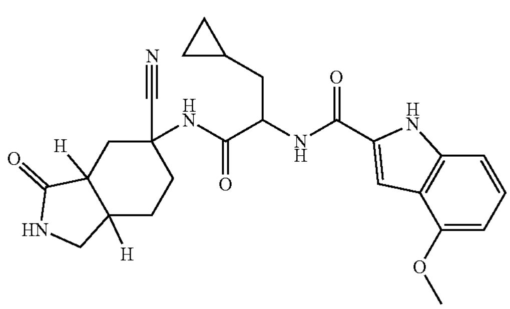 [SMILES: COc1cccc2[nH]c(C(=O)NC(CC3CC3)C(=O)NC3(C#N)CCC4CNC(=O)C4C3)cc12] |

TABLE 1-continued

Exemplary compounds.

| Compound No. | Structure |
|---|---|
| 287 | 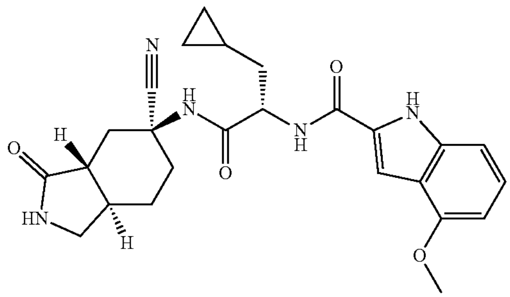 [SMILES: COc1cccc2[nH]c(C(=O)N[C@@H](CC3CC3)C(=O)N[C@@]3(C#N)CC[C@H]4CNC(=O)[C@@H]4C3)cc12] |
| 288 | 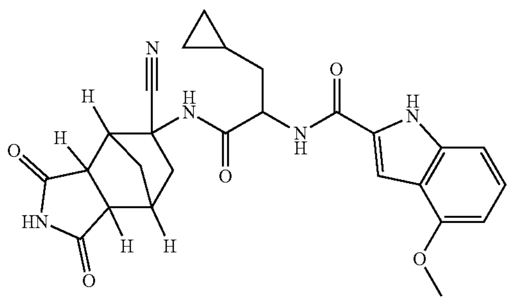 [SMILES: COc1cccc2[nH]c(C(=O)NC(CC3CC3)C(=O)NC3(C#N)CC4CC3C3C(=O)NC(=O)C43)cc12] |
| 289 | 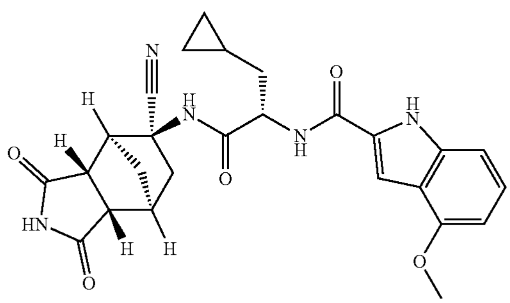 [SMILES: COc1cccc2[nH]c(C(=O)N[C@@H](CC3CC3)C(=O)N[C@@]3(C#N)C[C@@H]4C[C@H]3[C@H]3C(=O)NC(=O)[C@@H]43)cc12] |
| 290 | 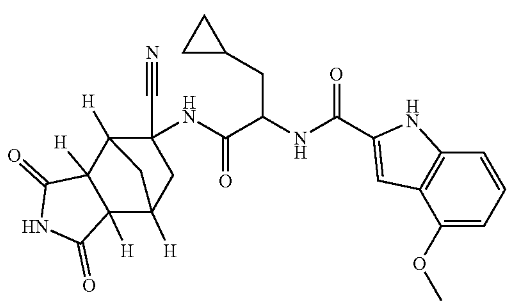 [SMILES: COc1cccc2[nH]c(C(=O)NC(CC3CC3)C(=O)NC3(C#N)CC4CC3C3C(=O)NC(=O)C43)cc12] |
| 291 | 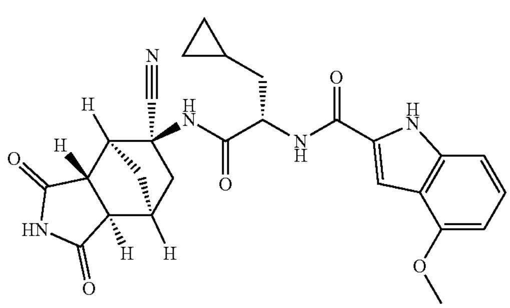 [SMILES: COc1cccc2[nH]c(C(=O)N[C@@H](CC3CC3)C(=O)N[C@@]3(C#N)C[C@@H]4C[C@H]3[C@H]3C(=O)NC(=O)[C@H]43)cc12] |

TABLE 1-continued

Exemplary compounds.

| Compound No. | Structure |
|---|---|
| 292 | 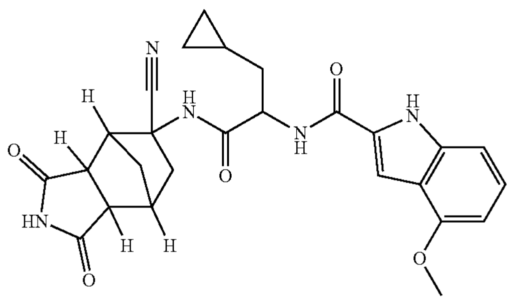 [SMILES: COc1cccc2[nH]c(C(=O)NC(CC3CC3)C(=O)NC3(C#N)CC4CC3C3C(=O)NC(=O)C43)cc12] |
| 293 | 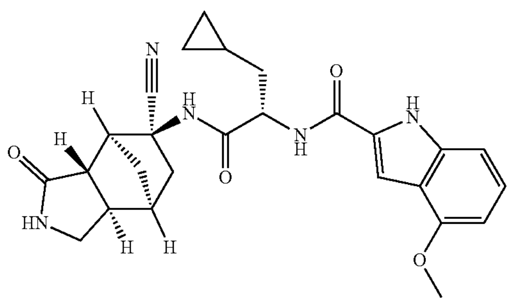 [SMILES: COc1cccc2[nH]c(C(=O)N[C@@H](CC3CC3)C(=O)N[C@@]3(C#N)C[C@@H]4C[C@H]3[C@H]3C(=O)NC[C@H]43)cc12] |
| 294 | 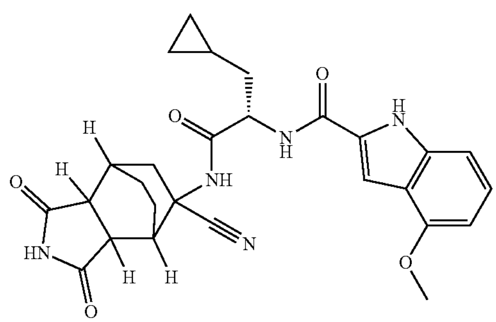 [SMILES: COc1cccc2[nH]c(C(=O)N[C@@H](CC3CC3)C(=O)NC3(C#N)CC4CCC3C3C(=O)NC(=O)C43)cc12] |
| 295 | 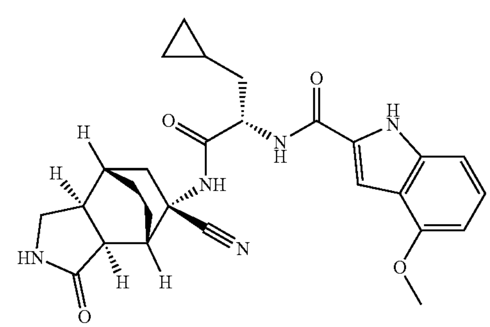 [SMILES: COc1cccc2[nH]c(C(=O)N[C@@H](CC3CC3)C(=O)N[C@@]3(C#N)C[C@@H]4CC[C@H]3[C@H]3C(=O)NC[C@@H]43)cc12] |

TABLE 1-continued

Exemplary compounds.

| Compound No. | Structure |
|---|---|
| 296 | 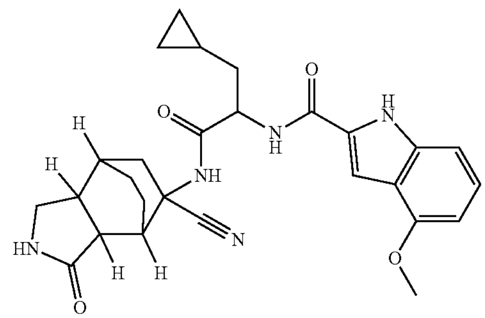 [SMILES: COc1cccc2[nH]c(C(=O)NC(CC3CC3)C(=O)NC3(C#N)CC4CCC3C3C(=O)NCC43)cc12] |
| 297 | 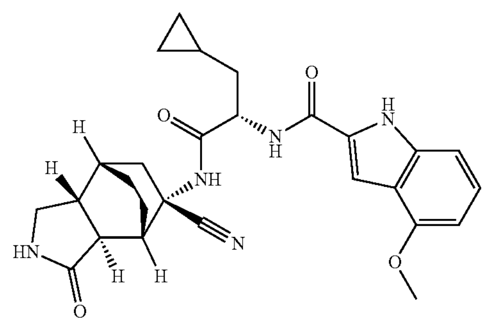 [SMILES: COc1cccc2[nH]c(C(=O)N[C@@H](CC3CC3)C(=O)N[C@@]3(C#N)C[C@@H]4CC[C@H]3[C@H]3C(=O)NC[C@H]43)cc12] |
| 298 | 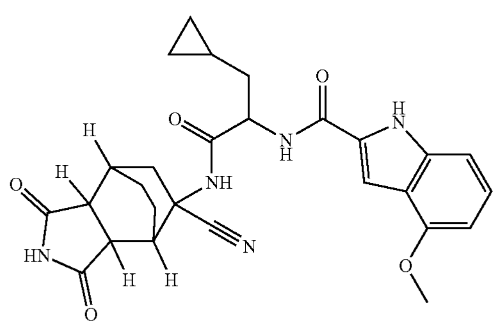 [SMILES: COc1cccc2[nH]c(C(=O)NC(CC3CC3)C(=O)NC3(C#N)CC4CCC3C3C(=O)NC(=O)C43)cc12] |
| 299 | 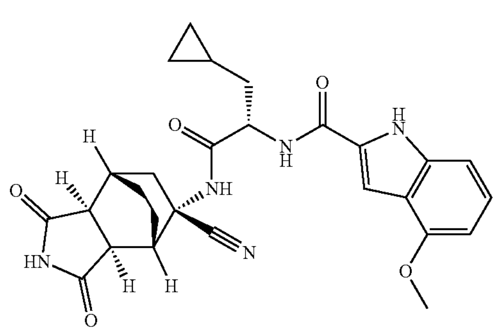 [SMILES: COc1cccc2[nH]c(C(=O)N[C@@H](CC3CC3)C(=O)N[C@@]3(C#N)C[C@@H]4CC[C@H]3[C@H]3C(=O)NC(=O)[C@@H]43)cc12] |

TABLE 1-continued
Exemplary compounds.
| Compound No. | Structure |
|---|---|
| 300 | 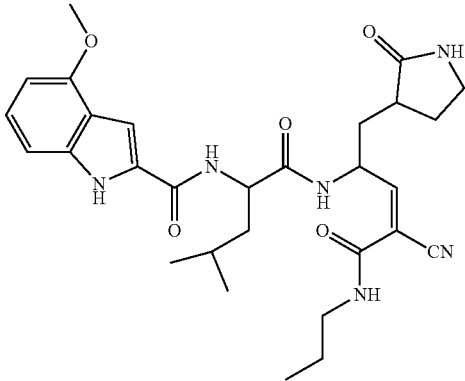 [SMILES: CCCNC(=O)/C(C#N)=C\C(CC1CCNC1=O)NC(=O)C(CC(C)C)NC(=O)c1cc2c(OC)cccc2[nH]1] |
| 301 | 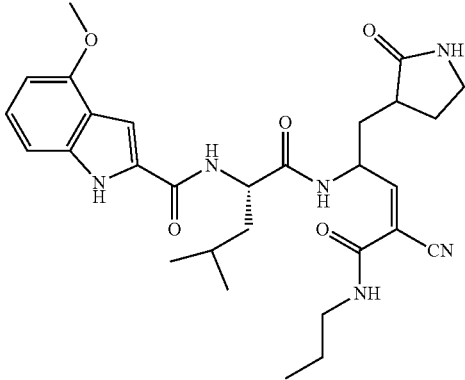 [SMILES: CCCNC(=O)/C(C#N)=C\C(CC1CCNC1=O)NC(=O)[C@H](CC(C)C)NC(=O)c1cc2c(OC)cccc2[nH]1] |
| 302 | 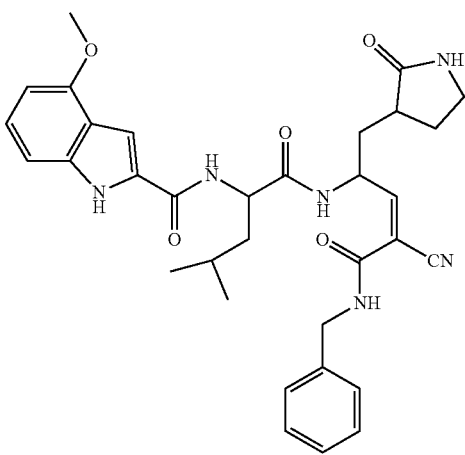 [SMILES: COc1cccc2[nH]c(C(=O)NC(CC(C)C)C(=O)NC(/C=C(/C#N)C(=O)NCc3ccccc3)CC3CCNC3=O)cc12] |

TABLE 1-continued
Exemplary compounds.
| Compound No. | Structure |
|---|---|
| 303 | 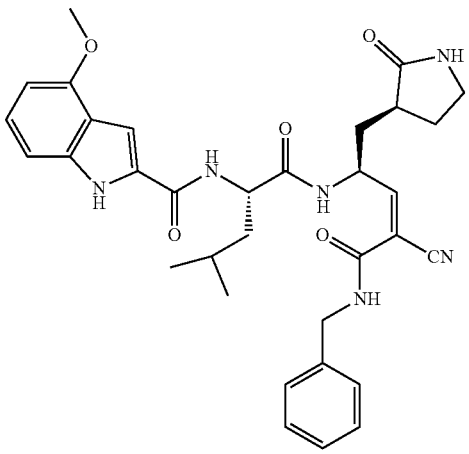 [SMILES: COc1cccc2[nH]c(C(=O)N[C@@H](CC(C)C)C(=O)N[C@H](/C=C(/C#N)C(=O)NCc3ccccc3)C[C@@H]3CCNC3=O)cc12] |
| 304 | 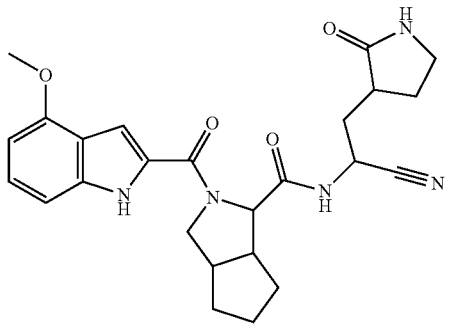 [SMILES: COc1cccc2[nH]c(C(=O)N3CC4CCCC4C3C(=O)NC(C#N)CC3CCNC3=O)cc12] |
| 305 | 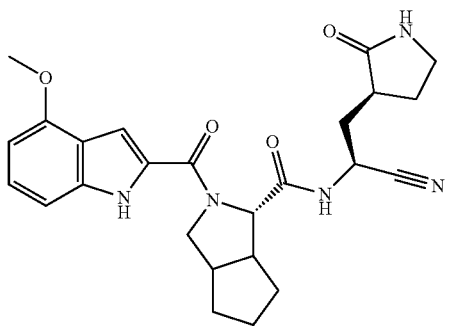 [SMILES: COc1cccc2[nH]c(C(=O)N3CC4CCCC4[C@H]3C(=O)N[C@H](C#N)C[C@@H]3CCNC3=O)cc12] |
| 306 | 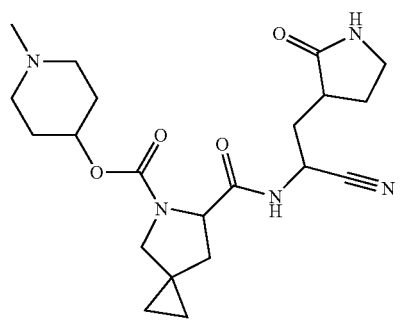 [SMILES: CN1CCC(OC(=O)N2CC3(CC3)CC2C(=O)NC(C#N)CC2CCNC2=O)CC1] |

TABLE 1-continued
Exemplary compounds.
| Compound No. | Structure |
|---|---|
| 307 | 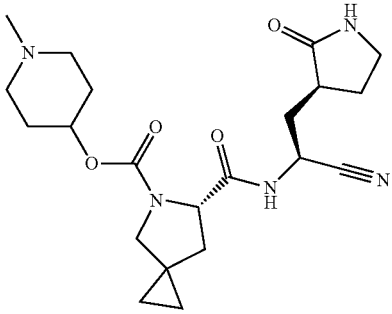 [SMILES: CN1CCC(OC(=O)N2CC3(CC3)C[C@H]2C(=O)N[C@H](C#N)C[C@@H]2CCNC2=O)CC1] |
| 308 | 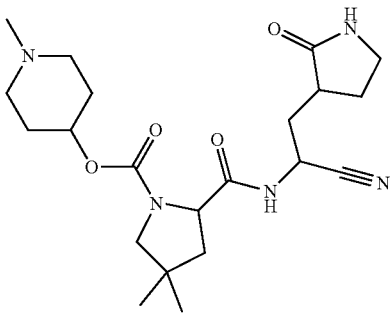 [SMILES: CN1CCC(OC(=O)N2CC(C)(C)CC2C(=O)NC(C#N)CC2CCNC2=O)CC1] |
| 309 | 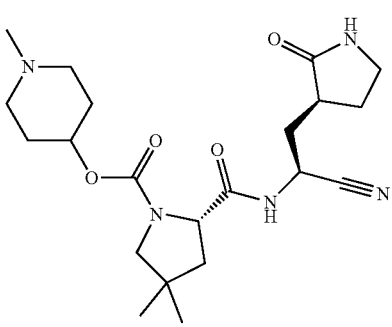 [SMILES: CN1CCC(OC(=O)N2CC(C)(C)C[C@H]2C(=O)N[C@H](C#N)C[C@@H]2CCNC2=O)CC1] |
| 310 | 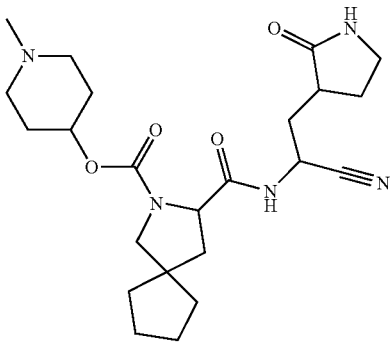 [SMILES: CN1CCC(OC(=O)N2CC3(CCCC3)CC2C(=O)NC(C#N)CC2CCNC2=O)CC1] |

TABLE 1-continued

Exemplary compounds.

| Compound No. | Structure |
| --- | --- |
| 311 | 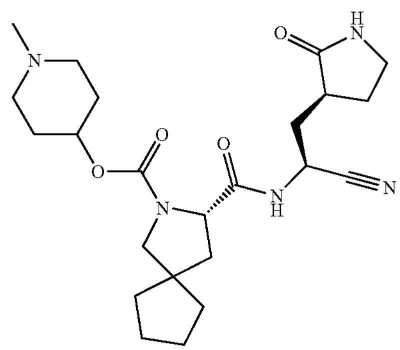 [SMILES: CN1CCC(OC(=O)N2CC3(CCCC3)C[C@H]2C(=O)N[C@H](C#N)C[C@@H]2CCNC2=O)CC1] |
| 312 | 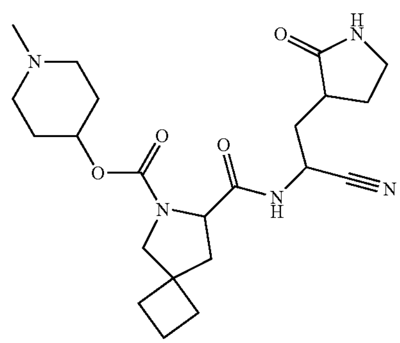 [SMILES: CN1CCC(OC(=O)N2CC3(CCC3)CC2C(=O)NC(C#N)CC2CCNC2=O)CC1] |
| 313 | 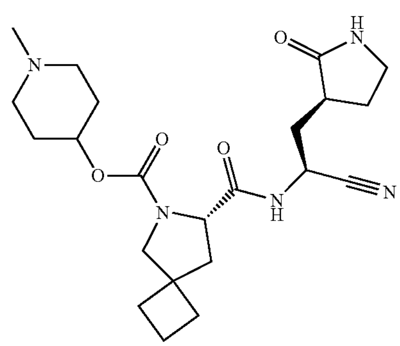 [SMILES: CN1CCC(OC(=O)N2CC3(CCC3)C[C@H]2C(=O)N[C@H](C#N)C[C@@H]2CCNC2=O)CC1] |
| 314 | 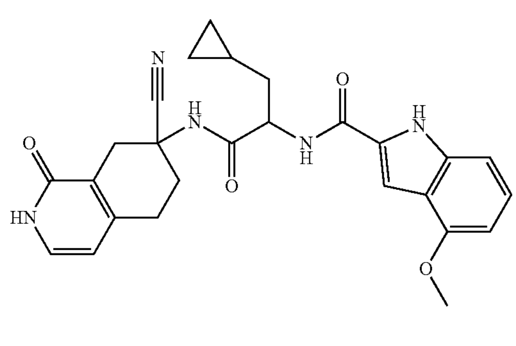 [SMILES: COc1cccc2[nH]c(C(=O)NC(CC3CC3)C(=O)NC3(C#N)CCc4cc[nH]c(=O)c4C3)cc12] |

TABLE 1-continued
Exemplary compounds.
| Compound No. | Structure |
|---|---|
| 315 | 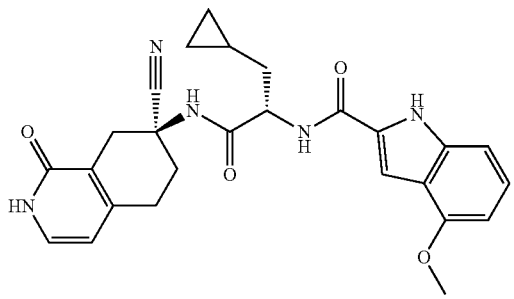 [SMILES: COc1cccc2[nH]c(C(=O)N[C@@H](CC3CC3)C(=O)N[C@@]3(C#N)CCc4cc[nH]c(=O)c4C3)cc12] |
| 316 | 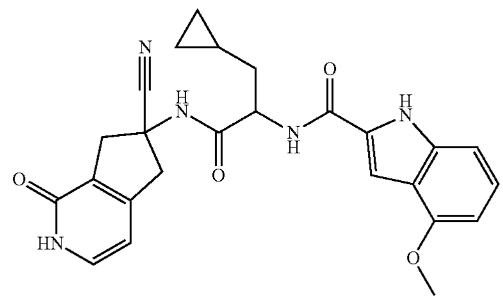 [SMILES: COc1cccc2[nH]c(C(=O)NC(CC3CC3)C(=O)NC3(C#N)Cc4cc[nH]c(=O)c4C3)cc12] |
| 317 | 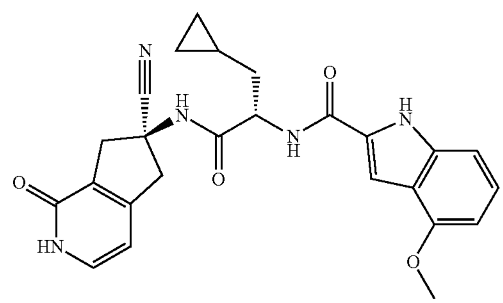 [SMILES: COc1cccc2[nH]c(C(=O)N[C@@H](CC3CC3)C(=O)N[C@@]3(C#N)Cc4cc[nH]c(=O)c4C3)cc12] |
| 318 | 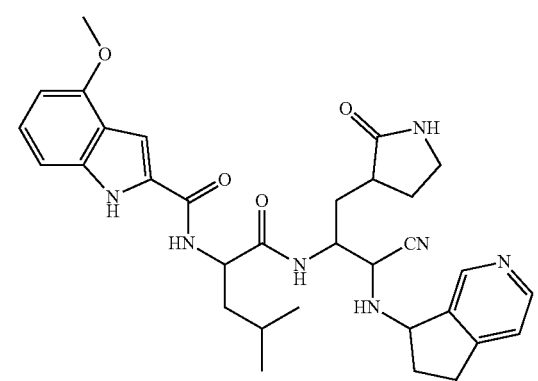 [SMILES: COc1cccc2[nH]c(C(=O)NC(CC(C)C)C(=O)NC(CC3CCNC3=O)C(C#N)NC3CCc4ccncc43)cc12] |

TABLE 1-continued
Exemplary compounds.
| Compound No. | Structure |
|---|---|
| 319 | 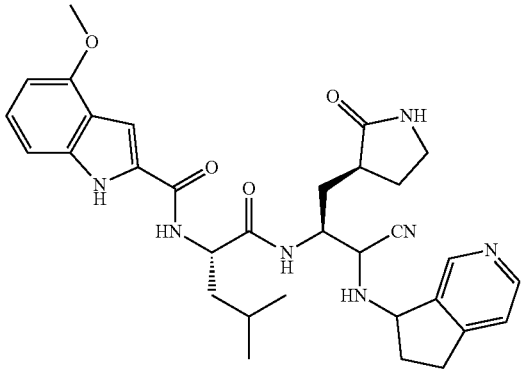 [SMILES: COc1cccc2[nH]c(C(=O)N[C@@H](CC(C)C)C(=O)N[C@@H](C[C@@H]3CCNC3=O)C(C#N)NC3CCc4ccncc43)cc12] |
| 320 | 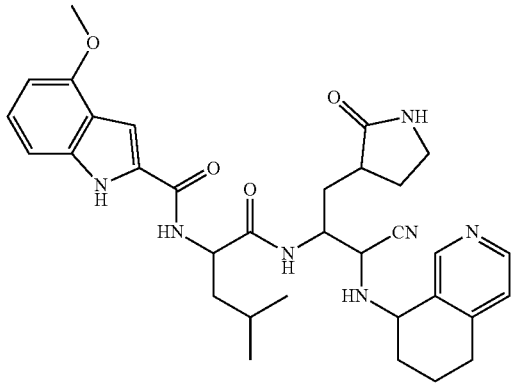 [SMILES: COc1cccc2[nH]c(C(=O)NC(CC(C)C)C(=O)NC(CC3CCNC3=O)C(C#N)NC3CCCc4ccncc43)cc12] |
| 321 | 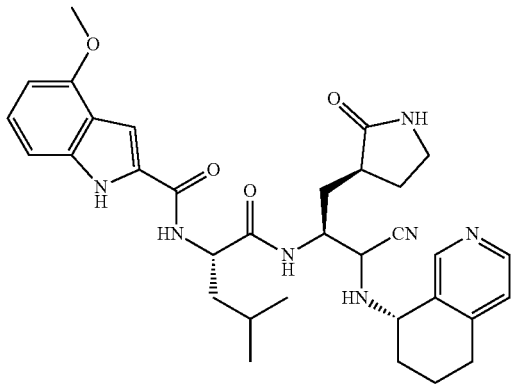 [SMILES: COc1cccc2[nH]c(C(=O)N[C@@H](CC(C)C)C(=O)N[C@@H](C[C@@H]3CCNC3=O)C(C#N)N[C@H]3CCCc4ccncc43)cc12] |
| 322 | 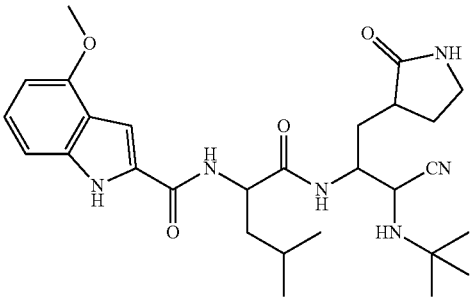 [SMILES: COc1cccc2[nH]c(C(=O)NC(CC(C)C)C(=O)NC(CC3CCNC3=O)C(C#N)NC(C)(C)C)cc12] |

TABLE 1-continued
Exemplary compounds.
| Compound No. | Structure |
|---|---|
| 323 | 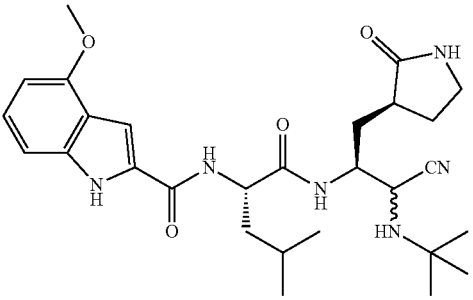 [SMILES: COc1cccc2[nH]c(C(=O)N[C@@H](CC(C)C)C(=O)N[C@@H](C[C@@H]3CCNC3=O)C(C#N)NC(C)(C)C)cc12] |
| 324 | 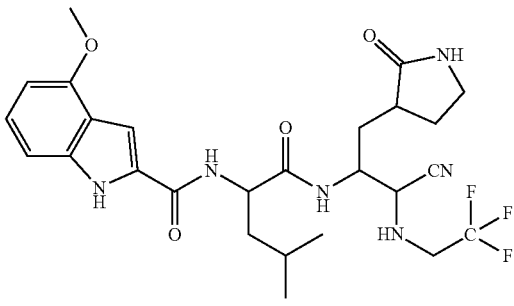 [SMILES: COc1cccc2[nH]c(C(=O)NC(CC(C)C)C(=O)NC(CC3CCNC3=O)C(C#N)NCC(F)(F)F)cc12] |
| 325 | 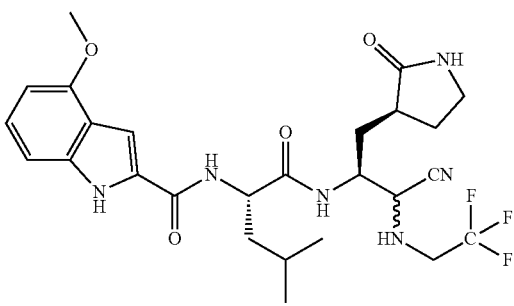 [SMILES: COc1cccc2[nH]c(C(=O)N[C@@H](CC(C)C)C(=O)N[C@@H](C[C@@H]3CCNC3=O)C(C#N)NCC(F)(F)F)cc12] |
| 326 | 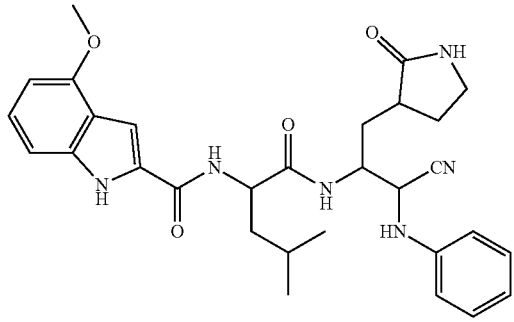 [SMILES: COc1cccc2[nH]c(C(=O)NC(CC(C)C)C(=O)NC(CC3CCNC3=O)C(C#N)Nc3ccccc3)cc12] |

TABLE 1-continued
Exemplary compounds.
| Compound No. | Structure |
|---|---|
| 327 | 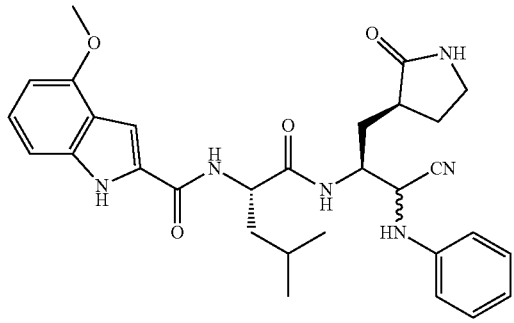 [SMILES: COc1cccc2[nH]c(C(=O)N[C@@H](CC(C)C)C(=O)N[C@@H](C[C@@H]3CCNC3=O)C(C#N)Nc3ccccc3)cc12] |
| 328 | 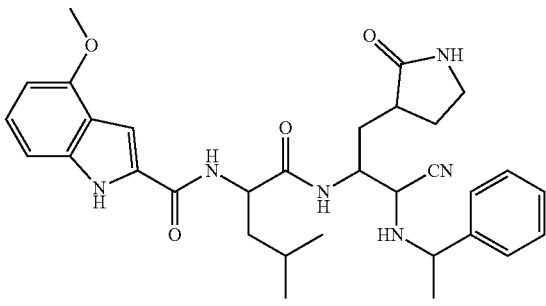 [SMILES: COc1cccc2[nH]c(C(=O)NC(CC(C)C)C(=O)NC(CC3CCNC3=O)C(C#N)NC(C)c3ccccc3)cc12] |
| 329 | 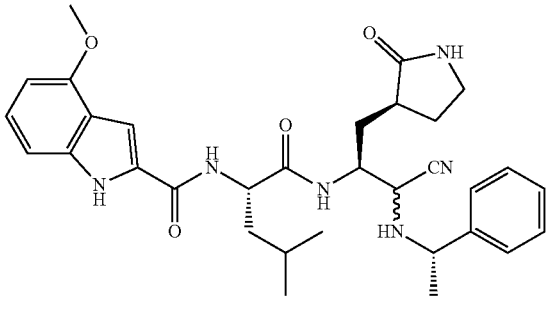 [SMILES: COc1cccc2[nH]c(C(=O)N[C@@H](CC(C)C)C(=O)N[C@@H](C[C@@H]3CCNC3=O)C(C#N)N[C@@H](C)c3ccccc3)cc12] |
| 330 | 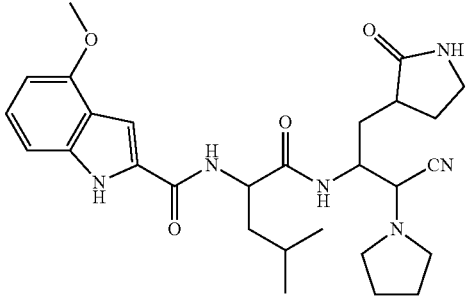 [SMILES: COc1cccc2[nH]c(C(=O)NC(CC(C)C)C(=O)NC(CC3CCNC3=O)C(C#N)N3CCCC3)cc12] |

TABLE 1-continued
Exemplary compounds.
| Compound No. | Structure |
|---|---|
| 331 | 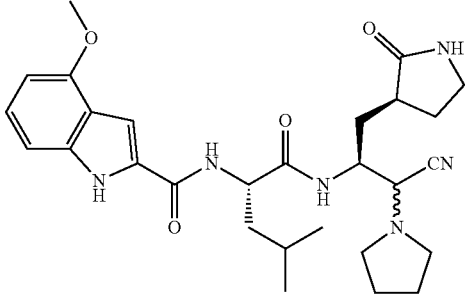 [SMILES: COc1cccc2[nH]c(C(=O)N[C@@H](CC(C)C)C(=O)N[C@@H](C[C@@H]3CCNC3=O)C(C#N)N3CCCC3)cc12] |
| 332 | 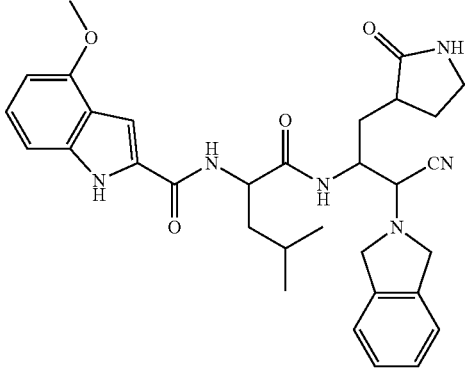 [SMILES: COc1cccc2[nH]c(C(=O)NC(CC(C)C)C(=O)NC(CC3CCNC3=O)C(C#N)N3Cc4ccccc4C3)cc12] |
| 333 | 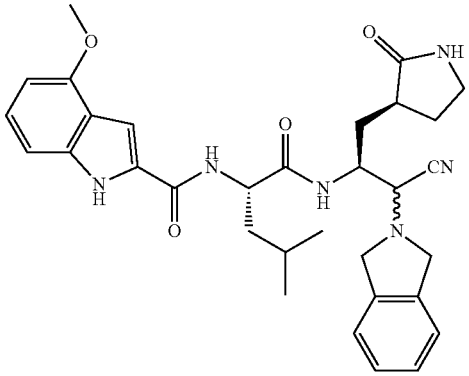 [SMILES: COc1cccc2[nH]c(C(=O)N[C@@H](CC(C)C)C(=O)N[C@@H](C[C@@H]3CCNC3=O)C(C#N)N3Cc4ccccc4C3)cc12] |
| 334 | 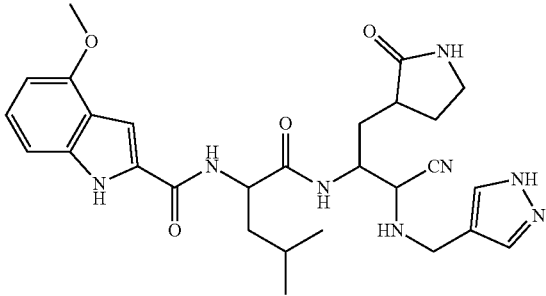 [SMILES: COc1cccc2[nH]c(C(=O)NC(CC(C)C)C(=O)NC(CC3CCNC3=O)C(C#N)NCc3cn[nH]c3)cc12] |

TABLE 1-continued
Exemplary compounds.
| Compound No. | Structure |
|---|---|
| 335 | 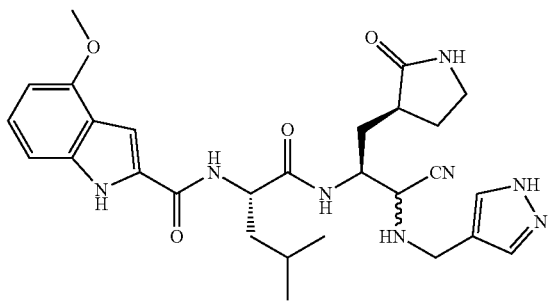 [SMILES: COc1cccc2[nH]c(C(=O)N[C@@H](CC(C)C)C(=O)N[C@@H](C[C@@H]3CCNC3=O)C(C#N)NCc3cn[nH]c3)cc12] |
| 336 | 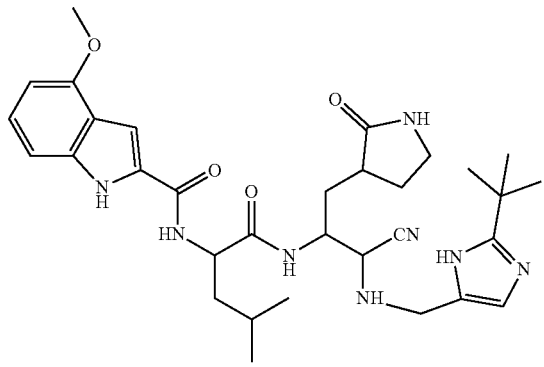 [SMILES: COc1cccc2[nH]c(C(=O)NC(CC(C)C)C(=O)NC(CC3CCNC3=O)C(C#N)NCc3cnc(C(C)(C)C)[nH]3)cc12] |
| 337 | 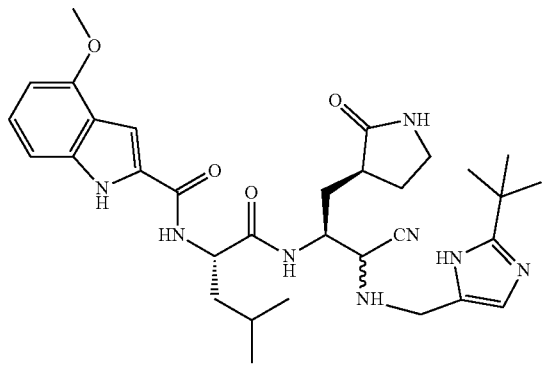 [SMILES: COc1cccc2[nH]c(C(=O)N[C@@H](CC(C)C)C(=O)N[C@@H](C[C@@H]3CCNC3=O)C(C#N)NCc3cnc(C(C)(C)C)[nH]3)cc12] |
| 338 | 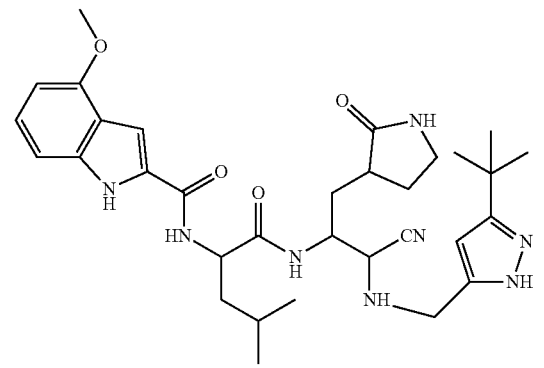 [SMILES: COc1cccc2[nH]c(C(=O)NC(CC(C)C)C(=O)NC(CC3CCNC3=O)C(C#N)NCc3cc(C(C)(C)C)n[nH]3)cc12] |

TABLE 1-continued
Exemplary compounds.
| Compound No. | Structure |
|---|---|
| 339 | 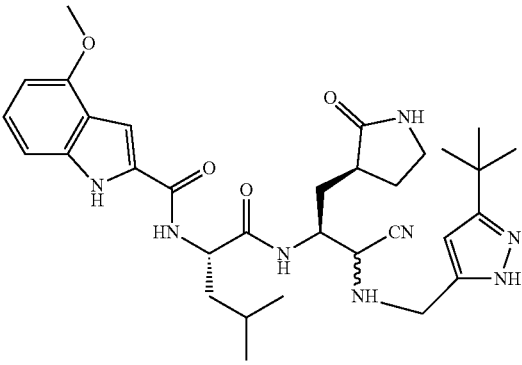 [SMILES: COc1cccc2[nH]c(C(=O)N[C@@H](CC(C)C)C(=O)N[C@@H](C[C@@H]3CCNC3=O)C(C#N)NCc3cc(C(C)(C)C)n[nH]3)cc12] |
| 340 | 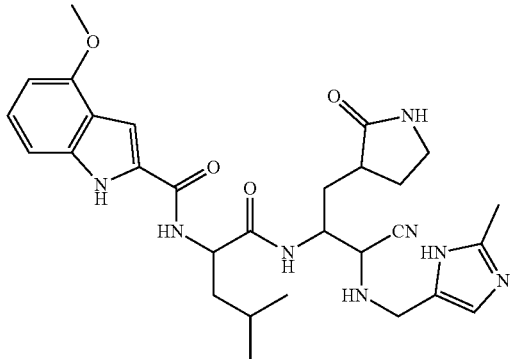 [SMILES: COc1cccc2[nH]c(C(=O)NC(CC(C)C)C(=O)NC(CC3CCNC3=O)C(C#N)NCc3cnc(C)[nH]3)cc12] |
| 341 | 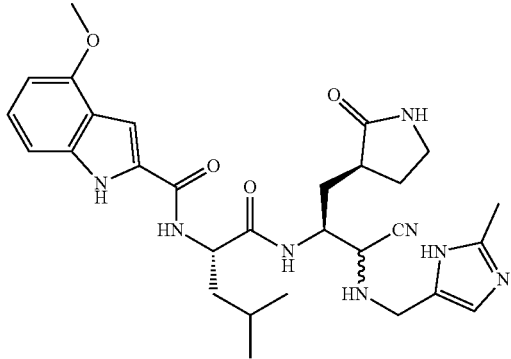 [SMILES: COc1cccc2[nH]c(C(=O)N[C@@H](CC(C)C)C(=O)N[C@@H](C[C@@H]3CCNC3=O)C(C#N)NCc3cnc(C)[nH]3)cc12] |
| 342 | 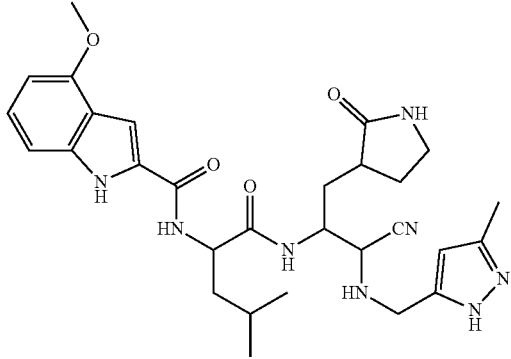 [SMILES: COc1cccc2[nH]c(C(=O)NC(CC(C)C)C(=O)NC(CC3CCNC3=O)C(C#N)NCc3cc(C)n[nH]3)cc12] |

TABLE 1-continued

Exemplary compounds.

| Compound No. | Structure |
|---|---|
| 343 | 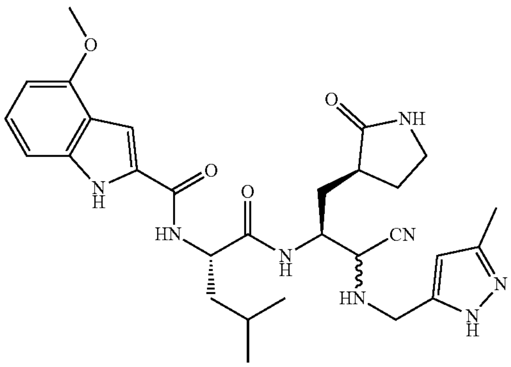 [SMILES: COc1cccc2[nH]c(C(=O)N[C@@H](CC(C)C)C(=O)N[C@@H](C[C@@H]3CCNC3=O)C(C#N)NCc3cc(C)n[nH]3)cc12] |
| 344 | 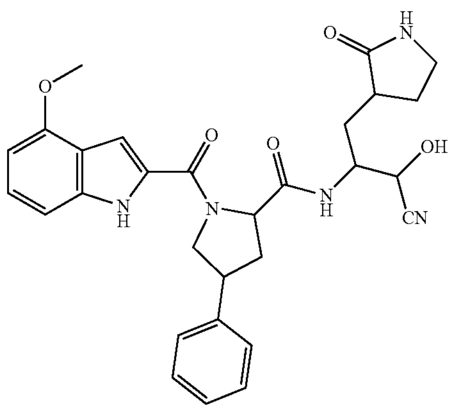 [SMILES: COc1cccc2[nH]c(C(=O)N3CC(c4ccccc4)CC3C(=O)NC(CC3CCNC3=O)C(O)C#N)cc12] |
| 345 | 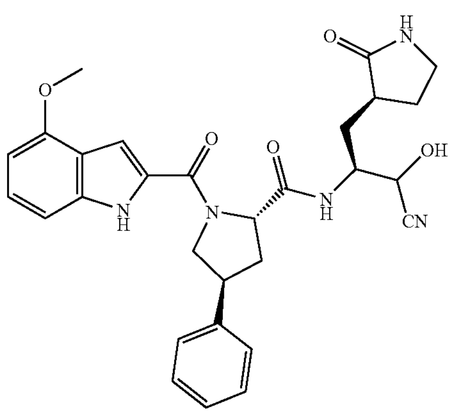 [SMILES: COc1cccc2[nH]c(C(=O)N3C[C@H](c4ccccc4)C[C@H]3C(=O)N[C@@H](C[C@@H]3CCNC3=O)C(O)C#N)cc12] |
| 346 | 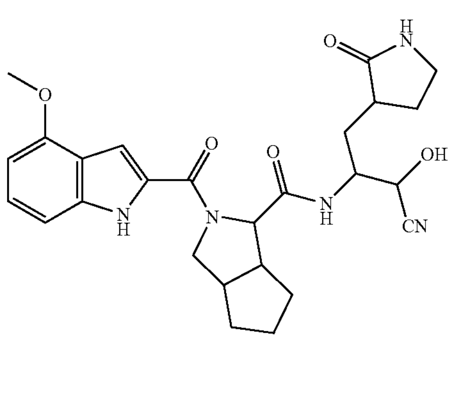 [SMILES: COc1cccc2[nH]c(C(=O)N3CC4CCCC4C3C(=O)NC(CC3CCNC3=O)C(O)C#N)cc12] |

TABLE 1-continued

Exemplary compounds.

| Compound No. | Structure |
|---|---|
| 347 | 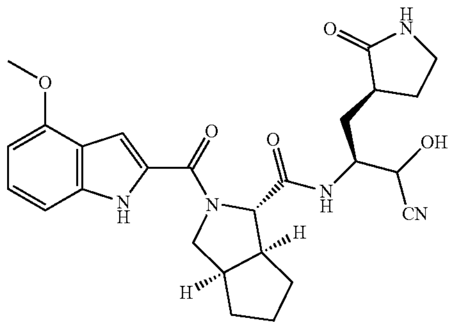 [SMILES: COc1cccc2[nH]c(C(=O)N3C[C@@H]4CCC[C@@H]4[C@H]3C(=O)N[C@@H](C[C@@H]3CCNC3=O)C(O)C#N)cc12] |
| 348 | 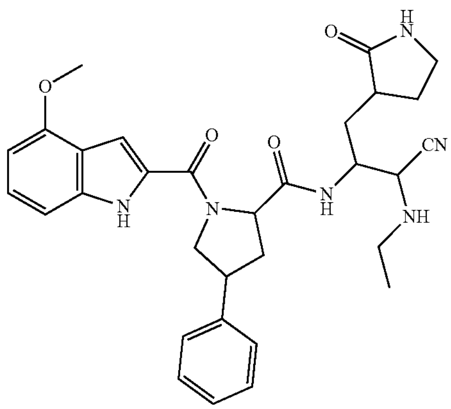 [SMILES: CCNC(C#N)C(CC1CCNC1=O)NC(=O)C1CC(c2ccccc2)CN1C(=O)c1cc2c(OC)cccc2[nH]1] |
| 349 | 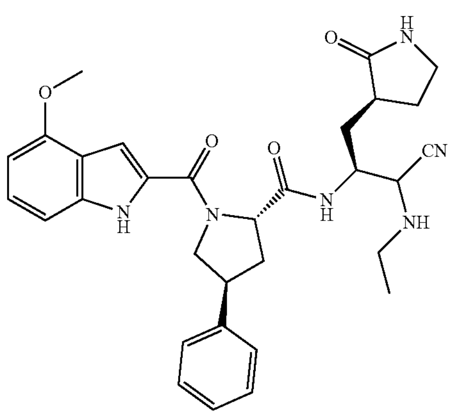 [SMILES: CCNC(C#N)[C@H](C[C@@H]1CCNC1=O)NC(=O)[C@@H]1C[C@@H](c2ccccc2)CN1C(=O)c1cc2c(OC)cccc2[nH]1] |
| 350 | 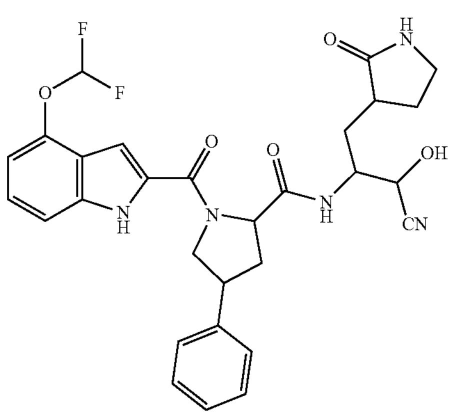 [SMILES: N#CC(O)C(CC1CCNC1=O)NC(=O)C1CC(c2ccccc2)CN1C(=O)c1cc2c(OC(F)F)cccc2[nH]1] |

TABLE 1-continued
Exemplary compounds.
| Compound No. | Structure |
|---|---|
| 351 | 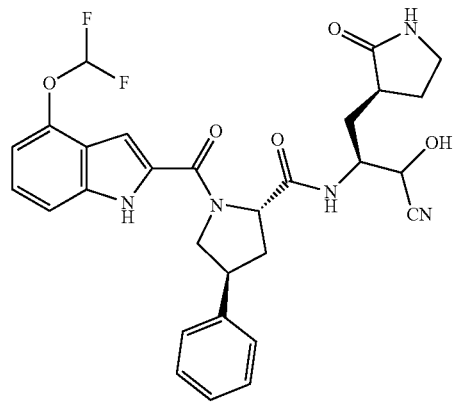 [SMILES: N#CC(O)[C@H](C[C@@H]1CCNC1=O)NC(=O)[C@@H]1C[C@@H](c2ccccc2)CN1C(=O)c1cc2c(OC(F)F)cccc2[nH]1] |
| 352 | 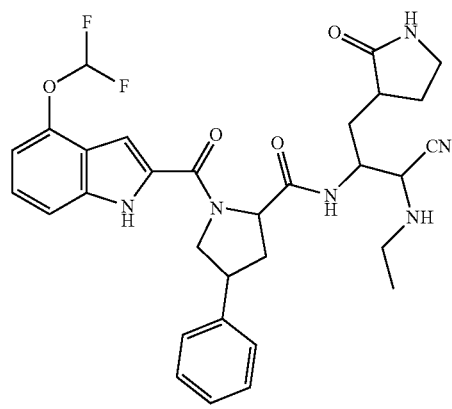 [SMILES: CCNC(C#N)C(CC1CCNC1=O)NC(=O)C1CC(c2ccccc2)CN1C(=O)c1cc2c(OC(F)F)cccc2[nH]1] |
| 353 | 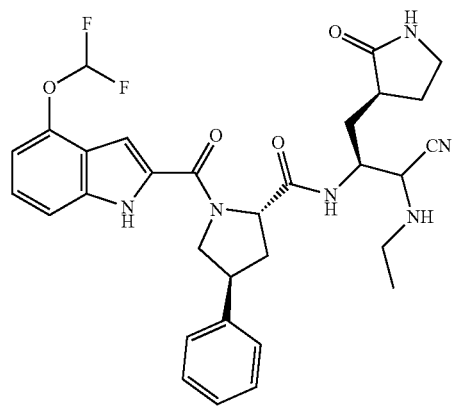 [SMILES: CCNC(C#N)[C@H](C[C@@H]1CCNC1=O)NC(=O)[C@@H]1C[C@@H](c2ccccc2)CN1C(=O)c1cc2c(OC(F)F)cccc2[nH]1] |

TABLE 1-continued
Exemplary compounds.
| Compound No. | Structure |
|---|---|
| 354 | 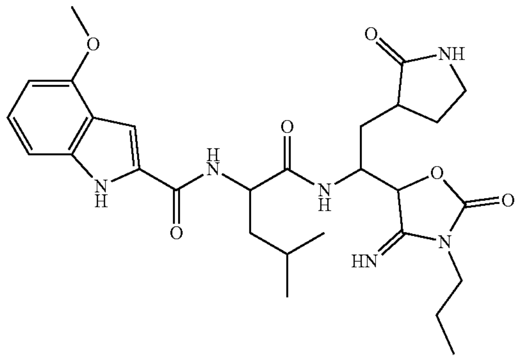 [SMILES: CCCN1C(=N)C(C(CC2CCNC2=O)NC(=O)C(CC(C)C)NC(=O)c2cc3c(OC)cccc3[nH]2)OC1=O] |
| 355 | 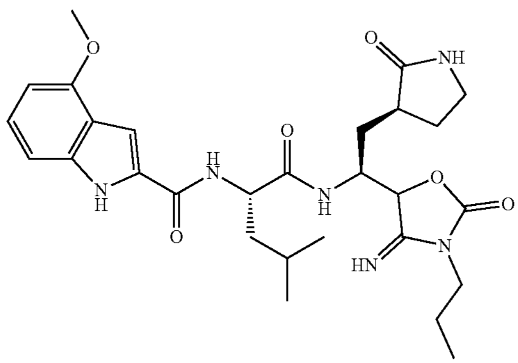 [SMILES: CCCN1C(=N)C([C@H](C[C@@H]2CCNC2=O)NC(=O)[C@H](CC(C)C)NC(=O)c2cc3c(OC)cccc3[nH]2)OC1=O] |
| 356 | 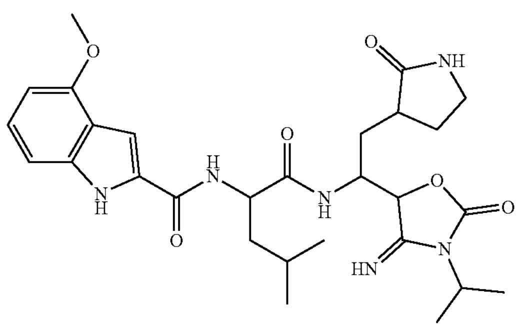 [SMILES: COc1cccc2[nH]c(C(=O)NC(CC(C)C)C(=O)NC(CC3CCNC3=O)C3OC(=O)N(C(C)C)C3=N)cc12] |
| 357 | 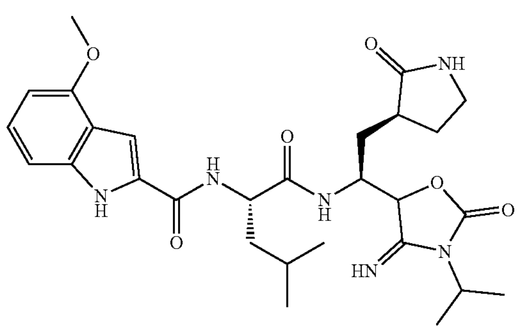 [SMILES: COc1cccc2[nH]c(C(=O)N[C@@H](CC(C)C)C(=O)N[C@@H](C[C@@H]3CCNC3=O)C3OC(=O)N(C(C)C)C3=N)cc12] |

TABLE 1-continued

Exemplary compounds.

| Compound No. | Structure |
|---|---|
| 358 | 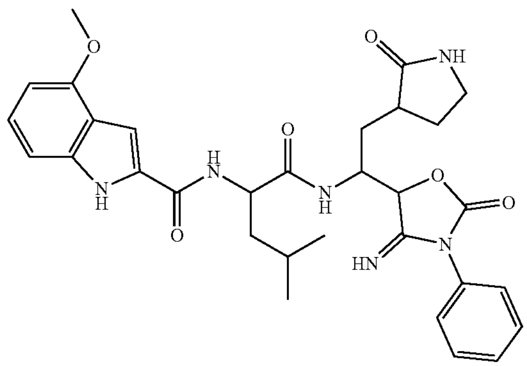 [SMILES: COc1cccc2[nH]c(C(=O)NC(CC(C)C)C(=O)NC(CC3CCNC3=O)C3OC(=O)N(c4ccccc4)C3=N)cc12] |
| 359 | 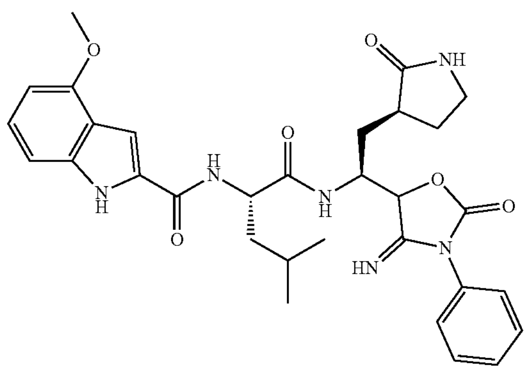 [SMILES: COc1cccc2[nH]c(C(=O)N[C@@H](CC(C)C)C(=O)N[C@@H](C[C@@H]3CCNC3=O)C3OC(=O)N(c4ccccc4)C3=N)cc12] |
| 360 | 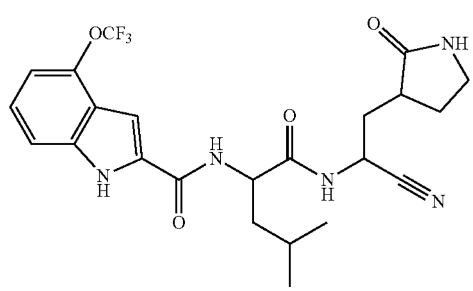 [SMILES: CC(C)CC(NC(=O)c1cc2c(OC(F)(F)F)cccc2[nH]1)C(=O)NC(C#N)CC1CCNC1=O] |
| 361 | 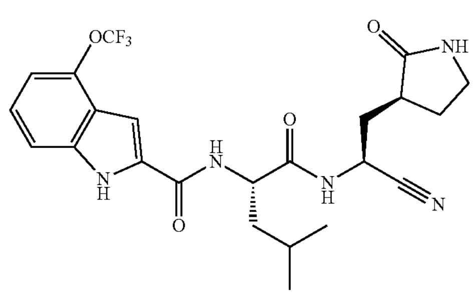 [SMILES: CC(C)C[C@H](NC(=O)c1cc2c(OC(F)(F)F)cccc2[nH]1)C(=O)N[C@H](C#N)C[C@@H]1CCNC1=O] |

TABLE 1-continued

Exemplary compounds.

| Compound No. | Structure |
|---|---|
| 362 | 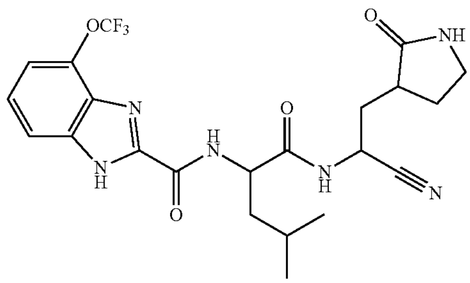 [SMILES: CC(C)CC(NC(=O)c1nc2c(OC(F)(F)F)cccc2[nH]1)C(=O)NC(C#N)CC1CCNC1=O] |
| 363 | 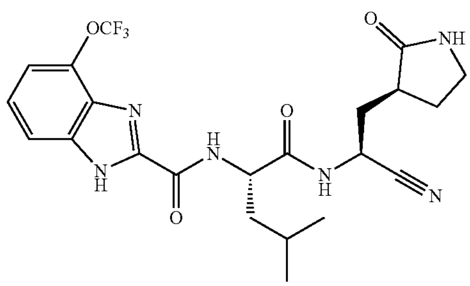 [SMILES: CC(C)C[C@H](NC(=O)c1nc2c(OC(F)(F)F)cccc2[nH]1)C(=O)N[C@H](C#N)C[C@@H]1CCNC1=O] |
| 364 | 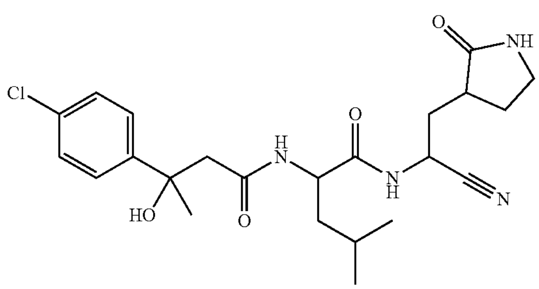 [SMILES: CC(C)CC(NC(=O)CC(C)(O)c1ccc(Cl)cc1)C(=O)NC(C#N)CC1CCNC1=O] |
| 365 | 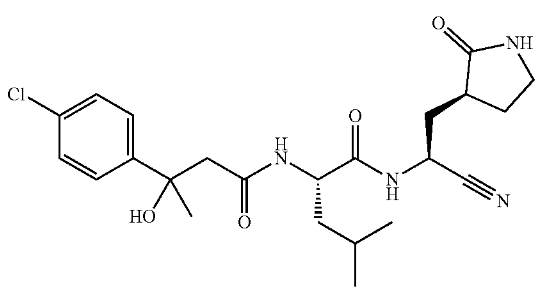 [SMILES: CC(C)C[C@H](NC(=O)CC(C)(O)c1ccc(Cl)cc1)C(=O)N[C@H](C#N)C[C@@H]1CCNC1=O] |
| 366 | 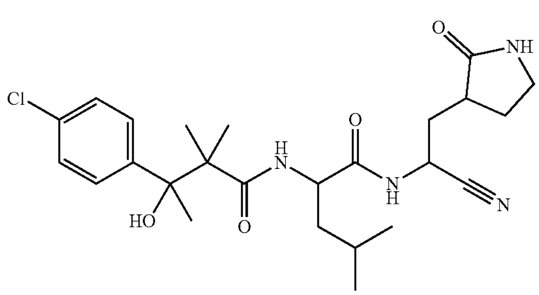 [SMILES: CC(C)CC(NC(=O)C(C)(C)C(C)(O)c1ccc(Cl)cc1)C(=O)NC(C#N)CC1CCNC1=O] |

TABLE 1-continued
Exemplary compounds.
| Compound No. | Structure |
|---|---|
| 367 | 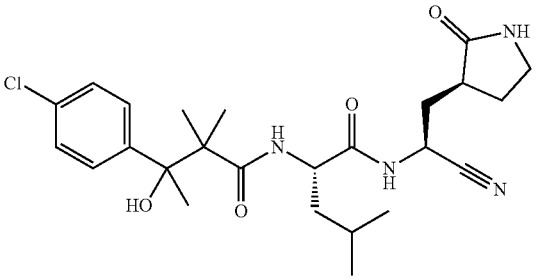 [SMILES: CC(C)C[C@H](NC(=O)C(C)(C)C(C)(O)c1ccc(Cl)cc1)C(=O)N[C@H](C#N)C[C@@H]1CCNC1=O] |
| 368 | 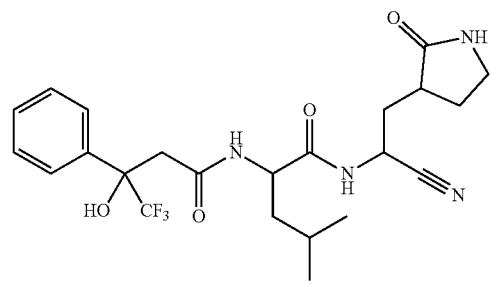 [SMILES: CC(C)CC(NC(=O)CC(O)(c1ccccc1)C(F)(F)F)C(=O)NC(C#N)CC1CCNC1=O] |
| 369 | 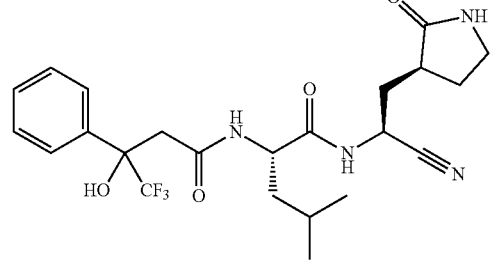 |
| 370 | 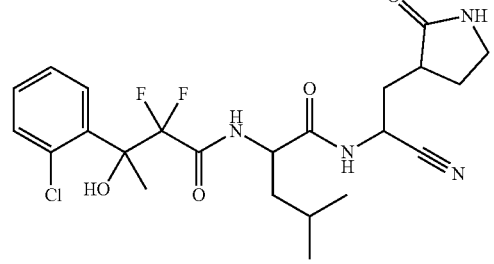 |
| 371 | 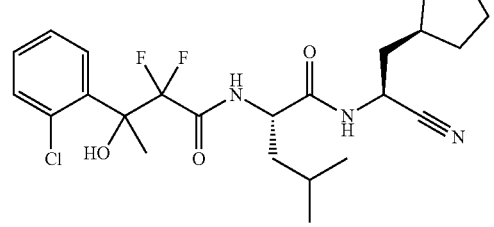 |

TABLE 1-continued
Exemplary compounds.
| Compound No. | Structure |
|---|---|
| 372 | 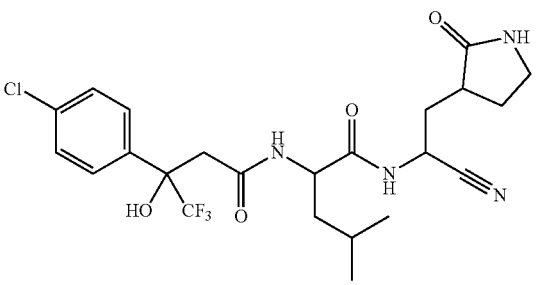 [SMILES: CC(C)CC(NC(=O)CC(O)(c1ccc(Cl)cc1)C(F)(F)F)C(=O)NC(C#N)CC1CCNC1=O] |
| 373 | 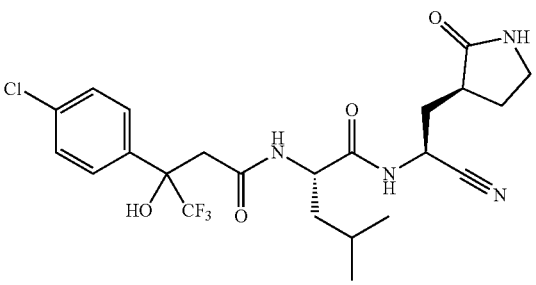 [SMILES: CC(C)C[C@H](NC(=O)CC(O)(c1ccc(Cl)cc1)C(F)(F)F)C(=O)N[C@H](C#N)C[C@@H]1CCNC1=O] |
| 374 | 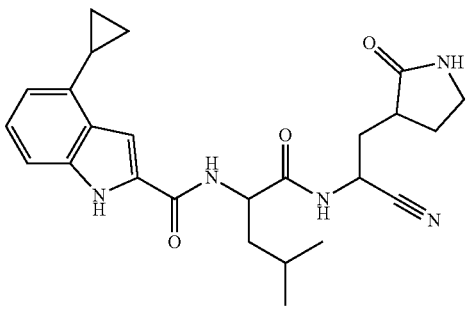 [SMILES: CC(C)CC(NC(=O)c1cc2c(C3CC3)cccc2[nH]1)C(=O)NC(C#N)CC1CCNC1=O] |
| 375 | 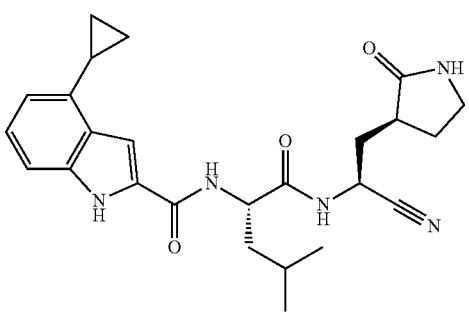 [SMILES: CC(C)C[C@H](NC(=O)c1cc2c(C3CC3)cccc2[nH]1)C(=O)N[C@H](C#N)C[C@@H]1CCNC1=O] |
| 376 | 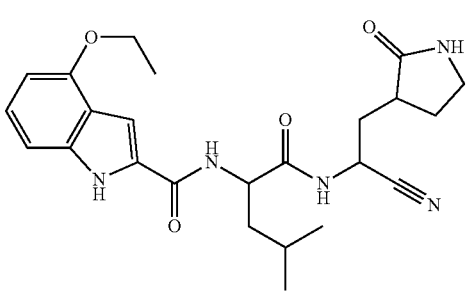 [SMILES: CCOc1cccc2[nH]c(C(=O)NC(CC(C)C)C(=O)NC(C#N)CC3CCNC3=O)cc12] |

TABLE 1-continued
Exemplary compounds.
| Compound No. | Structure |
|---|---|
| 377 | 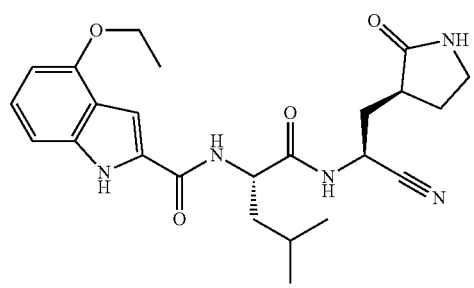 [SMILES: CCOc1cccc2[nH]c(C(=O)N[C@@H](CC(C)C)C(=O)N[C@H](C#N)C[C@@H]3CCNC3=O)cc12] |
| 378 | 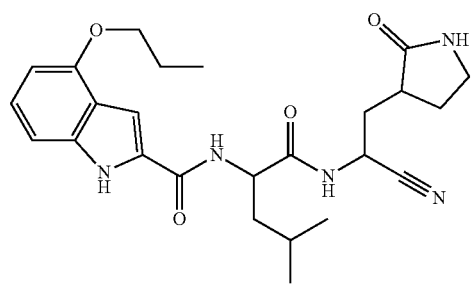 [SMILES: CCCOc1cccc2[nH]c(C(=O)NC(CC(C)C)C(=O)NC(C#N)CC3CCNC3=O)cc12] |
| 379 | 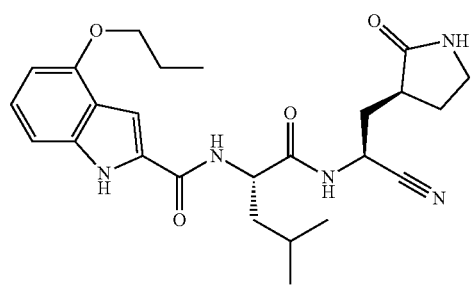 [SMILES: CCCOc1cccc2[nH]c(C(=O)N[C@@H](CC(C)C)C(=O)N[C@H](C#N)C[C@@H]3CCNC3=O)cc12] |
| 380 | 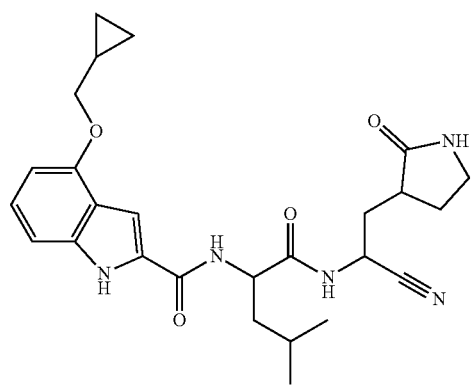 [SMILES: CC(C)CC(NC(=O)c1cc2c(OCC3CC3)cccc2[nH]1)C(=O)NC(C#N)CC1CCNC1=O] |

TABLE 1-continued
Exemplary compounds.
| Compound No. | Structure |
|---|---|
| 381 | 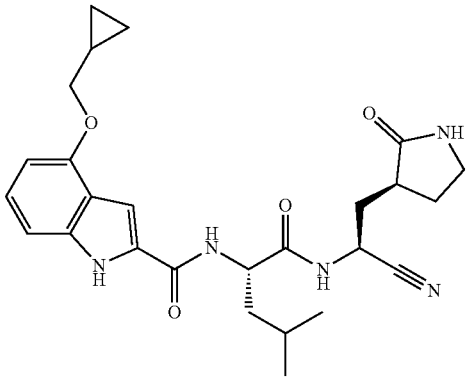 [SMILES: CC(C)C[C@H](NC(=O)c1cc2c(OCC3CC3)cccc2[nH]1)C(=O)N[C@H](C#N)C[C@@H]1CCNC1=O] |
| 382 | 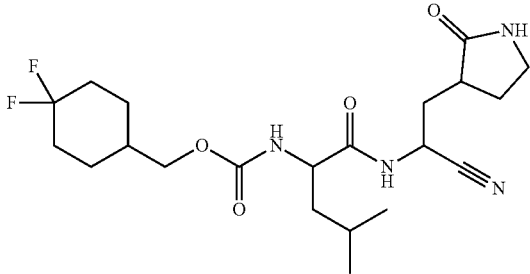 [SMILES: CC(C)CC(NC(=O)OCC1CCC(F)(F)CC1)C(=O)NC(C#N)CC1CCNC1=O] |
| 383 | 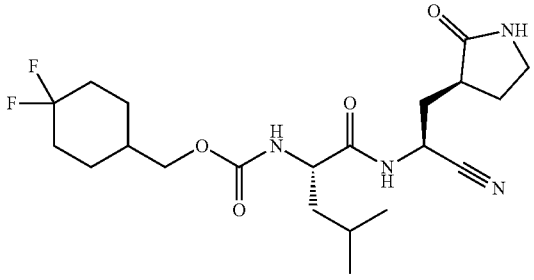 [SMILES: CC(C)C[C@H](NC(=O)OCC1CCC(F)(F)CC1)C(=O)N[C@H](C#N)C[C@@H]1CCNC1=O] |
| 384 | 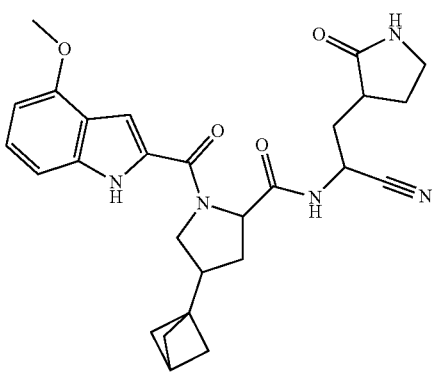 [SMILES: COc1cccc2[nH]c(C(=O)N3CC(C45CC(C4)C5)CC3C(=O)NC(C#N)CC3CCNC3=O)cc12] |

TABLE 1-continued

Exemplary compounds.

| Compound No. | Structure |
|---|---|
| 385 | 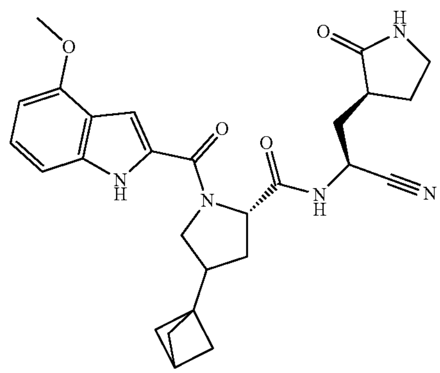 [SMILES: COc1cccc2[nH]c(C(=O)N3CC(C45CC(C4)C5)C[C@H]3C(=O)N[C@H](C#N)C[C@@H]3CCNC3=O)cc12] |
| 386 | 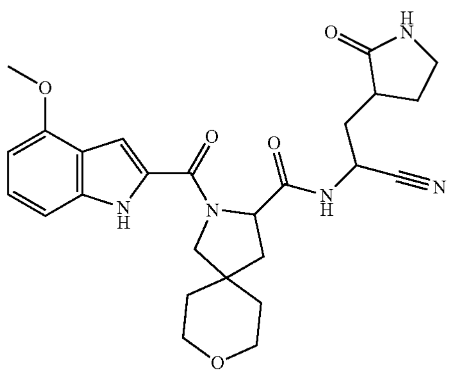 [SMILES: COc1cccc2[nH]c(C(=O)N3CC4(CCOCC4)CC3C(=O)NC(C#N)CC3CCNC3=O)cc12] |
| 387 | 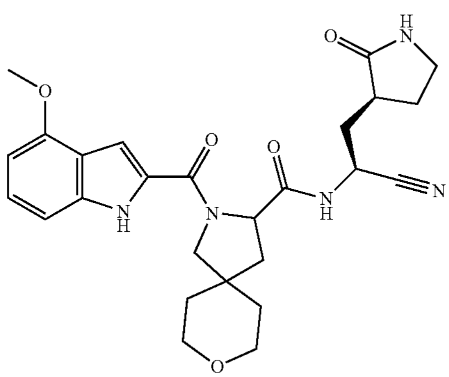 [SMILES: COc1cccc2[nH]c(C(=O)N3CC4(CCOCC4)CC3C(=O)N[C@H](C#N)C[C@@H]3CCNC3=O)cc12] |
| 388 | 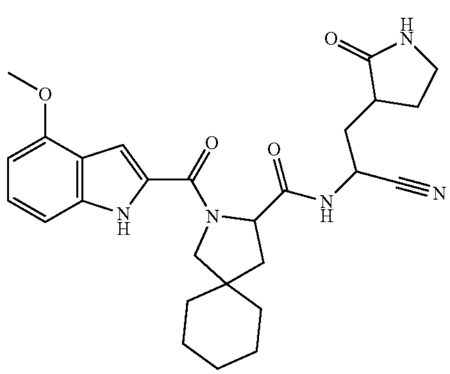 [SMILES: COc1cccc2[nH]c(C(=O)N3CC4(CCCCC4)CC3C(=O)NC(C#N)CC3CCNC3=O)cc12] |

TABLE 1-continued

Exemplary compounds.

| Compound No. | Structure |
|---|---|
| 389 | 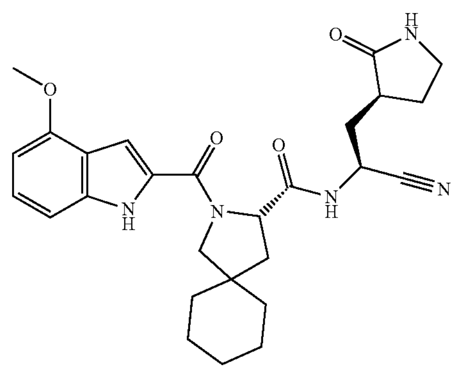 |
| 390 | 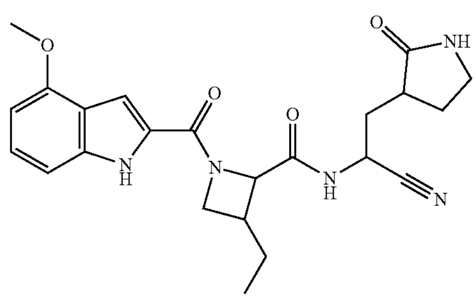 [SMILES: CCC1CN(C(=O)c2cc3c(OC)cccc3[nH]2)C1C(=O)NC(C#N)CC1CCNC1=O] |
| 391 | 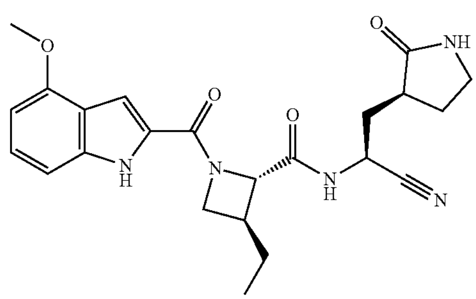 [SMILES: CC[C@H]1CN(C(=O)c2cc3c(OC)cccc3[nH]2)[C@@H]1C(=O)N[C@H](C#N)C[C@@H]1CCNC1=O] |
| 392 | 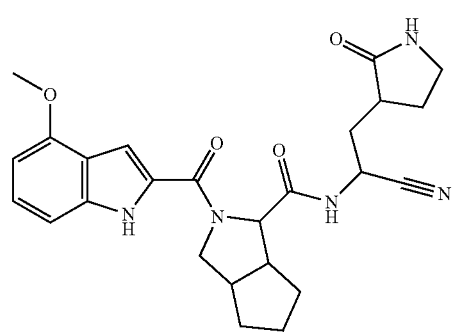 [SMILES: COc1cccc2[nH]c(C(=O)N3CC4CCCC4C3C(=O)NC(C#N)CC3CCNC3=O)cc12] |

TABLE 1-continued
Exemplary compounds.
| Compound No. | Structure |
|---|---|
| 393 | 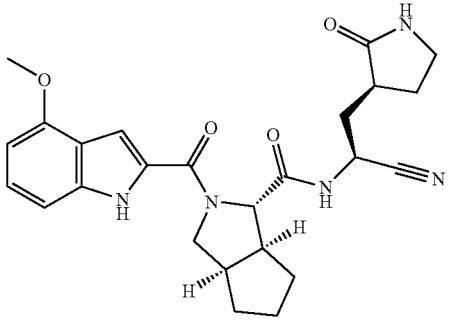 [SMILES: COc1cccc2[nH]c(C(=O)N3C[C@@H]4CCC[C@@H]4[C@H]3C(=O)N[C@H](C#N)C[C@@H]3CCNC3=O)cc12] |
| 394 | 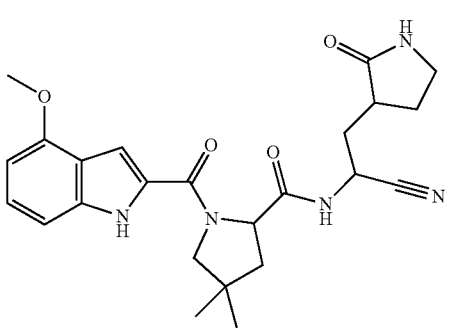 [SMILES: COc1cccc2[nH]c(C(=O)N3CC(C)(C)CC3C(=O)NC(C#N)CC3CCNC3=O)cc12] |
| 395 | 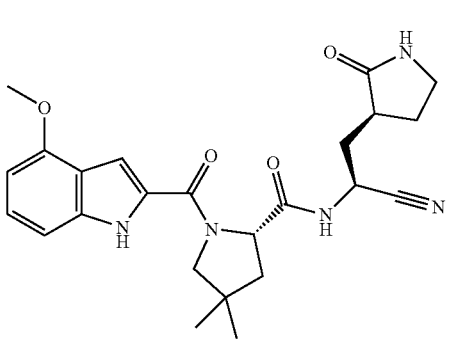 [SMILES: COc1cccc2[nH]c(C(=O)N3CC(C)(C)C[C@H]3C(=O)N[C@H](C#N)C[C@@H]3CCNC3=O)cc12] |
| 396 | 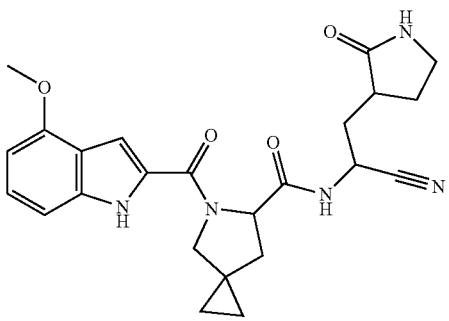 [SMILES: COc1cccc2[nH]c(C(=O)N3CC4(CC4)CC3C(=O)NC(C#N)CC3CCNC3=O)cc12] |

TABLE 1-continued

Exemplary compounds.

| Compound No. | Structure |
| --- | --- |
| 397 | 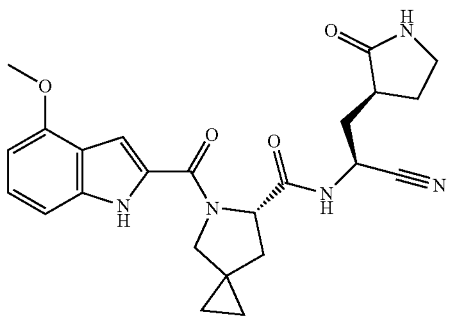 [SMILES: COc1cccc2[nH]c(C(=O)N3CC4(CC4)C[C@H]3C(=O)N[C@H](C#N)C[C@@H]3CCNC3=O)cc12] |
| 398 | 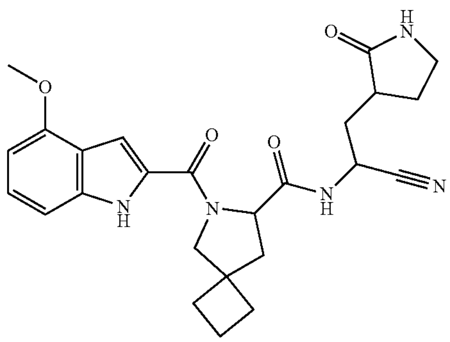 [SMILES: COc1cccc2[nH]c(C(=O)N3CC4(CCC4)CC3C(=O)NC(C#N)CC3CCNC3=O)cc12] |
| 399 | 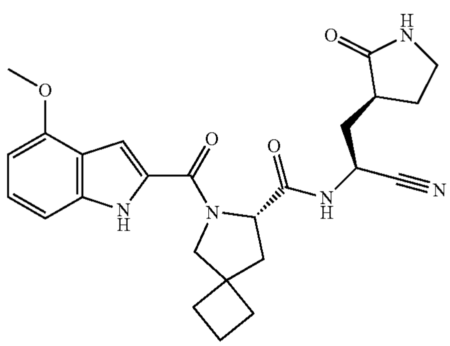 [SMILES: COc1cccc2[nH]c(C(=O)N3CC4(CCC4)C[C@H]3C(=O)N[C@H](C#N)C[C@@H]3CCNC3=O)cc12] |
| 400 | 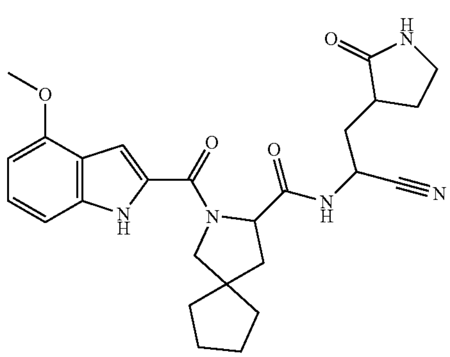 [SMILES: COc1cccc2[nH]c(C(=O)N3CC4(CCCC4)CC3C(=O)NC(C#N)CC3CCNC3=O)cc12] |

213
214
TABLE 1-continued
Exemplary compounds.
| Compound No. | Structure |
|---|---|
| 401 | 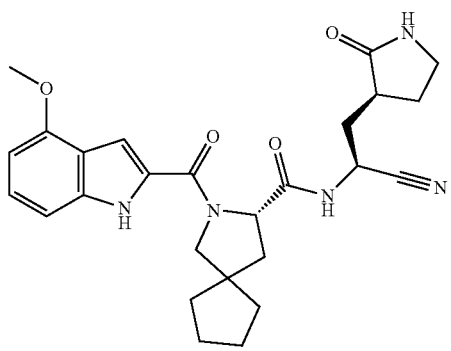 [SMILES: COc1cccc2[nH]c(C(=O)N3CC4(CCCC4)C[C@H]3C(=O)N[C@H](C#N)C[C@@H]3CCNC3=O)cc12] |
| 402 | 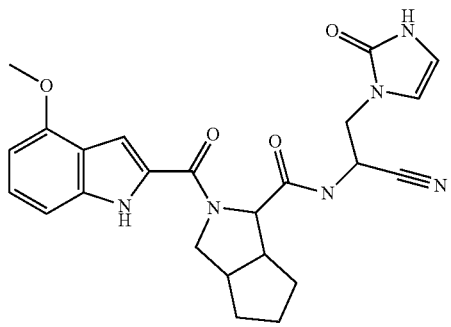 [SMILES: COc1cccc2[nH]c(C(=O)N3CC4CCCC4C3C(=O)NC(C#N)Cn3cc[nH]c3=O)cc12] |
| 403 | 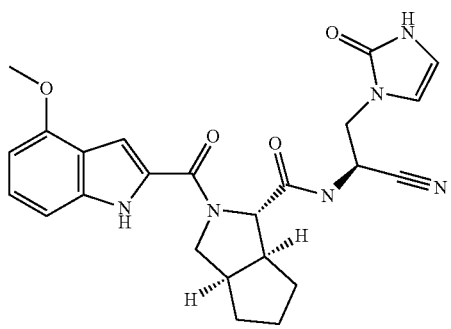 [SMILES: COc1cccc2[nH]c(C(=O)N3C[C@@H]4CCC[C@@H]4[C@H]3C(=O)N[C@H](C#N)Cn3cc[nH]c3=O)cc12] |
| 404 | 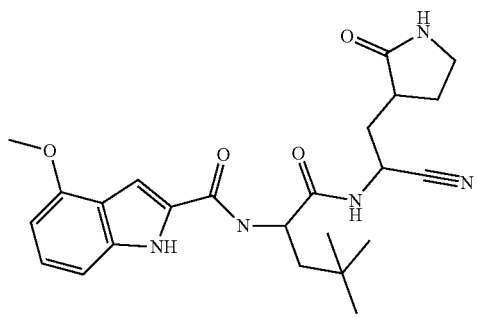 [SMILES: COc1cccc2[nH]c(C(=O)NC(CC(C)(C)C)C(=O)NC(C#N)CC3CCNC3=O)cc12] |

TABLE 1-continued
Exemplary compounds.
| Compound No. | Structure |
|---|---|
| 405 | 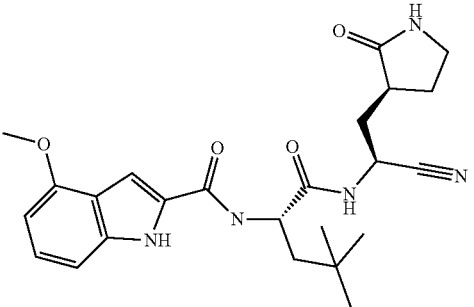 [SMILES: COc1cccc2[nH]c(C(=O)N[C@@H](CC(C)(C)C)C(=O)N[C@H](C#N)C[C@@H]3CCNC3=O)cc12] |
| 406 | 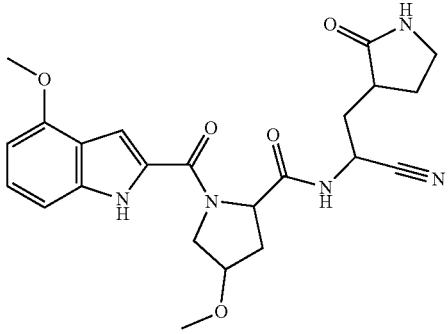 [SMILES: COc1cccc2[nH]c(C(=O)N3CC(OC)CC3C(=O)NC(C#N)CC3CCNC3=O)cc12] |
| 407 | 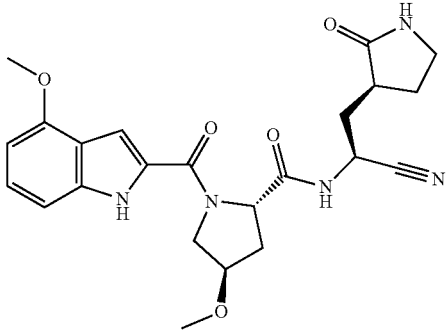 [SMILES: COc1cccc2[nH]c(C(=O)N3C[C@H](OC)C[C@H]3C(=O)N[C@H](C#N)C[C@@H]3CCNC3=O)cc12] |
| 408 | 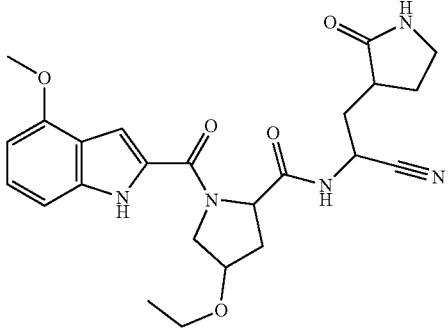 [SMILES: CCOC1CC(C(=O)NC(C#N)CC2CCNC2=O)N(C(=O)c2cc3c(OC)cccc3[nH]2)C1] |

TABLE 1-continued

Exemplary compounds.

| Compound No. | Structure |
|---|---|
| 409 | 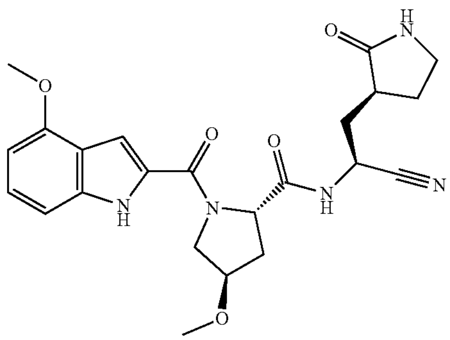 [SMILES: COc1cccc2[nH]c(C(=O)N3C[C@H](OC)C[C@H]3C(=O)N[C@H](C#N)C[C@@H]3CCNC3=O)cc12] |
| 410 | 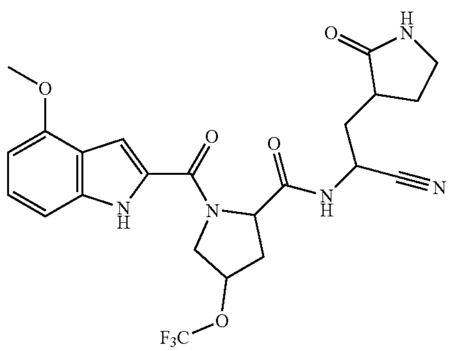 |
| 411 | 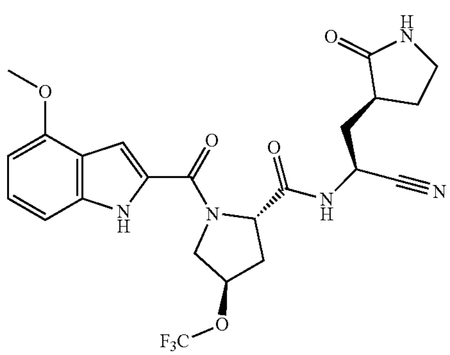 [SMILES: COc1cccc2[nH]c(C(=O)N3C[C@H](OC(F)(F)F)C[C@H]3C(=O)N[C@H](C#N)C[C@@H]3CCNC3=O)cc12] |
| 412 | 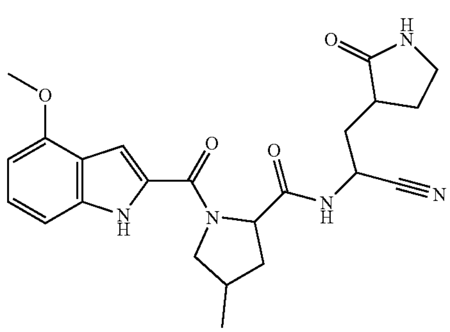 [SMILES: COc1cccc2[nH]c(C(=O)N3CC(C)CC3C(=O)NC(C#N)CC3CCNC3=O)cc12] |

TABLE 1-continued
Exemplary compounds.
| Compound No. | Structure |
|---|---|
| 413 | 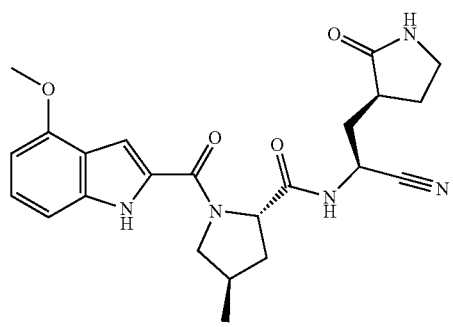 [SMILES: COc1cccc2[nH]c(C(=O)N3C[C@H](C)C[C@H]3C(=O)N[C@H](C#N)C[C@@H]3CCNC3=O)cc12] |
| 414 | 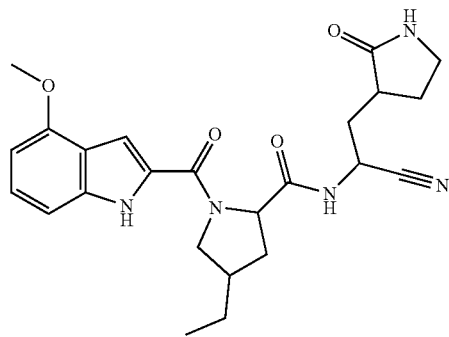 [SMILES: CCC1CC(C(=O)NC(C#N)CC2CCNC2=O)N(C(=O)c2cc3c(OC)cccc3[nH]2)C1] |
| 415 | 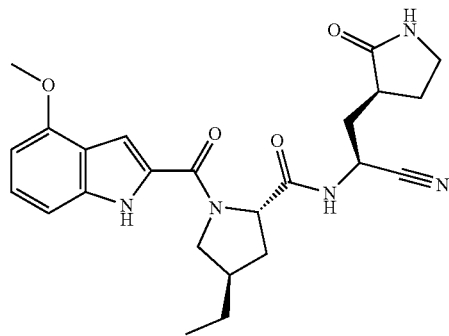 [SMILES: CC[C@@H]1C[C@@H](C(=O)N[C@H](C#N)C[C@@H]2CCNC2=O)N(C(=O)c2cc3c(OC)cccc3[nH]2)C1] |
| 416 | 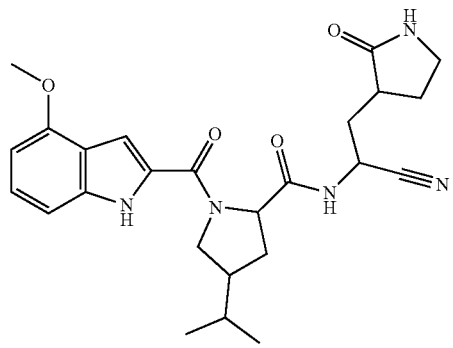 [SMILES: COc1cccc2[nH]c(C(=O)N3CC(C(C)C)CC3C(=O)NC(C#N)CC3CCNC3=O)cc12] |

TABLE 1-continued
Exemplary compounds.
| Compound No. | Structure |
|---|---|
| 417 | 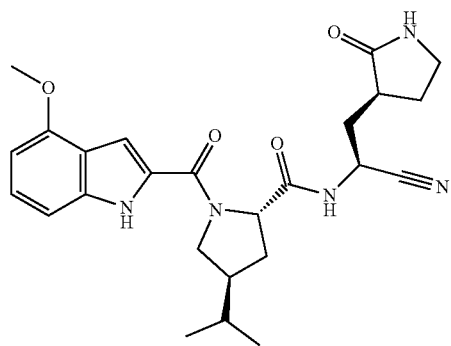 [SMILES: COc1cccc2[nH]c(C(=O)N3C[C@H](C(C)C)C[C@H]3C(=O)N[C@H](C#N)C[C@@H]3CCNC3=O)cc12] |
| 418 | 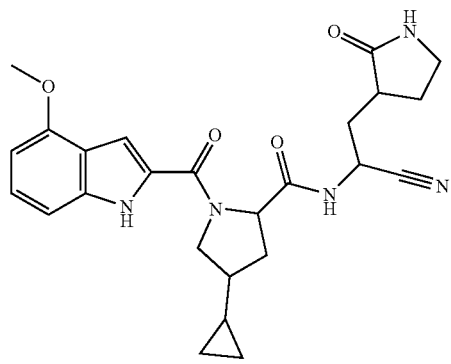 [SMILES: COc1cccc2[nH]c(C(=O)N3CC(C4CC4)CC3C(=O)NC(C#N)CC3CCNC3=O)cc12] |
| 419 | 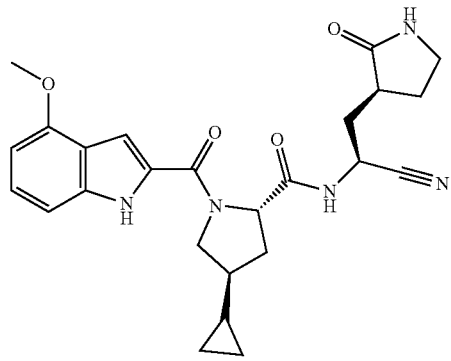 [SMILES: COc1cccc2[nH]c(C(=O)N3C[C@H](C4CC4)C[C@H]3C(=O)N[C@H](C#N)C[C@@H]3CCNC3=O)cc12] |
| 420 | 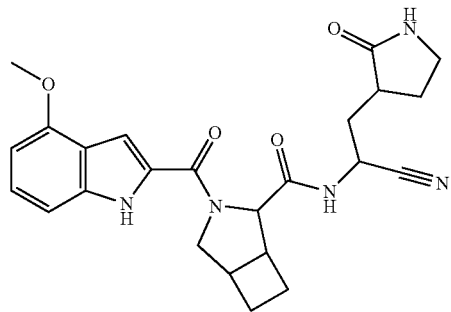 [SMILES: COc1cccc2[nH]c(C(=O)N3CC4CCC4C3C(=O)NC(C#N)CC3CCNC3=O)cc12] |

TABLE 1-continued

Exemplary compounds.

| Compound No. | Structure |
|---|---|
| 421 | 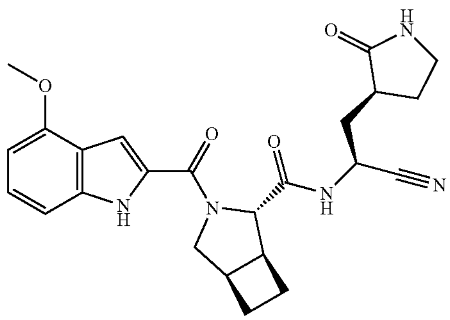 [SMILES: COc1cccc2[nH]c(C(=O)N3C[C@@H]4CC[C@@H]4[C@H]3C(=O)N[C@H](C#N)C[C@@H]3CCNC3=O)cc12] |
| 422 | 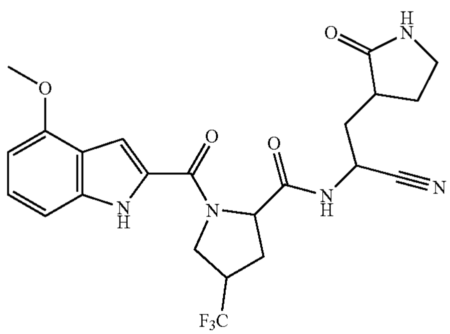 [SMILES: COc1cccc2[nH]c(C(=O)N3CC(C(F)(F)F)CC3C(=O)NC(C#N)CC3CCNC3=O)cc12] |
| 423 | 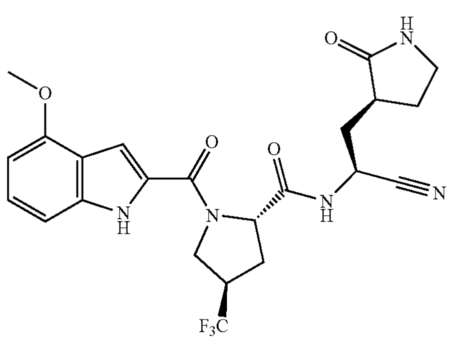 [SMILES: COc1cccc2[nH]c(C(=O)N3C[C@H](C(F)(F)F)C[C@H]3C(=O)N[C@H](C#N)C[C@@H]3CCNC3=O)cc12] |
| 424 | 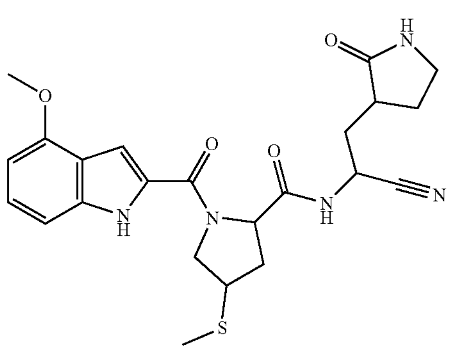 |

TABLE 1-continued

Exemplary compounds.

| Compound No. | Structure |
|---|---|
| 425 | 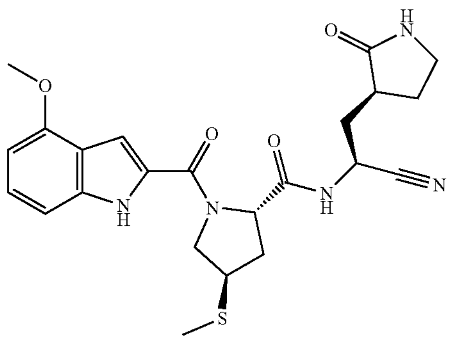 [SMILES: COc1cccc2[nH]c(C(=O)N3C[C@H](SC)C[C@H]3C(=O)N[C@H](C#N)C[C@@H]3CCNC3=O)cc12] |
| 426 | 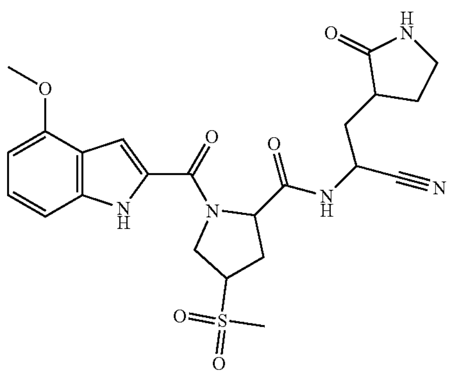 [SMILES: COc1cccc2[nH]c(C(=O)N3CC(S(C)(=O)=O)CC3C(=O)NC(C#N)CC3CCNC3=O)cc12] |
| 427 | 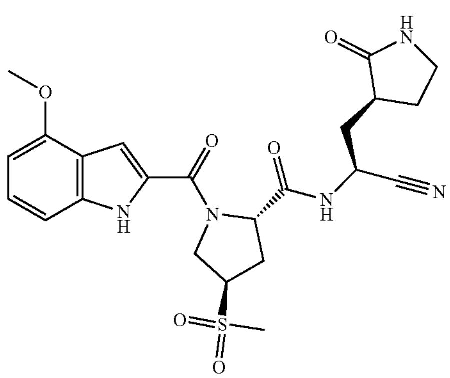 [SMILES: COc1cccc2[nH]c(C(=O)N3C[C@H](S(C)(=O)=O)C[C@H]3C(=O)N[C@H](C#N)C[C@@H]3CCNC3=O)cc12] |
| 428 | 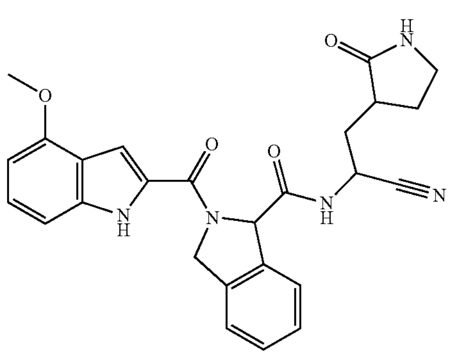 [SMILES: COc1cccc2[nH]c(C(=O)N3Cc4ccccc4C3C(=O)NC(C#N)CC3CCNC3=O)cc12] |

TABLE 1-continued
Exemplary compounds.
| Compound No. | Structure |
|---|---|
| 429 | 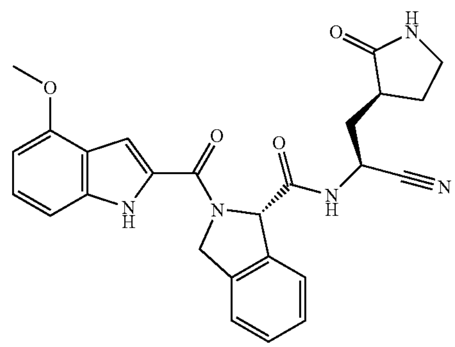 [SMILES: COc1cccc2[nH]c(C(=O)N3Cc4ccccc4[C@H]3C(=O)N[C@H](C#N)C[C@@H]3CCNC3=O)cc12] |
| 430 | 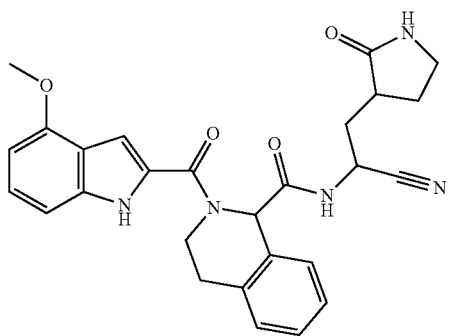 [SMILES: COc1cccc2[nH]c(C(=O)N3CCc4ccccc4C3C(=O)NC(C#N)CC3CCNC3=O)cc12] |
| 431 | 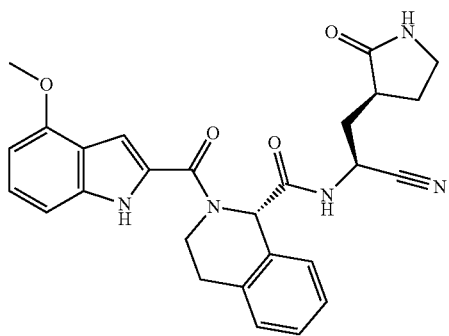 [SMILES: COc1cccc2[nH]c(C(=O)N3CCc4ccccc4[C@H]3C(=O)N[C@H](C#N)C[C@@H]3CCNC3=O)cc12] |
| 432 | 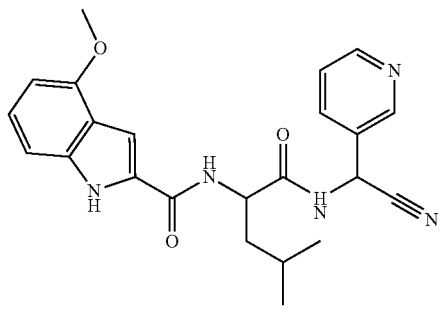 [SMILES: COc1cccc2[nH]c(C(=O)NC(CC(C)C)C(=O)NC(C#N)c3cccnc3)cc12] |

TABLE 1-continued
Exemplary compounds.
| Compound No. | Structure |
|---|---|
| 433 | 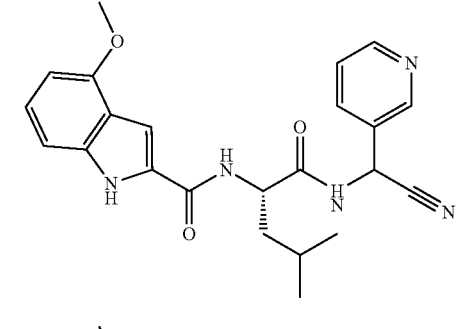 |
| 434 | 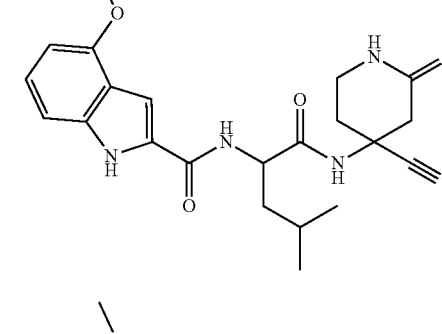 |
| 435 | 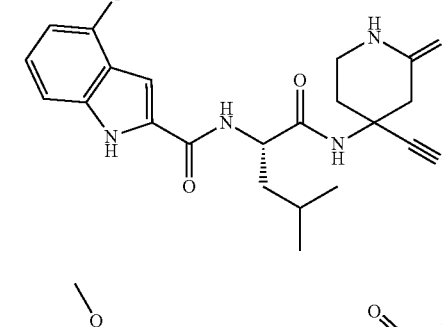 |
| 436 | 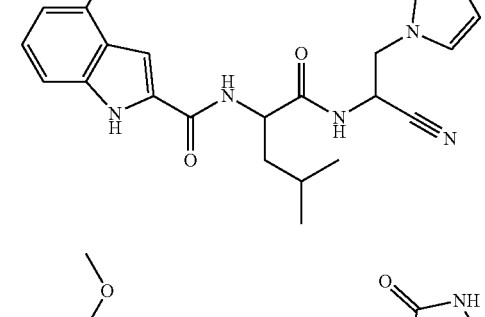 |
| 437 | 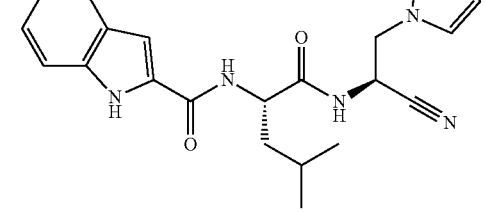 |

US 11,472,793 B2
231                                                                    232
TABLE 1-continued
Exemplary compounds.
| Compound No. | Structure |
|---|---|
| 438 | 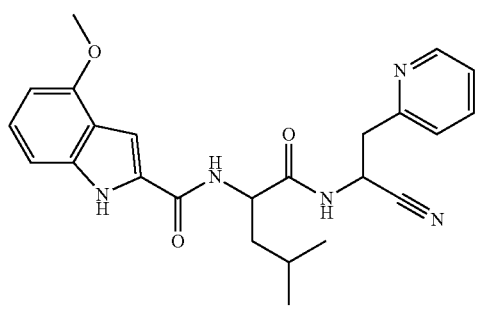 [SMILES: COc1cccc2[nH]c(C(=O)NC(CC(C)C)C(=O)NC(C#N)Cc3ccccn3)cc12] |
| 439 | 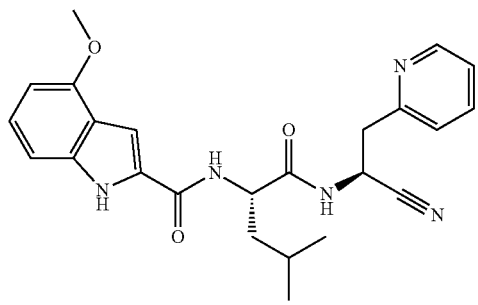 [SMILES: COc1cccc2[nH]c(C(=O)N[C@@H](CC(C)C)C(=O)N[C@H](C#N)Cc3ccccn3)cc12] |
| 440 | 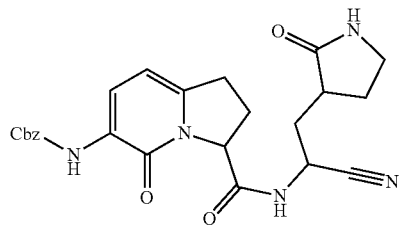 [SMILES: N#CC(CC1CCNC1=O)NC(=O)C1CCc2ccc(NC(=O)OCc3ccccc3)c(=O)n21] |
| 441 | 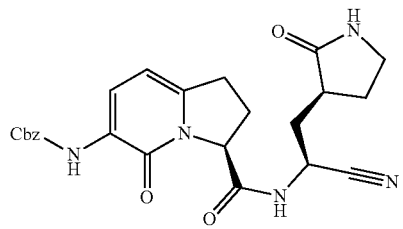 [SMILES: N#C[C@H](C[C@@H]1CCNC1=O)NC(=O)[C@@H]1CCc2ccc(NC(=O)OCc3ccccc3)c(=O)n21] |
| 442 | 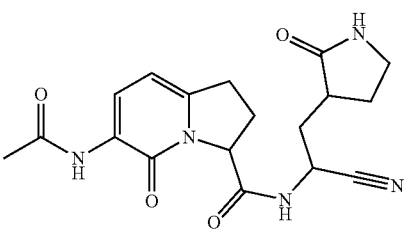 [SMILES: CC(=O)Nc1ccc2n(c1=O)C(C(=O)NC(C#N)CC1CCNC1=O)CC2] |

TABLE 1-continued

Exemplary compounds.

| Compound No. | Structure |
|---|---|
| 443 | 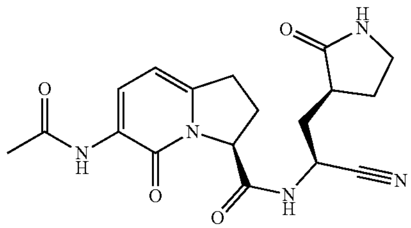 [SMILES: CC(=O)Nc1ccc2n(c1=O)[C@H](C(=O)N[C@H](C#N)C[C@@H]1CCNC1=O)CC2] |
| 444 | 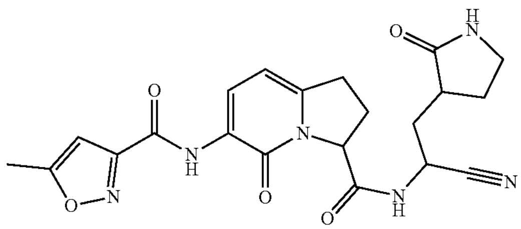 [SMILES: Cc1cc(C(=O)Nc2ccc3n(c2=O)C(C(=O)NC(C#N)CC2CCNC2=O)CC3)no1] |
| 445 | 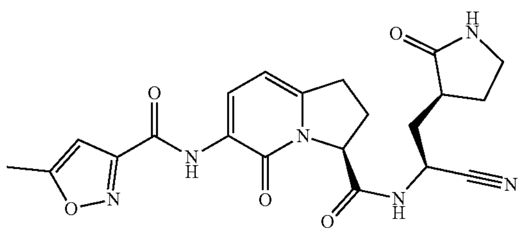 [SMILES: Cc1cc(C(=O)Nc2ccc3n(c2=O)[C@H](C(=O)N[C@H](C#N)C[C@@H]2CCNC2=O)CC3)no1] |
| 446 | 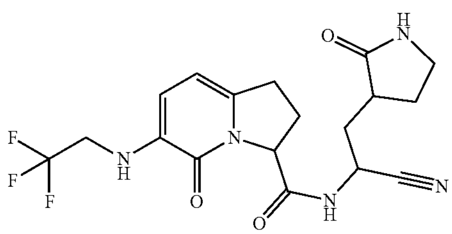 [SMILES: N#CC(CC1CCNC1=O)NC(=O)C1CCc2ccc(NCC(F)(F)F)c(=O)n21] |
| 447 | 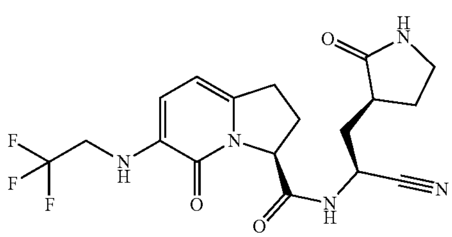 [SMILES: N#C[C@H](C[C@@H]1CCNC1=O)NC(=O)[C@@H]1CCc2ccc(NCC(F)(F)F)c(=O)n21] |
| 448 | 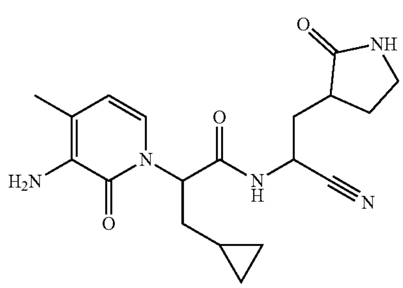 [SMILES: Cc1ccn(C(CC2CC2)C(=O)NC(C#N)CC2CCNC2=O)c(=O)c1N] |

TABLE 1-continued

Exemplary compounds.

| Compound No. | Structure |
|---|---|
| 449 | 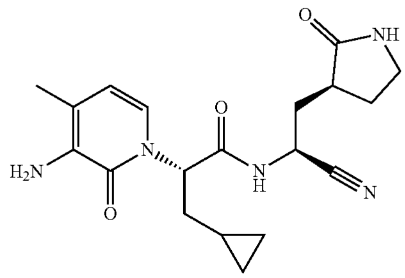 [SMILES: Cc1ccn([C@@H](CC2CC2)C(=O)N[C@H](C#N)C[C@@H]2CCNC2=O)c(=O)c1N] |
| 450 | 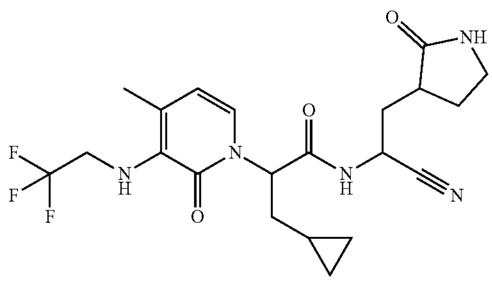 [SMILES: Cc1ccn(C(CC2CC2)C(=O)NC(C#N)CC2CCNC2=O)c(=O)c1NCC(F)(F)F] |
| 451 | 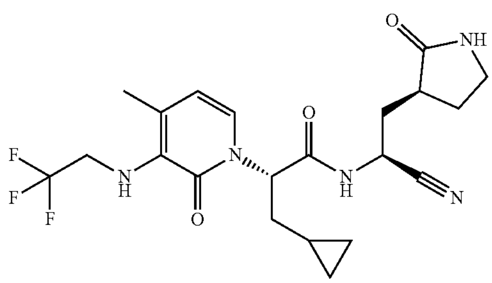 [SMILES: Cc1ccn([C@@H](CC2CC2)C(=O)N[C@H](C#N)C[C@@H]2CCNC2=O)c(=O)c1NCC(F)(F)F] |
| 452 | 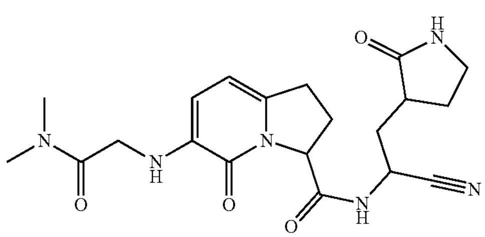 [SMILES: CN(C)C(=O)CNc1ccc2n(c1=O)C(C(=O)NC(C#N)CC1CCNC1=O)CC2] |
| 453 | 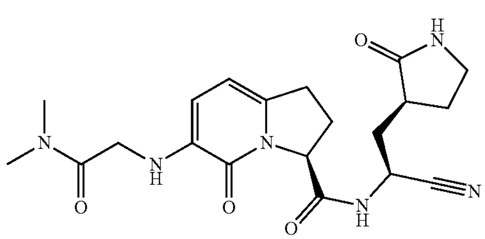 [SMILES: CN(C)C(=O)CNc1ccc2n(c1=O)[C@H](C(=O)N[C@H](C#N)C[C@@H]1CCNC1=O)CC2] |
| 454 | 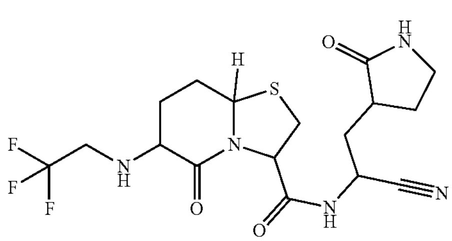 [SMILES: N#CC(CC1CCNC1=O)NC(=O)C1CSC2CCC(NCC(F)(F)F)C(=O)N21] |

TABLE 1-continued

Exemplary compounds.

| Compound No. | Structure |
|---|---|
| 455 | 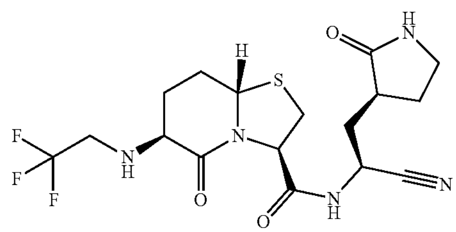 [SMILES: N#C[C@H](C[C@@H]1CCNC1=O)NC(=O)[C@@H]1CS[C@H]2CC[C@H](NCC(F)(F)F)C(=O)N21] |
| 456 | 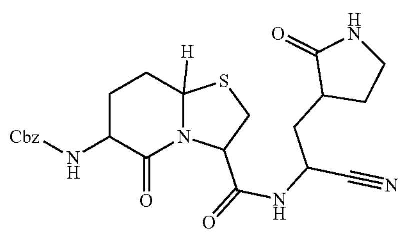 [SMILES: N#CC(CC1CCNC1=O)NC(=O)C1CSC2CCC(NC(=O)OCc3ccccc3)C(=O)N21] |
| 457 | 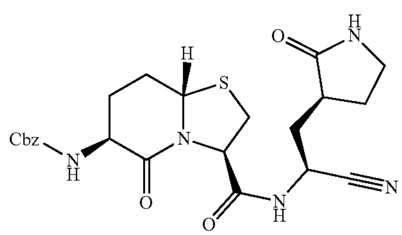 [SMILES: N#C[C@H](C[C@@H]1CCNC1=O)NC(=O)[C@@H]1CS[C@H]2CC[C@H](NC(=O)OCc3ccccc3)C(=O)N21] |
| 458 | 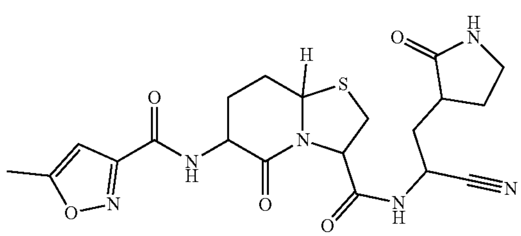 [SMILES: Cc1cc(C(=O)NC2CCC3SCC(C(=O)NC(C#N)CC4CCNC4=O)N3C2=O)no1] |
| 459 | 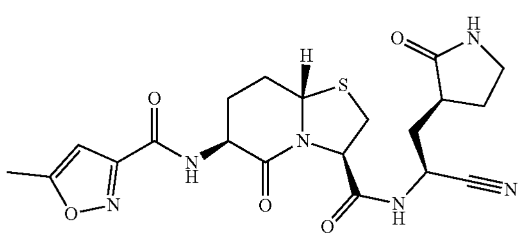 [SMILES: Cc1cc(C(=O)N[C@H]2CC[C@@H]3SC[C@@H](C(=O)N[C@H](C#N)C[C@@H]4CCNC4=O)N3C2=O)no1] |
| 460 | 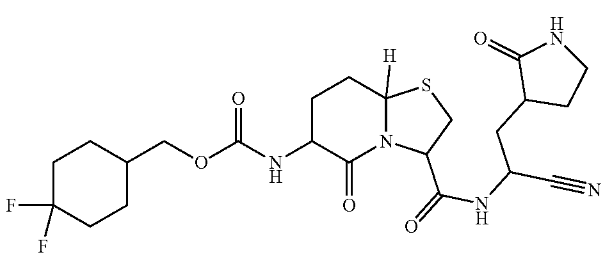 [SMILES: N#CC(CC1CCNC1=O)NC(=O)C1CSC2CCC(NC(=O)OCC3CCC(F)(F)CC3)C(=O)N21] |

TABLE 1-continued

Exemplary compounds.

| Compound No. | Structure |
|---|---|
| 461 | 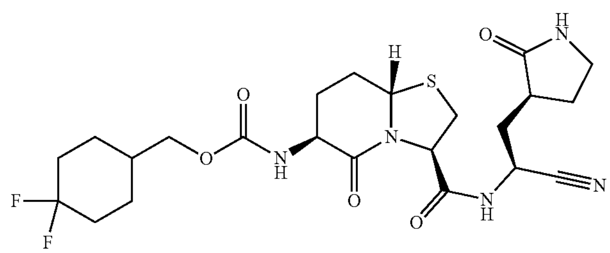 [SMILES: N#C[C@H](C[C@@H]1CCNC1=O)NC(=O)[C@@H]1CS[C@H]2CC[C@H](NC(=O)OCC3CCC(F)(F)CC3)C(=O)N21] |
| 462 | 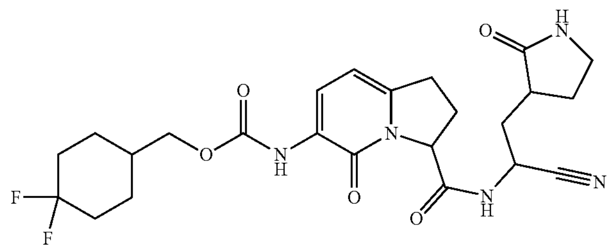 [SMILES: N#CC(CC1CCNC1=O)NC(=O)C1CCc2ccc(NC(=O)OCC3CCC(F)(F)CC3)c(=O)n21] |
| 463 | 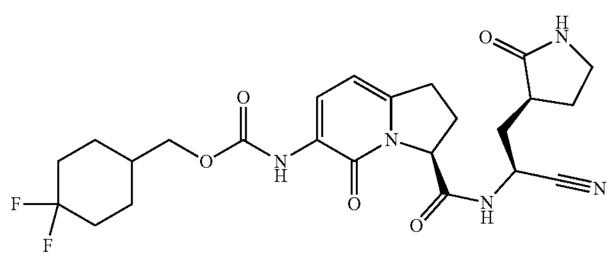 [SMILES: N#C[C@H](C[C@@H]1CCNC1=O)NC(=O)[C@@H]1CCc2ccc(NC(=O)OCC3CCC(F)(F)CC3)c(=O)n21] |
| 464 | 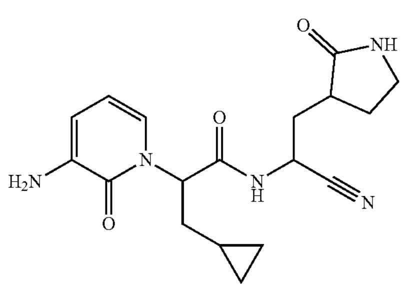 [SMILES: N#CC(CC1CCNC1=O)NC(=O)C(CC1CC1)n1cccc(N)c1=O] |
| 465 | 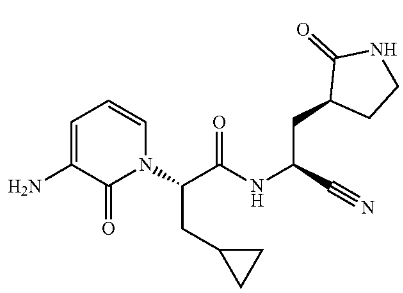 [SMILES: N#C[C@H](C[C@@H]1CCNC1=O)NC(=O)[C@H](CC1CC1)n1cccc(N)c1=O] |

TABLE 1-continued

Exemplary compounds.

| Compound No. | Structure |
|---|---|
| 466 | 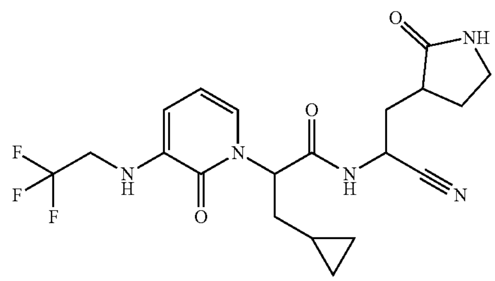 [SMILES: N#CC(CC1CCNC1=O)NC(=O)C(CC1CC1)n1cccc(NCC(F)(F)F)c1=O] |
| 467 | 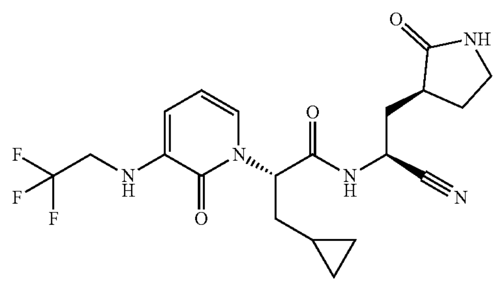 [SMILES: N#C[C@H](C[C@@H]1CCNC1=O)NC(=O)[C@H](CC1CC1)n1cccc(NCC(F)(F)F)c1=O] |
| 468 | 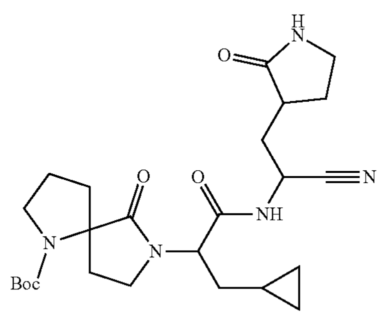 [SMILES: CC(C)(C)OC(=O)N1CCCC12CCN(C(CC1CC1)C(=O)NC(C#N)CC1CCNC1=O)C2=O] |
| 469 | 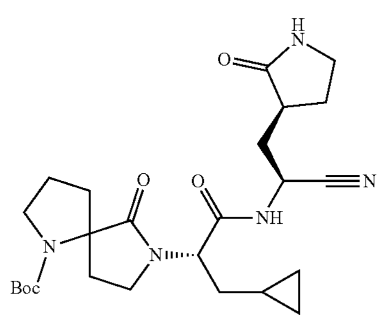 [SMILES: CC(C)(C)OC(=O)N1CCCC12CCN([C@@H](CC1CC1)C(=O)N[C@H](C#N)C[C@@H]1CCNC1=O)C2=O] |
| 470 | 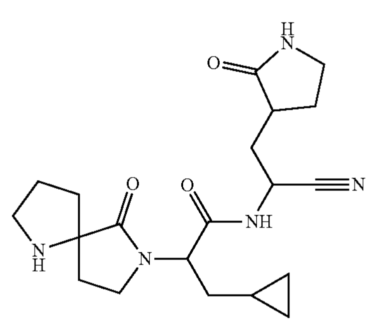 [SMILES: N#CC(CC1CCNC1=O)NC(=O)C(CC1CC1)N1CCC2(CCCN2)C1=O] |

TABLE 1-continued

Exemplary compounds.

| Compound No. | Structure |
|---|---|
| 471 | 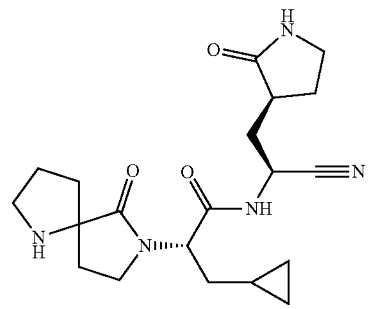 [SMILES: N#C[C@H](C[C@@H]1CCNC1=O)NC(=O)[C@H](CC1CC1)N1CCC2(CCCN2)C1=O] |
| 472 | 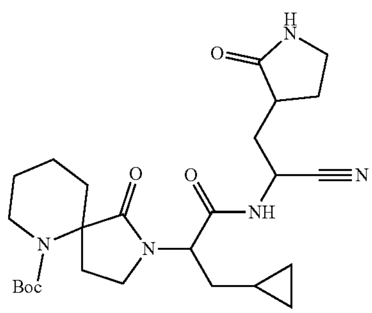 [SMILES: CC(C)(C)OC(=O)N1CCCCC12CCN(C(CC1CC1)C(=O)NC(C#N)CC1CCNC1=O)C2=O] |
| 473 | 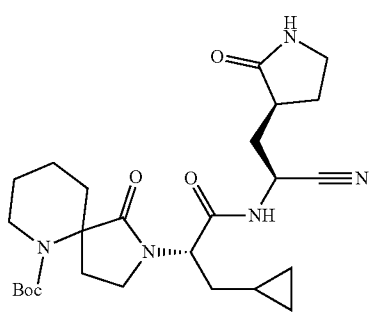 [SMILES: CC(C)(C)OC(=O)N1CCCCC12CCN([C@@H](CC1CC1)C(=O)N[C@H](C#N)C[C@@H]1CCNC1=O)C2=O] |
| 474 | 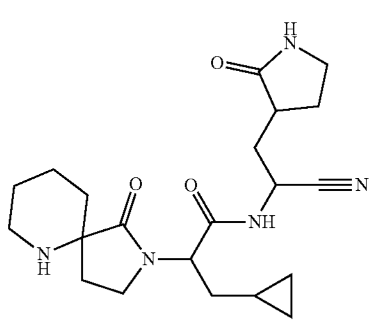 [SMILES: N#CC(CC1CCNC1=O)NC(=O)C(CC1CC1)N1CCC2(CCCCN2)C1=O] |

TABLE 1-continued

Exemplary compounds.

| Compound No. | Structure |
|---|---|
| 475 | 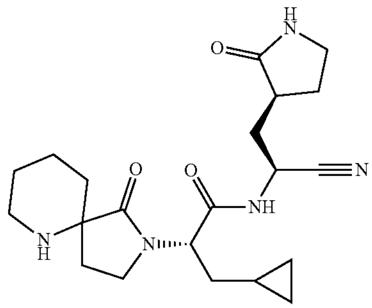 [SMILES: N#C[C@H](C[C@@H]1CCNC1=O)NC(=O)[C@H](CC1CC1)N1CCC2(CCCCN2)C1=O] |
| 476 | 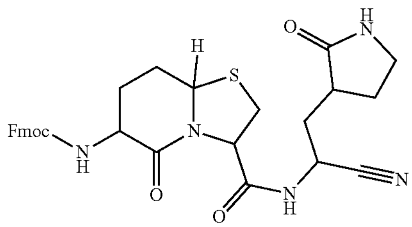 |
| 477 | 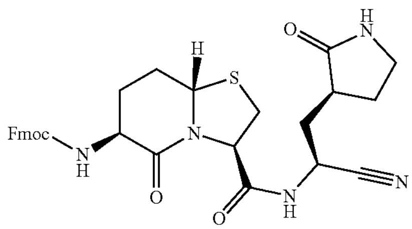 |
| 478 | 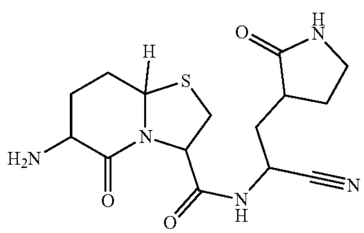 [SMILES: N#CC(CC1CCNC1=O)NC(=O)C1CSC2CCC(N)C(=O)N21] |
| 479 | 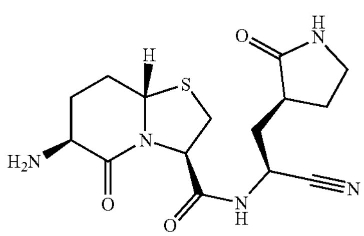 [SMILES: N#C[C@H](C[C@@H]1CCNC1=O)NC(=O)[C@@H]1CS[C@H]2CC[C@H](N)C(=O)N21] |
| 480 | 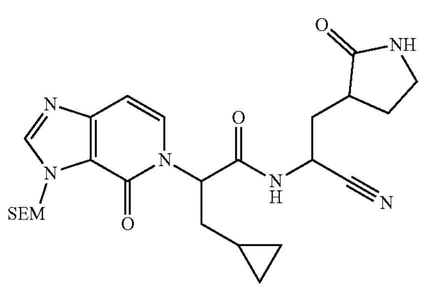 [SMILES: C[Si](C)(C)CCOCn1cnc2ccn(C(CC3CC3)C(=O)NC(C#N)CC3CCNC3=O)c(=O)c21] |

TABLE 1-continued

Exemplary compounds.

| Compound No. | Structure |
|---|---|
| 481 | 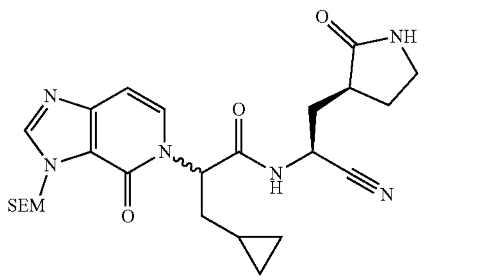 [SMILES: C[Si](C)(C)CCOCn1cnc2ccn(C(CC3CC3)C(=O)N[C@H](C#N)C[C@@H]3CCNC3=O)c(=O)c21] |
| 482 | 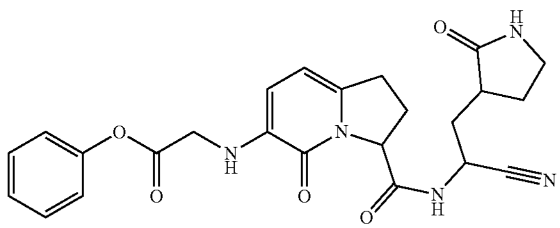 [SMILES: N#CC(CC1CCNC1=O)NC(=O)C1CCc2ccc(NCC(=O)Oc3ccccc3)c(=O)n21] |
| 483 | 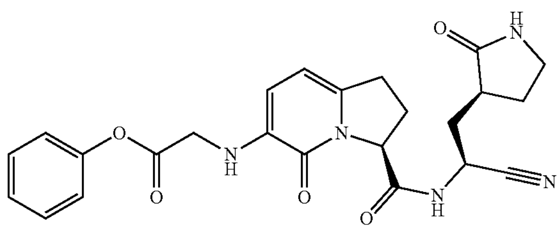 [SMILES: N#C[C@H](C[C@@H]1CCNC1=O)NC(=O)[C@@H]1CCc2ccc(NCC(=O)Oc3ccccc3)c(=O)n21] |
| 484 | 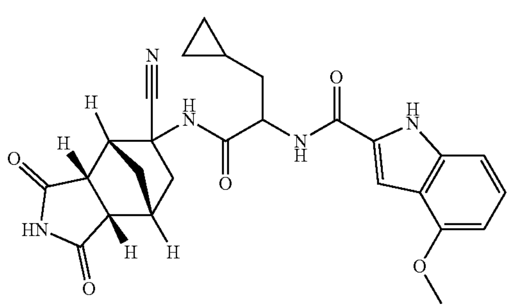 [SMILES: COc1cccc2[nH]c(C(=O)NC(CC3CC3)C(=O)NC3(C#N)C[C@H]4C[C@@H]3[C@H]3C(=O)NC(=O)[C@@H]43)cc12] |
| 485 | 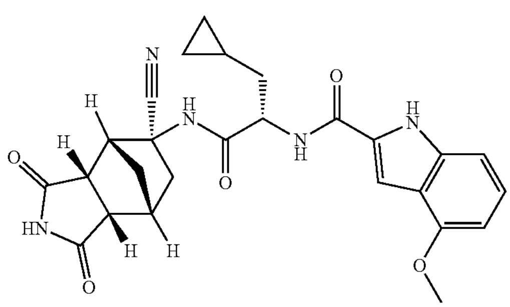 [SMILES: COc1cccc2[nH]c(C(=O)N[C@@H](CC3CC3)C(=O)N[C@@]3(C#N)C[C@H]4C[C@@H]3[C@H]3C(=O)NC(=O)[C@@H]43)cc12] |

TABLE 1-continued

Exemplary compounds.

| Compound No. | Structure |
|---|---|
| 486 | 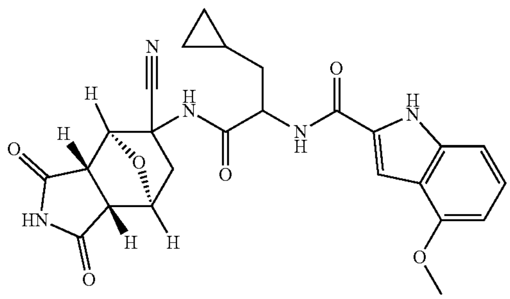 [SMILES: COc1cccc2[nH]c(C(=O)NC(CC3CC3)C(=O)NC3(C#N)C[C@@H]4O[C@H]3[C@H]3C(=O)NC(=O)[C@H]34)cc12] |
| 487 | 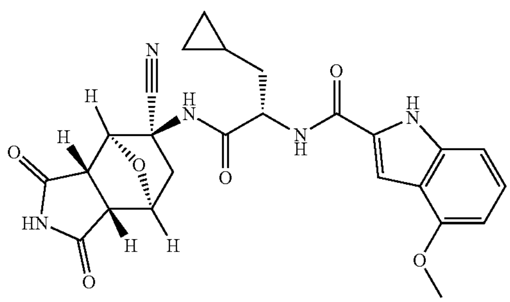 [SMILES: COc1cccc2[nH]c(C(=O)N[C@@H](CC3CC3)C(=O)N[C@@]3(C#N)C[C@@H]4O[C@H]3[C@H]3C(=O)NC(=O)[C@H]34)cc12] |
| 488 | 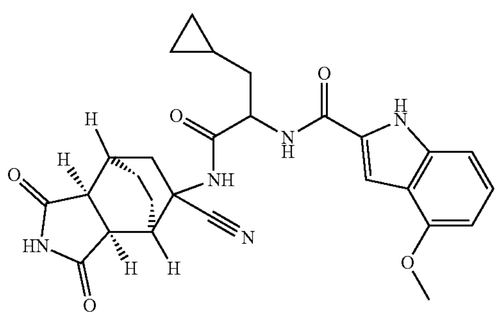 |
| 489 | 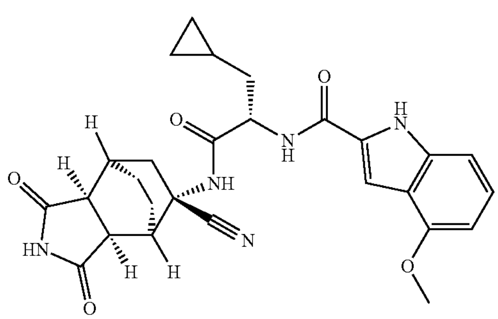 |
| 490 | 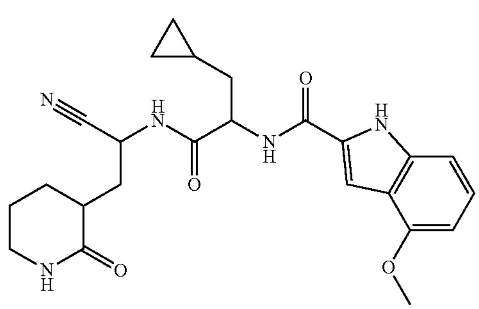 [SMILES: COc1cccc2[nH]c(C(=O)NC(CC3CC3)C(=O)NC(C#N)CC3CCCNC3=O)cc12] |

TABLE 1-continued

Exemplary compounds.

| Compound No. | Structure |
|---|---|
| 491 | 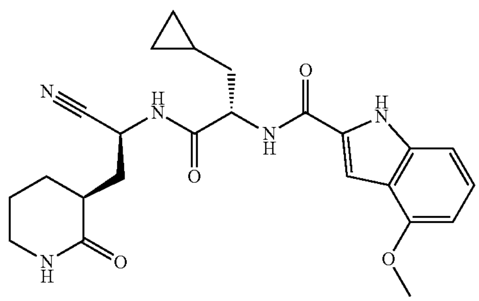 [SMILES: COc1cccc2[nH]c(C(=O)N[C@@H](CC3CC3)C(=O)N[C@H](C#N)C[C@@H]3CCCNC3=O)cc12] |
| 492 | 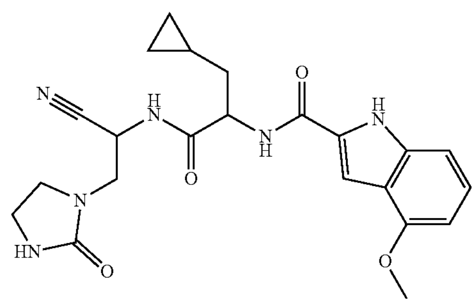 [SMILES: COc1cccc2[nH]c(C(=O)NC(CC3CC3)C(=O)NC(C#N)CN3CCNC3=O)cc12] |
| 493 | 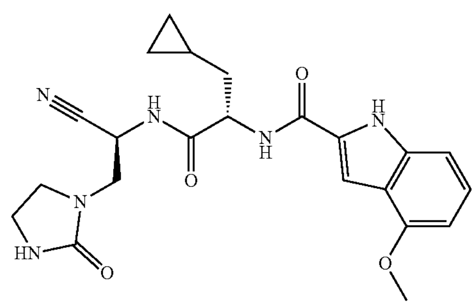 [SMILES: COc1cccc2[nH]c(C(=O)N[C@@H](CC3CC3)C(=O)N[C@H](C#N)CN3CCNC3=O)cc12] |
| 494 | 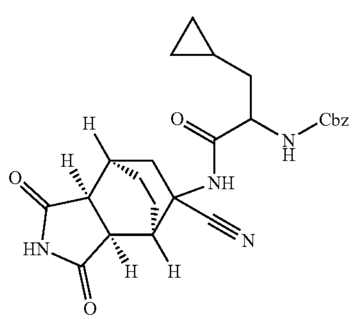 [SMILES: N#CC1(NC(=O)C(CC2CC2)NC(=O)OCc2ccccc2)C[C@H]2CC[C@@H]1[C@H]1C(=O)NC(=O)[C@@H]21] |
| 495 | 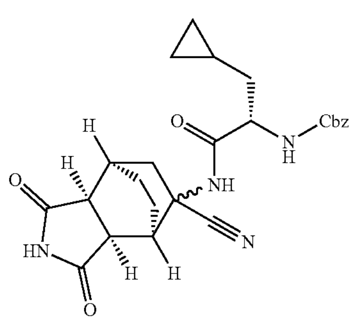 [SMILES: N#CC1(NC(=O)[C@H](CC2CC2)NC(=O)OCc2ccccc2)C[C@H]2CC[C@@H]1[C@H]1C(=O)NC(=O)[C@@H]21] |

TABLE 1-continued
Exemplary compounds.
| Compound No. | Structure |
|---|---|
| 496 | 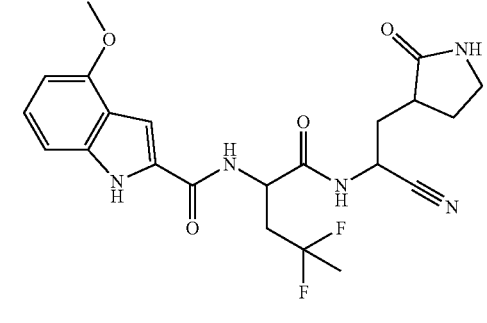 [SMILES: COc1cccc2[nH]c(C(=O)NC(CC(C)(F)F)C(=O)NC(C#N)CC3CCNC3=O)cc12] |
| 497 | 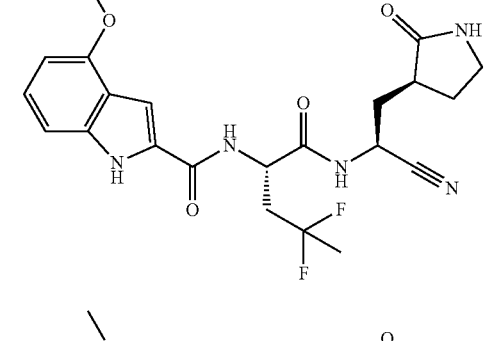 |
| 498 | 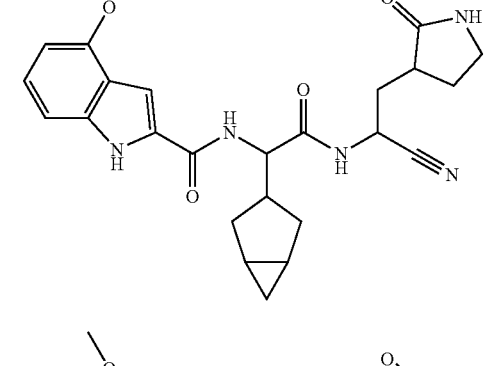 |
| 499 | 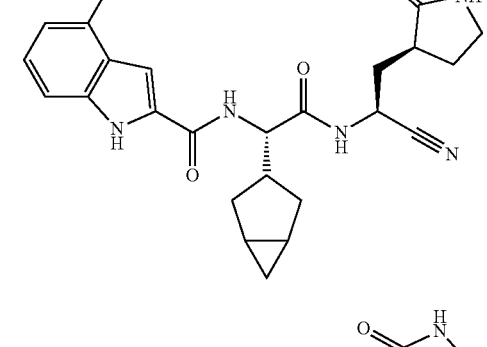 |
| 500 | 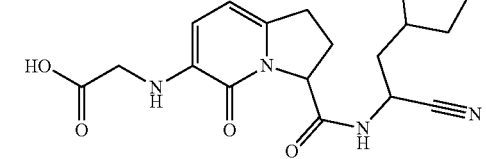 |

TABLE 1-continued

Exemplary compounds.

| Compound No. | Structure |
|---|---|
| 501 | 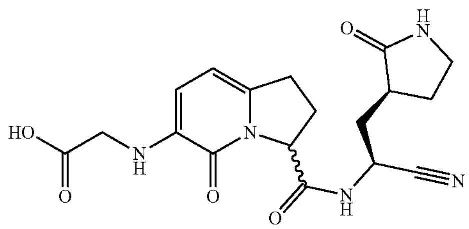 [SMILES: N#C[C@H](C[C@@H]1CCNC1=O)NC(=O)C1CCc2ccc(NCC(=O)O)c(=O)n21] |
| 502 | 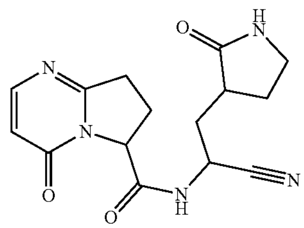 [SMILES: N#CC(CC1CCNC1=O)NC(=O)C1CCc2nccc(=O)n21] |
| 503 | 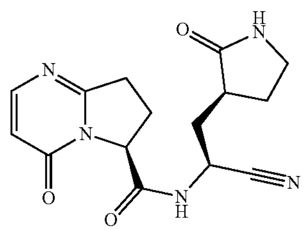 [SMILES: N#C[C@H](C[C@@H]1CCNC1=O)NC(=O)[C@@H]1CCc2nccc(=O)n21] |
| 504 | 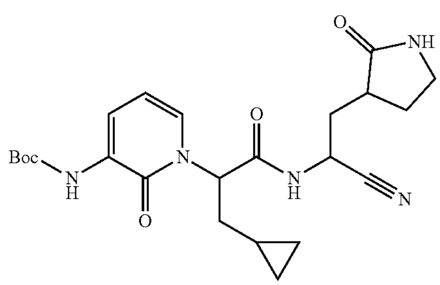 [SMILES: CC(C)(C)OC(=O)Nc1cccn(C(CC2CC2)C(=O)NC(C#N)CC2CCNC2=O)c1=O] |
| 505 | 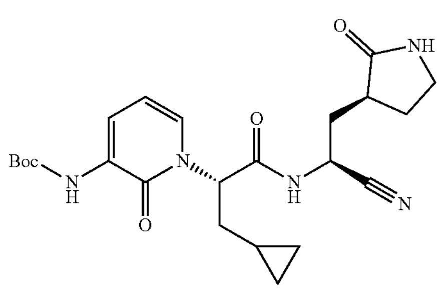 [SMILES: CC(C)(C)OC(=O)Nc1cccn([C@@H](CC2CC2)C(=O)N[C@H](C#N)C[C@@H]2CCNC2=O)c1=O] |

TABLE 1-continued

Exemplary compounds.

| Compound No. | Structure |
|---|---|
| 506 | 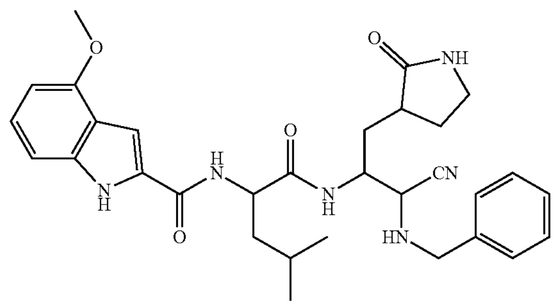 [SMILES: COc1cccc2[nH]c(C(=O)NC(CC(C)C)C(=O)NC(CC3CCNC3=O)C(C#N)NCc3ccccc3)cc12] |
| 507 | 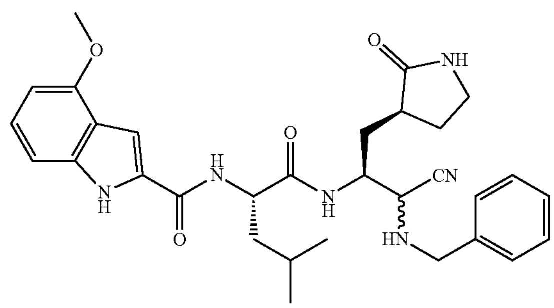 [SMILES: COc1cccc2[nH]c(C(=O)N[C@@H](CC(C)C)C(=O)N[C@@H](C[C@@H]3CCNC3=O)C(C#N)NCc3ccccc3)cc12] |
| 508 | 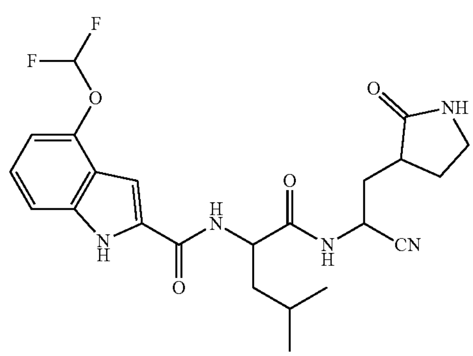 [SMILES: CC(C)CC(NC(=O)c1cc2c(OC(F)F)cccc2[nH]1)C(=O)NC(C#N)CC1CCNC1=O] |
| 509 | 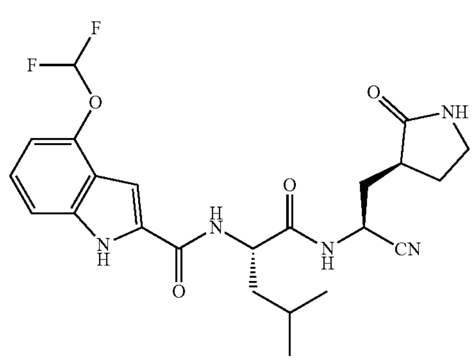 [SMILES: CC(C)C[C@H](NC(=O)c1cc2c(OC(F)F)cccc2[nH]1)C(=O)N[C@H](C#N)C[C@@H]1CCNC1=O] |

TABLE 1-continued

Exemplary compounds.

| Compound No. | Structure |
|---|---|
| 510 | 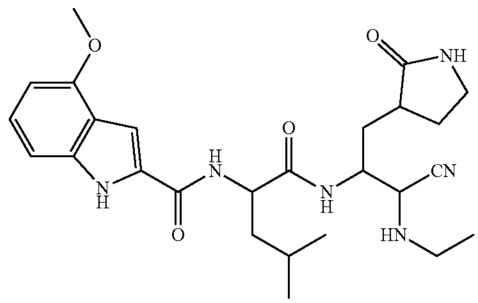 [SMILES: CCNC(C#N)C(CC1CCNC1=O)NC(=O)C(CC(C)C)NC(=O)c1cc2c(OC)cccc2[nH]1] |
| 511 | 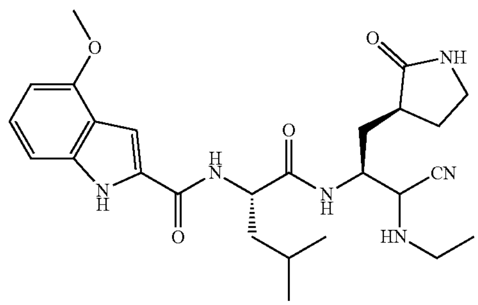 [SMILES: CCNC(C#N)[C@H](C[C@@H]1CCNC1=O)NC(=O)[C@H](CC(C)C)NC(=O)c1cc2c(OC)cccc2[nH]1] |
| 512 | 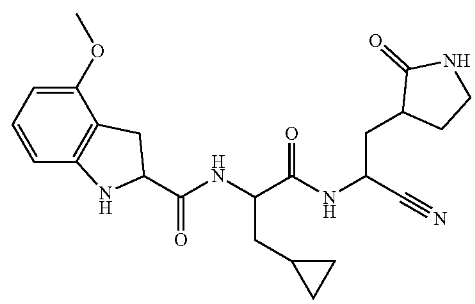 [SMILES: COc1cccc2c1CC(C(=O)NC(CC1CC1)C(=O)NC(C#N)CC1CCNC1=O)N2] |
| 513 | 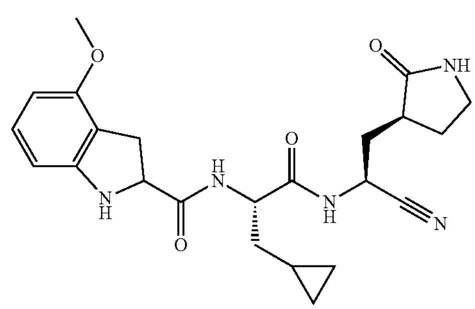 [SMILES: COc1cccc2c1CC(C(=O)N[C@@H](CC1CC1)C(=O)N[C@H](C#N)C[C@@H]1CCNC1=O)N2] |

TABLE 1-continued
Exemplary compounds.
| Compound No. | Structure |
|---|---|
| 514 | 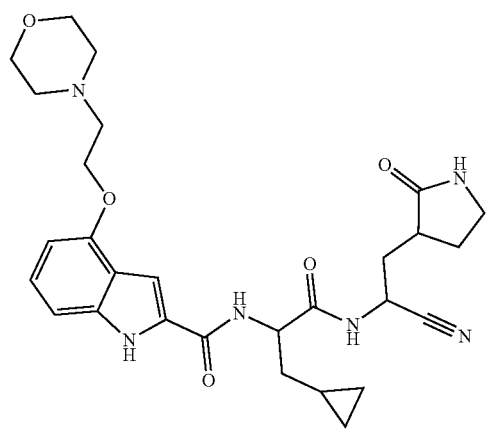 [SMILES: N#CC(CC1CCNC1=O)NC(=O)C(CC1CC1)NC(=O)c1cc2c(OCCN3CCOCC3)cccc2[nH]1] |
| 515 | 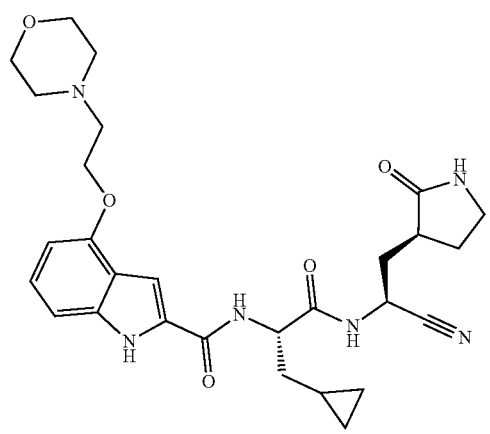 [SMILES: N#C[C@H](C[C@@H]1CCNC1=O)NC(=O)[C@H](CC1CC1)NC(=O)c1cc2c(OCCN3CCOCC3)cccc2[nH]1] |
| 516 | 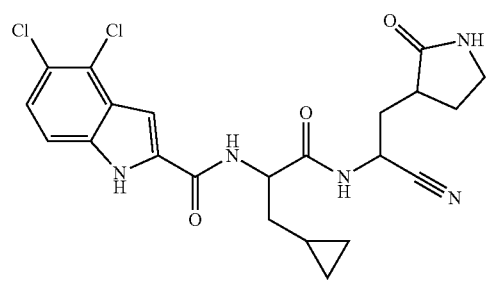 [SMILES: N#CC(CC1CCNC1=O)NC(=O)C(CC1CC1)NC(=O)c1cc2c(Cl)c(Cl)ccc2[nH]1] |
| 517 | 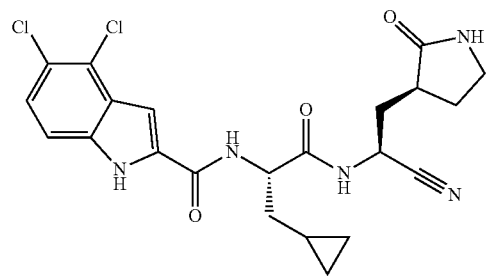 [SMILES: N#C[C@H](C[C@@H]1CCNC1=O)NC(=O)[C@H](CC1CC1)NC(=O)c1cc2c(Cl)c(Cl)ccc2[nH]1] |

TABLE 1-continued

Exemplary compounds.

| Compound No. | Structure |
|---|---|
| 518 | 5-chloro-1H-indole-2-carboxamide linked to cyclopropylalanine amide linked to 2-oxopyrrolidin-3-yl cyanomethyl group |
| 519 | 5-chloro-1H-indole-2-carboxamide linked to (S)-cyclopropylalanine amide linked to (S)-2-oxopyrrolidin-3-yl cyanomethyl group |
| 520 | 4,7-dichloro-1H-benzimidazole-2-carboxamide linked to cyclopropylalanine amide linked to 2-oxopyrrolidin-3-yl cyanomethyl group |
| 521 | 4,7-dichloro-1H-benzimidazole-2-carboxamide linked to (S)-cyclopropylalanine amide linked to (S)-2-oxopyrrolidin-3-yl cyanomethyl group |
| 522 | 4-methoxy-7-chloro-1H-benzimidazole-2-carboxamide linked to cyclopropylalanine amide linked to 2-oxopyrrolidin-3-yl cyanomethyl group |

TABLE 1-continued

Exemplary compounds.

| Compound No. | Structure |
|---|---|
| 523 | 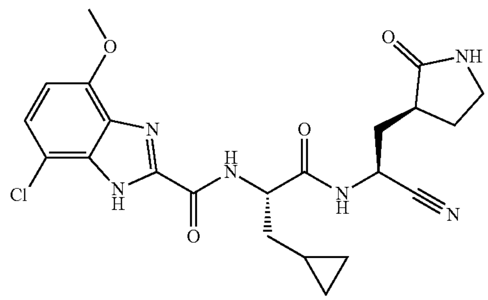 |
| 524 | 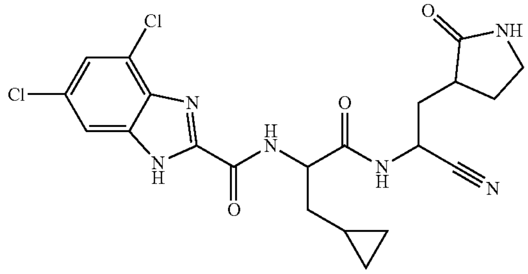 [SMILES: N#CC(CC1CCNC1=O)NC(=O)C(CC1CC1)NC(=O)c1nc2c(Cl)cc(Cl)cc2[nH]1] |
| 525 | 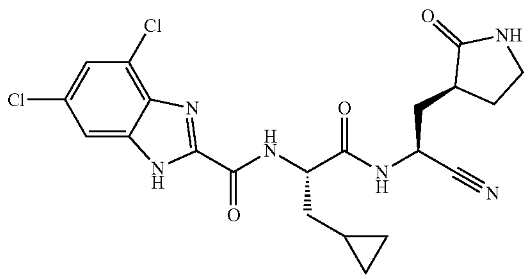 [SMILES: N#C[C@H](C[C@@H]1CCNC1=O)NC(=O)[C@H](CC1CC1)NC(=O)c1nc2c(Cl)cc(Cl)cc2[nH]1] |
| 526 | 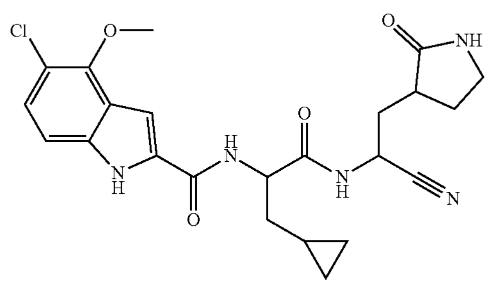 [SMILES: COc1c(Cl)ccc2[nH]c(C(=O)NC(CC3CC3)C(=O)NC(C#N)CC3CCNC3=O)cc12] |
| 527 | 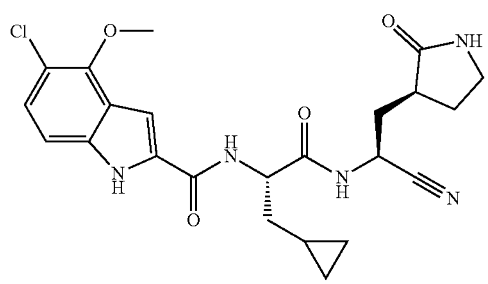 [SMILES: COc1c(Cl)ccc2[nH]c(C(=O)N[C@@H](CC3CC3)C(=O)N[C@H](C#N)C[C@@H]3CCNC3=O)cc12] |

TABLE 1-continued
Exemplary compounds.
| Compound No. | Structure |
|---|---|
| 528 | 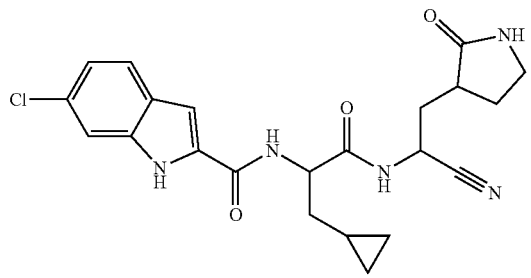 [SMILES: N#CC(CC1CCNC1=O)NC(=O)C(CC1CC1)NC(=O)c1cc2ccc(Cl)cc2[nH]1] |
| 529 | 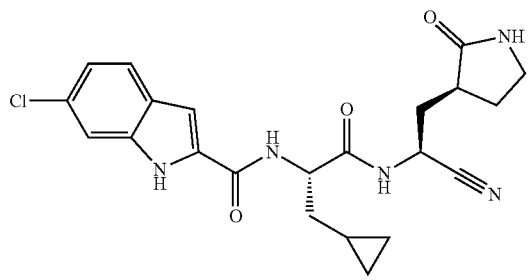 [SMILES: N#C[C@H](C[C@@H]1CCNC1=O)NC(=O)[C@H](CC1CC1)NC(=O)c1cc2ccc(Cl)cc2[nH]1] |
| 530 | 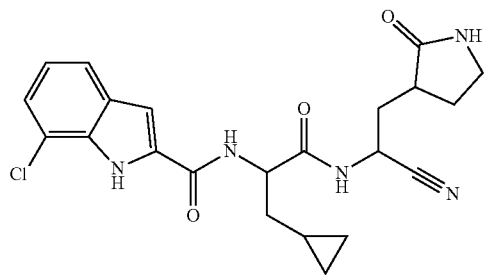 [SMILES: N#CC(CC1CCNC1=O)NC(=O)C(CC1CC1)NC(=O)c1cc2cccc(Cl)c2[nH]1] |
| 531 | 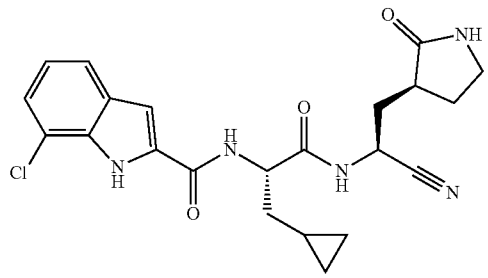 [SMILES: N#C[C@H](C[C@@H]1CCNC1=O)NC(=O)[C@H](CC1CC1)NC(=O)c1cc2cccc(Cl)c2[nH]1] |
| 532 | 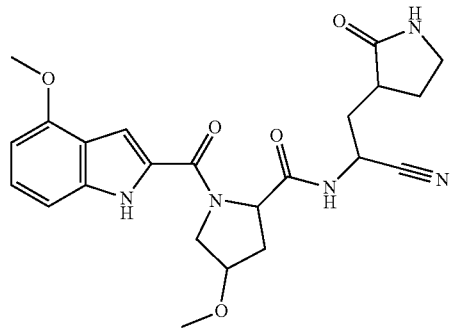 [SMILES: COc1cccc2[nH]c(C(=O)N3CC(OC)CC3C(=O)NC(C#N)CC3CCNC3=O)cc12] |

TABLE 1-continued

Exemplary compounds.

| Compound No. | Structure |
|---|---|
| 533 | 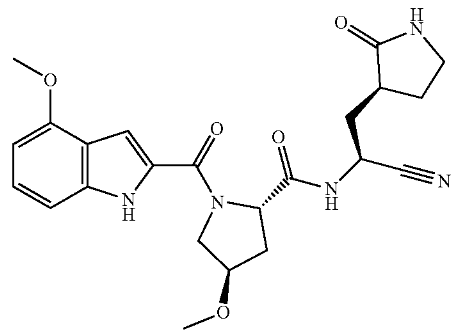 [SMILES: COc1cccc2[nH]c(C(=O)N3C[C@H](OC)C[C@H]3C(=O)N[C@H](C#N)C[C@@H]3CCNC3=O)cc12] |
| 534 | 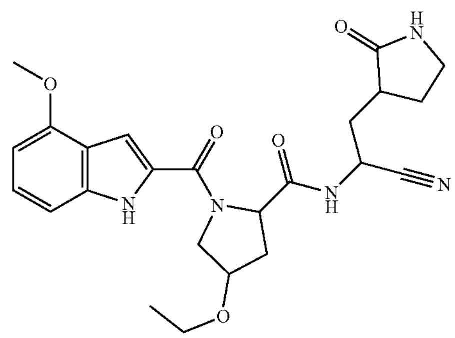 [SMILES: CCOC1CC(C(=O)NC(C#N)CC2CCNC2=O)N(C(=O)c2cc3c(OC)cccc3[nH]2)C1] |
| 535 | 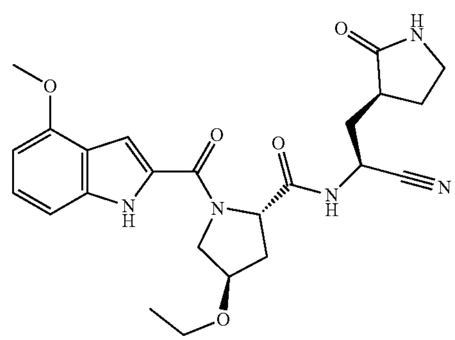 [SMILES: CCO[C@@H]1C[C@@H](C(=O)N[C@H](C#N)C[C@@H]2CCNC2=O)N(C(=O)c2cc3c(OC)cccc3[nH]2)C1] |
| 536 | 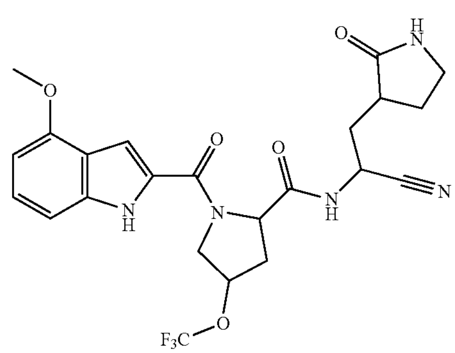 [SMILES: COc1cccc2[nH]c(C(=O)N3CC(OC(F)(F)F)CC3C(=O)NC(C#N)CC3CCNC3=O)cc12] |

TABLE 1-continued

Exemplary compounds.

| Compound No. | Structure |
|---|---|
| 537 | 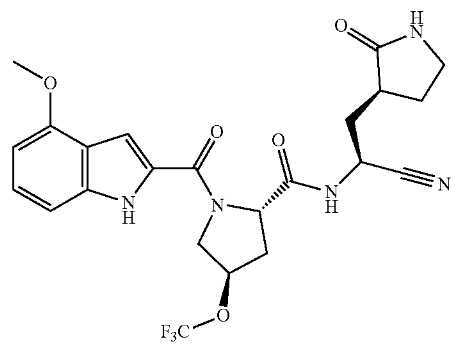 [SMILES: COc1cccc2[nH]c(C(=O)N3C[C@H](OC(F)(F)F)C[C@H]3C(=O)N[C@H](C#N)C[C@@H]3CCNC3=O)cc12] |
| 538 | 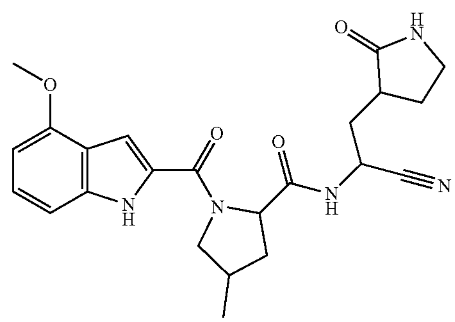 [SMILES: COc1cccc2[nH]c(C(=O)N3CC(C)CC3C(=O)NC(C#N)CC3CCNC3=O)cc12] |
| 539 | 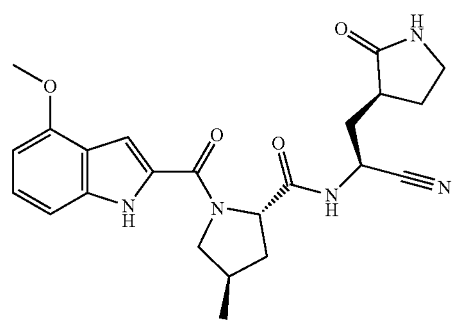 [SMILES: COc1cccc2[nH]c(C(=O)N3C[C@H](C)C[C@H]3C(=O)N[C@H](C#N)C[C@@H]3CCNC3=O)cc12] |
| 540 | 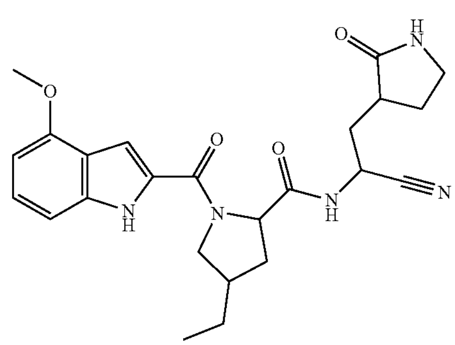 [SMILES: CCC1CC(C(=O)NC(C#N)CC2CCNC2=O)N(C(=O)c2cc3c(OC)cccc3[nH]2)C1] |

TABLE 1-continued
Exemplary compounds.
| Compound No. | Structure |
|---|---|
| 541 | 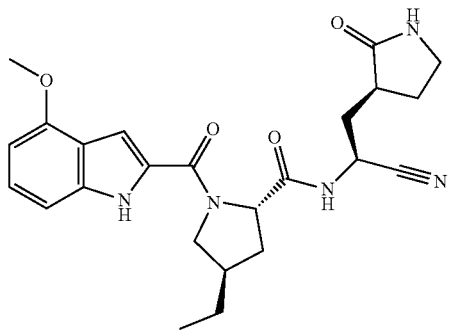 [SMILES: CC[C@@H]1C[C@@H](C(=O)N[C@H](C#N)C[C@@H]2CCNC2=O)N(C(=O)c2cc3c(OC)cccc3[nH]2)C1] |
| 542 | 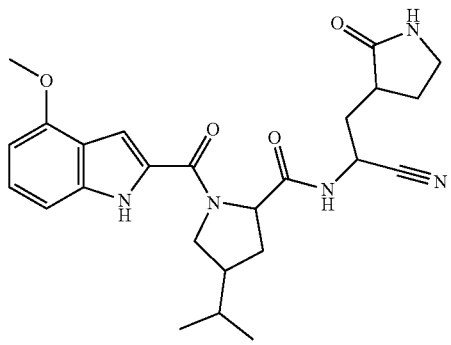 [SMILES: COc1cccc2[nH]c(C(=O)N3CC(C(C)C)CC3C(=O)NC(C#N)CC3CCNC3=O)cc12] |
| 543 | 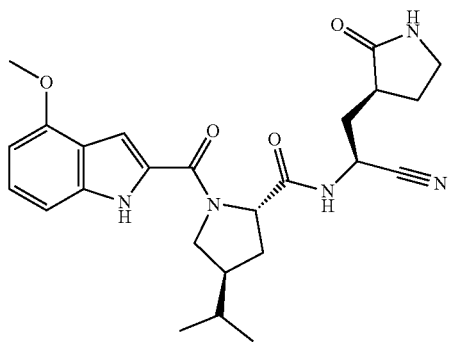 [SMILES: COc1cccc2[nH]c(C(=O)N3C[C@H](C(C)C)C[C@H]3C(=O)N[C@H](C#N)C[C@@H]3CCNC3=O)cc12] |
| 544 | 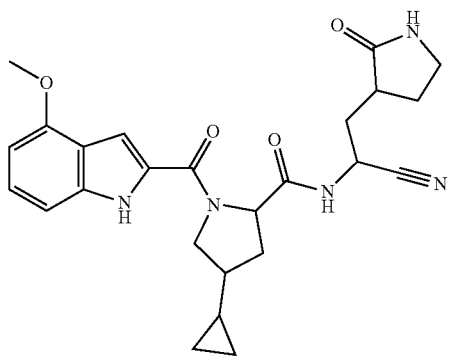 [SMILES: COc1cccc2[nH]c(C(=O)N3CC(C4CC4)CC3C(=O)NC(C#N)CC3CCNC3=O)cc12] |

TABLE 1-continued

Exemplary compounds.

| Compound No. | Structure |
|---|---|
| 545 | 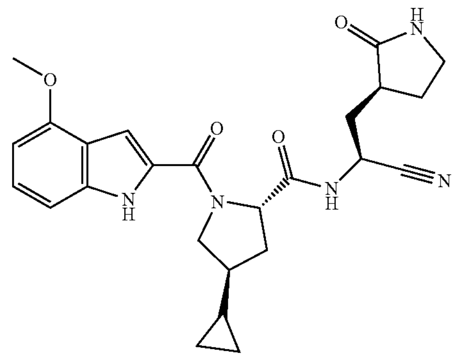 [SMILES: COc1cccc2[nH]c(C(=O)N3C[C@H](C4CC4)C[C@H]3C(=O)N[C@H](C#N)C[C@@H]3CCNC3=O)cc12] |
| 546 | 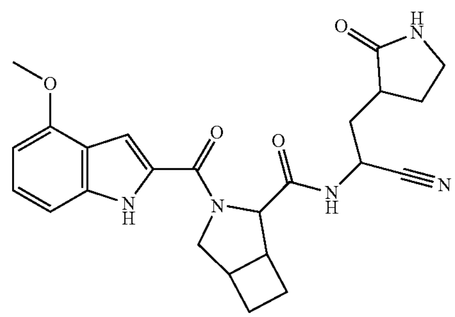 [SMILES: COc1cccc2[nH]c(C(=O)N3CC4CCC4C3C(=O)NC(C#N)CC3CCNC3=O)cc12] |
| 547 | 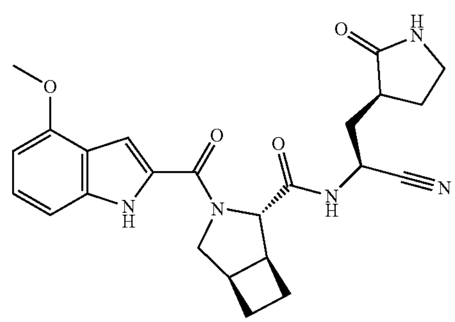 [SMILES: COc1cccc2[nH]c(C(=O)N3C[C@@H]4CC[C@@H]4[C@H]3C(=O)N[C@H](C#N)C[C@@H]3CCNC3=O)cc12] |
| 548 | 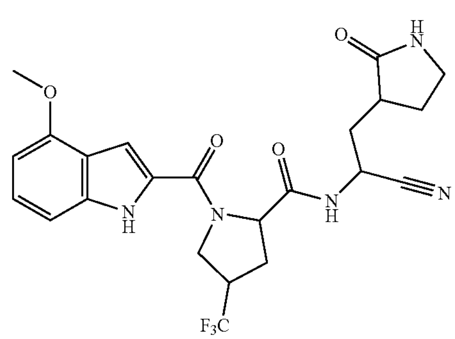 [SMILES: COc1cccc2[nH]c(C(=O)N3CC(C(F)(F)F)CC3C(=O)NC(C#N)CC3CCNC3=O)cc12] |

TABLE 1-continued

Exemplary compounds.

| Compound No. | Structure |
|---|---|
| 549 | 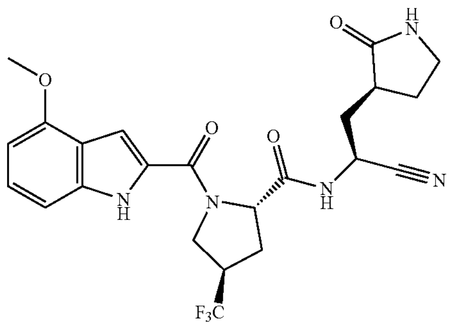 [SMILES: COc1cccc2[nH]c(C(=O)N3C[C@H](C(F)(F)F)C[C@H]3C(=O)N[C@H](C#N)C[C@@H]3CCNC3=O)cc12] |
| 550 | 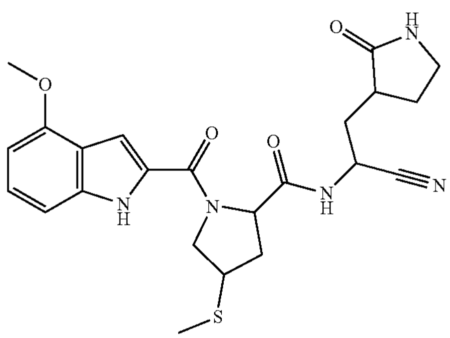 [SMILES: COc1cccc2[nH]c(C(=O)N3CC(SC)CC3C(=O)NC(C#N)CC3CCNC3=O)cc12] |
| 551 | 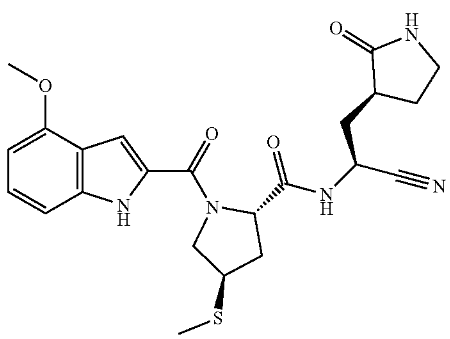 [SMILES: COc1cccc2[nH]c(C(=O)N3C[C@H](SC)C[C@H]3C(=O)N[C@H](C#N)C[C@@H]3CCNC3=O)cc12] |
| 552 | 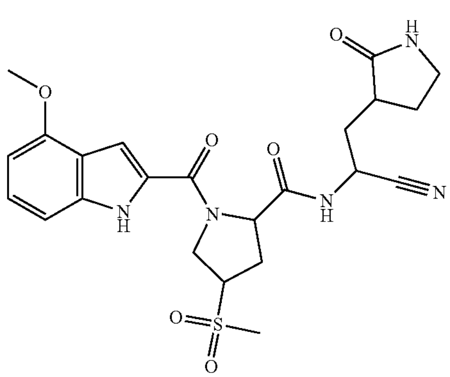 [SMILES: COc1cccc2[nH]c(C(=O)N3CC(S(C)(=O)=O)CC3C(=O)NC(C#N)CC3CCNC3=O)cc12] |

TABLE 1-continued
Exemplary compounds.
| Compound No. | Structure |
|---|---|
| 553 | 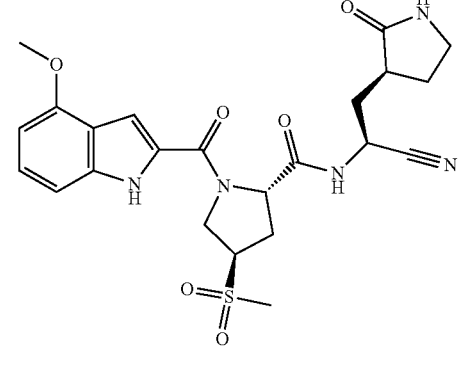 |
| 554 | 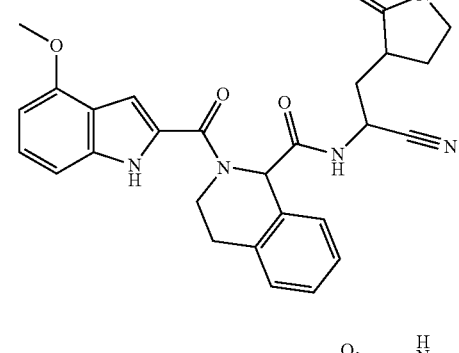 |
| 555 | 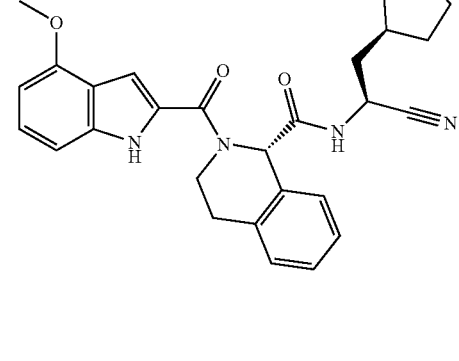 |
| 556 | 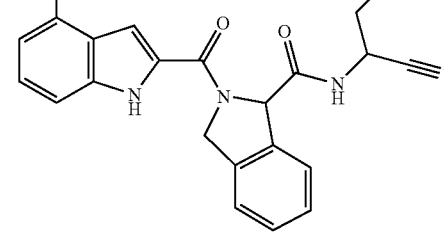 |

US 11,472,793 B2
281                                                                                            282
TABLE 1-continued
Exemplary compounds.
| Compound No. | Structure |
|---|---|
| 557 | 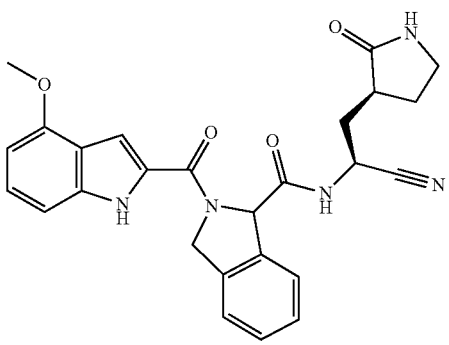 [SMILES: COc1cccc2[nH]c(C(=O)N3Cc4ccccc4C3C(=O)N[C@H](C#N)C[C@@H]3CCNC3=O)cc12] |
| 558 | 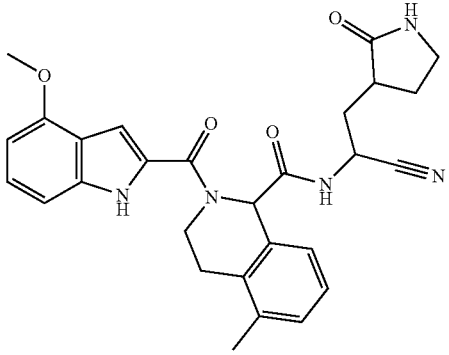 [SMILES: COc1cccc2[nH]c(C(=O)N3CCc4c(C)cccc4C3C(=O)NC(C#N)CC3CCNC3=O)cc12] |
| 559 | 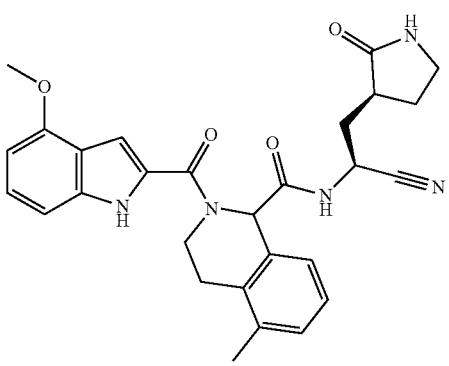 [SMILES: COc1cccc2[nH]c(C(=O)N3CCc4c(C)cccc4C3C(=O)N[C@H](C#N)C[C@@H]3CCNC3=O)cc12] |
| 560 | 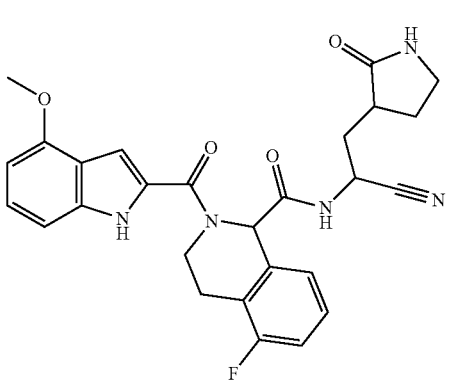 [SMILES: COc1cccc2[nH]c(C(=O)N3CCc4c(F)cccc4C3C(=O)NC(C#N)CC3CCNC3=O)cc12] |

TABLE 1-continued

Exemplary compounds.

| Compound No. | Structure |
|---|---|
| 561 | 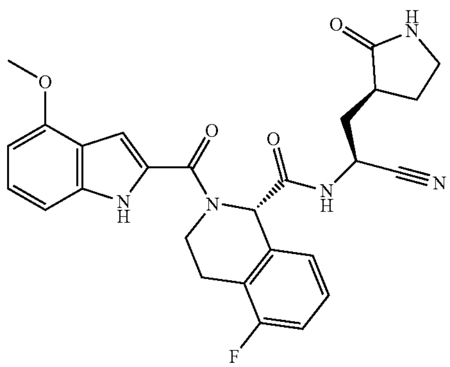 [SMILES: COc1cccc2[nH]c(C(=O)N3CCc4c(F)cccc4[C@H]3C(=O)N[C@H](C#N)C[C@@H]3CCNC3=O)cc12] |
| 562 | 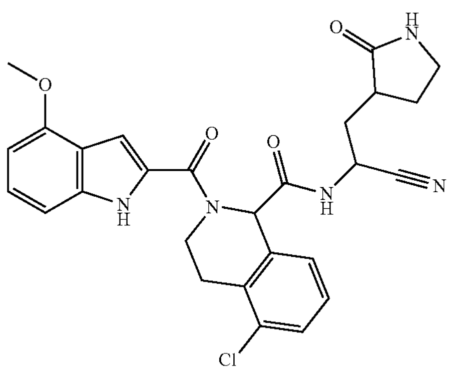 |
| 563 | 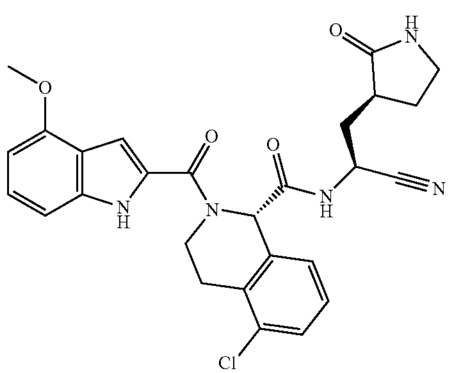 [SMILES: COc1cccc2[nH]c(C(=O)N3CCc4c(Cl)cccc4[C@H]3C(=O)N[C@H](C#N)C[C@@H]3CCNC3=O)cc12] |
| 564 | 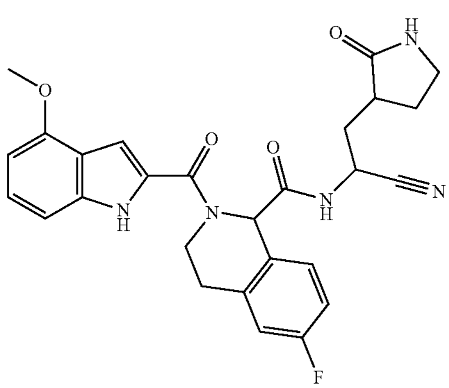 [SMILES: COc1cccc2[nH]c(C(=O)N3CCc4cc(F)ccc4C3C(=O)NC(C#N)CC3CCNC3=O)cc12] |

TABLE 1-continued
Exemplary compounds.
| Compound No. | Structure |
|---|---|
| 565 | 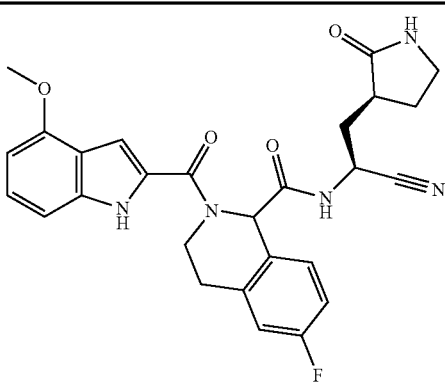 |
| 566 | 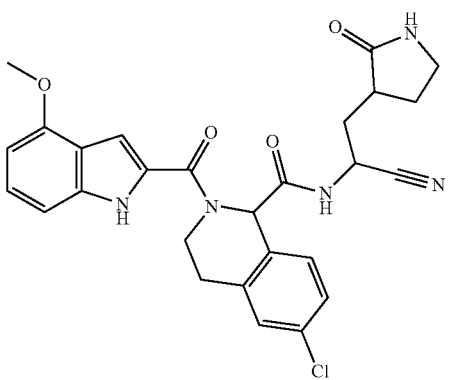 [SMILES: COc1cccc2[nH]c(C(=O)N3CCc4cc(Cl)ccc4C3C(=O)NC(C#N)CC3CCNC3=O)cc12] |
| 567 | 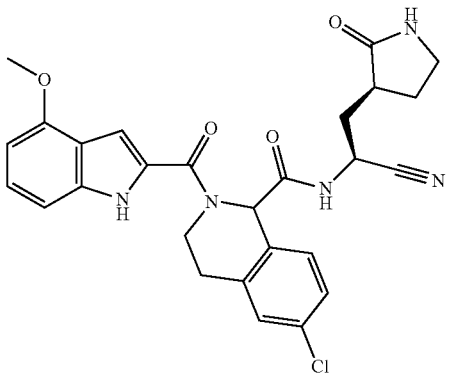 [SMILES: COc1cccc2[nH]c(C(=O)N3CCc4cc(Cl)ccc4C3C(=O)N[C@H](C#N)C[C@@H]3CCNC3=O)cc12] |
| 568 | 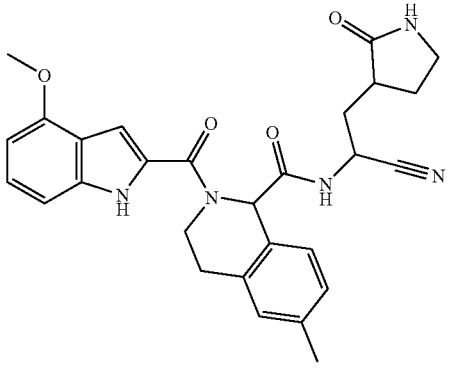 [SMILES: COc1cccc2[nH]c(C(=O)N3CCc4cc(C)ccc4C3C(=O)NC(C#N)CC3CCNC3=O)cc12] |

TABLE 1-continued
Exemplary compounds.
| Compound No. | Structure |
|---|---|
| 569 | 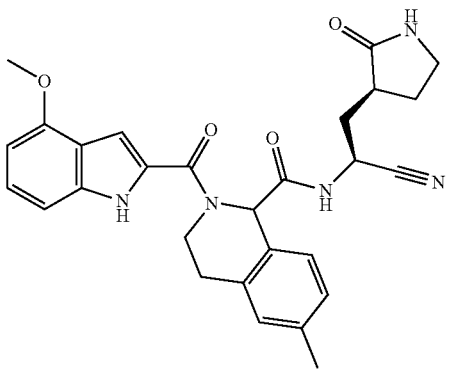 [SMILES: COc1cccc2[nH]c(C(=O)N3CCc4cc(C)ccc4C3C(=O)N[C@H](C#N)C[C@@H]3CCNC3=O)cc12] |
| 570 | 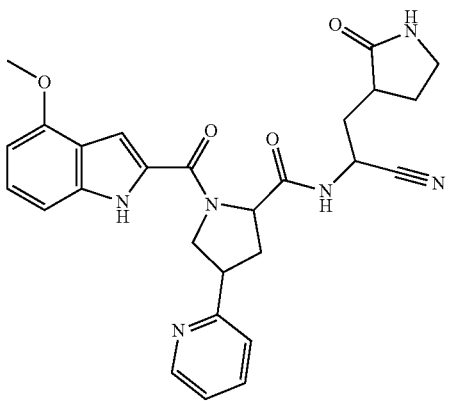 [SMILES: COc1cccc2[nH]c(C(=O)N3CC(c4ccccn4)CC3C(=O)NC(C#N)CC3CCNC3=O)cc12] |
| 571 | 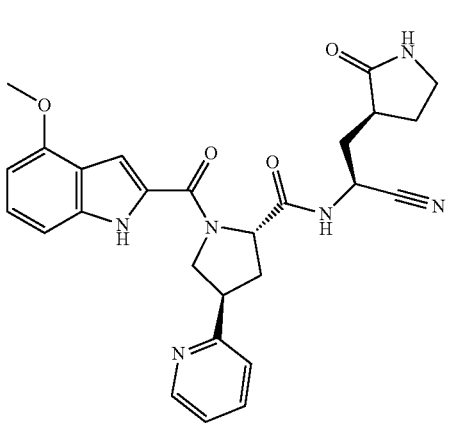 [SMILES: COc1cccc2[nH]c(C(=O)N3C[C@H](c4ccccn4)C[C@H]3C(=O)N[C@H](C#N)C[C@@H]3CCNC3=O)cc12] |

TABLE 1-continued

Exemplary compounds.

| Compound No. | Structure |
|---|---|
| 572 | 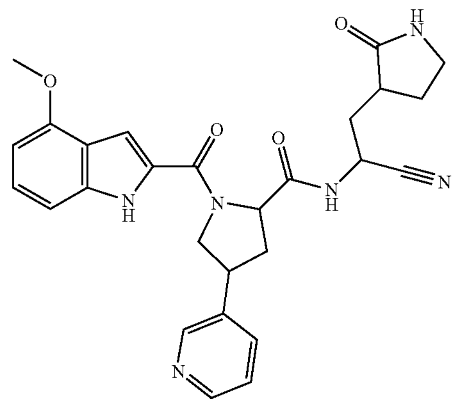 [SMILES: COc1cccc2[nH]c(C(=O)N3CC(c4cccnc4)CC3C(=O)NC(C#N)CC3CCNC3=O)cc12] |
| 573 | 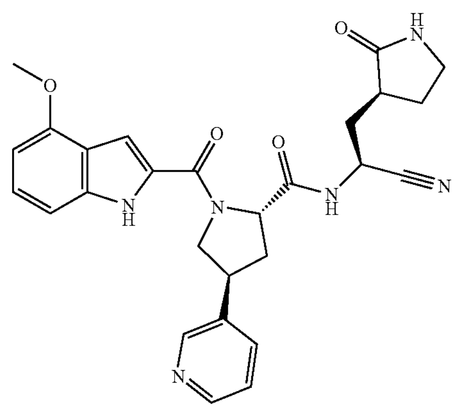 [SMILES: COc1cccc2[nH]c(C(=O)N3C[C@H](c4cccnc4)C[C@H]3C(=O)N[C@H](C#N)C[C@@H]3CCNC3=O)cc12] |
| 574 | 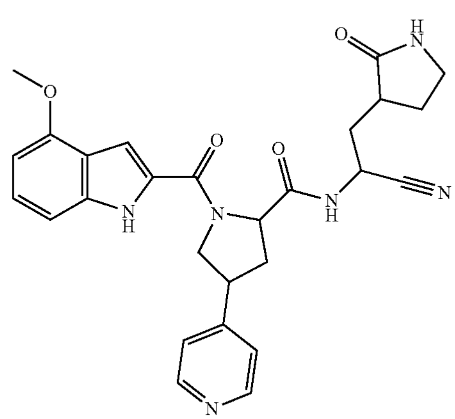 [SMILES: COc1cccc2[nH]c(C(=O)N3CC(c4ccncc4)CC3C(=O)NC(C#N)CC3CCNC3=O)cc12] |

TABLE 1-continued
Exemplary compounds.
| Compound No. | Structure |
|---|---|
| 575 | 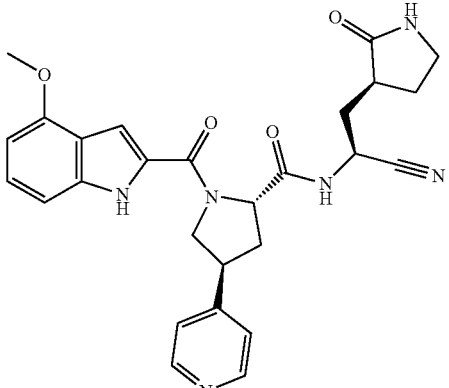 |
| 576 | 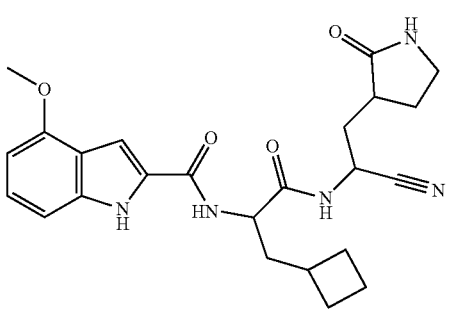 [SMILES: COc1cccc2[nH]c(C(=O)NC(CC3CCC3)C(=O)NC(C#N)CC3CCNC3=O)cc12] |
| 577 | 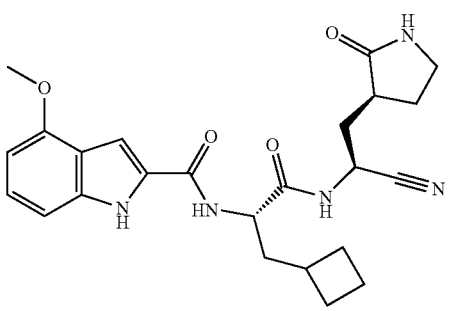 [SMILES: COc1cccc2[nH]c(C(=O)N[C@@H](CC3CCC3)C(=O)N[C@H](C#N)C[C@@H]3CCNC3=O)cc12] |
| 578 | 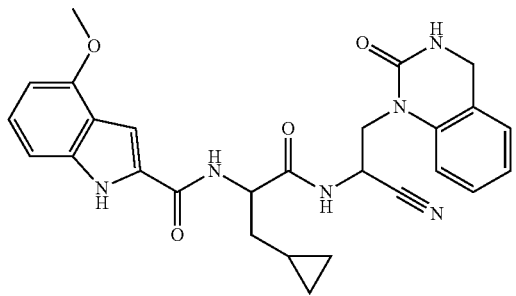 [SMILES: COc1cccc2[nH]c(C(=O)NC(CC3CC3)C(=O)NC(C#N)CN3C(=O)NCc4ccccc43)cc12] |

TABLE 1-continued

Exemplary compounds.

| Compound No. | Structure |
|---|---|
| 579 | 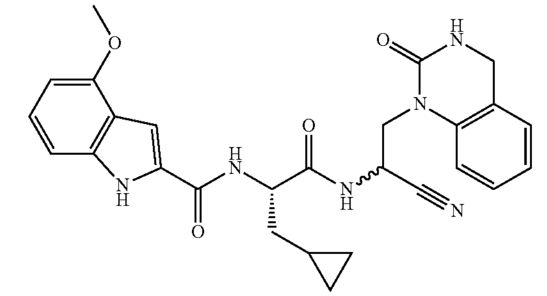 [SMILES: COc1cccc2[nH]c(C(=O)N[C@@H](CC3CC3)C(=O)NC(C#N)CN3C(=O)NCc4ccccc43)cc12] |
| 580 | 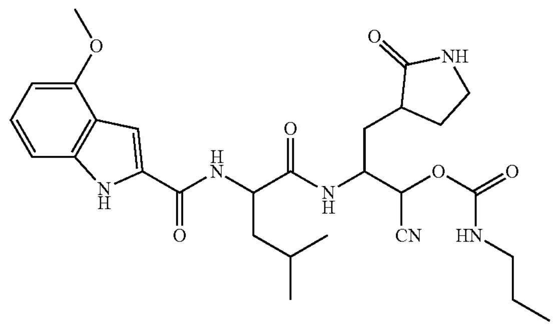 [SMILES: CCCNC(=O)OC(C#N)C(CC1CCNC1=O)NC(=O)C(CC(C)C)NC(=O)c1cc2c(OC)cccc2[nH]1] |
| 581 | 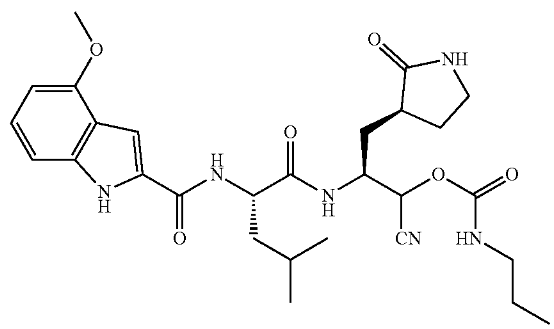 [SMILES: CCCNC(=O)OC(C#N)[C@H](C[C@@H]1CCNC1=O)NC(=O)[C@H](CC(C)C)NC(=O)c1cc2c(OC)cccc2[nH]1] |
| 582 | 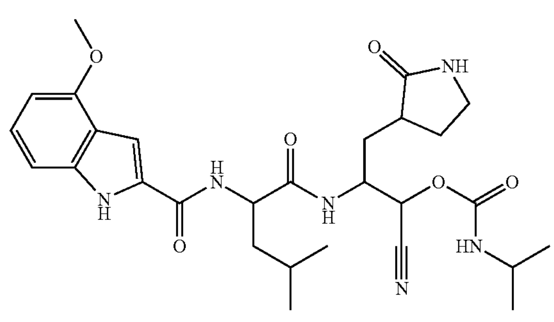 [SMILES: COc1cccc2[nH]c(C(=O)NC(CC(C)C)C(=O)NC(CC3CCNC3=O)C(C#N)OC(=O)NC(C)C)cc12] |

US 11,472,793 B2
TABLE 1-continued
Exemplary compounds.
| Compound No. | Structure |
|---|---|
| 583 | 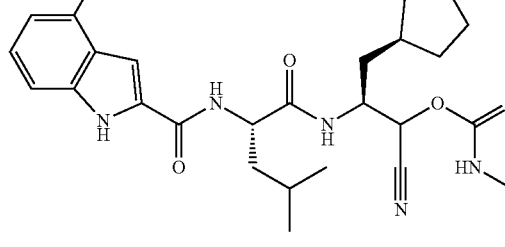 |
| 584 | 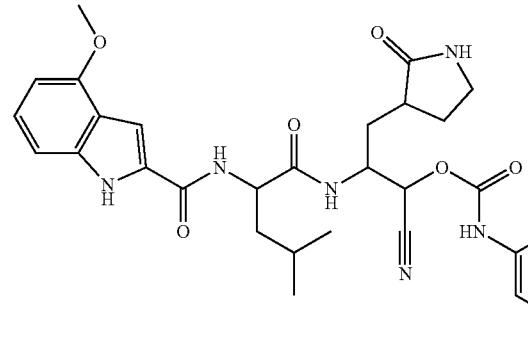 |
| 585 | 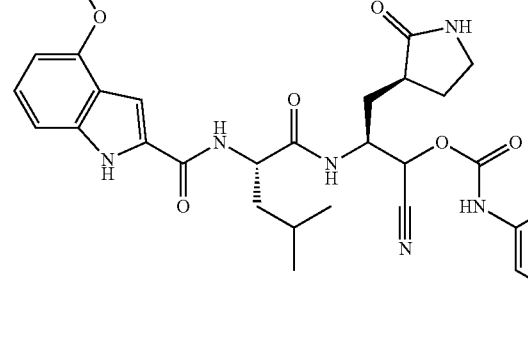 |
| 586 | 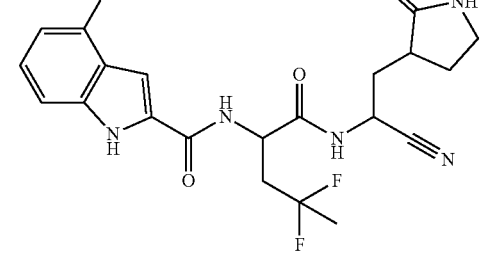 |

TABLE 1-continued
Exemplary compounds.
| Compound No. | Structure |
|---|---|
| 587 | 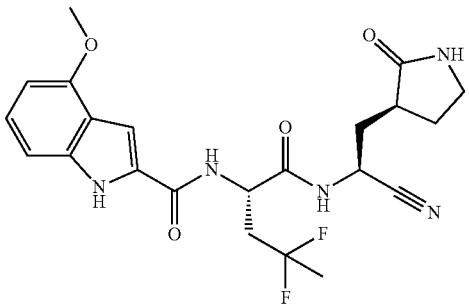 [SMILES: COc1cccc2[nH]c(C(=O)N[C@@H](CC(C)(F)F)C(=O)N[C@H](C#N)C[C@@H]3CCNC3=O)cc12] |
| 588 | 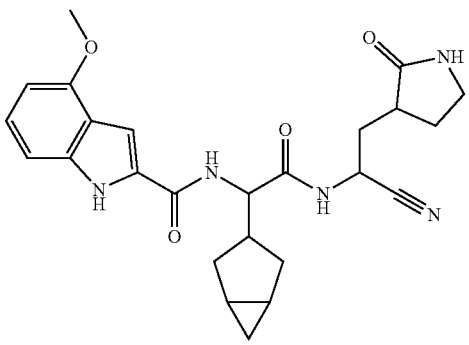 [SMILES: COc1cccc2[nH]c(C(=O)NC(C(=O)NC(C#N)CC3CCNC3=O)C3CC4CC4C3)cc12] |
| 589 | 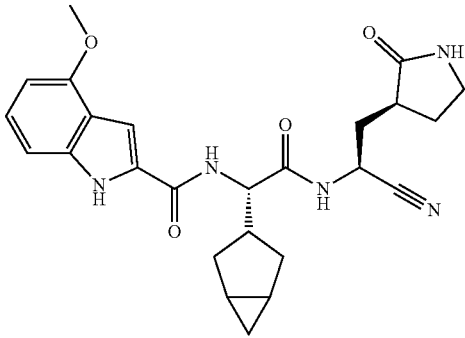 [SMILES: COc1cccc2[nH]c(C(=O)N[C@H](C(=O)N[C@H](C#N)C[C@@H]3CCNC3=O)C3CC4CC4C3)cc12] |
| 590 | 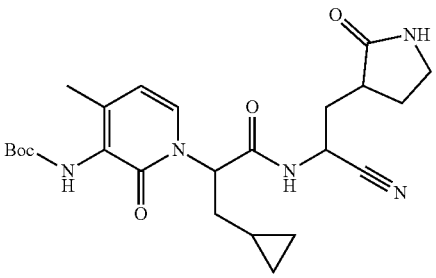 [SMILES: Cc1ccn(C(CC2CC2)C(=O)NC(C#N)CC2CCNC2=O)c(=O)c1NC(=O)OC(C)(C)C] |

TABLE 1-continued

Exemplary compounds.

| Compound No. | Structure |
|---|---|
| 591 | 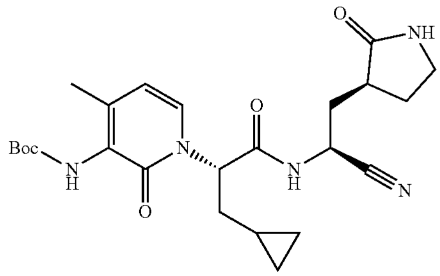 [SMILES: Cc1ccn([C@@H](CC2CC2)C(=O)N[C@H](C#N)C[C@@H]2CCNC2=O)c(=O)c1NC(=O)OC(C)(C)C] |
| 592 | 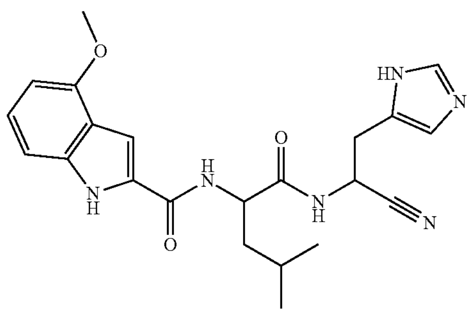 [SMILES: COc1cccc2[nH]c(C(=O)NC(CC(C)C)C(=O)NC(C#N)Cc3cnc[nH]3)cc12] |
| 593 | 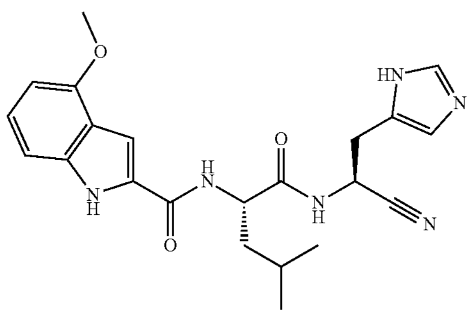 [SMILES: COc1cccc2[nH]c(C(=O)N[C@@H](CC(C)C)C(=O)N[C@H](C#N)Cc3cnc[nH]3)cc12] |
| 594 | 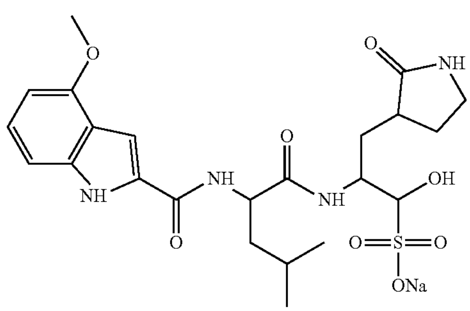 |
| 595 | 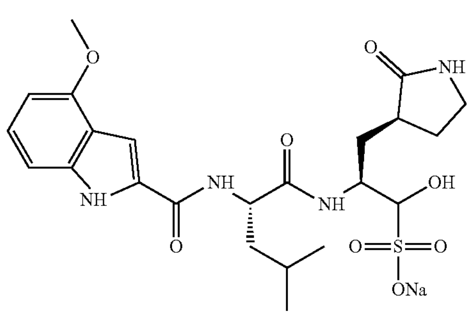 |

TABLE 1-continued

Exemplary compounds.

| Compound No. | Structure |
|---|---|
| 596 | 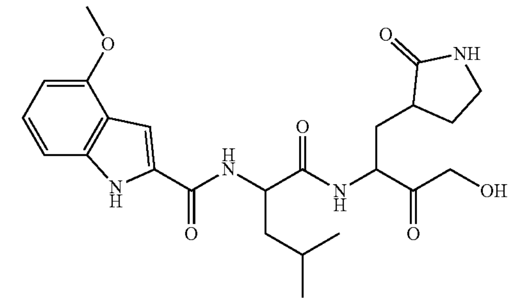 [SMILES: COc1cccc2[nH]c(C(=O)NC(CC(C)C)C(=O)NC(CC3CCNC3=O)C(=O)CO)cc12] |
| 597 | 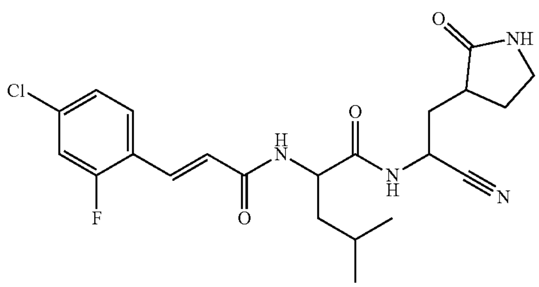 [SMILES: CC(C)CC(NC(=O)/C=C/c1ccc(Cl)cc1F)C(=O)NC(C#N)CC1CCNC1=O] |
| 598 | 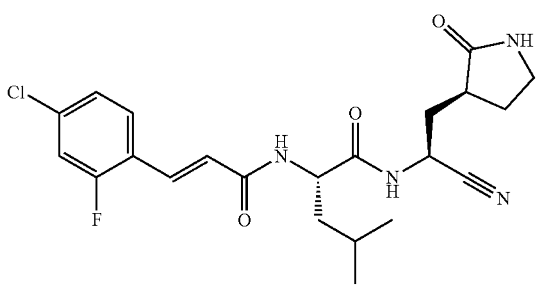 [SMILES: CC(C)C[C@H](NC(=O)/C=C/c1ccc(Cl)cc1F)C(=O)N[C@H](C#N)C[C@@H]1CCNC1=O] |
| 599A | 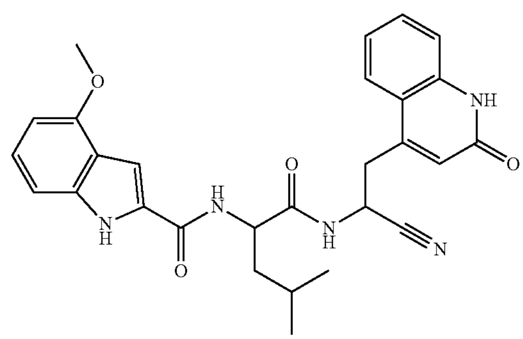 [SMILES: COc1cccc2[nH]c(C(=O)NC(CC(C)C)C(=O)NC(C#N)Cc3cc(=O)[nH]c4ccccc34)cc12] |
| 599 | 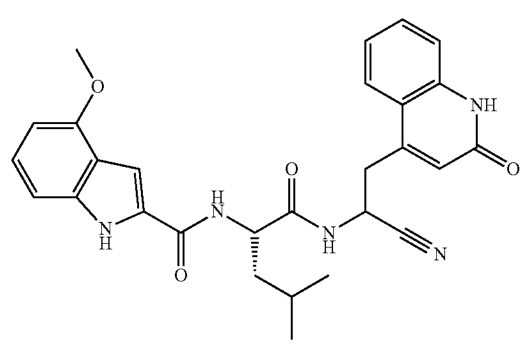 |

TABLE 1-continued
Exemplary compounds.
| Compound No. | Structure |
|---|---|
| 600A | 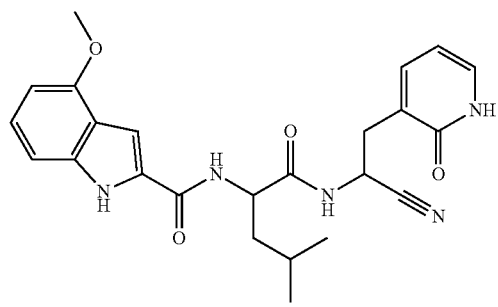 [SMILES: COc1cccc2[nH]c(C(=O)NC(CC(C)C)C(=O)NC(C#N)Cc3ccc[nH]c3=O)cc12] |
| 600 | 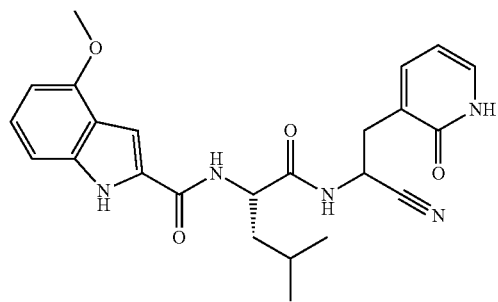 |
| 601A | 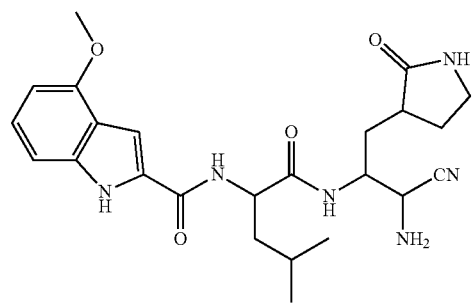 [SMILES: COc1cccc2[nH]c(C(=O)NC(CC(C)C)C(=O)NC(CC3CCNC3=O)C(N)C#N)cc12] |
| 601 | 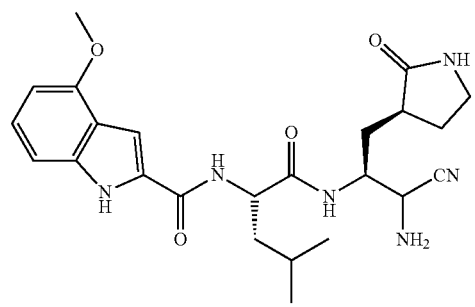 |

TABLE 1-continued

Exemplary compounds.

| Compound No. | Structure |
|---|---|
| 344A | 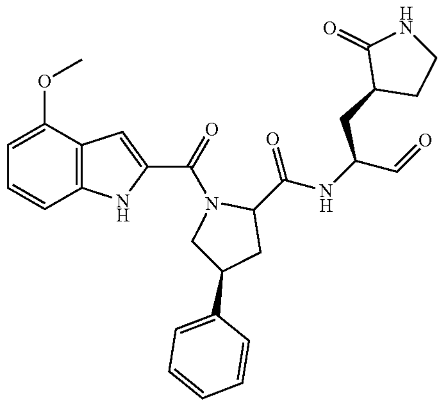 [SMILES: COc1cccc2[nH]c(C(=O)N3C[C@H](c4ccccc4)CC3C(=O)N[C@H](C=O)C[C@@H]3CCNC3=O)cc12] |
| 344B | 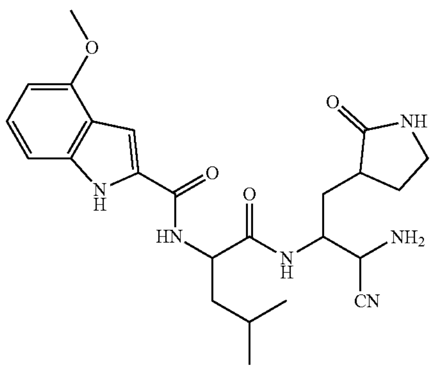 [SMILES: COc1cccc2[nH]c(C(=O)NC(CC(C)C)C(=O)NC(CC3CCNC3=O)C(N)C#N)cc12] |
| 344C | 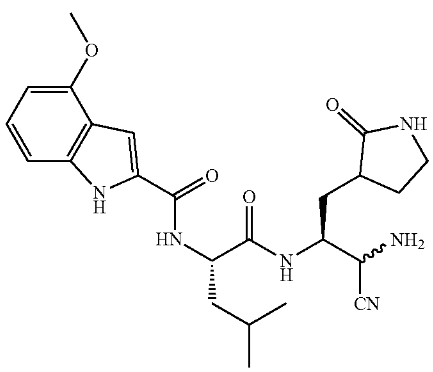 [SMILES: COc1cccc2[nH]c(C(=O)N[C@@H](CC(C)C)C(=O)N[C@@H](CC3CCNC3=O)C(N)C#N)cc12] |
| 344D | 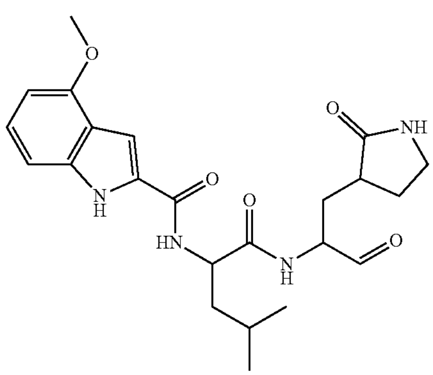 [SMILES: COc1cccc2[nH]c(C(=O)NC(CC(C)C)C(=O)NC(C=O)CC3CCNC3=O)cc12] |

TABLE 1-continued

Exemplary compounds.

| Compound No. | Structure |
|---|---|
| 602A | 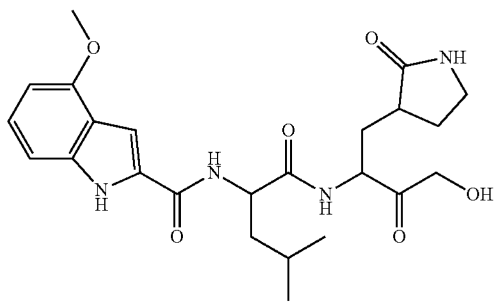 [SMILES: COc1cccc2[nH]c(C(=O)NC(CC(C)C)C(=O)NC(CC3CCNC3=O)C(=O)CO)cc12] |
| 602 | 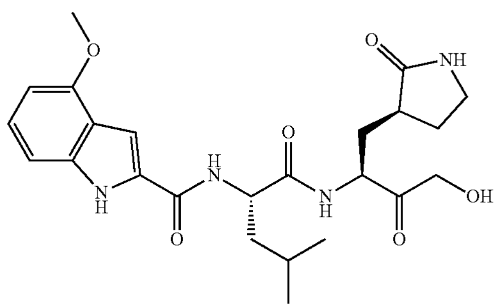 [SMILES: COc1cccc2[nH]c(C(=O)N[C@@H](CC(C)C)C(=O)N[C@@H](C[C@@H]3CCNC3=O)C(=O)CO)cc12] |
| 603 | 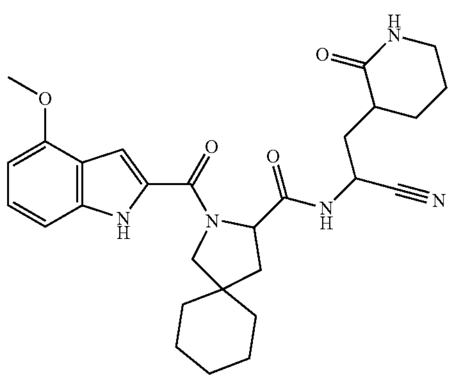 [SMILES: COc1cccc2[nH]c(C(=O)N3CC4(CCCCC4)CC3C(=O)NC(C#N)CC3CCCNC3=O)cc12] |
| 604 | 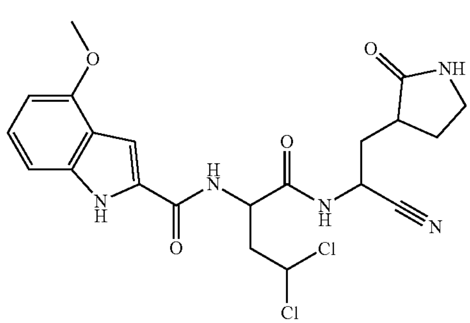 [SMILES: COc1cccc2[nH]c(C(=O)NC(CC(Cl)Cl)C(=O)NC(C#N)CC3CCNC3=O)cc12] |

TABLE 1-continued
Exemplary compounds.
| Compound No. | Structure |
|---|---|
| 605 | 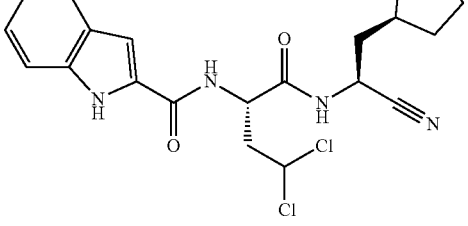 |
| 606 | 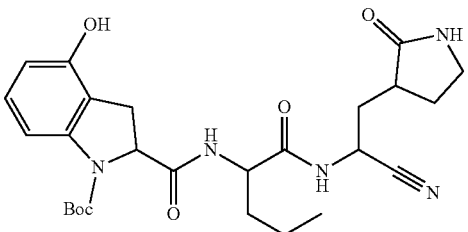 |
| 607 | 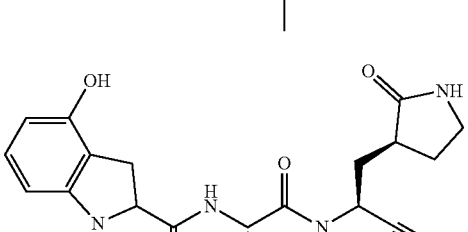 |
| 608 | 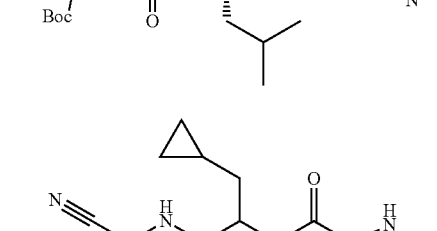 |
| 609 | 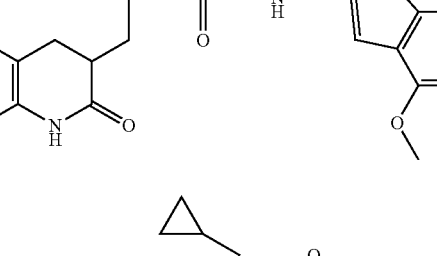 |

TABLE 1-continued
Exemplary compounds.
| Compound No. | Structure |
|---|---|
| 610 | 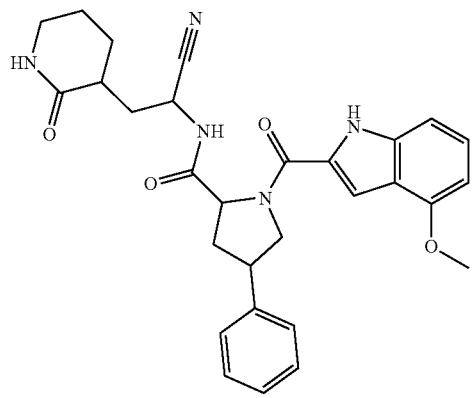 [SMILES: COc1cccc2[nH]c(C(=O)N3CC(c4ccccc4)CC3C(=O)NC(C#N)CC3CCCNC3=O)cc12] |
| 611 | 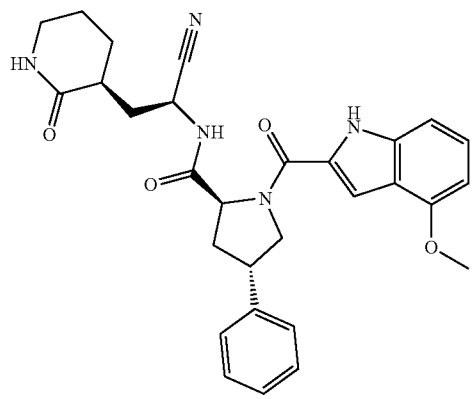 [SMILES: COc1cccc2[nH]c(C(=O)N3C[C@H](c4ccccc4)C[C@H]3C(=O)N[C@H](C#N)C[C@@H]3CCCNC3=O)cc12] |
| 612 | 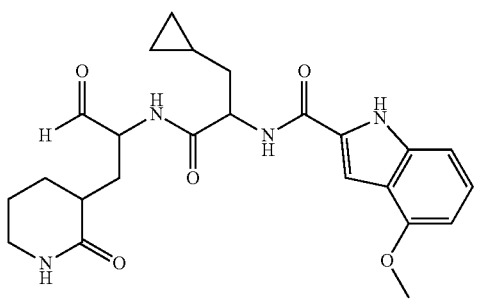 [SMILES: COc1cccc2[nH]c(C(=O)NC(CC3CC3)C(=O)NC(C=O)CC3CCCNC3=O)cc12] |
| 613 | 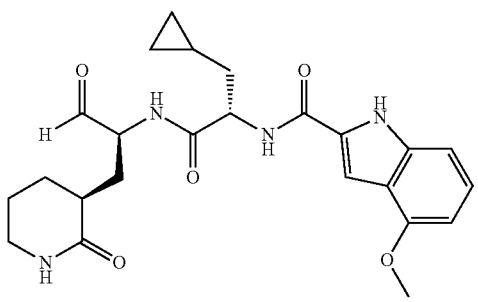 [SMILES: COc1cccc2[nH]c(C(=O)N[C@@H](CC3CC3)C(=O)N[C@H](C=O)C[C@@H]3CCCNC3=O)cc12] |

TABLE 1-continued

Exemplary compounds.

| Compound No. | Structure |
|---|---|
| 614 | 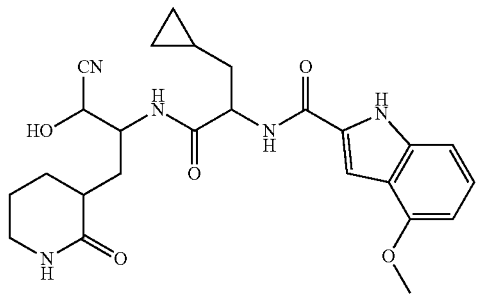 [SMILES: COc1cccc2[nH]c(C(=O)NC(CC3CC3)C(=O)NC(CC3CCCNC3=O)C(O)C#N)cc12] |
| 615 | 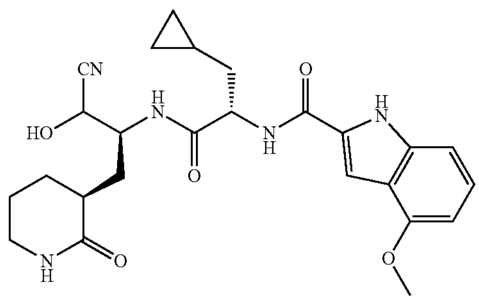 [SMILES: COc1cccc2[nH]c(C(=O)N[C@@H](CC3CC3)C(=O)N[C@@H](C[C@@H]3CCCNC3=O)C(O)C#N)cc12] |
| 616 | 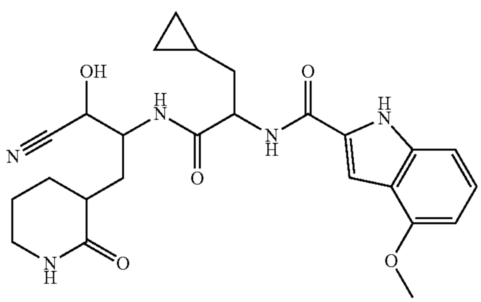 [SMILES: COc1cccc2[nH]c(C(=O)NC(CC3CC3)C(=O)NC(CC3CCCNC3=O)C(O)C#N)cc12] |
| 617 | 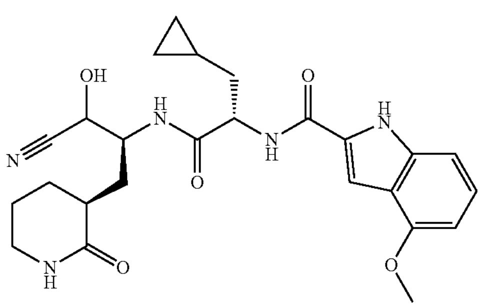 [SMILES: COc1cccc2[nH]c(C(=O)N[C@@H](CC3CC3)C(=O)N[C@@H](C[C@@H]3CCCNC3=O)C(O)C#N)cc12] |
| 618 | 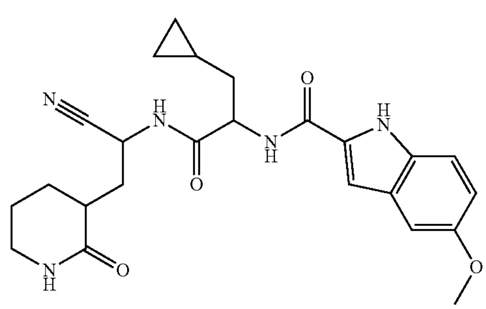 [SMILES: COc1ccc2[nH]c(C(=O)NC(CC3CC3)C(=O)NC(C#N)CC3CCCNC3=O)cc2c1] |

TABLE 1-continued

Exemplary compounds.

| Compound No. | Structure |
|---|---|
| 619 | 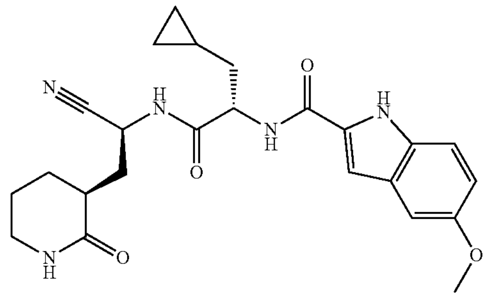 [SMILES: COc1ccc2[nH]c(C(=O)N[C@@H](CC3CC3)C(=O)N[C@H](C#N)C[C@@H]3CCCNC3=O)cc2c1] |
| 620 | 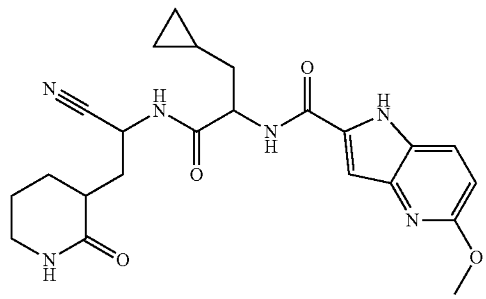 [SMILES: COc1ccc2[nH]c(C(=O)NC(CC3CC3)C(=O)NC(C#N)CC3CCCNC3=O)cc2n1] |
| 621 | 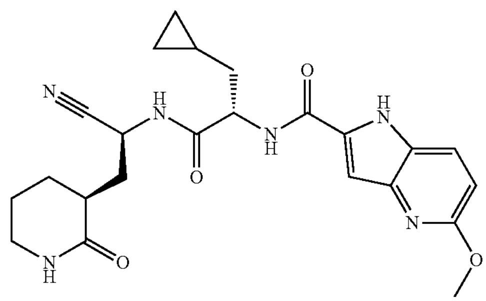 [SMILES: COc1ccc2[nH]c(C(=O)N[C@@H](CC3CC3)C(=O)N[C@H](C#N)C[C@@H]3CCCNC3=O)cc2n1] |
| 622 | 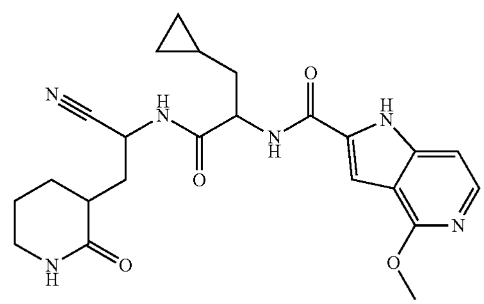 [SMILES: COc1nccc2[nH]c(C(=O)NC(CC3CC3)C(=O)NC(C#N)CC3CCCNC3=O)cc12] |
| 623 | 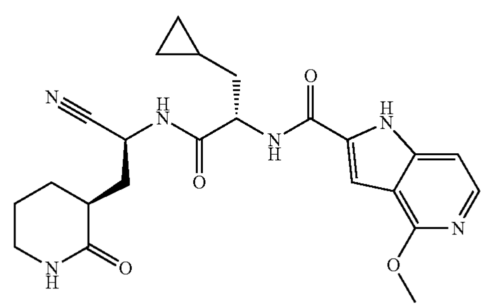 [SMILES: COc1nccc2[nH]c(C(=O)N[C@@H](CC3CC3)C(=O)N[C@H](C#N)C[C@@H]3CCCNC3=O)cc12] |

TABLE 1-continued
Exemplary compounds.
| Compound No. | Structure |
|---|---|
| 624 | 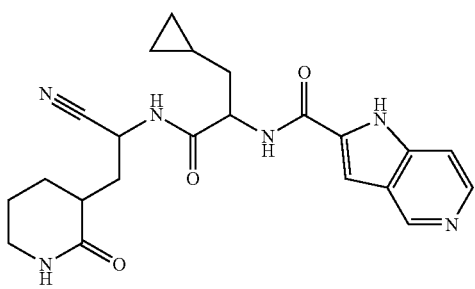 [SMILES: N#CC(CC1CCCNC1=O)NC(=O)C(CC1CC1)NC(=O)c1cc2cnccc2[nH]1] |
| 625 | 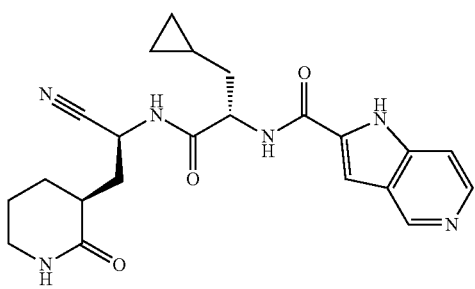 [SMILES: N#C[C@H](C[C@@H]1CCCNC1=O)NC(=O)[C@H](CC1CC1)NC(=O)c1cc2cnccc2[nH]1] |
| 626 | 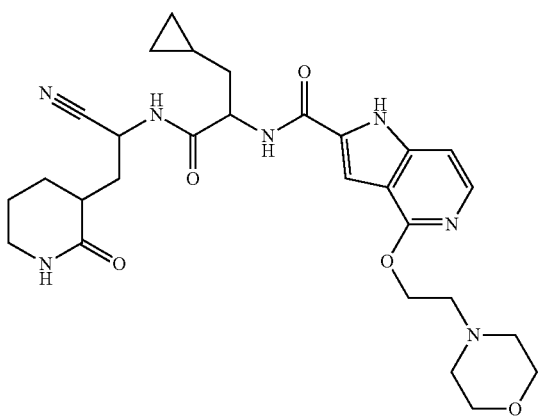 [SMILES: N#CC(CC1CCCNC1=O)NC(=O)C(CC1CC1)NC(=O)c1cc2c(OCCN3CCOCC3)nccc2[nH]1] |
| 627 | 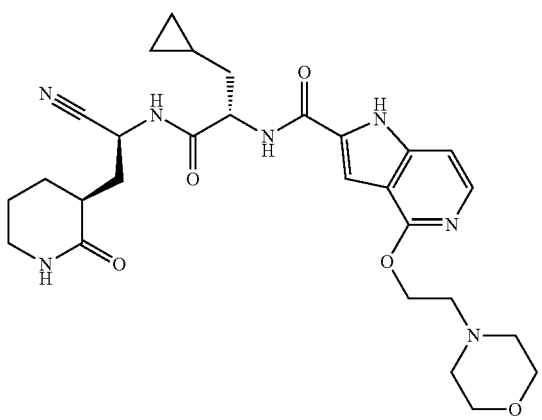 [SMILES: N#C[C@H](C[C@@H]1CCCNC1=O)NC(=O)[C@H](CC1CC1)NC(=O)c1cc2c(OCCN3CCOCC3)nccc2[nH]1] |

TABLE 1-continued
Exemplary compounds.
| Compound No. | Structure |
|---|---|
| 628 | 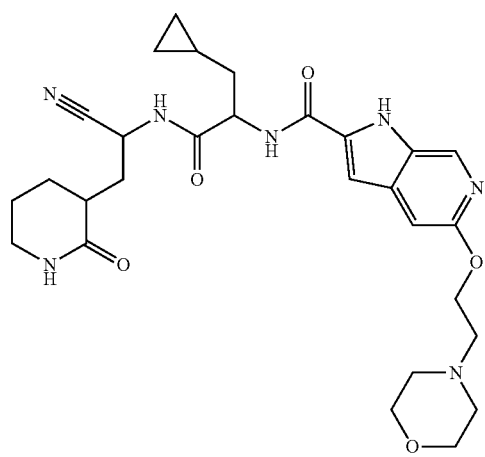 [SMILES: N#CC(CC1CCCNC1=O)NC(=O)C(CC1CC1)NC(=O)c1cc2cc(OCCN3CCOCC3)ncc2[nH]1] |
| 629 | 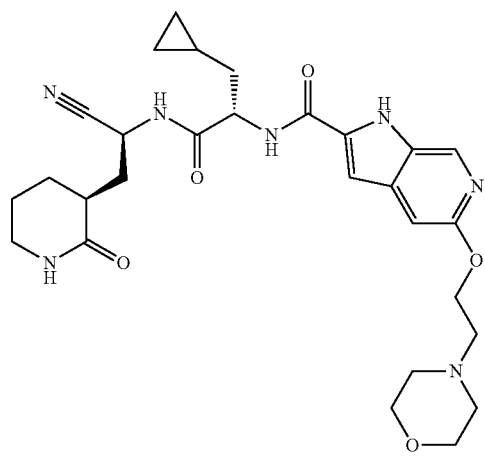 [SMILES: N#C[C@H](C[C@@H]1CCCNC1=O)NC(=O)[C@H](CC1CC1)NC(=O)c1cc2cc(OCCN3CCOCC3)ncc2[nH]1] |
| 630 | 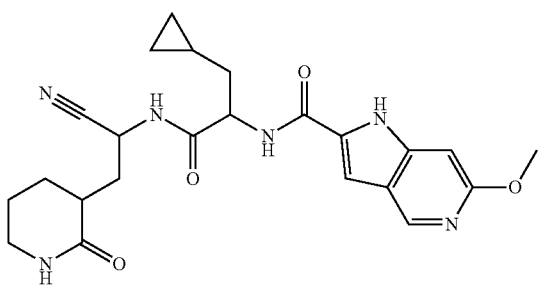 [SMILES: COc1cc2[nH]c(C(=O)NC(CC3CC3)C(=O)NC(C#N)CC3CCCNC3=O)cc2cn1] |
| 631 | 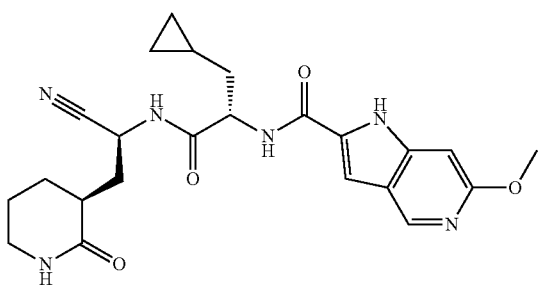 [SMILES: COc1cc2[nH]c(C(=O)N[C@@H](CC3CC3)C(=O)N[C@H](C#N)C[C@@H]3CCCNC3=O)cc2cn1] |

TABLE 1-continued
Exemplary compounds.
| Compound No. | Structure |
|---|---|
| 632 | 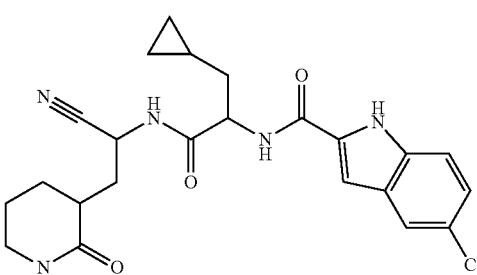 |
| 633 | 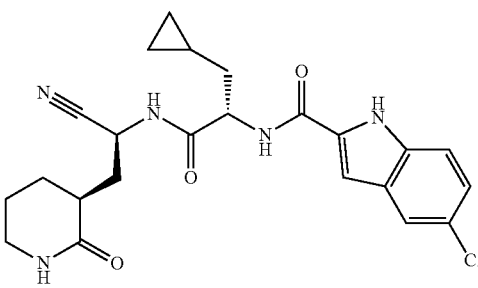 |
| 634 | 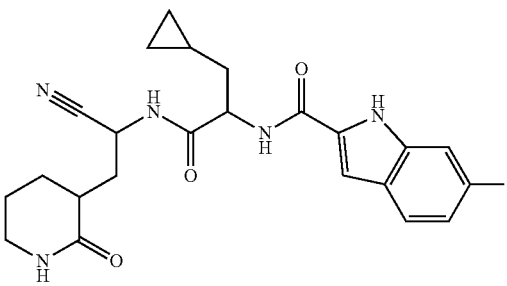 |
| 635 | 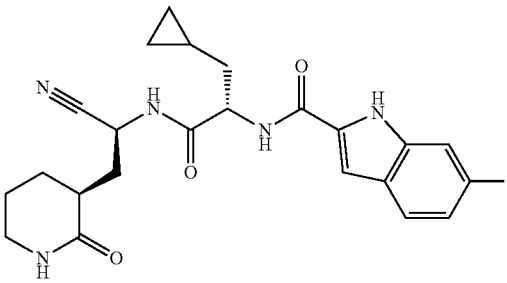 |
| 636 | 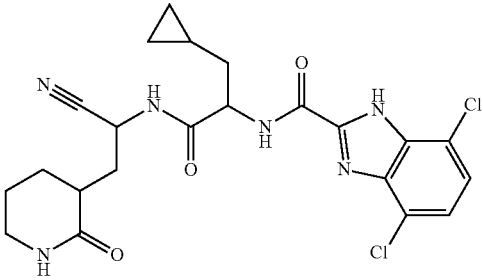 [SMILES: N#CC(CC1CCCNC1=O)NC(=O)C(CC1CC1)NC(=O)c1nc2c(Cl)ccc(Cl)c2[nH]1] |

TABLE 1-continued

Exemplary compounds.

| Compound No. | Structure |
|---|---|
| 637 | 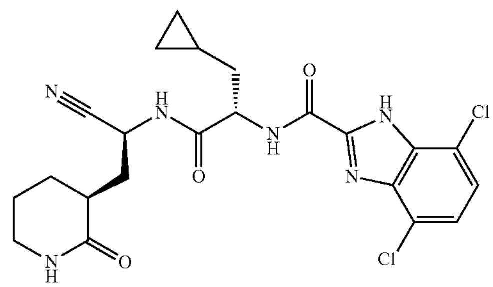 [SMILES: N#C[C@H](C[C@@H]1CCCNC1=O)NC(=O)[C@H](CC1CC1)NC(=O)c1nc2c(Cl)ccc(Cl)c2[nH]1] |
| 638 | 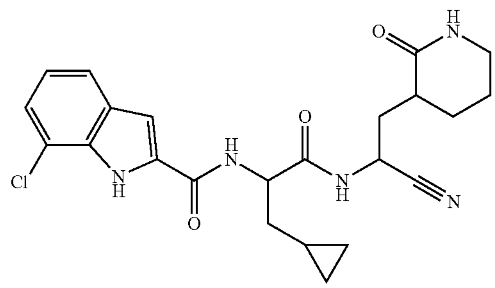 [SMILES: N#CC(CC1CCCNC1=O)NC(=O)C(CC1CC1)NC(=O)c1cc2cccc(Cl)c2[nH]1] |
| 639 | 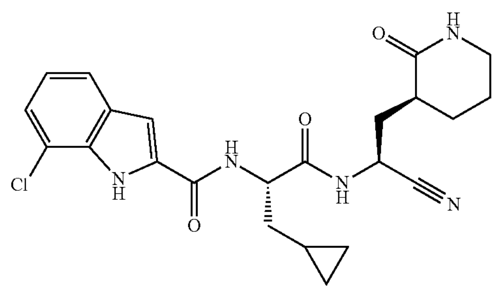 [SMILES: N#C[C@H](C[C@@H]1CCCNC1=O)NC(=O)[C@H](CC1CC1)NC(=O)c1cc2cccc(Cl)c2[nH]1] |
| 640 | 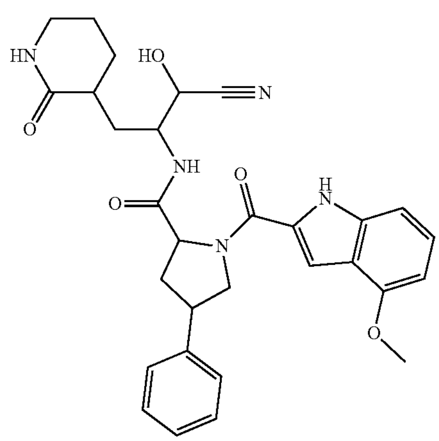 [SMILES: COc1cccc2[nH]c(C(=O)N3CC(c4ccccc4)CC3C(=O)NC(CC3CCCNC3=O)C(O)C#N)cc12] |

TABLE 1-continued

Exemplary compounds.

| Compound No. | Structure |
|---|---|
| 641 | 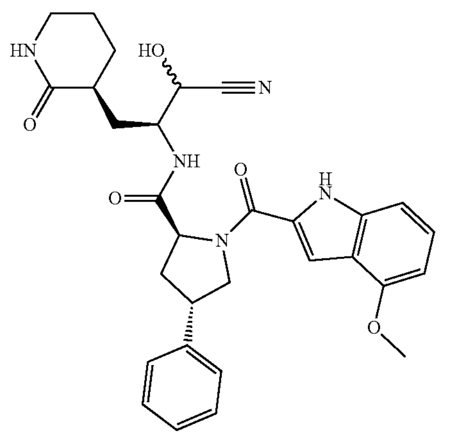 [SMILES: COc1cccc2[nH]c(C(=O)N3C[C@H](c4ccccc4)C[C@H]3C(=O)N[C@@H](C[C@@H]3CCCNC3=O)C(O)C#N)cc12] |
| 642 | 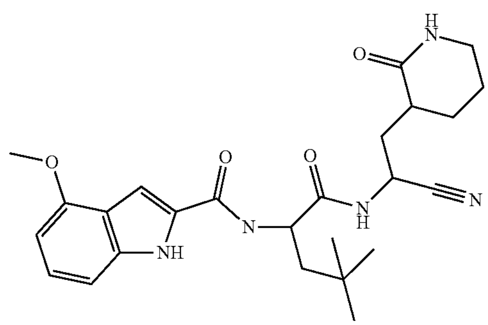 [SMILES: COc1cccc2[nH]c(C(=O)NC(CC(C)(C)C)C(=O)NC(C#N)CC3CCCNC3=O)cc12] |
| 643 | 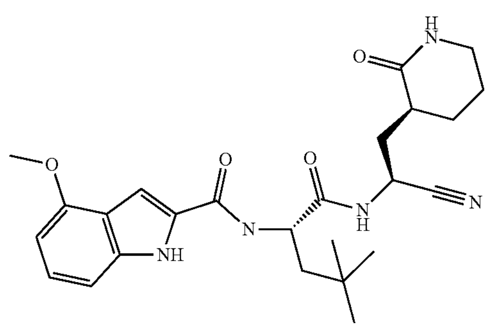 [SMILES: COc1cccc2[nH]c(C(=O)N[C@@H](CC(C)(C)C)C(=O)N[C@H](C#N)C[C@@H]3CCCNC3=O)cc12] |
| 644 | 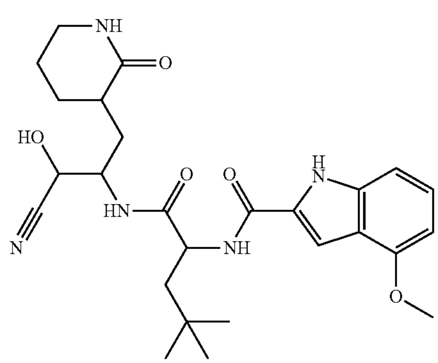 [SMILES: COc1cccc2[nH]c(C(=O)NC(CC(C)(C)C)C(=O)NC(CC3CCCNC3=O)C(O)C#N)cc12] |

TABLE 1-continued

Exemplary compounds.

| Compound No. | Structure |
|---|---|
| 645 | 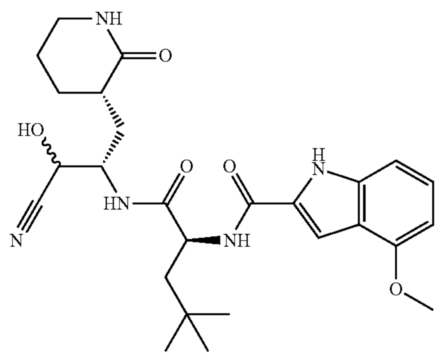 [SMILES: COc1cccc2[nH]c(C(=O)N[C@@H](CC(C)(C)C)C(=O)N[C@@H](C[C@@H]3CCCNC3=O)C(O)C#N)cc12] |
| 646 | 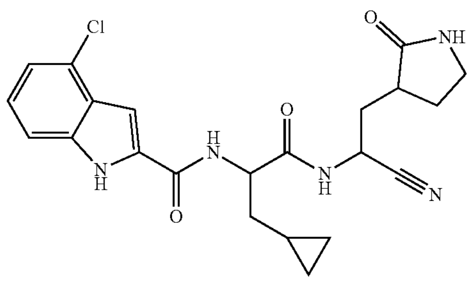 [SMILES: N#CC(CC1CCNC1=O)NC(=O)C(CC1CC1)NC(=O)c1cc2c(Cl)cccc2[nH]1] |
| 647 | 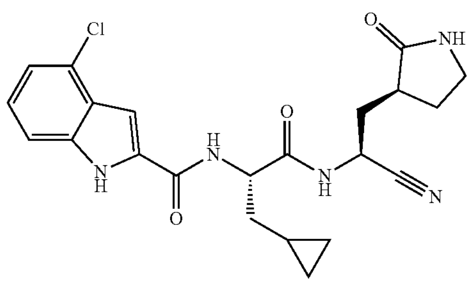 [SMILES: N#C[C@H](C[C@@H]1CCNC1=O)NC(=O)[C@H](CC1CC1)NC(=O)c1cc2c(Cl)cccc2[nH]1] |
| 648 | 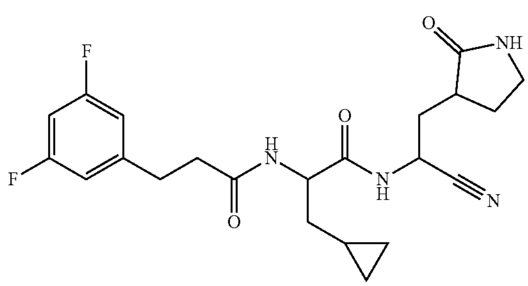 [SMILES: N#CC(CC1CCNC1=O)NC(=O)C(CC1CC1)NC(=O)CCc1cc(F)cc(F)c1] |
| 649 | 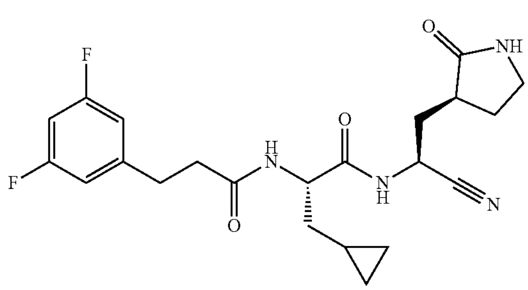 [SMILES: N#C[C@H](C[C@@H]1CCNC1=O)NC(=O)[C@H](CC1CC1)NC(=O)CCc1cc(F)cc(F)c1] |

TABLE 1-continued
Exemplary compounds.
| Compound No. | Structure |
|---|---|
| 650 | 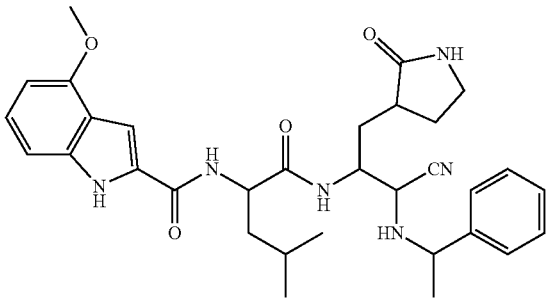 [SMILES: COc1cccc2[nH]c(C(=O)NC(CC(C)C)C(=O)NC(CC3CCNC3=O)C(C#N)NC(C)c3ccccc3)cc12] |
| 651 | 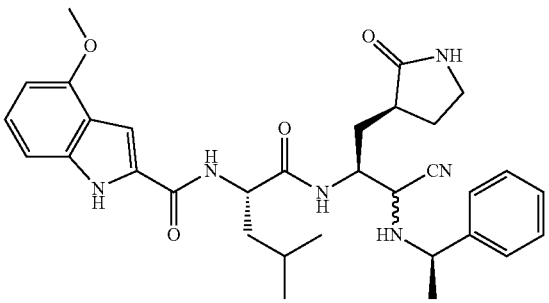 [SMILES: COc1cccc2[nH]c(C(=O)N[C@@H](CC(C)C)C(=O)N[C@@H](C[C@@H]3CCNC3=O)C(C#N)N[C@H](C)c3ccccc3)cc12] |
| 652 | 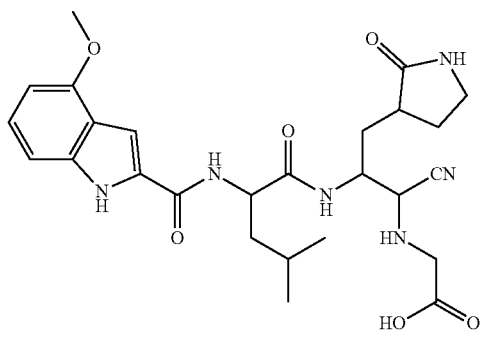 [SMILES: COc1cccc2[nH]c(C(=O)NC(CC(C)C)C(=O)NC(CC3CCNC3=O)C(C#N)NCC(=O)O)cc12] |
| 653 | 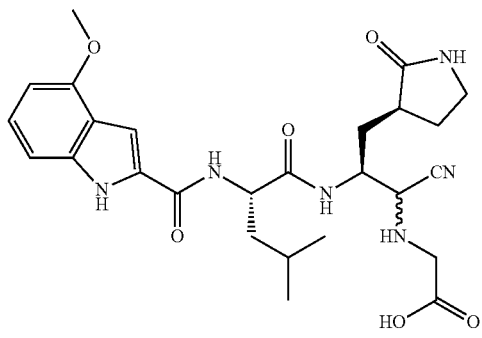 [SMILES: COc1cccc2[nH]c(C(=O)N[C@@H](CC(C)C)C(=O)N[C@@H](C[C@@H]3CCNC3=O)C(C#N)NCC(=O)O)cc12] |

TABLE 1-continued
Exemplary compounds.
| Compound No. | Structure |
| --- | --- |
| 654 | 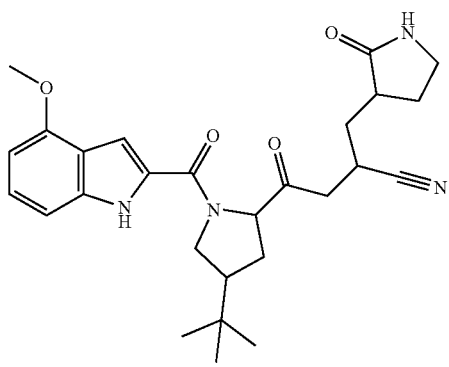 [SMILES: COc1cccc2[nH]c(C(=O)N3CC(C(C)(C)C)CC3C(=O)CC(C#N)CC3CCNC3=O)cc12] |
| 655 | 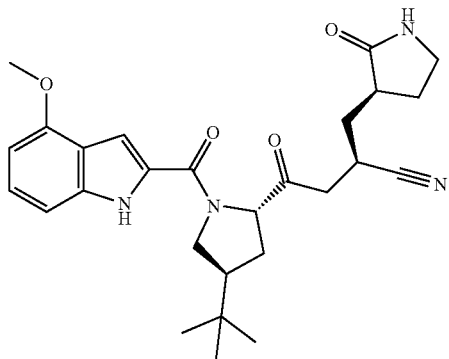 [SMILES: COc1cccc2[nH]c(C(=O)N3C[C@H](C(C)(C)C)C[C@H]3C(=O)C[C@H](C#N)C[C@@H]3CCNC3=O)cc12] |
| 656 | 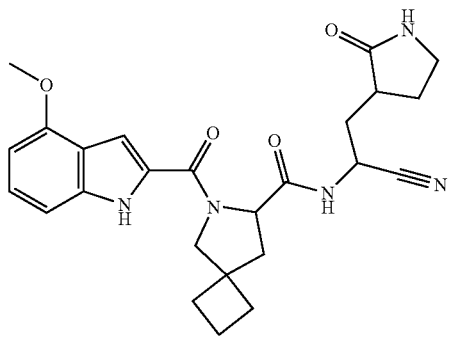 [SMILES: COc1cccc2[nH]c(C(=O)N3CC4(CCC4)CC3C(=O)NC(C#N)CC3CCNC3=O)cc12] |
| 657 | 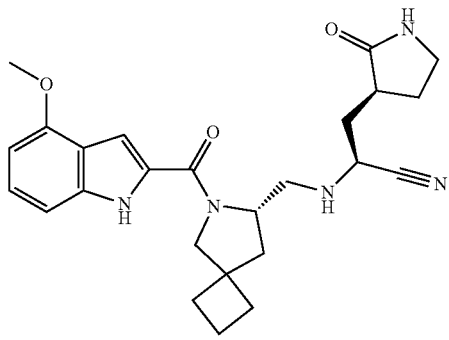 [SMILES: COc1cccc2[nH]c(C(=O)N3CC4(CCC4)C[C@H]3CN[C@H](C#N)C[C@@H]3CCNC3=O)cc12] |

TABLE 1-continued

Exemplary compounds.

| Compound No. | Structure |
|---|---|
| 658 | 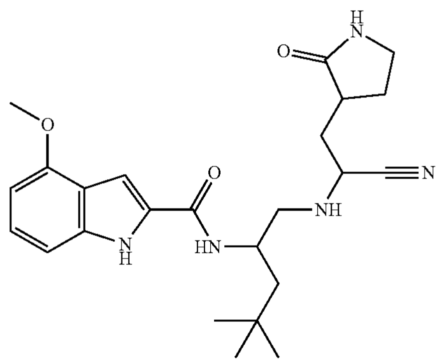 [SMILES: COc1cccc2[nH]c(C(=O)NC(CNC(C#N)CC3CCNC3=O)CC(C)(C)C)cc12] |
| 659 | 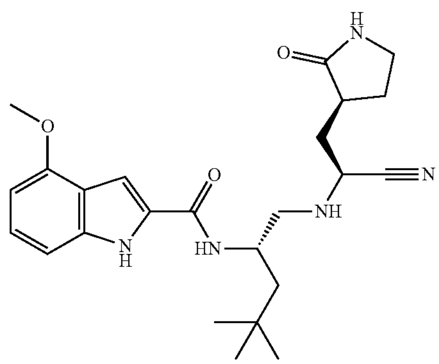 [SMILES: COc1cccc2[nH]c(C(=O)N[C@H](CN[C@H](C#N)C[C@@H]3CCNC3=O)CC(C)(C)C)cc12] |
| 660 | 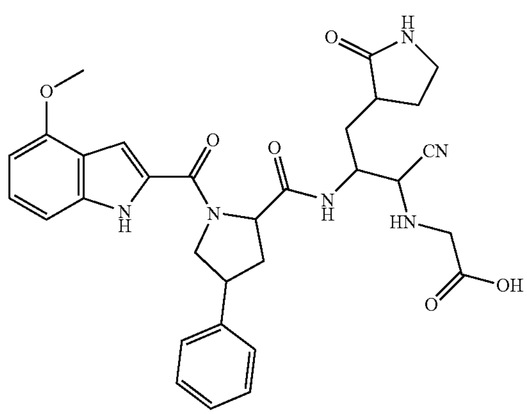 [SMILES: COc1cccc2[nH]c(C(=O)N3CC(c4ccccc4)CC3C(=O)NC(CC3CCNC3=O)C(C#N)NCC(=O)O)cc12] |
| 661 | 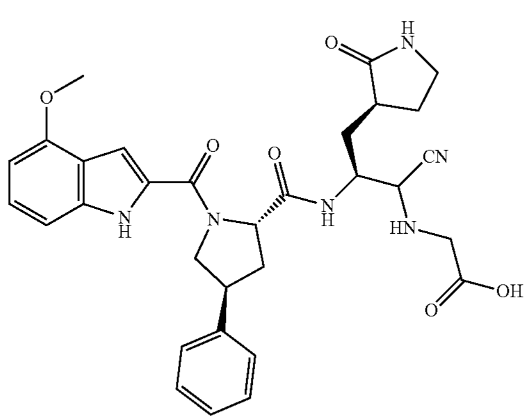 [SMILES: COc1cccc2[nH]c(C(=O)N3C[C@H](c4ccccc4)C[C@H]3C(=O)N[C@@H](C[C@@H]3CCNC3=O)C(C#N)NCC(=O)O)cc12] |

335 336
TABLE 1-continued
Exemplary compounds.
| Compound No. | Structure |
|---|---|
| 662 | 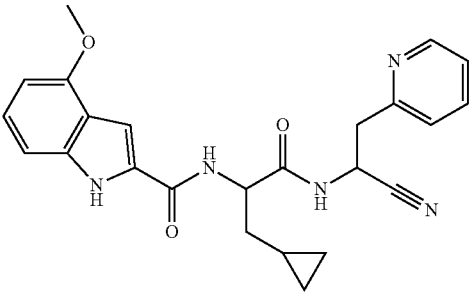 [SMILES: COc1cccc2[nH]c(C(=O)NC(CC3CC3)C(=O)NC(C#N)Cc3ccccn3)cc12] |
| 663 | 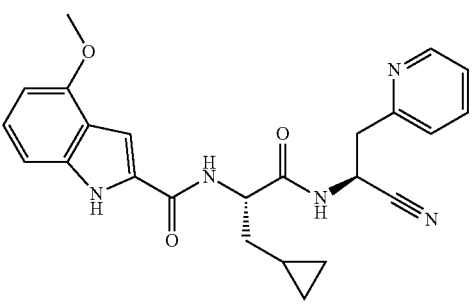 [SMILES: COc1cccc2[nH]c(C(=O)N[C@@H](CC3CC3)C(=O)N[C@H](C#N)Cc3ccccn3)cc12] |
| 664 | 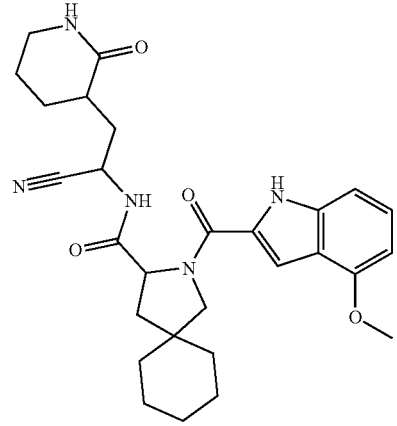 [SMILES: COc1cccc2[nH]c(C(=O)N3CC4(CCCCC4)CC3C(=O)NC(C#N)CC3CCCNC3=O)cc12] |
| 665 | 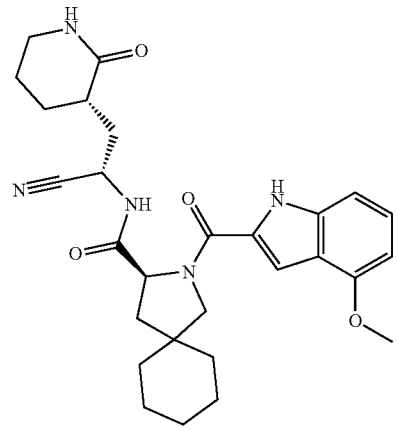 [SMILES: COc1cccc2[nH]c(C(=O)N3CC4(CCCCC4)C[C@H]3C(=O)N[C@H](C#N)C[C@@H]3CCCNC3=O)cc12] |

TABLE 1-continued

Exemplary compounds.

| Compound No. | Structure |
|---|---|
| 666 | 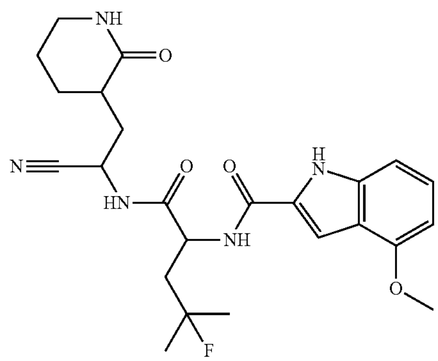 [SMILES: COc1cccc2[nH]c(C(=O)NC(CC(C)(C)F)C(=O)NC(C#N)CC3CCCNC3=O)cc12] |
| 667 | 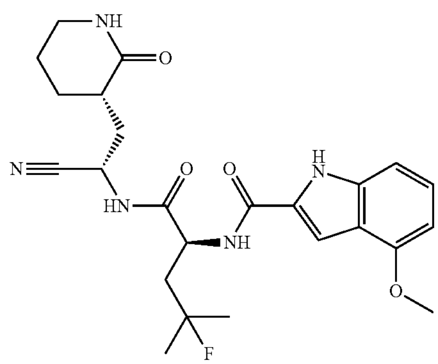 [SMILES: COc1cccc2[nH]c(C(=O)N[C@@H](CC(C)(C)F)C(=O)N[C@H](C#N)C[C@@H]3CCCNC3=O)cc12] |
| 668 | 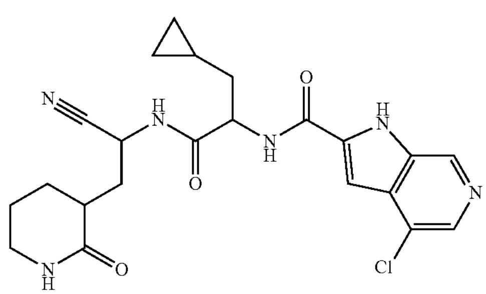 [SMILES: N#CC(CC1CCCNC1=O)NC(=O)C(CC1CC1)NC(=O)c1cc2c(Cl)cncc2[nH]1] |
| 669 | 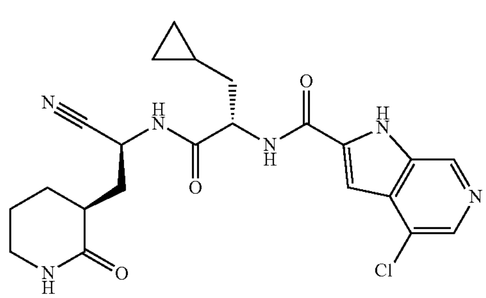 [SMILES: N#C[C@H](C[C@@H]1CCCNC1=O)NC(=O)[C@H](CC1CC1)NC(=O)c1cc2c(Cl)cncc2[nH]1] |

TABLE 1-continued
Exemplary compounds.
| Compound No. | Structure |
|---|---|
| 670 | 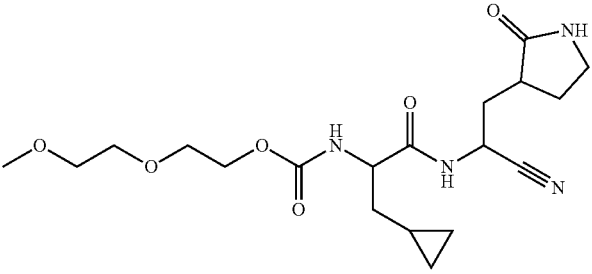 [SMILES: COCCOCCOC(=O)NC(CC1CC1)C(=O)NC(C#N)CC1CCNC1=O] |
| 671 | 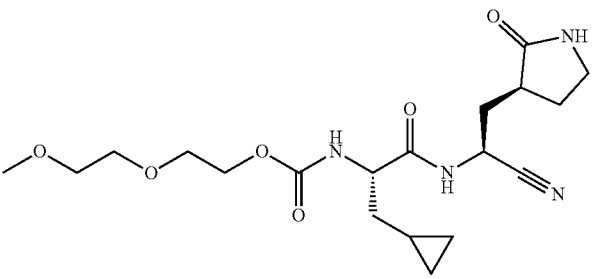 [SMILES: COCCOCCOC(=O)N[C@@H](CC1CC1)C(=O)N[C@H](C#N)C[C@@H]1CCNC1=O] |
| 672 | 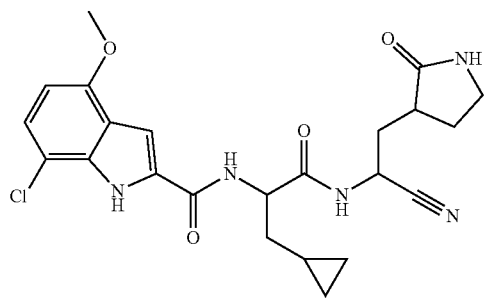 |
| 673 | 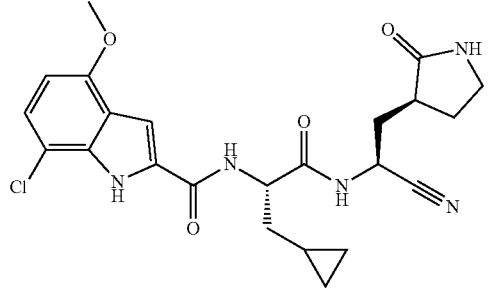 [SMILES: COc1ccc(Cl)c2[nH]c(C(=O)N[C@@H](CC3CC3)C(=O)N[C@H](C#N)C[C@@H]3CCNC3=O)cc12] |
| 674 | 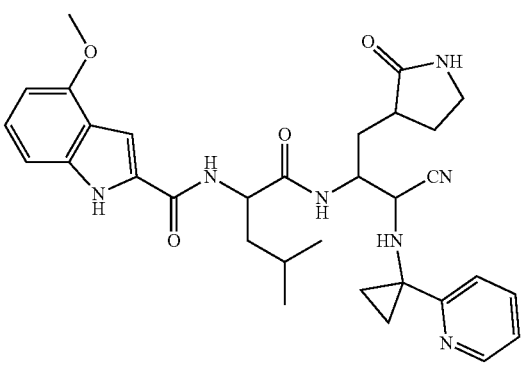 [SMILES: COc1cccc2[nH]c(C(=O)NC(CC(C)C)C(=O)NC(CC3CCNC3=O)C(C#N)NC3(c4ccccn4)CC3)cc12] |

341
342
TABLE 1-continued
Exemplary compounds.
| Compound No. | Structure |
|---|---|
| 675 | 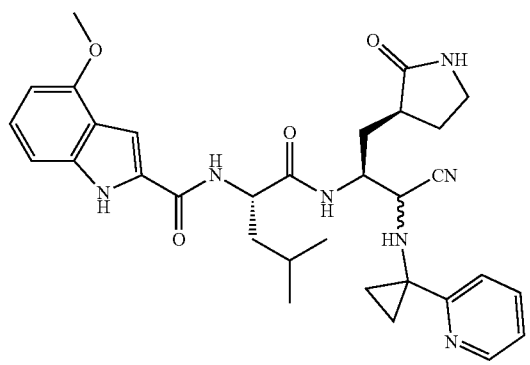 [SMILES: COc1cccc2[nH]c(C(=O)N[C@@H](CC(C)C)C(=O)N[C@@H](C[C@@H]3CCNC3=O)C(C#N)NC3(c4ccccn4)CC3)cc12] |
| 676 | 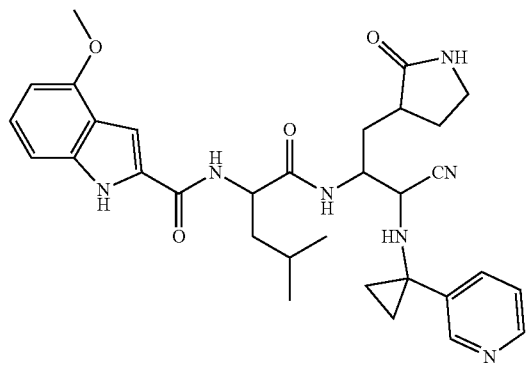 [SMILES: COc1cccc2[nH]c(C(=O)NC(CC(C)C)C(=O)NC(CC3CCNC3=O)C(C#N)NC3(c4cccnc4)CC3)cc12] |
| 677 | 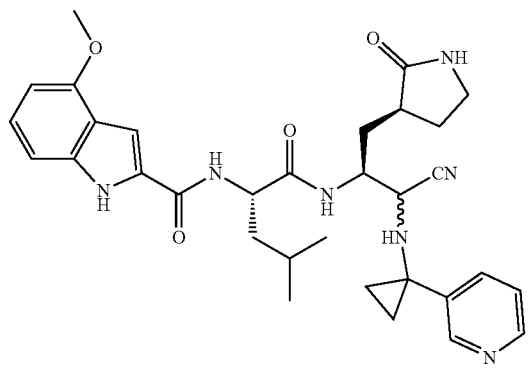 [SMILES: COc1cccc2[nH]c(C(=O)N[C@@H](CC(C)C)C(=O)N[C@@H](C[C@@H]3CCNC3=O)C(C#N)NC3(c4cccnc4)CC3)cc12] |
| 678 | 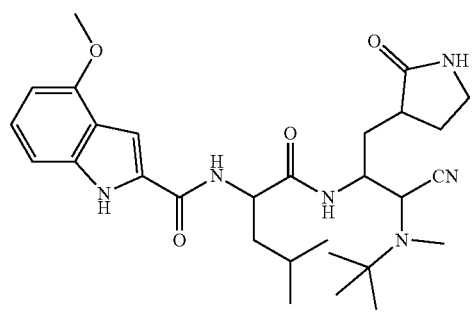 [SMILES: COc1cccc2[nH]c(C(=O)NC(CC(C)C)C(=O)NC(CC3CCNC3=O)C(C#N)N(C)C(C)(C)C)cc12] |

TABLE 1-continued

Exemplary compounds.

| Compound No. | Structure |
|---|---|
| 679 | 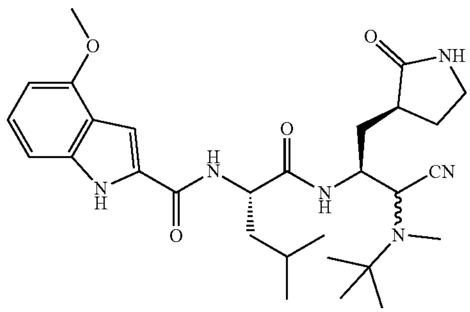 [SMILES: COc1cccc2[nH]c(C(=O)N[C@@H](CC(C)C)C(=O)N[C@@H](C[C@@H]3CCNC3=O)C(C#N)N(C)C(C)(C)C)cc12] |
| 680 | 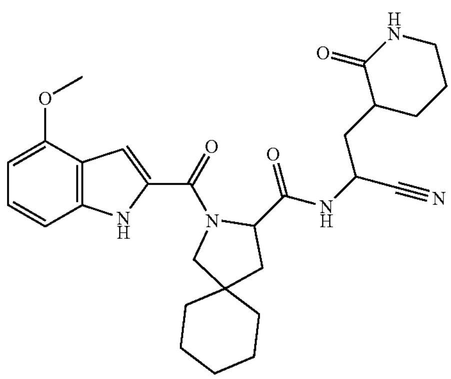 [SMILES: COc1cccc2[nH]c(C(=O)N3CC4(CCCCC4)CC3C(=O)NC(C#N)CC3CCCNC3=O)cc12] |
| 681 | 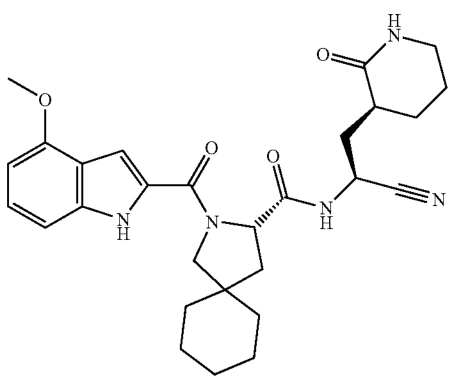 |
| 682 | 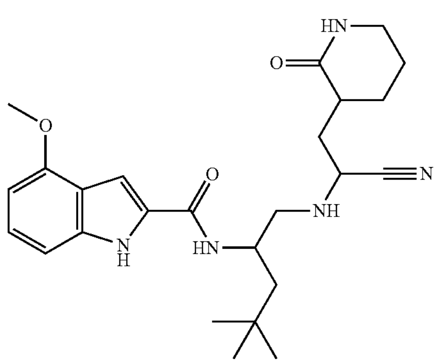 [SMILES: COc1cccc2[nH]c(C(=O)NC(CNC(C#N)CC3CCCNC3=O)CC(C)(C)C)cc12] |

TABLE 1-continued
Exemplary compounds.
| Compound No. | Structure |
|---|---|
| 683 | 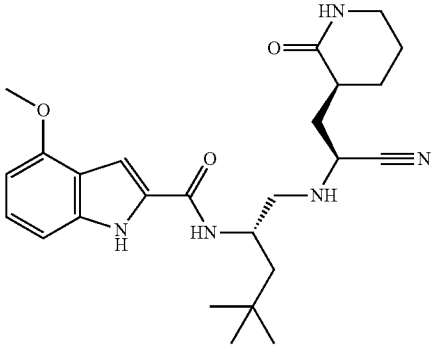 [SMILES: COc1cccc2[nH]c(C(=O)N[C@H](CN[C@H](C#N)C[C@@H]3CCCNC3=O)CC(C)(C)C)cc12] |
| 684 | 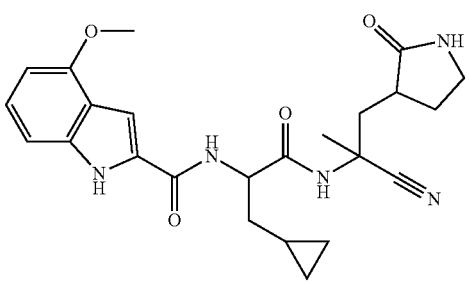 [SMILES: COc1cccc2[nH]c(C(=O)NC(CC3CC3)C(=O)NC(C)(C#N)CC3CCNC3=O)cc12] |
| 685 | 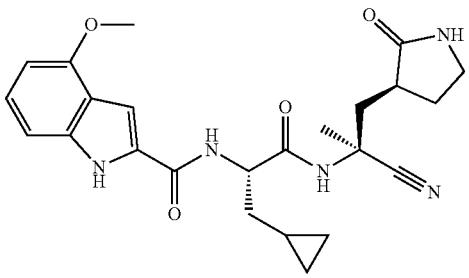 [SMILES: COc1cccc2[nH]c(C(=O)N[C@@H](CC3CC3)C(=O)N[C@](C)(C#N)C[C@@H]3CCNC3=O)cc12] |
| 686 | 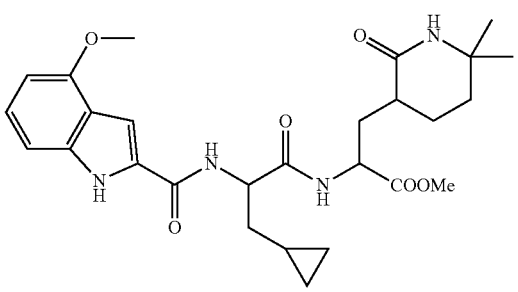 [SMILES: COC(=O)C(CC1CCC(C)(C)NC1=O)NC(=O)C(CC1CC1)NC(=O)c1cc2c(OC)cccc2[nH]1] |
| 687 | 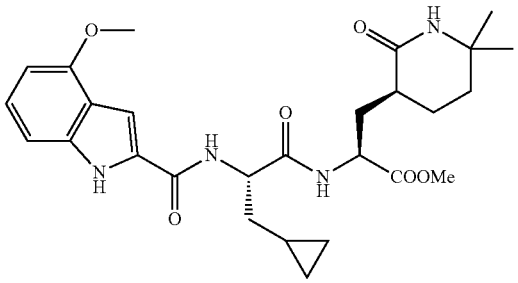 [SMILES: COC(=O)[C@H](C[C@@H]1CCC(C)(C)NC1=O)NC(=O)[C@H](CC1CC1)NC(=O)c1cc2c(OC)cccc2[nH]1] |

TABLE 1-continued

Exemplary compounds.

| Compound No. | Structure |
| --- | --- |
| 688 | 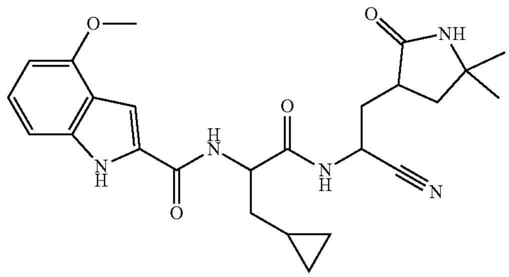 [SMILES: COc1cccc2[nH]c(C(=O)NC(CC3CC3)C(=O)NC(C#N)CC3CC(C)(C)NC3=O)cc12] |
| 689 | 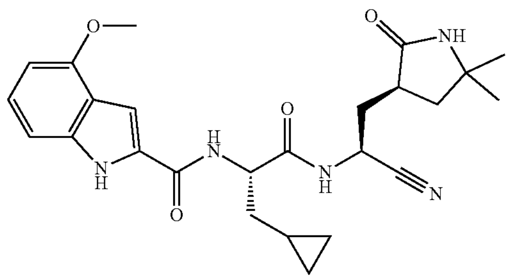 [SMILES: COc1cccc2[nH]c(C(=O)N[C@@H](CC3CC3)C(=O)N[C@H](C#N)C[C@@H]3CC(C)(C)NC3=O)cc12] |
| 690 | 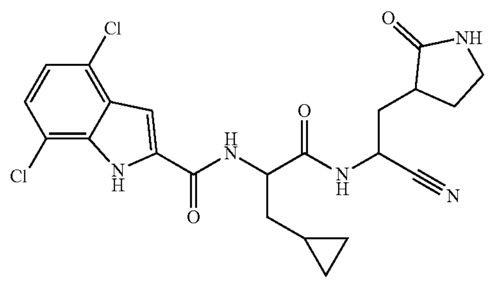 [SMILES: N#CC(CC1CCNC1=O)NC(=O)C(CC1CC1)NC(=O)c1cc2c(Cl)ccc(Cl)c2[nH]1] |
| 691 | 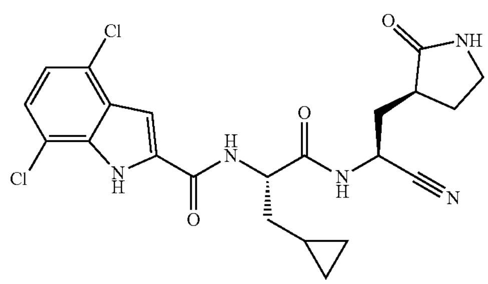 |
| 692 | 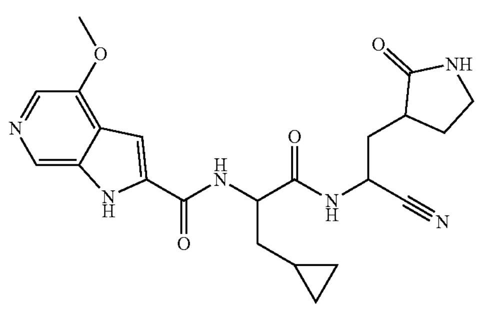 |

349
350
TABLE 1-continued
Exemplary compounds.
| Compound No. | Structure |
|---|---|
| 693 | 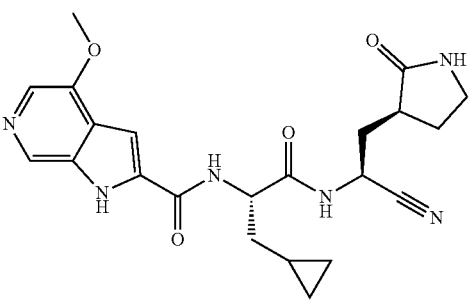 [SMILES: COc1cncc2[nH]c(C(=O)N[C@@H](CC3CC3)C(=O)N[C@H](C#N)C[C@@H]3CCNC3=O)cc12] |
| 694 | 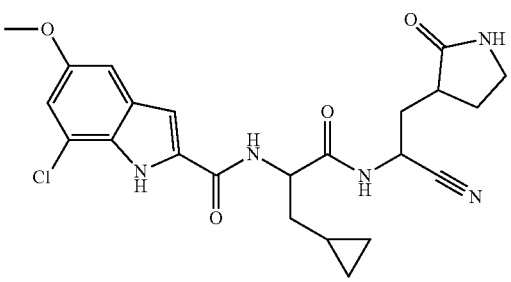 [SMILES: COc1cc(Cl)c2[nH]c(C(=O)NC(CC3CC3)C(=O)NC(C#N)CC3CCNC3=O)cc2c1] |
| 695 | 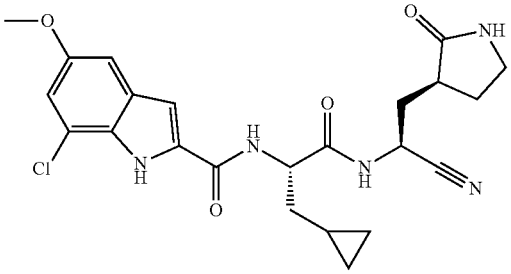 [SMILES: COc1cc(Cl)c2[nH]c(C(=O)N[C@@H](CC3CC3)C(=O)N[C@H](C#N)C[C@@H]3CCNC3=O)cc2c1] |
| 696 | 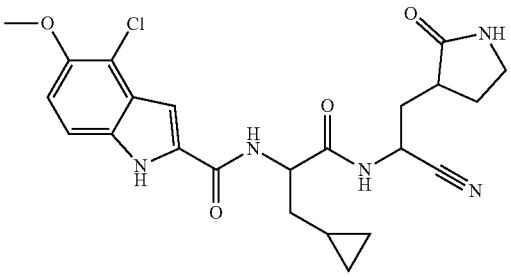 [SMILES: COc1ccc2[nH]c(C(=O)NC(CC3CC3)C(=O)NC(C#N)CC3CCNC3=O)cc2c1Cl] |
| 697 | 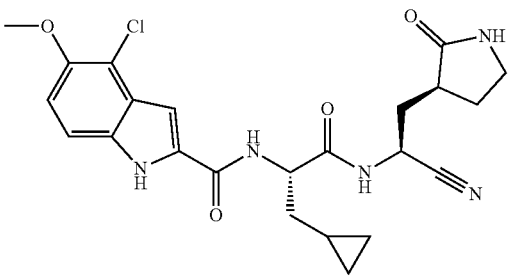 [SMILES: COc1ccc2[nH]c(C(=O)N[C@@H](CC3CC3)C(=O)N[C@H](C#N)C[C@@H]3CCNC3=O)cc2c1Cl] |

TABLE 1-continued
Exemplary compounds.
| Compound No. | Structure |
|---|---|
| 698 | 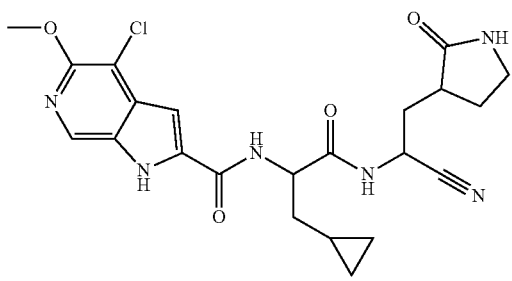 [SMILES: COc1ncc2[nH]c(C(=O)NC(CC3CC3)C(=O)NC(C#N)CC3CCNC3=O)cc2c1Cl] |
| 699 | 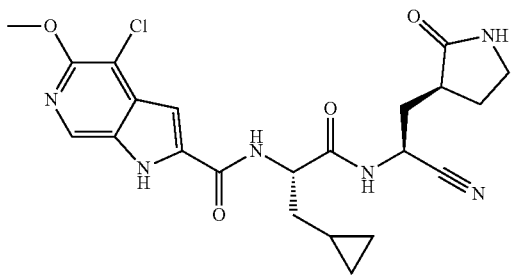 [SMILES: COc1ncc2[nH]c(C(=O)N[C@@H](CC3CC3)C(=O)N[C@H](C#N)C[C@@H]3CCNC3=O)cc2c1Cl] |
| 700 | 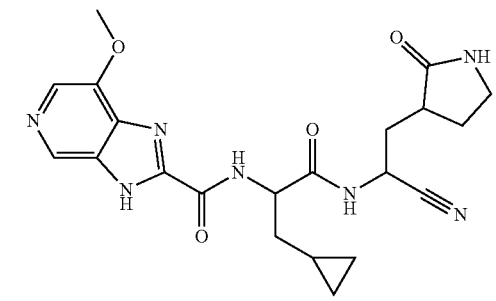 [SMILES: COc1cncc2[nH]c(C(=O)NC(CC3CC3)C(=O)NC(C#N)CC3CCNC3=O)nc12] |
| 701 | 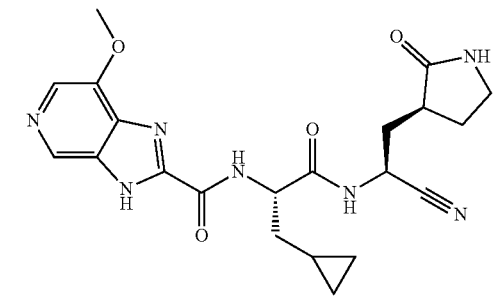 |
| 702 | 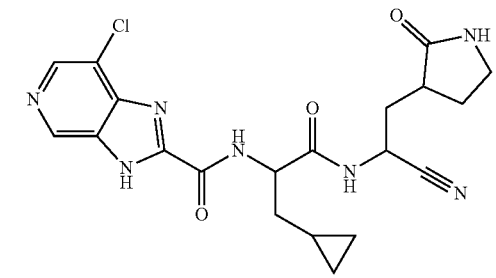 [SMILES: N#CC(CC1CCNC1=O)NC(=O)C(CC1CC1)NC(=O)c1nc2c(Cl)cncc2[nH]1] |

TABLE 1-continued

Exemplary compounds.

| Compound No. | Structure |
|---|---|
| 703 | 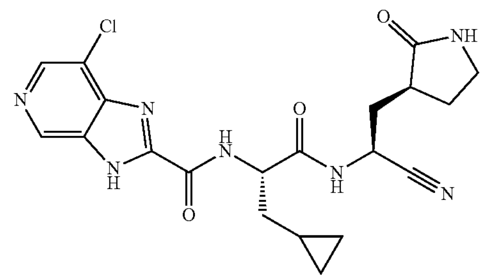 [SMILES: N#C[C@H](C[C@@H]1CCNC1=O)NC(=O)[C@H](CC1CC1)NC(=O)c1nc2c(Cl)cncc2[nH]1] |
| 704 | 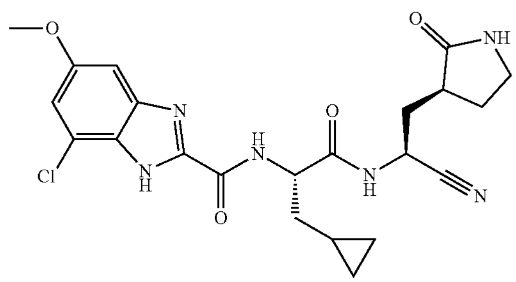 [SMILES: COc1cc(Cl)c2[nH]c(C(=O)N[C@@H](CC3CC3)C(=O)N[C@H](C#N)C[C@@H]3CCNC3=O)nc2c1] |
| 705 | 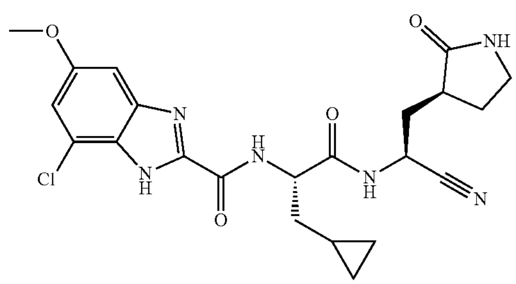 [SMILES: COc1cc(Cl)c2[nH]c(C(=O)N[C@@H](CC3CC3)C(=O)N[C@H](C#N)C[C@@H]3CCNC3=O)nc2c1] |
| 706 | 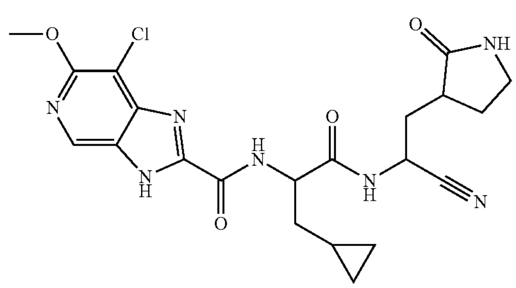 [SMILES: COc1ncc2[nH]c(C(=O)NC(CC3CC3)C(=O)NC(C#N)CC3CCNC3=O)nc2c1Cl] |
| 707 | 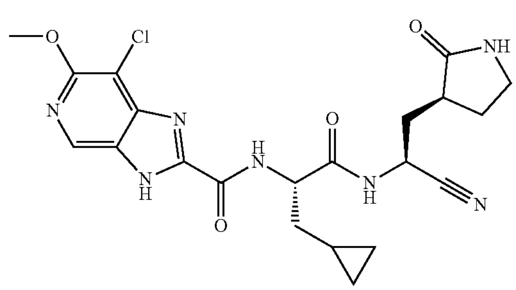 [SMILES: COc1ncc2[nH]c(C(=O)N[C@@H](CC3CC3)C(=O)N[C@H](C#N)C[C@@H]3CCNC3=O)nc2c1Cl] |

TABLE 1-continued

Exemplary compounds.

| Compound No. | Structure |
|---|---|
| 708 | 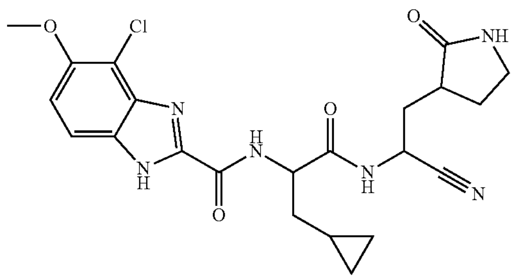 [SMILES: COc1ccc2[nH]c(C(=O)NC(CC3CC3)C(=O)NC(C#N)CC3CCNC3=O)nc2c1Cl] |
| 709 | 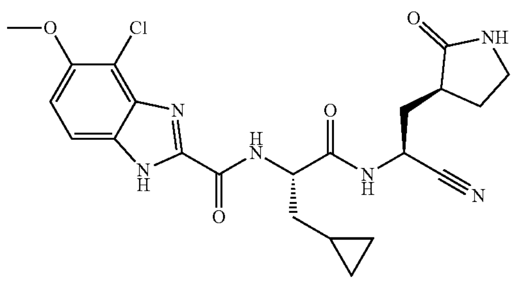 [SMILES: COc1ccc2[nH]c(C(=O)N[C@@H](CC3CC3)C(=O)N[C@H](C#N)C[C@@H]3CCNC3=O)nc2c1Cl] |
| 710 | 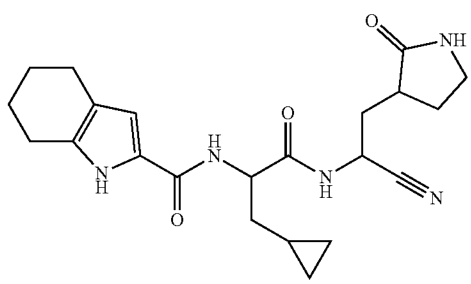 [SMILES: N#CC(CC1CCNC1=O)NC(=O)C(CC1CC1)NC(=O)c1cc2c([nH]1)CCCC2] |
| 711 | 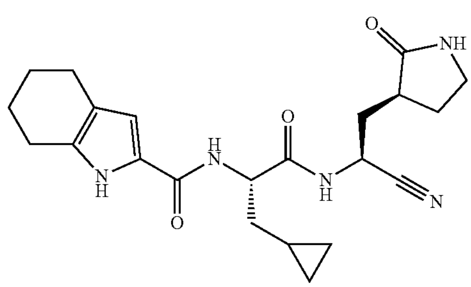 [SMILES: N#C[C@H](C[C@@H]1CCNC1=O)NC(=O)[C@H](CC1CC1)NC(=O)c1cc2c([nH]1)CCCC2] |
| 712 | 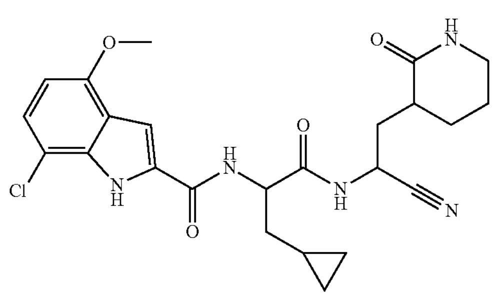 [SMILES: COc1ccc(Cl)c2[nH]c(C(=O)NC(CC3CC3)C(=O)NC(C#N)CC3CCCNC3=O)cc12] |

TABLE 1-continued

Exemplary compounds.

| Compound No. | Structure |
|---|---|
| 713 | 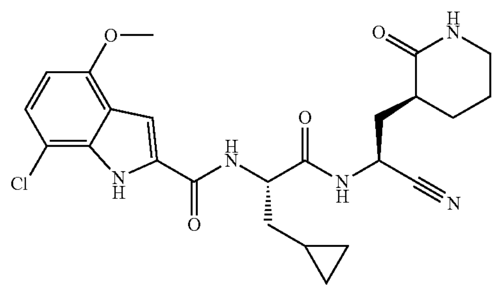 [SMILES: COc1ccc(Cl)c2[nH]c(C(=O)N[C@@H](CC3CC3)C(=O)N[C@H](C#N)C[C@@H]3CCCNC3=O)cc12] |
| 714 | 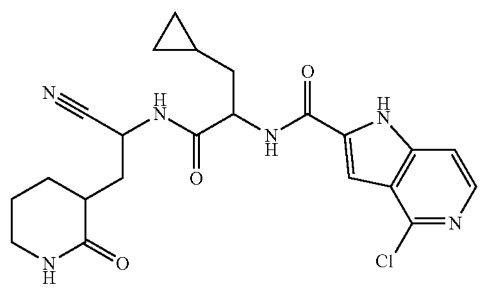 [SMILES: N#CC(CC1CCCNC1=O)NC(=O)C(CC1CC1)NC(=O)c1cc2c(Cl)nccc2[nH]1] |
| 715 | 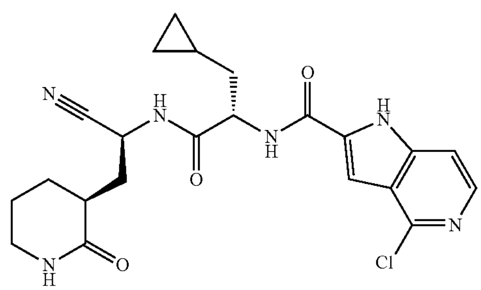 |
| 716 | 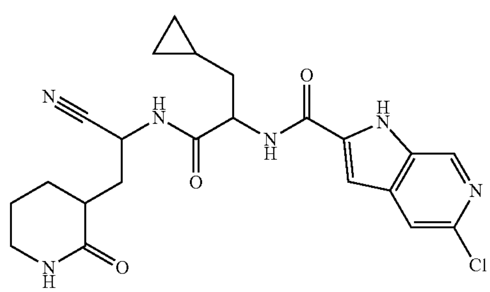 [SMILES: N#CC(CC1CCCNC1=O)NC(=O)C(CC1CC1)NC(=O)c1cc2cc(Cl)ncc2[nH]1] |
| 717 | 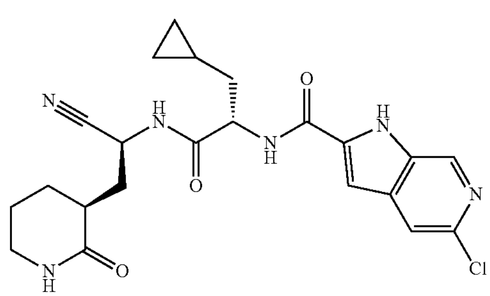 [SMILES: N#C[C@H](C[C@@H]1CCCNC1=O)NC(=O)[C@H](CC1CC1)NC(=O)c1cc2cc(Cl)ncc2[nH]1] |

TABLE 1-continued
Exemplary compounds.
| Compound No. | Structure |
|---|---|
| 718 | 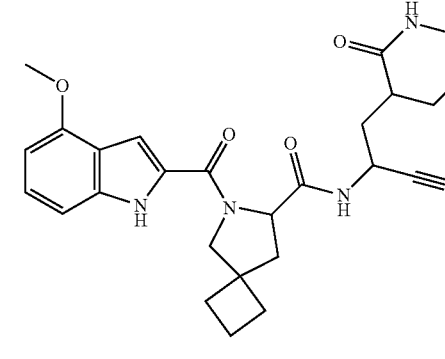 |
| 719 | 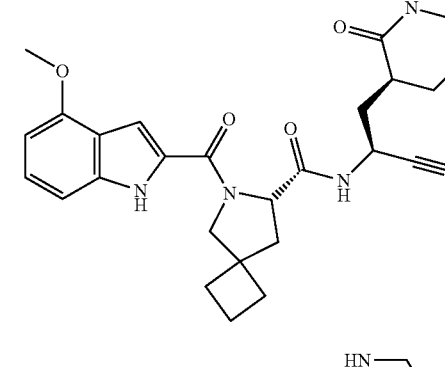 |
| 720 | 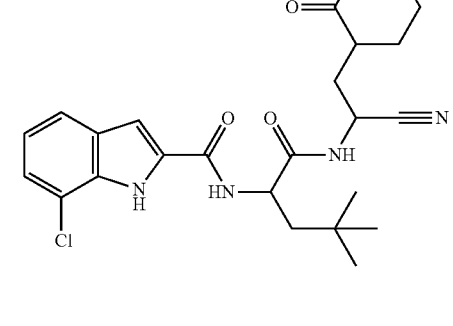 |
| 721 | 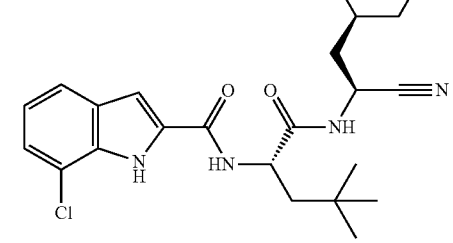 |

TABLE 1-continued
Exemplary compounds.
| Compound No. | Structure |
|---|---|
| 722 | 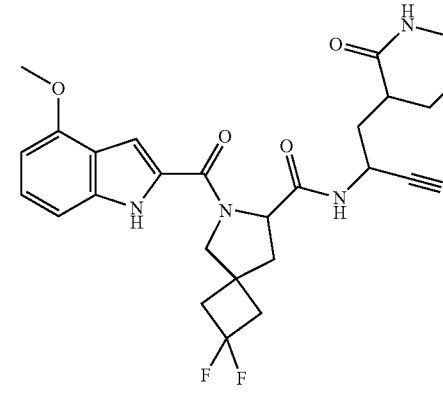 |
| 723 | 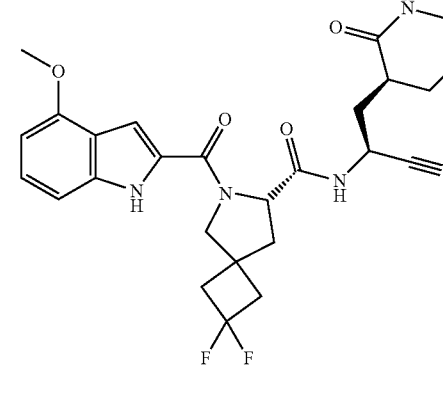 |
| 724 | 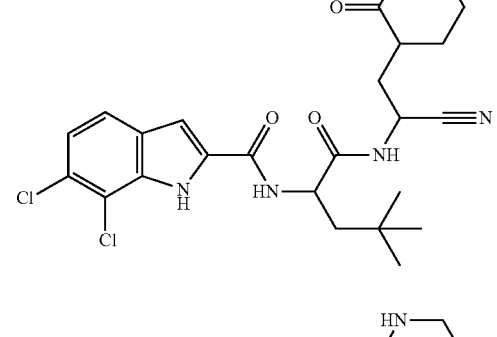 |
| 725 | 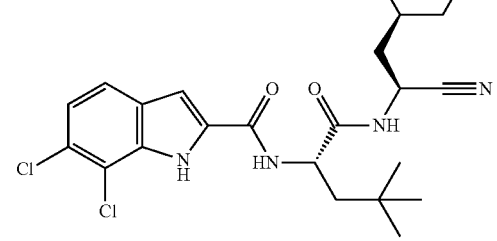 |

TABLE 1-continued

Exemplary compounds.

| Compound No. | Structure |
|---|---|
| 726 | 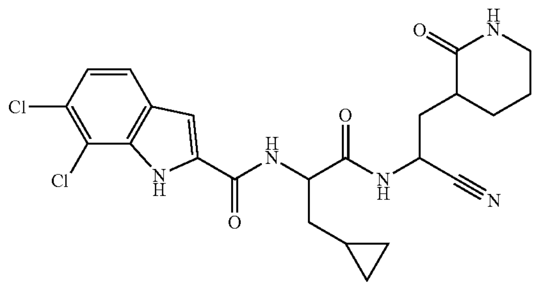 [SMILES: N#CC(CC1CCCNC1=O)NC(=O)C(CC1CC1)NC(=O)c1cc2ccc(Cl)c(Cl)c2[nH]1] |
| 727 | 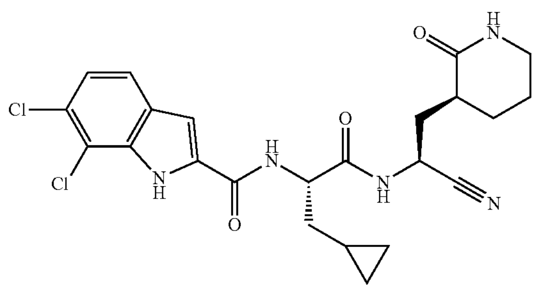 [SMILES: N#C[C@H](C[C@@H]1CCCNC1=O)NC(=O)[C@H](CC1CC1)NC(=O)c1cc2ccc(Cl)c(Cl)c2[nH]1] |
| 728 | 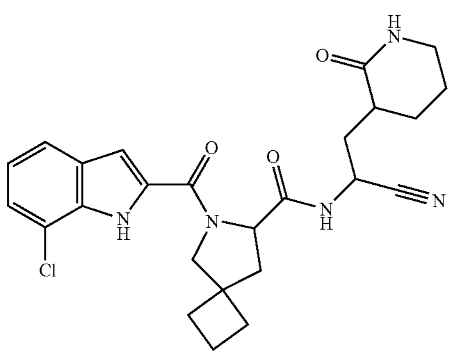 [SMILES: N#CC(CC1CCCNC1=O)NC(=O)C1CC2(CCC2)CN1C(=O)c1cc2cccc(Cl)c2[nH]1] |
| 729 | 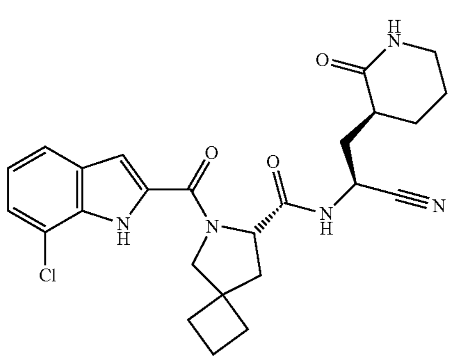 |

TABLE 1-continued
Exemplary compounds.
| Compound No. | Structure |
|---|---|
| 730 | 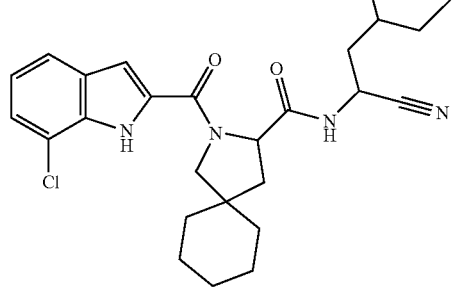 |
| 731 | 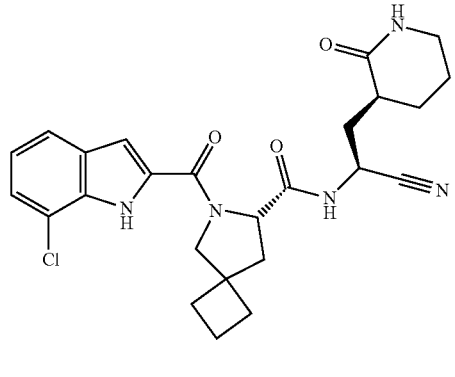 |
| 732 | 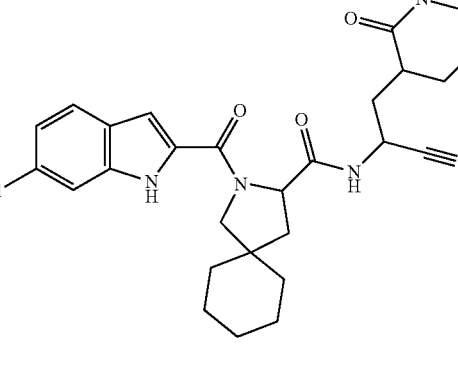 |
| 733 | 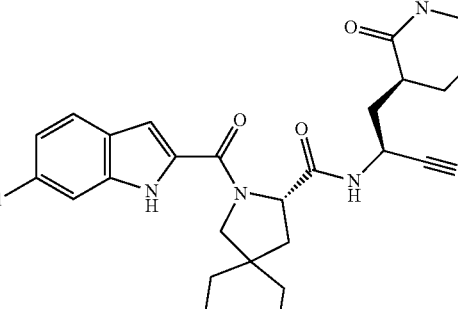 |

TABLE 1-continued

Exemplary compounds.

| Compound No. | Structure |
|---|---|
| 734 | 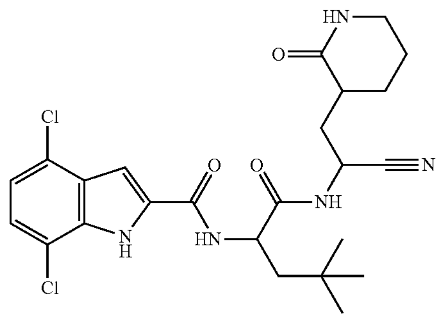 [SMILES: CC(C)(C)CC(NC(=O)c1cc2c(Cl)ccc(Cl)c2[nH]1)C(=O)NC(C#N)CC1CCCNC1=O] |
| 735 | 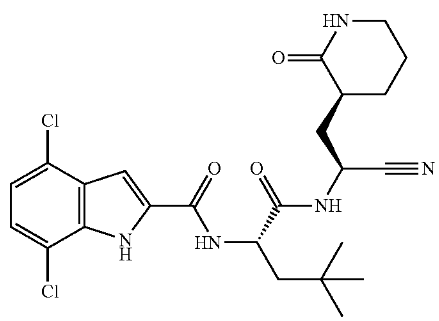 [SMILES: CC(C)(C)C[C@H](NC(=O)c1cc2c(Cl)ccc(Cl)c2[nH]1)C(=O)N[C@H](C#N)C[C@@H]1CCCNC1=O] |
| 736 | 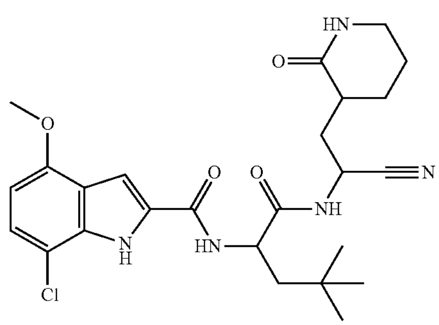 [SMILES: COc1ccc(Cl)c2[nH]c(C(=O)NC(CC(C)(C)C)C(=O)NC(C#N)CC3CCCNC3=O)cc12] |
| 737 | 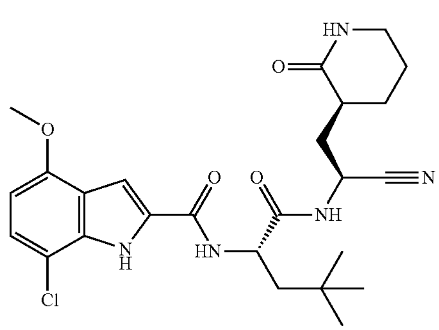 |

TABLE 1-continued
Exemplary compounds.
| Compound No. | Structure |
|---|---|
| 738 | 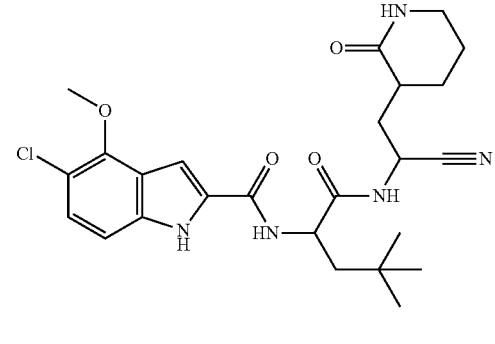 [SMILES: COc1c(Cl)ccc2[nH]c(C(=O)NC(CC(C)(C)C)C(=O)NC(C#N)CC3CCCNC3=O)cc12] |
| 739 | 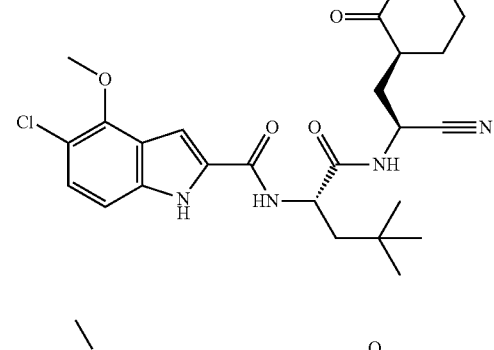 |
| 740 | 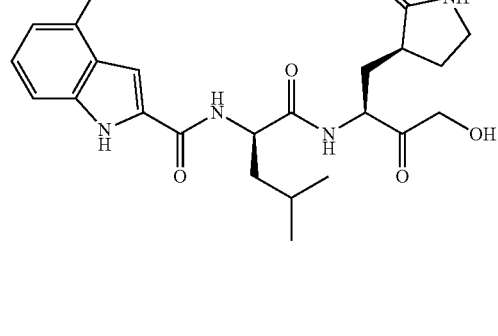 |
| 741 | 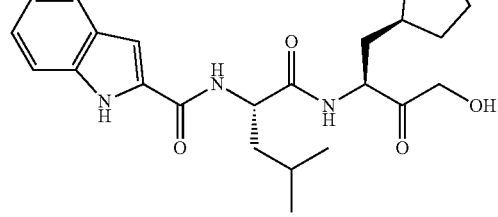 |

TABLE 1-continued
Exemplary compounds.
| Compound No. | Structure |
|---|---|
| 742 | 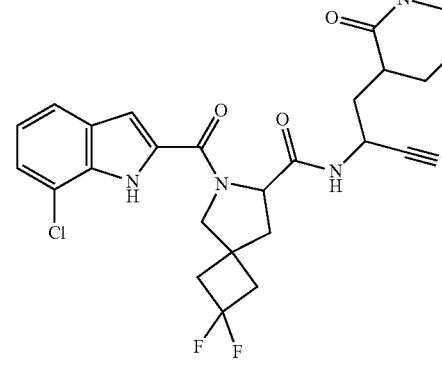 |
| 743 | 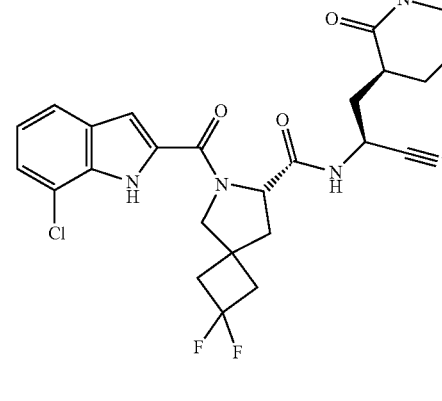 |
| 744 | 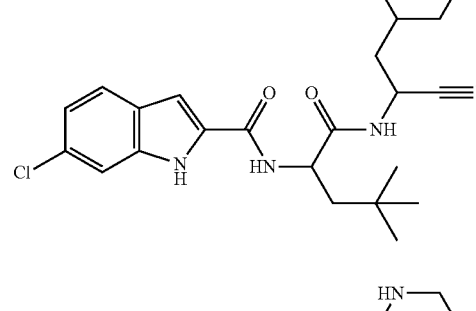 |
| 745 | 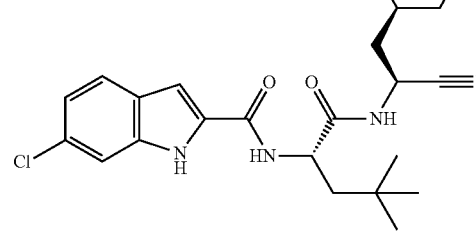 |

TABLE 1-continued
Exemplary compounds.
| Compound No. | Structure |
|---|---|
| 267A | 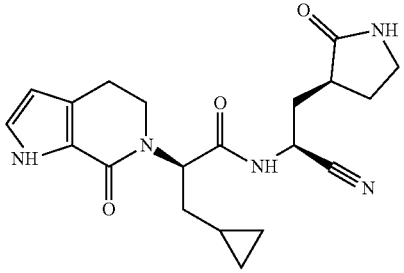 [SMILES: N#C[C@H](C[C@@H]1CCNC1=O)NC(=O)[C@@H](CC1CC1)N1CCc2cc[nH]c2C1=O] |
| 269A | 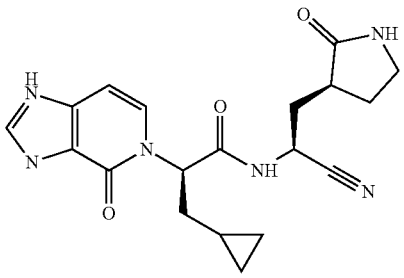 |
| 271A | 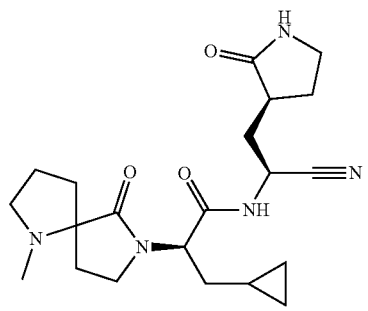 [SMILES: CN1CCCC12CCN([C@H](CC1CC1)C(=O)N[C@H](C#N)C[C@@H]1CCNC1=O)C2=O] |
| 273A | 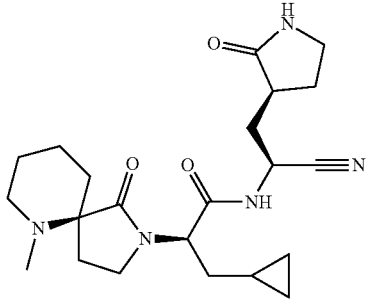 [SMILES: CN1CCCC[C@]12CCN([C@H](CC1CC1)C(=O)N[C@H](C#N)C[C@@H]1CCNC1=O)C2=O] |
| 273B | 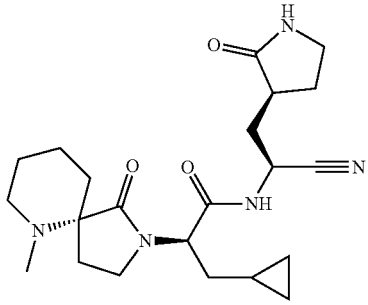 [SMILES: CN1CCCC[C@@]12CCN([C@H](CC1CC1)C(=O)N[C@H](C#N)C[C@@H]1CCNC1=O)C2=O] |

TABLE 1-continued

Exemplary compounds.

| Compound No. | Structure |
|---|---|
| 273C | 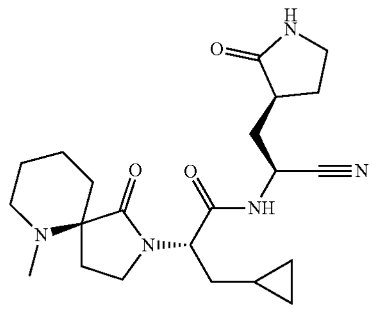 [SMILES: CN1CCCC[C@]12CCN([C@@H](CC1CC1)C(=O)N[C@H](C#N)C[C@@H]1CCNC1=O)C2=O] |
| 491A | 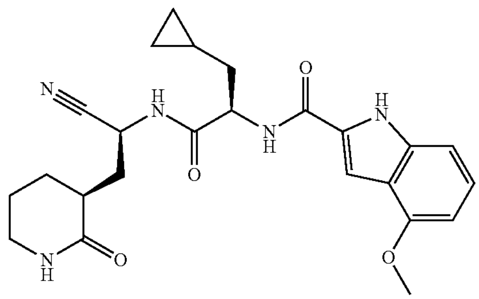 [SMILES: COc1cccc2[nH]c(C(=O)N[C@H](CC3CC3)C(=O)N[C@H](C#N)C[C@@H]3CCCNC3=O)cc12] |
| 375A | 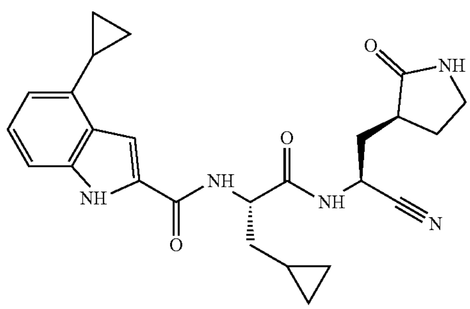 [SMILES: N#C[C@H](C[C@@H]1CCNC1=O)NC(=O)[C@H](CC1CC1)NC(=O)c1cc2c(C3CC3)cccc2[nH]1] |
| 389A | 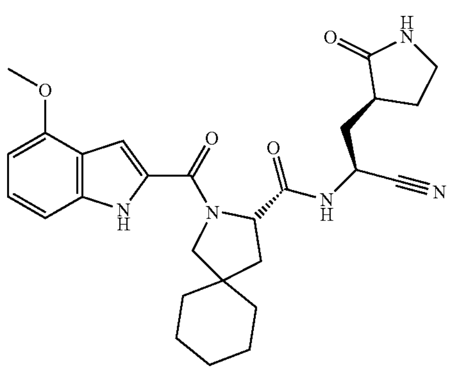 |

TABLE 1-continued

Exemplary compounds.

| Compound No. | Structure |
|---|---|
| 389B | 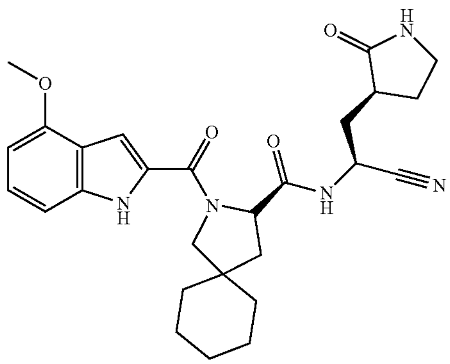 |
| 746 | 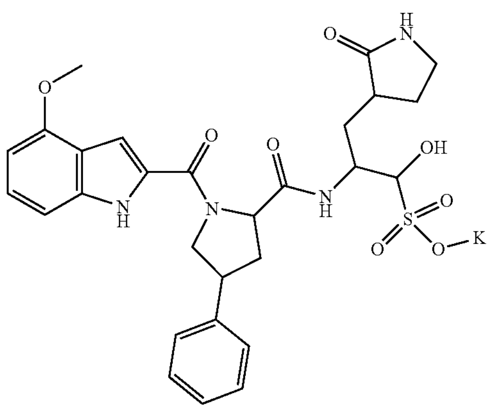 |
| 747 | 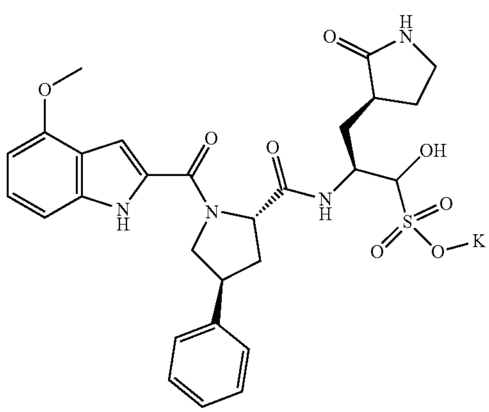 |
| 748 | 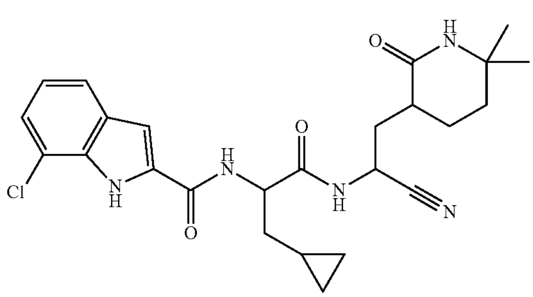 [SMILES: CC1(C)CCC(CC(C#N)NC(=O)C(CC2CC2)NC(=O)c2cc3cccc(Cl)c3[nH]2)C(=O)N1] |

TABLE 1-continued

Exemplary compounds.

| Compound No. | Structure |
|---|---|
| 749 | 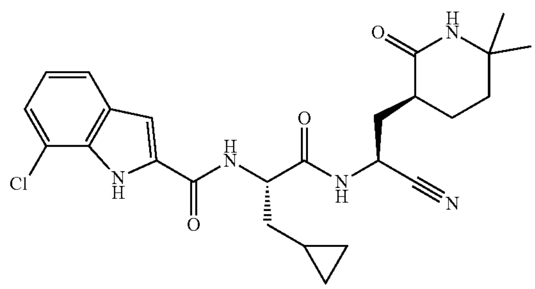 [SMILES: CC1(C)CC[C@@H](C[C@@H](C#N)NC(=O)[C@H](CC2CC2)NC(=O)c2cc3cccc(Cl)c3[nH]2)C(=O)N1] |
| 750 | 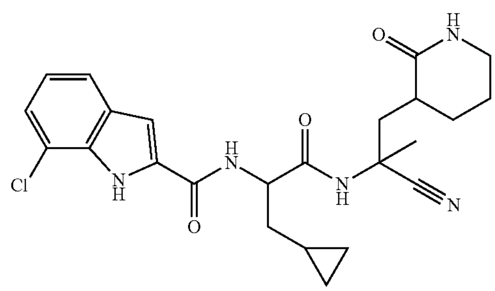 |
| 751 | 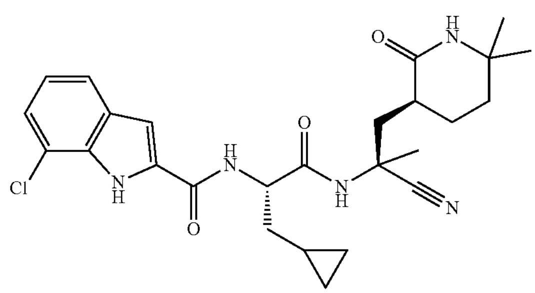 [SMILES: CC1(C)CC[C@@H](C[C@@](C)(C#N)NC(=O)[C@H](CC2CC2)NC(=O)c2cc3cccc(Cl)c3[nH]2)C(=O)N1] |
| 752 | 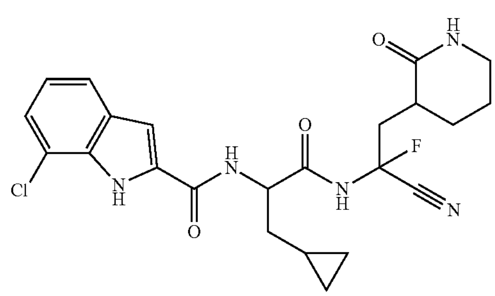 [SMILES: N#CC(F)(CC1CCCNC1=O)NC(=O)C(CC1CC1)NC(=O)c1cc2cccc(Cl)c2[nH]1] |
| 753 | 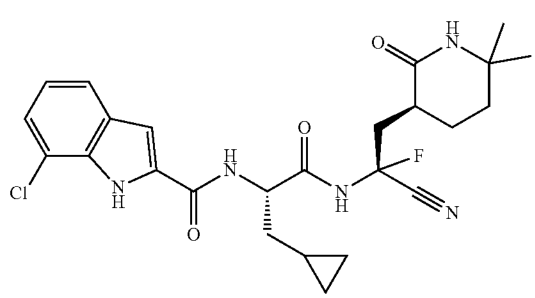 [SMILES: CC1(C)CC[C@@H](C[C@@](F)(C#N)NC(=O)[C@H](CC2CC2)NC(=O)c2cc3cccc(Cl)c3[nH]2)C(=O)N1] |

TABLE 1-continued
Exemplary compounds.
| Compound No. | Structure |
|---|---|
| 754 | 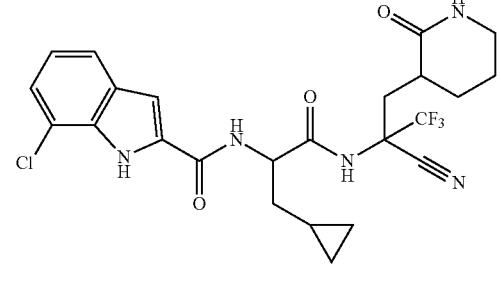 |
| 755 | 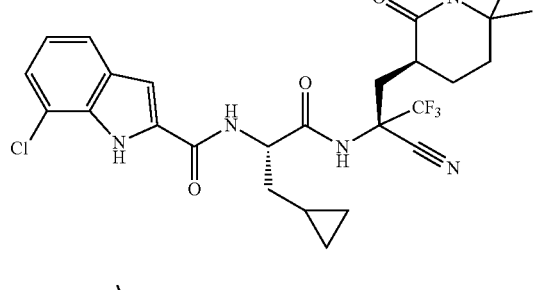 |
| 756 | 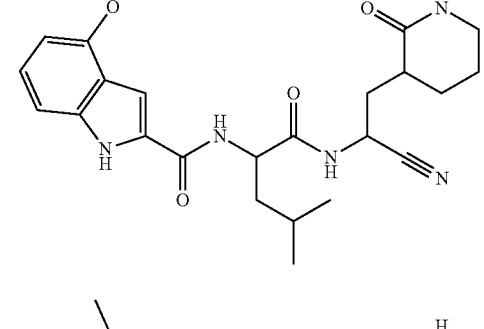 |
| 757 | 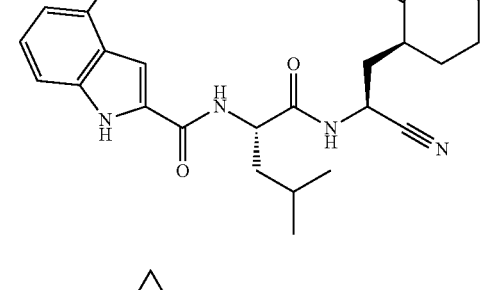 |
| 758 | 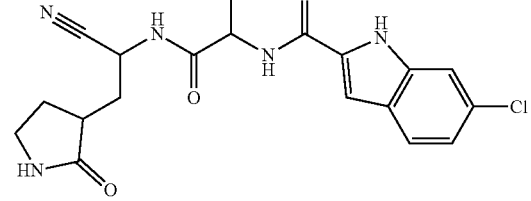 |

TABLE 1-continued

Exemplary compounds.

| Compound No. | Structure |
|---|---|
| 759 | 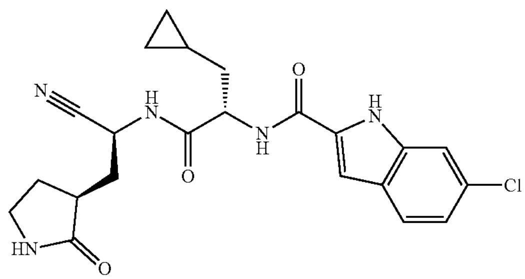 [SMILES: N#C[C@H](C[C@@H]1CCNC1=O)NC(=O)[C@H](CC1CC1)NC(=O)c1cc2ccc(Cl)cc2[nH]1] |
| 760 | 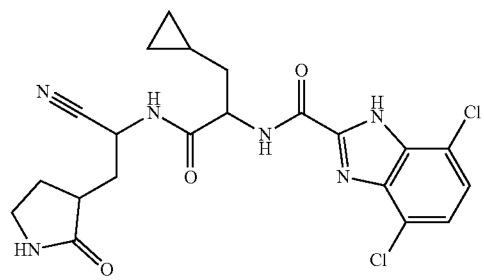 [SMILES: N#CC(CC1CCNC1=O)NC(=O)C(CC1CC1)NC(=O)c1nc2c(Cl)ccc(Cl)c2[nH]1] |
| 761 | 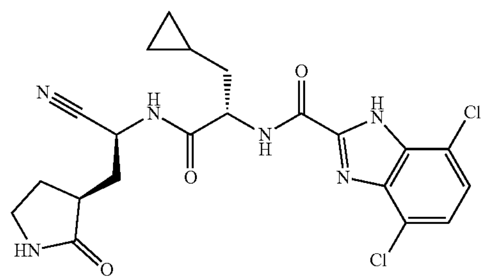 [SMILES: N#C[C@H](C[C@@H]1CCNC1=O)NC(=O)[C@H](CC1CC1)NC(=O)c1nc2c(Cl)ccc(Cl)c2[nH]1] |
| 762 | 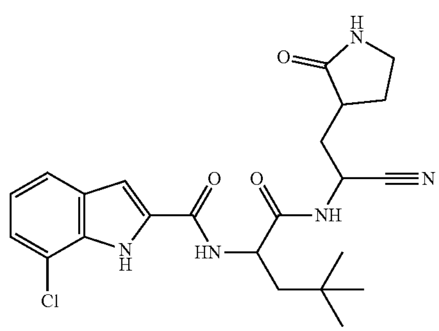 [SMILES: CC(C)(C)CC(NC(=O)c1cc2cccc(Cl)c2[nH]1)C(=O)NC(C#N)CC1CCNC1=O] |
| 763 | 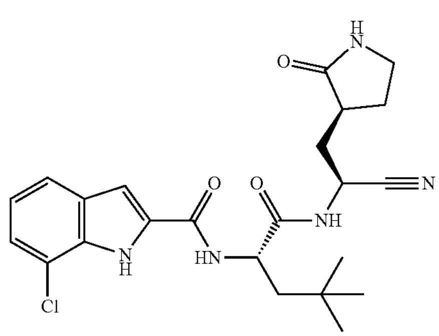 [SMILES: CC(C)(C)C[C@H](NC(=O)c1cc2cccc(Cl)c2[nH]1)C(=O)N[C@H](C#N)C[C@@H]1CCNC1=O] |

TABLE 1-continued

Exemplary compounds.

| Compound No. | Structure |
|---|---|
| 764 | 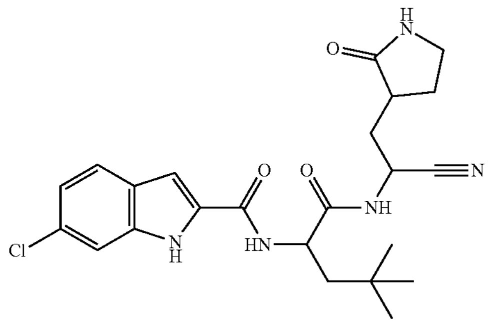 [SMILES: CC(C)(C)CC(NC(=O)c1cc2ccc(Cl)cc2[nH]1)C(=O)NC(C#N)CC1CCNC1=O] |
| 765 | 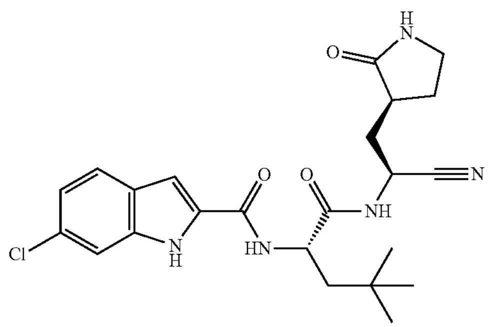 [SMILES: CC(C)(C)C[C@H](NC(=O)c1cc2ccc(Cl)cc2[nH]1)C(=O)N[C@H](C#N)C[C@@H]1CCNC1=O] |
| 766 | 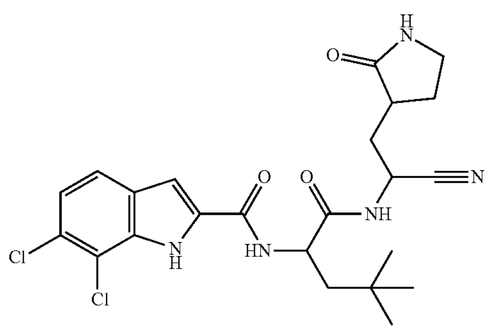 [SMILES: CC(C)(C)CC(NC(=O)c1cc2ccc(Cl)c(Cl)c2[nH]1)C(=O)NC(C#N)CC1CCNC1=O] |
| 767 | 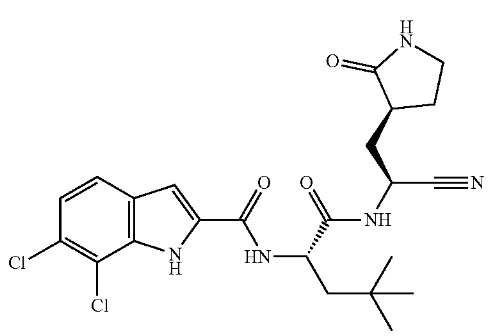 [SMILES: CC(C)(C)C[C@H](NC(=O)c1cc2ccc(Cl)c(Cl)c2[nH]1)C(=O)N[C@H](C#N)C[C@@H]1CCNC1=O] |

TABLE 1-continued

Exemplary compounds.

| Compound No. | Structure |
|---|---|
| 768 | 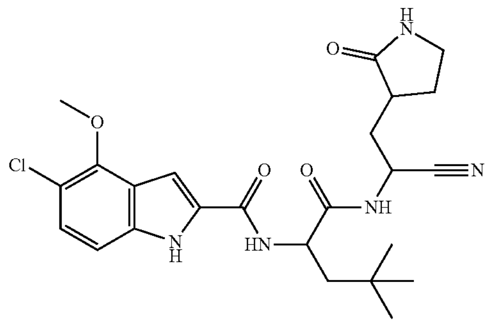 [SMILES: COc1c(Cl)ccc2[nH]c(C(=O)NC(CC(C)(C)C)C(=O)NC(C#N)CC3CCNC3=O)cc12] |
| 769 | 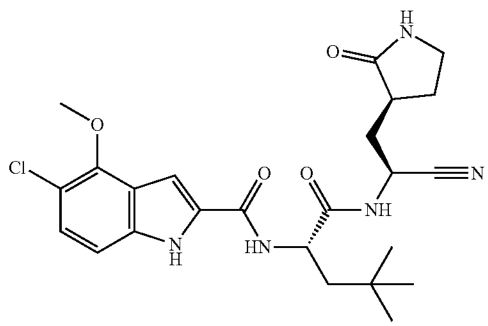 [SMILES: COc1c(Cl)ccc2[nH]c(C(=O)N[C@@H](CC(C)(C)C)C(=O)N[C@H](C#N)C[C@@H]3CCNC3=O)cc12] |
| 770 | 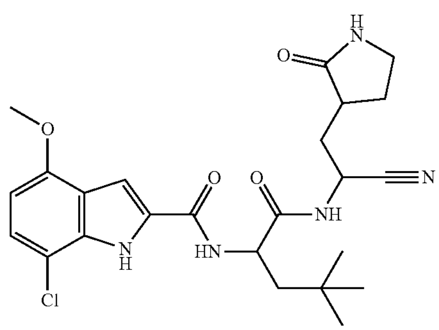 [SMILES: COc1ccc(Cl)c2[nH]c(C(=O)NC(CC(C)(C)C)C(=O)NC(C#N)CC3CCNC3=O)cc12] |
| 771 | 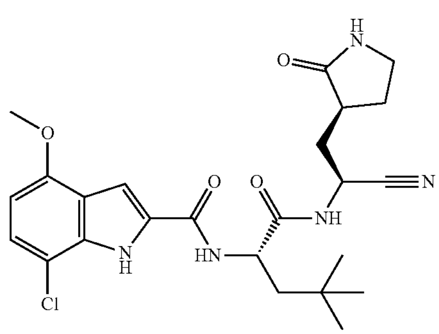 [SMILES: COc1ccc(Cl)c2[nH]c(C(=O)N[C@@H](CC(C)(C)C)C(=O)N[C@H](C#N)C[C@@H]3CCNC3=O)cc12] |

TABLE 1-continued

Exemplary compounds.

| Compound No. | Structure |
|---|---|
| 772 | 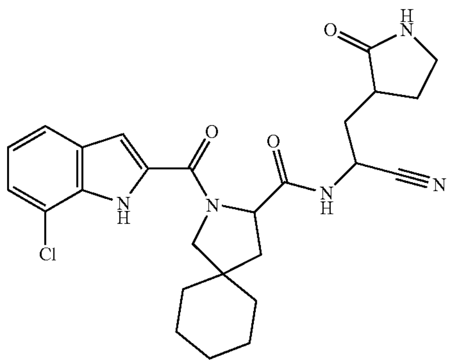 [SMILES: N#CC(CC1CCNC1=O)NC(=O)C1CC2(CCCCC2)CN1C(=O)c1cc2cccc(Cl)c2[nH]1] |
| 773 | 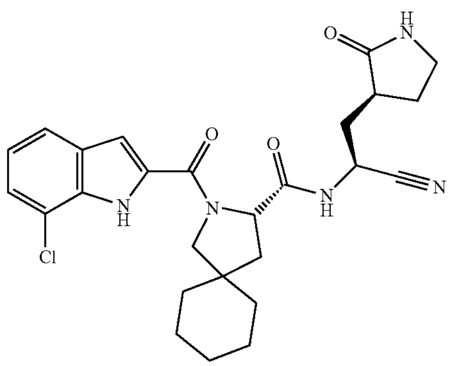 |
| 774 | 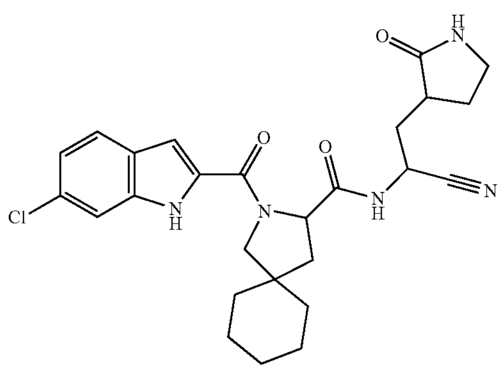 [SMILES: N#CC(CC1CCNC1=O)NC(=O)C1CC2(CCCCC2)CN1C(=O)c1cc2ccc(Cl)cc2[nH]1] |
| 775 | 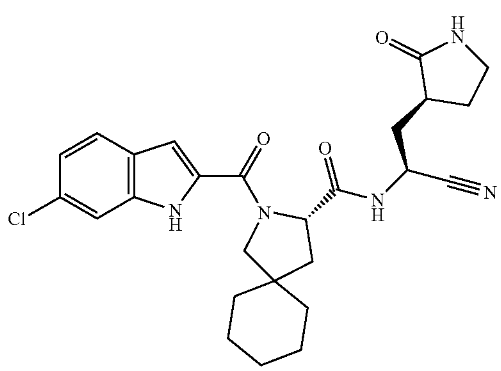 [SMILES: N#C[C@H](C[C@@H]1CCNC1=O)NC(=O)[C@@H]1CC2(CCCCC2)CN1C(=O)c1cc2ccc(Cl)cc2[nH]1] |

TABLE 1-continued
Exemplary compounds.
| Compound No. | Structure |
|---|---|
| 776 | 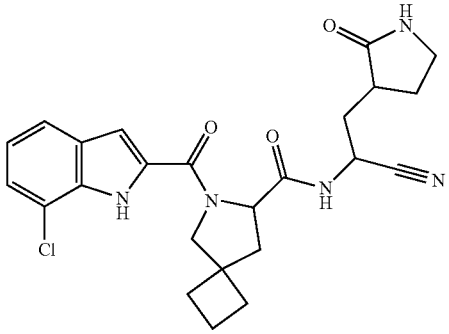 [SMILES: N#CC(CC1CCNC1=O)NC(=O)C1CC2(CCC2)CN1C(=O)c1cc2cccc(Cl)c2[nH]1] |
| 777 | 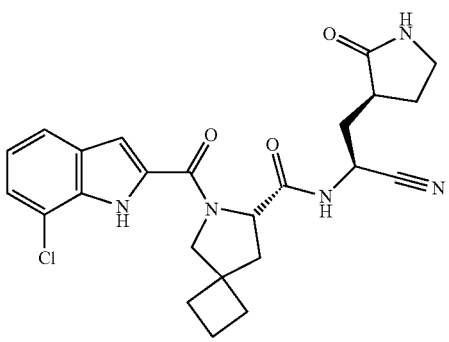 |
| 778 | 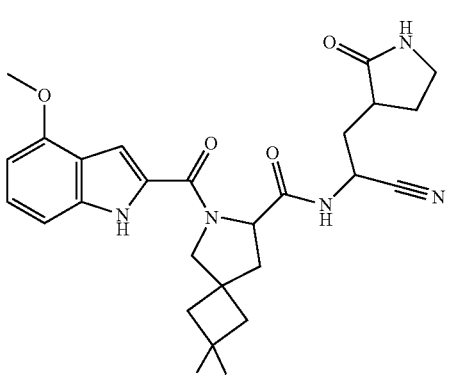 |
| 779 | 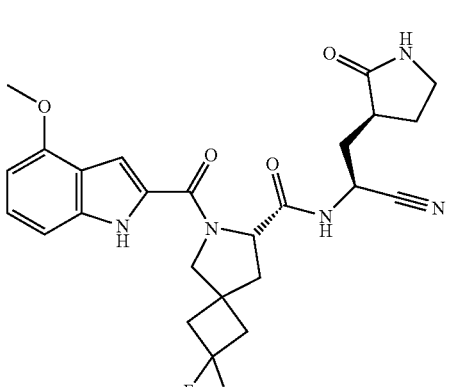 |

TABLE 1-continued

Exemplary compounds.

| Compound No. | Structure |
|---|---|
| 780 | *(chemical structure)* |
| 781 | *(chemical structure)* |
| 639A | *(chemical structure)* |

II. Methods

Another aspect of the disclosure provides methods of treating patients suffering from a viral infection, e.g., a coronaviral infection. In particular, in certain embodiments, the disclosure provides a method of treating the below medical indications comprising administering to a subject in need thereof a therapeutically effective amount of a compound described herein, such as a compound of Formula II, II-A, II-B, II-C, II-D-I, II-D-II, II-E, and II-I.

In certain embodiments, the disclosure provides a method of ameliorating or treating a viral infection in a patient in need thereof, comprising administering to the patient a therapeutically effective amount of any of the compounds described herein. In some embodiments, the viral infection is from a virus selected from the group consisting of an RNA virus, a DNA virus, a coronavirus, a papillomavirus, a pneumovirus, a picornavirus, an influenza virus, an adenovirus, a cytomegalovirus, a polyomavirus, a poxvirus, a flavivirus, an alphavirus, an ebola virus, a morbillivirus, an enterovirus, an orthopneumovirus, a lentivirus, arenavirus, a herpes virus, and a hepatovirus. In certain embodiments, the viral infection is a coronavirus infection. In some embodiments, the viral infection is a coronavirus selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2 (COVID-19). In embodiments, the viral infection is SARS-CoV-2.

In some embodiments, the viral infection is from a virus selected from the group consisting of calicivimses, MD145, murine norovirus, vesicular exanthema of swine virus, abbit hemorrhagic disease virus, porcine teschovirus, bovine coronavirus, feline infectious peritonitis virus, EV-68 virus, EV-71 virus, poliovirus, norovirus, human rhinovirus (HRV), hepatitis A virus (HAV) and foot-and-mouth disease virus (FMDV).

In embodiments, the viral infection is an arenavirus infection. In some embodiments, the arenavirus is selected from the group consisting of: Junin virus, Lassa virus, Lujo virus, Machupo virus, and Sabia virus. In some embodiments, the viral infection is an influenza infection. In some embodiments, the influenza is influenza H1N1, H3N2 or H5N1.

Another aspect of the disclosure provides methods of treating patients suffering from a viral infection, e.g., a noroviral infection. In some embodiments, the disclosure provides a method of treating a viral infection from a norovirus in a patient in need thereof, comprising administering to the patient a therapeutically effective amount of any of the compounds described herein.

Also provided herein, in certain embodiments, is a method of inhibiting transmission of a virus, a method of inhibiting viral replication, a method of minimizing expression of viral proteins, or a method of inhibiting virus release, comprising administering a therapeutically effective amount of a compound described herein to a patient suffering from the virus, and/or contacting an effective amount of a compound described herein with a virally infected cell. In some embodiments, the method further comprises administering another therapeutic. In some embodiments, the method further comprises administering an additional anti-viral therapeutic. In embodiments, the anti-viral therapeutic is selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of protease inhibitors, fusion inhibitors, M2 proton channel blockers, polymerase inhibitors, 6-endonuclease inhibitors, neuraminidase inhibitors, reverse transcriptase inhibitor, aciclovir, acyclovir, protease inhibitors, arbidol, atazanavir, atripla, boceprevir, cidofovir, combivir, darunavir, docosanol, edoxudine, entry inhibitors, entecavir, famciclovir, fomivirsen, fosamprenavir, foscarnet, fosfonet, ganciclovir, ibacitabine, immunovir, idoxuridine, imiquimod, inosine, integrase inhibitor, interferons, lopinavir, loviride, moroxydine, nexavir, nucleoside analogues, penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine. In embodiments, the additional anti-viral therapeutic is selected from the group consisting of lamivudine, an interferon alpha, a VAP anti-idiotypic antibody, enfuvirtide, amantadine, rimantadine, pleconaril, aciclovir, zidovudine, fomivirsen, a morpholino, a protease inhibitor, double-stranded RNA activated caspase oligomerizer (DRACO), rifampicin, zanamivir, oseltamivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine.

Contemplated patients include not only humans, but other animals such as companion animals (e.g. dogs, cats), domestic animals (e.g. cow, swine), and wild animals (e.g. monkeys, bats, snakes).

Accordingly, in one embodiment, described herein is a method of ameliorating or treating a viral infection in a patient in need thereof, comprising administering to the patient a therapeutically effective amount of a compound described herein (e.g., a compound of Formula II, II-A, II-B, II-C, II-D-I, II-D-II, II-E, or II-I, as described herein) or a pharmaceutically acceptable salt thereof.

Other contemplated methods of treatment include method of treating or ameliorating a virus infection condition or co-morbidity, by administering a compound disclosed herein to a subject.

Exemplary co-morbidities include lung diseases, cardiac disorders, endocrine disorders, respiratory disorders, hepatic disorders, skeletal disorders, psychiatric disorders, metabolic disorders, and reproductive disorders.

In some embodiments, the viral infection is from a virus selected from the group consisting of an RNA virus, a DNA virus, a coronavirus, a papillomavirus, a pneumovirus, a picornavirus, an influenza virus, an adenovirus, a cytomegalovirus, a polyomavirus, a poxvirus, a flavivirus, an alphavirus, an ebola virus, a morbillivirus, an enterovirus, an orthopneumovirus, a lentivirus, arenavirus, a herpes virus, and a hepatovirus. In some embodiments, the viral infection is a coronavirus infection. In some embodiments, the viral infection is a coronavirus selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2 (COVID-19). In some embodiments, the viral infection is SARS-CoV-2. In some embodiments, the viral infection is an arenavirus infection. In some embodiments, the arenavirus is selected from the group consisting of: Junin virus, Lassa virus, Lujo virus, Machupo virus, and Sabia virus. In some embodiments, the viral infection is an influenza infection. In some embodiments, the influenza is influenza H1N1, H3N2 or H5N1. In some embodiments, the viral infection is a respiratory viral infection. In some embodiments, the viral infection is an upper respiratory viral infection or a lower respiratory viral infection. In some embodiments, the method further comprises administering another therapeutic.

In certain embodiments, the virus is selected from the group consisting of a retrovirus (e.g., human immunodeficiency virus (HIV), simian immunodeficiency virus (SIV), human T-cell lymphotropic virus (HTLV)-1, HTLV-2, HTLV-3, HTLV-4), Ebola virus, hepatitis A virus, hepatitis B virus, hepatitis C virus, a herpes simplex virus (HSV) (e.g., HSV-1, HSV-2, varicella zoster virus, cytomegalovirus), an adenovirus, an orthomyxovirus (e.g., influenza virus A, influenza virus B, influenza virus C, influenza virus D, togavirus), a flavivirus (e.g., dengue virus, Zika virus), West Nile virus, Rift Valley fever virus, an arenavirus, Crimean-Congo hemorrhagic fever virus, an echovirus, a rhinovirus, coxsackie virus, a coronavirus (e.g., Severe acute respiratory syndrome coronavirus 2 (SARS-CoV-2), coronavirus disease 2019 (COVID-19), a respiratory syncytial virus, a mumps virus, a rotavirus, measles virus, rubella virus, a parvovirus (e.g., an adeno-associated virus), a vaccinia virus, a variola virus, a molluscum virus, bovine leukemia virus, bovine diarrhea virus, a poliovirus, St. Louis encephalitis virus, Japanese encephalitis virus, a tick-borne encephalitis virus, Murray Valley virus, Powassan virus, Rocio virus, louping-ill virus, Banzi virus, Ilheus virus, Kokobera virus, Kunjin virus, Alfuy virus, a rabies virus, a polyomavirus (e.g., JC virus, BK virus), an alphavirus, and a rubivirus (e.g., rubella virus).

In certain embodiments, the disease or disorder is a viral infection, e.g., a disease or disorder selected from the group consisting of acquired immune deficiency syndrome (AIDS), HTLV-1 associated myelopathy/tropical spastic paraparesis, Ebola virus disease, hepatitis A, hepatitis B, hepatitis C, herpes, herpes zoster, acute varicella, mononucleosis, respiratory infections, pneumonia, influenza, dengue fever, encephalitis (e.g., Japanese encephalitis, St. Louis encephalitis, or tick-borne encephalitis such as Powassan encephalitis), West Nile fever, Rift Valley fever, Crimean-Congo hemorrhagic fever, Kyasanur Forest disease, Yellow fever, Zika fever, aseptic meningitis, myocarditis, common cold, lung infections, molloscum contagiosum, enzootic bovine leucosis, coronavirus disease 2019 (COVID-19), mumps, gastroenteritis, measles, rubella, slapped-cheek disease, smallpox, warts (e.g., genital warts), molluscum contagiosum, polio, rabies, and *pityriasis rosea*.

In some embodiments, the virus is an RNA virus (having a genome that is composed of RNA). RNA viruses may be single-stranded RNA (ssRNA) or double-stranded RNA (dsRNA). RNA viruses have high mutation rates compared to DNA viruses, as RNA polymerase lacks proofreading capability (see Steinhauer D A, Holland J J (1987). "*Rapid evolution of RNA viruses*". *Annu. Rev. Microbiol.* 41: 409-33). In some embodiments, the RNA virus is a positive-strand RNA virus (e.g., a SARS-CoV virus, polio virus, Coxsackie virus, Enterovirus, Human rhinovirus, Foot/Mouth disease virus, encephalomyocarditis virus, Dengue virus, Zika virus, Hepatitis C virus, or New Castle Disease virus).

RNA viruses are classified by the type of genome (double-stranded, negative (−), or positive (+) single-stranded). Double-stranded RNA viruses contain a number of different RNA molecules, each coding for one or more viral proteins. Positive-sense ssRNA viruses utilize their genome directly as mRNA; ribosomes within the host cell translate mRNA into a single protein that is then modified to form the various proteins needed for viral replication. One such protein is RNA-dependent RNA polymerase (RNA replicase), which copies the viral RNA in order to form a double-stranded, replicative form. Negative-sense ssRNA viruses have their genome copied by an RNA replicase enzyme to produce positive-sense RNA for replication. Therefore, the virus comprises an RNA replicase enzyme. The resultant positive-sense RNA then acts as viral mRNA and is translated by the host ribosomes. In some embodiments, the virus is a dsRNA virus. In some embodiments, the virus is a negative ssRNA virus. In some embodiments, the virus is a positive ssRNA virus. In some embodiments, the positive ssRNA virus is a coronavirus.

SARS-CoV2, also sometimes referred to as the novel coronavirus of 2019 or 2019-nCoV, is a positive-sense single-stranded RNA virus. SARS-CoV-2 has four structural proteins, known as the S (spike), E (envelope), M (membrane), and N (nucleocapsid) proteins. The N protein holds the RNA genome together; the S, E, and M proteins form the viral envelope. Spike allows the virus to attach to the membrane of a host cell, such as the ACE2 receptor in human cells (Kruse R. L. (2020), Therapeutic strategies in an outbreak scenario to treat the novel coronavirus originating in Wuhan, China (version 2). *F1000Research,* 9:72). SARS-CoV2 is the highly contagious, causative viral agent of coronavirus disease 2019 (COVID19), a global pandemic.

In some embodiments, the virus is a DNA virus (having a genome that is composed of DNA). Exemplary DNA viruses include, without limitation, parvoviruses (e.g., adeno-associated viruses), adenoviruses, asfarviruses, herpesviruses (e.g., herpes simplex virus 1 and 2 (HSV-1 and HSV-2), Epstein-Barr virus (EBV), cytomegalovirus (CMV)), papillomaviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). Exemplary RNA viruses include, without limitation, bunyaviruses (e.g., hantavirus), coronaviruses, flaviviruses (e.g., yellow fever virus, west Nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, calicivirus, noroviruses (e.g., Norwalk virus), poliovirus, respiratory syncytial virus (RSV), retroviruses (e.g., human immunodeficiency virus-1 (HIV-1)) and toroviruses.

The methods described herein may inhibit viral replication transmission, replication, assembly, or release, or minimize expression of viral proteins. In one embodiment, described herein is a method of inhibiting transmission of a virus, a method of inhibiting viral replication, a method of minimizing expression of viral proteins, or a method of inhibiting virus release, comprising administering a therapeutically effective amount of a compound described herein, or a pharmaceutically acceptable salt thereof, to a patient suffering from the virus, and/or contacting an effective amount of a compound described herein or a pharmaceutically acceptable salt thereof, with a virally infected cell.

Also described herein is a method of treating a respiratory disorder in a subject in need thereof, comprising administering to the patient a therapeutically effective amount of a compound described herein (e.g., a compound of Formula II, II-A, II-B, II-C, II-D-I, II-D-II, II-E, or II-I, etc. described herein) or a pharmaceutically acceptable salt thereof. In embodiments, the respiratory disorder is selected from the group consisting of chronic obstructive pulmonary disease (COPD), asthma, fibrosis, chronic asthma, acute asthma, lung disease secondary to environmental exposures, acute lung infection, chronic lung infection, al antitrypsin disease, cystic fibrosis and an autoimmune disease.

Compounds described herein, e.g., a compound of Formula II, II-A, II-B, II-C, II-D-I, II-D-II, II-E, or II-I, etc. as defined herein, can be administered in combination with one or more additional therapeutic agents to treat a disorder described herein, such as an infection by a pathogen described herein, e.g., a virus, fungus, or protozoan. For clarity, contemplated herein are both a fixed composition comprising a disclosed compound and another therapeutic agent such as disclosed herein, and methods of administering, separately a disclosed compound and a disclosed therapeutic. For example, provided in the present disclosure is a pharmaceutical composition comprising a compound described herein, e.g., a compound of Formula II, II-A, II-B, II-C, II-D-I, II-D-II, II-E, or II-I as defined herein, one or more additional therapeutic agents, and a pharmaceutically acceptable excipient. In some embodiments, a compound of Formula II, II-A, II-B, II-C, II-D-I, II-D-II, II-E, or II-I as defined herein and one additional therapeutic agent is administered. In some embodiments, a disclosed compound as defined herein and two additional therapeutic agents are administered. In some embodiments, a disclosed compound as defined herein and three additional therapeutic agents are administered. Combination therapy can be achieved by administering two or more therapeutic agents, each of which is formulated and administered separately. For example, a compound of Formula II, II-A, II-B, II-C, II-D-I, II-D-II, II-E, or II-I, etc. as defined herein and an additional therapeutic agent can be formulated and administered separately. Combination therapy can also be achieved by administering two or more therapeutic agents in a single formulation, for example a pharmaceutical composition comprising a compound of Formula II, II-A, II-B, II-C, II-D-I, II-D-II, II-E, or II-I as one therapeutic agent and one or more additional therapeutic agents such as an antibiotic, a viral protease inhibitor, or an anti-viral nucleoside anti-metabolite. For example, a compound of Formula II, II-A, II-B, II-C, II-D-I, II-D-II, II-E, or II-I as defined herein and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

In some embodiments, the one or more additional therapeutic agents that may be administered in combination with a compound provided herein can be an antibiotic, a viral protease inhibitor, an anti-viral anti-metabolite, a lysosomotropic agent, a M2 proton channel blocker, a polymerase inhibitor (e.g., EIDD-2801), a neuraminidase inhibitor, a reverse transcriptase inhibitor, a viral entry inhibitor, an integrase inhibitor, interferons (e.g., types I, II, and III), or a nucleoside analogue.

In some embodiments, methods described herein further comprise administering an additional anti-viral therapeutic. In some embodiments, the anti-viral therapeutic is selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of protease inhibitors (e.g., nafamostat, camostat, gabexate, epsilon-aminocapronic acid and aprotinin), fusion inhibitors (e.g., BMY-27709, CL 61917, and CL 62554), M2 proton channel blockers (e.g., amantadine and rimantadine), polymerase inhibitors (e.g., 2-deoxy-2'fluoroguanosides (2'-fluoroGuo), 6-endonuclease inhibitors (e.g., L-735,822 and flutamide) neuraminidase inhibitors (e.g., zanamivir (Relenza), oseltamivir, peramivir and ABT-675 (A-315675), reverse transcriptase inhibitor (e.g., abacavir, adefovir, delavirdine, didanosine, efavirenz, emtricitabine, lamivudine, nevirapine, stavudine, tenofovir, tenofovir disoproxil, and zalcitabine), acyclovir, acyclovir, protease inhibitors (e.g., amprenavir, indinavir, nelfinavir, ritonavir, and saquinavir), arbidol, atazanavir, atripla, boceprevir, cidofovir, combivir, darunavir, docosanol, edoxudine, entry inhibitors (e.g., enfuvirtide and maraviroc), entecavir, famciclovir, fomivirsen, fosamprenavir, foscarnet, fosfonet, ganciclovir, ibacitabine, immunovir, idoxuridine, imiquimod, inosine, integrase inhibitor (e.g., raltegravir), interferons (e.g., types I, II, and III), lopinavir, loviride, moroxydine, nexavir, nucleoside analogues (e.g., aciclovir), penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine. In some embodiments, the additional anti-viral therapeutic is selected from the group consisting of lamivudine, an interferon alpha, a VAP anti-idiotypic antibody, enfuvirtide, amantadine, rimantadine, pleconaril, aciclovir, zidovudine, fomivirsen, a morpholino, a protease inhibitor, double-stranded RNA activated caspase oligomerizer (DRACO), rifampicin, zanamivir, oseltamivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VTR-576, and zalcitabine. In some embodiments, the another therapeutic is selected from the group consisting of quinine (optionally in combination with clindamycin), chloroquine, amodiaquine, artemisinin and its derivatives (e.g., artemether, artesunate, dihydroartemisinin, arteether), doxycycline, pyrimethamine, mefloquine, halofantrine, hydroxychloroquine, eflornithine, nitazoxanide, ornidazole, paromomycin, pentamidine, primaquine, pyrimethamine, proguanil (optionally in combination with atovaquone), a sulfonamide (e.g., sulfadoxine, sulfamethoxypyridazine), tafenoquine, tinidazole and a PPT1 inhibitor (including Lys05 and DC661). In some embodiments, the another therapeutic is an antibiotic. In some embodiments, the antibiotic is a penicillin antibiotic, a quinolone antibiotic, a tetracycline antibiotic, a macrolide antibiotic, a lincosamide antibiotic, a cephalosporin antibiotic, or an RNA synthetase inhibitor. In some embodiments, the antibiotic is selected from the group consisting of azithromycin, vancomycin, metronidazole, gentamicin, colistin, fidaxomicin, telavancin, oritavancin, dalbavancin, daptomycin, cephalexin, cefuroxime, cefadroxil, cefazolin, cephalothin, cefaclor, cefamandole, cefoxitin, cefprozil, ceftobiprole, cipro, Levaquin, floxin, tequin, avelox, norflox, tetracycline, minocycline, oxytetracycline, doxycycline, amoxicillin, ampicillin, penicillin V, dicloxacillin, carbenicillin, methicillin, ertapenem, doripenem, imipenem/cilastatin, meropenem, amikacin, kanamycin, neomycin, netilmicin, tobramycin, paromomycin, cefixime, cefdinir, cefditoren, cefoperazone, cefotaxime, ceftazidime, ceftibuten, ceftizoxime, ceftriaxone, cefoxotin, and streptomycin. In some embodiments, the antibiotic is azithromycin.

In some embodiments, the one or more additional therapeutic agents that may be administered in combination with a compound provided herein can be selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine.

In some embodiments, the compounds described herein (e.g. a compound of Formula II, II-A, II-B, II-C, II-D-I, II-D-II, II-E, or II-I, etc.) and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast-.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g. muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, anthelmintic agents, antimalarial agents, antiprotozoal agents and antituberculosis agents.

In some embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, sunitinib, pazopanib, sorafenib, regorafenib, sunitinib, axitinib, dasatinib, imatinib, nilotinib, ponatinib, idelalisib, ibrutinib, Loxo 292, larotrectinib, and quizartinib.

In some embodiments, the additional therapeutic agents can be therapeutic anti-viral vaccines.

In some embodiments, the additional therapeutic agents can be immunomodulatory agents including but not limited to anti-PD-1 or anti-PDL-1 therapeutics including pembrolizumab, nivolumab, atezolizumab, durvalumab, BMS-936559, or avelumab, anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or $R^{07009789}$, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles, anthracyclines including but not limited to doxorubicin or mitoxanthrone, hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone. In some embodiments, the additional therapeutic agent is a p2-adrenoreceptor agonist including, but not limited to, vilanterol, salmeterol, salbutamol.formoterol, salmefamol, fenoterol carmoterol, etanterol, naminterol, clenbuterol, pirbuterol.flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. In some embodiments, the additional therapeutic agent is an anticholinergic agent, including, but not limited to, umeclidinium (for example, as the bromide), ipratropium (for example, as the bromide), oxitropium (for example, as the bromide) and tiotropium (for example, as the bromide).

In particular, in certain embodiments, the disclosure provides a method of treating the above medical indications comprising administering a subject in need thereof a therapeutically effective amount of a compound described herein, such as a disclosed compound.

The term "boosting amount" or "boosting dose" is the amount of a compound needed to improve the pharmacokinetics of a second compound (or increase availability or exposure). The boosting amount or boosting dose may improve the pharmacokinetics (or increase availability or exposure) of the second compound to a level to therapeutic levels in a subject.

In one embodiment, the disclosure provides for a disclosed compound to be administered together with an anti-viral therapeutic such as disclosed herein, and e.g., thereby boosting the dose of the anti-viral therapeutic or therapeutics. Such a boost combination may be used, e.g., as prophylactic or therapeutic treatment of a viral infection in a subject in need thereof. In one embodiment, the protease inhibitor is a compound described herein (e.g. a compound of Formula II, II-A, II-B, II-C, II-D-I, II-D-II, II-E, or II-I, etc.).

III. Reversible or Irreversible Conjugates

In certain embodiments, provided herein are conjugates represented by Formula III:

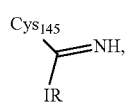

Formula III wherein Cys145 is cysteine at position 145 or equivalent active site cysteine on a CL or 3CL protease; IR is a viral protease inhibitor; and wherein the compound that forms the conjugate comprises a —CN warhead.

IV. Pharmaceutical Compositions and Kits

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this disclosure may be used in the form of a pharmaceutical preparation, for example, in solid, semisolid or liquid form, which contains one or more of the compound of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well-known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

Advantageously, the disclosure also provides kits for use by a e.g. a consumer in need of 3CL inhibitor. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well-known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent or administering a second active agent. For example, in addition to having a viral infection, a subject or patient can further have viral infection- or virus-related co-morbidities, i.e., diseases and other adverse health conditions associated with, exacerbated by, or precipitated by being infected by a virus. Contemplated herein are disclosed compounds in combination with at least one other agent that has previously been shown to treat these virus-related conditions.

Examples

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the disclosure.

$^1$H NMR spectra are recorded at ambient temperature using e.g., a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts are expressed in ppm relative to tetramethylsilane. The following abbreviations have been used: br=broad signal, s=singlet, d=doublet, dd=double doublet, dt=double triplet, ddd=double doublet, t=triplet, td=triple doublet, tdd=triple double doublet, q=quartet, m=multiplet.

Mass Spectrometry (LCMS) experiments to determine retention times and associated mass ions were performed using the following methods.

Abbreviations

AcOH Acetic acid
Boc tert-Butoxycarbonyl protecting group
DCM Dichloromethane
DIEA N,N-Diisopropylethylamine
DIPEA N,N-Diisopropylethylamine
DMAP 4-Dimethylaminopyridine
DMF Dimethylformamide
EA Ethyl Acetate
EtOAc Ethyl Acetate
EDCI 1-Ethyl-3-(3-dimethylaminopropyl)carbodiimide
EtOH Ethanol
HATU (1-[Bis(dimethylamino)methylene]-1H-1,2,3-triazolo[4,5-b]pyridinium 3-oxide hexafluorophosphate
HOBt Hydroxybenzotirazole
LiHMDS Lithium bis(trimethylsilyl)amide
MeOH Methanol
PE Petroleum Ether
PMA Phosphomolybdic acid
Pht Phthaloyl
T$_3$P Propanephosphonic acid anhydride
TEA Triethylamine
TFA Trifluoroacetic acid
TFAA Trifluoroacetic anhydride
THF Tetrahydrofuran General Chemistry Exemplary compounds described herein are available by the general synthetic method illustrated in the Scheme below, including preparations of Intermediates and preparation of accompanying Examples.

Synthetic Scheme(s)

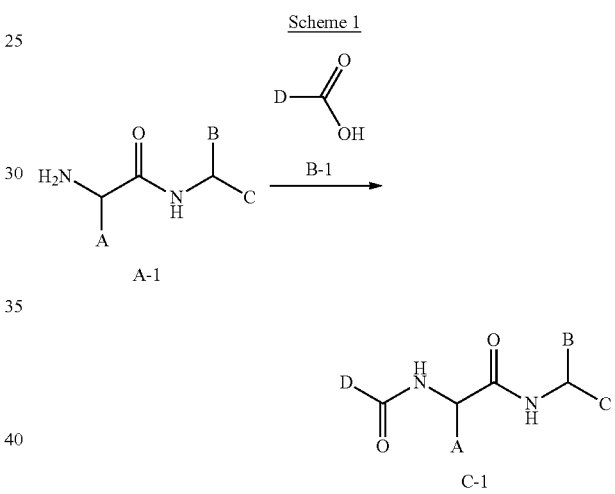

Scheme 1

Scheme 1 illustrates an exemplary preparation of C-1. Reacting a solution of amine A-1, and acid B-1 with a coupling agent such as T$_3$P, EDCI/HOBt, in the presence of a base such as TEA, DMAP and DIEA, and solvent such as DMF and DCM, affords C-1.

In Scheme 1, examples of A include a substituted or unsubstituted alkyl and a substituted or unsubstituted cycloalkyl, examples of B include a warhead moiety, such as cyano, aldehyde, hydroxymethylketone, ketoamide, heteroaryl-ketone, enone, and Michael acceptor warhead, examples of C include an alkyl substituted with a 4-, 5-, or 6-membered lactam, and examples of D include a substituted or unsubstituted bicyclic heteroaryl moiety. In Scheme 1, exemplary preparation of a cyano moiety at B include a dehydration of an amide to nitrile with a dehydration agent such as Burgess reagent.

Compounds of Table 1 have been prepared following general Scheme 1, which follows the examples described below, such as examples 19, 25, 27, 32, 39, and 41.

Example 1. Synthesis of Viral Protease Inhibitor Compound 103

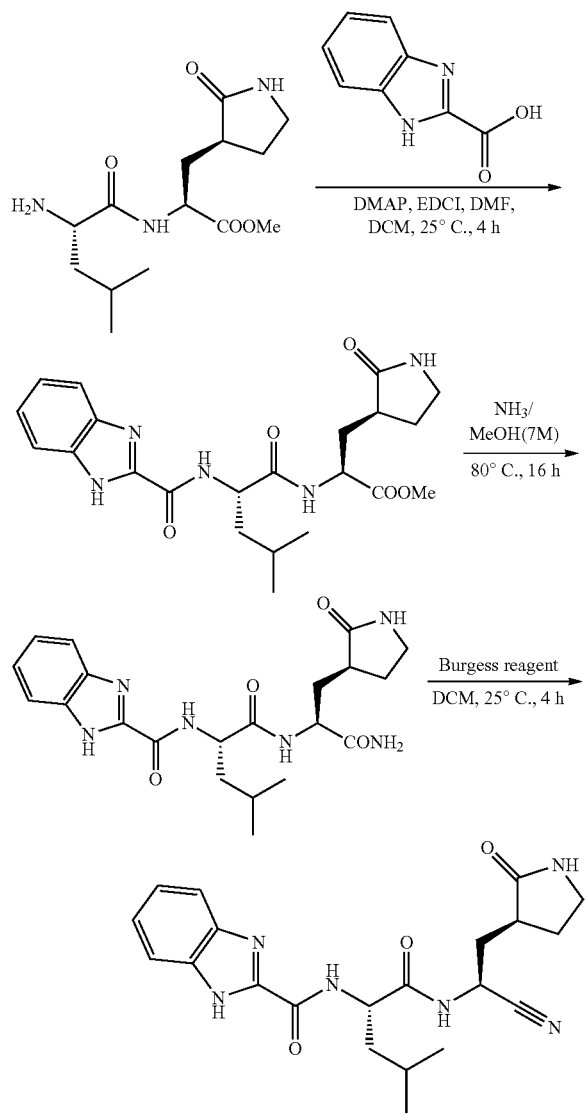

Step 1: (2S)-2-[[(2S)-2-(1H-benzimidazole-2-carbonylamino)-4-methyl-pentanoyl]amino]-3-[(3S)-2-oxopyrrolidin-3-yl]propanoate To a mixture of methyl (2S)-2-[[(2S)-2-amino-4-methyl-pentanoyl]amino]-3-[(3 S)-2-oxopyrrolidin-3-yl]propanoate (200 mg, 483.81 umol, 1 eq, TFA) and 1H-benzimidazole-2-carboxylic acid (94.14 mg, 580.57 umol, 1.2 eq) in DCM (2 mL) was added EDCI (185.49 mg, 967.61 umol, 2 eq) and DMAP (118.21 mg, 967.61 umol, 2 eq). The mixture was added DMF (1 mL) and stirred at 25° C. for 4 h. The resulting mixture was diluted with H₂O (20 mL) and extracted with DCM (10 mL*3). The combined organic layers were dried over Na₂SO₄, filtered and concentrated under reduced pressure to give a residue. The residue was purified by prep-TLC (SiO₂, DCM/MeOH=5/1), to give methyl (2S)-2-[[(2S)-2-(1H-benzimidazole-2-carbonylamino)-4-methyl-pentanoyl]amino]-3-[(3S)-2-oxopyrrolidin-3-yl]propanoate (150 mg, 338.22 umol) as a solid.

Step 2: N-[(1S)-3-methyl-1-[[(1S)-1-(nitrosomethyl)-2-[(3S)-2-oxopyrrolidin-3-yl]ethyl]carbamoyl]butyl]-1H-benzimidazole-2-carboxamide Methyl(2S)-2-[[(2S)-2-(1H-benzimidazole-2-carbonylamino)-4-methyl-pentanoyl]amino]-3-[(3S)-2-oxopyrrolidin-3-yl]propanoate (150 mg, 338.22 umol, 1 eq) was added NH₃/MeOH (7 M, 5 mL, 103.48 eq). The mixture was stirred at 80° C. for 16 h in a sealed tube. The reaction was concentrated in vacuo to dryness, give compound N-[(1S)-3-methyl-1-[[(1S)-1-(nitrosomethyl)-2-[(3S)-2-oxopyrrolidin-3-yl]ethyl]carbamoyl]butyl]-1H-benzimidazole-2-carboxamide (140 mg, crude) as a solid. The crude product was used directly in next step.

Step 3: N-[(1S)-1-[[(1S)-1-cyano-2-[(3S)-2-oxopyrrolidin-3-yl]ethyl]carbamoyl]-3-methyl-butyl]-1H-benzimidazole-2-carboxamide N-[(1S)-3-methyl-1-[[(1S)-1-(nitrosomethyl)-2-[(3S)-2-oxopyrrolidin-3-yl]ethyl]carbamoyl]butyl]-1H-benzimidazole-2-carboxamide (120.00 mg, 280.06 umol, 1 eq) in DCM (5 mL) was added Burgess reagent (150 mg, 629.45 umol, 2.25 eq). The mixture was stirred at 25° C. for 4 h. The reaction was blow-dried under N₂. The residue was purified by prep-HPLC (column: Waters Xbridge Prep OBD C₁₈ 150*40 mm*10 um; mobile phase: [water(10 mM NH4HCO3)—ACN]; B %: 20%-40%, 8 min), give N-[(1S)-1-[[(1S)-1-cyano-2-[(3S)-2-oxopyrrolidin-3-yl]ethyl]carbamoyl]-3-methyl-butyl]-1H-benzimidazole-2-carboxamide (40 mg, 97.45 umol) was obtained as a solid. MS (ESI) m/z 411.1 [M+H]⁺, ¹H NMR (400 MHz, DMSO-d₆) δ ppm 13.11 (br s, 1H), 8.97-8.81 (m, 2H), 7.90-7.64 (m, 2H), 7.54 (br s, 1H), 7.31 (br s, 2H), 5.08-4.93 (m, 1H), 4.62-4.43 (m, 1H), 3.19-3.05 (m, 2H), 2.44-2.29 (m, 1H), 2.23-2.05 (m, 2H), 1.91-1.50 (m, 5H), 0.91 (dd, J=6.3, 8.9 Hz, 6H).

Example 2. Synthesis of Viral Protease Inhibitor Compound 105

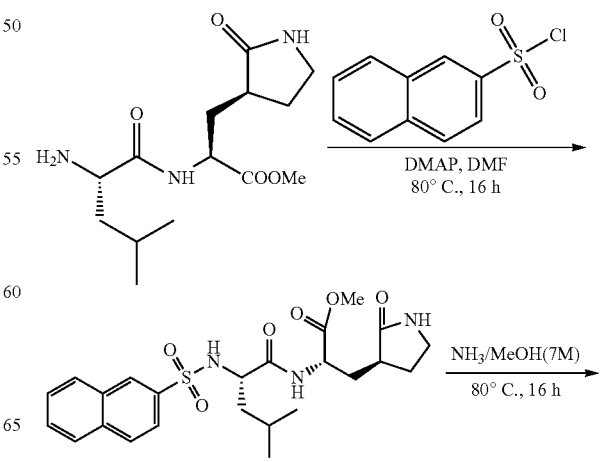

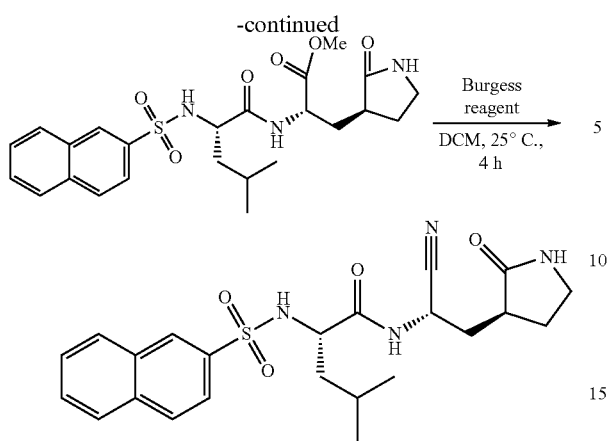

Step 1: (2S)-2-[[(2S)-4-methyl-2-(2-naphthylsulfonylamino)pentanoyl]amino]-3-[(3S)-2-oxopyrrolidin-3-yl]propanoate To a mixture of methyl (2S)-2-[[(2S)-2-amino-4-methylpentanoyl]amino]-3-[(3 S)-2-oxopyrrolidin-3-yl]propanoate (150 mg, 501.06 umol, 1 eq) in DMF (5 mL) was added naphthalene-2-sulfonyl chloride (227.16 mg, 1.00 mmol, 2 eq) and DMAP (155.35 mg, 1.27 mmol, 2.54 eq) and stirred at 25° C. Then the reaction was stirred at 80° C. for 16 h. The reaction mixture was diluted with $H_2O$ (20 mL) and extracted with EtOAc (10 mL*3). The combined organic layers were dried over $Na_2SO_4$, filtered and concentrated under reduced pressure to give a residue. The residue was purified by prep-TLC ($SiO_2$, DCM/MeOH=10/1). Give methyl (2S)-2-[[(2S)-4-methyl-2-(2-naphthylsulfonylamino)pentanoyl]amino]-3-[(3S)-2-oxopyrrolidin-3-yl] propanoate (70 mg, 142.98 umol) as an oil.

Step 2: (2S)—N-[(1S)-2-amino-2-oxo-1-[[(3S)-2-oxopyrrolidin-3-yl]methyl]ethyl]-4-methyl-2-(2-naphthylsulfonylamino)pentanamide To a mixture of methyl (2S)-2-[[(2S)-4-methyl-2-(2-naphthylsulfonylamino)pentanoyl]amino]-3-[(3S)-2-oxopyrrolidin-3-yl]propanoate (50 mg, 102.13 umol, 1 eq) was added $NH_3$/MeOH (7 M, 10 mL, 685.42 eq) and stirred at 80° C. for 16 h. The reaction was concentrated in vacuo to dryness to give the crude of (2S)—N-[(1 S)-2-amino-2-oxo-1-[[(3S)-2-oxopyrrolidin-3-yl]methyl]ethyl]-4-methyl-2-(2-naphthylsulfonylamino)pentanamide (50 mg, crude) as an oil.

Step 3: (2S)—N-[(1S)-1-cyano-2-[(3S)-2-oxopyrrolidin-3-yl]ethyl]-4-methyl-2-(2-naphthylsulfonylamino)pentanamide (2S)—N-[(1S)-2-amino-2-oxo-1-[[(3S)-2-oxopyrrolidin-3-yl]methyl]ethyl]-4-methyl-2-(2-naphthylsulfonylamino) pentanamide (70 mg, 147.50 umol, 1 eq) in DCM (0.5 mL) was added Burgess reagent (79.00 mg, 331.52 umol, 2.25 eq). The mixture was stirred at 25° C. for 4 h. The reaction was blow-dried under $N_2$. The residue was purified by prep-HPLC: column: Waters Xbridge Prep OBD $C_{18}$ 150*40 mm*10 um; mobile phase: [water(10 mM $NH_4HCO_3$)—ACN]; B %: 25%-55%, 8 min, give compound (2S)—N-[(1S)-1-cyano-2-[(3S)-2-oxopyrrolidin-3-yl]ethyl]-4-methyl-2-(2-naphthylsulfonylamino)pentanamide (30 mg, 65.71 umol) as a solid. MS (ESI) m/z 457.1 [M+H]+. $^1$H NMR (400 MHz, DMSO-$d_6$) δ ppm 8.81 (br d, J=7.5 Hz, 1H), 8.38 (s, 1H), 8.21 (br s, 1H), 8.12-8.03 (m, 2H), 8.00 (d, J=7.7 Hz, 1H), 7.82-7.72 (m, 1H), 7.71-7.56 (m, 3H), 4.64 (q, J=7.6 Hz, 1H), 3.78-3.67 (m, 1H), 3.09-3.01 (m, 1H), 3.00-2.89 (m, 1H), 2.08-1.96 (m, 1H), 1.90-1.78 (m, 1H), 1.71-1.60 (m, 1H), 1.58-1.33 (m, 4H), 1.31-1.19 (m, 1H), 0.78 (d, J=6.6 Hz, 3H), 0.63 (d, J=6.6 Hz, 3H).

Example 3. Synthesis of Benzyl N-[(1S)-1-[[(1S)-1-cyano-2-[(3S)-2-oxopyrrolidin-3-yl]ethyl]carbamoyl]-3-methyl-butyl] carbamate

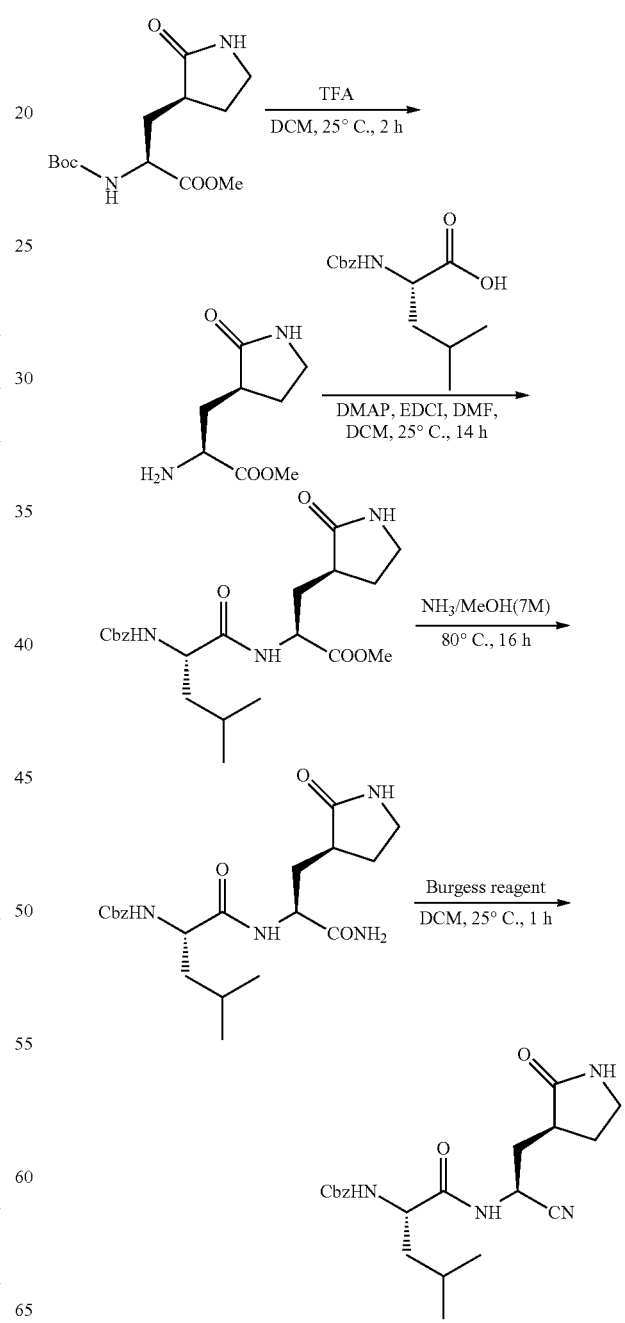

Step 1: methyl (2S)-2-amino-3-[(3S)-2-oxopyrrolidin-3-yl]propanoate

To a mixture of methyl (2S)-2-(tert-butoxycarbonylamino)-3-[(3S)-2-oxopyrrolidin-3-yl] propanoate (300 mg, 1.05 mmol, 1 eq) in DCM (5 mL) was added TFA (4.62 g, 40.52 mmol, 3 mL, 38.67 eq), then the mixture was stirred at 25° C. for 2 h. Once the reaction was completed, the reaction mixture was concentrated under reduced pressure to give a residue and used next step. Compound methyl (2S)-2-amino-3-[(3S)-2-oxopyrrolidin-3-yl]propanoate (180 mg, 918.33 umol) was obtained as a colorless oil. MS (ESI) m/z 187.1 [M+H]+

Step 2: methyl (2S)-2-[[(2S)-2-(tert-butoxycarbonylamino)-4-methyl-pentanoyl]amino]-3-[(3S)-2-oxopyrrolidin-3-yl]propanoate To a mixture of methyl (2S)-2-amino-3-[(3S)-2-oxopyrrolidin-3-yl]propanoate (189.47 mg, 966.66 umol) and (2S)-2-(benzyloxycarbonylamino)-4-methyl-pentanoic acid (256.46 mg, 966.66 umol, 1 eq) in DCM (2 mL) was added DMAP (236.19 mg, 1.93 mmol, 2 eq) and EDCI (370.62 mg, 1.93 mmol, 2 eq). The mixture was added with DMF (1 mL) and stirred at 25° C. for 14 h. Once the reaction was completed, the reaction mixture was diluted with H₂O (50 mL) and extracted with DCM (30 mL*3). The combined organic layers were washed with brine (50 mL), dried over Na₂SO₄, filtered and concentrated under reduced pressure to give a residue. The residue was purified by column chromatography (SiO₂, petroleum ether/EtOAc=3/1 to 0/1) to get the compound methyl (2S)-2-[[(2S)-2-(benzyloxycarbonylamino)-4-methyl-pentanoyl]amino]-3-[(3S)-2-oxopyrrolidin-3-yl]propanoate (250 mg, 461.36 umol) as a solid. MS (ESI) m/z 434.3 [M+H]+

Step 3: benzyl N-[(1S)-1-[[(1S)-2-amino-2-oxo-1-[[(3S)-2-oxopyrrolidin-3-yl]methyl]ethyl]carbamoyl]-3-methyl-butyl]carbamate Methyl (2S)-2-[[(2S)-2-(benzyloxycarbonylamino)-4-methyl-pentanoyl]amino]-3-[(3S)-2-oxopyrrolidin-3-yl] propanoate (200 mg, 369.09 umol, 1 eq) was added NH₃/MeOH (7 M, 58.14 mL, 1102.58 eq). The mixture was stirred at 80° C. for 16 h. Once the reaction was completed, the reaction mixture was concentrated under reduced pressure to give a residue and used directly next step. Compound benzyl N-[(1S)-1-[[(1S)-2-amino-2-oxo-1-[[(3S)-2-oxopyrrolidin-3-yl]methyl]ethyl]carbamoyl]-3-methyl-butyl]carbamate (150 mg, 322.59 umol) was obtained as a colorless oil.

Step 4: benzyl N-[(1S)-1-[[(S)-1-cyano-2-[(3S)-2-oxopyrrolidin-3-yl]ethyl]carbamoyl]-3-methyl-butyl]carbamate To a mixture of benzyl N-[(1S)-1-[[(1S)-2-amino-2-oxo-1-[[(3S)-2-oxopyrrolidin-3-yl]methyl]ethyl]carbamoyl]-3-methyl-butyl]carbamate (150 mg, 179.22 umol, 1 eq) in DCM (5 mL) was added Burgess reagent (42.71 mg, 179.22 umol, 1 eq). The mixture was stirred at 25° C. for 1 h. Once the reaction was completed, the reaction mixture was concentrated under reduced pressure to give a residue. The residue was purified by neutral prep-HPLC (column: Waters Xbridge BEH C₁₈ 100*30 mm*10 um; mobile phase: [water (10 mM NH₄HCO₃)—ACN]; B %: 20%-50%, 8 min) to get the compound benzyl N-[(1S)-1-[[(1S)-1-cyano-2-[(3S)-2-oxopyrrolidin-3-yl]ethyl]carbamoyl]-3-methyl-butyl]carbamate (28 mg, 69.92 umol) as a solid. MS (ESI) m/z 401.1 [M+H]+. ¹H NMR (400 MHz, DMSO-d₆) δ ppm 8.84 (br d, J=7.9 Hz, 1H), 7.70 (s, 1H), 7.54 (br d, J=7.8 Hz, 1H), 7.41-7.24 (m, 5H), 5.02 (s, 2H), 4.97-4.88 (m, 1H), 4.07-3.91 (m, 1H), 3.20-2.94 (m, 2H), 2.38-2.22 (m, 1H), 2.22-1.98 (m, 2H), 1.85-1.26 (m, 5H), 0.87 (br dd, J=6.5, 11.2 Hz, 6H)

Example 4. Synthesis of Viral Protease Inhibitor Compound 131

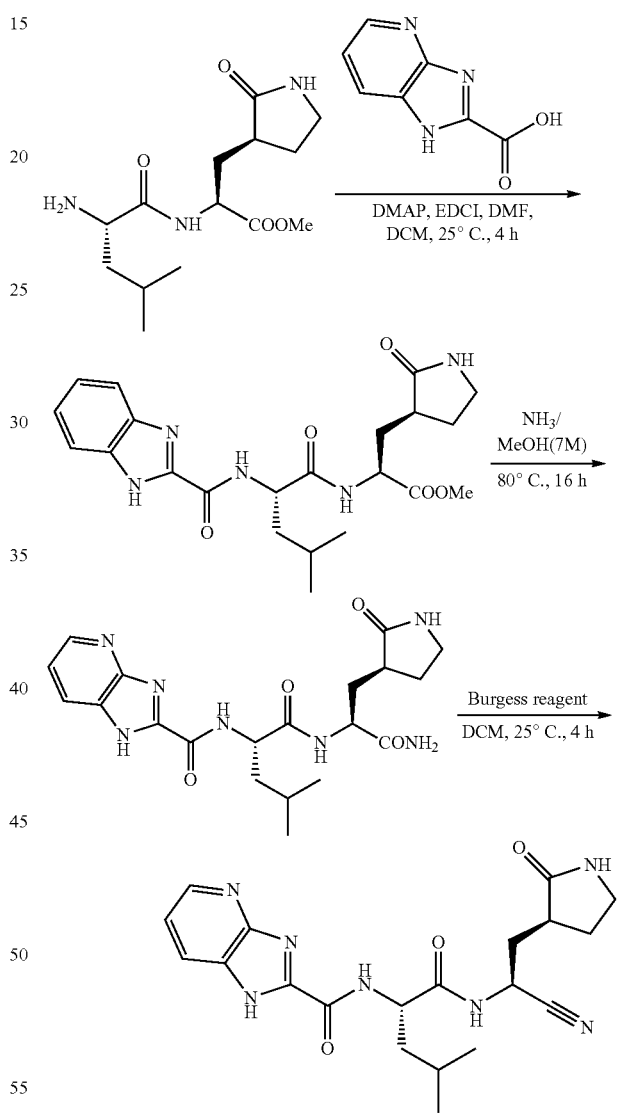

Step 1: (2S)-2-[[(2S)-2-(1H-imidazo[4,5-b]pyridine-2-carbonylamino)-4-methyl-pentanoyl]amino]-3-[(3S)-2-oxopyrrolidin-3-yl]propanoate To a mixture of methyl (2S)-2-[[(2S)-2-amino-4-methyl-pentanoyl]amino]-3-[(3 S)-2-oxopyrrolidin-3-yl]propanoate (250 mg, 604.76 umol, 1 eq, TFA) and 1H-imidazo[4,5-b]pyridine-2-carboxylic acid (118.39 mg, 725.71 umol, 1.2 eq) in DCM (4 mL) was added EDCI (231.86 mg, 1.21 mmol, 2 eq) and DMAP (147.77 mg, 1.21 mmol, 2 eq). The mixture was added with DMF (2 mL) and stirred at 25° C. for 4 h. The reaction mixture was diluted with H$_2$O (20 mL) and extracted with DCM (30 mL). The combined organic layers were dried over Na$_2$SO$_4$, filtered and concentrated under reduced pressure to give a residue. The residue was purified by prep-TLC (SiO$_2$, DCM/MeOH=5/1) to give compound methyl (2S)-2-[[(2S)-2-(1H-imidazo[4,5-b]pyridine-2-carbonylamino)-4-methyl-pentanoyl]amino]-3-[(3S)-2-oxopyrrolidin-3-yl]propanoate (100 mg, 224.98 umol) as a solid.

Step 2: N-[(1S)-1-[[(1S)-2-amino-2-oxo-1-[[(3S)-2-oxopyrrolidin-3-yl]methyl]ethyl]carbamoyl]-3-methyl-butyl]-1H-imidazo[4,5-b]pyridine-2-carboxamide To a mixture of methyl (2S)-2-[[(2S)-2-(1H-imidazo[4,5-b]pyridine-2-carbonylamino)-4-methyl-pentanoyl]amino]-3-[(3S)-2-oxopyrrolidin-3-yl]propanoate (100 mg, 224.98 umol, 1 eq) was added NH$_3$/MeOH (7 M, 27.54 mL, 856.77 eq) and stirred at 80° C. for 16 h. The reaction was concentrated in vacuo to dryness to give the crude of N-[(1S)-1-[[(1S)-2-amino-2-oxo-1-[[(3S)-2-oxopyrrolidin-3-yl]methyl]ethyl]carbamoyl]-3-methyl-butyl]-1H-imidazo[4,5-b]pyridine-2-carboxamide (90 mg, crude) as an oil.

Step 3: N-[(1S)-1-[[(1S)-1-cyano-2-[(3 S)-2-oxopyrrolidin-3-yl]ethyl]carbamoyl]-3-methyl-butyl]-1H-imidazo[4,5-b]pyridine-2-carboxamide N-[(1S)-1-[[(1S)-2-amino-2-oxo-1-[[(3S)-2-oxopyrrolidin-3-yl]methyl]ethyl]carbamoyl]-3-methyl-butyl]-1H-imidazo[4,5-b]pyridine-2-carboxamide (80 mg, 186.28 umol, 1 eq) in DCM (3 mL) was added Burgess reagent (100.00 mg, 419.62 umol, 2.25 eq). The mixture was stirred at 25° C. for 4 h. The reaction was blow-dried under N$_2$. The residue was purified by prep-HPLC (column: Waters Xbridge Prep OBD C$_{18}$ 150*40 mm*10 um; mobile phase: [water(10 mM NH$_4$HCO3)—ACN]; B %: 10%-35%, 8 min) to give N-[(1S)-1-[[(1S)-1-cyano-2-[(3S)-2-oxopyrrolidin-3-yl]ethyl]carbamoyl]-3-methyl-butyl]-1H-imidazo[4,5-b]pyridine-2-carboxamide (25 mg, 60.76 umol) as a solid. MS (ESI) m/z 412.1 [M+H]$^+$. $^1$H NMR (400 MHz, DMSO-d$_6$) δ ppm 13.58 (br s, 1H), 9.29-8.96 (m, 1H), 8.89 (d, J=7.9 Hz, 1H), 8.49 (br s, 1H), 8.28-7.84 (m, 1H), 7.71 (s, 1H), 7.36 (dd, J=4.6, 8.2 Hz, 1H), 5.06-4.93 (m, 1H), 4.61-4.44 (m, 1H), 3.20-3.06 (m, 2H), 2.43-2.31 (m, 1H), 2.20-2.07 (m, 2H), 1.90-1.53 (m, 5H), 0.92 (dd, J=6.4, 9.5 Hz, 6H).

Example 5. Synthesis of Viral Protease Inhibitor Compound 121

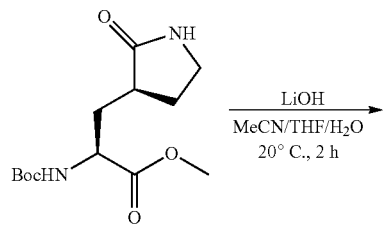

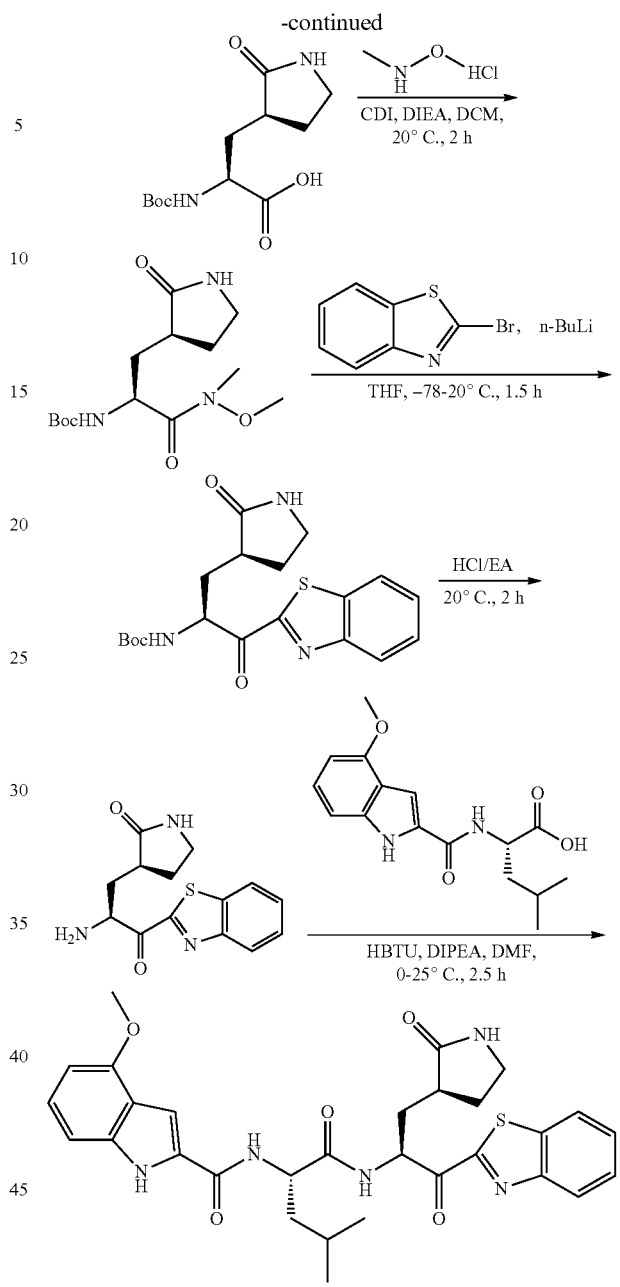

Step 1: (2S)-2-(tert-butoxycarbonylamino)-3-[(3S)-2-oxopyrrolidin-3-yl]propanoic acid To a mixture of methyl (2S)-2-(tert-butoxycarbonylamino)-3-[(3S)-2-oxopyrrolidin-3-yl]propanoate (1.2 g, 3.77 mmol) in THF (3 mL), ACN (3 mL) and H$_2$O (3 mL) was added LiOH.H$_2$O (158.29 mg, 3.77 mmol, 1 eq). The mixture was stirred at 25° C. for 2 h. Once the reaction was completed, the solution was concentrated to give a residue, and then the residue was adjusted to pH~4 with HCl. The resulting residue was extracted with EtOAc (20 mL*3) and brine (20 mL), and then concentrated to give a residue compound (2S)-2-(tert-butoxycarbonylamino)-3-[(3S)-2-oxopyrrolidin-3-yl]propaneic acid (1 g, 3.31 mmol) was obtained as an oil. MS (ESI) m/z 217.1 [M+H-56]$^+$.

Step 2: tert-butyl N—[(S)-2-[methoxy(methyl)amino]-2-oxo-1-[[(3S)-2-oxopyrrolidin-3-yl]methyl]ethyl]carbamate To a mixture of (2S)-2-(tert-butoxycarbonylamino)-3-[(3S)-2-oxopyrrolidin-3-yl]propanoic acid (1.0 g, 3.31 mmol) in DCM (20 mL) was added CDI (535.94 mg, 3.31 mmol, 1 eq). The mixture was stirred at 0° C. for 30 min, then added with DIEA (512.61 mg, 3.97 mmol, 690.85 uL, 1.2 eq) and N,O-DIMETHYLHYDROXYLAMINE HYDROCHLORIDE (322.40 mg, 3.31 mmol, 1 eq). The resulting mixture was stirred at 25° C. for 3 h. Once the reaction was complete, the reaction mixture was diluted with H₂O (30 mL) and extracted with ethyl acetate (30 mL*3). The combined organic layers were washed with brine (30 mL), dried over Na₂SO₄, filtered and concentrated under reduced pressure to give a residue. The residue was purified by column chromatography (SiO₂, petroleum ether/EtOAc=5/1 to 0/1) to get the compound tert-butyl N-[(1S)-2-[methoxy(methyl)amino]-2-oxo-1-[[(3S)-2-oxopyrrolidin-3-yl]methyl]ethyl]carbamate (0.9 g, 2.57 mmol) which was obtained as an oil. MS (ESI) m/z 316.2 [M+H]+

Step 3: tert-butyl N-[(1S)-2-(1,3-benzothiazol-2-yl)-2-oxo-1-[[(3S)-2-oxopyrrolidin-3-yl]methyl]ethyl]carbamate To a mixture of 2-bromo-1,3-benzothiazole (458.22 mg, 2.14 mmol, 1.5 eq) in THF (20 mL) was added n-BuLi (2.5 M, 684.92 uL, 1.2 eq) in one portion at −78° C. under N₂. The mixture was stirred at −78° C. for 30 min, and then added with tert-butyl N-[(1S)-2-[methoxy(methyl)amino]-2-oxo-1-[[(3S)-2-oxopyrrolidin-3-yl]methyl]ethyl]carbamate (500 mg, 1.43 mmol) at −78° C. The resulting mixture was stirred for 1 hour, and then the reaction mixture was quenched by the addition of NH₄Cl (10 mL) at 0° C., and then stirred for 10 min at 0° C. The resulting mixture was diluted with water (100 mL) and extracted with EtOAc (50 mL*3). The combined organic layers were washed with brine (50 mL), dried over Na₂SO₄, filtered and concentrated under reduced pressure to give a residue. The residue was purified by MPLC (SiO₂, petroleum ether/EtOAc-MeOH=10/1 to 0/1) to get the compound tert-butyl N-[(1S)-2-(1,3-benzothiazol-2-yl)-2-oxo-1-[[(3S)-2-oxopyrrolidin-3-yl]methyl]ethyl]carbamate (150 mg, 346.63 umol) as a colorless oil. MS (ESI) m/z 390.1 [M+H]⁺

Step 4: (3S)-3-[(2S)-2-amino-3-(1,3-benzothiazol-2-yl)-3-oxo-propyl]pyrrolidin-2-one To a mixture of tert-butyl N-[(1S)-2-(1,3-benzothiazol-2-yl)-2-oxo-1-[[(3S)-2-oxopyrrolidin-3-yl]methyl]ethyl]carbamate (150 mg, 346.63 umol) was added HCl/EtOAc (4 M, 86.66 uL, 1 eq). The resulting mixture was stirred at 20° C. for 2 h, and then concentrated under reduced pressure to give a residue (3S)-3-[(2S)-2-amino-3-(1, 3-benzothiazol-2-yl)-3-oxo-propyl]pyrrolidin-2-one (100 mg, crude) as an oil which was directly used in the next step. MS (ESI) m/z 290.1 [M+H]⁺

Step 5: N-[(1S)-1-[[(1S)-2-(1,3-benzothiazol-2-yl)-2-oxo-1-[[(3S)-2-oxopyrrolidin-3-yl]methyl]ethyl]carbamoyl]-3-methyl-butyl]-4-methoxy-1H-indole-2-carboxamide To a mixture of (2S)-2-[(4-methoxy-1H-indole-2-carbonyl)amino]-4-methyl-pentanoic acid (18.93 mg, 62.21 umol, 1 eq) in DMF (1 mL) was added 1-methylimidazole (25.54 mg, 311.04 umol, 24.79 uL, 5 eq) and [chloro(dimethylamino)methylene]-dimethyl-ammonium hexafluorophosphate (20.95 mg, 74.65 umol, 1.2 eq) at 0° C. The resulting mixture was stirred at 0° C. for 30 min, and then added with (3S)-3-[(2S)-2-amino-3-(1,3-benzothiazol-2-yl)-3-oxo-propyl]pyrrolidin-2-one (18 mg, 62.21 umol, 1 eq). The resulting mixture was stirred at 25° C. for 2 h. Once the reaction was completed, the reaction mixture was filtered and concentrated under reduced pressure to give a residue. The crude was purified by neutral prep-HPLC (column: Waters Xbridge BEH C₁₈ 100*30 mm*10 um; mobile phase: [water (10 mMNH4HCO3)— ACN]; B %: 35%-65%, 10 min) and SFC (column: DAICEL CHIRALCEL OX (250 mm*30 mm, 10 um); mobile phase: [0.1% NH₃H2O MEOH]; B %: 50%-50%, 12 min) separation to get the compound N-[(1S)-1-[[(1S)-2-(1,3-benzothiazol-2-yl)-2-oxo-1-[[(3S)-2-oxopyrrolidin-3-yl]methyl]ethyl]carbamoyl]-3-methyl-butyl]-4-methoxy-1H-indole-2-carboxamide (8 mg, 13.48 umol) as a solid. MS (ESI) m/z 576.3 [M+H]⁺. ¹H NMR (400 MHz, DMSO-d₆) δ=11.69 (s, 1H), 8.75-8.51 (m, 2H), 8.08 (d, J=7.9 Hz, 1H), 7.95 (d, J=8.2 Hz, 1H), 7.68 (s, 1H), 7.50 (t, J=7.4 Hz, 1H), 7.44-7.37 (m, 1H), 7.19-7.07 (m, 4H), 6.93 (d, J=8.2 Hz, 1H), 6.49 (d, J=7.7 Hz, 1H), 3.89 (s, 3H), 3.15-2.99 (m, 2H), 2.46-2.30 (m, 1H), 2.21-1.94 (m, 4H), 1.93-1.74 (m, 1H), 1.57-1.40 (m, 2H), 0.83-0.71 (m, 6H).

Example 6. Synthesis of Viral Protease Inhibitor Compound 185

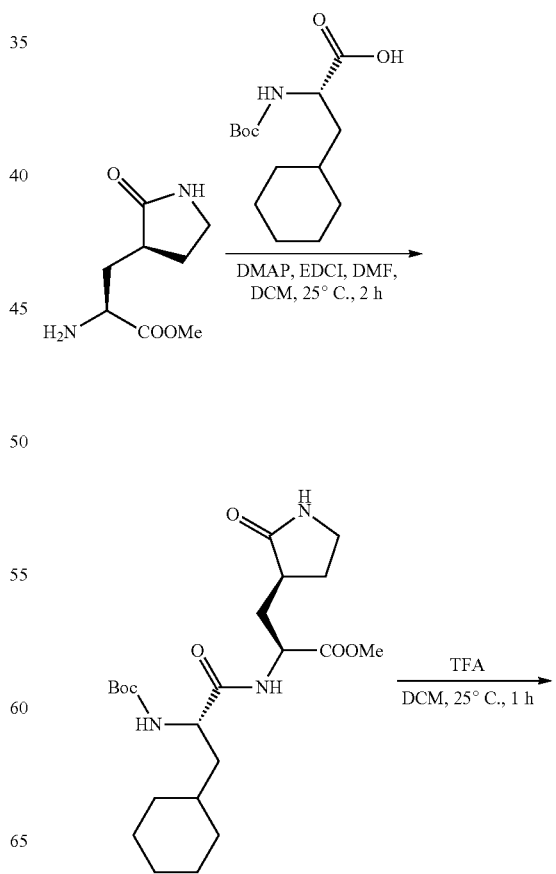

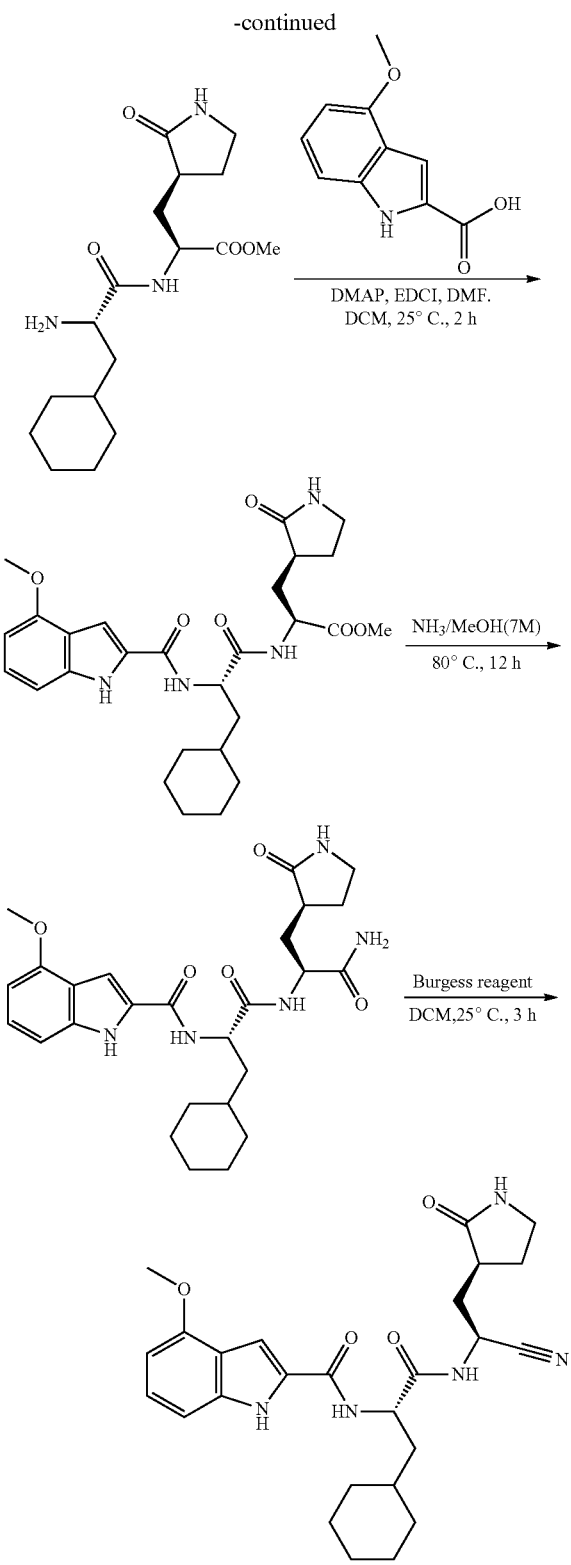

Step 1: (S)-methyl 2-((S)-2-((tert-butoxycarbonyl)amino)-3-cyclohexylpropanamido)-3-((S)-2-oxopyrrolidin-3-yl)propanoate To a solution of methyl (2S)-2-amino-3-[(3S)-2-oxopyrrolidin-3-yl]propanoate (170 mg, 763.47 umol, 1 eq, HCl) and (2S)-2-(tert-butoxycarbonylamino)-3-cyclohexyl-propanoic acid (207.17 mg, 763.47 umol, 1 eq) in DMF (2 mL) was added DMAP (186.55 mg, 1.53 mmol, 2 eq) and EDCI (292.71 mg, 1.53 mmol, 2 eq). The mixture was added DCM (3 mL) and stirred at 25° C. for 2 h. LCMS showed the reaction was completed, and desired MS was observed. The reaction mixture was quenched by addition $H_2O$ (30 mL) at 0° C., and then extracted with DCM (20 mL*3). The combined organic layers were washed with brine (10 mL), dried over $Na_2SO_4$, filtered and concentrated under reduced pressure to give a residue. The residue was purified by prep-TLC ($SiO_2$, petroleum ether/EtOAc=0/1) to get the product methyl (2S)-2-[[(2S)-2-(tert-butoxycarbonylamino)-3-cyclohexyl-propanoyl]amino]-3-[(3S)-2-oxopyrrolidin-3-yl]propanoate (250 mg, 568.77 umol, 74.50% yield) was obtained as a solid. MS (ESI) m/z 440.3 $[M+H]^+$ Step 2: (S)-methyl 2-((S)-2-amino-3-cyclohexylpropanamido)-3-((S)-2-oxopyrrolidin-3-yl)propanoate A solution of methyl (2S)-2-[[(2S)-2-(tert-butoxycarbonylamino)-3-cyclohexyl-propanoyl]amino]-3-[(3S)-2-oxopyrrolidin-3-yl]propanoate (200 mg, 455.02 umol, 1 eq) in EtOAc (0.5 mL) was added drop-wise HCl/EtOAc (4 M, 2.00 mL, 17.58 eq) at 25° C. The mixture was stirred at 25° C. for 1 h. The reaction mixture was concentrated under reduced pressure to give a product methyl (2S)-2-[[(2S)-2-amino-3-cyclohexyl-propanoyl]amino]-3-[(3S)-2-oxopyrrolidin-3-yl]propanoate (150 mg, crude, HCl) was obtained as a solid and used directly next step. MS (ESI) m/z 340.1 $[M+H]^+$ Step 3: ((S)-methyl 2-((S)-3-cyclohexyl-2-(4-methoxy-1H-indole-2-carboxamido)propanamido)-3-((S)-2-oxopyrrolidin-3-yl)propanoate A solution of 4-methoxy-1H-indole-2-carboxylic acid (99.18 mg, 518.77 umol, 1.3 eq) and methyl (2S)-2-[[(2S)-2-amino-3-cyclohexyl-propanoyl]amino]-3-[(3S)-2-oxopyrrolidin-3-yl]propanoate (150 mg, 399.05 umol, 1 eq, HCl) in DMF (2 mL) was added DMAP (97.50 mg, 798.11 umol, 2.0 eq) and EDCI (153.00 mg, 798.11 umol, 2 eq). The mixture was added DCM (4 mL) and stirred at 25° C. for 2 h. The reaction mixture was quenched by addition $H_2O$ (20 mL) at 0° C., and then extracted with DCM (20 mL*3). The combined organic layers were washed with brine (20 mL), dried over $Na_2SO_4$, filtered and concentrated under reduced pressure to give a residue. The residue was purified by column chromatography ($SiO_2$, DCM:MeOH=1:0 to 10:1) to get a product methyl (2S)-2-[[(2S)-3-cyclohexyl-2-[(4-methoxy-1H-indole-2-carbonyl)amino]propanoyl]amino]-3-[(3S)-2-oxopyrrolidin-3-yl]propanoate (150 mg, 292.63 umol, 73.33% yield) was obtained as a solid.

$^1$H NMR (METHANOL-$d_4$, 400 MHz): δ ppm 7.26 (s, 1H), 7.09-7.20 (m, 1H), 7.02 (d, J=8.3 Hz, 1H), 6.51 (d, J=7.6 Hz, 1H), 4.66 (br dd, J=9.0, 6.3 Hz, 1H), 4.52-4.58 (m, 1H), 3.93 (s, 3H), 3.72 (s, 3H), 3.22-3.29 (m, 2H), 2.54-2.62 (m, 1H), 2.26-2.33 (m, 1H), 2.15-2.23 (m, 1H), 1.66-1.87 (m, 9H), 1.47-1.54 (m, 1H), 1.25-1.40 (m, 3H), 0.96-1.06 (m, 2H)

Step 4: N—((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide A solution of methyl (2S)-2-[[(2S)-3-cyclohexyl-2-[(4-methoxy-1H-indole-2-carbonyl)amino]propanoyl]amino]-

3-[(3S)-2-oxopyrrolidin-3-yl]propanoate (150 mg, 292.63 umol, 1 eq) in ammonia (15.30 g, 898.39 mmol, 15.00 mL, 3070.07 eq) was heated at 80° C. for 12 hours in a sealed tube. The reaction mixture was concentrated under reduced pressure to get a product N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (140 mg, crude) was obtained as a solid. MS (ESI) m/z 498.2 [M+H]$^+$ $^1$H NMR (METHANOL-d$_4$, 400 MHz): δ ppm 7.27-7.34 (m, 1H), 7.13-7.20 (m, 1H), 7.05 (d, J=8.3 Hz, 1H), 6.53 (d, J=7.7 Hz, 1H), 4.62 (t, J=7.6 Hz, 1H), 4.42-4.51 (m, 1H), 3.95 (s, 3H), 3.22-3.30 (m, 2H), 2.53 (td, J=9.2, 4.5 Hz, 1H), 2.33 (ddd, J=9.2, 6.4, 3.4 Hz, 1H), 2.17 (ddd, J=14.1, 11.4, 4.6 Hz, 1H), 1.71-1.88 (m, 9H), 1.46-1.53 (m, 1H), 1.21-1.32 (m, 3H), 0.97-1.09 (m, 2H)

Step 5: N—((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide To a solution of N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (80 mg, 160.78 umol, 1 eq) in DCM (3 mL) was added Burgess reagent (114.94 mg, 482.33 umol, 3 eq), and then the resulting mixture was stirred at 25° C. for 3 h. The reaction mixture was concentrated under reduced pressure to give a residue. The residue was purified by neutral prep-HPLC to give a product N-[(1S)-2-[[(1S)-1-cyano-2-[(3S)-2-oxopyrrolidin-3-yl]ethyl]amino]-1-(cyclohexylmethyl)-2-oxo-ethyl]-4-methoxy-1H-indole-2-carboxamide (20.02 mg, 41.75 umol) was obtained as a solid. MS (ESI) m/z 480.1 [M+H]$^+$.

Prep-HPLC condition: column: Waters Xbridge BEH C$_{18}$ 100*25 mm*5 um; mobile phase: [water(10 mM NH$_4$HCO$_3$)—ACN]; B %: 30%-60%, 10 min H NMR (METHANOL-d$_4$, 400 MHz): δ ppm 7.28 (s, 1H), 7.11-7.18 (m, 1H), 7.02 (d, J=8.3 Hz, 1H), 6.51 (d, J=7.6 Hz, 1H), 5.05 (dd, J=10.1, 5.9 Hz, 1H), 4.56-4.61 (m, 1H), 3.93 (s, 3H), 3.22-3.30 (m, 2H), 2.55-2.66 (m, 1H), 2.23-2.40 (m, 2H), 1.65-1.94 (m, 9H), 1.41-1.52 (m, 1H), 1.17-1.36 (m, 3H), 0.94-1.10 (m, 2H).

Example 7. Synthesis of Viral Protease Inhibitor Compound 101

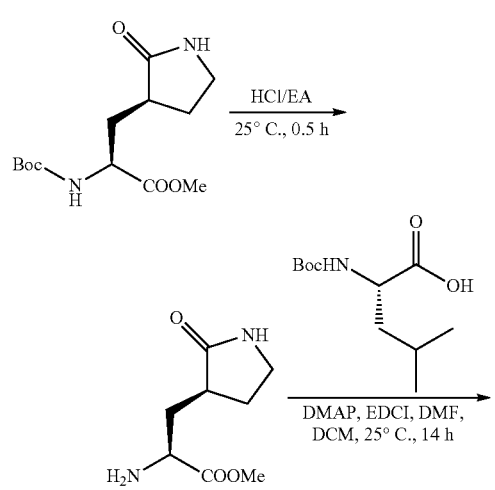

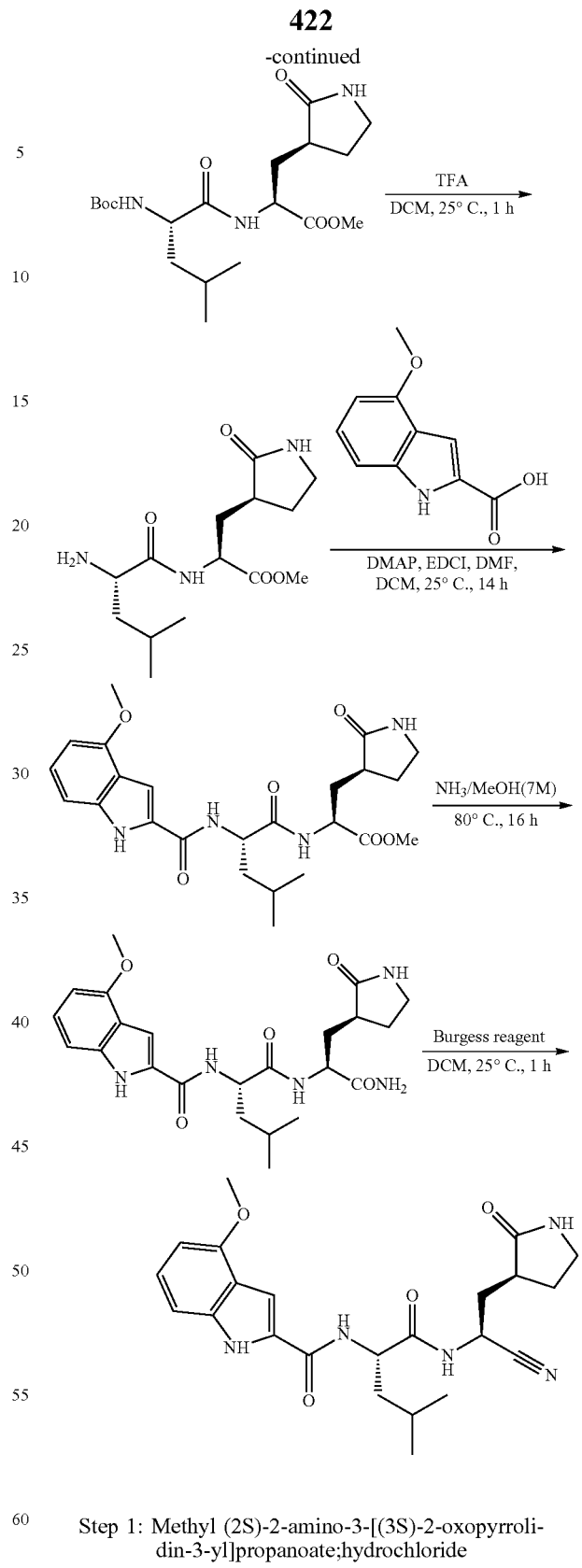

Step 1: Methyl (2S)-2-amino-3-[(3S)-2-oxopyrrolidin-3-yl]propanoate;hydrochloride Methyl (2S)-2-(tert-butoxycarbonylamino)-3-[(3S)-2-oxopyrrolidin-3-yl]propanoate (500 mg, 1.75 mmol, 1 eq) was added HCl/EtOAc (4 M, 10 mL, 22.91 eq) at 25° C. The mixture was stirred at 25° C. for 0.5 h. The resulting mixture was concentrated under reduced pressure to give a product methyl (2S)-2-amino-3-[(3S)-2-oxopyrrolidin-3-yl]propanoate; hydrochloride (300 mg, 1.28 mmol, 73.29% yield, 95% purity) as a solid and used directly next step. MS (ESI) m z 187.1 [M+H]$^+$ Step 2: methyl (2S)-2-[[(2S)-2-(tert-butoxycarbonylamino)-4-methyl-pentanoyl]amino]-3-[(3S)-2-oxopyrrolidin-3-yl]propanoate To a mixture of methyl (2S)-2-amino-3-[(3S)-2-oxopyrrolidin-3-yl]propanoate; hydrochloride (157.89 mg, 673.65 umol, 95% purity, 1 eq) and (2S)-2-(tert-butoxycarbonylamino)-4-methyl-pentanoic acid (155.81 mg, 673.65 umol, 1 eq) in DMF (2 mL) was added EDCI (258.28 mg, 1.35 mmol, 2 eq) and DMAP (164.60 mg, 1.35 mmol, 2 eq). The mixture was added DCM (3 mL) and stirred at 25° C. for 14 h. The resulting mixture was diluted with H$_2$O (50 mL) and extracted with DCM (30 mL*3). The combined organic layers were washed with brine, dried over Na$_2$SO$_4$, filtered and concentrated under reduced pressure to give a residue. The residue was purified by column chromatography (SiO2, petroleum ether/EtOAc=3/1 to 1/1) to get the product methyl (2S)-2-[[(2S)-2-(tert-butoxycarbonylamino)-4-methyl-pentanoyl]amino]-3-[(3S)-2-oxopyrrolidin-3-yl]propanoate (250 mg, 500.65 umol, 74.32% yield, 80% purity) was obtained as a solid. MS (ESI) m/z 400.3 [M+H]$^+$ Step 3: (2S)-2-amino-N-[(1S)-1-cyano-2-[(3S)-2-oxopyrrolidin-3-yl]ethyl]-4-methyl-pentanamide tert-butylN-[(1S)-1-[[(1S)-1-cyano-2-[(3S)-2-oxopyrrolidin-3-yl]ethyl]carbamoyl]-3-methyl-butyl]carbamate (200 mg, 491.19 umol, 90% purity, 1 eq) in DCM (5 mL) was added TFA (770.00 mg, 6.75 mmol, 0.5 mL, 13.75 eq) at 25° C. The mixture was stirred at 25° C. for 1 h. The resulting mixture was concentrated under reduced pressure to give a product (2S)-2-amino-N-[(1S)-1-cyano-2-[(3S)-2-oxopyrrolidin-3-yl]ethyl]-4-methyl-pentanamide (120 mg, 405.50 umol, 82.55% yield, 90% purity) as an oil and used directly next step. MS (ESI) m z 300.2 [M+H]$^+$ Step 4: methyl(2S)-2-[[(2S)-2-[(4-methoxy-1H-indole-2-carbonyl)amino]-4-methyl-pentanoyl]amino]-3-[(3S)-2-oxopyrrolidin-3-yl]propanoate To a mixture of 4-methoxy-1H-indole-2-carboxylic acid (120 mg, 627.67 umol, 1 eq) and methyl (2S)-2-[[(2S)-2-amino-4-methyl-pentanoyl]amino]-3-[(3 S)-2-oxopyrrolidin-3-yl]propanoate (208.78 mg, 627.67 umol, 90% purity, 1 eq) in DCM (1 mL) was added EDCI (240.65 mg, 1.26 mmol, 2 eq) and DMAP (153.36 mg, 1.26 mmol, 2 eq). The mixture was added DMF (0.5 mL) and stirred at 25° C. for 14 h. The resulting mixture was diluted with H$_2$O (50 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO2, petroleum ether/EtOAc=3/1 to 0/1) to get the compound methyl(2S)-2-[[(2S)-2-[(4-methoxy-1H-indole-2-carbonyl)amino]-4-methyl-pentanoyl]amino]-3-[(3S)-2-oxopyrrolidin-3-yl]propanoate (160 mg, 304.74 umol, 48.55% yield, 90% purity) as a solid. MS (ESI) m/z 473.3 [M+H]$^+$ Step 5: N-[(1S)-1-[[(1S)-2-amino-2-oxo-1-[[(3S)-2-oxopyrrolidin-3-yl]methyl]ethyl]carbamoyl]-3-methyl-butyl]-4-methoxy-1H-indole-2-carboxamide methyl (2S)-2-[[(2S)-2-[(4-methoxy-1H-indole-2-carbonyl)amino]-4-methyl-pentanoyl]amino]3-[(3S)-2-oxopyrrolidin-3-yl]propanoate (180 mg, 342.83 umol, 90% purity, 1 eq) was added NH$_3$/MeOH (7 M, 54.00 mL, 1102.58 eq), The mixture was stirred at 80° C. for 16 h. The resulting mixture was concentrated under reduced pressure to give a residue N-[(1S)-1-[[(1S)-2-amino-2-oxo-1-[[(3S)-2-oxopyrrolidin-3-yl]methyl]ethyl]carbamoyl]-3-methyl-butyl]-4-methoxy-1H-indole-2-carboxamide (130 mg, 255.73 umol, 74.59% yield, 90% purity) as an oil. MS (ESI) m/z 458.3 [M+H]$^+$ 1H NMR (400 MHz, METHANOL-d4) δ ppm 0.97-1.02 (dd, J=14.55, 6.11 Hz, 6H) 1.74-1.82 (m, 5H) 2.15 (ddd, J=14.03, 11.34, 4.58 Hz, 1H) 2.25-2.37 (m, 1H) 2.52 (ddt, J=13.82, 9.41, 4.71, 4.71 Hz, 1H) 3.17-3.29 (m, 2H) 3.90 (s, 3H) 4.46 (dd, J=11.25, 4.16 Hz, 1H) 4.60 (dd, J=9.66, 5.01 Hz, 1H) 6.50-6.52 (d, J=7.70 Hz, 1H) 7.02-7.04 (d, J=8.31 Hz, 1H) 7.15-7.17 (m, 1H) 7.28-7.29 (d, J=0.73 Hz, 1H)

Step 6: N-[(1S)-1-[[(1S)-1-cyano-2-[(3S)-2-oxopyrrolidin-3-yl]ethyl]carbamoyl]-3-methyl-butyl]-4-methoxy-1H-indole-2-carboxamide To a mixture of N-[(1S)-1-[[(1S)-2-amino-2-oxo-1-[[(3S)-2-oxopyrrolidin-3-yl]methyl]ethyl]carbamoyl]-3-methyl-butyl]-4-methoxy-1H-indole-2-carboxamide (100 mg, 196.71 umol, 90% purity, 1 eq) in DCM (4 mL) was added Burgess reagent (93.75 mg, 393.42 umol, 2 eq). The mixture was stirred at 25° C. for 1 h. The resulting mixture was concentrated under reduced pressure to give a residue. The residue was purified by neutral prep-HPLC to get the product N-[(1S)-1-[[(1S)-1-cyano-2-[(3S)-2-oxopyrrolidin-3-yl]ethyl]carbamoyl]-3-methyl-butyl]-4-methoxy-1H-indole-2-carboxamide (23 mg, 49.50 umol, 25.16% yield, 94.59% purity) as a solid. MS (ESI) m/z 440.1 [M+H]$^+$.

Prep-HPLC Condition:
column: Waters Xbridge BEH C$_{18}$ 100*30 mm*10 um; mobile phase: [water(10 mM NH4HCO3)—ACN]; B %: 27%-57%, 10 min 1H NMR (400 MHz, DMSO-d6) δ ppm 0.88-0.94 (m, 6H) 1.67-1.74 (m, 5H) 2.11-2.13 (m, 2H) 2.14-2.34 (m, 1H) 3.09-3.14 (m, 2H) 3.88 (s, 3H) 4.36-4.57 (m, 1H) 4.90-5.00 (m, 1H) 6.49-6.51 (d, J=7.58 Hz, 1H) 6.99-7.01 (m, 2H) 7.38 (s, 1H) 7.70 (s, 1H) 8.45-8.47 (br d, J=7.70 Hz, 1H) 8.89-8.91 (br d, J=7.95 Hz, 1H) 11.57 (br s, 1H)

Example 8. Synthesis of Viral Protease Inhibitor Compound 593

-continued

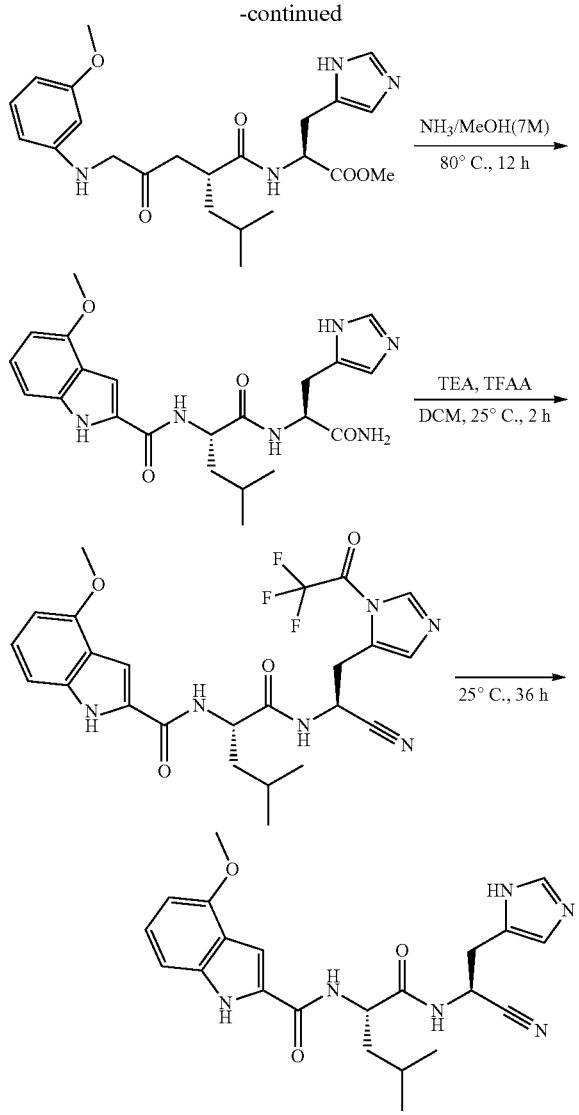

Step 1: methyl (2S)-2-amino-3-(1H-imidazol-5-yl) propanoate

To the solution of (2S)-2-(tert-butoxycarbonylamino)-3-(1H-imidazol-5-yl)propanoic acid (0.5 g, 1.96 mmol, 1 eq) in MeOH (0.6 mL) was added HCl/MeOH (4 M, 4.90 mL, 10 eq) at 25° C. The reaction mixture was stirred at 25° C. for 12 h. The reaction mixture was concentrated to get the product. Methyl (2S)-2-amino-3-(1H-imidazol-5-yl) propanoate (400 mg, crude, HCl) was obtained as a solid and used directly next step. MS (ESI) m/z 170.1 [M+H]$^+$

Step 2: methyl (2S)-3-(1H-imidazol-5-yl)-2-[[(2S)-2-[(4-methoxy-1H-indole-2-carbonyl)amino]-4-methyl-pentanoyl]amino]propanoate To a mixture of (2S)-2-[(4-methoxy-1H-indole-2-carbonyl)amino]-4-methyl-pentanoic acid (741.86 mg, 1.77 mmol, 1 eq, TFA) and methyl (2S)-2-amino-3-(1H-imidazol-5-yl)propanoate (0.3 g, 1.77 mmol, 1 eq, HCl), DIPEA (1.15 g, 8.87 mmol, 1.54 mL, 5 eq) in THF (0.3 mL) and DCM (0.3 mL) was added T3P (1.69 g, 2.66 mmol, 1.58 mL, 50% purity, 1.5 eq) at 0° C. under N$_2$. The mixture was stirred at 25° C. for 12 h. The reaction mixture was added saturated sodium bicarbonate solution (10 mL) and extracted with DCM (10 mL*2) to get the organic phase. The organic phase was washed with brine (3 mL*3) and dried over anhydrous sodium sulfate and concentrated to get the crude product. Methyl (2S)-3-(1H-imidazol-5-yl)-2-[[(2S)-2-[(4-methoxy-1H-indole-2-carbonyl)amino]-4-methyl-pentanoyl]amino]propanoate (300 mg, crude) was obtained as a solid and used directly next step. MS (ESI) m/z 456.2 [M+H]$^+$ 1H NMR (400 MHz, METHANOL-d$_4$) δ ppm 7.48 (s, 1H), 7.27 (s, 1H), 7.11-7.18 (m, 1H), 7.02 (d, J=8.16 Hz, 1H), 6.85 (s, 1H), 6.51 (d, J=7.72 Hz, 1H), 4.60-4.71 (m, 2H), 3.93 (s, 3H), 3.68 (s, 3H), 3.00-3.17 (m, 3H), 1.62-1.78 (m, 3H), 0.97 (dd, J=13.78, 6.06 Hz, 6H)

Step 3: N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide To methyl (2S)-3-(1H-imidazol-5-yl)-2-[[(2S)-2-[(4-methoxy-1H-indole-2-carbonyl)amino]-4-methyl-pentanoyl]amino]propanoate (200 mg, 439.07 umol, 1 eq) was added NH$_3$/MeOH (7 M, 11.76 mL, 187.56 eq) in one portion at 25° C. under N2. The mixture was stirred at 80° C. and stirred for 12 h. The reaction mixture was cooled to 25° C. and concentrated to get the crude product. N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide (170 mg, 378.83 umol, 86.28% yield, 98.16% purity) was obtained as a solid and used directly next step. MS (ESI) m z 441.2 [M+H]$^+$

Step 4: N-[(1S)-1-[[(1S)-1-cyano-2-(H-imidazol-5-yl)ethyl]carbamoyl]-3-methyl-butyl]-4-methoxy-1H-indole-2-carboxamide To a mixture of N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide (140 mg, 317.82 umol, 1 eq) in DCM (2 mL) was added TFAA (133.51 mg, 635.65 umol, 88.41 uL, 2 eq) at 25° C. under N$_2$. The mixture was stirred at 25° C. for 2 h. The reaction mixture was concentrated to get the crude product. Crude product turned into compound 593 after 36 h in storage. The residue was purified by prep-HPLC. N-[(1S)-1-[[(1S)-1-cyano-2-(1H-imidazol-5-yl)ethyl]carbamoyl]-3-methyl-butyl]-4-methoxy-1H-indole-2-carboxamide (23.89 mg, 56.31 umol, 17.72% yield, 99.581% purity) was obtained as a solid. MS (ESI) m/z 423.2 [M+H]$^+$ Prep-HPLC Condition:
column: Waters Xbridge BEH C$_{18}$ 100*25 mm*5 um; mobile phase: [water(10 mM NH$_4$HCO$_3$)—ACN]; B %: 25%-55%, 10 min $^1$H NMR (400 MHz, METHANOL-d$_4$) δ ppm 7.58 (s, 1H), 7.30 (s, 1H), 7.12-7.21 (m, 1H), 6.99-7.09 (m, 2H), 6.52 (d, J=7.72 Hz, 1H), 5.05 (t, J=7.06 Hz, 1H), 4.61 (br dd, J=9.70, 4.85 Hz, 1H), 3.94 (s, 3H), 3.06-3.21 (m, 2H), 1.60-1.83 (m, 3H), 0.99 (dd, J=13.89, 6.17 Hz, 6H)

Step 5: tert-butyl (2S)-2-[(4-methoxy-1H-indole-2-carbonyl)amino]-4-methyl-pentanoate To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under N₂. The mixture was stirred at 25° C. and stirred for 2 h. The reaction mixture was added water (90 mL) and extracted with EtOAc (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography (SiO₂, petroleum ether: EtOAc=30:1 to 10:1). Tert-butyl (2S)-2-[(4-methoxy-1H-indole-2-carbonyl) amino]-4-methyl-pentanoate (5.93 g, 16.45 mmol, 62.91% yield) was obtained as a solid. MS (ESI) m/z 361.2 [M+H]⁺

¹H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 6: (2S)-2-[(4-methoxy-1H-indole-2-carbonyl) amino]-4-methyl-pentanoic acid

To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and H₂O (666.67 mg, 37.01 mmol, 666.67 uL, 6.67 eq) in one portion at 0° C. under N₂. The mixture was stirred at 25° C. and stirred for 4 h. The reaction mixture was concentrated to get the crude product. (2S)-2-[(4-methoxy-1H-indole-2-carbonyl)amino]-4-methyl-pentanoic acid (2.24 g, 5.35 mmol, 96.50% yield, TFA) was obtained as a solid and used directly next step. MS (ESI) m/z 305.1 [M+H]⁺

Example 9. Synthesis of Viral Protease Inhibitor Compounds 135, 595 and 136

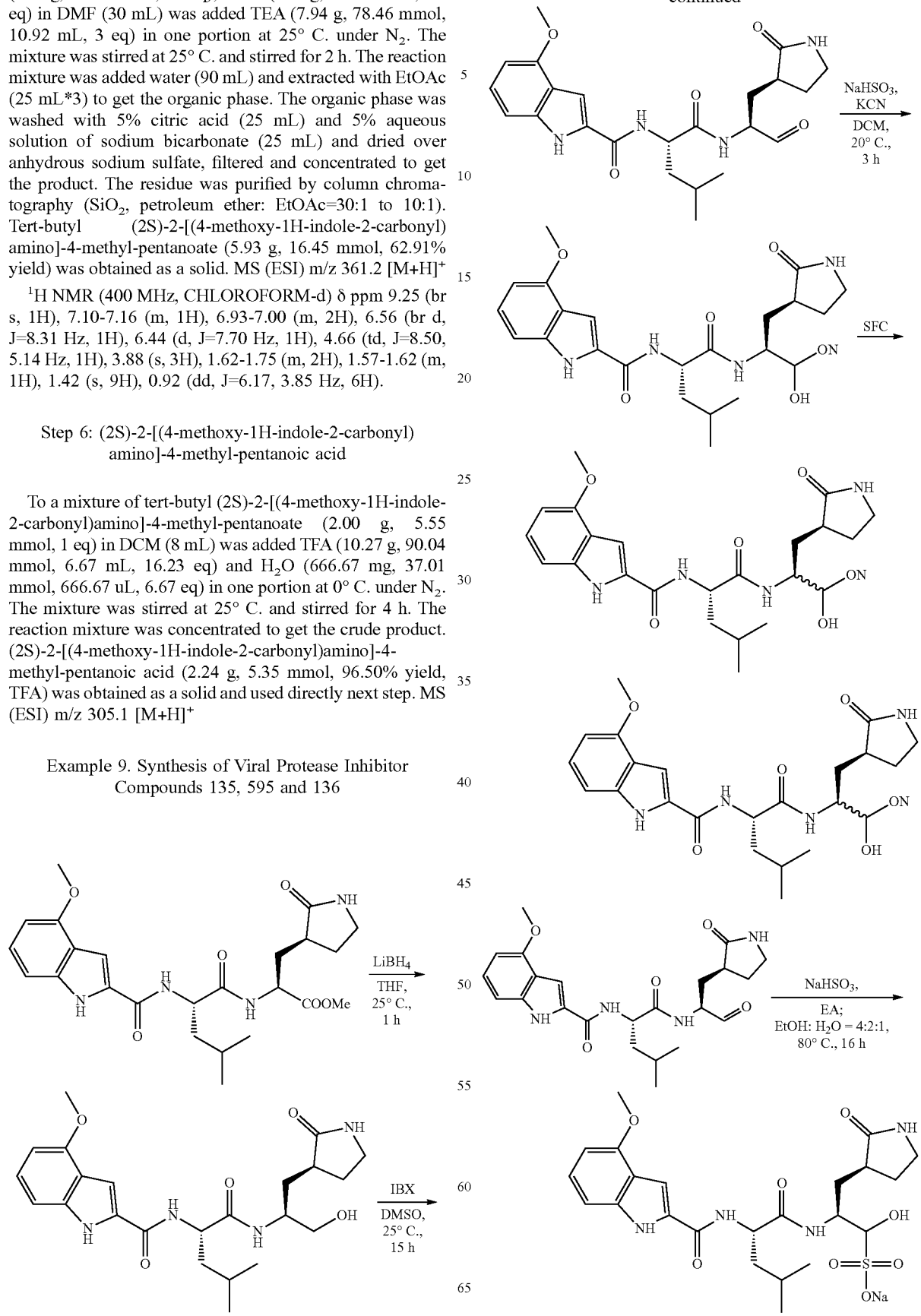

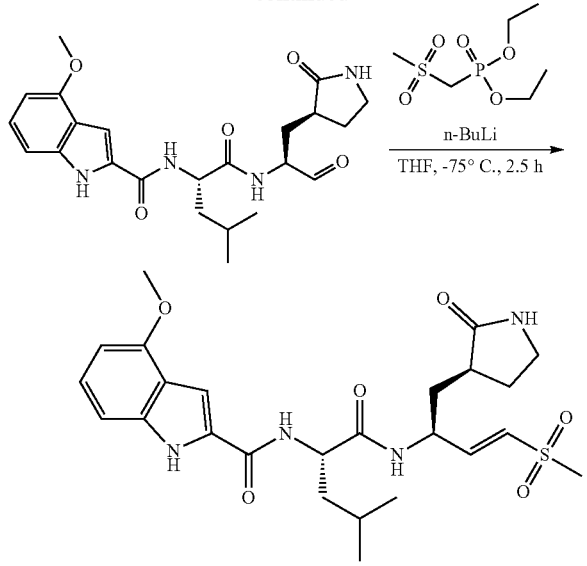

Step 1: N-[(1S)-1-[[(S)-1-(hydroxymethyl)-2-[(3S)-2-oxopyrrolidin-3-yl]ethyl]carbamoyl]-3-methyl-butyl]-4-methoxy-1H-indole-2-carboxamide To a mixture of methyl (2S)-2-[[(2S)-2-[(4-methoxy-1H-indole-2-carbonyl)amino]-4-methyl-pentanoyl]amino]-3-[(3S)-2-oxopyrrolidin-3-yl]propanoate (1.5 g, 2.86 mmol, 90% purity, 1 eq) in THF (20 mL) was added LiBH₄ (124.45 mg, 5.71 mmol, 2 eq). The mixture was stirred at 25° C. for 2 h. Once the reaction was completed, the reaction mixture was quenched by addition H₂O (10 mL) at 0° C., and extracted with EtOAc (30 mL*3). The combined organic layers were washed with brine (30 mL), dried over Na₂SO₄, filtered and concentrated under reduced pressure to give a residue compound N-[(1S)-1-[[(1S)-1-(hydroxymethyl)-2-[(3S)-2-oxopyrrolidin-3-yl]ethyl]carbamoyl]-3-methyl-butyl]-4-methoxy-1H-indole-2-carboxamide (1.0 g, 2.25 mmol, 78.74% yield) was obtained as a solid. MS (ESI) m/z 445.1 [M+H]⁺. ¹H NMR (400 MHz, METHANOL-d₄) δ=7.27 (s, 1H), 7.19-7.10 (m, 1H), 7.02 (d, J=8.3 Hz, 1H), 6.51 (d, J=7.7 Hz, 1H), 4.65-4.53 (m, 1H), 4.05-3.97 (m, 1H), 3.93 (s, 3H), 3.60-3.43 (m, 2H), 3.27-3.10 (m, 2H), 2.59-2.43 (m, 1H), 2.39-2.19 (m, 1H), 2.08-1.89 (m, 1H), 1.85-1.63 (m, 4H), 1.60-1.46 (m, 1H), 1.00 (dd, J=6.1, 12.5 Hz, 6H).

Step 2: N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide To a mixture of N-[(1S)-1-[[(1S)-1-(hydroxymethyl)-2-[(3S)-2-oxopyrrolidin-3-yl]ethyl]carbamoyl]-3-methyl-butyl]-4-methoxy-1H-indole-2-carboxamide (674 mg, 1.52 mmol, 1 eq) in DMSO (25 mL) was added IBX (849.14 mg, 3.03 mmol, 2 eq). The mixture was stirred at 25° C. for 15 h. Once the reaction was completed, the reaction mixture was diluted with H₂O (30 mL) and extracted with EtOAc (30 mL*2). The combined organic layers were washed with brine (30 mL), dried over Na₂SO₄, filtered and concentrated under reduced pressure to give a residue. The residue was added EA (10 mL) and filtered to give the product N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (420 mg, 759.31 umol, 50.08% yield, 80% purity) as a solid. MS (ESI) m/z 443.1 [M+H]⁺. ¹H NMR (400 MHz, METHANOL-d₄) δ=7.27 (s, 1H), 7.20-7.09 (m, 1H), 7.02 (d, J=8.3 Hz, 1H), 6.51 (d, J=7.7 Hz, 1H), 4.60 (dt, J=5.5, 9.9 Hz, 1.5H), 4.47 (dd, J=1.4, 4.1 Hz, 0.5H), 4.02-3.94 (m, 1H), 3.93 (s, 3H), 3.28-3.15 (m, 2H), 2.54-2.39 (m, 1H), 2.37-2.21 (m, 1H), 2.10-1.93 (m, 1H), 1.89-1.49 (m, 5H), 1.17-0.91 (m, 6H).

Step 3: N-[(1S)-1-[[(S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (400 mg, 723.15 umol, 80% purity, 1 eq) in DCM (10 mL) was added saturated NaHSO₃ (301.01 mg, 2.89 mmol, 203.38 uL, 4 eq). The mixture was stirred at 25° C. for 30 min, and then an aq solution of KCN (42 mg, 644.96 umol, 27.63 uL, 8.92e-1 eq) in H₂O (0.8 mL) was added. The mixture was stirred at 25° C. for 3 h. Once the reaction was completed, the organic phase was collected and the aqueous layer was extracted with DCM (30 mL*3). The combined organic phase was washed with brine (30 mL*2), dried over Na₂SO₄, and concentrated to get the crude. The liquid was added NaOH to pH=9, then quenched by adding aq NaCl, then added NaOH to pH >14. The crude was purified by HCl prep-HPLC to get the mixture 120 mg, and SFC separation to get compound N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (34 mg, 70.96 umol, 9.81% yield, 97.99% purity) and compound N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (64 mg, 131.75 umol, 18.22% yield, 96.66% purity) as a solid. MS (ESI) m z 470.2[M+H]⁺.
prep-HPLC condition: column: Phenomenex luna C₁₈ 80*40 mm*3 um; mobile phase: [water (0.04% HCl)—ACN]; B %: 26%-50%, 7 min
SFC condition: column: REGIS (R,R)WHELK-O1 (250 mm*25 mm, 10 um); mobile phase: [Neu-IPA]; B %: 35%-35%, 11 min
Compound 134 Isomer 1: ¹H NMR (400 MHz, DMSO-d₆) δ=11.57 (d, J=1.8 Hz, 1H), 8.40 (d, J=7.9 Hz, 1H), 8.13 (d, J=9.3 Hz, 1H), 7.57 (s, 1H), 7.36 (d, J=1.5 Hz, 1H), 7.13-7.06 (m, 1H), 7.03-6.97 (m, 1H), 6.69 (d, J=7.3 Hz, 1H), 6.50 (d, J=7.7 Hz, 1H), 4.50-4.40 (m, 1H), 4.33 (t, J=7.8 Hz, 1H), 4.10-3.97 (m, 1H), 3.88 (s, 3H), 3.16-2.98 (m, 2H), 2.39-2.26 (m, 1H), 2.15-2.01 (m, 1H), 1.92-1.80 (m, 1H), 1.80-1.63 (m, 2H), 1.62-1.40 (m, 3H), 0.90 (dd, J=6.3, 15.5 Hz, 6H).
Compound 134 Isomer 2: ¹H NMR (400 MHz, DMSO-d₆) δ=11.55 (br d, J=1.5 Hz, 1H), 8.35 (d, J=7.9 Hz, 1H), 8.21 (d, J=8.6 Hz, 1H), 7.60 (s, 1H), 7.34 (d, J=1.8 Hz, 1H), 7.12-7.06 (m, 1H), 7.03-6.97 (m, 1H), 6.64 (d, J=6.0 Hz, 1H), 6.50 (d, J=7.5 Hz, 1H), 4.60-4.49 (m, 2H), 4.12-3.96 (m, 1H), 3.88 (s, 3H), 3.19-2.98 (m, 2H), 2.41-2.26 (m, 1H), 2.16-1.95 (m, 2H), 1.92-1.35 (m, 5H), 0.98-0.82 (m, 6H).

Step 4: [(2S)-1-hydroxy-2-[[(2S)-2-[(4-methoxy-1H-indole-2-carbonyl)amino]-4-methyl-pentanoyl]amino]-3-[(3S)-2-oxopyrrolidin-3-yl]propyl]sulfonyloxysodium To a mixture of N-[(1S)-1-[[(1S)-1-formyl-2-[(3S)-2-oxopyrrolidin-3-yl]ethyl]carbamoyl]-3-methyl-butyl]-4- methoxy-1H-indole-2-carboxamide (50 mg, 112.99 umol, 1 eq) in EtOH (0.4 mL), EtOAc (0.2 mL) and H₂O (0.1 mL) was added NaHSO₃ (11.76 mg, 112.99 umol, 7.94 uL, 1 eq). The mixture was stirred at 80° C. for 16 h. Once the reaction was completed, the reaction mixture was concentrated under reduced pressure to give a residue. The residue was added DCM (3 mL) and ACN (3 mL), filtered to get the compound [(2S)-1-hydroxy-2-[[(2S)-2-[(4-methoxy-1H-indole-2-carbonyl)amino]-4-methyl-pentanoyl]amino]-3-[(3S)-2-oxopyrrolidin-3-yl]propyl]sulfonyloxysodium (5 mg, 5.26 umol, 4.66% yield, 57.5% purity) as a solid. (ESI) m/z 525.1 [M+H]⁺

¹H NMR (400 MHz, DMSO-d6) δ=11.67-11.44 (m, 1H), 9.42 (s, 0.02H), 8.52-8.27 (m, 1H), 7.74-7.59 (m, 1H), 7.43 (s, 1H), 7.32 (dd, J=1.8, 4.9 Hz, 1H), 7.15-6.93 (m, 2H), 6.50 (d, J=7.7 Hz, 1H), 5.40-5.24 (m, 1H), 4.61-4.33 (m, 1H), 4.31-4.15 (m, 0.5H), 4.11-3.96 (m, 0.5H), 3.94 (dd, J=2.4, 5.7 Hz, 0.5H), 3.88 (s, 3H), 3.85-3.81 (m, 0.5H), 3.19-2.94 (m, 2H), 2.27-1.87 (m, 3H), 1.85-1.42 (m, 5H), 0.99-0.79 (m, 6H)

Step 5: 4-methoxy-N-[(1S)-3-methyl-1-[[(E,]S)-3-methylsulfonyl-1-[[(3S)-2-oxopyrrolidin-3-yl]methyl]allyl]carbamoyl]butyl]-1H-indole-2-carboxamide To a mixture of 1-[ethoxy(methylsulfonylmethyl)phosphoryl]oxyethane (130.06 mg, 564.96 umol, 5 eq) in THF (2 mL) was added n-BuLi (2.5 M, 180.79 uL, 4 eq) at 0° C. under N₂. The mixture was stirred at −75° C. for 30 min, then added N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (50 mg, 112.99 umol, 1 eq). The mixture was stirred at −75° C. for 2 h. Once the reaction was completed, the reaction mixture was quenched by addition H₂O (10 mL) at 0° C., and then concentrated under reduced pressure to give a residue. The residue was purified by prep-HPLC to get the compound 4-methoxy-N-[(1S)-3-methyl-1-[[(E,1S)-3-methylsulfonyl-1-[[(3S)-2-oxopyrrolidin-3-yl]methyl]allyl]carbamoyl]butyl]-1H-indole-2-carboxamide (15 mg, 28.82 umol, 25.50% yield, 99.638% purity) as a solid. (ESI) m/z 519.1 [M+H]⁺ column: Phenomenex luna C₁₈ 80*40 mm*3 um; mobile phase: [water (0.04% HCl)—ACN]; B %: 26%-52%, 7 min ¹H NMR (400 MHz, METHANOL-d₄) δ=7.33-7.26 (m, 1H), 7.20-7.10 (m, 1H), 7.03 (d, J=8.3 Hz, 1H), 6.85 (dd, J=4.8, 15.3 Hz, 1H), 6.68 (dd, J=1.6, 15.3 Hz, 1H), 6.52 (d, J=7.7 Hz, 1H), 4.77-4.67 (m, 1H), 4.61-4.50 (m, 1H), 3.99-3.83 (m, 3H), 3.28-3.18 (m, 2H), 3.01-2.88 (m, 3H), 2.65-2.50 (m, 1H), 2.39-2.22 (m, 1H), 2.15-1.97 (m, 1H), 1.91-1.62 (m, 5H), 1.09-0.92 (m, 6H)

Example 10. Synthesis of Viral Protease Inhibitor Compound 740 and 741

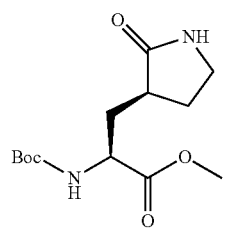

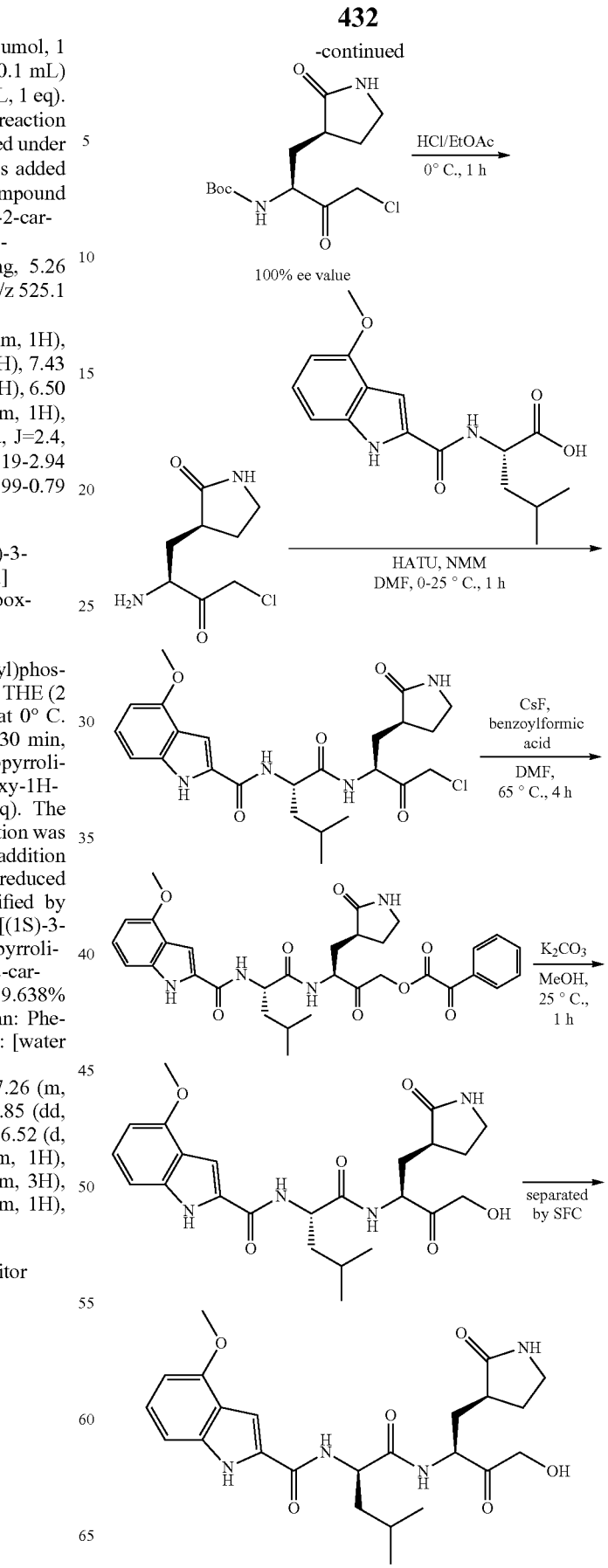

-continued

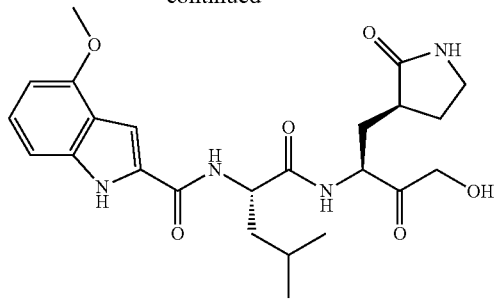

Step 1: tert-butyl ((S)-4-chloro-3-oxo-1-((S)-2-oxopyrrolidin-3-yl)butan-2-yl)carbamate To a solution of methyl (2S)-2-(tert-butoxycarbonylamino)-3-[(3S)-2-oxopyrrolidin-3-yl]propanoate (0.6 g, 2.10 mmol, 1 eq) in THF (24 mL) was added chloro(iodo)methane (1.48 g, 8.38 mmol, 608.42 uL, 4 eq), then the solution was cooled to −70° C. and LDA (2 M, 6.29 mL, 6 eq) was added drop-wise. The reaction was stirred at −70° C. for 1 h. Upon completion, the reaction mixture was quenched by addition a mixture of AcOH (4.5 mL) and THF (22 mL) at −70° C., and then diluted with ethyl acetate (50 mL) and extracted with water (30 mL*2), sat. NaHCO$_3$ (30 mL). The organic layers were washed dried over Na$_2$SO$_4$, filtered and concentrated under reduced pressure to give a residue. The residue was purified by column chromatography (SiO$_2$, petroleum ether: EtOAc=2:1 to 0:1) and then triturated with methyl tertiary butyl ether:petroleum ether=4:1 (3 mL) to give tert-butyl N-[(1S)-3-chloro-2-oxo-1-[[(3S)-2-oxopyrrolidin-3-yl]methyl]propyl]carbamate (0.35 g, 1.03 mmol, 49.32% yield, 90% purity) as a solid. MS (ESI) m/z 308.0 [M+H]$^+$.

$^1$H NMR (400 MHz, DMSO-d$_6$) δ=7.66 (br s, 1H), 7.53 (br d, J=7.7 Hz, 1H), 4.61 (d, J=2.2 Hz, 2H), 4.22-4.10 (m, 1H), 3.21-3.11 (m, 2H), 2.34-2.06 (m, 2H), 1.93-1.80 (m, 1H), 1.73-1.54 (m, 2H), 1.39 (s, 9H).

Step 2: (S)-3-((S)-2-amino-4-chloro-3-oxobutyl) pyrrolidin-2-one

A solution of tert-butyl N-[(1S)-3-chloro-2-oxo-1-[[(3S)-2-oxopyrrolidin-3-yl]methyl]propyl]carbamate (0.33 g, 1.08 mmol, 1 eq) in HCl/EtOAc (4 M, 5 mL, 18.47 eq) was stirred at 0° C. for 1 h. Upon completion, the reaction mixture was concentrated under reduced pressure to give (3S)-3-[(2S)-2-amino-4-chloro-3-oxo-butyl]pyrrolidin-2-one (0.3 g, crude, HCl) as an oil. MS (ESI) m/z 205.0 [M+H]$^+$.

$^1$H NMR (400 MHz, DMSO-d$_6$) δ=8.75 (br s, 3H), 7.97 (br s, 1H), 4.96-4.91 (m, 1H), 4.77 (s, 1H), 4.37-4.23 (m, 1H), 3.26-3.07 (m, 2H), 2.60 (br d, J=8.6 Hz, 1H), 2.37-2.27 (m, 1H), 1.96-1.90 (m, 1H), 1.79-1.66 (m, 1H).

Step 3: N—((S)-1-(((S)-4-chloro-3-oxo-1-((S)-2-oxopyrrolidin-3-yl)butan-2-yl)amino)-4-methyl-1-oxopentan-2-yl)-4-methoxy-1H-indole-2-carboxamide A solution of (2S)-2-[(4-methoxy-1H-indole-2-carbonyl)amino]-4-methyl-pentanoic acid (416.53 mg, 1.37 mmol, 1.1 eq) in DMF (5 mL) was added HATU (946.18 mg, 2.49 mmol, 2 eq) and NMM (251.71 mg, 2.49 mmol, 273.59 uL, 2 eq), the solution was stirred at 0° C. for 0.5 h. Then a solution of (3S)-3-[(2S)-2-amino-4-chloro-3-oxo-butyl]pyrrolidin-2-one (0.3 g, 1.24 mmol, 1 eq, HCl) in DMF (5 mL) was added drop-wise at 0° C. The reaction was stirred at 25° C. for 0.5 h. Upon completion, the reaction mixture was diluted with water (50 mL) at 0° C. drop-wise and extracted with EtOAc (20 mL*3). The combined organic layers were dried over Na$_2$SO$_4$, filtered and concentrated under reduced pressure to give a residue. The residue was purified by column chromatography (SiO$_2$, petroleum ether: EtOAc=2:1 to 0:1). To give N-[(1S)-1-[[(1S)-3-chloro-2-oxo-1-[[(3S)-2-oxopyrrolidin-3-yl]methyl]propyl]carbamoyl]-3-methyl-butyl]-4-methoxy-1H-indole-2-carboxamide (0.3 g, 549.92 umol, 44.20% yield, 90% purity) as a solid. MS (ESI) m/z 491.1 [M+H]$^+$.

$^1$H NMR (400 MHz, DMSO-d$_6$) δ=11.58 (br s, 1H), 8.74-8.57 (m, 1H), 8.44 (br d, J=5.0 Hz, 1H), 7.65 (br d, J=4.5 Hz, 1H), 7.37 (br s, 1H), 7.15-7.06 (m, 1H), 7.01 (br d, J=8.1 Hz, 1H), 6.50 (br d, J=7.6 Hz, 1H), 4.75-4.60 (m, 1H), 4.59-4.55 (m, 1H), 4.44 (br d, J=9.2 Hz, 2H), 3.88 (s, 3H), 3.13-3.01 (m, 2H), 2.34-2.18 (m, 1H), 2.09 (br dd, J=2.5, 3.9 Hz, 1H), 1.99-1.90 (m, 1H), 1.78-1.49 (m, 5H), 0.97-0.81 (m, 6H).

Step 4: (S)-3-((S)-2-(4-methoxy-1H-indole-2-carboxamido)-4-methylpentanamido)-2-oxo-4-((S)-2-oxopyrrolidin-3-yl)butyl 2-oxo-2-phenylacetate To a solution of N-[(1S)-1-[[(1S)-3-chloro-2-oxo-1-[[(3S)-2-oxopyrrolidin-3-yl]methyl]propyl]carbamoyl]-3-methyl-butyl]-4-methoxy-1H-indole-2-carboxamide (0.25 g, 509.19 umol, 1 eq) in DMF (6 mL) was added benzoyl-formic acid (99.38 mg, 661.94 umol, 1.3 eq) and CsF (177.89 mg, 1.17 mmol, 43.18 uL, 2.3 eq). The reaction was stirred at 65° C. for 4 h under N$_2$ atmosphere. Upon completion, the reaction mixture was diluted with water (20 mL) and extracted with EtOAc (10 mL*3). The combined organic layers were dried over Na$_2$SO$_4$, filtered and concentrated under reduced pressure to give [(3S)-3-[[(2S)-2-[(4-methoxy-1H-indole-2-carbonyl)amino]-4-methyl-pentanoyl]amino]-2-oxo-4-[(3S)-2-oxopyrrolidin-3-yl]butyl]2-oxo-2-phenyl-acetate (0.3 g, crude) as an oil. MS (ESI) m/z 605.2 [M+H]$^+$.

Step 5&6: N-[(1R)-1-[[(3S)-2-oxopyrrolidin-3-yl]methyl]propyl]carbamoyl]-3-methyl-butyl]-4-methoxy-1H-indole-2-carboxamide N-[(1S)-1-[[(1S)-3-hydroxy-2-oxo-1-[[(3S)-2-oxopyrrolidin-3-yl]methyl]propyl] carbamoyl]-3-methyl-butyl]-4-methoxy-1H-indole-2-carboxamide To a solution of [(3S)-3-[[(2S)-2-[(4-methoxy-1H-indole-2-carbonyl)amino]-4-methyl-pentanoyl]amino]-2-oxo-4-[(3 S)-2-oxopyrrolidin-3-yl]butyl]2-oxo-2-phenyl-acetate (0.3 g, 496.16 umol, 1 eq) in MeOH (10 mL) was added K$_2$CO$_3$ (3.43 mg, 24.81 umol, 0.05 eq). The reaction was stirred at 25° C. for 1 h. Upon completion, the reaction mixture was concentrated under reduced pressure to give a residue. The residue was purified by prep-TLC (SiO$_2$, DCM:MeOH=10:1) to give the product.

$^1$H NMR (400 MHz, DMSO-d$_6$) δ=11.58 (s, 1H), 8.50 (d, J=7.8 Hz, 1H), 8.41 (d, J=7.9 Hz, 1H), 7.63 (s, 1H), 7.35 (d, J=1.5 Hz, 1H), 7.14-7.05 (m, 1H), 7.04-6.94 (m, 1H), 6.50 (d, J=7.7 Hz, 1H), 5.05-4.98 (m, 1H), 4.57-4.46 (m, 1H), 4.41 (ddd, J=4.0, 7.7, 11.2 Hz, 1H), 4.34-4.25 (m, 1H), 4.22-4.13 (m, 1H), 3.88 (s, 3H), 3.18-3.01 (m, 2H), 2.25-

2.14 (m, 1H), 2.13-2.04 (m, 1H), 1.99-1.84 (m, 1H), 1.77-1.48 (m, 5H), 0.93 (br d, J=6.2 Hz, 3H), 0.89 (br d, J=6.4 Hz, 3H).

To give N-[(1S)-1-[[(1S)-3-hydroxy-2-oxo-1-[[(3S)-2-oxopyrrolidin-3-yl]methyl]propyl]carbamoyl]-3-methyl-butyl]-4-methoxy-1H-indole-2-carboxamide (23.86 mg, 49.08 umol, 9.89% yield, 97.2% purity) as a solid. MS (ESI) m/z 473.2 [M+H]$^+$. The product was separated by chiral-SFC (column: DAICEL CHIRALCEL OJ (250 mm*30 mm, 10 um); mobile phase: [Neu-MeOH]; B %: 20%-20%, 15 min) to give N-[(1R)-1-[[(1S)-3-hydroxy-2-oxo-1-[[(3S)-2-oxopyrrolidin-3-yl]methyl]propyl]carbamoyl]-3-methyl-butyl]-4-methoxy-1H-indole-2-carboxamide (15.43 mg, 31.22 umol, 6.29% yield, 95.6% purity) as a solid. MS (ESI) m/z 473.2 [M+H]$^+$.

$^1$H NMR (400 MHz, DMSO-d$_6$) δ=11.57 (s, 1H), 8.45 (br d, J=8.1 Hz, 1H), 8.41 (br d, J=7.8 Hz, 1H), 7.62 (s, 1H), 7.36 (d, J=1.3 Hz, 1H), 7.14-7.05 (m, 1H), 7.04-6.97 (m, 1H), 6.50 (d, J=7.6 Hz, 1H), 5.06 (br s, 1H), 4.62-4.38 (m, 2H), 4.30-4.19 (m, 1H), 4.19-4.09 (m, 1H), 3.88 (s, 3H), 3.19-3.01 (m, 2H), 2.37-2.22 (m, 1H), 2.09 (br dd, J=3.2, 6.2 Hz, 1H), 1.99-1.86 (m, 1H), 1.80-1.43 (m, 5H), 0.94 (d, J=6.2 Hz, 3H), 0.89 (d, J=6.2 Hz, 3H).

Example 11. Synthesis of Viral Protease Inhibitor Compound 143

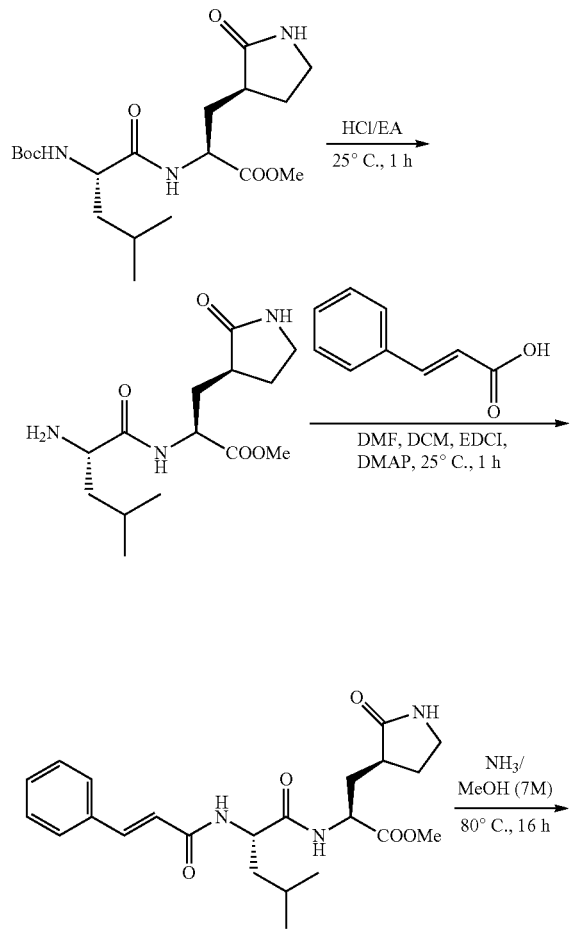

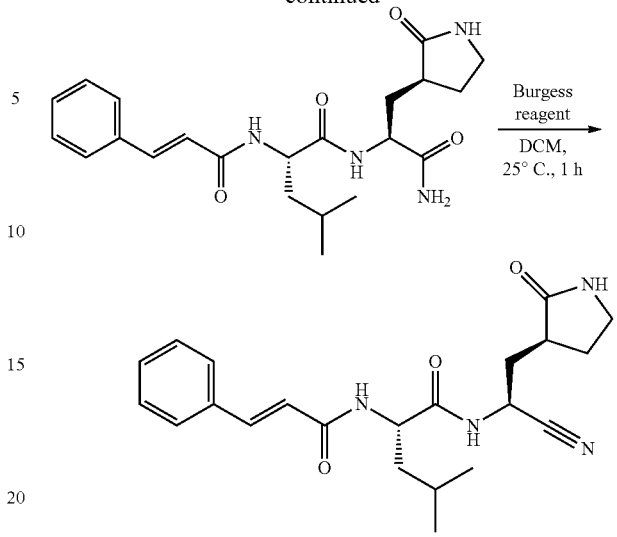

Step 1: methyl (2S)-2-[[(2S)-2-amino-4-methyl-pentanoyl]amino]-3-[(3S)-2-oxopyrrolidin-3-yl]propanoate A mixture of methyl (2S)-2-[[(2S)-2-(tert-butoxycarbonylamino)-4-methyl-pentanoyl]amino]-3-[(3S)-2-oxopyrrolidin-3-yl]propanoate (250 mg, 625.81 umol, 1 eq) was added HCl/EtOAc (8 mL) at 25° C. for 1 h. Upon completion, the reaction mixture was concentrated under reduced pressure to give a residue get a product methyl (2S)-2-[[(2S)-2-amino-4-methyl-pentanoyl]amino]-3-[(3S)-2-oxopyrrolidin-3-yl]propanoate (230 mg, crude) as an oil. MS (ESI) m/z 300.0 [M+H]$^+$.

Step 2: methyl (2S)-2-[[(2S)-4-methyl-2-[[(E)-3-phenylprop-2-enoyl]amino]pentanoyl]amino]-3-[(3S)-2-oxopyrrolidin-3-yl]propanoate A mixture of methyl (2S)-2-[[(2S)-2-amino-4-methyl-pentanoyl]amino]-3-[(3S)-2-oxopyrrolidin-3-yl]propanoate (230 mg, 684.88 umol, 1 eq, HCl) and (E)-3-phenylprop-2-enoic acid (202.94 mg, 1.37 mmol, 162.35 uL, 2 eq) in DMF (2 mL) and DCM (4 mL), and added EDCI (262.59 mg, 1.37 mmol, 2 eq) and DMAP (167.34 mg, 1.37 mmol, 2 eq). The mixture was stirred at 25° C. for 1 h. Upon completion, the reaction mixture was diluted with H$_2$O (10 mL) and extracted with DCM (10 mL*3). The combined organic layers were washed with brine (50 mL), dried over Na$_2$SO$_4$, filtered and concentrated under reduced pressure to give a residue. The residue was purified by silica gel chromatography (SiO$_2$, petroleum ether:EtOAc=1:1) to get a product methyl (2S)-2-[[(2S)-4-methyl-2-[[(E)-3-phenylprop-2-enoyl]amino]pentanoyl]amino]-3-[(3S)-2-oxopyrrolidin-3-yl]propanoate (200 mg, 465.65 umol, 67.99% yield) as an oil. MS (ESI) m/z 430.1 [M+H]$^+$.

Step 3: (2S)—N-[(1S)-2-amino-2-oxo-1-[[(3S)-2-oxopyrrolidin-3-yl]methyl]ethyl]-4-methyl-2-[[(E)-3-phenylprop-2-enoyl]amino]pentanamide A mixture of methyl (2S)-2-[[(2S)-4-methyl-2-[[(E)-3-phenylprop-2-enoyl]amino]pentanoyl]amino]-3-[(3S)-2-oxopyrrolidin-3-yl]propanoate (200 mg, 465.65 umol, 1 eq)

in NH₃/MeOH (7 M, 7 mL, 97% purity, 105.23 eq) heated to 80° C. for 16 h in the sealed tube. Upon completion, the reaction mixture was concentrated under reduced pressure to give a residue to get the product (2S)—N-[(1S)-2-amino-2-oxo-1-[[(3S)-2-oxopyrrolidin-3-yl]methyl]ethyl]-4-methyl-2-[[(E)-3-phenylprop-2-enoyl]amino]pentanamide (200 mg, crude) as an oil. MS (ESI) m/z 415.1 [M+H]⁺.

Step 4: (2S)—N-[(1S)-1-cyano-2-[(3S)-2-oxopyrrolidin-3-yl]ethyl]-4-methyl-2-[[(E)-3-phenylprop-2-enoyl]amino]pentanamide A mixture of (2S)—N-[(1S)-2-amino-2-oxo-1-[[(3S)-2-oxopyrrolidin-3-yl]methyl]ethyl]-4-methyl-2-[[(E)-3-phenylprop-2-enoyl]amino]pentanamide (200 mg, 482.51 umol, 1 eq) in DCM (2 mL) was added methoxycarbonyl-(triethylammonio)sulfonyl-azanide (574.93 mg, 2.41 mmol, 5 eq), the mixture was stirred at 25° C. for 1 h. Upon completion, the reaction mixture was concentrated under reduced pressure to give a residue. The residue was purified by prep-HPLC (column: Waters Xbridge Prep OBD C₁₈ 150*40 mm*10 um; mobile phase: [water(10 mM NH₄HCO₃)—ACN]; B %: 25%-55%, 8 min) to give a product (2S)—N-[(1S)-1-cyano-2-[(3S)-2-oxopyrrolidin-3-yl]ethyl]-4-methyl-2-[[(E)-3-phenylprop-2-enoyl]amino]pentanamide (23.1 mg, 58.26 umol, 12.07% yield, 100% purity) as a solid. MS (ESI) m/z 397.2 [M+H]⁺.

¹H NMR (400 MHz, CDCl₃)=8.70 (br d, J=6.6 Hz, 1H), 7.66-7.55 (m, 1H), 7.54-7.44 (m, 2H), 7.35 (br s, 3H), 6.72-6.52 (m, 2H), 6.47 (d, J=15.7 Hz, 1H), 5.02-4.67 (m, 2H), 3.49-3.22 (m, 2H), 2.56-2.27 (m, 3H), 2.02-1.88 (m, 1H), 1.88-1.80 (m, 1H), 1.75-1.61 (m, 3H), 1.07-0.87 (m, 6H)

Example 12. Synthesis of Viral Protease Inhibitor Compound 598

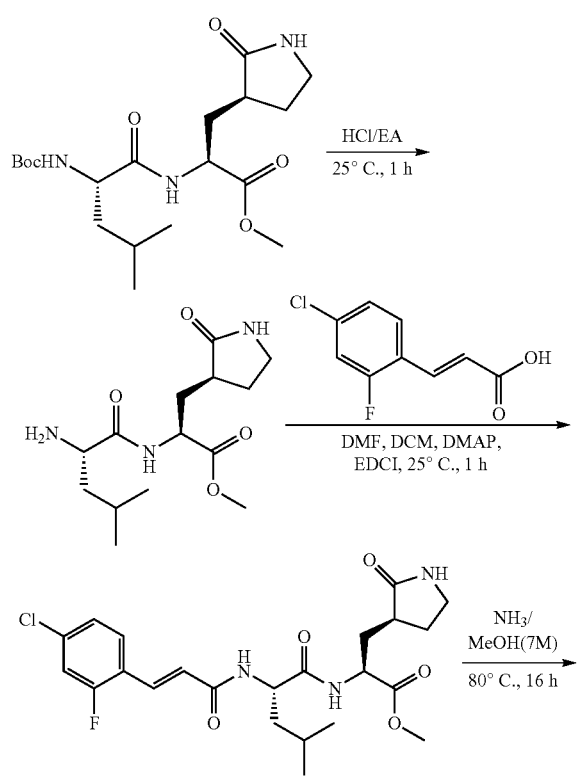

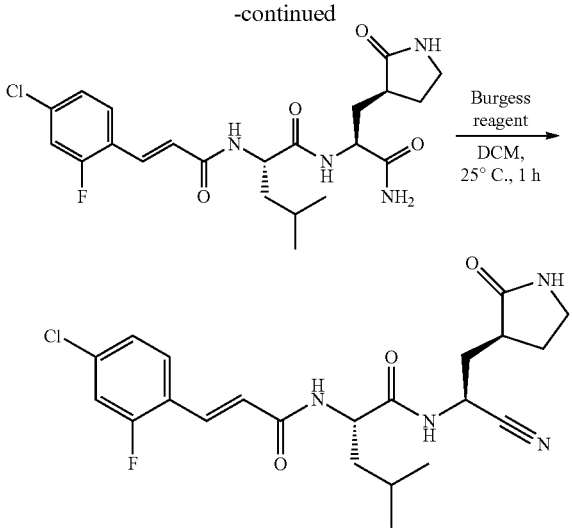

Step 1: methyl (2S)-2-[[(2S)-2-amino-4-methyl-pentanoyl]amino]-3-[(3S)-2-oxopyrrolidin-3-yl]propanoate A mixture of methyl (2S)-2-[[(2S)-2-(tert-butoxycarbonylamino)-4-methyl-pentanoyl]amino]-3-[(3S)-2-oxopyrrolidin-3-yl]propanoate (300 mg, 750.98 umol, 1 eq) was added HCl/EtOAc (4 M, 6 mL, 31.96 eq) at 25° C. for 1 h. Upon completion, the product blow-dried directly with N₂ to get the product methyl (2S)-2-[[(2S)-2-amino-4-methyl-pentanoyl]amino]-3-[(3S)-2-oxopyrrolidin-3-yl]propanoate (260 mg, crude) as an oil. MS (ESI) m/z 300.1 [M+H]⁺.

Step 2: methyl (2S)-2-[[(2S)-2-[[(E)-3-(4-chloro-2-fluoro-phenyl)prop-2-enoyl]amino]-4-methyl-pentanoyl]amino]-3-[(3S)-2-oxopyrrolidin-3-yl]propanoate A mixture of methyl (2S)-2-[[(2S)-2-amino-4-methyl-pentanoyl]amino]-3-[(3S)-2-oxopyrrolidin-3-yl]propanoate (250 mg, 744.43 umol, 1 eq, HCl) and (E)-3-(4-chloro-2-fluoro-phenyl)prop-2-enoic acid (298.66 mg, 1.49 mmol, 81.96 uL, 2 eq) in DMF (2 mL) and DCM (4 mL) was added EDCI (285.42 mg, 1.49 mmol, 2 eq) and DMAP (181.89 mg, 1.49 mmol, 2 eq). The mixture was stirred at 25° C. for 1 h. Upon completion, the reaction mixture was diluted with H₂O (10 mL) and extracted with DCM (10 mL*3). The combined organic layers were washed with brine (50 mL), dried over Na₂SO₄, filtered and concentrated under reduced pressure to give a residue. The residue was purified by silica gel chromatography (SiO₂, petroleum ether:EtOAc=0:1) to get a product methyl (2S)-2-[[(2S)-2-[[(E)-3-(4-chloro-2-fluoro-phenyl)prop-2-enoyl]amino]-4-methyl-pentanoyl]amino]-3-[(3S)-2-oxopyrrolidin-3-yl]propanoate (80 mg, 165.99 umol, 22.30% yield) as an oil. MS (ESI) m/z 482.1 [M+H]⁺.

Step 3: (2S)—N-[(1S)-2-amino-2-oxo-1-[[(3S)-2-oxopyrrolidin-3-yl]methyl]ethyl]-2-[[(E)-3-(4-chloro-2-fluoro-phenyl)prop-2-enoyl]amino]-4-methyl-pentanamide A mixture of methyl (2S)-2-[[(2S)-2-[[(E)-3-(4-chloro-2-fluoro-phenyl)prop-2-enoyl]amino]-4-methyl-pentanoyl]

amino]-3-[(3S)-2-oxopyrrolidin-3-yl]propanoate (70 mg, 145.25 umol, 1 eq) in NH₃/MeOH (7 M, 6 mL, 97% purity, 289.17 eq) was stirred at 80° C. for 16 h. Upon completion, the reaction mixture was concentrated under reduced pressure to give the product (2S)—N-[(1S)-2-amino-2-oxo-1-[[(3S)-2-oxopyrrolidin-3-yl]methyl]ethyl]-2-[[(E)-3-(4-chloro-2-fluoro-phenyl)prop-2-enoyl]amino]-4-methyl-pentanamide (70 mg, crude) as an oil. MS (ESI) m/z 467.1 [M+H]$^+$.

Step 4: (2S)-2-[[(E)-3-(4-chloro-2-fluoro-phenyl)prop-2-enoyl]amino]-N-[(1S)-1-cyano-2-[(3S)-2-oxopyrrolidin-3-yl]ethyl]-4-methyl-pentanamide A mixture of (2S)—N-[(1S)-2-amino-2-oxo-1-[[(3S)-2-oxopyrrolidin-3-yl]methyl]ethyl]-2-[[(E)-3-(4-chloro-2-fluoro-phenyl)prop-2-enoyl]amino]-4-methyl-pentanamide (70 mg, 149.91 umol, 1 eq) in DCM (1.5 mL) was added methoxycarbonyl-(triethylammonio)sulfonyl-azanide (160.77 mg, 674.62 umol, 4.5 eq), the mixture was stirred at 25° C. for 1 h. Upon completion, the reaction mixture was concentrated under reduced pressure to give a residue. The residue was purified by prep-HPLC (column: Waters Xbridge Prep OBD C₁₈ 150*40 mm*10 um; mobile phase: [water(10 mM NH₄HCO₃)—ACN]; B %: 30%-60%, 8 min) to get product (2S)—N-[(1S)-1-cyano-2-[(3S)-2-oxopyrrolidin-3-yl]ethyl]-4-methyl-2-[[(E)-3-phenylprop-2-enoyl]amino]pentanamide (13.4 mg, 58.26 umol, 12.07% yield, 100% purity) as a solid. MS (ESI) m/z 449.1 [M+H]$^+$.

$^1$H NMR (400 MHz, CDCl₃) δ=8.67 (br d, J=5.7 Hz, 1H), 7.63 (d, J=15.7 Hz, 1H), 7.42 (t, J=8.3 Hz, 1H), 7.19-7.06 (m, 2H), 6.55 (d, J=15.7 Hz, 1H), 6.34 (br s, 1H), 6.19 (br s, 1H), 4.83-4.67 (m, 2H), 3.47-3.33 (m, 2H), 2.58-2.28 (m, 3H), 2.04 (br s, 1H), 1.95-1.82 (m, 1H), 1.81-1.62 (m, 3H), 0.99 (d, J=6.0 Hz, 6H)

Example 13. Synthesis of Viral Protease Inhibitor Compound 149

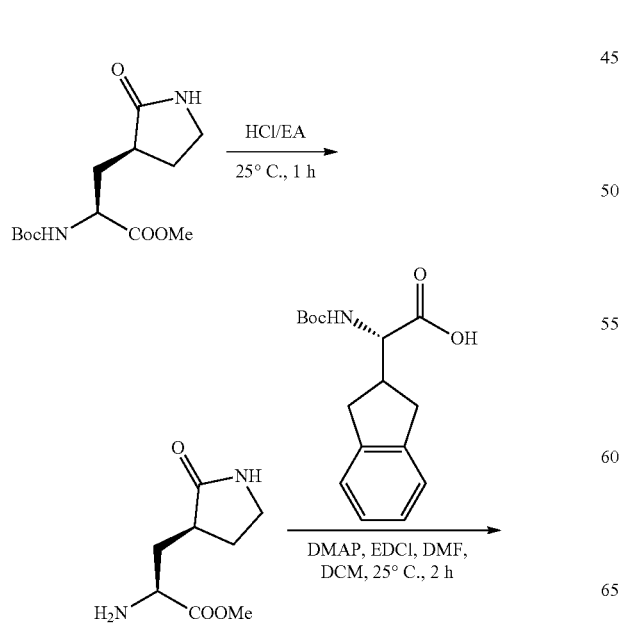

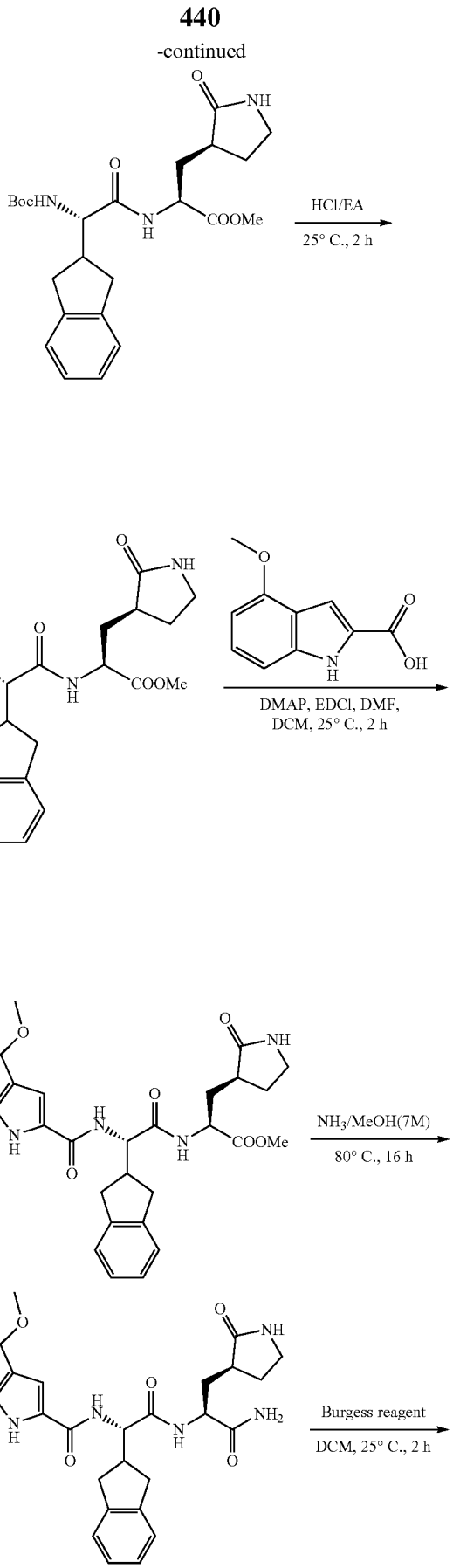

-continued

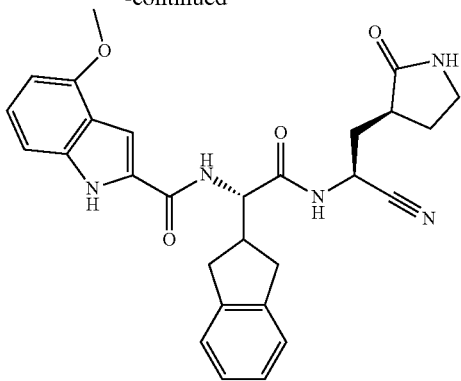

Step 1: methyl (2S)-2-amino-3-[(3S)-2-oxopyrrolidin-3-yl]propanoate

To a mixture of methyl (2S)-2-(tert-butoxycarbonylamino)-3-[(3S)-2-oxopyrrolidin-3-yl]propanoate (500 mg, 1.75 mmol, 1 eq) in HCl/EtOAc (4 M, 20 mL). The mixture was stirred at 25° C. and stirred for 1 h. Once the reaction was completed, the reaction was concentrated to give the crude methyl (2S)-2-amino-3-[(3S)-2-oxopyrrolidin-3-yl]propanoate (400 mg, crude) (oil). The crude product was used directly without further purification. MS (ESI) m/z 187.1 [M+H]$^+$

Step 2: methyl (2S)-2-[[(2S)-2-(tert-butoxycarbonylamino)-2-indan-2-yl-acetyl]amino]-3-[(3S)-2-oxopyrrolidin-3-yl]propanoate To a mixture of methyl (2S)-2-amino-3-[(3S)-2-oxopyrrolidin-3-yl]propanoate (190 mg, 1.02 mmol, 1 eq) and (2S)-2-(tert-butoxycarbonylamino)-2-indan-2-yl-acetic acid (297.27 mg, 1.02 mmol, 1 eq) in DCM (9 mL) and DMF (3 mL) was added DMAP (249.31 mg, 2.04 mmol, 2 eq) and EDCI (391.21 mg, 2.04 mmol, 2 eq). The mixture was stirred at 25° C. for 2 h. Once the reaction was completed, the reaction was poured into ice-water (30 mL) and extracted with EtOAc (20 mL*3). The combined organic phase was dried with anhydrous Na$_2$SO$_4$, filtered and concentrated in vacuum. The residue was purified by silica gel chromatography (column height: 250 mm, diameter: 100 mm, 100-200 mesh silica gel, petroleum ether/EtOAc=1/1, 0/1) to give methyl (2S)-2-[[(2S)-2-(tert-butoxycarbonylamino)-2-indan-2-yl-acetyl]amino]-3-[(3S)-2-oxopyrrolidin-3-yl]propanoate (300 mg, 522.27 umol, 51.18% yield, 80% purity) (solid). MS (ESI) m/z 460.3 [M+H]$^+$

Step 3: methyl (2S)-2-[[(2S)-2-(tert-butoxycarbonylamino)-2-indan-2-yl-acetyl]amino]-3-[(3S)-2-oxopyrrolidin-3-yl]propanoate To a mixture of (S)-methyl 2-((tert-butoxycarbonyl)amino)-3-((S)-2-oxopyrrolidin-3-yl)propanoate (400 mg, 870.4 umol, 1 eq) in HCl/EtOAc (4 M, 20 mL). The mixture was stirred at 25° C. for 2 h. Once the reaction was completed, the reaction mixture was concentrated to get the product methyl (2S)-2-[[(2S)-2-(tert-butoxycarbonylamino)-2-indan-2-yl-acetyl]amino]-3-[(3S)-2-oxopyrrolidin-3-yl]propanoate (330 mg, crude) was obtained as an oil and used directly next step. MS (ESI) m/z 360.2 [M+H]$^+$

Step 4: methyl (2S)-2-[[(2S)-2-amino-2-indan-2-yl-acetyl]amino]-3-[(3S)-2-oxopyrrolidin-3-yl]propanoate To a mixture of methyl (2S)-2-[[(2S)-2-(tert-butoxycarbonylamino)-2-indan-2-yl-acetyl]amino]-3-[(3S)-2-oxopyrrolidin-3-yl]propanoate (300 mg, 652.84 umol, 1 eq) and 4-methoxy-1H-indole-2-carboxylic acid (149.77 mg, 783.40 umol, 1.2 eq) in DCM (6 mL) and DMF (2 mL) was added DMAP (159.51 mg, 1.31 mmol, 2 eq) and EDCI (250.30 mg, 1.31 mmol, 2 eq). The mixture was stirred at 25° C. and stirred for 2 h. Once the reaction was completed, the reaction was poured into ice-water (30 mL) and extracted with ethyl acetate (20 mL*3). The combined organic phase was dried with anhydrous Na$_2$SO$_4$, filtered and concentrated in vacuum. The residue was purified by silica gel chromatography (column height: 250 mm, diameter: 100 mm, 100-200 mesh silica gel, petroleum ether/ethyl acetate=1/1, 0/1) to give methyl (2S)-2-[[(2S)-2-amino-2-indan-2-yl-acetyl]amino]-3-[(3S)-2-oxopyrrolidin-3-yl]propanoate (300 mg, 506.96 umol, 77.66% yield, 90% purity) (solid). MS (ESI) m/z 533.2 [M+H]$^+$

Step 5: N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide To a mixture of (S)-methyl 2-((S)-2-(2,3-dihydro-1H-inden-2-yl)-2-(4-methoxy-1H-indole-2-carboxamido)acetamido)-3-((S)-2-oxopyrrolidin-3-yl)propanoate (100 mg, 187.76 umol, 1 eq) was added ammonia (3.20 mg, 187.76 umol, 3.13 uL, 1 eq). The mixture was stirred at 80° C. and stirred for 16 h. Once the reaction was completed, the reaction was concentrated to give the crude N—((S)-2-(((S)-1-amino-1-oxo-3-((S)-2-oxopyrrolidin-3-yl)propan-2-yl)amino)-1-(2,3-dihydro-1H-inden-2-yl)-2-oxoethyl)-4-methoxy-1H-indole-2-carboxamide (70 mg, 108.20 umol, 57.62% yield, 80% purity) as a solid. Crude product was used directly without further purification. MS (ESI) m/z 518.2 [M+H]$^+$

Step 6: N-[(1S)-2-[[(1S)-1-cyano-2-[(3S)-2-oxopyrrolidin-3-yl]ethyl]amino]-1-indan-2-yl-2-oxo-ethyl]-4-methoxy-1H-indole-2-carboxamide To a mixture of N-[(1S)-2-[[(1S)-2-amino-2-oxo-1-[[(3S)-2-oxopyrrolidin-3-yl]methyl]ethyl]amino]-1-indan-2-yl-2-oxo-ethyl]-4-methoxy-1H-indole-2-carboxamide (60 mg, 115.93 umol, 1 eq) and methoxycarbonyl-(triethylammonio)sulfonyl-azanide (55.25 mg, 231.85 umol, 2 eq) in DCM (0.5 mL). The mixture was stirred at 25° C. and stirred for 2 h. Once the reaction was completed, the reaction was poured into ice-water (30 mL) and extracted with DCM (20 mL*3). The combined organic phase was dried with anhydrous Na$_2$SO$_4$, filtered and concentrated in vacuum. The residue was purified by prep-HPLC (column: Phenomenex Gemini-NX 80*40 mm*3 um; mobile phase: [water(10 Mm NH$_4$HCO$_3$)—ACN]; B %: 20%-50%, 8 min) to give N-[(1S)-2-[[(1S)-1-cyano-2-[(3S)-2-oxopyrrolidin-3-yl]ethyl]amino]-1-indan-2-yl-2-oxo-ethyl]-4-methoxy-1H-indole-2-carboxamide (23.83 mg, 47.70 umol, 41.15% yield, 100% purity) (solid). MS (ESI) m/z 500.3 [M+H]$^+$.

$^1$H NMR (400 MHz, METHANOL-d$_4$) δ ppm 7.26 (s, 1H), 7.13-7.17 (m, 2H), 7.11-7.12 (m, 3H), 7.03 (s, 1H), 6.55-6.52 (d, J=12.4 Hz, 1H), 5.05-5.01 (m, 1H), 4.85-5.00

(m, 1H), 3.92 (s, 3H), 3.25-3.26 (m, 3H), 3.21-3.24 (m, 2H), 2.90-3.01 (m, 2H), 2.88-2.89 (m, 1H), 2.31-3.33 (m, 2H), 1.81-1.92 (m, 2H)

Example 14. Synthesis of Viral Protease Inhibitor Compound 165

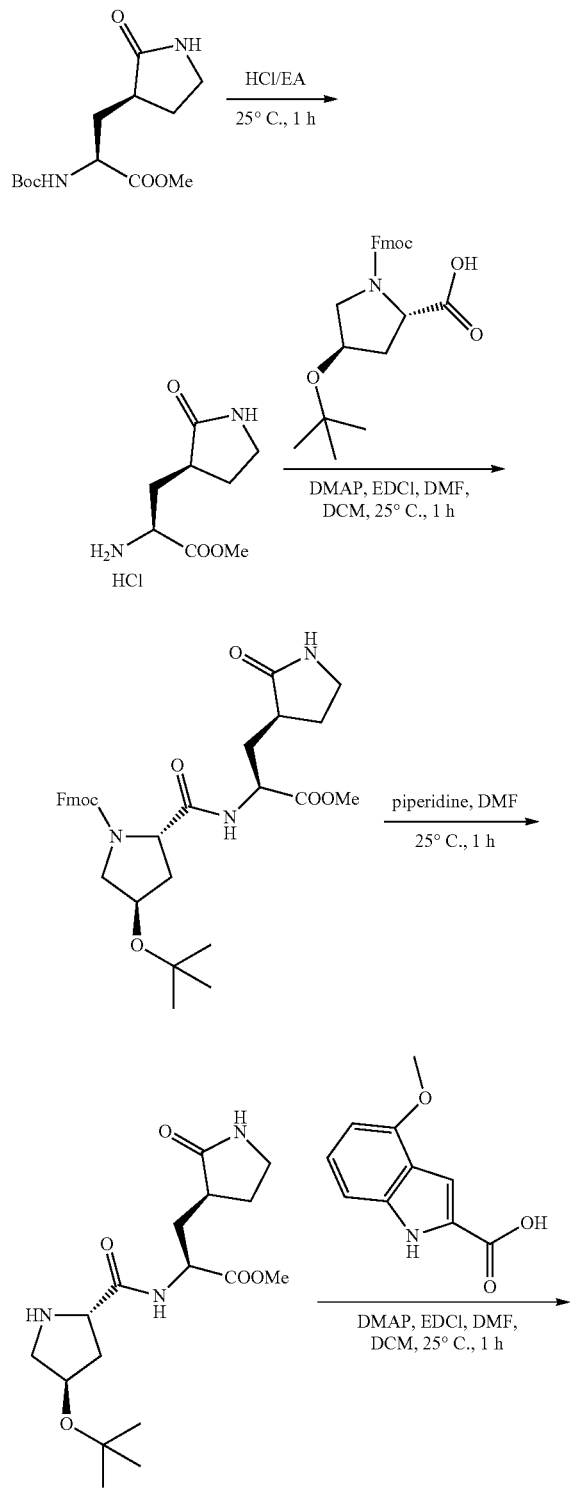

-continued

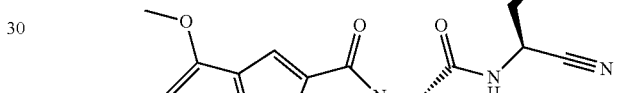
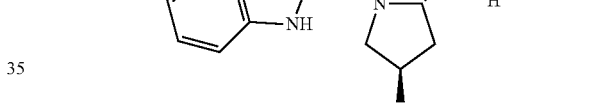

Step 1: methyl (2S)-2-amino-3-[(3S)-2-oxopyrrolidin-3-yl]propanoate; hydrochloride Methyl (2S)-2-(tert-butoxycarbonylamino)-3-[(3S)-2-oxopyrrolidin-3-yl]propanoate (250 mg, 873.14 umol, 1 eq) was added HCl/EtOAc (4 M, 30 mL) at 25° C. The mixture was stirred at 25° C. for 1 h. The reaction mixture was concentrated under reduced pressure to give a product methyl (2S)-2-amino-3-[(3S)-2-oxopyrrolidin-3-yl]propanoate; hydrochloride (200 mg, crude) as a solid and used directly for next step.

Step 2: (2S,4R)-(9H-fluoren-9-yl)methyl-4-(tert-butoxy)-2-(((S)-1-methoxy-1-oxo-3-((S)-2-oxopyrrolidin-3-yl)propan-2-yl)carbamoyl)pyrrolidine-1-carboxylate A mixture of methyl (2S)-2-amino-3-[(3S)-2-oxopyrrolidin-3-yl]propanoate (190 mg, 853.29 umol, 1 eq, HCl), (2S,4R)-4-tert-butoxy-1-(9H-fluoren-9-ylmethoxycarbonyl)pyrrolidine-2-carboxylic acid (349.40 mg, 853.29 umol, 1 eq), EDCI (327.15 mg, 1.71 mmol, 2 eq), DMAP (208.49 mg, 1.71 mmol, 2 eq), DMF (3 mL) and DCM (6 mL) was stirred at 25° C. for 1 h. The reaction mixture was diluted with H₂O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the product (2S,4R)-(9H-fluoren-9-yl)methyl-4-(tert-butoxy)-2-(((S)-1-methoxy-1-oxo-3-((S)-2-oxopyrrolidin-3-yl)propan-2-yl)carbamoyl)pyrrolidine-1-carboxylate (230 mg, 319.96 umol, 37.50% yield, 80.36% purity), as an oil. MS (ESI) m/z 578.2 [M+H]$^+$ Step 3: (S)-methyl-2-((2S,4R)-4-(tert-butoxy)pyrrolidine-2-carboxamido)-3-((S)-2-oxopyrrolidin-3-yl)propanoate A mixture of (2S,4R)-(9H-fluoren-9-yl)methyl-4-(tert-butoxy)-2-(((S)-1-methoxy-1-oxo-3-((S)-2-oxopyrrolidin-3-yl)propan-2-yl)carbamoyl)pyrrolidine-1-carboxylate (170 mg, 294.29 umol, 1 eq), piperidine (3.76 g, 8.83 mmol, 4.36 mL, 20% purity, 30 eq), DMF (1 mL) was stirred at 25° C. for 1 h. The reaction mixture was concentrated under reduced pressure to give a residue. The residue was purified by prep-TLC (DCM/MeOH=10/1) to get the product (S)-methyl-2-((2S,4R)-4-(tert-butoxy)pyrrolidine-2-carboxamido)-3-((S)-2-oxopyrrolidin-3-yl)propanoate (40 mg, 112.54 umol, 38.24% yield) as an oil.

Step 4: (S)-methyl-2-((2S,4R)-4-(tert-butoxy)-1-(4-methoxy-1H-indole-2-carbonyl)pyrrolidine-2-carboxamido)-3-((S)-2-oxopyrrolidin-3-yl)propanoate A mixture of (S)-methyl-2-((2S,4R)-4-(tert-butoxy)pyrrolidine-2-carboxamido)-3-((S)-2-oxopyrrolidin-3-yl)propanoate (40 mg, 112.54 umol, 1 eq), 4-methoxy-1H-indole-2-carboxylic acid (21.52 mg, 112.54 umol, 1 eq), EDCI (43.15 mg, 225.08 umol, 2 eq), DMAP (27.50 mg, 225.08 umol, 2 eq), DMF (0.5 mL) and DCM (1 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the compound (S)-methyl-2-((2S,4R)-4-(tert-butoxy)-1-(4-methoxy-1H-indole-2-carbonyl)pyrrolidine-2-carboxamido)-3-((S)-2-oxopyrrolidin-3-yl)propanoate (30 mg, 22.33 umol, 19.84% yield), as an oil.

Step 5: (2S,4R)—N—((S)-1-amino-1-oxo-3-((S)-2-oxopyrrolidin-3-yl)propan-2-yl)-4-(tert-butoxy)-1-(4-methoxy-1H-indole-2-carbonyl)pyrrolidine-2-carboxamide A mixture of (S)-methyl-2-((2S,4R)-4-(tert-butoxy)-1-(4-methoxy-1H-indole-2-carbonyl)pyrrolidine-2-carboxamido)-3-((S)-2-oxopyrrolidin-3-yl)propanoate (27 mg, 20.10 umol, 39.35% purity, 1 eq) and NH$_3$/MeOH (7 M, 3 mL) was stirred at 80° C. for 16 h. The reaction mixture was concentrated under reduced pressure to give a product (2S,4R)—N—((S)-1-amino-1-oxo-3-((S)-2-oxopyrrolidin-3-yl)propan-2-yl)-4-(tert-butoxy)-1-(4-methoxy-1H-indole-2-carbonyl)pyrrolidine-2-carboxamide (22 mg, crude) as a solid. MS (ESI) m/z 514.2 [M+H]$^+$ Step 6: (2S,4R)-4-(tert-butoxy)-N—((S)-1-cyano-2-((S)-2-oxopyrrolidin-3-yl)ethyl)-1-(4-methoxy-1H-indole-2-carbonyl)pyrrolidine-2-carboxamide A mixture of (2S,4R)—N—((S)-1-amino-1-oxo-3-((S)-2-oxopyrrolidin-3-yl)propan-2-yl)-4-(tert-butoxy)-1-(4-methoxy-1H-indole-2-carbonyl)pyrrolidine-2-carboxamide (20 mg, 38.94 umol, 1 eq), Burgess reagent (27.84 mg, 116.83 umol, 3 eq) and DCM (1 mL) was stirred at 25° C. for 4 h. The reaction mixture was concentrated under reduced pressure to give a residue. The residue was purified by prep-HPLC (column: Phenomenex Gemini-NX C$_{18}$ 75*30 mm*3 um; mobile phase: [water(0.05% NH$_3$H$_2$O+10 mM NH$_4$HCO$_3$)—ACN]; B %: 20%-40%, 8 min) to get the product (2S,4R)-4-(tert-butoxy)-N—((S)-1-cyano-2-((S)-2-oxopyrrolidin-3-yl)ethyl)-1-(4-methoxy-1H-indole-2-carbonyl)pyrrolidine-2-carboxamide (5 mg, 10.09 umol, 25.91% yield, 100% purity), as a solid. MS (ESI) m/z 496.3 [M+H]$^+$.

$^1$H NMR (400 MHz, DMSO-d$_6$) δ=11.73-11.43 (m, 1H), 9.26-8.84 (m, 1H), 7.84-7.49 (m, 1H), 7.19-7.07 (m, 1H), 7.05-6.96 (m, 1H), 6.94-6.65 (m, 1H), 6.57-6.41 (m, 1H), 5.08-4.92 (m, 1H), 4.85-4.40 (m, 2H), 4.34-4.08 (m, 1H), 3.98-3.75 (m, 3H), 3.74-3.50 (m, 1H), 3.22-2.80 (m, 2H), 2.47-2.37 (m, 1H), 2.27-2.04 (m, 3H), 2.03-1.87 (m, 1H), 1.86-1.36 (m, 2H), 1.15 (s, 9H)

Example 15. Synthesis of Viral Protease Inhibitor Compound 167

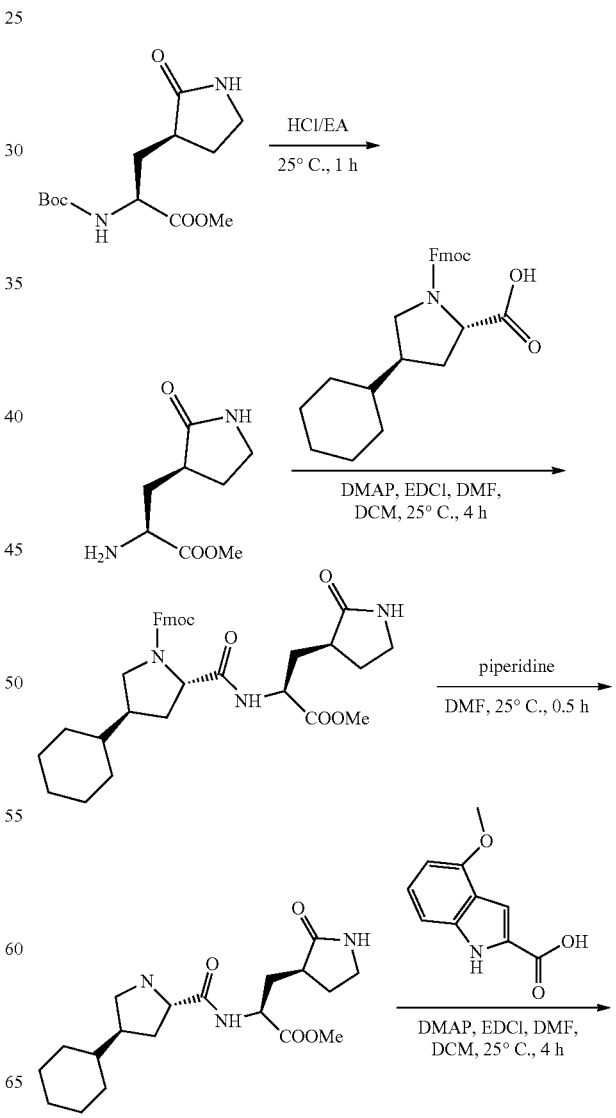

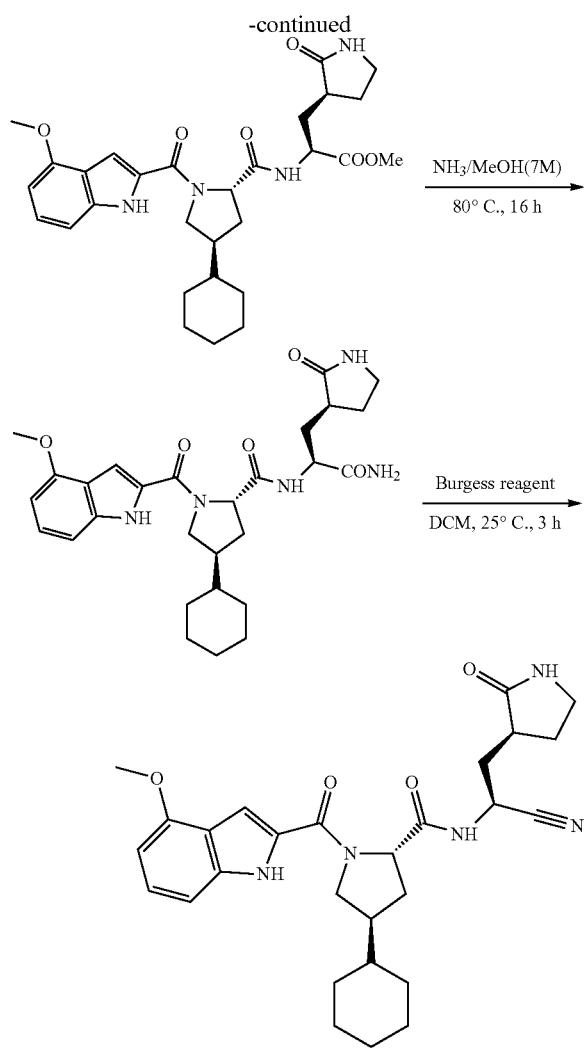

Step 1: (S)-methyl 2-amino-3-((S)-2-oxopyrrolidin-3-yl)propanoate

Methyl (2S)-2-(tert-butoxycarbonylamino)-3-[(3S)-2-oxopyrrolidin-3-yl]propanoate (300 mg, 1.05 mmol, 1 eq) in HCl/EtOAc (4 M, 5 mL, 19.09 eq) was stirred at 25° C. for 1 h. Upon completion, the mixture was concentrated under the reduced pressure affording the product methyl (2S)-2-amino-3-[(3S)-2-oxopyrrolidin-3-yl]propanoate (HCl salt, 210 mg, crude) as a solid.

Step 2: (2S,4S)-(9H-fluoren-9-yl)methyl4-cyclohexyl-2-(((S)-1-methoxy-1-oxo-3-((S)-2-oxopyrrolidin-3-yl)propan-2-yl)carbamoyl)pyrrolidine-1-carboxylate Methyl (2S)-2-amino-3-[(3S)-2-oxopyrrolidin-3-yl]propanoate (200 mg, 1.07 mmol, 1 eq) and (2S,4S)-4-cyclohexyl-1-(9Hfluoren-9-ylmethoxycarbonyl)pyrrolidine-2-carboxylic acid (450.58 mg, 1.07 mmol, 1 eq) in DMF (1 mL) and DCM (2 mL) was added DMAP (262.43 mg, 2.15 mmol, 2 eq) and EDCI (411.80 mg, 2.15 mmol, 2 eq). The mixture was stirred at 25° C. for 4 h. Upon completion, the reaction mixture was quenched by addition H$_2$O (10 mL), and then extracted with EtOAc (10 mL*3). The combined organic layers were washed with brine (10 mL), dried over Na$_2$SO$_4$, filtered and concentrated under reduced pressure to give a residue. The residue was purified by column chromatography (SiO$_2$, petroleum ether: EtOAc=5:1 to 1:1) affording the product 9H-fluoren-9-ylmethyl (2S,4S)-4-cyclohexyl-2-[[(1S)-2-methoxy-2-oxo-1-[[(3S)-2-oxopyrrolidin-3-yl]methyl]ethyl]carbamoyl]pyrrolidine-1-carboxylate (500 mg, 850.77 umol, 79.21% yield) as a solid. MS (ESI) m/z 588.3 [M+H]$^+$ Step 3: (S)-methyl2-((2S,4S)-4-cyclohexylpyrrolidine-2-carboxamido)-3-((S)-2-oxopyrrolidin-3-yl)propanoate 9H-fluoren-9-ylmethyl (2S,4S)-4-cyclohexyl-2-[[(1S)-2-methoxy-2-oxo-1-[[(3S)-2-oxopyrrolidin-3-yl]methyl]ethyl]carbamoyl]pyrrolidine-1-carboxylate (480 mg, 816.74 umol, 1 eq) in DMF (4 mL) and PIPERIDINE (862.20 mg, 10.13 mmol, 1 mL, 12.40 eq) was stirred at 25° C. for 0.5 h. Upon completion, the mixture was drying with N$_2$ and then diluted with DCM (10 mL), concentrated under the reduced pressure to give a residue. The residue was purified by prep-TLC (SiO$_2$, DCM:MeOH=10:1) affording the product methyl (2S)-2-[[(2S,4S)-4-cyclohexylpyrrolidine-2-carbonyl]amino]-3-[(3S)-2-oxopyrrolidin-3-yl]propanoate (210 mg, 574.61 umol, 70.35% yield) as a solid.

Step 4: (S)-methyl2-((2S,4S)-4-cyclohexyl-1-(4-methoxy-1H-indole-2-carbonyl)pyrrolidine-2-carboxamido)-3-((S)-2-oxopyrrolidin-3-yl)propanoate Methyl(2S)-2-[[(2S,4S)-4-cyclohexylpyrrolidine-2-carbonyl]amino]-3-[(3S)-2-oxopyrrolidin-3-yl]propanoate (200 mg, 547.25 umol, 1 eq) and 4-methoxy-1H-indole-2-carboxylic acid (104.62 mg, 547.25 umol, 1 eq) in DMF (2 mL) and DCM (3 mL) was added DMAP (133.71 mg, 1.09 mmol, 2 eq) and EDCI (209.82 mg, 1.09 mmol, 2 eq). The mixture was stirred at 25° C. for 4 h. Upon completion, the reaction mixture was quenched by addition H$_2$O (10 mL), and then extracted with DCM (10 mL*3). The combined organic layers were washed with brine (10 mL), dried over Na$_2$SO$_4$, filtered and concentrated under reduced pressure to give a residue. The residue was purified by prep-TLC (SiO$_2$, petroleum ether:EtOAc=0:1) affording the product methyl (2S)-2-[[(2S,4S)-4-cyclohexyl-1-(4-methoxy-1H-indole-2-carbonyl)pyrrolidine-2-carbonyl]amino]-3-[(3S)-2-oxopyrrolidin-3-yl]propanoate (210 mg, 389.88 umol, 71.24% yield) as a solid. MS (ESI) m/z 539.2 [M+H]$^+$ Step 5: (2S,4S)—N—((S)-1-amino-1-oxo-3-((S)-2-oxopyrrolidin-3-yl)propan-2-yl)-4-cyclohexyl-]-(4-methoxy-1H-indole-2-carbonyl)pyrrolidine-2-carboxamide Methyl(2S)-2-[[(2S,4S)-4-cyclohexyl-1-(4-methoxy-1H-indole-2-carbonyl)pyrrolidine-2-carbonyl]amino]-3-[(3S)-2-oxopyrrolidin-3-yl]propanoate (200 mg, 371.31 umol, 1 eq) was in NH$_3$/MeOH (7 M, 10 mL, 188.52 eq). The mixture was stirred at 80° C. for 16 h. Upon completion, the mixture was concentrated under the reduced pressure affording the product (2S,4S)—N-[(1S)-2-amino-2-oxo-1-[[(3S)-2-oxopyrrolidin-3-yl]methyl]ethyl]-4-cyclohexyl-1-(4- methoxy-1Hindole-2-carbonyl)pyrrolidine-2-carboxamide (110 mg, crude) as a solid. MS (ESI) m/z 524.2 [M+H]⁺

Step 6: (2S,4S)—N—((S)-1-cyano-2-((S)-2-oxopyrrolidin-3-yl)ethyl)-4-cyclohexyl-1-(4-methoxy-1H-indole-2-carbonyl)pyrrolidine-2-carboxamide (2S,4S)—N-[(1S)-2-amino-2-oxo-1-[[(3S)-2-oxopyrrolidin-3-yl]methyl]ethyl]-4-cyclohexyl-1-(4-methoxy-1H-indole-2-carbonyl)pyrrolidine-2-carboxamide (100 mg, 190.98 umol, 1 eq) in DCM (1 mL) was added methoxycarbonyl-(triethylammonio)sulfonyl-azanide (227.55 mg, 954.89 umol, 5 eq). The mixture was stirred at 25° C. for 3 h. Upon completion, the mixture was concentrated under the reduced pressure to give a residue. The residue was purified by prep-HPLC (column: Waters Xbridge BEH C₁₈ 100*25 mm*5 um; mobile phase: [water (10 mM NH₄HCO₃)—ACN]; B %: 30%-60%, 10 min) affording the product (2S,4S)—N-[(1S)-1-cyano-2-[(3S)-2-oxopyrrolidin-3-yl]ethyl]-4-cyclohexyl-1-(4-methoxy-1H-indole-2-carbonyl)pyrrolidine-2-carboxamide (30.7 mg, 60.17 umol, 31.51% yield, 99.1% purity) as a solid. MS (ESI) m/z 506.3 [M+H]⁺

¹H NMR (400 MHz, MeOD-d₄) δ=7.23-6.82 (m, 3H), 6.60-6.36 (m, 1H), 5.21-4.96 (m, 1H), 4.72-4.56 (m, 1H), 4.34-4.07 (m, 1H), 4.00-3.80 (m, 3H), 3.57 (br t, J=9.4 Hz, 1H), 3.02-2.54 (m, 1H), 2.46-0.92 (m, 20H)

Example 16. Synthesis of Viral Protease Inhibitor Compound 209

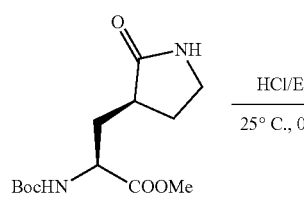

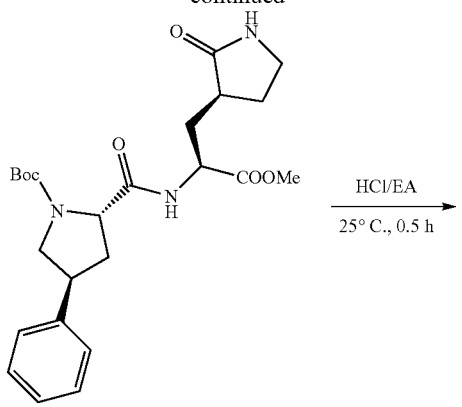

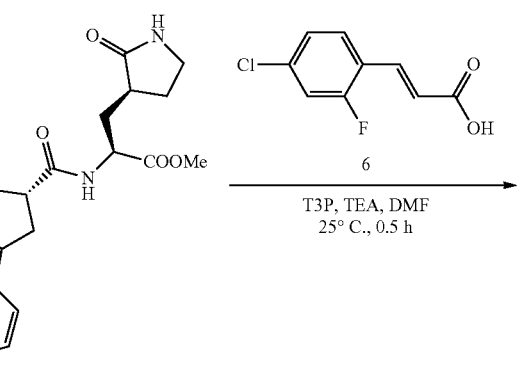

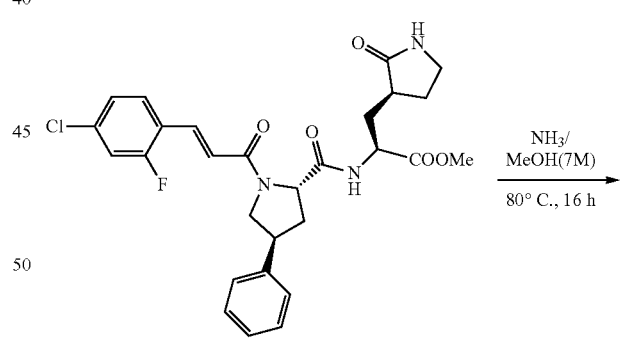

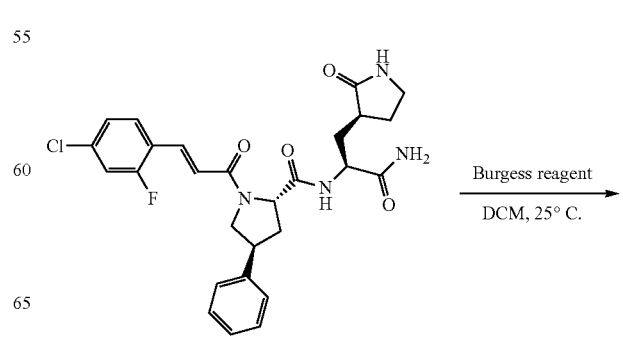

-continued

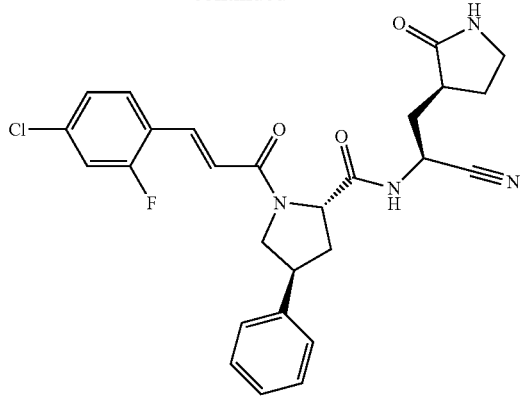

Step 1: (S)-methyl 2-amino-3-((S)-2-oxopyrrolidin-3-yl)propanoate

A mixture of methyl (2S)-2-(tert-butoxycarbonylamino)-3-[(3S)-2-oxopyrrolidin-3-yl]propanoate (0.55 g, 1.92 mmol, 1 eq) and HCl/EtOAc (4 M, 10 mL, 20.82 eq) was stirred at 25° C. for 0.5 h. Upon completion, the reaction mixture was concentrated under reduced pressure to give (S)-methyl 2-amino-3-((S)-2-oxopyrrolidin-3-yl)propanoate (0.35 g, crude) as an oil.

Step 2: (2S,4S)-tert-butyl 2-(((S)-1-methoxy-1-oxo-3-((S)-2-oxopyrrolidin-3-yl)propan-2-yl)carbamoyl)-4-phenylpyrrolidine-1-carboxylate A mixture of (S)-methyl 2-amino-3-((S)-2-oxopyrrolidin-3-yl)propanoate (0.15 g, 805.55 umol, 1 eq), (2S,4S)-1-tert-butoxycarbonyl-4-phenyl-pyrrolidine-2-carboxylic acid (234.69 mg, 805.55 umol, 1 eq), DMAP (196.83 mg, 1.61 mmol, 2 eq), EDCI (308.85 mg, 1.61 mmol, 2 eq) in DMF (1 mL) and DCM (2 mL) was stirred at 25° C. for 0.5 h. Upon completion, the reaction mixture was diluted with water (10 mL) and extracted with ethyl acetate (5 mL*3). The combined organic layers were dried over Na$_2$SO$_4$, filtered and concentrated under reduced pressure to give a residue. The residue was purified by column chromatography (SiO$_2$, petroleum ether: EtOAc=2:1 to 0:1) to give (2S,4S)-tert-butyl 2-[[(1S)-2-methoxy-2-oxo-1-[[(3S)-2-oxopyrrolidin-3-yl]methyl]ethyl]carbamoyl]-4-phenyl-pyrrolidine-1-carboxylate (0.25 g, 500.51 umol, 62.13% yield, 92% purity) as a colorless oil. MS (ESI) m/z 460.1 [M+H]$^+$.

Step 3: (S)-methyl 3-((S)-2-oxopyrrolidin-3-yl)-2-((2S,4S)-4-phenylpyrrolidine-2-carboxamido)propanoate A mixture of tert-butyl (2S,4S)-2-[[(1S)-2-methoxy-2-oxo-1-[[(3S)-2-oxopyrrolidin-3-yl]methyl]ethyl]carbamoyl]-4-phenyl-pyrrolidine-1-carboxylate (0.25 g, 544.03 umol, 1 eq) and HCl/EtOAc (4 M, 10 mL, 73.53 eq) was stirred at 25° C. for 0.5 h. Upon completion, the reaction mixture was concentrated under reduced pressure to give methyl (2S)-3-[(3S)-2-oxopyrrolidin-3-yl]-2-[[(2S,4S)-4-phenylpyrrolidine-2-carbonyl]amino]propanoate (0.2 g, crude) as an oil. MS (ESI) m/z 360.1 [M+H]$^+$.

Step 4: (S)-methyl 2-((2S,4S)-1-((E)-3-(4-chloro-2-fluorophenyl)acryloyl)-4-phenylpyrrolidine-2-carboxamido)-3-((S)-2-oxopyrrolidin-3-yl)propanoate A mixture of methyl (2S)-3-[(3S)-2-oxopyrrolidin-3-yl]-2-[[(2S,4S)-4-phenylpyrrolidine-2-carbonyl]amino]propanoate (0.17 g, 472.99 umol, 1 eq), (E)-3-(4-chloro-2-fluoro-phenyl)prop-2-enoic acid (94.88 mg, 472.99 umol, 1 eq), T3P (451.48 mg, 709.48 umol, 421.95 uL, 50% purity, 1.5 eq), TEA (143.58 mg, 1.42 mmol, 197.50 uL, 3 eq) in DMF (4 mL) was degassed stirred at 25° C. for 0.5 h. Upon completion, the reaction mixture was diluted with water (20 mL) and extracted with ethyl acetate (10 mL*3). The combined organic layers were dried over Na$_2$SO$_4$, filtered and concentrated under reduced pressure to give a residue. The residue was purified by column chromatography (SiO$_2$, petroleum ether: EtOAc=2:1 to 0:1) to give methyl (2S)-2-[[(2S,4S)-1-[(E)-3-(4-chloro-2-fluoro-phenyl)prop-2-enoyl]-4-phenyl-pyrrolidine-2-carbonyl]amino]-3-[(3S)-2-oxopyrrolidin-3-yl]propanoate (0.11 g, 162.36 umol, 34.33% yield, 80% purity) as a solid. MS (ESI) m/z 542.1 [M+H]$^+$.

Step 5: (2S,4S)—N—((S)-1-amino-1-oxo-3-((S)-2-oxopyrrolidin-3-yl)propan-2-yl)-1-((E)-3-(4-chloro-2-fluorophenyl)acryloyl)-4-phenylpyrrolidine-2-carboxamide A mixture of methyl (2S)-2-[[(2S,4S)-1-[(E)-3-(4-chloro-2-fluoro-phenyl)prop-2-enoyl]-4-phenyl-pyrrolidine-2-carbonyl]amino]-3-[(3S)-2-oxopyrrolidin-3-yl]propanoate (0.1 g, 184.50 umol, 1 eq) in NH$_3$/MeOH (7M, 3 mL) was stirred at 80° C. for 16 h in the sealed tube. Upon completion, the reaction mixture was concentrated under reduced pressure to give (2S,4S)—N-[(1S)-2-amino-2-oxo-1-[[(3S)-2-oxopyrrolidin-3-yl]methyl]ethyl]-1-[(E)-3-(4-chloro-2-fluoro-phenyl)prop-2-enoyl]-4-phenyl-pyrrolidine-2-carboxamide (0.09 g, crude) as a yellow oil. MS (ESI) m/z 527.0 [M+H]$^+$.

Step 6: (2S,4S)-1-((E)-3-(4-chloro-2-fluorophenyl)acryloyl)-N—((S)-1-cyano-2-((S)-2-oxopyrrolidin-3-yl)ethyl)-4-phenylpyrrolidine-2-carboxamide To a solution of (2S,4S)—N-[(1S)-2-amino-2-oxo-1-[[(3S)-2-oxopyrrolidin-3-yl]methyl]ethyl]-1-[(E)-3-(4-chloro-2-fluoro-phenyl)prop-2-enoyl]-4-phenyl-pyrrolidine-2-carboxamide (0.09 g, 170.78 umol, 1 eq) in DCM (1 mL) was added Burgess reagent (203.50 mg, 853.91 umol, 5 eq), the solution was stirred at 25° C. for 1 h. Upon completion, the reaction mixture was concentrated under reduced pressure to give a residue. The residue was purified by prep-HPLC (column: Waters Xbridge BEH C$_{18}$ 100*25 mm*5 um; mobile phase: [water(10 mM NH$_4$HCO$_3$)—ACN]; B %: 30%-60%, 10 min) to give (2S,4S)-1-[(E)-3-(4-chloro-2-fluoro-phenyl)prop-2-enoyl]-N-[(1S)-1-cyano-2-[(3S)-2-oxopyrrolidin-3-yl]ethyl]-4-phenyl-pyrrolidine-2-carboxamide (29.73 mg, 56.89 umol, 33.31% yield, 97.4% purity) as a solid. MS (ESI) m/z 509.1 [M+H]$^+$.

$^1$H NMR (400 MHz, DMSO-d$_6$) δ=9.17-8.86 (m, 1H), 8.07-7.75 (m, 1H), 7.75-7.65 (m, 1H), 7.62-7.49 (m, 2H), 7.48-7.30 (m, 5H), 7.26 (tt, J=3.0, 5.6 Hz, 1H), 7.22-6.73 (m, 1H), 5.09-4.83 (m, 1H), 4.69-4.47 (m, 1H), 4.40-4.01 (m, 1H), 3.77-3.50 (m, 3H), 3.19-3.04 (m, 2H), 2.44-2.31 (m, 2H), 2.22-2.09 (m, 2H), 1.88-1.59 (m, 2H).

Example 17. Synthesis of Viral Protease Inhibitor Compound 183

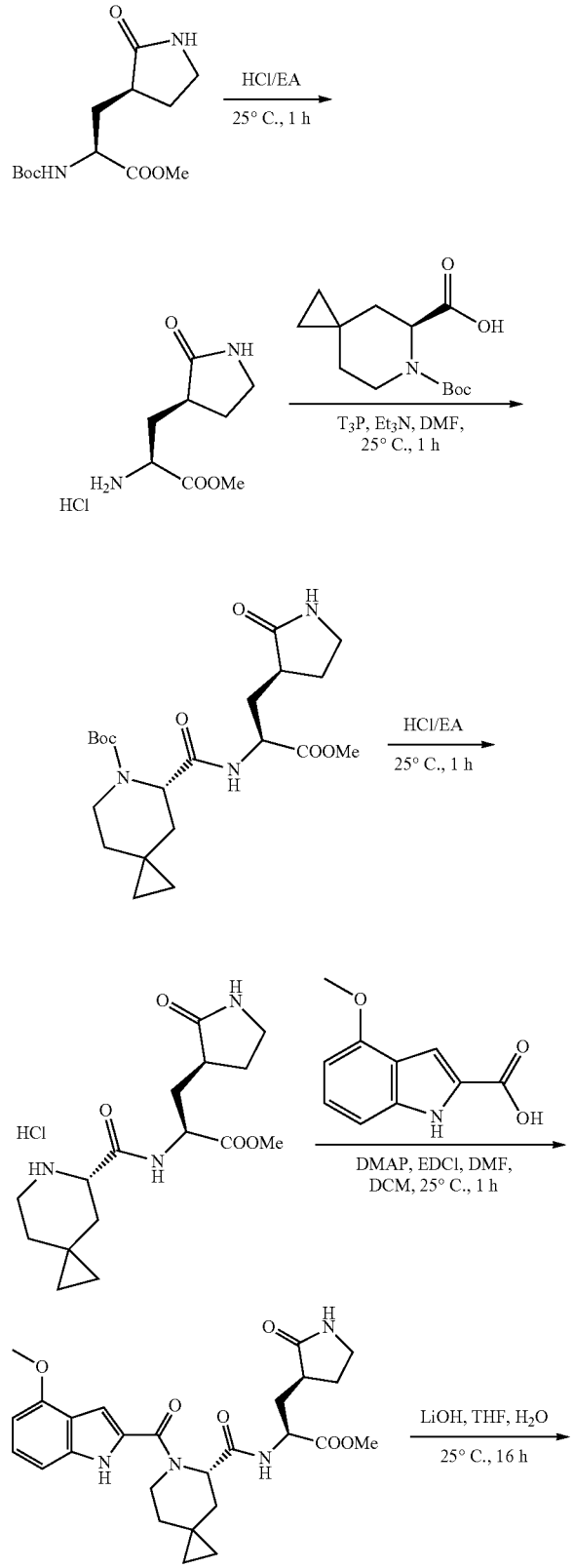

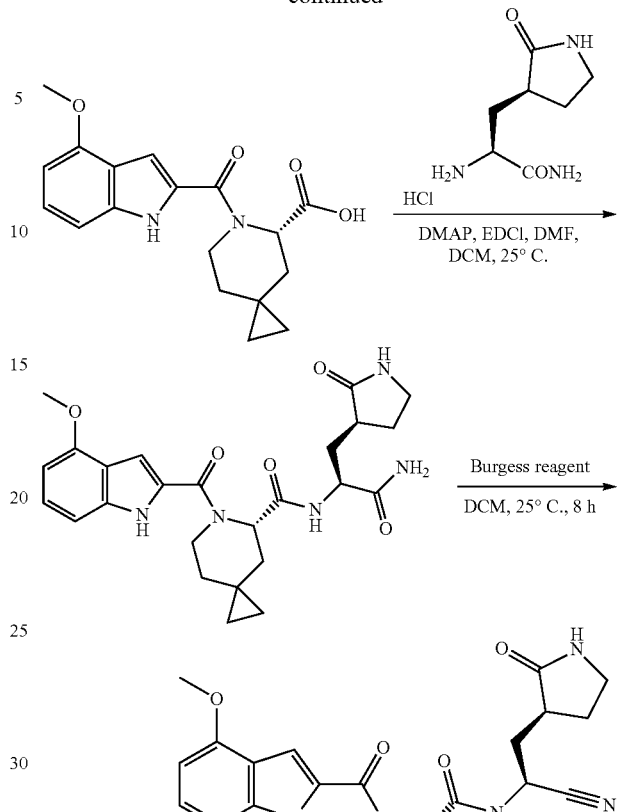

Step 1: methyl (2S)-2-amino-3-[(3S)-2-oxopyrrolidin-3-yl]propanoate; hydrochloride Methyl (2S)-2-(tert-butoxycarbonylamino)-3-[(3S)-2-oxopyrrolidin-3-yl]propanoate (300 mg, 1.05 mmol, 1 eq) was added HCl/EtOAc (4 M, 30 mL) at 25° C. The mixture was stirred at 25° C. for 1 h. The reaction mixture was concentrated under reduced pressure to give a product methyl (2S)-2-amino-3-[(3S)-2-oxopyrrolidin-3-yl]propanoate:HCl (230 mg, crude) as an oil and used directly for next step.

Step 2: (S)-tert-butyl 5-(((S)-1-methoxy-1-oxo-3-((S)-2-oxopyrrolidin-3-yl)propan-2-yl)carbamoyl)-6-azaspiro[2.5]octane-6-carboxylate A mixture of methyl (2S)-2-amino-3-[(3S)-2-oxopyrrolidin-3-yl]propanoate (230 mg, 1.03 mmol, 1 eq, HCl), (7S)-6-tert-butoxycarbonyl-6-azaspiro[2.5]octane-7-carboxylic acid (263.72 mg, 1.03 mmol, 1 eq), $T_3P$ (657.31 mg, 2.07 mmol, 614.31 uL, 2 eq), $Et_3N$ (522.60 mg, 5.16 mmol, 718.85 uL, 5 eq) and DMF (5 mL) was stirred at 25° C. for 1 h. The reaction mixture was diluted with $H_2O$ (30 mL) and extracted with DCM (30 mL*3). The combined organic layers were washed with brine (50 mL), dried over $Na_2SO_4$, filtered and concentrated under reduced pressure to give a residue. The residue was purified by column chromatography ($SiO_2$, petroleum ether/EtOAc=0/1) to get the product (S)-tert-butyl 5-(((S)-1-methoxy-1-oxo-3-((S)-2-oxopyrrolidin-3-yl)propan-2-yl)carbamoyl)-6-azaspiro[2.5]octane-6-carboxylate (300 mg, 708.38 umol, 68.58% yield), as yellow oil. MS (ESI) m/z 424.1 [M+H]$^+$

Step 3: (S)-methyl 3-((S)-2-oxopyrrolidin-3-yl)-2-((S)-6-azaspiro[2.5]octane-5-carboxamido)propanoate A mixture of (S)-tert-butyl 5-(((S)-1-methoxy-1-oxo-3-((S)-2-oxopyrrolidin-3-yl)propan-2-yl)carbamoyl)-6-azaspiro[2.5]octane-6-carboxylate (290 mg, 684.77 umol, 1 eq) and HCl/EtOAc (4 M, 30 mL) was stirred at 25° C. for 1 h. The reaction mixture was concentrated under reduced pressure to give a product (S)-methyl 3-((S)-2-oxopyrrolidin-3-yl)-2-((S)-6-azaspiro[2.5]octane-5-carboxamido)propanoate (240 mg, crude, HCl) as a an oil and used directly for next step.

Step 4: (S)-methyl 2-((S)-6-(4-methoxy-1H-indole-2-carbonyl)-6-azaspiro[2.5]octane-5-carboxamido)-3-((S)-2-oxopyrrolidin-3-yl)propanoate A mixture of (S)-methyl 3-((S)-2-oxopyrrolidin-3-yl)-2-((S)-6-azaspiro[2.5]octane-5-carboxamido)propanoate (240 mg, 666.95 umol, 1 eq, HCl), 4-methoxy-1H-indole-2-carboxylic acid (127.51 mg, 666.95 umol, 1 eq), DMAP (162.96 mg, 1.33 mmol, 2 eq), EDCI (255.71 mg, 1.33 mmol, 2 eq), DMF (2 mL) and DCM (4 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the compound (S)-methyl 2-((S)-6-(4-methoxy-1H-indole-2-carbonyl)-6-azaspiro[2.5]octane-5-carboxamido)-3-((S)-2-oxopyrrolidin-3-yl)propanoate (150 mg, 275.74 umol, 41.34% yield, 91.28% purity) as an oil. MS (ESI) m/z 495.2 [M–H]$^-$

Step 5: (S)-6-(4-methoxy-1H-indole-2-carbonyl)-6-azaspiro[2.5]octane-5-carboxylic acid A mixture of (S)-methyl 2-((S)-6-(4-methoxy-1H-indole-2-carbonyl)-6-azaspiro[2.5]octane-5-carboxamido)-3-((S)-2-oxopyrrolidin-3-yl)propanoate, LiOH (24.12 mg, 1.01 mmol, 5 eq), H$_2$O (1 mL) and THF (4 mL) was stirred at 25° C. for 16 h. The reaction mixture was concentrated under reduced pressure to give a product (S)-6-(4-methoxy-1H-indole-2-carbonyl)-6-azaspiro[2.5]octane-5-carboxylic acid (65 mg, crude) as a solid. MS (ESI) m z 327.1 [M–H]$^-$

Step 6: tert-butyl ((S)-1-amino-1-oxo-3-((S)-2-oxopyrrolidin-3-yl)propan-2-yl)carbamate A mixture of methyl (2S)-2-(tert-butoxycarbonylamino)-3-[(3S)-2-oxopyrrolidin-3-yl]propanoate (400 mg, 1.40 mmol, 1 eq) and NH$_3$/MeOH (7 M, 10 mL) was stirred at 80° C. for 16 h. The reaction mixture was concentrated under reduced pressure to give a product tert-butyl ((S)-1-amino-1-oxo-3-((S)-2-oxopyrrolidin-3-yl)propan-2-yl)carbamate (380 mg, crude) as a solid.

Step 7: (S)-2-amino-3-((S)-2-oxopyrrolidin-3-yl)propanamide

A mixture of tert-butyl ((S)-1-amino-1-oxo-3-((S)-2-oxopyrrolidin-3-yl)propan-2-yl)carbamate (300 mg, 1.11 mmol, 1 eq) and HCl/EtOAc (4 M, 15 mL, 54.26 eq) was stirred at 25° C. for 0.5 h. The reaction mixture was concentrated under reduced pressure to give a product (S)-2-amino-3-((S)-2-oxopyrrolidin-3-yl)propanamide (190 mg, crude) as a solid and used directly for next step.

Step 8: (S)—N—((S)-1-amino-1-oxo-3-((S)-2-oxopyrrolidin-3-yl)propan-2-yl)-6-(4-methoxy-1H-indole-2-carbonyl)-6-azaspiro[2.5]octane-5-carboxamide A solution of (S)-6-(4-methoxy-1H-indole-2-carbonyl)-6-azaspiro[2.5]octane-5-carboxylic acid (65 mg, 197.95 umol, 1 eq), (S)-2-amino-3-((S)-2-oxopyrrolidin-3-yl)propanamide (33.89 mg, 197.95 umol, 1 eq), DMAP (48.37 mg, 395.91 umol, 2 eq), EDCI (75.90 mg, 395.91 umol, 2 eq), DMF (1 mL) and DCM (3 mL) was stirred at 25° C. for 16 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by prep-HPLC (column: Phenomenex Gemini-NX C$_{18}$ 75*30 mm*3 um; mobile phase: [water(0.05% NH$_3$H$_2$O+10 mM NH$_4$HCO$_3$)—ACN]; B %: 10%-40%, 8 min) to get the compound (S)—N—((S)-1-amino-1-oxo-3-((S)-2-oxopyrrolidin-3-yl)propan-2-yl)-6-(4-methoxy-1H-indole-2-carbonyl)-6-azaspiro[2.5]octane-5-carboxamide (45 mg, 79.43 umol, 40.13% yield, 85% purity) as a solid. MS (ESI) m/z 480.2 [M–H]$^-$

Step 9: (S)—N—((S)-1-cyano-2-((S)-2-oxopyrrolidin-3-yl)ethyl)-6-(4-methoxy-1H-indole-2-carbonyl)-6-azaspiro[2.5]octane-5-carboxamide A mixture of (S)—N—((S)-1-amino-1-oxo-3-((S)-2-oxopyrrolidin-3-yl)propan-2-yl)-6-(4-methoxy-1H-indole-2-carbonyl)-6-azaspiro[2.5]octane-5-carboxamide (40 mg, 83.07 umol, 1 eq), Burgess reagent (237.55 mg, 996.80 umol, 12 eq) and DCM (20 mL) was stirred at 25° C. for 8 h. The reaction mixture was concentrated under reduced pressure to give a residue. The residue was purified by prep-HPLC (column: Phenomenex Gemini-NX C18 75*30 mm*3 um; mobile phase: [water(0.05% NH$_3$H$_2$O+10 mM NH4HCO$_3$)—ACN]; B %: 20%-40%, 8 min) to get the product (S)—N—((S)-1-cyano-2-((S)-2-oxopyrrolidin-3-yl)ethyl)-6-(4-methoxy-1H-indole-2-carbonyl)-6-azaspiro[2.5]octane-5-carboxamide (17 mg, 34.79 umol, 41.89% yield, 94.87% purity), as a solid. MS (ESI) m/z 462.2 [M–H]$^-$.

$^1$H NMR (400 MHz, DMSO-d$_6$) δ=11.64 (s, 1H), 9.26-8.52 (m, 1H), 7.87-7.61 (m, 1H), 7.18-7.07 (m, 1H), 7.06-6.96 (m, 1H), 6.85-6.60 (m, 1H), 6.51 (d, 1H), 5.30-4.93 (m, 2H), 4.61-4.41 (m, 1H), 3.85 (s, 3H), 3.21-2.96 (m, 2H), 2.39-2.03 (m, 5H), 1.96-1.56 (m, 4H), 0.99 (d, 1H), 0.45-0.15 (m, 4H)

Example 18. Synthesis of Viral Protease Inhibitor Compound 185

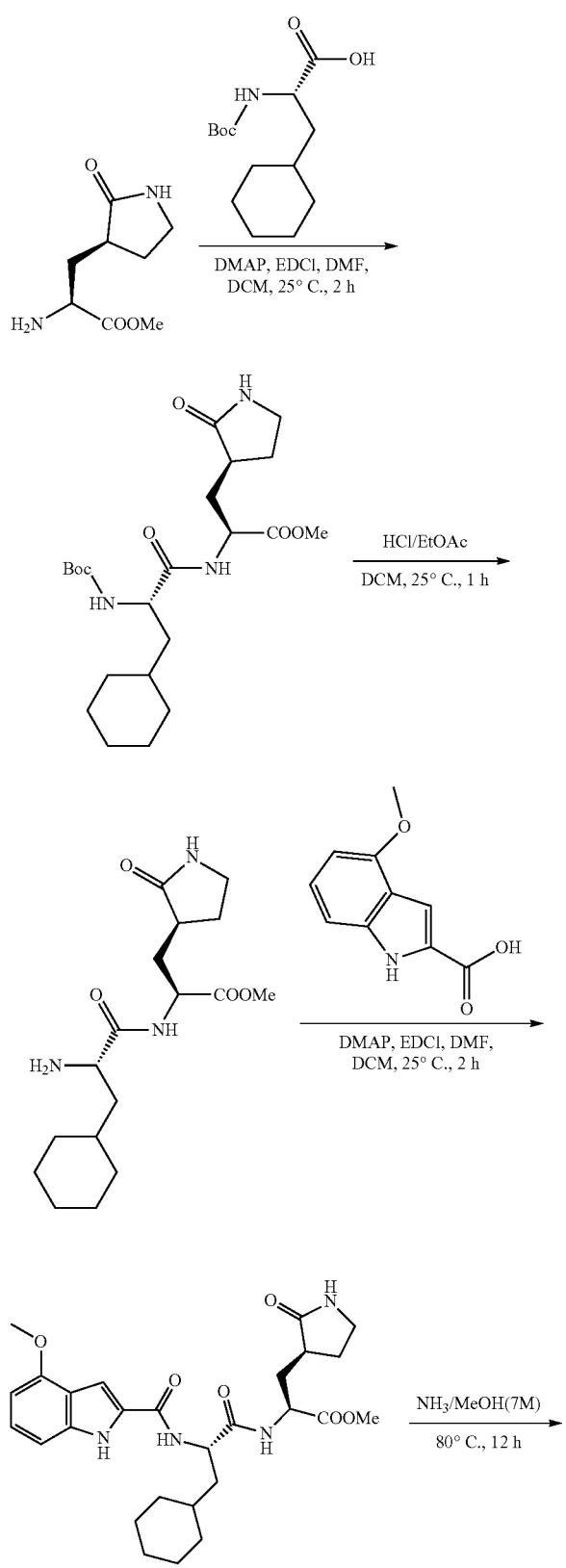

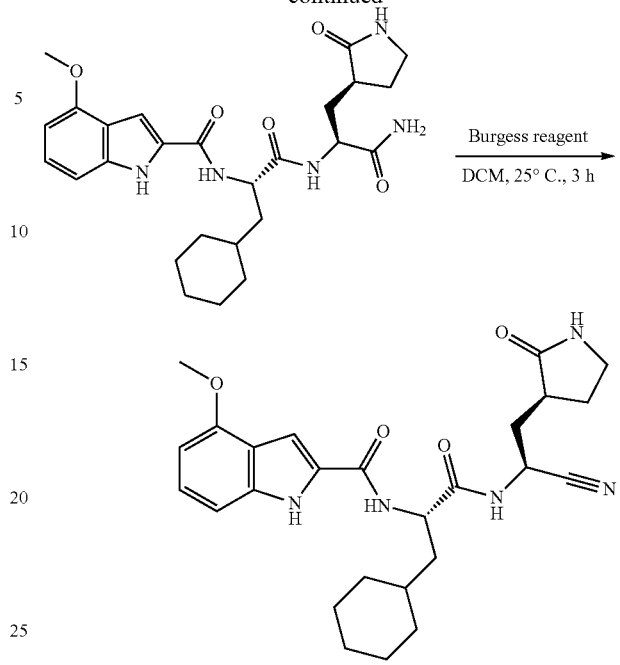

Step 1: (S)-methyl 2-((S)-2-((tert-butoxycarbonyl)amino)-3-cyclohexylpropanamido)-3-((S)-2-oxopyrrohidin-3-yl)propanoate To a solution of methyl (2S)-2-amino-3-[(3S)-2-oxopyrrolidin-3-yl]propanoate (170 mg, 763.47 umol, 1 eq, HCl) and (2S)-2-(tert-butoxycarbonylamino)-3-cyclohexyl-propanoic acid (207.17 mg, 763.47 umol, 1 eq) in DMF (2 mL) was added DMAP (186.55 mg, 1.53 mmol, 2 eq) and EDCI (292.71 mg, 1.53 mmol, 2 eq). The mixture was added DCM (3 mL) and stirred at 25° C. for 2 h. The reaction mixture was quenched by addition H$_2$O (30 mL) at 0° C., and then extracted with DCM (20 mL*3). The combined organic layers were washed with brine, dried over Na$_2$SO$_4$, filtered and concentrated under reduced pressure to give a residue. The residue was purified by prep-TLC (SiO$_2$, petroleum ether/EtOAc=0/1) to get the product methyl (2S)-2-[[(2S)-2-(tert-butoxycarbonylamino)-3-cyclohexyl-propanoyl]amino]-3-[(3 S)-2-oxopyrrolidin-3-yl]propanoate (250 mg, 568.77 umol, 74.50% yield) was obtained as a solid. MS (ESI) m/z 440.3 [M+H]H Step 2: (S)-methyl 2-((S)-2-amino-3-cyclohexylpropanamido)-3-((S)-2-oxopyrrolidin-3-pronyl)propanoate A solution of methyl (2S)-2-[[(2S)-2-(tert-butoxycarbonylamino)-3-cyclohexyl-propanoyl]amino]-3-[(3S)-2-oxopyrrolidin-3-yl]propanoate (200 mg, 455.02 umol, 1 eq) in EtOAc (0.5 mL) was added drop-wise HCl/EtOAc (4 M, 2.00 mL, 17.58 eq) at 25° C. The mixture was stirred at 25° C. for 1 h. The reaction mixture was concentrated under reduced pressure to give a product methyl (2S)-2-[[(2S-2-amino-cyclohexyl-propanoyl]amino]-3-[(3S)-2-oxopyrrolidin-3-yl]propanoate (150 mg, crude, HCl) was obtained as a solid and used directly next step. MS (ESI) m/z 340.1 [M+H]$^+$

Step 3: ((S)-methyl 2-((S)-3-cyclohexyl-2-(4-methoxy-1H-indole-2-carboxamido)propanamido)-3-((S)-2-oxopyrrolidin-3-yl)propanoate A solution of 4-methoxy-1H-indole-2-carboxylic acid (99.18 mg, 518.77 umol, 1.3 eq) and methyl (2S)-2-[[(2S)-2-amino-3-cyclohexyl-propanoyl]amino]-3-[(3S)-2-oxopyrrolidin-3-yl]propanoate (150 mg, 399.05 umol, 1 eq, HCl) in DMF (2 mL) was added DMAP (97.50 mg, 798.11 umol, 2.0 eq) and EDCI (153.00 mg, 798.11 umol, 2 eq). The mixture was added DCM (4 mL) and stirred at 25° C. for 2 h. The reaction mixture was quenched by addition $H_2O$ (20 mL) at 0° C., and then extracted with DCM (20 mL*3). The combined organic layers were washed with brine (20 mL), dried over $Na_2SO_4$, filtered and concentrated under reduced pressure to give a residue. The residue was purified by column chromatography ($SiO_2$, DCM:MeOH=1:0 to 10:1) to get a product methyl (2S)-2-[[(2S)-3-cyclohexyl-2-[(4-methoxy-1H-indole-2-carbonyl)amino]propanoyl]amino]-3-[(3S)-2-oxopyrrolidin-3-yl]propanoate (150 mg, 292.63 umol, 73.33% yield) was obtained as a solid.

$^1$H NMR (METHANOL-$d_4$, 400 MHz): δ ppm 7.26 (s, 1H), 7.09-7.20 (m, 1H), 7.02 (d, J=8.3 Hz, 1H), 6.51 (d, J=7.6 Hz, 1H), 4.66 (br dd, J=9.0, 6.3 Hz, 1H), 4.52-4.58 (m, 1H), 3.93 (s, 3H), 3.72 (s, 3H), 3.22-3.29 (m, 2H), 2.54-2.62 (m, 1H), 2.26-2.33 (m, 1H), 2.15-2.23 (m, 1H), 1.66-1.87 (m, 9H), 1.47-1.54 (m, 1H), 1.25-1.40 (m, 3H), 0.96-1.06 (m, 2H)

Step 4: N—((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide To a solution of methyl (2S)-2-[[(2S)-3-cyclohexyl-2-[(4-methoxy-1H-indole-2-carbonyl)amino]propanoyl]amino]-3-[(3S)-2-oxopyrrolidin-3-yl]propanoate (150 mg, 292.63 umol, 1 eq) in ammonia (15.30 g, 898.39 mmol, 15.00 mL, 3070.07 eq) was heated to 80° C. for 12 h in a sealed tube. The reaction mixture was concentrated under reduced pressure to get a product N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (140 mg, crude) was obtained as a solid. MS (ESI) m/z 498.2 $[M+H]^+$ $^1$H NMR (METHANOL-$d_4$, 400 MHz): δ ppm 7.27-7.34 (m, 1H), 7.13-7.20 (m, 1H), 7.05 (d, J=8.3 Hz, 1H), 6.53 (d, J=7.7 Hz, 1H), 4.62 (t, J=7.6 Hz, 1H), 4.42-4.51 (m, 1H), 3.95 (s, 3H), 3.22-3.30 (m, 2H), 2.53 (td, J=9.2, 4.5 Hz, 1H), 2.33 (ddd, J=9.2, 6.4, 3.4 Hz, 1H), 2.17 (ddd, J=14.1, 11.4, 4.6 Hz, 1H), 1.71-1.88 (m, 9H), 1.46-1.53 (m, 1H), 1.21-1.32 (m, 3H), 0.97-1.09 (m, 2H)

Step 5: N—((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide To a solution of N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (80 mg, 160.78 umol, 1 eq) in DCM (3 mL) was added Burgess reagent (114.94 mg, 482.33 umol, 3 eq), then the mixture was stirred at 25° C. for 3 h. The reaction mixture was concentrated under reduced pressure to give a residue. The residue was purified by neutral prep-HPLC to get a product N-[(1S)-2-[[(1S)-1-cyano-2-[(3S)-2-oxopyrrolidin-3-yl]ethyl]amino]-1-(cyclohexylmethyl)-2-oxo-ethyl]-4-methoxy-1H-indole-2-carboxamide (20.02 mg, 41.75 umol, 25.97% yield, 100% purity) was obtained as a solid. MS (ESI) m/z 480.1 $[M+H]^+$.

Prep-HPLC condition: column: Waters Xbridge BEH C18 100*25 mm*5 um; mobile phase: [water(10 mM $NH_4HCO_3$)—ACN]; B %: 30%-60%, 10 min $^1$H NMR (METHANOL-$d_4$, 400 MHz): δ ppm 7.28 (s, 1H), 7.11-7.18 (m, 1H), 7.02 (d, J=8.3 Hz, 1H), 6.51 (d, J=7.6 Hz, 1H), 5.05 (dd, J=10.1, 5.9 Hz, 1H), 4.56-4.61 (m, 1H), 3.93 (s, 3H), 3.22-3.30 (m, 2H), 2.55-2.66 (m, 1H), 2.23-2.40 (m, 2H), 1.65-1.94 (m, 9H), 1.41-1.52 (m, 1H), 1.17-1.36 (m, 3H), 0.94-1.10 (m, 2H).

Example 19. Synthesis of Viral Protease Inhibitor Compound 197

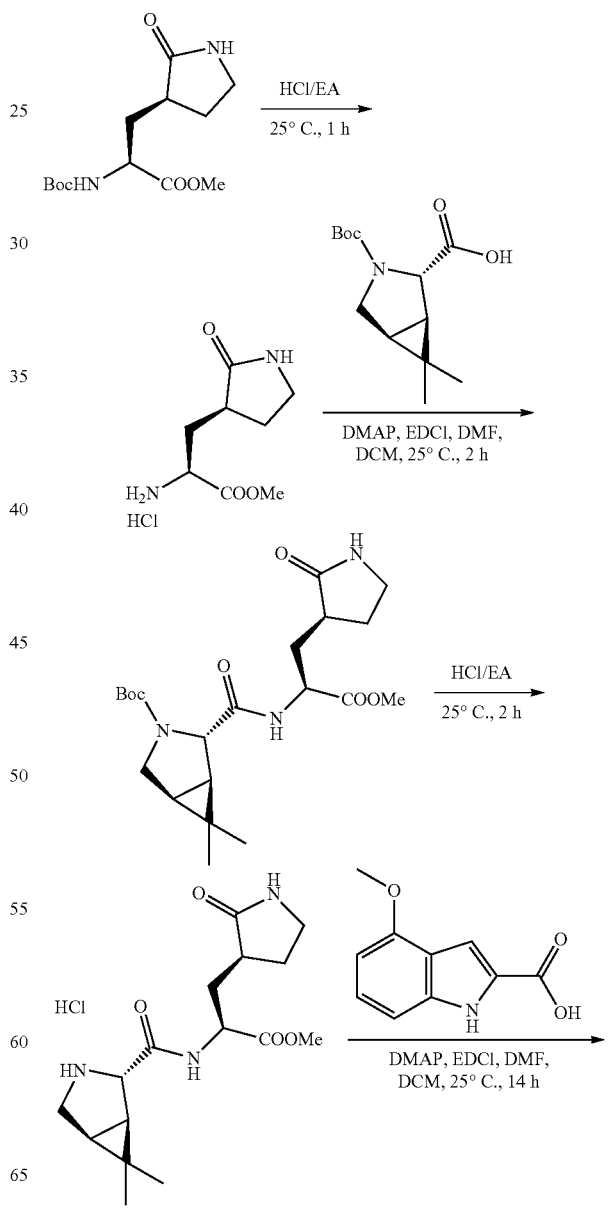

-continued

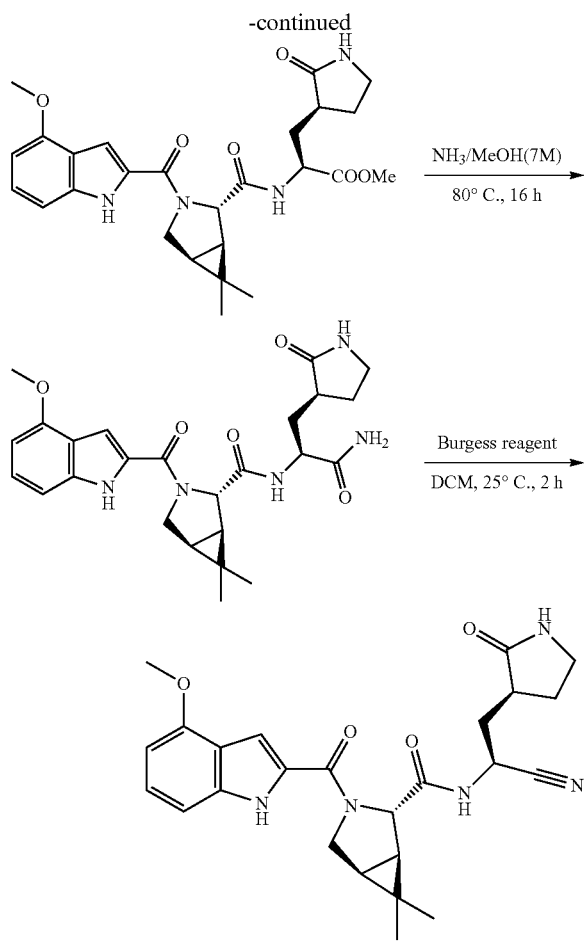

Step 1: methyl (2S)-2-amino-3-[(3S)-2-oxopyrrolidin-3-yl]propanoate

To a mixture of methyl (2S)-2-(tert-butoxycarbonylamino)-3-[(3S)-2-oxopyrrolidin-3-yl]propanoate (500 mg, 1.75 mmol, 1 eq) in HCl/EtOAc (4M, 20 mL). The mixture was stirred at 25° C. and stirred for 1 h. Once the reaction was completed, the reaction was concentrated to give the crude methyl (2S)-2-amino-3-[(3S)-2-oxopyrrolidin-3-yl]propanoate (400 mg, crude, an oil). The crude product was used directly without further purification. MS (ESI) m/z 187.1 [M+H]$^+$ Step 2: tert-butyl (2S,5S)-2-[[(1S)-2-methoxy-2-oxo-1-[[(3S)-2-oxopyrrolidin-3-yl]methyl]ethyl]carbamoyl]-6,6-dimethyl-3-azabicyclo[3.1.0]hexane-3-carboxylate To a mixture of methyl (2S)-2-amino-3-[(3S)-2-oxopyrrolidin-3-yl]propanoate (230 mg, 1.24 mmol, 1 eq) and (2S,5S)-3-tert-butoxycarbonyl-6,6-dimethyl-3-azabicyclo[3.1.0]hexane-2-carboxylic acid (315.35 mg, 1.24 mmol, 1 eq) in DCM (4.5 mL) and DMF (1.5 mL) was added EDCI (473.57 mg, 2.47 mmol, 2 eq) and DMAP (301.80 mg, 2.47 mmol, 2 eq). The mixture was stirred at 25° C. for 2 h. Once the reaction was completed, the reaction was concentrated and purified by prep-HPLC (column: Waters Xbridge BEH C18 100*30 mm*10 um; mobile phase: [water(10 mM NH$_4$HCO$_3$)—ACN]; B %: 25%-55%, 10 min) to give tert-butyl (2S,5S)-2-[[(1S)-2-methoxy-2-oxo-1-[[(3S)-2-oxopyrrolidin-3-yl]methyl]ethyl]carbamoyl]-6,6-dimethyl-3-azabicyclo[3.1.0]hexane-3-carboxylate (200 mg, 425.03 umol, 34.41% yield, 90% purity) (solid). MS (ESI) m/z 424.1 [M+H]$^+$ Step 3: (S)-methyl 2-((1S,2S,5S)-6,6-dimethyl-3-azabicyclo[3.1.0]hexane-2-carboxamido)-3-((S)-2-oxopyrrolidin-3-yl)propanoate To a mixture of (1S,2S,5S)-tert-butyl 2-(((S)-1-methoxy-1-oxo-3-((S)-2-oxopyrrolidin-3-yl)propan-2-yl)carbamoyl)-6,6-dimethyl-3-azabicyclo[3.1.0]hexane-3-carboxylate (200 mg, 236.13 umol, 50% purity, 1 eq) in HCl/EtOAc (4M, 20 mL). The mixture was stirred at 25° C. and stirred for 2 h. Once the reaction was completed, the reaction was concentrated to give the crude (S)-methyl 2-((1S,2S,5S)-6,6-dimethyl-3-azabicyclo[3.1.0]hexane-2-carboxamido)-3-((S)-2-oxopyrrolidin-3-yl)propanoate (150 mg, crude, an oil). Crude product was used directly without further purification. MS (ESI) m/z 324.1 [M+H]$^+$ Step 4: methyl (2S)-2-[[(2S,5S)-3-(4-methoxy-1H-indole-2-carbonyl)-6,6-dimethyl-3-azabicyclo[3.1.0]hexane-2-carbonyl]amino]-3-[(3S)-2-oxopyrrolidin-3-yl]propanoate To a mixture of (S)-methyl 2-((1S,2S,5S)-6,6-dimethyl-3-azabicyclo[3.1.0]hexane-2-carboxamido)-3-((S)-2-oxopyrrolidin-3-yl)propanoate (150 mg, 463.84 umol, 1 eq) and 4-methoxy-1H-indole-2-carboxylic acid (88.68 mg, 463.84 umol, 1 eq) in DCM (3 mL) and DMF (1 mL) was added EDCI (177.84 mg, 927.68 umol, 2 eq) and DMAP (113.33 mg, 927.68 umol, 2 eq). The mixture was stirred at 25° C. and stirred for 14 h. Once the reaction was completed, the mixture was poured into water (50 mL) and extracted with DCM (20 mL*3). The combined organic phase was washed with brine (60 mL*3), dried with anhydrous Na$_2$SO$_4$, filtered and concentrated in vacuum. The residue was purified by silica gel chromatography (column height: 250 mm, diameter: 100 mm, 100-200 mesh silica gel, petroleum ether/ethyl acetate=1/1, 0/1) to afford methyl (2S)-2-[[(2S,5S)-3-(4-methoxy-1H-indole-2-carbonyl)-6,6-dimethyl-3-azabicyclo[3.1.0]hexane-2-carbonyl]amino]-3-[(3S)-2-oxopyrrolidin-3-yl]propanoate (50 mg, 80.56 umol, 17.37% yield, 80% purity) as solid. MS (ESI) m/z 497.2 [M+H]$^+$ Step 5: (2S,5S)—N-[(1S)-2-amino-2-oxo-1-[[(3S)-2-oxopyrrolidin-3-yl]methyl]ethyl]-3-(4-methoxy-1H-indole-2-carbonyl)-6,6-dimethyl-3-azabicyclo[3.1.0]hexane-2-carboxamide To a mixture of methyl (2S)-2-[[(2S,5S)-3-(4-methoxy-1H-indole-2-carbonyl)-6,6-dimethyl-3-azabicyclo[3.1.0]hexane-2-carbonyl]amino]-3-[(3S)-2-oxopyrrolidin-3-yl]propanoate (100 mg, 201.39 umol, 1 eq) in ammonia (5.10 g, 299.46 mmol, 5 mL, 1486.99 eq). The mixture was stirred at 80° C. and stirred for 16 h. Once the reaction was completed, the reaction was concentrated to give the crude (2S,5S)—N-[(1S)-2-amino-2-oxo-1-[[(3S)-2-oxopyrrolidin-3-yl]methyl]ethyl]-3-(4-methoxy-1H-indole-2-carbonyl)-6,6-dimethyl-3-azabicyclo[3.1.0]hexane-2-carboxamide (100 mg, crude) (solid). Crude product was used directly without further purification. MS (ESI) m/z 482.3[M+H]$^+$

Step 6: (2S,5S)—N-[(1S)-1-cyano-2-[(3S)-2-oxopyrrolidin-3-yl]ethyl]-3-(4-methoxy-1H-indole-2-carbonyl)-6,6-dimethyl-3-azabicyclo[3.1.0]hexane-2-carboxamide To a mixture of (2S,5S)—N-[(1S)-2-amino-2-oxo-1-[[(3S)-2-oxopyrrolidin-3-yl]methyl]ethyl]-3-(4-methoxy-1H-indole-2-carbonyl)-6,6-dimethyl-3-azabicyclo[3.1.0]hexane-2-carboxamide (50 mg, 103.83 umol, 1 eq) in DCM (3 mL) was added methoxycarbonyl-(triethylammonio)sulfonyl-azanide (49.49 mg, 207.67 umol, 2 eq). The mixture was stirred at 25° C. for 2 h. Once the reaction was completed, the reaction was concentrated and purified by prep-HPLC (column: Phenomenex Gemini-NX 80*40 mm*3 um; mobile phase: [water(10 mM NH4HCO3)—ACN]; B %: 20%-40%, 8 min) to give (2S,5S)—N-[(1S)-1-cyano-2-[(3S)-2-oxopyrrolidin-3-yl]ethyl]-3-(4-methoxy-1H-indole-2-carbonyl)-6,6-dimethyl-3-azabicyclo[3.1.0]hexane-2-carboxamide (14.44 mg, 31.15 umol, 30.00% yield, 100% purity) as a solid. MS (ESI) m/z 464.2[M+H]$^+$.

1H NMR (400 MHz, METHANOL-d4): δ ppm 7.16-7.18 (m, 1H), 7.11-7.14 (m, 2H), 6.4-6.88 (m, 1H), 5.05-5.08 (m, 0.5H), 4.06 (s, 2H), 3.94-3.98 (m, 0.5H), 3.77-3.86 (m, 4H), 3.28 (s, 2H), 2.61-3.69 (m, 1H), 2.27-2.32 (m, 1H), 2.25-2.26 (m, 1H), 1.78-2.00 (m, 1H), 1.74-1.75 (m, 1H) 1.35-1.64 (m, 2H), 0.97-1.15 (m, 6H)

Example 20. Synthesis of Viral Protease Inhibitor Compound 213

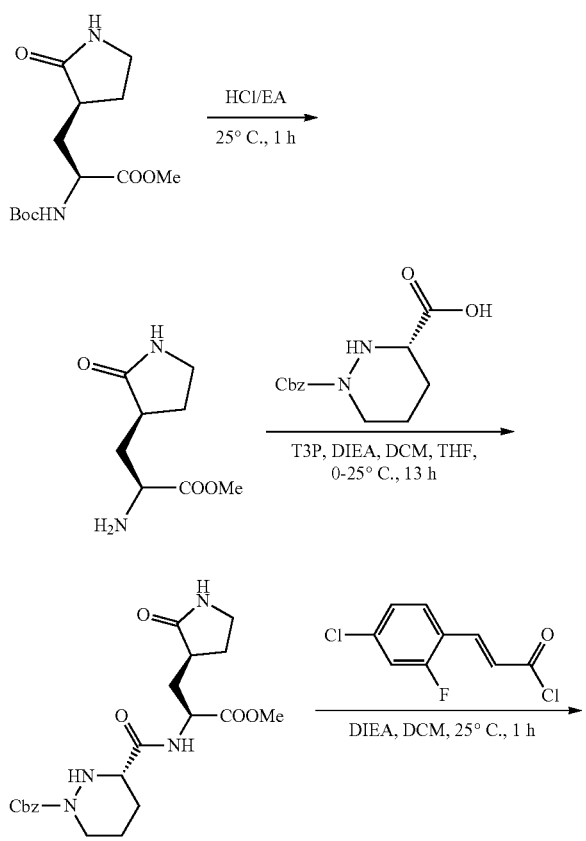

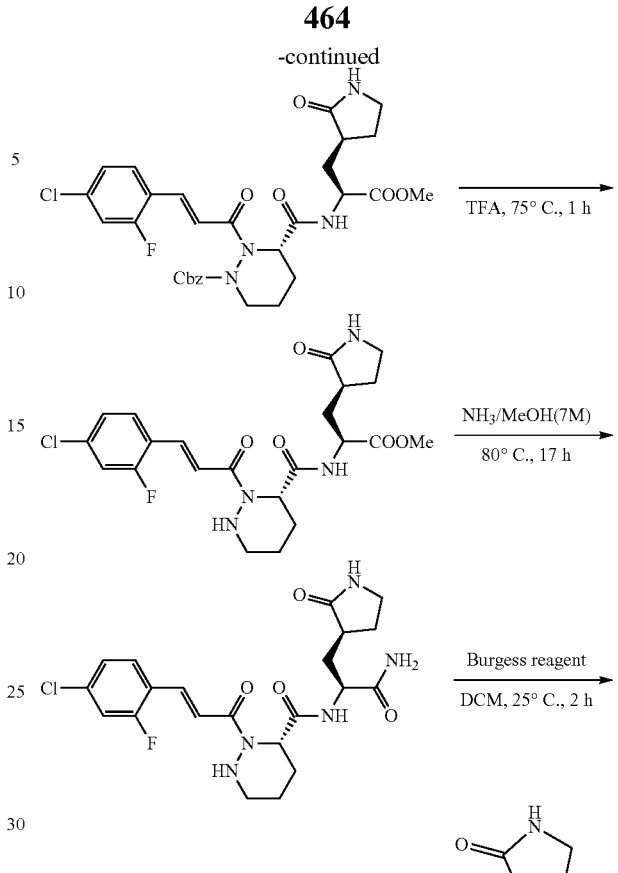

Step 1: (S)-Methyl 2-amino-3-((S)-2-oxopyrrolidin-3-yl)propanoate

Methyl (2S)-2-(tert-butoxycarbonylamino)-3-[(3S)-2-oxopyrrolidin-3-yl]propanoate (501 mg, 1.75 mmol, 1 eq) in HCl/EtOAc (4 M, 10.02 mL, 22.91 eq) was stirred at 25° C. for 1 h. Upon completion, the solution was concentrated. The crude was used to next step directly and without further purification. Methyl (2S)-2-amino-3-[(3S)-2-oxopyrrolidin-3-yl]propanoate (300 mg, crude) was obtained as yellow oil.

Step 2: (S)-benzyl 3-(((S)-1-methoxy-1-oxo-3-((S)-2-oxopyrrolidin-3-yl)propan-2-yl)carbamoyl)tetrahydropyridazine-](2H)-carboxylate Methyl (2S)-2-amino-3-[(3S)-2-oxopyrrolidin-3-yl]propanoate (295.93 mg, 1.59 mmol, 1.4 eq) and (3S)-1-benzyloxycarbonylhexahydropyridazine-3-carboxylic acid (300 mg, 1.14 mmol, 1 eq) in DCM (2 mL)/THF (2 mL) was cooled to 0° C., then the T3P (1.08 g, 1.70 mmol, 1.01 mL, 50% purity, 1.5 eq) and DIEA (440.14 mg, 3.41 mmol, 593.18 uL, 3 eq) was added and the solution was stirred at 25° C. for 13 h. Upon completion, the solution was diluted with H$_2$O (20 mL), extracted with Ethyl acetate (30 mL*3), the combined organic phase was dried over Na₂SO₄, filtrated and concentrated to give the crude. The crude was used to next step directly and without further purification. Benzyl (3S)-3-[[(1S)-2-methoxy-2-oxo-1-[[(3S)-2-oxopyrrolidin-3-yl]methyl]ethyl]carbamoyl]hexahydropyridazine-1-carboxylate (455 mg, crude) was obtained as yellow oil. MS (ESI) m/z 433.1 [M+H]⁺.

Step 3: (S)-benzyl 2-((E)-3-(4-chloro-2-fluorophenyl)acryloyl)-3-(((S)-1-methoxy-1-oxo-3-((S)-2-oxopyrrolidin-3-yl)propan-2-yl)carbamoyl)tetrahydropyridazine-1(2H)-carboxylate Benzyl (3S)-3-[[(1S)-2-methoxy-2-oxo-1-[[(3S)-2-oxopyrrolidin-3-yl]methyl]ethyl]carbamoyl]hexahydropyridazine-1-carboxylate (200 mg, 462.46 umol, 1 eq) in DCM (2 mL) was added the DIEA (119.54 mg, 924.92 umol, 161.10 uL, 2 eq), (E)-3-(4-chloro-2-fluoro-phenyl)prop-2-enoyl chloride (121.56 mg, 554.95 umol, 1.2 eq) was added and the solution was stirred at 25° C. for 1 h. Upon completion, the solution was diluted with H₂O (10 mL), extracted with DCM (20 mL*3), the combined organic phase was dried over Na₂SO₄, filtrated and concentrated to give the crude. The residue was purified by prep-TLC (SiO₂, DCM: MeOH=10:1). Benzyl (3S)-2-[(E)-3-(4-chloro-2-fluoro-phenyl) prop-2-enoyl]-3-[[(1S)-2-methoxy-2-oxo-1-[[(3S)-2-oxopyrrolidin-3-yl]methyl]ethyl]carbamoyl]hexahydropyridazine-1-carboxylate (160 mg, 248.88 umol, 53.82% yield, 95.67% purity) was obtained as yellow oil. MS (ESI) m/z 433.1 [M+H]⁺.

Step 4: (S)-methyl 2-((S)-2-((E)-3-(4-chloro-2-fluorophenyl)acryloyl)hexahydropyridazine-3-carboxamido)-3-((S)-2-oxopyrrolidin-3-yl)propanoate Benzyl (3S)-2-[(E)-3-(4-chloro-2-fluoro-phenyl)prop-2-enoyl]-3-[[(1S)-2-methoxy-2-oxo-1-[[(3S)-2-oxopyrrolidin-3-yl]methyl]ethyl]carbamoyl]hexahydropyridazine-1-carboxylate (160 mg, 260.14 umol, 1 eq) in TFA (5 mL) was stirred at 75° C. for 1 h. Upon completion, the solution was concentrated to remove the TFA, diluted with the solution of NaHCO₃, extracted with EtOAc (20 mL*3), the combined organic phase was dried over Na₂SO₄, filtrated and concentrated to give the crude. The crude was used to next step directly and without further purification. Methyl (2S)-2-[[(3S)-2-[(E)-3-(4-chloro-2-fluoro-phenyl) prop-2-enoyl]hexahydropyridazine-3-carbonyl]amino]-3-[(3S)-2-oxopyrrolidin-3-yl]propanoate (80 mg, crude) was obtained as solid. MS (ESI) m/z 481.0 [M+H]⁺.

Step 5: (S)—N—((S)-1-amino-1-oxo-3-((S)-2-oxopyrrolidin-3-yl)propan-2-yl)-2-((E)-3-(4-chloro-2-fluorophenyl)acryloyl)hexahydropyridazine-3-carboxamide Methyl (2S)-2-[[(3S)-2-[(E)-3-(4-chloro-2-fluoro-phenyl)prop-2-enoyl]hexahydropyridazine-3-carbonyl]amino]-3-[(3S)-2-oxopyrrolidin-3-yl]propanoate (80 mg, 166.35 umol, 1 eq) in NH₃/MeOH (7 M, 4.00 mL, 168.32 eq) was stirred at 80° C. for 17 h. Upon completion, the solution was concentrated to remove the MeOH. The crude was used to next step directly and without further purification. (3S)—N-[(1S)-2-amino-2-oxo-1-[[(3S)-2-oxopyrrolidin-3-yl]methyl]ethyl]-2-[(E)-3-(4-chloro-2-fluoro-phenyl) prop-2-enoyl]hexahydropyridazine-3-carboxamide (75 mg, crude) was obtained as yellow oil. MS (ESI) m/z 481.0 [M+H]⁺.

Step 6: (S)-2-((E)-3-(4-chloro-2-fluorophenyl)acryloyl)-N—((S)-1-cyano-2-((S)-2-oxopyrrolidin-3-yl)ethyl)hexahydropyridazine-3-carboxamide (3S)—N-[(1S)-2-amino-2-oxo-1-[[(3S)-2-oxopyrrolidin-3-yl]methyl]ethyl]-2-[(E)-3-(4-chloro-2-fluoro-phenyl) prop-2-enoyl]hexahydropyridazine-3-carboxamide (75 mg, 160.98 umol, 1 eq) in DCM (0.5 mL) was added the Burgess reagent (76.72 mg, 321.95 umol, 2 eq) and the solution was stirred at 25° C. for 2 h. Upon completion, the solution was concentrated to remove the DCM. The residue was purified by prep-HPLC (neutral condition). Column: Phenomenex Gemini-NX 80*40 mm*3 um; mobile phase: [water (10 mM NH₄HCO3)—ACN]; B %: 25%-45%, 8 min. (3S)-2-[(E)-3-(4-chloro-2-fluoro-phenyl)prop-2-enoyl]-N-[(1S)-1-cyano-2-[(3S)-2-oxopyrrolidin-3-yl]ethyl]hexahydropyridazine-3-carboxamide (20 mg, 44.65 umol, 27.74% yield, 100% purity) was obtained as a solid. ¹H NMR (400 MHz, METHANOL-d₄) δ=7.79-7.60 (m, 3H), 7.32-7.22 (m, 2H), 5.17 (dd, J=2.2, 6.0 Hz, 1H), 5.07 (dd, J=6.4, 9.7 Hz, 1H), 3.38-3.32 (m, 2H), 3.12 (br d, J=13.7 Hz, 1H), 2.90-2.74 (m, 1H), 2.56 (dq, J=5.8, 9.0 Hz, 1H), 2.44-2.14 (m, 3H), 2.08-1.79 (m, 3H), 1.75-1.53 (m, 2H). MS (ESI) m/z 448.2 [M+H]⁺.

Step 7: (E)-3-(4-chloro-2-fluorophenyl)acryloyl chloride (E)-3-(4-chloro-2-fluoro-phenyl)prop-2-enoic acid (120 mg, 598.22 umol, 1 eq) in DCM (0.5 mL) was added the DMF (437.26 ug, 5.98 umol, 0.46 uL, 0.01 eq) and cooled to 0° C., then the (COCl)₂ (151.86 mg, 1.20 mmol, 104.73 uL, 2 eq) was added and the solution was stirred at 25° C. for 1 h. Upon completion, the solution was concentrated to remove the DCM and give the crude. The crude was used to next step directly and without further purification. (E)-3-(4-chloro-2-fluoro-phenyl)prop-2-enoyl chloride (125 mg, crude) was obtained as a solid.

Example 21. Synthesis of Viral Protease Inhibitor Compound 201

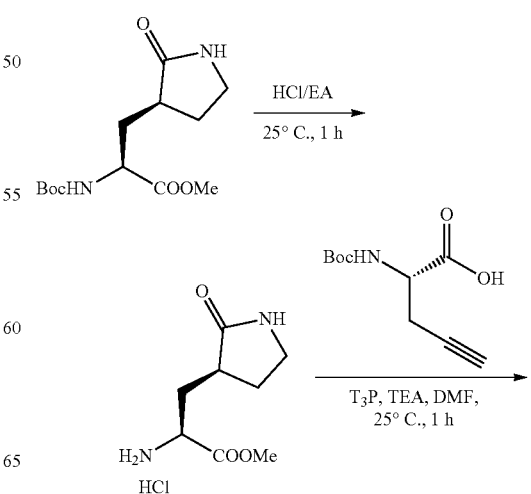

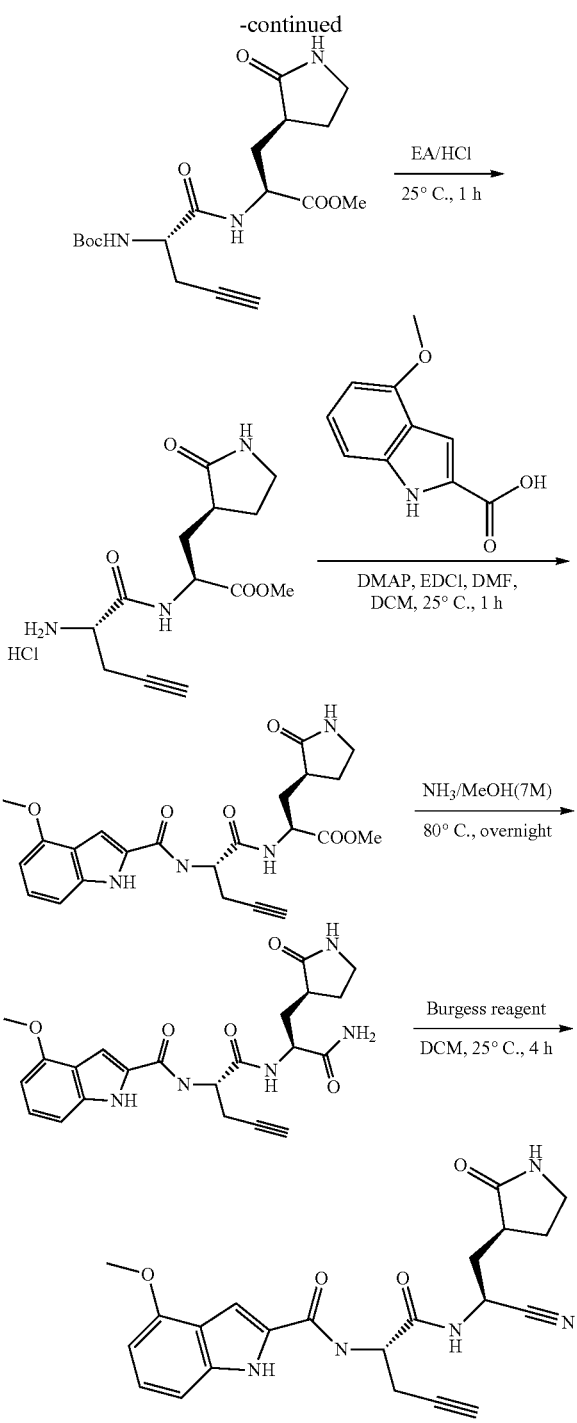

Step 1: methyl (2S)-2-amino-3-[(3S)-2-oxopyrrolidin-3-yl]propanoate; hydrochloride Methyl (2S)-2-(tert-butoxycarbonylamino)-3-[(3S)-2-oxopyrrolidin-3-yl]propanoate (250 mg, 873.14 umol, 1 eq) was added HCl/EtOAc (4 M, 30 mL) at 25° C. The mixture was stirred at 25° C. for 1 h. The reaction mixture was concentrated under reduced pressure to give a product methyl (2S)-2-amino-3-[(3S)-2-oxopyrrolidin-3-yl]propanoate; hydrochloride (200 mg, crude) as a solid and used directly for next step.

Step 2: (S)-methyl-2-((S)-2-((tert-butoxycarbonyl)amino)pent-4-ynamido)-3-((S)-2-oxopyrrolidin-3-yl)propanoate A mixture of methyl (2S)-2-amino-3-[(3S)-2-oxopyrrolidin-3-yl]propanoate; hydrochloride (180 mg, 808.38 umol, 1 eq), (2S)-2-(tert-butoxycarbonylamino)pent-4-ynoic acid (172.37 mg, 808.38 umol, 1 eq), TEA (572.59 mg, 5.66 mmol, 787.61 uL, 7 eq), T$_3$P (1.03 g, 1.62 mmol, 961.53 uL, 50% purity, 2 eq) and DMF (3 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO, petroleum ether/EtOAc=0/1) to afford the product (S)-methyl-2-((S)-2-((tert-butoxycarbonyl)amino)pent-4-ynamido)-3-((S)-2-oxopyrrolidin-3-yl)propanoate (150 mg, 393.26 umol, 48.65% yield), as an oil. MS (ESI) m/z 382.1 [M+H]$^+$ Step 3: (S)-methyl 2-((S)-2-aminopent-4-ynamido)-3-((S)-2-oxopyrrolidin-3-yl)propanoate A mixture of (S)-methyl-2-((S)-2-((tert-butoxycarbonyl)amino)pent-4-ynamido)-3-((S)-2-oxopyrrolidin-3-yl)propanoate (140 mg, 367.05 umol, 1 eq) and HCl/EtOAc (4 M, 30 mL) was stirred at 25° C. for 1 h. The reaction mixture was concentrated under reduced pressure to give a product (S)-methyl 2-((S)-2-aminopent-4-ynamido)-3-((S)-2-oxopyrrolidin-3-yl)propanoate (120 mg, crude, HCl) as an oil and used directly for next step.

Step 4: (S)-methyl-2-((S)-2-(4-methoxy-1H-indole-2-carboxamido)pent-4-ynamido)-3-((S)-2-oxopyrrolidin-3-yl)propanoate A mixture of (S)-methyl 2-((S)-2-aminopent-4-ynamido)-3-((S)-2-oxopyrrolidin-3-yl)propanoate (120 mg, 377.63 umol, 1 eq, HCl), 4-methoxy-1H-indole-2-carboxylic acid (72.20 mg, 377.63 umol, 1 eq), EDCI (144.78 mg, 755.27 umol, 2 eq), DMAP (92.27 mg, 755.27 umol, 2 eq), DMF (2 mL) and DCM (4 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the compound (S)-methyl-2-((S)-2-(4-methoxy-1H-indole-2-carboxamido)pent-4-ynamido)-3-((S)-2-oxopyrrolidin-3-yl)propanoate (90 mg, 160.56 umol, 42.52% yield, 81.08% purity), as an oil. MS (ESI) m/z 455.1 [M+H]$^+$ Step 5: N—((S)-1-(((S)-1-amino-1-oxo-3-((S)-2-oxopyrrolidin-3-yl)propan-2-yl)amino)-1-oxopent-4-yn-2-yl)-4-methoxy-1H-indole-2-carboxamide A mixture of (S)-methyl-2-((S)-2-(4-methoxy-1H-indole-2-carboxamido)pent-4-ynamido)-3-((S)-2-oxopyrrolidin-3-yl)propanoate (85 mg, 187.03 umol, 1 eq) and NH$_3$/MeOH (7 M, 10 mL) was stirred at 80° C. for 16 h. The reaction mixture was concentrated under reduced pressure to give a product N—((S)-1-(((S)-1-amino-1-oxo-3-((S)-2-oxopyrrolidin-3-yl)propan-2-yl)amino)-1-oxopent-4-yn-2-yl)-4- methoxy-1H-indole-2-carboxamide (85 mg, crude) as a solid. MS (ESI) m/z 440.2 [M+H]+

Step 6: N—((S)-1-(((S)-1-cyano-2-((S)-2-oxopyrrolidin-3-yl)ethyl)amino)-1-oxopent-4-yn-2-yl)-4-methoxy-1H-indole-2-carboxamide A mixture of N—((S)-1-(((S)-1-amino-1-oxo-3-((S)-2-oxopyrrolidin-3-yl)propan-2-yl)amino)-1-oxopent-4-yn-2-yl)-4-methoxy-1H-indole-2-carboxamide (80 mg, 182.04 umol, 1 eq), Burgess reagent (216.91 mg, 910.20 umol, 5 eq) and DCM (5 mL) was stirred at 25° C. for 4 h. The reaction mixture was concentrated under reduced pressure to give a residue. The residue was purified by prep-HPLC (column: Waters Xbridge BEH C18 100*30 mm*10 um; mobile phase: [water(0.04% NH3H2O+10 mM NH4HCO3)—ACN]; B %: 20%-50%, 10 min) to get the product N—((S)-1-(((S)-1-cyano-2-((S)-2-oxopyrrolidin-3-yl)ethyl)amino)-1-oxopent-4-yn-2-yl)-4-methoxy-1H-indole-2-carboxamide (20 mg, 47.46 umol, 26.07% yield, 100% purity), as solid. MS (ESI) m/z 422.2 [M+H]+.

1H NMR (400 MHz, DMSO-d6) δ=11.61 (d, J=1.8 Hz, 1H), 9.18-8.93 (m, 1H), 8.74-8.58 (m, 1H), 7.78-7.62 (m, 1H), 7.37-7.29 (m, 1H), 7.15-7.07 (m, 1H), 7.05-6.97 (m, 1H), 6.51 (d, J=7.5 Hz, 1H), 5.03-4.91 (m, 1H), 4.65-4.50 (m, 1H), 3.89 (s, 3H), 3.20-3.05 (m, 2H), 2.91-2.85 (m, 1H), 2.78-2.59 (m, 2H), 2.43-2.29 (m, 1H), 2.21-2.06 (m, 2H), 1.88-1.59 (m, 2H)

Example 22. Synthesis of Viral Protease Inhibitor Compound 205

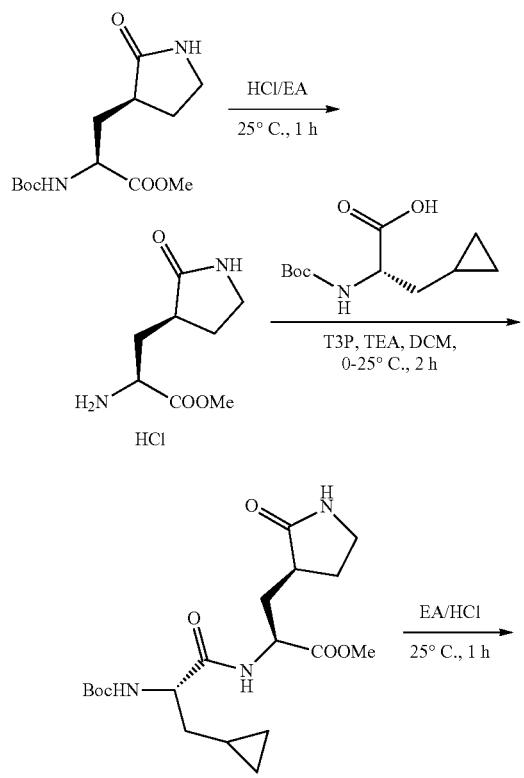

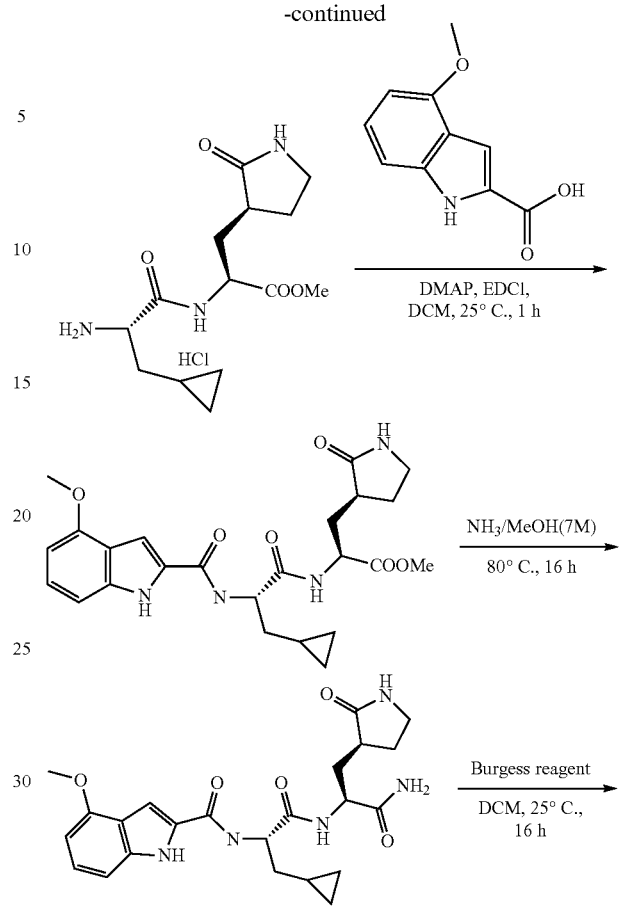

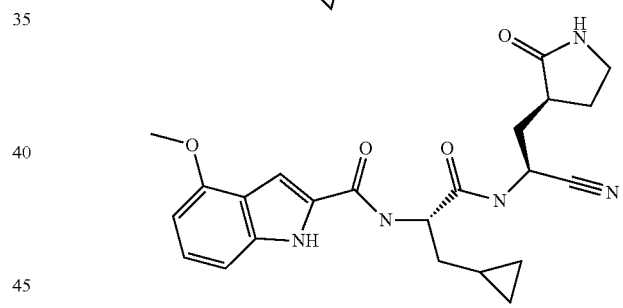

Step 1: (S)-2-((tert-butoxycarbonyl)amino)-3-cyclopropylpropanoic acid

To a solution of (2S)-2-amino-3-cyclopropyl-propanoic acid (1 g, 7.74 mmol, 1 eq) in THF (5 mL) and H2O (5 mL), was added K2CO3 (3.75 g, 27.10 mmol, 3.5 eq) and (Boc)2O (2.20 g, 10.07 mmol, 2.31 mL, 1.3 eq). Additional water was added to the mixture, and then the mixture was stirred at 25° C. for 16 h. The organic solvent was then evaporated and the aqueous solution was washed with petroleum ether (10 mL) and acidified to pH ~3 with 1N aqueous citric acid (30 mL). The solution was extracted with DCM (30 mL*3) and was concentrated in vacuum to afford (S)-2-((tert-butoxycarbonyl) amino)-3-cyclopropyl propanoic acid (1.8 g, crude) as an oil.

Step 2: (S)-methyl 2-amino-3-((S)-2-oxopyrrolidin-3-yl)propanoate (S)-methyl 2-((tert-butoxycarbonyl) amino)-3-((S)-2-oxopyrrolidin-3-yl) propanoate (500 mg, 1.75 mmol, 1 eq)

was added HCl/EtOAc (4 M, 5 mL) at 25° C. The mixture was stirred at 25° C. for 1 h. The reaction mixture was concentrated under reduced pressure to give a product (S)-methyl 2-amino-3-((S)-2-oxopyrrolidin-3-yl) propanoate (350 mg, HCl, crude) as a yellow gum and used to next step directly.

Step 3: (S)-methyl2-((S)-2-((tert-butoxycarbonyl) amino)-3-cyclopropylpropanamido)-3-((S)-2-oxopyrrolidin-3-yl)propanoate To a mixture of (S)-methyl 2-amino-3-((S)-2-oxopyrrolidin-3-yl) propanoate (250 mg, 1.12 mmol, 1 eq, HCl) and (S)-2-((tert-butoxycarbonyl) amino)-3-cyclopropyl propanoic acid (386.12 mg, 1.68 mmol, 1.5 eq) in DCM (5 mL) was added TEA (568.05 mg, 5.61 mmol, 781.36 uL, 5 eq) at 0° C., the mixture was added T3P (2.14 g, 3.37 mmol, 2.00 mL, 50% purity, 3 eq) at 0° C., then the mixture was stirred at 25° C. for 2 h. The reaction mixture was quenched by water (10 mL) and was extracted with DCM (5 mL*3). The resulting solution was dried with Na$_2$SO$_4$, filtered and concentration in vacuum to give a residue. The residue was purified by column chromatography (SiO$_2$, petroleum ether: EtOAc=1:0 to 0:1) to afford the product (S)-methyl 2-((S)-2-((tert-butoxycarbonyl)amino)-3-cyclopropylpropanamido)-3-((S)-2-oxopyrrolidin-3-yl)propanoate (400 mg, 905.74 umol, 80.67% yield, 90% purity) was obtained as a gum.
$^1$H NMR (400 MHz, CDCl$_3$) δ ppm 7.60 (d, J=5.6 Hz, 1H), 5.96 (s, 1H), 5.24 (d, J=7.5 Hz, 1H), 4.65-4.47 (m, 1H), 4.24 (d, J=6.6 Hz, 1H), 3.73 (s, 3H), 3.44-3.27 (m, 2H), 2.51-2.36 (m, 2H), 2.25-2.13 (m, 1H), 1.98-1.82 (m, 1H), 1.66-1.58 (m, 1H), 1.44 (s, 9H), 1.30-1.21 (m, 1H), 0.86-0.71 (m, 1H), 0.49 (d, J=7.9 Hz, 2H), 0.13 (d, J=4.4 Hz, 2H).

Step 4: (S)-methyl 2-((S)-2-amino-3-cyclopropylpropanamido)-3-((S)-2-oxopyrrolidin-3-yl)propanoate A solution of (S)-methyl2-((S)-2-((tert-butoxycarbonyl) amino)-3-cyclopropylpropanamido)-3-((S)-2-oxopyrrolidin-3-yl)propanoate in HCl/EtOAc (4M, 4 mL), the mixture was stirred at 25° C. for 1 h. The reaction mixture was concentrated under reduced pressure to give a product (S)-methyl 2-((S)-2-amino-3-cyclopropylpropanamido)-3-((S)-2-oxopyrrolidin-3-yl) propanoate (330 mg, crude, HCl) as a yellow gum and used directly next step.
1H NMR (400 MHz, MeOD-d$_4$) δ ppm 4.57 (dd, J=4.1, 11.0 Hz, 1H), 3.94 (t, J=6.7 Hz, 1H), 3.73 (s, 3H), 3.40-3.33 (m, 2H), 2.55-2.33 (m, 2H), 2.19-2.07 (m, 1H), 2.03-2.00 (m, 1H), 1.93-1.84 (m, 2H), 1.24 (t, J=7.1 Hz, 1H), 0.89-0.79 (m, 1H), 0.59 (dd, J=4.5, 7.9 Hz, 2H), 0.26-0.17 (m, 2H).

Step 5: (S)-methyl2-((S)-3-cyclopropyl-2-(4-methoxy-1H-indole-2-carboxamido)propanamido)-3-((S)-2-oxopyrrolidin-3-yl)propanoate To a mixture of 4-methoxy-1H-indole-2-carboxylic acid (257.73 mg, 1.35 mmol, 1.5 eq) and (S)-methyl 2-((S)-2-amino-3-cyclopropylpropanamido)-3-((S)-2-oxopyrrolidin-3-yl) propanoate (300 mg, 898.71 umol, 1 eq, HCl) in DCM (8 mL) was added EDCI (861.43 mg, 4.49 mmol, 5 eq) and DMAP (329.38 mg, 2.70 mmol, 3 eq), then the mixture was stirred at 25° C. for 2 h. The combined organic layers were quenched with water (10 mL) and were extracted with DCM (4 mL*3). The resulting solution was dried over Na$_2$SO$_4$, filtered and concentrated under reduced pressure to give a residue. The residue was purified by column chromatography (SiO$_2$, EtOAc) to get the compound (S)-methyl2-((S)-3-cyclopropyl-2-(4-methoxy-1H-indole-2-carboxamido) propanamido)-3-((S)-2-oxopyrrolidin-3-yl)propanoate (250 mg, 425.06 umol, 47.30% yield, 80% purity) as yellow oil. MS (ESI) m/z 471.1 [M+H]$^+$ Step 6: N—((S)-1-(((S)-1-amino-1-oxo-3-((S)-2-oxopyrrolidin-3-yl)propan-2-yl)amino)-3-cyclopropyl-1-oxopropan-2-yl)-4-methoxy-1H-indole-2-carboxamide (S)-Methyl2-((S)-3-cyclopropyl-2-(4-methoxy-1H-indole-2-carboxamido)propanamido)-3-((S)-2-oxopyrrolidin-3-yl)propanoate (250 mg, 531.33 umol, 1 eq) was added with NH$_3$/MeOH (7M, 6.00 mL). The mixture was stirred at 80° C. for 16 h. The resulting mixture was concentrated under reduced pressure to give a residue N—((S)-1-(((S)-1-amino-1-oxo-3-((S)-2-oxopyrrolidin-3-yl)propan-2-yl) amino)-3-cyclopropyl-1-oxopropan-2-yl)-4-methoxy-1H-indole-2-carboxamide (200 mg, crude) as a solid. MS (ESI) m/z 456.1 [M+H]$^+$ Step 7: N—((S)-1-(((S)-1-cyano-2-((S)-2-oxopyrrolidin-3-yl)ethyl)amino)-3-cyclopropyl-1-oxopropan-2-yl)-4-methoxy-1H-indole-2-carboxamide To a mixture of N—((S)-1-(((S)-1-amino-1-oxo-3-((S)-2-oxopyrrolidin-3-yl)propan-2-yl) amino)-3-cyclopropyl-1-oxopropan-2-yl)-4-methoxy-1H-indole-2-carboxamide (100 mg, crude) in DCM (4 mL) was added Burgess reagent (104.63 mg, 439.07 umol, 2 eq). The mixture was stirred at 25° C. for 16 h. The reaction mixture was quenched by water (0.5 mL) and was dried by blowing N$_2$. The residue was purified by neutral prep-HPLC to get the product N—((S)-1-(((S)-1-cyano-2-((S)-2-oxopyrrolidin-3-yl)ethyl)amino)-3-cyclopropyl-1-oxopropan-2-yl)-4-methoxy-1H-indole-2-carboxamide (15 mg, 34.29 umol, 15.62% yield, 100% purity) as a solid. MS (ESI) m/z 438.2 [M+H]$^+$.
Prep-HPLC Condition:
column: Waters Xbridge BEH C18 100*25 mm*5 um; mobile phase: [water (10 mM NH$_4$HCO$_3$)—ACN]; B %: 20%-50%, 10 min.
$^1$H NMR (400 MHz, DMSO-d$_6$) δ ppm 11.57 (d, J=1.8 Hz, 1H), 8.90 (d, J=8.2 Hz, 1H), 8.50 (d, J=7.5 Hz, 1H), 7.78-7.65 (m, 1H), 7.36 (d, J=1.5 Hz, 1H), 7.13-7.04 (m, 1H), 7.03-6.96 (m, 1H), 6.50 (d, J=7.8 Hz, 1H), 5.04-4.94 (m, 1H), 4.54-4.38 (m, 1H), 3.89 (s, 3H), 3.19-3.06 (m, 2H), 2.44-2.33 (m, 1H), 2.22-2.07 (m, 2H), 1.90-1.75 (m, 2H), 1.74-1.63 (m, 1H), 1.54-1.41 (m, 1H), 0.87-0.73 (m, 1H), 0.47-0.34 (m, 2H), 0.25-0.15 (m, 1H), 0.14-0.04 (m, 1H).

Example 23. Synthesis of Viral Protease Inhibitor Compound 401

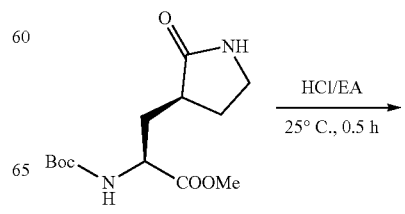

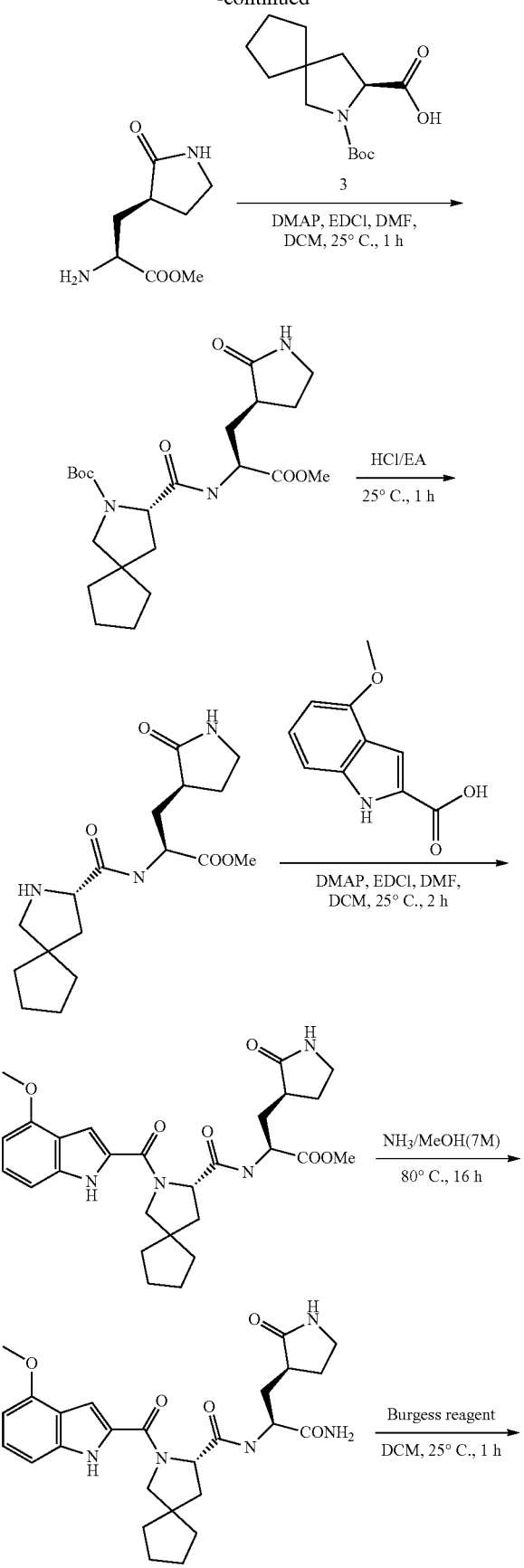

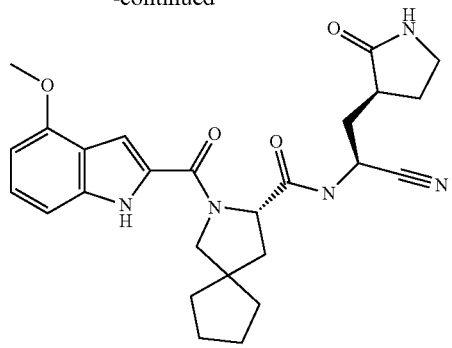

Step 1: (S)-methyl 2-amino-3-((S)-2-oxopyrrolidin-3-yl)propanoate

Methyl (2S)-2-(tert-butoxycarbonylamino)-3-[(3S)-2-oxopyrrolidin-3-yl]propanoate (400 mg, 1.40 mmol, 1 eq) in HCl/EtOAc (4 M, 10 mL, 28.63 eq) was stirred at 25° C. for 0.5 h. Upon completion, the mixture was concentrated under the reduced pressure affording the product methyl (2S)-2-amino-3-[(3S)-2-oxopyrrolidin-3-yl]propanoate (300 mg, crude, HCl) as a solid.

Step 2: (S)-tert-butyl3-(((S)-1-methoxy-1-oxo-3-((S)-2-oxopyrrolidin-3-yl)propan-2-yl)carbamoyl)-2-azaspiro[4.4]nonane-2-carboxylate Methyl (2S)-2-amino-3-[(3S)-2-oxopyrrolidin-3-yl]propanoate (300 mg, 1.35 mmol, 1 eq, HCl) and (3S)-2-tertbutoxycarbonyl-2-azaspiro[4.4]nonane-3-carboxylic acid (362.87 mg, 1.35 mmol, 1 eq) in DMF (2 mL) and DCM (5 mL) was added DMAP (329.19 mg, 2.69 mmol, 2 eq) and EDCI (516.56 mg, 2.69 mmol, 2 eq). The mixture was stirred at 25° C. for 1 h. Upon completion, the reaction mixture was quenched by addition H₂O (10 mL), and then extracted with DCM (10 mL*3). The combined organic layers were washed with brine (10 mL), dried over Na₂SO₄, filtered and concentrated under reduced pressure to give a residue. The residue was purified by column chromatography (SiO₂, petroleum ether: EtOAc=5:1 to 0:1) affording the product tert-butyl(3S)-3-[[(1S)-2-methoxy-2-oxo-1-[[(3S)-2-oxopyrrolidin-3-yl]methyl]ethyl]carbamoyl]-2-azaspiro[4.4]nonane-2-carboxylate (340 mg, 777.09 umol, 57.68% yield) as an oil.

Step 3: (S)-methyl3-((S)-2-oxopyrrolidin-3-yl)-2-((S)-2-azaspiro[4.4]nonane-3-carboxamido)propanoate tert-Butyl(3S)-3-[[(1S)-2-methoxy-2-oxo-1-[[(3S)-2-oxopyrrolidin-3-yl]methyl]ethyl]carbamoyl]-2-azaspiro[4.4]nonane-2-carboxylate (340 mg, 777.09 umol, 1 eq) in HCl/EtOAc (4 M, 10 mL, 51.47 eq) was stirred at 25° C. for 1 h. Upon completion, the mixture was concentrated under the reduced pressured affording the product methyl(2S)-2-[[(3S)-2-azaspiro[4.4]nonane-3-carbonyl]amino]-3-[(3S)-2-oxopyrrolidin-3-yl]propanoate (250 mg, crude, HCl) as an oil.

Step 4: (S)-methyl2-((S)-2-(4-methoxy-1H-indole-2-carbonyl)-2-azaspiro[4.4]nonane-3-carboxamido)-3-((S)-2-oxopyrrolidin-3-yl)propanoate Methyl(2S)-2-[[(3S)-2-azaspiro[4.4]nonane-3-carbonyl]amino]-3-[(3S)-2-oxopyrrolidin-3-yl]propanoate (250 mg, 668.67 umol, 1 eq, HCl) and 4-methoxy-1H-indole-2-carboxylic acid (127.84 mg, 668.67 umol, 1 eq) in DMF (2 mL) and DCM (6 mL) was added DMAP (163.38 mg, 1.34 mmol, 2 eq) and EDCI (256.37 mg, 1.34 mmol, 2 eq). The mixture was stirred at 25° C. for 2 h. Upon completion, the reaction mixture was quenched by addition H₂O (10 mL), and then extracted with DCM (10 mL*3). The combined organic layers were washed with brine (10 mL), dried over Na₂SO₄, filtered and concentrated under reduced pressure to give a residue. The residue was purified by prep-TLC (SiO₂, petroleum ether:EtOAc=0:1) affording the product methyl (2S)-2-[[(3S)-2-(4-methoxy-1H-indole-2-carbonyl)-2-azaspiro[4.4]nonane-3-carbonyl]amino]-3-[(3S)-2-oxopyrrolidin-3-yl]propanoate (180 mg, 352.54 umol, 52.72% yield) as an oil. MS (ESI) m/z 511.2 [M+H]⁺

Step 5: (S)—N—((S)-1-amino-1-oxo-3-((S)-2-oxopyrrolidin-3-yl)propan-2-yl)-2-(4-methoxy-1H-indole-2-carbonyl)-2-azaspiro[4.4]nonane-3-carboxamide Methyl(2S)-2-[[(3S)-2-(4-methoxy-1H-indole-2-carbonyl)-2-azaspiro[4.4]nonane-3-carbonyl]amino]-3-[(3S)-2-oxopyrrolidin-3-yl]propanoate (180 mg, 352.54 umol, 1 eq) in ammonia (7 M, 20 mL, 397.12 eq) was stirred at 80° C. for 16 h. Upon completion, the mixture was concentrated under the reduced pressure affording the product (3S)—N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.4]nonane-3-carboxamide (170 mg, crude) as an oil.

Step 6: (S)—N—((S)-1-cyano-2-((S)-2-oxopyrrolidin-3-yl)ethyl)-2-(4-methoxy-1H-indole-2-carbonyl)-2-azaspiro[4.4]nonane-3-carboxamide (3S)—N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.4]nonane-3-carboxamide (170 mg, 343.04 umol, 1 eq) in DCM (3 mL) was added methoxycarbonyl-(triethylammonio)sulfonyl-azanide (408.74 mg, 1.72 mmol, 5 eq). The mixture was stirred at 25° C. for 1 h. Upon completion, the mixture was concentrated under the reduced pressure to give a residue. The residue was purified by prep-HPLC (column: Waters Xbridge BEH C18 100*25 mm*5 um; mobile phase: [water(10 mM NH₄HCO₃)—ACN]; B %: 30%-60%, 10 min) affording the product (3S)—N-[(1S)-1-cyano-2-[(3S)-2-oxopyrrolidin-3-yl]ethyl]-2-(4-methoxy-1H-indole-2-carbonyl)-2-azaspiro[4.4]nonane-3-carboxamide (25 mg, 51.09 umol, 14.89% yield, 97.6% purity) as a solid. MS (ESI) m/z 478.2 [M+H]⁺

¹H NMR (400 MHz, MMeOD-d₄) δ=7.22-7.12 (m, 1H), 7.11-6.98 (m, 2H), 6.58-6.45 (m, 1H), 5.11-4.95 (m, 1H), 4.65-4.52 (m, 1H), 3.94 (s, 3H), 3.93-3.80 (m, 2H), 3.28-3.18 (m, 1H), 2.54-2.02 (m, 4H), 2.01-1.48 (m, 12H).

Example 24. Synthesis of Viral Protease Inhibitor Compound 225

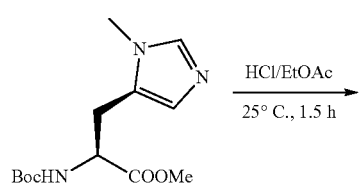

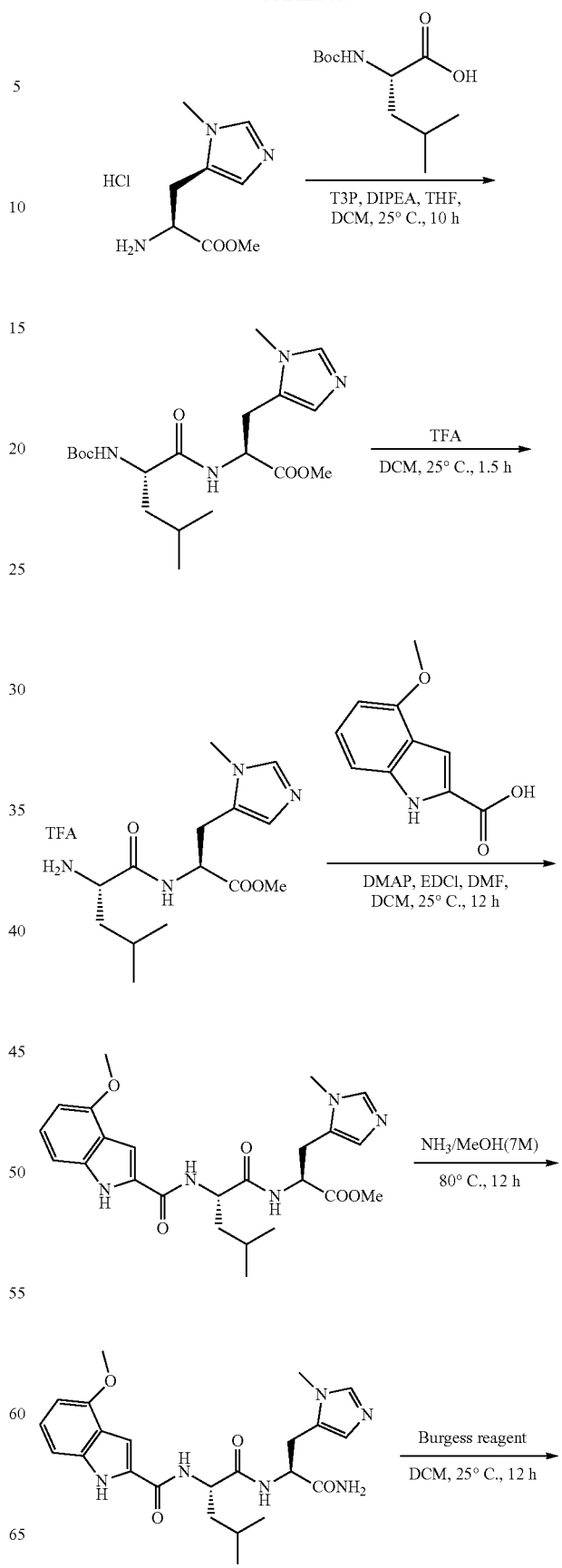

-continued

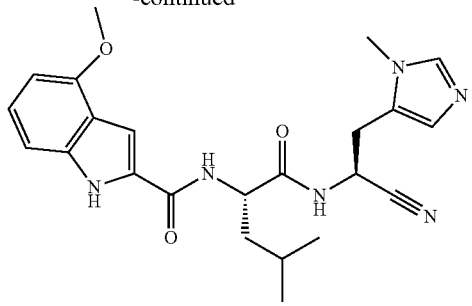

Step 1: methyl (2S)-2-amino-3-(3-methylimidazol-4-yl)propanoate

To the solution of (2S)-2-(tert-butoxycarbonylamino)-3-(3-methylimidazol-4-yl)propanoic acid (300 mg, 1.11 mmol, 1 eq) in EtOAc (1.2 mL) was added HCl/EtOAc (4 M, 2.79 mL, 10 eq) at 25° C. The reaction mixture was stirred at 25° C. for 1.5 h. The resulting mixture was concentrated to get the product. Methyl (2S)-2-amino-3-(3-methylimidazol-4-yl)propanoate (250 mg, crude, HCl) was obtained as a solid and used directly next step. MS (ESI) m/z 183.2 [M+H]

$^1$H NMR (400 MHUz, METHANOL-dl$_4$) δ ppm 8.94 (s, 1H), 7.56 (s, 1H), 4.51 (t, J=7.17 Hz, 1H), 3.93 (s, 3H), 3.87 (s, 3H), 3.46-3.55 (m, 1H), 3.32-3.42 (in, 1H).

Step 2: methyl (2S)-2-[[(2S)-2-(tert-butoxycarbonylamino)-4-methyl-pentanoyl]amino]-3-(3-methyl-imidazol-4-yl)propanoate To a mixture of methyl (2S)-2-amino-3-(3-methylimidazol-4-yl)propanoate (250 mg, 1.14 mmol, 1 eq, HCl) and (2S)-2-(tert-butoxycarbonylamino)-4-methyl-pentanoic acid (263.22 mg, 1.14 mmol, 1 eq) in THF (1 mL) and DCM (1 mL) and DIPEA (441.26 mg, 3.41 mmol, 594.69 uL, 3 eq) was added T3P (1.09 g, 1.71 mmol, 1.02 mL, 500% purity, 1.5 eq) at 0° C. under N$_2$. The mixture was stirred at 25° C. for 10 h. LCMS showed the reaction mixture was completed. The reaction mixture was added saturated sodium bicarbonate solution (10 mL) and extracted with DCM (10 mL×2) to get the organic phase. The organic phase was washed with brine (3 mL×3), dried over anhydrous sodium sulfate and concentrated to get the crude product. Methyl (2S)-2-[[(2S)-2-(tert-butoxy carbonyl amino)-4-methyl-pentanoyl]amino]-3-(3-methylimidazol-4-yl)propanoate (360 mg, crude) was obtained as an oil and used directly next step. MS (ESI) m/z 397.3 [M+H]$^+$

Step 3: methyl(2S)-2-[[(2S)-2-amino-4-methyl-pentanoyl]amino]-3-(3-methylimidazol-4-yl)propanoate To a mixture of methyl (2S)-2-[[(2S)-2-(tert-butoxycarbonylamino)-4-methyl-pentanoyl]amino]-3-(3-methylimidazol-4-yl)propanoate (360 mg, 907.99 umol, 1 eq) in DCM (3.3 mL) was added TFA (1.04 g, 9.08 mmol, 672.27 uL, 10 eq) at 25° C. under N$_2$. The mixture was stirred at 25° C. for 1.5 h. LCMS showed the reaction mixture was completed. The reaction mixture was concentrated to get the product. Methyl (2S)-2-[[(2S)-2-amino-4-methyl-pentanoyl]amino]-3-(3-methylimidazol-4-yl) propanoate (370 mg, crude, TFA) was obtained as an oil and used directly next step. MS (ESI) m/z 297.2 [M+H]$^+$

Step 4: methyl (2S)-2-[[(2S)-2-[(4-methoxy-1H-indole-2-carbonyl)amino]-4-methyl-pentanoyl]amino]-3-(3-methylimidazol-4-yl)propanoate To a mixture of methyl (2S)-2-[[(2S)-2-amino-4-methyl-pentanoyl]amino]-3-(3-methylimidazol-4-yl)propanoate (370 mg, 1.25 mmol, 1 eq, TFA) and 4-methoxy-1H-indole-2-carboxylic acid (238.69 mg, 1.25 mmol, 1 eq) in DMF (1.5 mL) and DCM (1.5 mL) was added EDCI (478.66 mg, 2.50 mmol, 2 eq) and DMAP (305.05 mg, 2.50 mmol, 2 eq) in one portion at 25° C. under N$_2$. The mixture was stirred at 25° C. for 12 h. The resulting mixture was added with water (10 mL) and extracted with DCM (10 mL*2) to get the organic phase. The organic phase was washed with brine (3 mL*3) and dried over anhydrous sodium sulfate and concentrated to get the crude product. The residue was purified by column chromatography (SiO2, petroleum ether/EtOAc=2/1 to EtOAc/Methanol=10/1). Methyl (2S)-2-[[(2S)-2-[(4-methoxy-1H-indole-2-carbonyl)amino]-4-methyl-pentanoyl]amino]-3-(3-methylimidazol-4-yl)propanoate (270 mg, crude) was obtained as an oil. MS (ESI) m/z 469.5 [M+H]$^+$

Step 5: N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide To methyl (2S)-2-[[(2S)-2-[(4-methoxy-1H-indole-2-carbonyl)amino]-4-methyl-pentanoyl]amino]-3-(3-methylimidazol-4-yl)propanoate (235.00 mg, 500.50 umol, 1 eq) was added NH$_3$/MeOH (7 M, 1.94 mL, 27.14 eq) in one portion at 25° C. under N$_2$. The mixture was stirred at 80° C. and stirred for 12 h. LCMS showed the reaction mixture was completed. The reaction mixture was cooled to 25° C. and concentrated to get the crude product. The residue was purified by prep-TLC. N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide (170 mg, crude) was obtained as a solid. MS (ESI) m/z 455.3 [M+H]$^+$

Step 6: N-[(1S)-1-[[(S)-1-cyano-2-(3-methylimidazol-4-yl)ethyl]carbamoyl]-3-methyl-butyl]-4-methoxy-1H-indole-2-carboxamide To a mixture of N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide (140 mg, 308.02 umol, 1 eq) in DCM (2 mL) was added Burgess reagent (293.61 mg, 1.23 mmol, 4 eq) at 25° C. under N$_2$. The mixture was stirred at 25° C. for 12 h, and then concentrated to get the crude product. The crude product was purified by pre-HPLC. N-[(1S)-1-[[(1S)-1-cyano-2-(3-methylimidazol-4-yl)ethyl]carbamoyl]-3-methyl-butyl]-4-methoxy-1H-indole-2-carboxamide (10.59 mg, 23.82 umol, 7.73% yield, 98.2% purity) was obtained as a solid. MS (ESI) m/z 437.2 [M+H]$^+$.

Prep-HPLC Condition:
column: Phenomenex Gemini-NX C18 75*30 mm*3 um; mobile phase: [water(10 mM NH$_4$HCO$_3$)—ACN]; B %: 25%-50%, 6 min
column: Waters Xbridge BEH C18 100*30 mm*10 um; mobile phase: [water(10 mM NH$_4$HCO$_3$)—ACN]; B %: 20%-45%, 8 min $^1$H NMR (400 MHz, METHANOL-d$_4$) δ ppm 7.52-7.57 (m, 1H), 7.28 (s, 1H), 7.12-7.18 (m, 1H), 7.03 (d, J=8.38 Hz, 1H), 6.85-6.96 (m, 1H), 6.52 (d, J=7.72 Hz, 1H), 5.05-5.13

(m, 1H), 4.55-4.62 (m, 1H), 3.86-3.99 (m, 3H), 3.68 (s, 3H), 3.21 (tt, J=15.24, 7.80 Hz, 2H), 1.55-1.81 (m, 3H), 0.86-1.07 (m, 6H)

Example 25. Synthesis of Viral Protease Inhibitor Compound 227

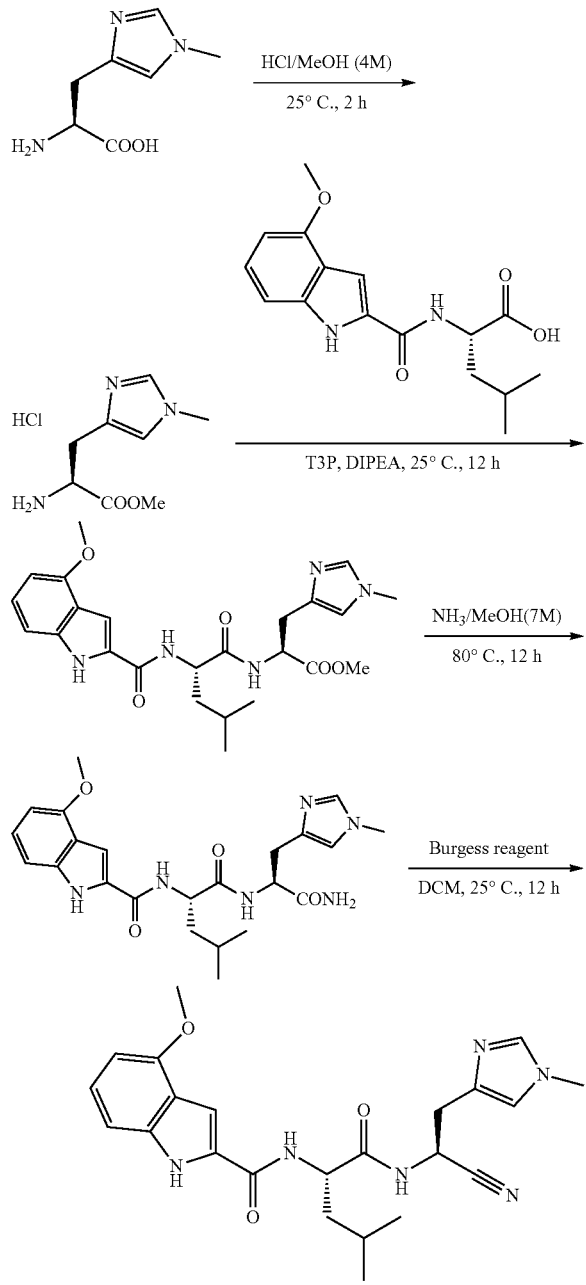

Step 1: methyl (2S)-2-amino-3-(1-methylimidazol-4-yl)propanoate

To a mixture of (2S)-2-amino-3-(1-methylimidazol-4-yl) propanoic acid (0.5 g, 2.96 mmol, 1 eq) was added HCl/MeOH (4 M, 7.39 mL, 10 eq) in one portion at 25° C. under $N_2$. The mixture was stirred at 25° C. for 2 h. The reaction mixture was concentrated to get the product. Methyl (2S)-2-amino-3-(1-methylimidazol-4-yl)propanoate (0.6 g, crude, HCl) was obtained as a solid and used directly next step. MS (ESI) m/z 184.1 [M+H]$^+$ Step 2: methyl (2S)-2-[[(2S)-2-[(4-methoxy-1H-indole-2-carbonyl)amino]-4-methyl-pentanoyl]amino]-3-(1-methylimidazol-4-yl)propanoate To a mixture of (2S)-2-[(4-methoxy-1H-indole-2-carbonyl)amino]-4-methyl-pentanoic acid (498.76 mg, 1.64 mmol, 1.2 eq) and methyl (2S)-2-amino-3-(1-methylimidazol-4-yl)propanoate (0.3 g, 1.37 mmol, 1 eq, HCl), DIPEA (882.53 mg, 6.83 mmol, 1.19 mL, 5 eq) in THF (0.9 mL) and DCM (0.9 mL) was added T3P (1.30 g, 2.05 mmol, 1.22 mL, 50% purity, 1.5 eq) at 0° C. under $N_2$. The mixture was stirred at 25° C. for 12 h. The reaction mixture was added to saturated sodium bicarbonate solution (10 mL) and extracted with DCM (10 mL*2) to get the organic phase. The organic phase was washed with brine (3 mL*3) and dried over anhydrous sodium sulfate and concentrated to get the crude product. The residue was purified by prep-HPLC. Methyl (2S)-2-[[(2S)-2-[(4-methoxy-1H-indole-2-carbonyl)amino]-4-methyl-pentanoyl]amino]-3-(1-methylimidazol-4-yl)propanoate (100 mg, 202.97 umol, 14.86% yield, 95.3% purity) was obtained as a solid. MS (ESI) m/z 470.2 [M+H]$^+$ Prep-HPLC Condition:
column: Kromasil $C_{18}$ (250*50 mm*10 um); mobile phase: [water(10 mM $NH_4HCO_3$)—ACN]; B %: 25%-50%, 10 min Step 3: N-[(1S)-1-[[(1S)-2-amino-1-[(1-methylimidazol-4-yl)methyl]-2-oxo-ethyl]carbamoyl]-3-methyl-butyl]-4-methoxy-1H-indole-2-carboxamide To methyl (2S)-2-[[(2S)-2-[(4-methoxy-1H-indole-2-carbonyl)amino]-4-methyl-pentanoyl]amino]-3-(1-methylimidazol-4-yl)propanoate (100 mg, 212.98 umol, 1 eq) was added $NH_3$/MeOH (7 M, 10.00 mL, 328.67 eq) in one portion at 25° C. under $N_2$. The mixture was stirred at 80° C. for 12 h. The reaction mixture was cooled to 25° C. and concentrated to get the product. N-[(1S)-1-[[(1S)-2-amino-1-[(1-methylimidazol-4-yl)methyl]-2-oxo-ethyl]carbamoyl]-3-methyl-butyl]-4-methoxy-1H-indole-2-carboxamide (95.5 mg, 190.57 umol, 89.48% yield, 90.7% purity) was obtained as a solid and used directly next step. MS (ESI) m/z 455.2 [M+H]$^+$ Step 4: N-[(1S)-1-[[(1S)-1-cyano-2-(1-methylimidazol-4-yl)ethyl]carbamoyl]-3-methyl-butyl]-4-methoxy-]H-indole-2-carboxamide To a mixture of N-[(1S)-1-[[(1S)-2-amino-1-[(1-methylimidazol-4-yl)methyl]-2-oxo-ethyl]carbamoyl]-3-methyl-butyl]-4-methoxy-1H-indole-2-carboxamide (80.00 mg, 176.01 umol, 1 eq) in DCM (1 mL) was added Burgess reagent (83.89 mg, 352.02 umol, 2 eq) in one portion at 25° C. under $N_2$. The mixture was stirred at 25° C. for 12 h. The reaction mixture was added the water (0.3 mL) and stirred for 10 min. Then the reaction mixture was concentrated to get the crude product. The crude product was purified by prep-HPLC. N-[(1S)-1-[[(1S)-1-cyano-2-(1-methylimidazol-4-yl)ethyl]carbamoyl]-3-methyl-butyl]-4-methoxy-1H-indole-2-carboxamide (26.39 mg, 60.27 umol, 34.24% yield, 99.684% purity) was obtained as a solid. MS (ESI) m/z 437.2 [M+H]$^+$ Prep-HPLC Condition:
column: Waters Xbridge BEH $C_{18}$ 100*25 mm*5 um; mobile phase: [water(10 mM $NH_4HCO_3$) —ACN]; B %: 25%-55%, 10 min $^1$H NMR (400 MHz, METHANOL-$d_4$) δ ppm 7.35 (s, 1H), 7.28 (s, 1H), 7.12-7.20 (m, 1H), 7.05 (d, J=8.38 Hz, 1H), 6.91-6.98 (m, 1H), 6.53 (d, J=7.72 Hz, 1H), 5.01 (t, J=7.06 Hz, 1H), 4.63 (br dd, J=9.59, 4.96 Hz, 1H), 3.94 (s, 3H), 3.46-3.59 (m, 3H), 3.00-3.13 (m, 2H), 1.61-1.81 (m, 3H), 0.89-1.07 (m, 6H)

Step 5: tert-butyl (2S)-2-[(4-methoxy-1H-indole-2-carbonyl)amino]-4-methyl-pentanoate To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under $N_2$. The mixture was stirred at 25° C. and stirred for 2 h. The reaction mixture was added water (90 mL) and extracted with EtOAc (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography ($SiO_2$, petroleum ether: EtOAc=30:1 to 10:1). Tert-butyl (2S)-2-[(4-methoxy-1H-indole-2-carbonyl)amino]-4-methyl-pentanoate (5.93 g, 16.45 mmol, 62.91% yield) was obtained as solid. MS (ESI) m/z 361.2 [M+H]$^+$ $^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 6: (2S)-2-[(4-methoxy-1H-indole-2-carbonyl)amino]-4-methyl-pentanoic acid

To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and $H_2O$ (666.67 mg, 37.01 mmol, 666.67 uL, 6.67 eq) in one portion at 0° C. under $N_2$. The mixture was stirred at 25° C. and stirred for 4 h. The reaction mixture was concentrated to get the crude product. (2S)-2-[(4-methoxy-1H-indole-2-carbonyl)amino]-4-methyl-pentanoic acid (2.24 g, 5.35 mmol, 96.50% yield, TFA) was obtained as a solid and used directly next step. MS (ESI) m/z 305.1 [M+H]$^+$ Example 26. Synthesis of Viral Protease Inhibitor Compound 231

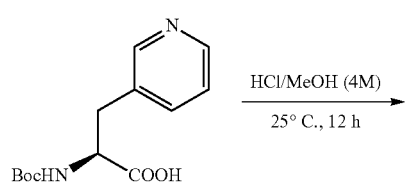

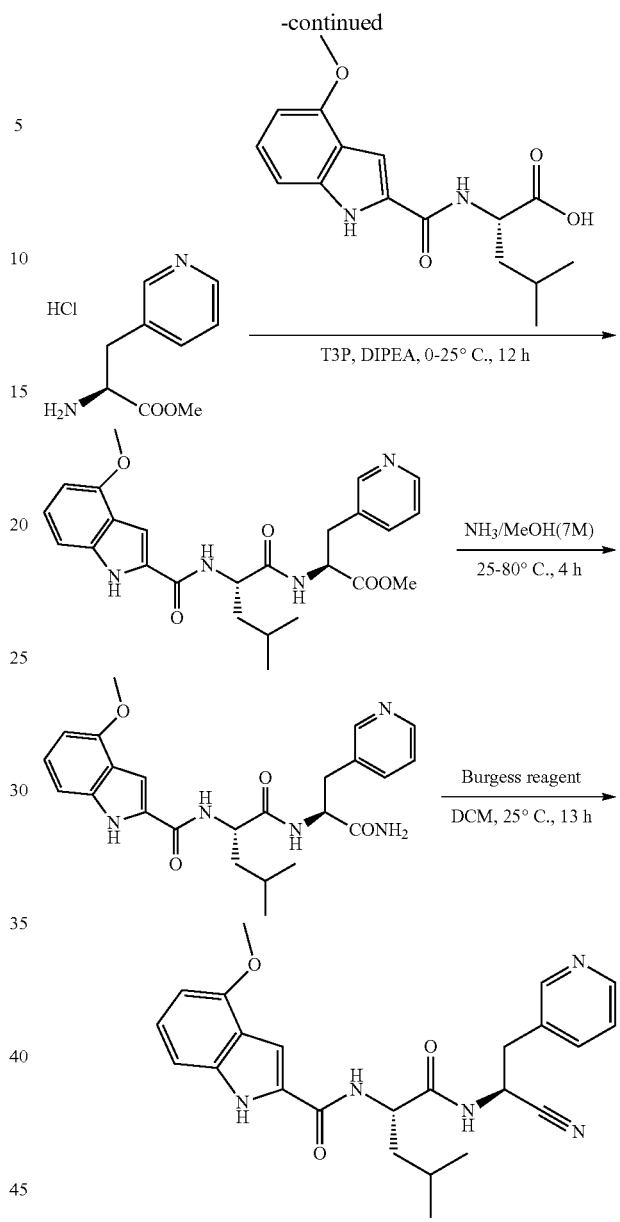

Step 1: (S)-methyl 2-amino-3-(pyridin-3-yl)propanoate hydrochloride

To a mixture of (2S)-2-(tert-butoxycarbonylamino)-3-(3-pyridyl)propanoic acid (500 mg, 1.88 mmol, 1 eq) was added HCl/MeOH (4 M, 20.80 mL, 44.31 eq) in one portion at 25° C. under $N_2$. The mixture was stirred at 25° C. and stirred for 12 h. Upon completion, the reaction mixture was concentrated to get methyl (2S)-2-amino-3-(3-pyridyl)propanoate (400 mg, crude, HCl) as an oil and used directly for the next step. MS (ESI) m/z 181.1 [M+H]$^+$ Step 2: (S)-methyl 2-((S)-2-(4-methoxy-1H-indole-2-carboxamido)-4-methylpentanamido)-3-(pyridine-3-yl)propanoate To a mixture of methyl (2S)-2-amino-3-(3-pyridyl)propanoate (0.3 g, 1.66 mmol, 1 eq, HCl) and (2S)-2-[(4-methoxy-1H-indole-2-carbonyl)amino]-4-methyl-pentanoic acid (506.66 mg, 1.66 mmol, 1 eq), DIPEA (1.08 g, 8.32 mmol, 1.45 mL, 5 eq) in THF (0.6 mL) and DCM (0.6 mL) was added T3P (1.59 g, 2.50 mmol, 1.49 mL, 50% purity, 1.5 eq) at 0° C. under N2. The mixture was stirred at 25° C. for 12 h. Upon completion, the reaction mixture was added saturated sodium bicarbonate solution (10 mL) and extracted with DCM (10 mL*2) to get the organic phase. The organic phase was concentrated to get the crude product. The residue was purified by pulping with petroleum ether (20 mL) and filtered to get the filter cake as the product. Methyl (2S)-2-[[(2S)-2-[(4-methoxy-1H-indole-2-carbonyl)amino]-4-methyl-pentanoyl]amino]-3-(3-pyridyl)propanoate (0.4 g, crude) was obtained as a solid and used directly next step. MS (ESI) m/z 467.1 [M+H]$^+$ Step 3: N—((S)-1-(((S)-1-amino-1-oxo-3-(pyridin-3-yl)propan-2-yl)amino)-4-methyl-1-oxopentan-2-yl)-4-methoxy-1H-indole-2-carboxamide To a mixture of methyl (2S)-2-[[(2S)-2-[(4-methoxy-1H-indole-2-carbonyl)amino]-4-methyl-pentanoyl]amino]-3-(3-pyridyl)propanoate (200.00 mg, 428.70 umol, 1 eq) was added NH$_3$/MeOH (7 M, 5 mL, 81.64 eq) in one portion at 25° C. under N$_2$. The mixture was stirred at 80° C. for 4 h. Upon completion, the reaction mixture was cooled to 25° C. and concentrated to get N-[(1S)-1-[[(1S)-2-amino-2-oxo-1-(3-pyridylmethyl)ethyl]carbamoyl]-3-methyl-butyl]-4-methoxy-1H-indole-2-carboxamide (0.18 g, 339.65 umol, 79.23% yield, 85.2% purity) as a solid and used directly next step. MS (ESI) m/z 452.2 [M+H]$^+$ Step 3: N—((S)-1-(((S)-1-cyano-2-(pyridin-3-yl)ethyl)amino)-4-methyl-1-oxopentan-2-yl)-4-methoxy-1H-indole-2-carboxamide To a mixture of N-[(1S)-1-[[(1S)-2-amino-2-oxo-1-(3-pyridylmethyl)ethyl]carbamoyl]-3-methyl-butyl]-4-methoxy-1H-indole-2-carboxamide (0.1 g, 221.48 umol, 1 eq) in DCM (1 mL) was added Burgess reagent (105.56 mg, 442.95 umol, 2 eq) in one portion at 25° C. under N$_2$. The mixture was stirred at 25° C. for 12 h. The Burgess reagent (105.56 mg, 442.95 umol, 2 eq) was re-added into the above solution at 25° C. and the reaction mixture was stirred at 25° C. for 1 h. Upon completion, the reaction mixture was added the water (0.5 mL) and stirred for 10 min. Then the mixture was concentrated to get the crude product. The crude product was purified by pre-HPLC to give N-[(1S)-1-[[(1S)-1-cyano-2-(3-pyridyl)ethyl]carbamoyl]-3-methyl-butyl]-4-methoxy-1H-indole-2-carboxamide (23.18 mg, 52.94 umol, 23.90% yield, 99.009% purity) as a solid. MS (ESI) m/z 434.2 [M+H]$^+$ Prep-HPLC Condition:
column: Waters Xbridge BEH C18 100*25 mm*5 um; mobile phase: [water(10 mM NH$_4$HCO$_3$)—ACN]; B %: 30%-60%, 10 min $^1$H NMR (400 MHz, METHANOL-d$_4$) δ ppm 8.47-8.52 (m, 1H), 8.34-8.45 (m, 1H), 7.77-7.84 (m, 1H), 7.28-7.38 (m, 1H), 7.23-7.28 (m, 1H), 7.12-7.19 (m, 1H), 6.99-7.07 (m, 1H), 6.52 (d, J=7.63 Hz, 1H), 5.08-5.18 (m, 1H), 4.48-4.61 (m, 1H), 3.94 (s, 3H), 3.12-3.29 (m, 2H), 1.41-1.76 (m, 3H), 0.87-1.03 (m, 6H).

Step 5: (S)-tert-butyl 2-(4-methoxy-1H-indole-2-carboxamido)-4-methylpentanoate

To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under N$_2$. The mixture was stirred at 25° C. and stirred for 2 h. Upon completion, the reaction mixture was added water (90 mL) and extracted with ethyl acetate (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the crude product. The residue was purified by column chromatography (SiO$_2$, petroleum ether: EtOAc=30:1 to 10:1) to give tert-butyl (2S)-2-[(4-methoxy-1H-indole-2-carbonyl)amino]-4-methyl-pentanoate (5.93 g, 16.45 mmol, 62.91% yield) as a solid. MS (ESI) m/z 361.2 [M+H]$^+$ $^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 6: (S)-2-(4-methoxy-1H-indole-2-carboxamido)-4-methylpentanoic acid

To a mixture of tert-butyl (2S)-2-[(4-methoxy-1H-indole-2-carbonyl)amino]-4-methyl-pentanoate (0.5 g, 1.39 mmol, 1 eq) in DCM (0.33 mL) was added TFA (2.57 g, 22.51 mmol, 1.67 mL, 16.23 eq) and H$_2$O (166.71 mg, 9.25 mmol, 166.71 uL, 6.67 eq) in one portion at 0° C. under N$_2$. The mixture was stirred at 25° C. and stirred for 2 h. Upon completion, the reaction mixture was concentrated to give (S)-2-(4-methoxy-1H-indole-2-carboxamido)-4-methylpentanoic acid (400 mg, crude, TFA) as a solid and used directly next step. MS (ESI) m z 305.1 [M+H]$^+$ Example 27. Synthesis of Viral Protease Inhibitor Compound 599

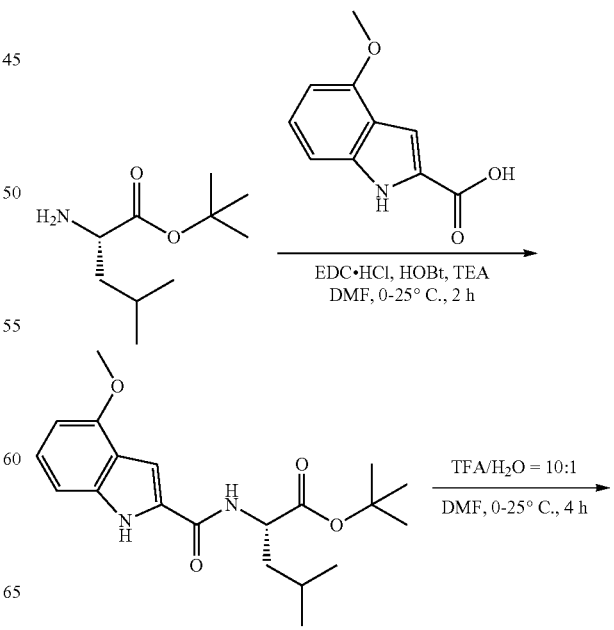

-continued

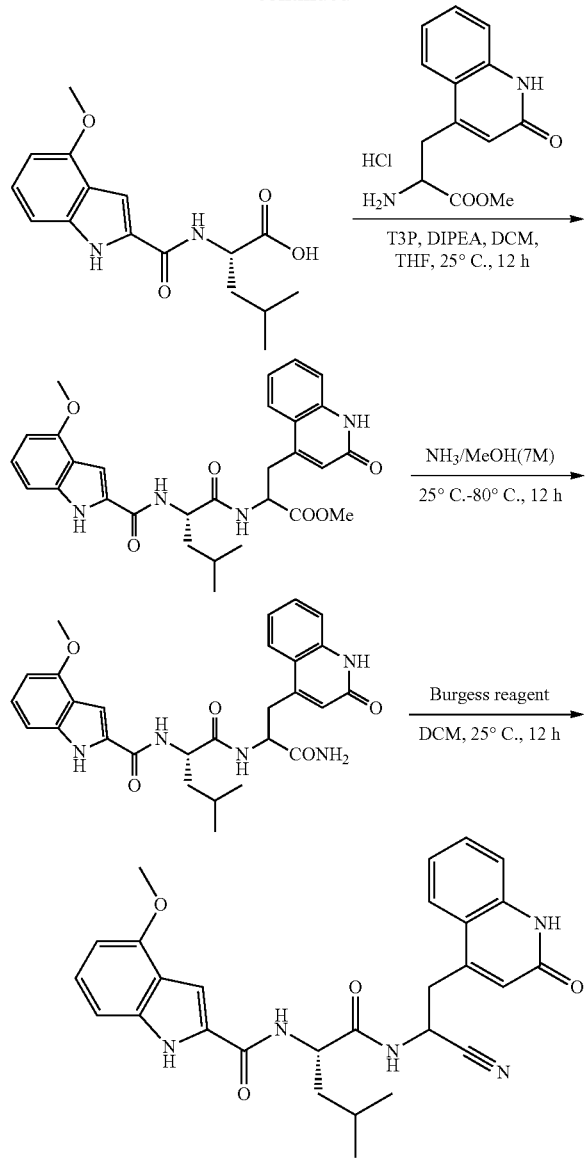

Step 1: tert-butyl (2S)-2-[(4-methoxy-1H-indole-2-carbonyl)amino]-4-methyl-pentanoate To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under $N_2$. The mixture was stirred at 25° C. and stirred for 2 h. The reaction mixture was added with water (90 mL) and extracted with EtOAc (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography ($SiO_2$, petroleum ether: EtOAc=30:1 to 10:1). Tert-butyl (2S)-2-[(4-methoxy-1H-indole-2-carbonyl) amino]-4-methyl-pentanoate (5.93 g, 16.45 mmol, 62.91% yield) was obtained as a solid. MS (ESI) m/z 361.2 $[M+H]^+$ $^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 2: (2S)-2-[(4-methoxy-1H-indole-2-carbonyl) amino]-4-methyl-pentanoic acid

To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and $H_2O$ (666.67 mg, 37.01 mmol, 666.67 uL, 6.67 eq) in one portion at 0° C. under $N_2$. The mixture was stirred at 25° C. and stirred for 4 h. The reaction mixture was concentrated to get the crude product. (2S)-2-[(4-methoxy-1H-indole-2-carbonyl)amino]-4-methyl-pentanoic acid (2.24 g, 5.35 mmol, 96.50% yield, TFA) was obtained as a solid and used directly next step. MS (ESI) m/z 305.1 $[M+H]^+$ Step 3: methyl 2-[[(2S)-2-[(4-methoxy-1H-indole-2-carbonyl)amino]-4-methyl-pentanoyl]amino]-3-(2-oxo-1H-quinolin-4-yl)propanoate To a mixture of (2S)-2-[(4-methoxy-1H-indole-2-carbonyl)amino]-4-methyl-pentanoic acid (568.23 mg, 1.36 mmol, 1.2 eq, TFA) and methyl 2-amino-3-(2-oxo-1H-quinolin-4-yl)propanoate (320 mg, 1.13 mmol, 1 eq, HCl), DIPEA (731.40 mg, 5.66 mmol, 985.72 uL, 5 eq) in THF (1 mL) and DCM (1 mL) was added T3P (1.08 g, 1.70 mmol, 1.01 mL, 50% purity, 1.5 eq) at 0° C. under $N_2$. The mixture was stirred at 25° C. for 12 h. The reaction mixture was added with saturated sodium bicarbonate solution (10 mL) and extracted with DCM (10 mL*2) to get the organic phase. The organic phase was concentrated to get the crude product. The residue was purified by prep-HPLC. Methyl 2-[[(2S)-2-[(4-methoxy-1H-indole-2-carbonyl)amino]-4-methyl-pentanoyl]amino]-3-(2-oxo-1H-quinolin-4-yl)propanoate (0.2 g, 375.53 umol, 33.18% yield) was obtained as a solid. MS (ESI) m/z 533.2 $[M+H]^+$ Prep-HPLC Condition:

column: Kromasil C18 (250*50 mm*10 um); mobile phase: [water(10 mM $NH_4HCO_3$)—ACN]; B %: 30%-60%, 10 min Step 4: N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide To a mixture of methyl 2-[[(2S)-2-[(4-methoxy-1H-indole-2-carbonyl)amino]-4-methyl-pentanoyl]amino]-3-(2-oxo-1H-quinolin-4-yl)propanoate (200.00 mg, 375.53 umol, 1 eq) was added $NH_3$/MeOH (7 M, 10.00 mL, 186.41 eq) in one portion at 25° C. under $N_2$. The mixture was stirred at 80° C. for 12 h. The reaction mixture was cooled to 25° C. and concentrated to get the product. N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide (180 mg, 326.21 umol, 86.87% yield, 93.8% purity) was obtained as a solid and used directly next step. MS (ESI) m/z 518.2 $[M+H]^+$

Step 5: N-[(1S)-1-[[I-cyano-2-(2-oxo-1H-quinolin-4-yl)ethyl]carbamoyl]-3-methyl-butyl]-4-methoxy-1H-indole-2-carboxamide To a mixture of N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide (90 mg, 173.89 umol, 1 eq) in DCM (5 mL) was added Burgess reagent (207.19 mg, 869.44 umol, 5 eq) in one portion at 25° C. under N₂. The mixture was stirred at 25° C. for 12 h, and then concentrated to get the crude product.

The residue was purified by prep-HPLC. N-[(1S)-1-[[1-cyano-2-(2-oxo-1H-quinolin-4-yl)ethyl]carbamoyl]-3-methyl-butyl]-4-methoxy-1H-indole-2-carboxamide (20.74 mg, 41.13 umol, 23.66% yield, 99.079% purity) was obtained as a solid. MS (ESI) m/z 500.2 [M+H]⁺

Prep-HPLC Condition:
column: Waters Xbridge BEH C18 100*25 mm*5 um; mobile phase: [water(10 mM NH₄HCO₃)—ACN]; B %: 30%-65%, 10 min ¹H NMR (400 MHz, METHANOL-d₄) δ ppm 7.93 (br d, J=8.16 Hz, 1H), 7.50-7.58 (m, 1H), 7.28-7.40 (m, 2H), 7.26 (dd, J=11.47, 0.66 Hz, 1H), 7.11-7.19 (m, 1H), 7.04 (dd, J=8.27, 4.08 Hz, 1H), 6.59-6.70 (m, 1H), 6.46-6.56 (m, 1H), 5.24-5.34 (m, 1H), 4.53 (td, J=10.31, 5.18 Hz, 1H), 3.93 (d, J=4.41 Hz, 3H), 3.40-3.59 (m, 3H), 1.72 (ddd, J=15.16, 9.87, 5.18 Hz, 1H), 1.53-1.66 (m, 2H), 1.40-1.50 (m, 1H), 0.87-1.01 (m, 5H)

Step 6: methyl 2-amino-3-(2-oxo-1H-quinolin-4-yl)propanoate

To 2-amino-3-(2-oxo-1H-quinolin-4-yl)propanoic acid (400 mg, 1.72 mmol, 1 eq) was added HCl/MeOH (4 M, 4.31 mL, 10 eq) in one portion at 25° C. under N₂. The mixture was stirred at 25° C. and stirred for 1 h. The reaction mixture was concentrated to get the product. Methyl 2-amino-3-(2-oxo-1H-quinolin-4-yl)propanoate (370 mg, crude, HCl) was obtained as a solid and used directly next step.

Example 28. Synthesis of Viral Protease Inhibitor Compound 249

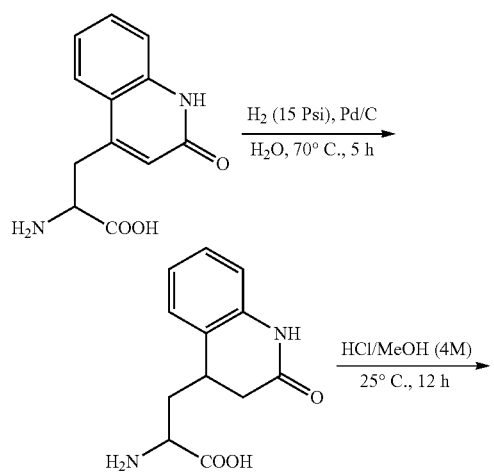

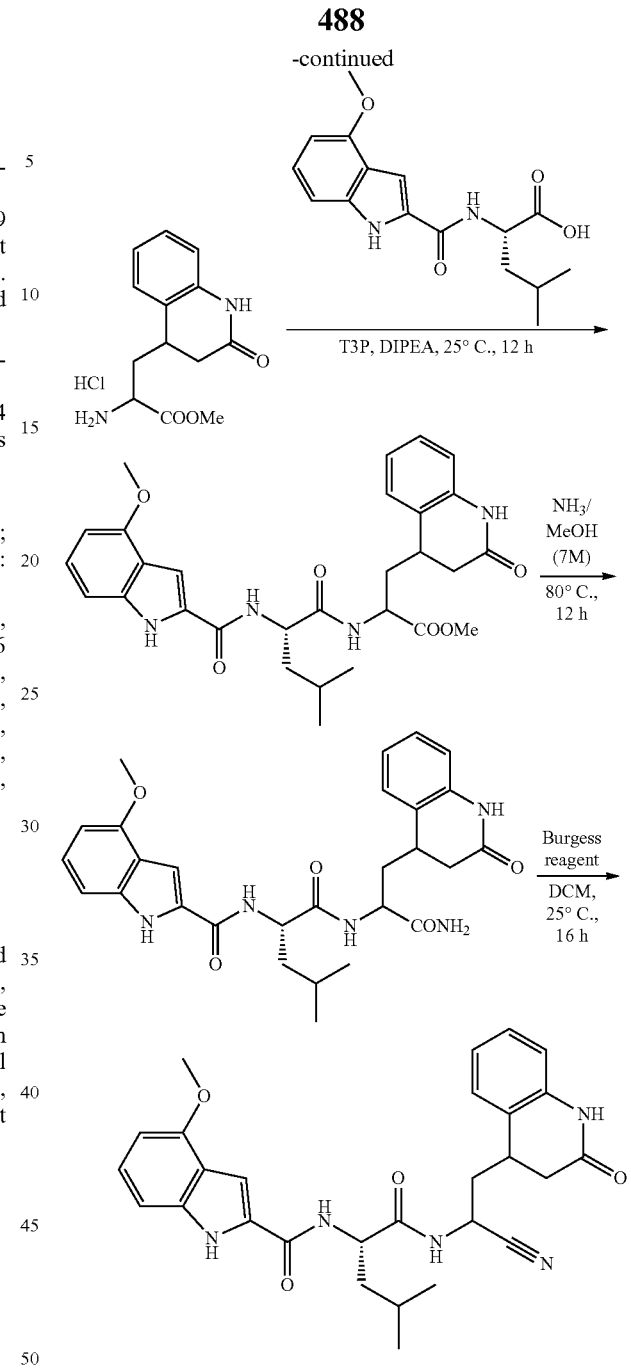

Step 1: 2-amino-3-(2-oxo-3,4-dihydro-1H-quinolin-4-yl)propanoic acid

To a solution of 2-amino-3-(2-oxo-1H-quinolin-4-yl)propanoic acid (200 mg, 861.20 umol, 1 eq) in H₂O (1 mL) was added Pd/C (20 mg, 861.20 umol, 10% purity) at 25° C. under N₂. The suspension was degassed under vacuum and purged with H₂ several times. The mixture was stirred under H₂ (861.20 umol) (15 psi) at 70° C. for 5 h. The reaction mixture was cooled to 25° C. and filtered to get the filtrate. The filtrate was concentrated to get the product. 2-amino-3-(2-oxo-3,4-dihydro-1H-quinolin-4-yl)propanoic acid (200 mg, crude) was obtained as a solid and used directly next step. MS (ESI) m/z 235.0 [M+H]⁺

¹H NMR (400 MHz, METHANOL-d₄) δ ppm 1.92-2.03 (m, 1H) 2.06-2.21 (m, 1H) 2.45-2.62 (m, 1H) 2.86 (dd, J=16.43, 6.06 Hz, 1H) 3.32-3.40 (m, 1H) 3.83 (br dd, J=8.49, 5.84 Hz, 1H) 3.93 (br t, J=6.95 Hz, 1H) 6.93 (d, J=7.72 Hz, 1H) 7.01-7.10 (m, 1H) 7.24 (br t, J=7.72 Hz, 1H) 7.36 (d, J=7.06 Hz, 1H)

Step 2: methyl 2-amino-3-(2-oxo-3,4-dihydro-1H-quinolin-4-yl)propanoate

To 2-amino-3-(2-oxo-3,4-dihydro-1H-quinolin-4-yl)propanoic acid (200 mg, 853.79 umol, 1 eq) was added HCl/MeOH (4 M, 9.91 mL, 46.45 eq) in one portion at 25° C. under $N_2$. The mixture was stirred at 25° C. for 12 h. The reaction mixture was concentrated to get the crude product. Methyl 2-amino-3-(2-oxo-3,4-dihydro-1H-quinolin-4-yl)propanoate (260 mg, crude, HCl) was obtained as the yellow oil and used directly next step. MS (ESI) m/z 249.1 [M+H]$^+$

Step 3: methyl 2-[[(2S)-2-[(4-methoxy-1H-indole-2-carbonyl)amino]-4-methyl-pentanoyl]amino]-3-(2-oxo-3,4-dihydro-1H-quinolin-4-yl)propanoate To a mixture of methyl 2-amino-3-(2-oxo-3,4-dihydro-1H-quinolin-4-yl)propanoate (260 mg, 913.12 umol, 1 eq, HCl) and (2S)-2-[(4-methoxy-1H-indole-2-carbonyl)amino]-4-methyl-pentanoic acid (277.90 mg, 913.12 umol, 1 eq), DIPEA (590.07 mg, 4.57 mmol, 795.24 uL, 5 eq) in THF (0.6 mL) and DCM (0.6 mL) was added T3P (871.61 mg, 1.37 mmol, 814.59 uL, 50% purity, 1.5 eq) at 0° C. under $N_2$. The mixture was stirred at 25° C. for 12 h. The reaction mixture was added saturated sodium bicarbonate solution (10 mL) and extracted with DCM (10 mL*2) to get the organic phase. The organic phase was concentrated to get the crude product. The residue was purified by pre-HPLC. Methyl 2-[[(2S)-2-[(4-methoxy-1H-indole-2-carbonyl)amino]-4-methyl-pentanoyl]amino]-3-(2-oxo-3,4-dihydro-1H-quinolin-4-yl)propanoate (85 mg, 151.05 umol, 16.54% yield, 95% purity) was obtained as a solid. MS (ESI) m/z 535.2 [M+H]$^+$
Prep-HPLC Condition:
column: Phenomenex Gemini-NX 80*40 mm*3 um; mobile phase: [water(10 mM NH$_4$HCO3)—ACN]; B %: 27%-47%, 8 min

Step 4: N-[(1S)-1-[[2-amino-2-oxo-1-[(2-oxo-3,4-dihydro-1H-quinolin-4-yl)methyl]ethyl]carbamoyl]-3-methyl-butyl]-4-methoxy-1H-indole-2-carboxamide To a mixture of methyl 2-[[(2S)-2-[(4-methoxy-1H-indole-2-carbonyl)amino]-4-methyl-pentanoyl]amino]-3-(2-oxo-3,4-dihydro-1H-quinolin-4-yl)propanoate (55 mg, 102.88 umol, 1 eq) was added NH$_3$/MeOH (7 M, 1.83 mL, 124.74 eq) in one portion at 25° C. under $N_2$. The mixture was stirred at 80° C. for 12 h. The reaction mixture was cooled to the 25° C. and concentrated to get the product. N-[(1S)-1-[[2-amino-2-oxo-1-[(2-oxo-3,4-dihydro-1H-quinolin-4-yl)methyl]ethyl]carbamoyl]-3-methyl-butyl]-4-methoxy-1H-indole-2-carboxamide (55 mg, crude) was obtained as a solid and used directly next step. MS (ESI) m/z 518.2 [M+H]$^+$

Step 5: N-[(1S)-1-[[1-cyano-2-(2-oxo-1H-quinolin-4-yl)ethyl]carbamoyl]-3-methyl-butyl]-4-methoxy-1H-indole-2-carboxamide To a mixture of N-[(1S)-1-[[2-amino-2-oxo-1-[(2-oxo-3,4-dihydro-1H-quinolin-4-yl)methyl]ethyl]carbamoyl]-3-methyl-butyl]-4-methoxy-1H-indole-2-carboxamide (75 mg, 144.34 umol, 1 eq) in DCM (0.1 mL) was added Burgess reagent (103.19 mg, 433.03 umol, 3 eq) in one portion at 25° C. under $N_2$. The mixture was stirred at 25° C. and stirred for 16 h. The reaction mixture was added with water (0.5 mL) and stirred for 10 min. Then the mixture was concentrated to get the crude product. The crude product was purified by pre-HPLC. N-[(1S)-1-[[1-cyano-2-(2-oxo-3,4-dihydro-1H-quinolin-4-yl) ethyl]carbamoyl]-3-methyl-butyl]-4-methoxy-1H-indole-2-carboxamide (26.51 mg, 52.85 umol, 36.62% yield, 100% purity) was obtained as a solid. MS (ESI) m/z 502.2 [M+H]$^+$
Prep-HPLC Condition:
column: Waters Xbridge BEH C18 100*25 mm*5 um; mobile phase: [water(10 mM NH$_4$HCO3)—ACN]; B %: 30%-60%, 10 min $^1$H NMR (400 MHz, DMSO-d$_6$) δ ppm 11.51-11.61 (m, 1H), 10.14-10.20 (m, 1H), 8.84-9.01 (m, 1H), 8.42-8.59 (m, 1H), 7.32-7.42 (m, 1H), 7.05-7.22 (m, 3H), 6.81-7.04 (m, 3H), 6.50 (dd, J=7.64, 3.85 Hz, 1H), 4.37-4.66 (m, 2H), 3.83-3.95 (m, 3H), 2.95-3.12 (m, 1H), 2.63-2.82 (m, 1H), 2.26-2.42 (m, 1H), 1.88-2.08 (m, 2H), 1.45-1.82 (m, 3H), 0.81-1.02 (m, 6H)

Step 6: (S)-tert-butyl 2-(4-methoxy-1H-indole-2-carboxamido)-4-methylpentanoate To a mixture of 4-methoxy-1H-indole-2-carboxylic acid (15 g, 78.46 mmol, 1 eq) and tert-butyl (2S)-2-amino-4-methyl-pentanoate (21.07 g, 94.15 mmol, 1.2 eq, HCl) in DMF (150 mL) was added EDCI (19.55 g, 102.00 mmol, 1.3 eq), HOBt (13.78 g, 102.00 mmol, 1.3 eq), TEA (23.82 g, 235.38 mmol, 32.76 mL, 3 eq) at 25° C. under $N_2$. The mixture was stirred at 25° C. and stirred for 2 h. The reaction mixture was added water (450 mL) and extracted with EtOAc (250 mL*3) to get the organic phase. The organic phase was washed with 5% citric acid (300 mL) and 5% aqueous solution of sodium bicarbonate (300 mL) and dried over anhydrous sodium sulfate, filtered and concentrated to get the product. The residue was purified by column chromatography (SiO$_2$, petroleum ether: EtOAc=30:1 to 10:1). tert-butyl (2S)-2-[(4-methoxy-1H-indole-2-carbonyl)amino]-4-methyl-pentanoate (24 g, 66.58 mmol, 84.87% yield) was obtained as a solid. MS (ESI) m/z 361.2 [M+H1+

Step 7: (S)-2-(4-methoxy-1H-indole-2-carboxamido)-4-methylpentanoic acid

To a mixture of tert-butyl (2S)-2-[(4-methoxy-1H-indole-2-carbonyl)amino]-4-methyl-pentanoate (10 g, 27.74 mmol, 1 eq) in DCM (30 mL) was added TFA (61.60 g, 540.26 mmol, 40 mL, 19.47 eq) and H$_2$O (4.00 g, 221.98 mmol, 4.00 mL, 8.00 eq) in one portion at 0° C. under $N_2$. The mixture was stirred at 25° C. for 2 h. The reaction mixture was concentrated to get the crude product. The crude product was purified with petroleum ether:ethyl acetate=10:1 (20 mL) and filtered to get the product. (2S)-2-[(4-methoxy-1H-indole-2-carbonyl)amino]-4-methyl-pentanoic acid (6 g, 19.22 mmol, 69.27% yield, 97.48% purity) was obtained as a solid. MS (ESI) m/z 305.1 [M+H]$^+$

Example 29. Synthesis of Viral Protease Inhibitor Compound 600

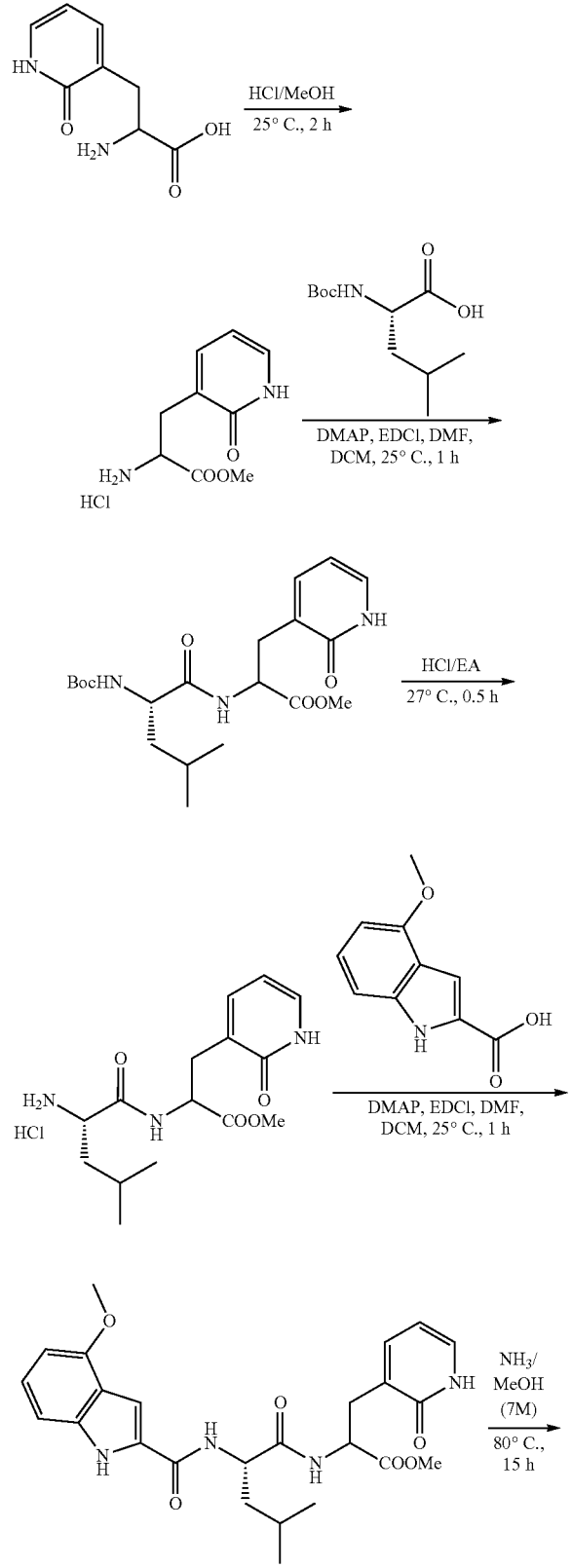

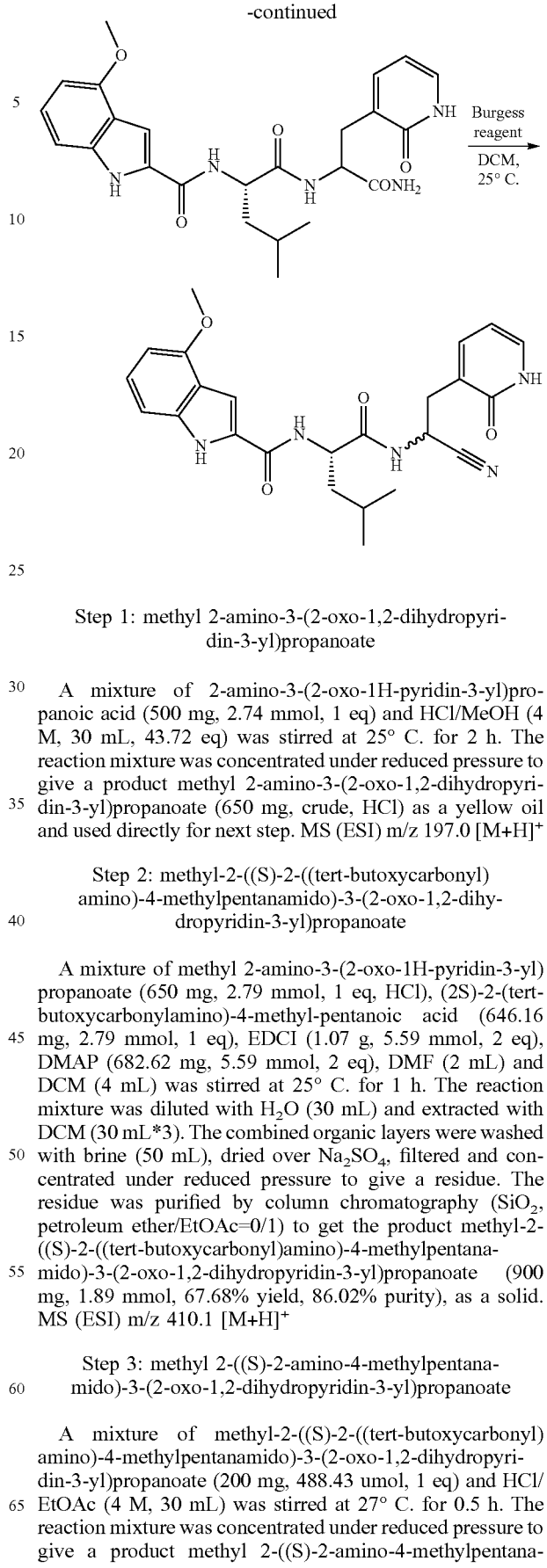

Step 1: methyl 2-amino-3-(2-oxo-1,2-dihydropyridin-3-yl)propanoate

A mixture of 2-amino-3-(2-oxo-1H-pyridin-3-yl)propanoic acid (500 mg, 2.74 mmol, 1 eq) and HCl/MeOH (4 M, 30 mL, 43.72 eq) was stirred at 25° C. for 2 h. The reaction mixture was concentrated under reduced pressure to give a product methyl 2-amino-3-(2-oxo-1,2-dihydropyridin-3-yl)propanoate (650 mg, crude, HCl) as a yellow oil and used directly for next step. MS (ESI) m/z 197.0 [M+H]$^+$

Step 2: methyl-2-((S)-2-((tert-butoxycarbonyl)amino)-4-methylpentanamido)-3-(2-oxo-1,2-dihydropyridin-3-yl)propanoate A mixture of methyl 2-amino-3-(2-oxo-1H-pyridin-3-yl)propanoate (650 mg, 2.79 mmol, 1 eq, HCl), (2S)-2-(tert-butoxycarbonylamino)-4-methyl-pentanoic acid (646.16 mg, 2.79 mmol, 1 eq), EDCI (1.07 g, 5.59 mmol, 2 eq), DMAP (682.62 mg, 5.59 mmol, 2 eq), DMF (2 mL) and DCM (4 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the product methyl-2-((S)-2-((tert-butoxycarbonyl)amino)-4-methylpentanamido)-3-(2-oxo-1,2-dihydropyridin-3-yl)propanoate (900 mg, 1.89 mmol, 67.68% yield, 86.02% purity), as a solid. MS (ESI) m/z 410.1 [M+H]$^+$

Step 3: methyl 2-((S)-2-amino-4-methylpentanamido)-3-(2-oxo-1,2-dihydropyridin-3-yl)propanoate A mixture of methyl-2-((S)-2-((tert-butoxycarbonyl)amino)-4-methylpentanamido)-3-(2-oxo-1,2-dihydropyridin-3-yl)propanoate (200 mg, 488.43 umol, 1 eq) and HCl/EtOAc (4 M, 30 mL) was stirred at 27° C. for 0.5 h. The reaction mixture was concentrated under reduced pressure to give a product methyl 2-((S)-2-amino-4-methylpentanamido)-3-(2-oxo-1,2-dihydropyridin-3-yl)propanoate (170 mg, crude, HCl) as a solid and used directly for next step.

Step 4: methyl 2-((S)-2-(4-methoxy-1H-indole-2-carboxamido)-4-methylpentanamido)-3-(2-oxo-1,2-dihydropyridin-3-yl)propanoate A mixture of methyl 2-((S)-2-amino-4-methylpentanamido)-3-(2-oxo-1,2-dihydropyridin-3-yl)propanoate (170 mg, 491.58 umol, 1 eq, HCl), 4-methoxy-1H-indole-2-carboxylic acid (93.98 mg, 491.58 umol, 1 eq), EDCI (188.47 mg, 983.17 umol, 2 eq), DMAP (120.11 mg, 983.17 umol, 2 eq), DMF (2 mL) and DCM (4 mL) was stirred at 25° C. for 1 h. The reaction mixture was diluted with H₂O (30 mL) and then extracted with DCM (30 mL*3). The combined organic layers were washed with brine (50 mL), dried over Na₂SO₄, filtered and concentrated under reduced pressure to give a residue. The residue was purified by column chromatography (SiO₂, petroleum ether/EtOAc=0/1) to get the compound methyl 2-((S)-2-(4-methoxy-1H-indole-2-carboxamido)-4-methylpentanamido)-3-(2-oxo-1,2-dihydropyridin-3-yl)propanoate (130 mg, 269.41 umol, 54.81% yield), as a solid. MS (ESI) m/z 483.1 [M+H]⁺

Step 5: N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide A mixture of methyl 2-((S)-2-(4-methoxy-1H-indole-2-carboxamido)-4-methylpentanamido)-3-(2-oxo-1,2-dihydropyridin-3-yl)propanoate (190 mg, 393.76 umol, 1 eq), NH₃/MeOH (7 M, 10 mL) was stirred at 80° C. for 15 h. The reaction mixture was concentrated under reduced pressure to give N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide (190 mg, crude) as a solid. MS (ESI) m/z 468.2 [M+H]⁺

Step 6: N-((2S)-1-((]-cyano-2-(2-oxo-1,2-dihydropyridin-3-yl)ethyl)amino)-4-methyl-]-oxopentan-2-yl)-4-methoxy-1H-indole-2-carboxamide A mixture of N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide (180 mg, 385.01 umol, 1 eq), Burgess reagent (917.53 mg, 3.85 mmol, 10 eq) and DCM (30 mL) was stirred at 25° C. for 8 h. The reaction mixture was concentrated under reduced pressure to give a residue. The residue was purified by prep-HPLC (column: Phenomenex Gemini-NX C₁₈ 75*30 mm*3 um; mobile phase: [water(0.05% NH₃H₂O+10 mM NH₄HCO₃)—ACN]; B %: 25%-45%, 8 min) to get the product N-((2S)-1-((1-cyano-2-(2-oxo-1,2-dihydropyridin-3-yl)ethyl)amino)-4-methyl-1-oxopentan-2-yl)-4-methoxy-1H-indole-2-carboxamide (24 mg, 52.18 umol, 13.55% yield, 97.73% purity), as a solid. MS (ESI) m/z 450.2 [M+H]⁺.

¹H NMR (400 MHz, DMSO-d₆) δ=11.90-11.40 (m, 2H), 9.08-8.85 (m, 1H), 8.55-8.35 (m, 1H), 7.51-7.26 (m, 3H), 7.16-7.05 (m, 1H), 7.04-6.94 (m, 1H), 6.51 (d, J=7.5 Hz, 1H), 6.15 (t, J=6.6 Hz, 1H), 5.19-5.01 (m, 1H), 4.55-4.33 (m, 1H), 3.89 (s, 3H), 3.02-2.78 (m, 2H), 1.75-1.33 (m, 3H), 0.98-0.72 (m, 6H)

Example 30. Synthesis of Viral Protease Inhibitor Compounds 344C, 344D, 507 and 511

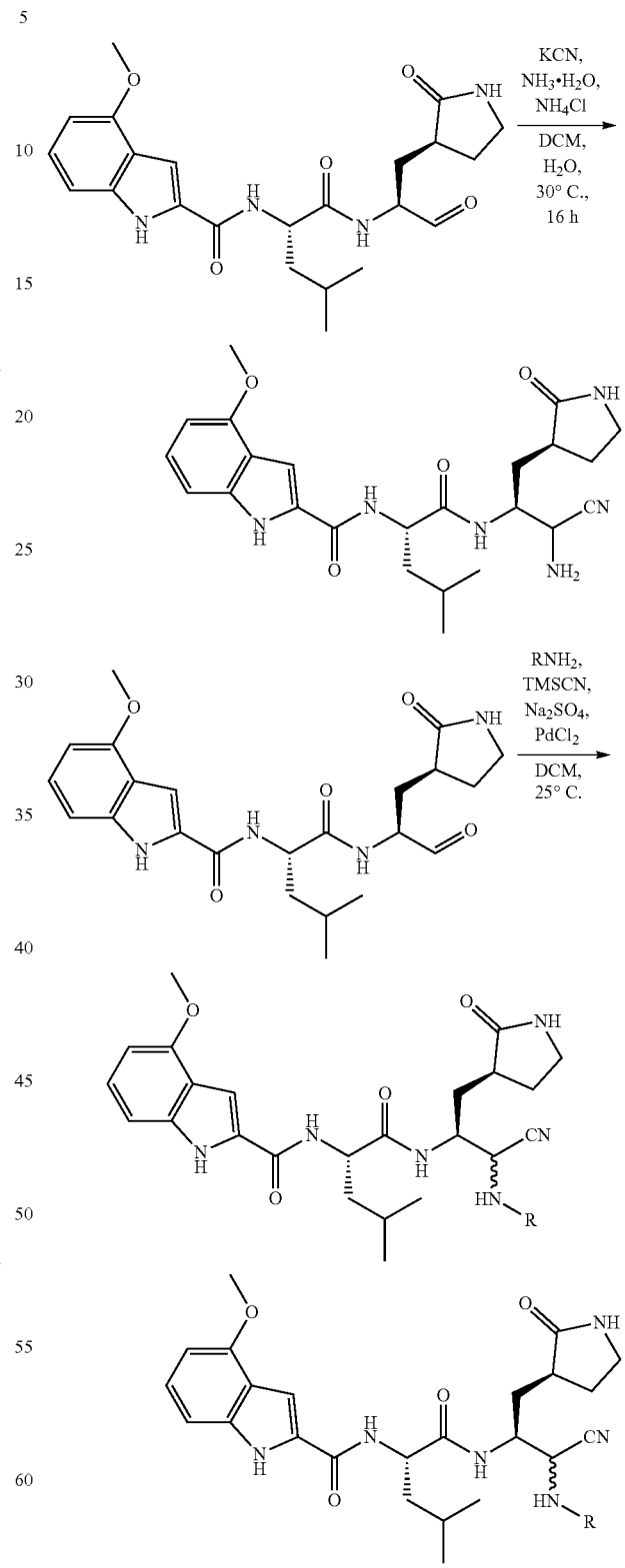

Compound 511: R = Et;
Compound 507: R = Bn

Step for compound 344C: N-[(1S)-1-[[(S)-2-amino-2-cyano-1-[[(3S)-2-oxopyrrolidin-3-yl]methyl]ethyl]carbamoyl]-3-methyl-butyl]-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (100 mg, 180.79 umol, 80% purity, 1 eq) in DCM (10 mL) was added NH$_3$.H$_2$O (46.93 mg, 361.58 umol, 51.57 uL, 27% purity, 2 eq) and NH$_4$Cl (19.34 mg, 361.58 umol, 2 eq). The mixture was stirred at 25° C. for 30 min, then added KCN (94.18 mg, 1.45 mmol, 61.96 uL) in H$_2$O (0.2 mL), the mixture was stirred at 30° C. for 16 h. Once the reaction was completed, the reaction mixture was then quenched by addition H$_2$O (10 mL) at 0° C., and then diluted with H$_2$O (10 mL) and extracted with EtOAc (30 mL*2). The combined organic layers were washed with brine (30 mL), dried over Na$_2$SO$_4$, filtered and concentrated under reduced pressure to give a residue. The liquid water was added with NaOH to adjust pH=9, quenched with aq NaCl, and then added with NaOH to adjust pH >14. The residue was purified by HCl prep-HPLC to get the compound N-[(1S)-1-[[(1S)-2-amino-2-cyano-1-[[(3S)-2-oxopyrrolidin-3-yl]methyl]ethyl]carbamoyl]-3-methyl-butyl]-4-methoxy-1H-indole-2-carboxamide (50 mg, 103.83 umol, 57.43% yield, 97.3% purity) as a solid. MS (ESI) m/z 469.2 [M+H]$^+$
Prep-HPLC Condition:
column: Phenomenex luna C18 80*40 mm*3 um; mobile phase: [water(0.04% HCl)—ACN]; B %: 15%-40%, 7 min
$^1$H NMR (400 MHz, DMSO-d6) δ=11.59 (dd, J=1.9, 5.0 Hz, 1H), 9.16-8.58 (m, 2H), 8.54-8.26 (m, 2H), 7.66 (d, J=9.0 Hz, 1H), 7.37 (dd, J=2.0, 4.2 Hz, 1H), 7.14-7.06 (m, 1H), 7.04-6.97 (m, 1H), 6.51 (d, J=7.5 Hz, 1H), 4.61-4.42 (m, 2H), 4.39-4.21 (m, 1H), 3.88 (s, 3H), 3.20-2.98 (m, 2H), 2.48-2.34 (m, 1H), 2.14-1.88 (m, 2H), 1.82-1.47 (m, 5H), 0.92 (dd, J=6.0, 14.8 Hz, 6H) Step for compound 511: N-[(1S)-1-[[(1S)-2-cyano-2-(ethylamino)-1-[[(3S)-2-oxopyrrolidin-3-yl]methyl]ethyl]carbamoyl]-3-methyl-butyl]-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (80 mg, 108.47 umol, 60% purity, 1 eq) in DCM (5 mL) was added PdCl$_2$ (3.85 mg, 21.69 umol, 0.2 eq), Na$_2$SO$_4$ (53.93 mg, 379.66 umol, 38.52 uL, 3.5 eq), and ethanamine (9.78 mg, 216.95 umol, 14.19 uL, 2 eq). The resulting mixture was stirred at 25° C. for 30 min, and then added with TMSCN (21.52 mg, 216.95 umol, 27.14 uL, 2 eq). The resulting mixture was stirred at 25° C. for 1 h. Once the reaction was completed, the reaction mixture was filtered and concentrated under reduced pressure to give a residue. The residue was purified by HCl prep-HPLC to yield 70 mg of the mixture. The mixture was purified by SFC to get the N-[(1S)-1-[[(1S)-2-cyano-2-(ethylamino)-1-[[(3S)-2-oxo pyrrolidin-3-yl]methyl]ethyl]carbamoyl]-3-methyl-butyl]-4-methoxy-1H-indole-2-carboxamide (16 mg, 28.20 umol, 26.00% yield, 87.525% purity) as an oil and N-[(1S)-1-[[(1S)-2-cyano-2-(ethylamino)-1-[[(3S)-2-oxopyrrolidin-3-yl]methyl]ethyl]carbamoyl]-3-methyl-butyl]-4-methoxy-1H-indole-2-carboxamide (16 mg, 31.44 umol, 28.98% yield, 97.569% purity) as a solid. MS (ESI) m/z 497.3 [M+H]$^+$ Prep-HPLC Condition:
column: Phenomenex luna C18 80*40 mm*3 um; mobile phase: [water(0.04% HCl)—ACN]; B %: 25%-40%, 7 min
SFC Condition:
column: DAICEL CHIRALCEL OX (250 mm*30 mm, 10 um); mobile phase: [Neu-ETOH]; B %: 38%-38%, 9 min Compound 511 Isomer 1: $^1$H NMR (400 MHz, DMSO-d6) δ=11.56 (br s, 1H), 8.37 (br d, J=7.7 Hz, 1H), 8.29-8.20 (m, 1H), 7.80-7.48 (m, 3H), 7.35 (br d, J=2.0 Hz, 1H), 7.17-6.96 (m, 2H), 6.50 (d, J=7.7 Hz, 1H), 4.53-4.40 (m, 1H), 4.05 (td, J=3.9, 7.7 Hz, 1H), 3.88 (s, 3H), 3.77 (br dd, J=4.9, 10.1 Hz, 1H), 3.18-2.97 (m, 2H), 2.88-2.63 (m, 2H), 2.40-2.24 (m, 1H), 2.14-2.06 (m, 2H), 1.82-1.31 (m, 5H), 1.09-0.98 (m, 3H), 0.91 (br dd, J=6.2, 16.1 Hz, 6H)

Compound 511 Isomer 2: $^1$H NMR (400 MHz, DMSO-d6) δ=11.58 (d, J=1.5 Hz, 1H), 8.41 (br d, J=7.9 Hz, 1H), 8.17 (br s, 1H), 7.63-7.50 (m, 1H), 7.37 (d, J=1.8 Hz, 1H), 7.14-7.05 (m, 1H), 7.00 (d, J=8.2 Hz, 1H), 6.50 (d, J=7.5 Hz, 1H), 4.58-4.37 (m, 1H), 4.25-3.99 (m, 1H), 3.88 (s, 3H), 3.81-3.51 (m, 1H), 3.16-2.96 (m, 2H), 2.89-2.54 (m, 2H), 2.43-2.23 (m, 1H), 2.20-1.99 (m, 1H), 1.95-1.43 (m, 6H), 1.10-0.98 (m, 3H), 0.91 (dd, J=6.4, 15.2 Hz, 6H) Step for compound 507: N-[(1S)-1-[[(1S)-2-(benzylamino)-2-cyano-1-[[(3S)-2-oxopyrrolidin-3-yl]methyl]ethyl]carbamoyl]-3-methyl-butyl]-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (150 mg, 271.18 umol, 80% purity, 1 eq) in DCM (15 mL) was added PdCl$_2$ (9.62 mg, 54.24 umol, 0.2 eq), Na$_2$SO$_4$ (134.82 mg, 949.14 umol, 96.30 uL, 3.5 eq) and BnNH$_2$ (58.11 mg, 542.36 umol, 59.12 uL, 2 eq). The mixture was stirred at 25° C. for 30 min, then added with TMSCN (53.81 mg, 542.36 umol, 67.85 uL, 2 eq). The mixture was stirred at 25° C. for 2 hours. Once the reaction was completed, the reaction mixture was filtered and concentrated under reduced pressure to give a residue. The residue was purified by HCl prep-HPLC to get the compound N-[(1S)-1-[[(1S)-2-(benzylamino)-2-cyano-1-[[(3S)-2-oxopyrrolidin-3-yl]methyl]ethyl]carbamoyl]-3-methyl-butyl]-4-methoxy-1H-indole-2-carboxamide (30 mg, 51.71 umol, 19.07% yield, 96.291% purity) and N-[(1S)-1-[[(1S)-2-(benzylamino)-2-cyano-1-[[(3S)-2-oxopyrrolidin-3-yl]methyl]ethyl]carbamoyl]-3-methyl-butyl]-4-methoxy-1H-indole-2-carboxamide (18 mg, 31.04 umol, 11.44% yield, 96.329% purity) as a solid. MS (ESI) m/z 559.3 [M+H]$^+$
Prep-HPLC Condition:
column: Phenomenex luna C$_{18}$ 80*40 mm*3 um; mobile phase: [water(0.04% HCl)—ACN]; B %: 38%-62%, 7 min Compound 507 Isomer 1: $^1$H NMR: (400 MHz, DMSO-d6) δ=11.58 (d, J=1.8 Hz, 1H), 8.48-8.34 (m, 1H), 8.23 (br d, J=9.5 Hz, 1H), 7.69-7.53 (m, 1H), 7.51-7.23 (m, 5H), 7.14-7.05 (m, 1H), 7.02-6.97 (m, 1H), 6.50 (d, J=7.7 Hz, 1H), 4.56-4.37 (m, 1H), 4.23 (br d, J=9.3 Hz, 1H), 4.13-3.91 (m, 2H), 3.88 (s, 3H), 3.84 (br d, J=13.2 Hz, 1H), 3.17-2.95 (m, 2H), 2.42-2.24 (m, 1H), 2.16-1.98 (m, 1H), 1.93-1.44 (m, 6H), 0.90 (dd, J=6.3, 16.2 Hz, 6H)

Compound 507 Isomer 2: $^1$H NMR (400 MHz, DMSO-d6) δ=11.56 (br d, J=1.5 Hz, 1H), 8.52-8.14 (m, 2H), 7.69-7.55 (m, 1H), 7.49-7.22 (m, 6H), 7.13-7.05 (m, 1H), 7.00 (d, J=8.4 Hz, 1H), 6.50 (d, J=7.5 Hz, 1H), 4.56-4.41 (m, 1H), 4.21 (br s, 1H), 4.06-3.94 (m, 2H), 3.88 (s, 3H), 3.83 (br d, J=12.8 Hz, 1H), 3.17-2.97 (m, 2H), 2.42-2.29 (m, 1H), 2.17-2.00 (m, 2H), 1.83-1.44 (m, 5H), 0.90 (dd, J=6.3, 17.8 Hz, 6H)

Example 31. Synthesis of Viral Protease Inhibitor Compound 129

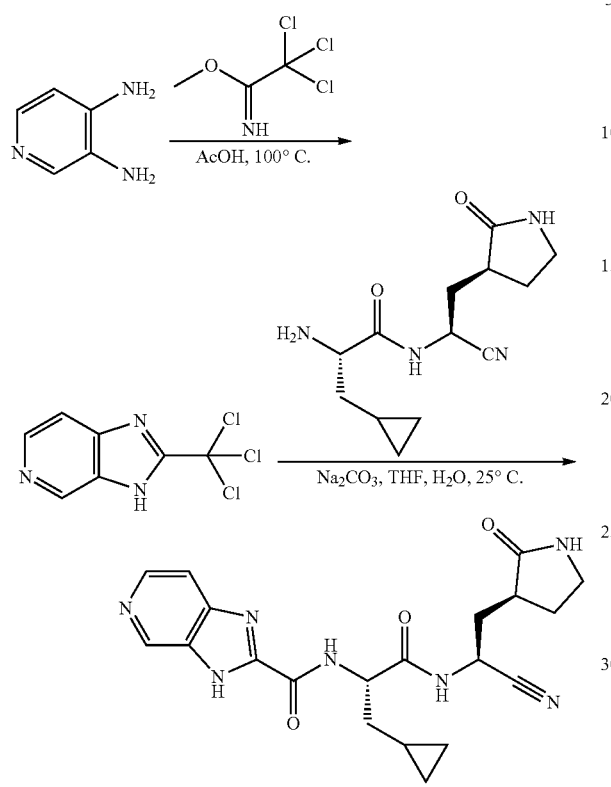

Step 1. 2-(trichloromethyl)-3H-imidazo[4,5-c]pyridine

To a solution of pyridine-3,4-diamine (2 g, 18.33 mmol, 1 eq) in AcOH (25 mL) was added methyl 2,2,2-trichloroethanimidate (3.88 g, 21.99 mmol, 2.71 mL, 1.2 eq). The solution was stirred for 5 h at 100° C. The reaction was added with H$_2$O (90 mL) and extracted with ethyl acetate (70 mL*3) and washed with NaHCO$_3$ (90 mL*2). The organic layer was cautiously concentrated to give crude 2-(trichloromethyl)-3H-imidazo[4,5-c]pyridine (800 mg, crude) was obtained as a yellow solid. The crude was used directly for the next step. MS (ESI) m z 235.9 [M+H]$^+$

Step 2: N-[(1S)-2-[[(1S)-1-cyano-2-[(3S)-2-oxopyrrolidin-3-yl]ethyl]amino]-1-(cyclopropylmethyl)-2-oxo-ethyl]-3H-imidazo[4,5-c]pyridine-2-carboxamide To a solution of 2-(trichloromethyl)-3H-imidazo[4,5-c]pyridine (150 mg, 634.29 umol, 1 eq) and (2S)-2-amino-N-[(1S)-1-cyano-2-[(3S)-2-oxopyrrolidin-3-yl]ethyl]-3-cyclopropyl-propanamide(167.66 mg, 634.29 umol, 1 eq) in THF (5 mL) and H$_2$O (2.5 mL) was added Na$_2$CO$_3$ (201.68 mg, 1.90 mmol, 3 eq). The solution was stirred for 1 h at 20° C. The solution was added with H$_2$O (20 mL), extracted with ethyl acetate (40 mL*3) and concentrated to give crude. The crude was purified by pre-HPLC(Column: Waters Xbridge BEH C18 100*30 mm*10 um; mobile phase: [water (10 mM NH$_4$HCO$_3$)—ACN]; B %: 1%-23%, 8 min) to give 70% purity product and then continue purified by pre-HPLC (Column: Phenomenex Luna C$_{18}$ 75*30 mm*3 um; mobile phase: [water (0.2% FA)—ACN]; B %: 1%-30%, 8 min) to give product N-[(1S)-2-[[(1S)-1-cyano-2-[(3S)-2-oxopyrrolidin-3-yl]ethyl]amino]-1-(cyclopropylmethyl)-2-oxo-ethyl]-3H-imidazo[4,5-c]pyridine-2-carboxamide (3 mg, 6.96 umol, 1.10% yield, 95% purity) was obtained as a solid. MS (ESI) m/z 410.1 [M+H]$^+$. $^1$H NMR (400 MHz, DMSO-d$_6$) δ=8.89-8.81 (m, 2H), 8.77 (d, J=7.9 Hz, 1H), 8.21 (d, J=5.4 Hz, 2H), 7.54 (s, 1H), 7.43 (br d, J=5.4 Hz, 1H), 4.91-4.76 (m, 1H), 4.44-4.32 (m, 1H), 3.02-2.92 (m, 2H), 2.25-2.16 (m, 1H), 2.03-1.91 (m, 2H), 1.78-1.38 (m, 4H), 0.59 (br s, 1H), 0.25 (br d, J=7.9 Hz, 2H), 0.05-0.11 (m, 2H).

Example 32. Synthesis of Viral Protease Inhibitor Compound 389A and 389B

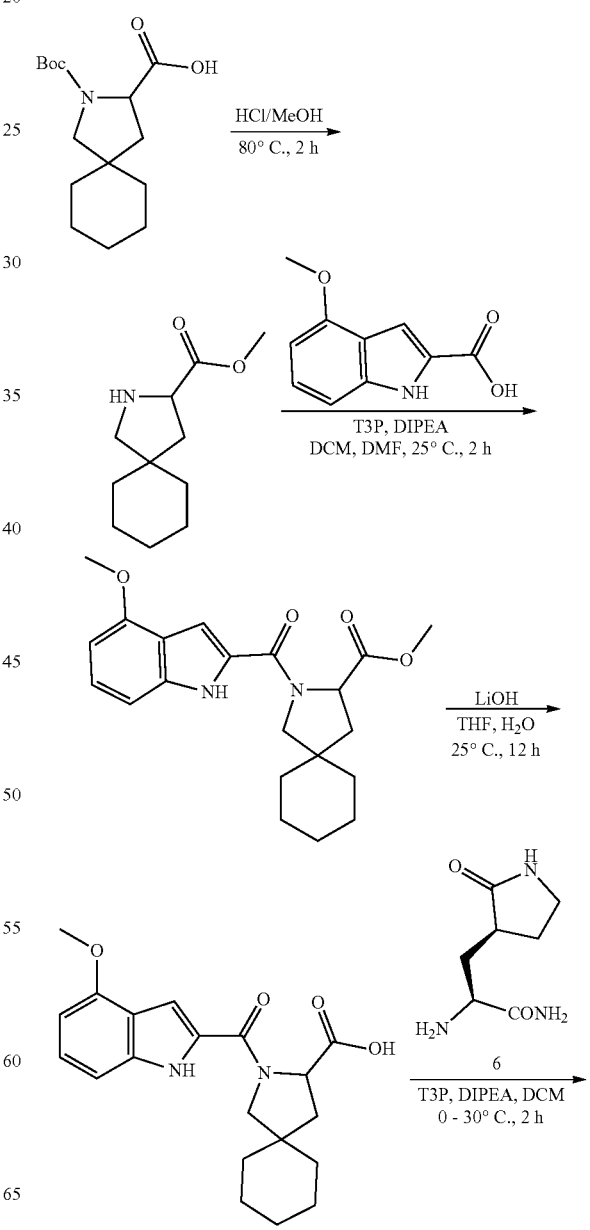

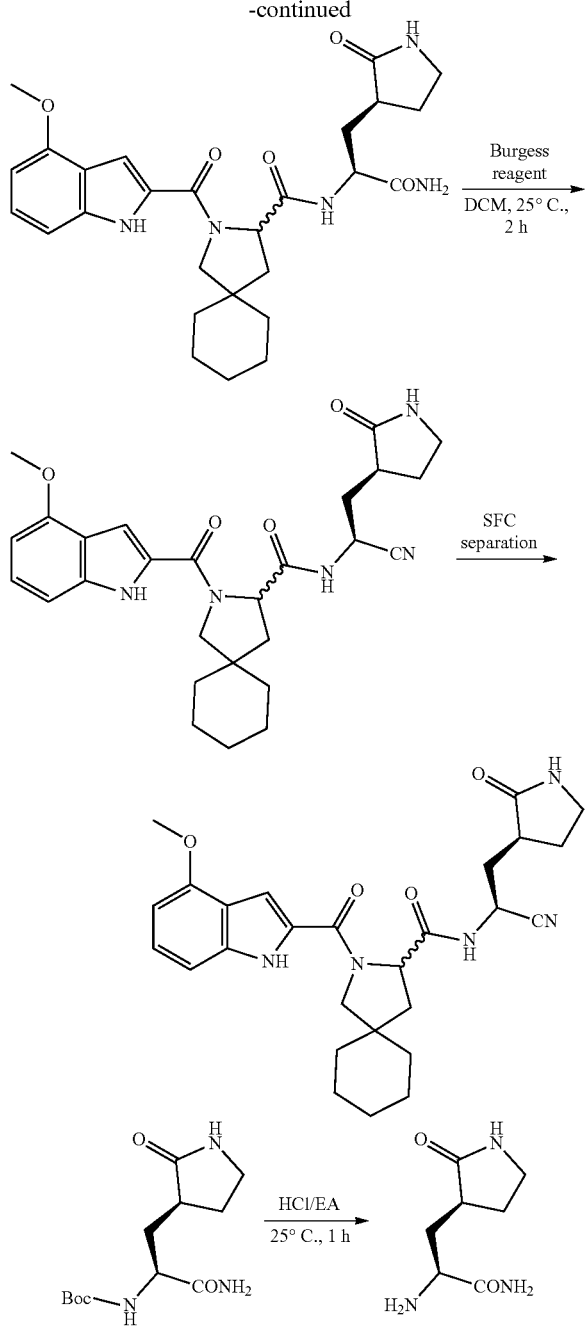

Step 1: (S)-2-amino-3-((S)-2-oxopyrrolidin-3-yl)propanamide tert-Butyl N-[(1S)-2-amino-2-oxo-1-[[(3S)-2-oxopyrrolidin-3-yl]methyl]ethyl]carbamate (2 g, 7.37 mmol, 1 eq) in HCl/EtOAc (4 M, 50 mL, 27.13 eq) was stirred at 25° C. for 1 h. Upon completion, the mixture was concentrated under the reduced pressure affording the product (2S)-2-amino-3-[(3S)-2-oxopyrrolidin-3-yl]propanamide (1.2 g, crude) as a solid.

Step 2: Methyl 2-azaspiro[4.5]decane-3-carboxylate

A solution of 2-tert-butoxycarbonyl-2-azaspiro[4.5]decane-3-carboxylic acid (3 g, 10.59 mmol, 1 eq) in HCl/MeOH (4 M, 50 mL, 18.89 eq) was stirred at 80° C. for 2 h. The mixture was concentrated under the reduced pressure to afford the product methyl 2-azaspiro[4.5]decane-3-carboxylate (2 g, crude) as a yellow oil.

Step 3: Methyl 2-(4-methoxy-1H-indole-2-carbonyl)-2-azaspiro[4.5]decane-3-carboxylate To a solution of methyl 2-azaspiro[4.5]decane-3-carboxylate (2 g, 10.14 mmol, 1 eq) and 4-methoxy-1H-indole-2-carboxylic acid (2.33 g, 12.17 mmol, 1.2 eq) in DCM (30 mL) and DMF (5 mL) was added T3P (12.90 g, 20.28 mmol, 12.06 mL, 50% purity, 2 eq) and DIEA (3.93 g, 30.41 mmol, 5.30 mL, 3 eq). The mixture was stirred at 25° C. for 2 h. Upon completion, the reaction mixture was quenched by addition H$_2$O (100 mL), and extracted with DCM (50 mL*3). The combined organic layers were washed with brine (50 mL), dried over Na$_2$SO$_4$, filtered and concentrated under reduced pressure to give a residue. The residue was purified by column chromatography (SiO$_2$, Petroleum ether: Ethyl acetate=10:1 to 0:1) to afford the product methyl 2-(4-methoxy-1H-indole-2-carbonyl)-2-azaspiro[4.5]decane-3-carboxylate (3 g, 8.10 mmol, 79.88% yield) as a solid. MS (ESI) m/z 371.1 [M+H]$^+$ Step 4: 2-(4-methoxy-1H-indole-2-carbonyl)-2-azaspiro[4.5]decane-3-carboxylic acid To a solution of methyl 2-(4-methoxy-1H-indole-2-carbonyl)-2-azaspiro[4.5]decane-3-carboxylate (3 g, 8.10 mmol, 1 eq) in THF (45 mL) and H$_2$O (15 mL) was added LiOH.H$_2$O (1.70 g, 40.49 mmol, 5 eq). The mixture was stirred at 25° C. for 12 h. Upon completion, the mixture was quenched by addition H$_2$O (50 mL), and then added aq. HCl (1 M) to adjust the pH=3-4, and then extracted with ethyl acetate (50 mL*3). The combined organic layers were washed with brine (30 mL), dried over Na$_2$SO$_4$, filtered and concentrated under reduced pressure affording the product 2-(4-methoxy-1H-indole-2-carbonyl)-2-azaspiro[4.5]decane-3-carboxylic acid (2.6 g, crude) as a white solid. MS (ESI) m/z 357.1 [M+H]$^+$ Step 5: N—((S)-1-amino-1-oxo-3-((S)-2-oxopyrrolidin-3-yl)propan-2-yl)-2-(4-methoxy-1H-indole-2-carbonyl)-2-azaspiro[4.5]decane-3-carboxamide To a solution of 2-(4-methoxy-1H-indole-2-carbonyl)-2-azaspiro[4.5]decane-3-carboxylic acid (1 g, 2.81 mmol, 1 eq) and (2S)-2-amino-3-[(3S)-2-oxopyrrolidin-3-yl]propanamide (720.49 mg, 4.21 mmol, 1.5 eq) in DCM (30 mL) was added T3P (3.57 g, 5.61 mmol, 3.34 mL, 50% purity, 2 eq) and DIEA (1.09 g, 8.42 mmol, 1.47 mL, 3 eq) at 0° C. The mixture was stirred at 30° C. for 1 h. Upon completion, the mixture was quenched by addition H$_2$O (100 mL), and then extracted with DCM (50 mL*3). The combined organic layers were washed with brine (50 mL), dried over Na$_2$SO$_4$, filtered and concentrated under reduced pressure to give a residue. The residue was purified by column chromatography (SiO$_2$, DCM:MeOH=1:0 to 10:1) affording the product N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.5]decane-3-carboxamide (700 mg, 1.37 mmol, 48.96% yield) as a white solid. MS (ESI) m/z 510.3 [M+H]$^+$ Step 6: N—((S)-1-cyano-2-((S)-2-oxopyrrolidin-3-yl)ethyl)-2-(4-methoxy-1H-indole-2-carbonyl)-2-azaspiro[4.5]decane-3-carboxamide To a solution of N-[(1S)-2-amino-2-oxo-1-[[(3S)-2-oxopyrrolidin-3-yl]methyl]ethyl]-2-(4-methoxy-1H-indole- 2-carbonyl)-2-azaspiro[4.5]decane-3-carboxamide (700 mg, 1.37 mmol, 1 eq) in DCM (10 mL) was added Burgess reagent (982.03 mg, 4.12 mmol, 3 eq). The mixture was stirred at 25° C. for 2 h. Upon completion, the mixture was concentrated under the reduced pressure to give a residue. The residue was purified by prep-HPLC (column: Kromasil $C_{18}$ (250*50 mm*10 um); mobile phase: [water (10 mM $NH_4HCO_3$)—ACN]; B %: 30%-60%, 10 min) affording the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide (500 mg, 1.02 mmol, 74.05% yield) as a white solid. MS (ESI) m/z 492.3 [M+H]$^+$ Step 7: N—((S)-1-cyano-2-((S)-2-oxopyrrolidin-3-yl)ethyl)-2-(4-methoxy-1H-indole-2-carbonyl)-2-azaspiro[4.5]decane-3-carboxamide N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide (500 mg, 1.02 mmol) was separated by SFC (column: DAICEL CHIRALPAK AD (250 mm*30 mm, 10 um); mobile phase: [0.1% $NH_3H_2O$ IPA]; B %: 55%-55%, 9 min) to afford the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide, Isomer 1 (264 mg, 537.04 umol, 52.80% yield) as a solid. MS (ESI) m/z 492.3 [M+H]$^+$; $^1$H NMR (400 MHz, METHANOL-$d_4$) δ=7.28-6.76 (m, 3H), 6.60-6.38 (m, 1H), 5.05 (br dd, J=5.2, 10.2 Hz, 1H), 4.63-4.60 (m, 1H), 4.03-3.85 (m, 5H), 3.74-3.28 (m, 1H), 2.73 (br dd, J=5.0, 8.6 Hz, 1H), 2.51-2.28 (m, 2H), 2.27-2.08 (m, 1H), 1.96-1.72 (m, 2H), 1.69-1.38 (m, 11H), 1.37-1.09 (m, 1H); and
N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide, Isomer 2 (140 mg, 284.51 umol, 27.97% yield) as a solid. MS (ESI) m/z 492.3 [M+H]$^+$; $^1$H NMR (400 MHz, METHANOL-$d_4$) δ=7.30-6.81 (m, 3H), 6.53 (br d, J=2.0 Hz, 1H), 5.12-4.95 (m, 2H), 4.70-4.55 (m, 2H), 4.08-3.86 (m, 4H), 3.84-3.72 (m, 1H), 2.62-2.40 (m, 1H), 2.36-2.18 (m, 2H), 1.94-1.69 (m, 3H), 1.68-1.34 (m, 11H).

Example 33. Synthesis of Viral Protease Inhibitor Compound 399

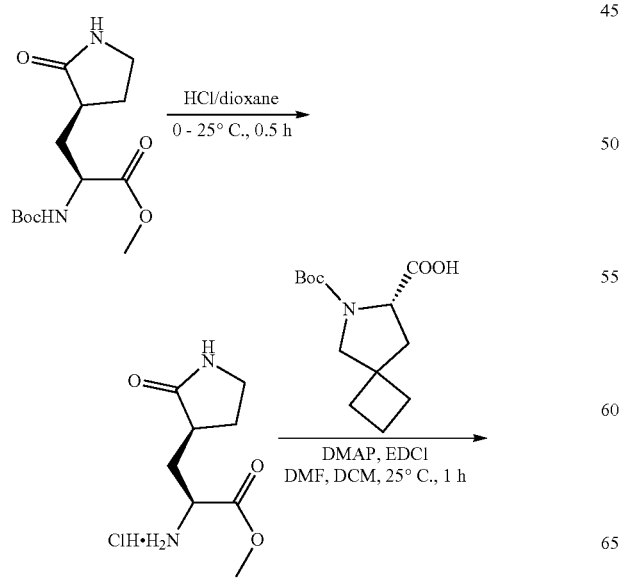

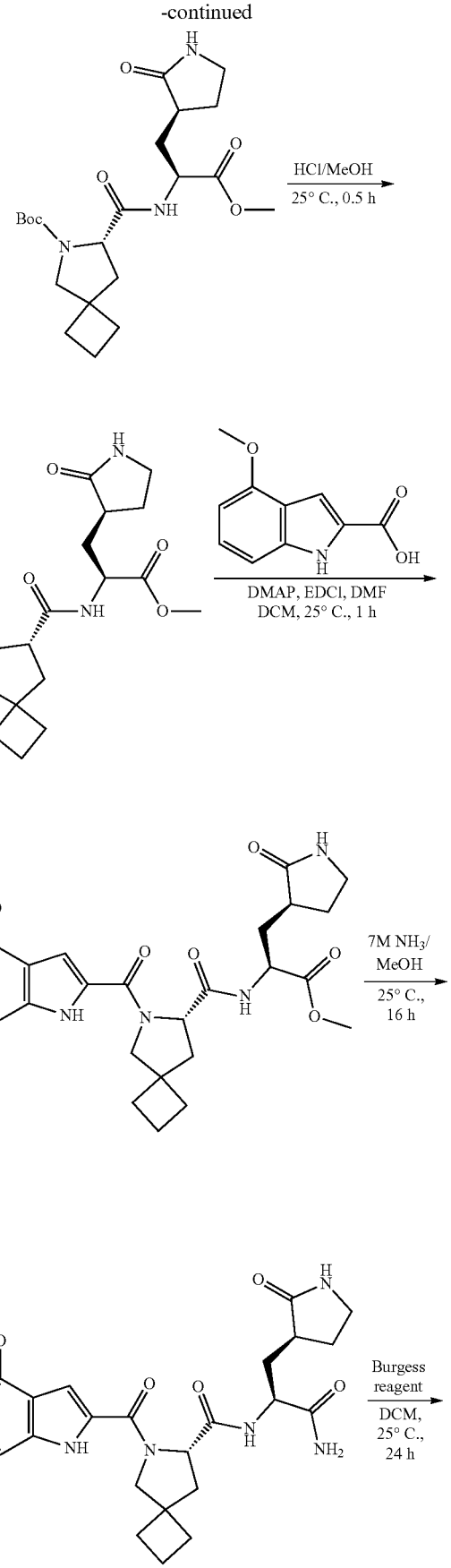

-continued

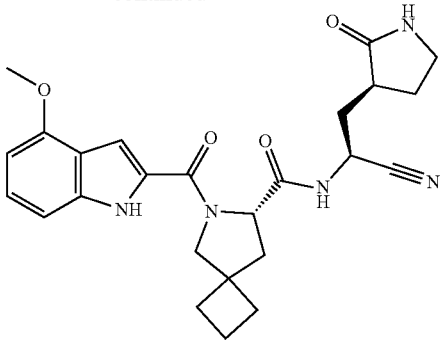

Step 1: (S)-methyl 2-amino-3-((S)-2-oxopyrrolidin-3yl)propanoate hydrochloride

To a solution of methyl (2S)-2-(tert-butoxycarbonylamino)-3-[(3S)-2-oxopyrrolidin-3-yl]propanoate (130 mg, 454.03 umol, 1 eq) in HCl/dioxane (4 M, 2.27 mL, 20 eq) was stirred at 25° C. for 0.5 h. The reaction mixture was concentrated under reduced pressure to get the product methyl (2S)-2-amino-3-[(3S)-2-oxopyrrolidin-3-yl]propanoate (173.4 mg, 451.67 umol, 99.48% yield, HCl) was obtained as yellow liquid.

Step 2: (S)-tert-butyl 7-(((S)-1-methoxy-1-oxo-3-((S)-2-oxopyrrolidin-3-yl)propan-2-yl)carbamoyl)-6-azaspiro[3.4]octane-6-carboxylate To a solution of (7S)-6-tert-butoxycarbonyl-6-azaspiro[3.4]octane-7-carboxylic acid (105.34 mg, 412.59 umol, 1 eq) and methyl (2S)-2-amino-3-[(3S)-2-oxopyrrolidin-3-yl]propanoate (158.4 mg, 412.59 umol, 1 eq, HCl) in DCM (1.2 mL) and DMF (0.4 mL) was added DMAP (100.81 mg, 825.19 umol, 2 eq) and EDCI (158.19 mg, 825.19 umol, 2 eq). The reaction mixture was stirred at 25° C. for 1 h. The residue was diluted with H₂O (6 mL) and extracted with ethyl acetate (3 mL). The combined organic layers were washed with ethyl acetate (3 mL*3), dried over Na₂SO₄, filtered and concentrated under reduced pressure to give a residue. The residue was purified by prep-TLC (SiO₂, petroleum ether/ethyl acetate=0/1) to get the product tert-butyl (7S)-7-[[(1S)-2-methoxy-2-oxo-1-[[(3S)-2-oxopyrrolidin-3-yl]methyl]ethyl]carbamoyl]-6-azaspiro[3.4]octane-6-carboxylate (66.3 mg, 156.55 umol, 37.94% yield) was obtained as a liquid. MS (ESI) m/z 424.0 [M+H]⁺

Step 3: (S)-methyl 3-((S)-2-oxopyrrolidin-3-yl)-2-((S)-6-azaspiro[3.4]octane-7-carboxamido)propanoate A solution of tert-butyl (7S)-7-[[(1S)-2-methoxy-2-oxo-1-[[(3S)-2-oxopyrrolidin-3-yl]methyl]ethyl]carbamoyl]-6-azaspiro[3.4]octane-6-carboxylate (66.3 mg, 156.55 umol, 1 eq) in HCl/MeOH (4 M, 782.76 uL, 20 eq) was stirred at 25° C. for 0.5 h. The reaction mixture was concentrated under reduced pressure to get the product methyl (2S)-2-[[(7S)-6-azaspiro[3.4]octane-7-carbonyl]amino]-3-[(3S)-2-oxopyrrolidin-3-yl]propanoate (71.1 mg, 156.09 umol, 99.71% yield, 79% purity, HCl) was obtained as a yellow liquid.

Step 4: (S)-methyl 2-((S)-6-(4-methoxy-1H-indole-2-carbonyl)-6-azaspiro[3.4]octane-7-carboxamido)-3-((S)-2-oxopyrrolidin-3-yl)propanoate To a solution of methyl (2S)-2-[[(7S)-6-azaspiro[3.4]octane-7-carbonyl]amino]-3-[(3S)-2-oxopyrrolidin-3-yl]propanoate (62.8 mg, 137.87 umol, 1 eq, HCl) and 4-methoxy-1H-indole-2-carboxylic acid (26.36 mg, 137.87 umol, 1 eq) in DCM (1.2 mL) and DMF (0.4 mL) was added DMAP (33.69 mg, 275.74 umol, 2 eq) and EDCI (52.86 mg, 275.74 umol, 2 eq) at 25° C. for 1 h. The residue was diluted with brine (6 mL) and extracted with ethyl acetate (3 mL*3). The combined organic layers were dried over Na₂SO₄, filtered and concentrated under reduced pressure to give a residue. The residue was purified by prep-TLC (SiO₂, petroleum ether/ethyl acetate=0/1) to get the product methyl (2S)-2-[[(7S)-6-(4-methoxy-1H-indole-2-carbonyl)-6-azaspiro [3.4]octane-7-carbonyl]amino]-3-[(3S)-2-oxopyrrolidin-3-yl]propanoate (33.2 mg, 66.86 umol, 48.50% yield) was obtained as a white solid. MS (ESI) m/z 497.1 [M+H]⁺

Step 5: (S)—N—((S)-1-amino-1-oxo-3-((S)-2-oxopyrrolidin-3-yl)propan-2-yl)-6-(4-methoxy-1H-indole-2-carbonyl)-6-azaspiro[3.4]octane-7-carboxamide A mixture of methyl (2S)-2-[[(7S)-6-(4-methoxy-1H-indole-2-carbonyl)-6-azaspiro[3.4]octane-7-carbonyl]amino]-3-[(3S)-2-oxopyrrolidin-3-yl]propanoate (23.0 mg, 46.32 umol, 1 eq) and ammonia (7 M, 4 mL, 604.50 eq) was stirred at 25° C. for 16 h. The reaction mixture was concentrated under reduced pressure to get the product (7S)—N-[(1S)-2-amino-2-oxo-1-[[(3S)-2-oxopyrrolidin-3-yl]methyl]ethyl]-6-(4-methoxy-1H-indole-2-carbonyl)-6-azaspiro[3.4]octane-7-carboxamide (15 mg, crude) was obtained as a yellow solid. MS (ESI) m z 482.2 [M+H]⁺

Step 6: (S)—N—((S)-1-cyano-2-((S)-2-oxopyrrolidin-3-yl)ethyl)-6-(4-methoxy-1H-indole-2-carbonyl)-6-azaspiro[3.4]octane-7-carboxamide A solution of (7S)—N-[(1S)-2-amino-2-oxo-1-[[(3S)-2-oxopyrrolidin-3-yl]methyl]ethyl]-6-(4-methoxy-1H-indole-2-carbonyl)-6-azaspiro[3.4]octane-7-carboxamide (15 mg, 28.66 umol, 1 eq) and Burgess reagent (13.66 mg, 57.32 umol, 2 eq) was stirred at 25° C. for 24 h. The reaction mixture was concentrated under reduced pressure to give a residue. The residue was purified by prep-HPLC (column: Waters Xbridge BEH C18 100*30 mm*10 um; mobile phase: [water(10 mM NH₄HCO₃)—ACN]; B %: 20%-45%, 8 min) to get the product (7S)—N-[(1S)-1-cyano-2-[(3S)-2-oxopyrrolidin-3-yl]ethyl]-6-(4-methoxy-1H-indole-2-carbonyl)-6-azaspiro[3.4]octane-7-carboxamide (3.01 mg, 6.49 umol, 22.66% yield) was obtained as a solid. MS (ESI) m/z 464.3 [M+H]⁺ ¹H NMR (400 MHz, METHANOL-d₄) δ ppm 6.95-7.24 (m, 3H) 6.47-6.58 (m, 1H) 5.01 (br dd, J=10.67, 5.19 Hz, 1H) 4.58 (t, J=7.09 Hz, 1H) 3.82-4.19 (m, 5H) 3.19 (br t, J=8.52 Hz, 1H) 2.93-3.07 (m, 1H) 2.28-2.56 (m, 3H) 2.16-2.27 (m, 2H) 1.94-2.14 (m, 6H) 1.47-1.86 (m, 2H).

Example 34. Synthesis of Viral Protease Inhibitor Compound 405

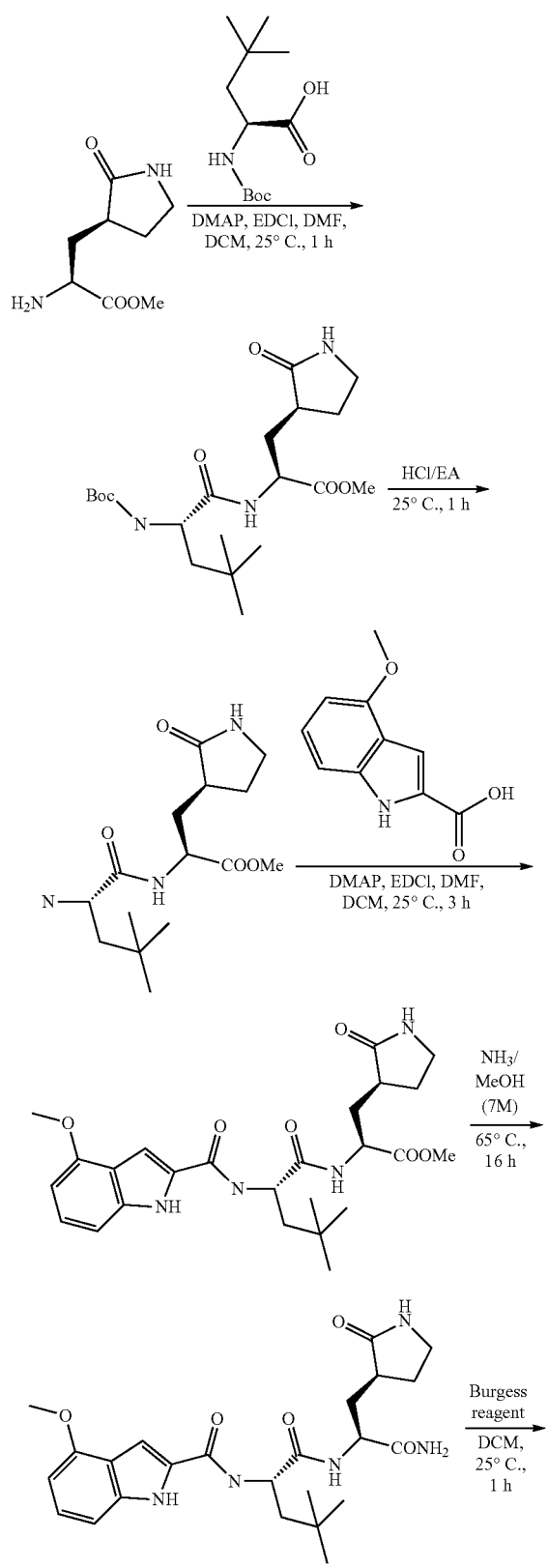

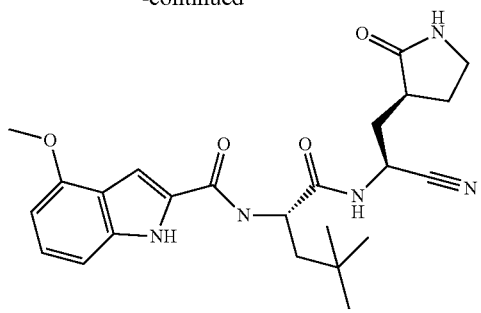

Step 1: methyl (2S)-2-[[(2S)-2-(tert-butoxycarbonylamino)-4,4-dimethyl-pentanoyl]amino]-3-[(3S)-2-oxopyrrolidin-3-yl]propanoate To a solution of methyl (2S)-2-amino-3-[(3S)-2-oxopyrrolidin-3-yl]propanoate (225 mg, 1.21 mmol, 1 eq) in DMF (2 mL) and DCM (4 mL) was added TEA (733.62 mg, 7.25 mmol, 1.01 mL, 6 eq) and T3P (1.15 g, 3.62 mmol, 1.08 mL, 3 eq) and (2S)-2-(tert-butoxycarbonylamino)-4,4-dimethyl-pentanoic acid (296.42 mg, 1.21 mmol, 1 eq). The solution was stirred for 1 h at 25° C. The reaction was added with H$_2$O (40 mL) and extracted with ethyl acetate (50 mL*3) and the organic layer was cautiously concentrated to give crude compound methyl (2S)-2-[[(2S)-2-(tert-butoxycarbonylamino)-4,4-dimethyl-pentanoyl]amino]-3-[(3S)-2-oxopyrrolidin-3-yl]propanoate (440 mg, crude) as a solid used directly for the next step. MS (ESI) m/z 414.1 [M+H]$^+$ Step 2: methyl (2S)-2-[[(2S)-2-amino-4,4-dimethyl-pentanoyl]amino]-3-[(3S)-2-oxopyrrolidin-3-yl]propanoate A solution of methyl (2S)-2-[[(2S)-2-(tert-butoxycarbonylamino)-4,4-dimethyl-pentanoyl]amino]-3-[(3S)-2-oxopyrrolidin-3-yl]propanoate (440 mg, 1.06 mmol, 1 eq) in HCl/MeOH (10 mL) was stirred for 1 h at 25° C. TLC (DCM:MeOH=10:1). The reaction was cautiously concentrated to give crude. Compound methyl (2S)-2-[[(2S)-2-amino-4,4-dimethyl-pentanoyl]amino]-3-[(3S)-2-oxopyrrolidin-3-yl]propanoate (310 mg, crude) as a solid used directly for the next step. MS (ESI) m/z 314.3 [M+H]$^+$ Step 3: methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate To a solution of methyl (2S)-2-[[(2S)-2-amino-4,4-dimethyl-pentanoyl]amino]-3-[(3S)-2-oxopyrrolidin-3-yl]propanoate (310 mg, 989.18 umol, 1 eq) in DMF (4 mL) and DCM (4 mL) was added EDCI (379.25 mg, 1.98 mmol, 2 eq) and DMAP (241.70 mg, 1.98 mmol, 2 eq) and 4-methoxy-1H-indole-2-carboxylic acid (189.11 mg, 989.18 umol, 1 eq) was added. The solution was stirred for 3 h at 25° C. The reaction was added with H$_2$O (40 mL) and extracted with ethyl acetate (80 mL*3) and the organic layer was cautiously concentrated to give crude. The crude was purified by pre-TLC(SiO$_2$, ethyl acetate:MeOH=10:1) to afford methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate (200 mg, 411.05 umol, 41.55% yield). MS (ESI) m/z 487.2 [M−H]$^+$

Step 4: N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide A solution of methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate (135 mg, 277.46 umol, 1 eq) in NH$_3$/MeOH (7 M, 8 mL, 201.83 eq) was stirred for 16 h at 65° C. The reaction was cautiously concentrated to give crude. Compound N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide (130 mg, crude) as a solid used directly for the next step. MS (ESI) m/z 472.3 [M+H]$^+$; Prep-HPLC condition: column: Phenomenex Gemini-NX C18 75*30 mm*3 um; mobile phase: [water(0.05% NH3H2O+10 mM NH$_4$HCO$_3$)—ACN]; B %: 35%-55%, 8 min

Step 5: N-[(1S)-1-[[(S)-1-cyano-2-[(3S)-2-oxopyrrolidin-3-yl]ethyl]carbamoyl]-3,3-dimethyl-butyl]-4-methoxy-1H-indole-2-carboxamide To a solution of N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide (130 mg, 275.69 umol, 1 eq) in DCM (7 mL) was added Burgess reagent (197.09 mg, 827.06 umol, 3 eq). The solution was stirred for 1 h at 25° C. The reaction was cautiously concentrated to give crude. The crude was purified by pre-HPLC(TFA) to afford N-[(1S)-1-[[(1S)-1-cyano-2-[(3S)-2-oxopyrrolidin-3-yl]ethyl]carbamoyl]-3,3-dimethyl-butyl]-4-methoxy-1H-indole-2-carboxamide (36 mg, 75.41 umol, 27.35% yield, 95% purity) as a solid. MS (ESI) m/z 454.1 [M+H]$^+$. Prep-HPLC condition: column: Phenomenex luna C18 80*40 mm*3 um; mobile phase: [water(0.04% HCl)—ACN]; B %: 30%-55%, 7 min; $^1$H NMR (400 MHz, METHANOL-d$_4$) δ ppm 1.02 (s, 9H) 1.74-1.94 (m, 4H) 2.21-2.37 (m, 2H) 2.52-2.63 (m, 1H) 3.16-3.26 (m, 2H) 3.92 (s, 3H) 4.63 (dd, J=8.49, 4.30 Hz, 1H) 4.98-5.06 (m, 1H) 6.50 (d, J=7.72 Hz, 1H) 7.02 (d, J=8.38 Hz, 1H) 7.10-7.16 (m, 1H) 7.23 (d, J=0.88 Hz, 1H).

Example 35. Synthesis of Viral Protease Inhibitor Compound 491 and 491A

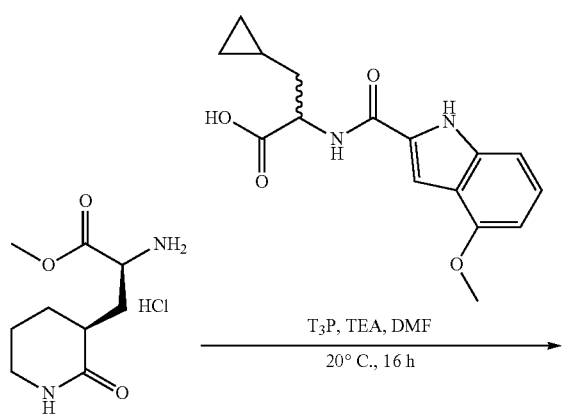

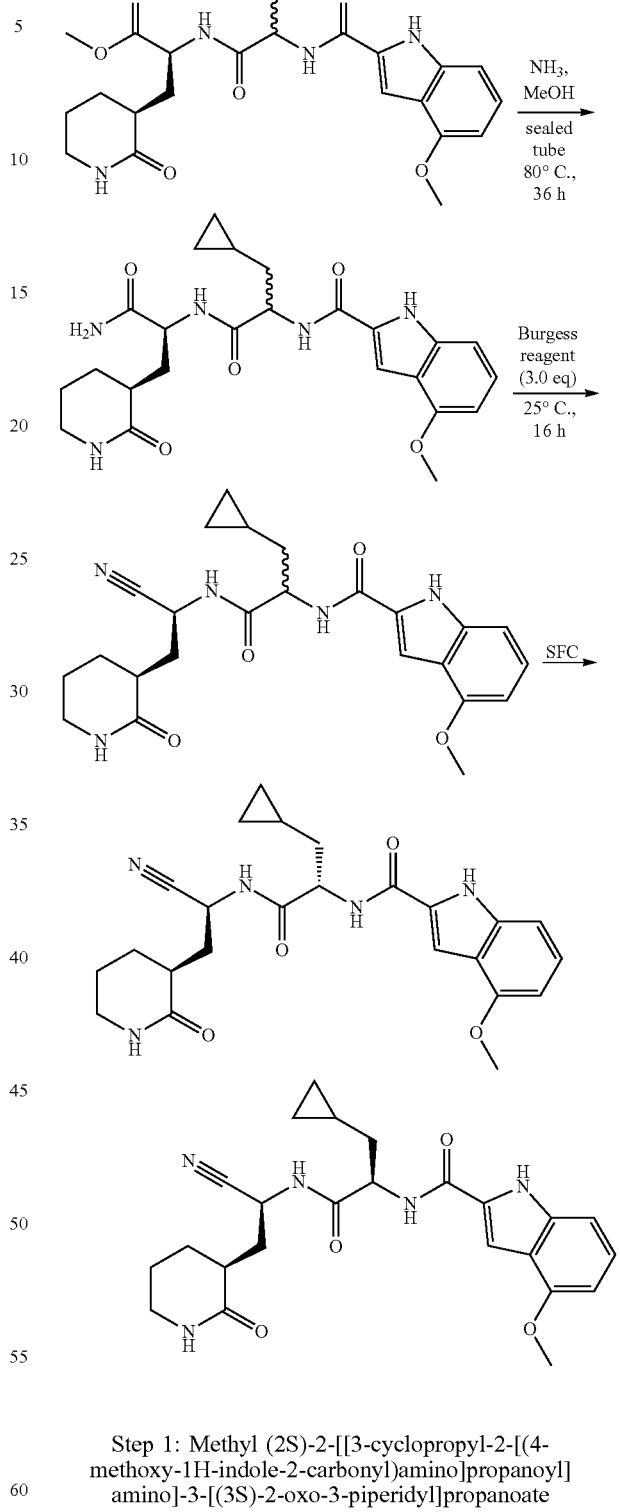

Step 1: Methyl (2S)-2-[[3-cyclopropyl-2-[(4-methoxy-1H-indole-2-carbonyl)amino]propanoyl]amino]-3-[(3S)-2-oxo-3-piperidyl]propanoate To the mixture of methyl (2S)-2-amino-3-[(3S)-2-oxo-3-piperidyl]propanoate (1 g, 4.22 mmol, 1 eq, HCl), 3-cyclopropyl-2-[(4-methoxy-1H-indole-2-carbonyl)amino]propanoic acid (1.5 g, 5.06 mmol, 1.2 eq, HCl) and TEA (1.7 g, 16.88 mmol, 2.35 mL, 4 eq) in DMF (5 mL) was added T$_3$P (5.3 g, 8.44 mmol, 5.02 mL, 50% purity, 2 eq) at 25° C. The mixture was stirred at 25° C. for 16 h. TLC (DCM: MeOH=10:1/UV254 nm) showed new spot was detected. The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by flash silica gel chromatography (ISCO®; 12 g SepaFlash® Silica Flash Column, Eluent of 100~25% Ethyl acetate/MeOH@ 30 mL/min). Compound methyl (2S)-2-[[3-cyclopropyl-2-[(4-methoxy-1H-indole-2-carbonyl)amino]propanoyl]amino]-3-[(3 S)-2-oxo-3-piperidyl]propanoate (1.9 g, 3.84 mmol, 91.0% yield) was obtained as a solid. Methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (50 mg, 0.10 mmol, 1 eq) was purified by prep-HPLC (column: Phenomenex Gemini-NX 80*30 mm*3 um; mobile phase: [water(0.05% NH₃H₂O+10 mM NH₄HCO₃)—ACN]; B %: 20%-50%, 9.5 min). Compound methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (50 mg, 0.10 mmol, 1 eq) was obtained as a solid.

Step 2: N-[2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide The mixture of methyl (2S)-2-[[3-cyclopropyl-2-[(4-methoxy-1H-indole-2-carbonyl)amino]propanoyl]amino]-3-[(3S)-2-oxo-3-piperidyl]propanoate (1.00 g, 1.73 mmol, 84% purity, 1 eq) in NH₃ (7 M, 24.77 mL, 100 eq) (7M in MeOH) was stirred at 80° C. for 36 h. Then, the reaction mixture was concentrated in vacuum. Compound N-[2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (813 mg, crude) was obtained as yellow solid.

N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (50 mg, 0.10 mmol, 1 eq) was purified by prep-HPLC (column: Phenomenex Gemini-NX 80*40 mm*3 um; mobile phase: [water (0.05% NH₃H₂O+10 mM NH₄HCO₃)—ACN]; B %: 23%-53%, 7.8 min). Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (20.3 mg, 42.5 umol, 39.9% yield, 98.4% purity) was obtained as white solid.

Step 3: N-[2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide A mixture of N-[2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (663.0 mg, 1.41 mmol, 1 eq) and methoxycarbonyl-(triethylammonio)sulfonyl-azanide (673.0 mg, 2.82 mmol, 2 eq) in DCM (8 mL) was stirred at 25° C. for 16 h. Then, methoxycarbonyl-(triethylammonio)sulfonyl-azanide (336.5 mg, 1.41 mmol, 1 eq) was added at the mixture and the mixture was stirred at 25° C. for 16 hr. LC-MS showed that the desired compound was detected. TLC (petroleum ether: ethyl acetate=0:1/I₂) showed new spots were detected. The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by prep-HPLC (column: Phenomenex Gemini-NX 80*30 mm*3 um; mobile phase: [water (0.05% NH₃H₂O+10 mM NH₄HCO₃)—ACN]; B %: 23%-53%, 9.5 min). Compound N-[2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (450 mg, 0.98 mmol, 69.9% yield) was obtained as yellow solid.

Step 4: N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide N-[2-[[1-cyano-2-[(3S)-2-oxo-3-piperidyl]ethyl]amino]-1-(cyclopropylmethyl)-2-oxo-ethyl]-4-methoxy-1H-indole-2-carboxamide (550.0 mg, 1.22 mmol, 1 eq) was purified by SFC(column: DAICEL CHIRALPAK AD (250 mm*30 mm, 10 um); mobile phase: [0.1% NH₃H₂O ETOH]; B %: 55%-55%, min). Compound N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide, Isomer 1 (147.1 mg, 0.25 mmol, 22.1% yield) was obtained as a solid. LCMS: Rt=0.756 min; for C₂₄H₂₉N₅O₄ MS Calcd: 451.22, MS Found:452.1 [M+H]⁺. ¹H NMR (400 MHz, DMSO-d₆) δ 11.56 (br s, 1H), 8.90 (br d, J=8.0 Hz, 1H), 8.49 (br d, J=7.4 Hz, 1H), 7.52 (br s, 1H), 7.36 (s, 1H), 7.12-7.06 (m, 1H), 7.03-6.98 (m, 1H), 6.50 (d, J=7.6 Hz, 1H), 5.17-4.96 (m, 1H), 4.56-4.33 (m, 1H), 3.88 (s, 3H), 3.09 (br s, 2H), 2.33-2.19 (m, 2H), 1.88-1.76 (m, 3H), 1.70 (br dd, J=3.8, 8.3 Hz, 1H), 1.57 (br s, 1H), 1.50-1.35 (m, 2H), 0.80 (br s, 1H), 0.41 (br d, J=6.6 Hz, 2H), 0.25-0.03 (m, 2H); and N-[(1R)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamidem, Isomer 2 (113.1 mg, 0.32 mmol, 28.8% yield, 100% purity) was obtained as a solid. LCMS: Rt=0.761 min; for C₂₄H₂₉N₅O₄ MS Calcd: 451.22, MS Found:452.0 [M+H]⁺. ¹H NMR (400 MHz, DMSO-d₆) δ 11.57 (s, 1H), 8.89 (br d, J=8.0 Hz, 1H), 8.49 (br d, J=7.6 Hz, 1H), 7.51 (br s, 1H), 7.36 (d, J=1.6 Hz, 1H), 7.13-7.06 (m, 1H), 7.03-6.97 (m, 1H), 6.50 (d, J=7.5 Hz, 1H), 5.08-4.99 (m, 1H), 4.52-4.42 (m, 1H), 3.88 (s, 3H), 3.08 (br s, 2H), 2.23-2.13 (m, 2H), 1.90-1.68 (m, 4H), 1.64-1.36 (m, 3H), 0.85-0.70 (m, 1H), 0.45-0.33 (m, 2H), 0.24-0.11 (m, 1H), 0.13-0.03 (m, 1H).

Example 36. Synthesis of Viral Protease Inhibitor Compound 531

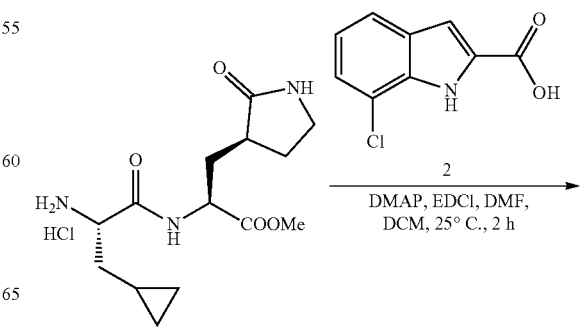

511

-continued

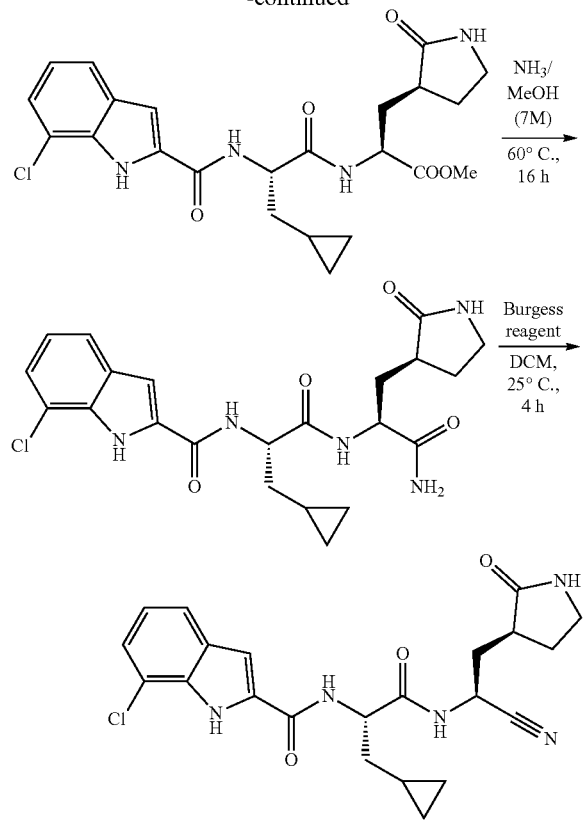

Step 1: methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (500 mg, 1.68 mmol, 1 eq) in DCM (10 mL) and DMF (2.5 mL), was added DMAP (616.30 mg, 5.04 mmol, 3 eq) in one portion at 25° C. The mixture was added 7-chloro-1H-indole-2-carboxylic acid (394.69 mg, 2.02 mmol, 1.2 eq) and EDCI (967.04 mg, 5.04 mmol, 3 eq). The resulting mixture was stirred at 25° C. for 2 h. Then, the mixture was concentrated under reduced pressure to give the crude product. The crude was purified by column chromatography (SiO$_2$, Petroleum ether/Ethyl acetate=5/1 to 0/1) to give methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate (550 mg, 1.16 mmol, 68.87% yield) as a white solid. MS (ESI) m/z 475.1 [M+H]$^+$

Step 2: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide A mixture of methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate (500 mg, 1.05 mmol, 1 eq) in NH$_3$/MeOH (7 M, 10 mL, 66.49 eq) was stirred at 60° C. for 16 h. The reaction mixture was concentrated under reduced pressure to give N-[(1S)-2-[[(1S)-2-amino-2-oxo-1-[[(3S)-2-oxopyrrolidin-3-yl]methyl]ethyl]

512 amino]-1-(cyclopropylmethyl)-2-oxo-ethyl]-7-chloro-1H-indole-2-carboxamide (440 mg, 956.68 umol, 90.87% yield) as a solid. MS (ESI) m/z 460.3 [M+H]$^+$

Step 3: 7-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide (430 mg, 934.94 umol, 1 eq) in DCM (6 mL) was added Burgess reagent (445.61 mg, 1.87 mmol, 2 eq) in one portion at 25° C. The mixture was stirred at 25° C. for 4 h. The reaction mixture was concentrated under reduced pressure to give the crude product. The crude was purified by prep-HPLC (column: Phenomenex Gemini-NX C$_{18}$ 75*30 mm*3 um; mobile phase: [water(0.05% NH$_3$H$_2$O+10 mM NH$_4$HCO$_3$)—ACN]; B %: 30%-60%, 8 min) to give 7-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide (180 mg, 407.32 umol, 43.57% yield) as a solid. MS (ESI) m/z 442.2 [M+H]$^+$; $^1$H NMR (400 MHz, DMSO-d$_6$) δ=11.71 (br s, 1H), 9.01 (d, J=7.9 Hz, 1H), 8.72 (d, J=7.5 Hz, 1H), 7.71 (s, 1H), 7.63 (dd, J=0.7, 7.9 Hz, 1H), 7.34-7.25 (m, 2H), 7.07 (t, J=7.8 Hz, 1H), 5.00 (q, J=7.9 Hz, 1H), 4.58-4.49 (m, 1H), 3.13 (quin, J=9.2 Hz, 2H), 2.42-2.31 (m, 1H), 2.22-2.05 (m, 2H), 1.89-1.64 (m, 3H), 1.57-1.46 (m, 1H), 0.89-0.75 (m, 1H), 0.50-0.37 (m, 2H), 0.25-0.07 (m, 2H).

Example 37. Synthesis of Viral Protease Inhibitor Compound 635

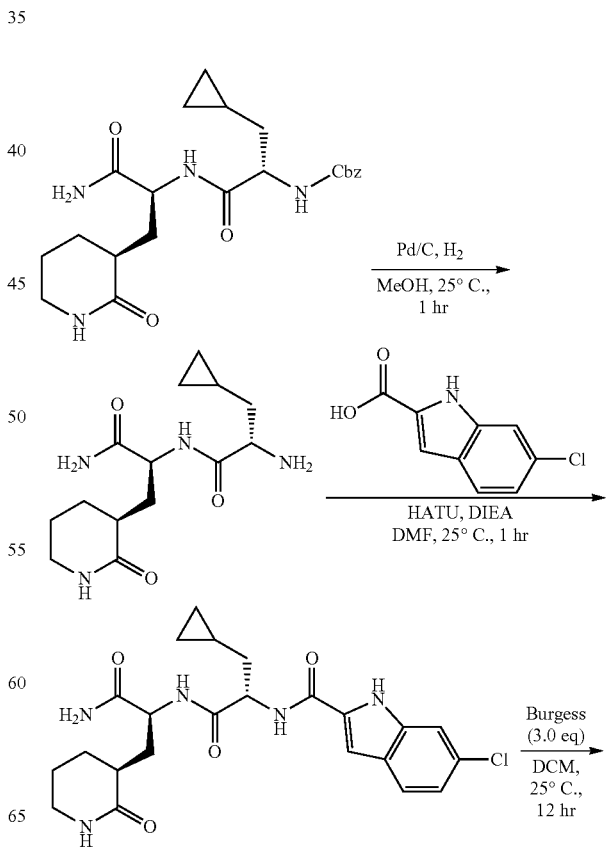

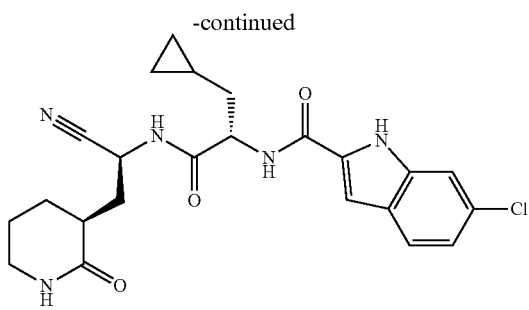

Step 1: (2S)-2-amino-N-[(1S)-2-amino-2-oxo-1-[[(3S)-2-oxo-3-piperidyl]methyl]ethyl]-3-cyclopropyl-propanamide To a solution of benzyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (400 mg, 0.92 mmol, 1 eq) in MeOH (5 mL) was added Pd (200 mg, 10% purity) and $H_2$ (0.92 mmol). The mixture was stirred at 25° C. under 15 psi for 1 hr. The mixture was filtered to give the filter liquor. The mixture was concentrated under reduce pressure to give compound (2S)-2-amino-N-[(1S)-2-amino-2-oxo-1-[[(3S)-2-oxo-3-piperidyl]methyl]ethyl]-3-cyclopropyl-propanamide (274 mg, 0.92 mmol, 99.5% yield) as a solid.

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide To a solution of (2S)-2-amino-N-[(1S)-2-amino-2-oxo-1-[[(3S)-2-oxo-3-piperidyl]methyl]ethyl]-3-cyclopropyl-propanamide (137 mg, 0.46 mmol, 1 eq) and 6-chloro-1H-indole-2-carboxylic acid (90.4 mg, 0.46 mmol, 1 eq) in DMF (2 mL) was added DIPEA (119.4 mg, 0.92 mmol, 0.16 mL, 2 eq) and HATU (210.9 mg, 0.55 mmol, 1.2 eq). The mixture was stirred at 25° C. for 1 hr. LCMS showed one peak with desired MS was detected. The mixture was concentrated under reduce pressure. The residue was purified by flash silica gel chromatography (ISCO®; 12 g SepaFlash® Silica Flash Column, Eluent of 0~10% DCM/MeOH @ 30 mL/min) to give Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide (200 mg, 89.0% yield) as a solid. LCMS: Rt=0.780 min; for $C_{23}H_{28}ClN_5O_4$ MS Calcd.: 473.18; MS Found: 474.1 [M+H]$^+$].

Step 3: 6-Chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide (47.5 mg, 0.1 mmol, 1 eq) in DCM (1 mL) was added Burgess reagent (71.6 mg, 0.3 mmol, 3 eq) at 0° C. The mixture was stirred at 25° C. for 12 hr. The mixture was concentrated under reduce pressure. The residue was purified by prep-HPLC (column: Phenomenex Gemini-NX 80*40 mm*3 um; mobile phase: [water(0.05% $NH_3H_2O$+10 mM $NH_4HCO_3$)—ACN]; B %: 31%-61%, 7.8 min) to give compound 6-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide(64.33 mg, 34.7% yield) as a solid. LCMS: Rt=0.832 min; for $C_{23}H_{26}ClN_5O_3$; MS Calcd.:455.17; MS Found: 456.1 [M+H]$^+$]. $^1$H NMR (400 MHz, DMSO-d$_6$) δ 11.73 (br s, 1H), 8.95 (br d, J=8.0 Hz, 1H), 8.66 (br d, J=7.5 Hz, 1H), 7.66 (d, J=8.5 Hz, 1H), 7.53 (br s, 1H), 7.44 (s, 1H), 7.31 (s, 1H), 7.05 (dd, J=1.8, 8.5 Hz, 1H), 5.11-4.96 (m, 1H), 4.52-4.42 (m, 1H), 3.09 (br s, 2H), 2.34-2.21 (m, 2H), 1.89-1.75 (m, 3H), 1.74-1.65 (m, 1H), 1.56 (br s, 1H), 1.51-1.29 (m, 2H), 0.79 (br s, 1H), 0.42 (br d, J=7.0 Hz, 2H), 0.23-0.01 (m, 2H)

Example 38. Synthesis of Viral Protease Inhibitor Compound 637

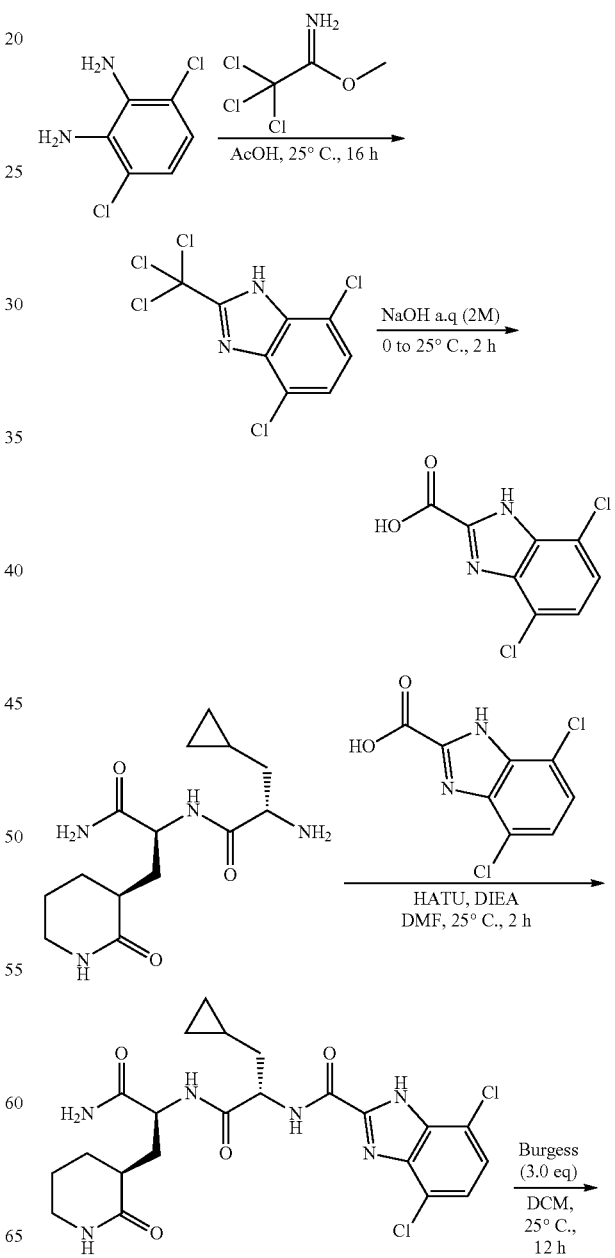

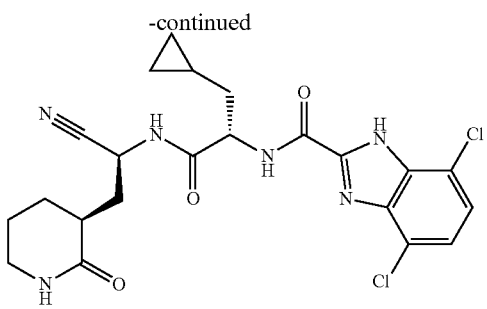

Step 1: 4,7-Dichloro-2-(trichloromethyl)-1H-benzimidazole

To a solution of 3,6-dichlorobenzene-1,2-diamine (0.3 g, 1.69 mmol, 1 eq) in AcOH (12.57 g, 209.2 mmol, 11.97 mL, 123.8 eq) was added methyl 2,2,2-trichloroacetimidate (313.0 mg, 1.77 mmol, 0.21 mL, 1.05 eq) at 0° C. The mixture was stirred at 25° C. for 16 hr. The resulting mixture was diluted with H₂O (40 mL) and filtered to give 4,7-dichloro-2-(trichloromethyl)-1H-benzo[d]imidazole (300 mg, crude) as a solid.

Step 2: 4,7-Dichloro-1H-benzimidazole-2-carboxylic acid

To a solution of NaOH (0.8 g, 20.0 mmol, 20.2 eq) in H₂O (10 mL) was added 4,7-dichloro-2-(trichloromethyl)-1H-benzo[d]imidazole (0.3 g, 985.58 umol, 1 eq) at 0° C. The mixture was stirred at 25° C. for 1 hr. The pH of the mixture was adjusted with HCl (2 M) to pH=2-3 and then the mixture was filtered to give 4,7-dichloro-1H-benzo[d]imidazole-2-carboxylic acid (0.2 g, crude) as a solid.

Step 3: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,6-dichloro-1H-benzimidazole-2-carboxamide To a solution of (S)-2-amino-N—((S)-1-amino-1-oxo-3-((S)-2-oxopiperidin-3-yl)propan-2-yl)-3-cyclopropylpropanamide (130 mg, 0.43 mmol, 1 eq) and 4,7-dichloro-1H-benzo[d]imidazole-2-carboxylic acid (101.3 mg, 0.43 mmol, 1.0 eq) in DMF (3 mL) was added HATU (250.1 mg, 0.65 mmol, 1.5 eq) and DIPEA (113.3 mg, 0.87 mmol, 0.15 mL, 2.0 eq). The mixture was stirred at 25° C. for 1 hr. TLC (Dichloromethane: Methanol=10/1) indicated 4,7-dichloro-1H-benzo[d]imidazole-2-carboxylic acid was consumed completely and one new spot formed. The reaction mixture was concentrated under reduced pressure to give a residue. The residue was purified by column chromatography (SiO₂, Petroleum ether/Ethyl acetate=100/1 to 10/1) to give N—((S)-1-(((S)-1-amino-1-oxo-3-((S)-2-oxopiperidin-3-yl)propan-2-yl)amino)-3-cyclopropyl-1-oxopropan-2-yl)-4,7-dichloro-1H-benzo[d]imidazole-2-carboxamide (0.2 g, 0.39 mmol, 89% yield) as a solid.

Step 4: 4,7-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-benzimidazole-2-carboxamide To a solution of N—((S)-1-(((S)-1-amino-1-oxo-3-((S)-2-oxopiperidin-3-yl)propan-2-yl)amino)-3-cyclopropyl-1-oxopropan-2-yl)-4,7-dichloro-1H-benzo[d]imidazole-2-carboxamide (100.00 mg, 0.19 mmol, 1 eq) in DCM (3.0 mL) was added Burgess Reagent (140.3 mg, 0.58 mmol, 3.0 eq). The mixture was stirred at 25° C. for 1 hr. The reaction mixture was concentrated under reduced pressure to give a residue. The residue was purified by prep-HPLC (column: Phenomenex Gemini-NX 80*40 mm*3 um; mobile phase: [water (0.05% NH3H2O+10 mM NH₄HCO3)—ACN]; B %: 20%-50%, 7.8 min) to give the product (22.11 mg, 22% yield) as a solid. LCMS: Rt=0.824 min; for C₂₂H₂₄Cl₂N₆O₃ MS Calcd.: 490.13; MS Found: 491.1 [M+H]⁺]. ¹H NMR (400 MHz, CD₃OD) δ 7.30 (s, 2H), 5.22-5.09 (m, 1H), 4.60 (t, J=7.1 Hz, 1H), 3.27-3.19 (m, 2H), 2.56-2.37 (m, 2H), 2.06-1.88 (m, 3H), 1.87-1.79 (m, 1H), 1.73 (td, J=7.2, 14.0 Hz, 2H), 1.60-1.44 (m, 1H), 0.96-0.75 (m, 1H), 0.54 (d, J=6.9 Hz, 2H), 0.21 (dd, J=4.8, 10.4 Hz, 2H).

Example 39. Synthesis of Viral Protease Inhibitor Compound 639 and 639A

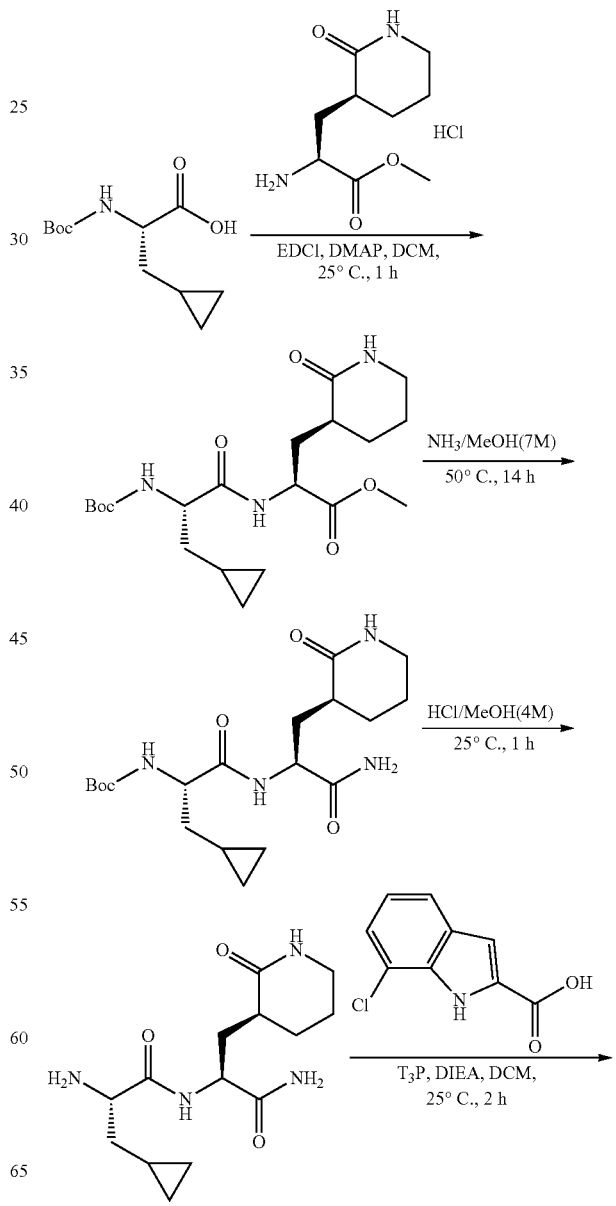

517
-continued

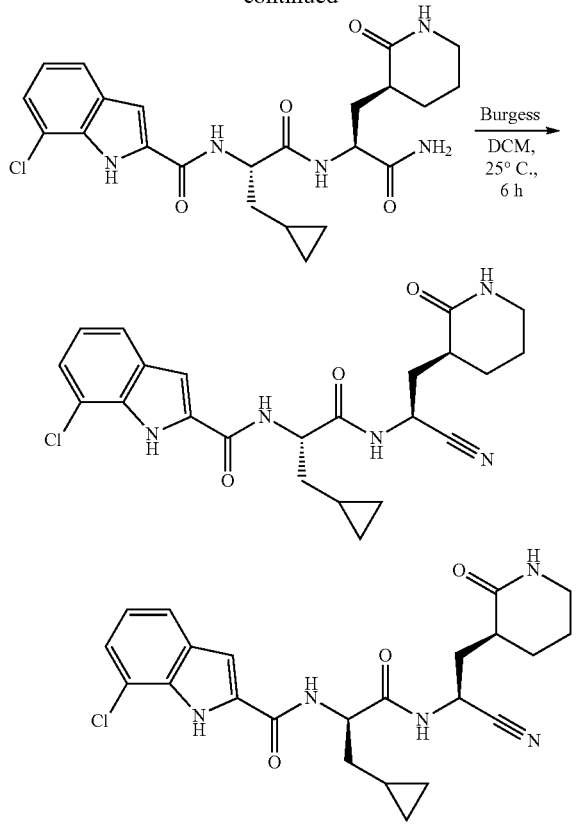

Step 1: Methyl (2S)-2-[[(2S)-2-(tert-butoxycarbonylamino)-3-cyclopropyl-propanoyl]amino]-3-[(3S)-2-oxo-3-piperidyl]propanoate To a solution of (2S)-2-(tert-butoxycarbonylamino)-3-cyclopropyl-propanoic acid (1.07 g, 4.65 mmol, 1.1 eq) and methyl (2S)-2-amino-3-[(3S)-2-oxo-3-piperidyl]propanoate (1 g, 4.22 mmol, 1 eq, HCl) in DCM (10 mL) was added DMAP (1.55 g, 12.67 mmol, 3 eq) and EDCI (1.62 g, 8.45 mmol, 2 eq). The resulting mixture was stirred at 25° C. for 1 h. Upon completion, the solution was added with H$_2$O (30 mL), and then extracted with ethyl acetate (30 mL*3). The combined organic phase was dried over Na$_2$SO$_4$, filtrated and concentrated. The residue was purified by column chromatography (SiO$_2$, DCM/MeOH=30/1 to 10/1) to give methyl (2S)-2-[[(2S)-2-(tert-butoxycarbonylamino)-3-cyclopropyl-propanoyl]amino]-3-[(3S)-2-oxo-3-piperidyl] propanoate (1.2 g, 2.92 mmol, 68.97% yield, 100% purity) was obtained as yellow oil. MS (ESI) m/z 412.3 [M+H]$^+$.

Step 2: (2R)—N-(4-(tert-butyl)phenyl)-N-(2-oxo-1-(pyridin-3-yl)-2-((pyridin-4-ylmethyl)amino)ethyl)pyrrolidine-2-carboxamide Methyl (2S)-2-[[(2S)-2-(tert-butoxycarbonylamino)-3-cyclopropyl-propanoyl]amino]-3-[(3S)-2-oxo-3-piperidyl] propanoate (600 mg, 1.46 mmol, 1 eq) in ammonia (7 M, 7.2 mL, 8.30 eq) was stirred at 50° C. for 14 h. Upon completion, the solution was concentrated to give tert-butyl N-[(1S)-2-[[(1S)-2-amino-2-oxo-1-[[(3S)-2-oxo-3-piperidyl]methyl]ethyl]amino]-1-(cyclopropylmethyl)-2-oxoethyl]carbamate (580 mg, crude) as yellow oil. MS (ESI) m/z 397.3 [M+H]$^+$.

518

Step 3: (2S)-2-amino-N-[(1S)-2-amino-2-oxo-1-[[(3S)-2-oxo-3-piperidyl]methyl]ethyl]-3-cyclopropyl-propanamide Tert-butyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (580 mg, 1.46 mmol, 1 eq) in HCl/MeOH (4 M, 10.00 mL, 7.93 eq) was stirred at 25° C. for 1 h. Upon completion, the solution was concentrated to give (2S)-2-amino-N-[(1S)-2-amino-2-oxo-1-[[(3S)-2-oxo-3-piperidyl]methyl]ethyl]-3-cyclopropyl-propanamide (380 mg, crude) was obtained as yellow oil. MS (ESI) m/z 297.2 [M+H]$^+$.

Step 4: (2S)-2-amino-N-[(1S)-2-amino-2-oxo-1-[[(3S)-2-oxo-3-piperidyl]methyl]ethyl]-3-cyclopropyl-propanamide To a solution of (2S)-2-amino-N-[(1S)-2-amino-2-oxo-1-[[(3S)-2-oxo-3-piperidyl]methyl]ethyl]-3-cyclopropyl-propanamide (380 mg, 1.28 mmol, 1 eq) in DCM (3 mL) was added 7-chloro-1H-indole-2-carboxylic acid (275.88 mg, 1.41 mmol, 1.1 eq), T$_3$P (1.22 g, 1.93 mmol, 1.14 mL, 50% purity, 1.5 eq), and DIEA (331.44 mg, 2.56 mmol, 446.68 uL, 2 eq). The mixture was stirred at 25° C. for 2 h. Upon completion, the solution was diluted with H$_2$O (20 mL), extracted with DCM (30 mL*3), the combined organic phase was dried over Na$_2$SO$_4$, filtrated and concentrated. The residue was purified by prep-TLC (SiO$_2$, DCM: MeOH=10:1) to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (350 mg, 738.47 umol, 57.59% yield, 100% purity) as yellow oil. MS (ESI) m/z 474.3 [M+H]$^+$.

Step 5: 7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (350 mg, 738.47 umol, 1 eq) in DCM (4 mL) was added Burgess reagent (527.94 mg, 2.22 mmol, 3 eq), and the solution was stirred at 25° C. for 6 h. Upon completion, DCM was removed using blow dry. The residue was purified by prep-HPLC (column: Waters Xbridge Prep OBD C18 150*40 mm*10 um; mobile phase: [water(0.05% NH$_3$H$_2$O+10 mM NH4HCO$_3$)—ACN]; B %: 25%-55%, 8 min) to afford the product as a solid, which was further separated by SFC (column: DAICEL CHIRALPAK AS (250 mm*30 mm, 10 um); mobile phase: [0.1% NH$_3$H$_2$O ETOH]; B %: 33%-33%, 8 min) to give:

7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (250 mg, 530.89 umol, 74.25% yield, 96.82% purity) as a solid. MS (ESI) m/z 456.2 [M+H]$^+$. $^1$H NMR (400 MHz, METHANOL-d$_4$) δ=7.58 (d, J=7.9 Hz, 1H), 7.35-7.20 (m, 2H), 7.06 (t, J=7.8 Hz, 1H), 5.22-5.05 (m, 1H), 4.57 (t, J=7.5 Hz, 1H), 3.27-3.14 (m, 2H), 2.61-2.34 (m, 2H), 2.09-1.61 (m, 6H), 1.59-1.43 (m, 1H), 0.98-0.76 (m, 1H), 0.55 (dd, J=1.3, 8.2 Hz, 2H), 0.31-0.09 (m, 2H); and 7-chloro-N-[(1R)-2-[[(1S)-1-cyano-2-[(3S)-2-oxo-3-piperidyl]ethyl]amino]-1-(cyclopropylmethyl)-2-oxo-ethyl]-1H-indole-2-carboxamide (45 mg, 98.70 umol, 13.37% yield, 100% purity) as a solid. MS (ESI) m/z 456.2 [M+H]$^+$.

¹H NMR (400 MHz, METHANOL-d₄) δ =7.59 (dd, J=0.9, 7.9 Hz, 1H), 7.32-7.21 (m, 2H), 7.07 (t, J=7.8 Hz, 1H), 5.12-5.02 (m, 1H), 4.59 (dd, J=6.4, 7.9 Hz, 1H), 3.21 (dd, J=4.6, 7.7 Hz, 2H), 2.44-2.23 (m, 2H), 2.09-1.62 (m, 6H), 1.60-1.47 (m, 1H), 0.94-0.78 (m, 1H), 0.62-0.43 (m, 2H), 0.27-0.11 (m, 2H).

Example 40. Synthesis of Viral Protease Inhibitor Compound 643

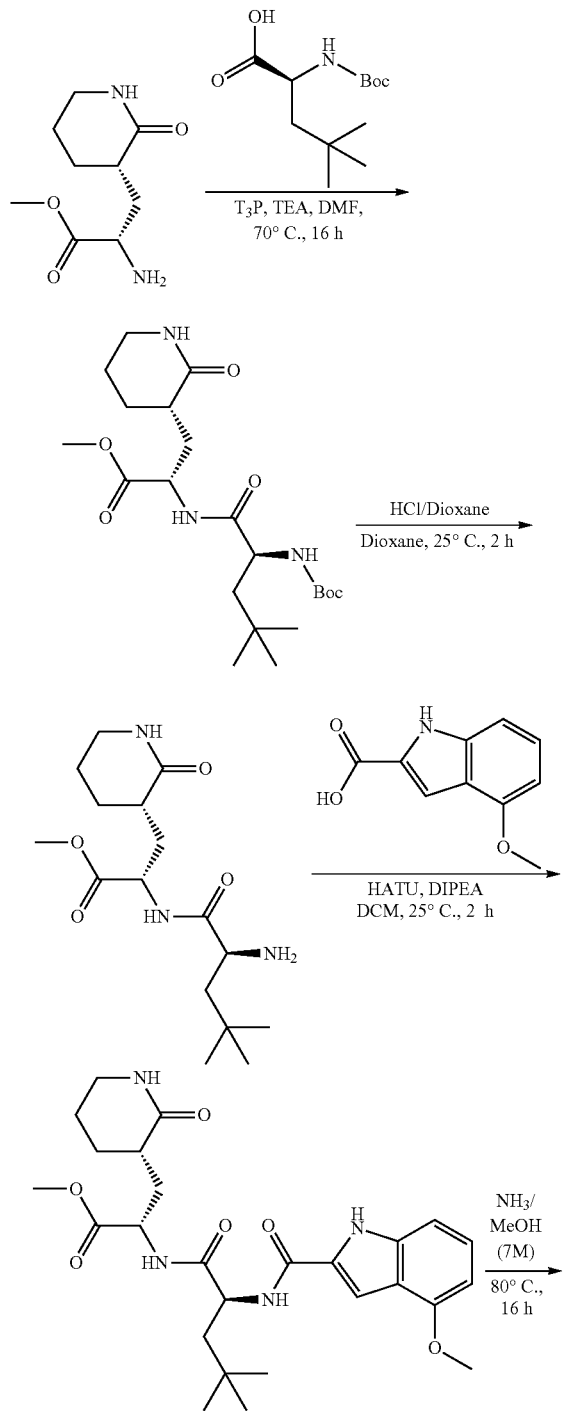

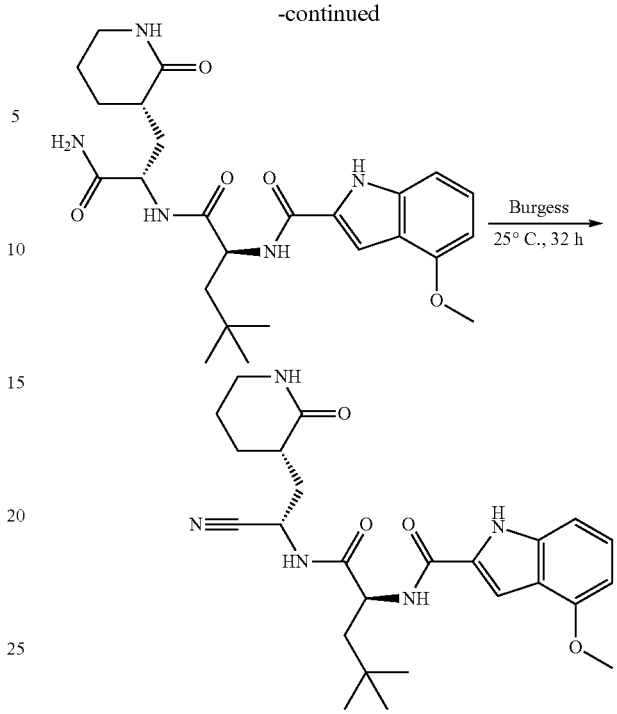

Step 1: Methyl (2S)-2-[[(2S)-2-(tert-butoxycarbonylamino)-4,4-dimethyl-pentanoyl]amino]-3-[(3S)-2-oxo-3-piperidyl]propanoate T₃P (2.69 g, 4.22 mmol, 2.51 mL, 50% purity, 2 eq) was added to a mixture of methyl (2S)-2-amino-3-[(3S)-2-oxo-3-piperidyl]propanoate (500 mg, 2.11 mmol, 1 eq, HCl), (2S)-2-(tert-butoxycarbonylamino)-4,4-dimethyl-pentanoic acid (570.0 mg, 2.32 mmol, 1.1 eq) and TEA (855.0 mg, 8.45 mmol, 1.18 mL, 4 eq) in DMF (5 mL). The resulting mixture was stirred at 70° C. for 16 hr. TLC (petroleum ether: ethyl acetate=0:1/PMA) showed new spots were detected. The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by flash silica gel chromatography (ISCO®; 20 g SepaFlash® Silica Flash Column, Eluent of 0-100% Ethyl acetate/Petroleum ethergradient @30 mL/min). Compound methyl (2S)-2-[[(2S)-2-(tert-butoxycarbonylamino)-4,4-dimethyl-pentanoyl]amino]-3-[(3S)-2-oxo-3-piperidyl]propanoate (436 mg, 0.99 mmol, 47.2% yield, 97.9% purity) was obtained as a solid.

Step 2: Methyl (2S)-2-[[(2S)-2-amino-4,4-dimethyl-pentanoyl]amino]-3-[(3S)-2-oxo-3-piperidyl]propanoate Methyl (2S)-2-[[(2S)-2-(tert-butoxycarbonylamino)-4,4-dimethyl-pentanoyl]amino]-3-[(3S)-2-oxo-3-piperidyl]propanoate (300 mg, 0.70 mmol, 1 eq) in HCl/dioxane (4 M, 175.42 uL, 1 eq) was stirred at 25° C. for 2 hr. Compound methyl (2S)-2-[[(2S)-2-amino-4,4-dimethyl-pentanoyl]amino]-3-[(3S)-2-oxo-3-piperidyl]propanoate (250 mg, crude, HCl) was obtained as a solid and was used into next step without further purification.

Step 3: Methyl (2S)-2-[[(2S)-2-[(4-methoxy-1H-indol-2-carbonyl)amino]-4,4-dimethyl-pentanoyl]amino]-3-[(3S)-2-oxo-3-piperidyl]propanoate A mixture of methyl (2S)-2-[[(2S)-2-amino-4,4-dimethyl-pentanoyl]amino]-3-[(3S)-2-oxo-3-piperidyl]propanoate (310 mg, 0.85 mmol, 1 eq, HCl), 4-methoxy-1H-indole-2-carboxylic acid (179.1 mg, 0.93 mmol, 1.1 eq), HATU (647.8 mg, 1.70 mmol, 2 eq) and DIPEA (440.4 mg, 3.41 mmol, 0.60 mL, 4 eq) in DCM (4 mL) was stirred at 25° C. for 2 hr. TLC (petroleum ether/ethyl acetate=0:1/UV 254 nm) showed new spots were detected. The reaction mixture was diluted with H$_2$O (10 mL) and the mixture was extracted with ethyl acetate (10 mL*3). The combined organic phase was washed with brine (10 mL*2), dried with anhydrous Na$_2$SO$_4$, filtered and concentrated in vacuum. The residue was purified by flash silica gel chromatography (ISCO®; 12 g SepaFlash® Silica Flash Column, Eluent of 0~100% Ethyl acetate/Petroleum ethergradient @ 30 mL/min). Compound methyl (2S)-2-[[(2S)-2-[(4-methoxy-1H-indole-2-carbonyl)amino]-4,4-dimethyl-pentanoyl]amino]-3-[(3S)-2-oxo-3-piperidyl]propanoate (451 mg, 0.68 mmol, 80.1% yield) was obtained as an oil and confirmed by LC-MS.

Step 4: N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide NH$_3$ (7 M, 11.42 mL, 100 eq) was added to a mixture of methyl (2S)-2-[[(2S)-2-[(4-methoxy-1H-indole-2-carbonyl)amino]-4,4-dimethyl-pentanoyl]amino]-3-[(3S)-2-oxo-3-piperidyl]propanoate (400 mg, 0.79 mmol, 1 eq) in MeOH. Then, the mixture was stirred at 80° C. for 16 hr. TLC (DCM:MeOH=10:1/UV 254 nm) showed new spot was detected. The reaction mixture was concentrated in vacuum. The residue was purified by flash silica gel chromatography (ISCO®; 12 g SepaFlash® Silica Flash Column, Eluent of 0~50% Ethyl acetate/MeOH @30 mL/min). Compound N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide (295 mg, 0.60 mmol, 75.1% yield, 98.9% purity) was obtained as a solid.

Step 5: N-[(1S)-1-[[(1S)-1-cyano-2-[(3S)-2-oxo-3-piperidyl]ethyl]carbamoyl]-3,3-dimethyl-butyl]-4-methoxy-1H-indole-2-carboxamide Methoxycarbonyl-(triethylammonio)sulfonyl-azanide (284.6 mg, 1.19 mmol, 2 eq) was added at the mixture of N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide (290 mg, 0.59 mmol, 1 eq) in DCM (3 mL) at 25° C. Then the mixture was stirred at 25° C. for 16 hr. Then methoxycarbonyl-(triethylammonio)sulfonyl-azanide (142.3 mg, 0.59 mmol, 1 eq) was added to the mixture and the mixture was stirred at 25° C. for anther 16 hr. The reaction mixture was diluted with H$_2$O (10 mL) and the mixture was extracted with ethyl acetate (10 mL*3). The combined organic phase was washed with brine (10 mL*2), dried with anhydrous Na$_2$SO$_4$, filtered and concentrated in vacuum. The residue was purified by prep-HPLC (column: Welch Xtimate C$_{18}$ 150*25 mm*5 um; mobile phase: [water (0.05% ammonia hydroxide v/v)—MeOH]; B %: 55%-85%, 9.5 min). Compound N-[(1S)-1-[[(1S)-1-cyano-2-[(3S)-2-oxo-3-piperidyl]ethyl]carbamoyl]-3,3-dimethyl-butyl]-4-methoxy-1H-indole-2-carboxamide (28.1 mg, 59.3 umol, 9.9% yield, 98.7% purity) was obtained as a solid. Rt=0.832 min; for C$_{25}$H$_{33}$N$_5$O$_4$ MS Calcd.: 467.25, MS Found: 468.2 [M+H]$^+$. $^1$H NMR (400 MHz, CD$_3$OD) δ 7.26-7.22 (m, 1H), 7.18-7.12 (m, 1H), 7.05-7.00 (m, 1H), 6.51 (d, J=7.5 Hz, 1H), 5.08 (dd, J=6.3, 9.8 Hz, 1H), 4.67-4.63 (m, 1H), 3.93 (s, 3H), 3.21-3.15 (m, 2H), 2.47-2.38 (m, 2H), 1.98-1.72 (m, 6H), 1.70-1.58 (m, 1H), 1.54-1.43 (m, 1H), 1.02 (s, 8H), 1.04-1.01 (m, 2H).

Example 41. Synthesis of Viral Protease Inhibitor Compound 681

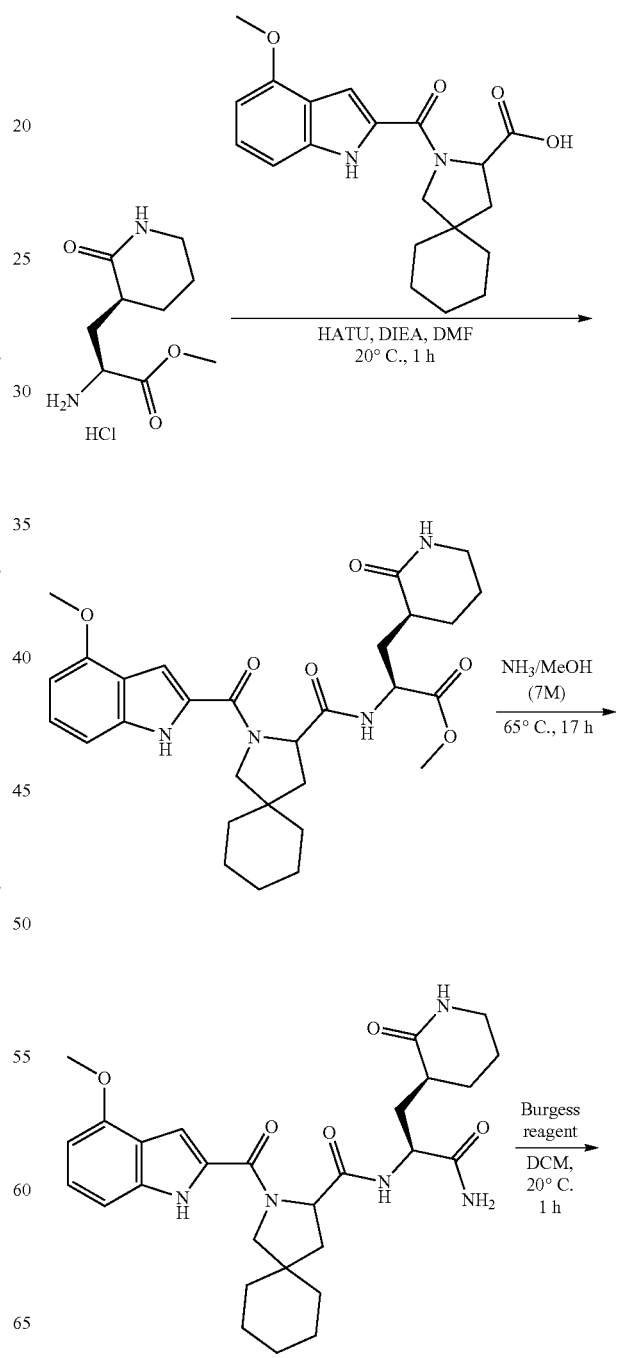

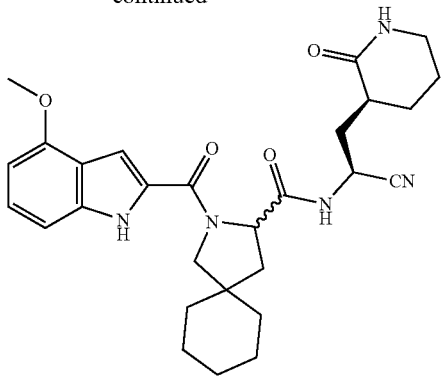

Step 1: (2S)-methyl2-(2-(4-methoxy-1H-indole-2-carbonyl)-2-azaspiro[4.5]decane-3-carboxamido)-3-((S)-2-oxopiperidin-3-yl)propanoate To a solution of methyl (2S)-2-amino-3-[(3S)-2-oxo-3-piperidyl]propanoate (500 mg, 2.11 mmol, 1.1 eq, HCl) and 2-(4-methoxy-1H-indole-2-carbonyl)-2-azaspiro[4.5]decane-3-carboxylic acid (684.45 mg, 1.92 mmol, 1 eq) in DMF (15 mL) was added N,N-diisopropylethylamine (DIEA) (744.57 mg, 5.76 mmol, 1.00 mL, 3 eq) and (1-[bis(dimethylamino)methylene]-1H-1,2,3-triazolo[4,5-b]pyridinium 3-oxide hexafluorophosphate (HATU) (730.19 mg, 1.92 mmol, 1 eq). The mixture was stirred at 20° C. for 1 h. Upon completion, the two batch reaction mixture was quenched by addition H$_2$O (80 mL), and extracted with ethyl acetate (40 mL*3). The combined organic layers were washed with brine 40 mL, dried over Na$_2$SO$_4$, filtered and concentrated under reduced pressure to get the product methyl (2S)-2-[[2-(4-methoxy-1H-indole-2-carbonyl)-2-azaspiro[4.5]decane-3-carbonyl]amino]-3-[(3S)-2-oxo-3-piperidyl]propanoate (1.35 g, crude) was obtained as white solid. MS (ESI) m/z 539.3 [M+H]$^+$.

Step 2: N—((S)-1-amino-1-oxo-3-((S)-2-oxopiperidin-3-yl)propan-2-yl)-2-(4-methoxy-1H-indole-2-carbonyl)-2-azaspiro[4.5]decane-3-carboxamide A solution of methyl (2S)-2-[[2-(4-methoxy-1H-indole-2-carbonyl)-2-azaspiro[4.5]decane-3-carbonyl]amino]-3-[(3S)-2-oxo-3-piperidyl]propanoate (650 mg, 1.21 mmol, 1 eq) in NH$_3$/MeOH (7 M, 3.45 mL, 20 eq) was stirred at 65° C. for 17 h. Upon completion, the two batch reaction mixture was concentrated under reduced pressure to get the product N-[(1S)-2-amino-2-oxo-1-[[(3S)-2-oxo-3-piperidyl]methyl]ethyl]-2-(4-methoxy-1H-indole-2-carbonyl)-2-azaspiro[4.5]decane-3-carboxamide (1.22 g, crude) as colorless oil. MS (ESI) m/z 524.3 [M+H]$^+$.

Step 3: N—((S)-1-cyano-2-((S)-2-oxopiperidin-3-yl)ethyl)-2-(4-methoxy-1H-indole-2-carbonyl)-2-azaspiro[4.5]decane-3-carboxamide To a solution of N-[(1S)-2-amino-2-oxo-1-[[(3S)-2-oxo-3-piperidyl]methyl]ethyl]-2-(4-methoxy-1H-indole-2-carbonyl)-2-azaspiro[4.5]decane-3-carboxamide (1.22 g, 2.33 mmol, 1 eq) in DCM (20 mL) was added Burgess reagent (1.39 g, 5.82 mmol, 2.5 eq). The mixture was stirred at 20° C. for 1 h. Upon completion, the reaction mixture was quenched by the addition of H$_2$O (3 mL) and then concentrated under reduced pressure to give a residue. The residue was purified by prep-HPLC (column: Agela DuraShell C18 250*70 mm*10 um; mobile phase: [water(10 mM NH$_4$HCO$_3$)—ACN]; B %: 43%-63%, 20 min) to give desired compound (490 mg) as a solid, which was further separated by SFC (column: DAICEL CHIRALPAK AD (250 mm*30 mm, 10 um); mobile phase: [0.1% NH$_3$H$_2$O IPA]; B %: 58%-58%, 10 min) to afford the product N-[(1S)-1-cyano-2-[(3 S)-2-oxo-3-piperidyl]ethyl]-2-(4-methoxy-1H-indole-2-carbonyl)-2-azaspiro[4.5]decane-3-carboxamide, Isomer 1 (201.77 mg, 394.36 umol, 16.93% yield) was obtained as white solid. MS (ESI) m/z 506.3[M+H]$^+$. $^1$H NMR (400 MHz, DMSO-d$_6$) δ ppm 11.26 (br s, 1H) 8.50-8.85 (m, 1H) 7.23 (br s, 1H) 7.00-7.16 (m, 2H) 6.89 (br s, 1H) 6.52 (br d, J=7.46 Hz, 1H) 4.86-5.06 (m, 1H) 4.48-4.79 (m, 1H) 3.80-3.98 (m, 4H) 3.59 (br d, J=4.65 Hz, 1H) 3.09 (br s, 2H) 2.15-2.31 (m, 3H) 1.73-2.01 (m, 2H) 1.67 (br dd, J=12.17, 8.62 Hz, 2H) 1.33-1.61 (m, 12H); and N-[(1S)-1-cyano-2-[(3S)-2-oxo-3-piperidyl]ethyl]-2-(4-methoxy-1H-indole-2-carbonyl)-2-azaspiro[4.5]decane-3-carboxamide, Isomer 2 (200.95 mg, 394.35 umol, 16.93% yield) was obtained as white solid. MS (ESI) m/z 506.3[M+H]$^+$. $^1$H NMR (400 MHz, DMSO-d$_6$) δ ppm 11.27 (br s, 1H) 8.61 (br d, J=1.22 Hz, 1H) 7.02-7.26 (m, 3H) 6.91 (br s, 1H) 6.53 (d, J=7.46 Hz, 1H) 4.91-5.06 (m, 1H) 4.62 (br s, 1H) 3.82-3.98 (m, 4H) 3.52-3.75 (m, 1H) 3.09 (br s, 2H) 2.09-2.28 (m, 3H) 1.63-1.92 (m, 4H) 1.33-1.62 (m, 12H).

Example 42. Synthesis of Viral Protease Inhibitor Compound 721

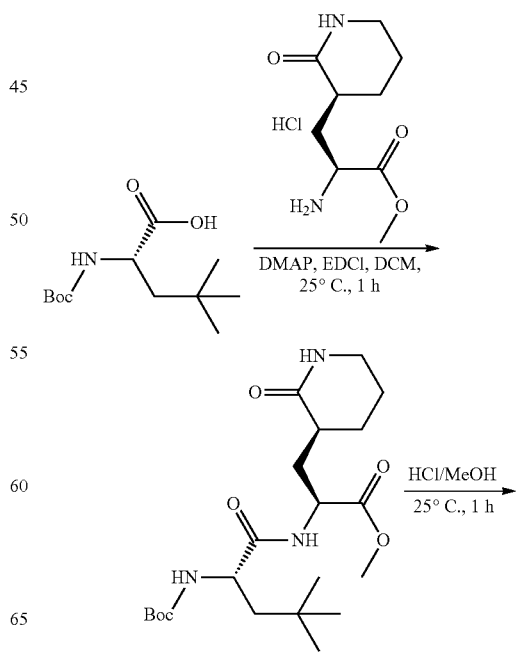

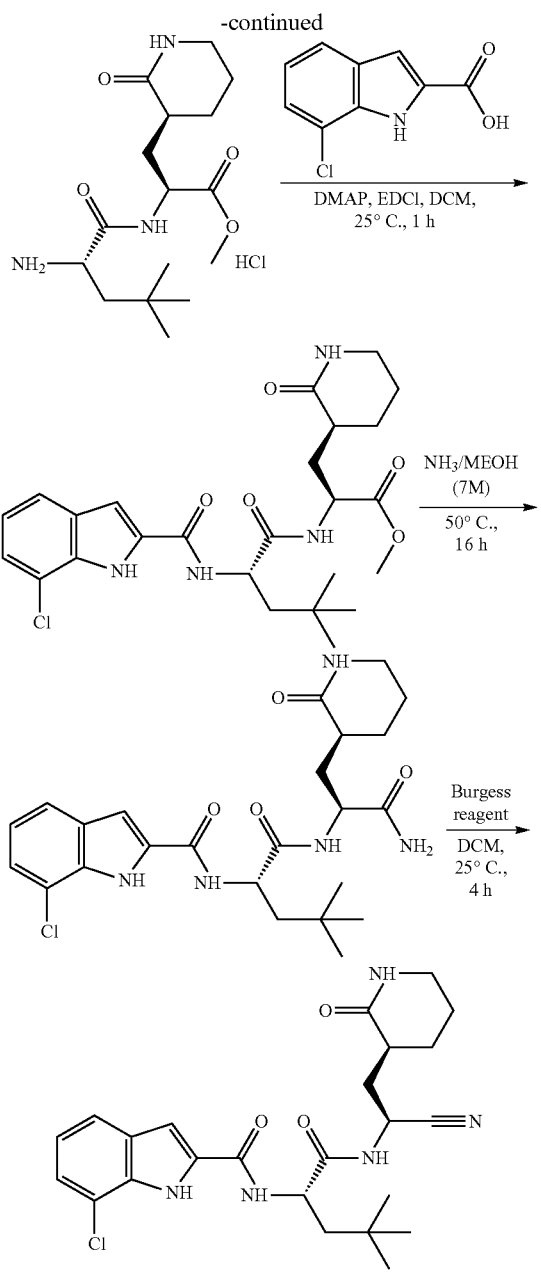

Step 1: (S)-methyl2-((S)-2-((tert-butoxycarbonyl)amino)-4,4-dimethylpentanamido)-3-((S)-2-oxopiperidin-3-yl)propanoate To a solution of (2S)-2-(tert-butoxycarbonylamino)-4,4-dimethyl-pentanoic acid (2.49 g, 10.14 mmol, 1.2 eq) and methyl (2S)-2-amino-3-[(3S)-2-oxo-3-piperidyl]propanoate (2 g, 8.45 mmol, 1 eq, HCl) in DCM (60 mL) was added DMAP (3.10 g, 25.35 mmol, 3 eq). Then, EDCI (3.24 g, 16.90 mmol, 2 eq) was added, and the resulting mixture was stirred at 25° C. for 1 h. Upon the reaction complement, the mixture was quenched by water (400 mL), extracted with DCM (150 mL*3), and then was dried by sat. NaCl (50 mL). The resulting solution was concentrated in vacuum and was purified by column (SiO₂, petroleum ether:ethyl acetate=2:1 to 0:1). The resulting residue was washed with HCl (1 M, 150 mL), extracted with DCM (50 mL*3), and then the pH of the solution was adjust pH=~8 with sat. NaHCO₃ (30 mL). The resulting mixture was extracted with DCM (100 mL), and then concentrated under vacuum to afford (S)-methyl 2-((S)-2-((tert-butoxycarbonyl)amino)-4,4-dimethylpentanamido)-3-((S)-2-oxopiperidin-3-yl) propanoate (3 g, 6.32 mmol, 74.74% yield) as a solid. $^1$H NMR (400 MHz, CDCl$_3$-d) δ ppm 7.61 (d, J=7.0 Hz, 1H), 6.85-6.51 (m, 1H), 6.22 (s, 1H), 5.06-4.85 (m, 1H), 4.63-4.47 (m, 1H), 4.30-4.02 (m, 1H), 3.79-3.66 (m, 3H), 3.35-3.25 (m, 2H), 2.42-2.24 (m, 1H), 2.14-2.05 (m, 1H), 1.96-1.66 (m, 4H), 1.63-1.52 (m, 1H), 1.43 (s, 9H), 1.03-0.90 (m, 9H).

Step 2: (S)-methyl 2-((S)-2-amino-4,4-dimethylpentanamido)-3-((S)-2-oxopiperidin-3-yl)propanoate A solution of (S)-methyl 2-((S)-2-((tert-butoxycarbonyl)amino)-4,4-dimethylpentanamido)-3-((S)-2-oxopiperidin-3-yl) propanoate (1.5 g, 3.51 mmol, 1 eq) in HCl/MeOH (4 M, 20 mL) was stirred at 25° C. for 1 h. Upon the reaction complement, the mixture was concentrated under vacuum to obtain (S)-methyl 2-((S)-2-amino-4,4-dimethylpentanamido)-3-((S)-2-oxopiperidin-3-yl)propanoate (1.1 g, crude, HCl) as a solid. $^1$H NMR (400 MHz, D$_2$O) δ ppm 4.57 (dd, J=4.8, 10.3 Hz, 1H), 3.98 (dd, J=5.2, 7.8 Hz, 1H), 3.78-3.65 (m, 3H), 3.29-3.14 (m, 2H), 2.75-2.33 (m, 1H), 2.24-1.47 (m, 8H), 1.04-0.86 (m, 9H).

Step 3: (S)-methyl2-((S)-2-(7-chloro-1H-indole-2-carboxamido)-4,4-dimethylpentanamido)-3-((S)-2-oxopiperidin-3-yl)propanoate To a solution of (S)-methyl 2-((S)-2-amino-4,4-dimethylpentanamido)-3-((S)-2-oxopiperidin-3-yl)propanoate (550 mg*2, HCl salt, 1.68 mmol, 1 eq) and 7-chloro-1H-indole-2-carboxylic acid (394.29 mg, 2.02 mmol, 1.2 eq) in DCM (6 mL) was added DMAP (615.66 mg, 5.04 mmol, 3 eq). EDCI (644.05 mg, 3.36 mmol, 2 eq) was added to the mixture at 25° C., and the mixture was stirred at 25° C. for 1 h. Upon the reaction complement, the mixture was quenched by water (200 mL), extracted with DCM (70 mL*3), and then concentrated under vacuum. The resulting residue was purified by column (SiO₂, petroleum ether: ethyl acetate=1:1 to 0:1), concentrated in vacuum, and then was washed with 1M HCl (100 mL) and extracted with DCM (30 mL*3). The organic phase was adjusted to pH=~7 with sat. NaHCO₃ (30 mL), and then concentrated in vacuum to obtain (S)-methyl 2-((S)-2-(7-chloro-1H-indole-2-carboxamido)-4,4-dimethylpentanamido)-3-((S)-2-oxopiperidin-3-yl)propanoate (650 mg, 1.16 mmol, 40% yield) as a solid. MS (ESI) m/z 505.2 [M+H]⁺; $^1$H NMR (400 MHz, MeOD-d$_4$) δ ppm 7.58 (d, J=7.8 Hz, 1H), 7.32-7.17 (m, 2H), 7.06 (t, J=7.8 Hz, 1H), 4.73 (dd, J=3.8, 8.6 Hz, 1H), 4.55 (dd, J=4.0, 11.7 Hz, 1H), 3.71 (s, 3H), 3.35 (s, 1H), 3.24-3.01 (m, 2H), 2.49-2.22 (m, 2H), 2.02-1.40 (m, 8H), 1.08-0.96 (m, 9H).

Step 4: N—((S)-1-(((S)-1-amino-1-oxo-3-((S)-2-oxopiperidin-3-yl)propan-2-yl)amino)-4,4-dimethyl-1-oxopentan-2-yl)-7-chloro-1H-indole-2-carboxamide A solution of (S)-methyl 2-((S)-2-(7-chloro-1H-indole-2-carboxamido)-4,4-dimethylpentanamido)-3-((S)-2-oxopiperidin-3-yl)propanoate (650 mg, 1.29 mmol, 1 eq) in NH₃/MeOH (7M, 10 mL) was stirred at 50° C. for 16 h. Upon the reaction complement, the mixture was concentrated in vacuum to obtain N—((S)-1-(((S)-1-amino-1-oxo-3-((S)-2- oxopiperidin-3-yl) propan-2-yl) amino)-4,4-dimethyl-1-oxopentan-2-yl)-7-chloro-1H-indole-2-carboxamide (450 mg, crude) as a light yellow solid. MS (ESI) m/z 490.3 [M+H]$^+$ Step 5: 7-chloro-N—((S)-1-(((S)-1-cyano-2-((S)-2-oxopiperidin-3-yl)ethyl)amino)-4,4-dimethyl-1-oxopentan-2-yl)-1H-indole-2-carboxamide To a solution of N—((S)-1-(((S)-1-amino-1-oxo-3-((S)-2-oxopiperidin-3-yl) propan-2-yl) amino)-4,4-dimethyl-1-oxopentan-2-yl)-7-chloro-1H-indole-2-carboxamide (430 mg, 877.56 umol, 1 eq) in DCM (10 mL) was added Burgess reagent (627.38 mg, 2.63 mmol, 3 eq). The reaction mixture was stirred at 25° C. for 4 h. Upon the reaction complement, the mixture was quenched by water (10 mL), dried with a stream of N$_2$ and purified by prep-HPLC (column: Kromasil C18 (250*50 mm*10 um); mobile phase: [water (10 mM NH$_4$HCO$_3$)—ACN]; B %: 35%-65%, 10 min) to obtain 7-chloro-N—((S)-1-(((S)-1-cyano-2-((S)-2-oxopiperidin-3-yl)ethyl)amino)-4,4-dimethyl-1-oxopentan-2-yl)-1H-indole-2-carboxamide (205 mg, 424.79 umol, 48.41% yield) as a white solid. MS (ESI) m/z 472.2 [M+H]$^+$; 1H NMR (400 MHz, DMSO-d$_6$) δ ppm 11.70 (s, 1H), 9.02 (d, J=8.0 Hz, 1H), 8.71 (d, J=8.0 Hz, 1H), 7.63 (d, J=8.0 Hz, 1H), 7.52 (s, 1H), 7.34-7.23 (m, 2H), 7.07 (t, J=7.8 Hz, 1H), 5.05 (q, J=8.2 Hz, 1H), 4.63-4.54 (m, 1H), 3.07 (s, 2H), 2.30-2.18 (m, 2H), 1.88-1.32 (m, 7H), 0.95 (s, 9H).

Example 43. Evaluation of Antiviral Activity of Compounds Against COVID-19 (nCoV-2019, SARS-CoV2) Mpro in the Enzymatic Assay Compounds were assayed using standard methods to assess compound activity and IC50. As an exemplary for assessment of the SARS-COV2 Mpro, the C-His6-tagged Mpro (NC_045512) was cloned, expressed in E. coli and purified. The assay buffer contained 20 mM of Tris-HCl (pH 7.3), 100 mM of NaCl, 1 mM of EDTA, 5 mM of TCEP and 0.1% BSA. The final concentrations of the Mpro protein and substrate were 25 nM and 25 μM, respectively, in the Mpro enzymatic assay. The Km of the Mpro substrate for the protease was 13.5 μM.

The compounds were added to an assay plate. For 100% inhibition control (HPE, hundred percent effect), 1 μM GC376 was added. For no inhibition control (ZPE, zero percent effect), no compound was added. Each activity testing point had a relevant background control to normalize the fluorescence interference of compound.

IC50 values of compounds were calculated with the GraphPad Prism software using the nonlinear regression model of log(inhibitor) vs. response—Variable slope (four parameters). The inhibition activity was calculated using the formula below, IC50 values was calculated using the Inhibition % data.

Inhibition %=[(Sample−Average ZPE)/(Average HPE−Average ZPE)]*100%

HEP: Hundred percent effect controls. Containing substrate+enzyme+1 μM GC376.

ZPE: Zero percent effective controls. Containing enzyme+substrate, no compound.

Sample: Compound activity testing wells. Containing compound+enzyme+substrate.

BG: Compound background control wells. Containing compound+substrate, no enzyme.

Example 44. Evaluation of Antiviral Activity of Compounds Against Human Coronavirus (HCov) 229E and OC43 in the Cytopathic Effect (CPE) Assays Compounds were assayed using standard methods against multiple coronaviral strains, including HCoV 229E and OC43 strains. The antiviral activity of compounds was calculated based on the protection of the virus-induced CPE at each concentration normalized by the virus control.

Reagents and instruments used in this assay include luminescent cell viability assay kit CellTiter Glo (Promega) and Microplate Reader Synergy2 (BioTek).

Virus—HCoV 229E

Cytopathic effect (CPE) was measured by CellTiter Glo following the manufacturer's manual. The antiviral activity of compounds was calculated based on the protection of the virus-induced CPE at each concentration normalized by the virus control.

Virus—HCov OC43

Reference compound used was remdesivir; detection reagent: CellTiter Glo.) The CPE were measured by CellTiter Glo following the manufacturer's manual. The antiviral activity of compounds was calculated based on the protection of the virus-induced CPE at each concentration normalized by the virus control.

The cytotoxicity of compounds was assessed under the same conditions, but without virus infection, in parallel. Cell viability was measured with CellTiter Glo. The antiviral activity and cytotoxicity of compounds were expressed as % Inhibition and % Viability, respectively, and calculated with formulas.

Table 2, Table 3 and Table 4 below show activity data.

TABLE 2

Activity data for compounds.

| Compound No. | 229E mPRO IC50 (μM) | Sars CoV2 mPRO IC50 (μM) |
|---|---|---|
| 101 | D | D |
| 103 | D | D |
| 127 | B | C |
| 129 | C | D |
| 131 | D | D |
| 133 | D | D |
| 134 | D | D |
| 134 (Isomer 1) | D | D |
| 134 (Isomer 2) | D | D |
| 135 | D | D |
| 135 (Isomer 1) | C | C |
| 135 (Isomer 2) | D | D |
| 136 | D | D |
| 143 | C | C |
| 145 | D | D |
| 147 | A | D |
| 149 | C | D |
| 153 | B | D |
| 165 | A | B |
| 167 | C | C |
| 171 | D | D |
| 183 | C | D |
| 185 | D | D |
| 197 | D | D |
| 201 | C | C |
| 205 | D | D |
| 209 | B | C |
| 213 | A | B |

TABLE 2-continued

Activity data for compounds.

| Compound No. | 229E mPRO IC50 (μM) | Sars CoV2 mPRO IC50 (μM) |
|---|---|---|
| 223 (Isomer 1) | B | B |
| 223 (Isomer 2) | A | A |
| 225 | A | A |
| 227 | A | C |
| 231 | A | A |
| 237 | A | A |
| 241 | A | A |
| 245 | A | C |
| 249 | A | A |
| 253 | C | C |
| 265 | C | C |
| 267 | A | A |
| 267A | D | D |
| 269 | A | A |
| 269 | A | A |
| 271 | | |
| 271A (Isomer 1) | A | A |
| 271A (Isomer 2) | A | A |
| 271A (Isomer 3) | A | A |
| 271A (Isomer 4) | A | A |
| 273A | A | A |
| 273B | A | A |
| 273C | C | A |
| 279 | A | A |
| 305 | D | D |
| 323 (Isomer 1) | D | D |
| 323 (Isomer 2) | D | D |
| 325 | B | B |
| 327 | D | D |
| 329 | D | D |
| 331 (Isomer 1) | D | D |
| 331 (Isomer 2) | D | D |
| 344D | D | D |
| 344C | D | D |
| 344A | D | D |
| 345 | D | D |
| 345 (Isomer 1) | D | D |
| 345 (Isomer 2) | D | D |
| 355 | C | D |
| 357 | A | B |
| 359 | B | C |
| 361 | D | D |
| 363 | D | D |
| 365 (Isomer 1) | C | D |
| 365 (Isomer 2) | C | B |
| 369 (Isomer 1) | B | B |
| 369 (Isomer 2) | C | C |
| 375A | D | D |
| 377 | D | D |
| 379 | D | D |
| 383 | C | C |
| 385 (Isomer 1) | D | D |
| 385 (Isomer 2) | D | C |
| 387 | A | B |
| 389A (Isomer 1) | D | D |
| 391 | A | A |
| 393 | D | D |
| 395 (Isomer 1) | D | D |
| 395 (Isomer 2) | D | D |
| 397 | D | D |
| 399 (Isomer 1) | D | D |
| 401 | D | D |
| 401 (Isomer 1) | D | D |
| 401 (Isomer 2) | C | C |
| 405 | D | D |
| 407 | D | C |
| 433 | D | D |
| 439 | A | B |
| 449 | B | B |
| 449 (Isomer 1) | A | A |
| 449 (Isomer 2) | B | C |
| 451 (Isomer 1) | A | A |
| 451 (Isomer 2) | B | C |
| 455 | A | B |
| 457 | A | A |
| 459 | A | A |
| 465 | B | B |
| 465 (Isomer 1) | A | A |
| 465 (Isomer 2) | B | C |
| 467 (Isomer 1) | C | C |
| 469 | A | B |
| 469 (Isomer 1 & Isomer 2) | A | A |
| 469 (Isomer 3) | A | A |
| 469 (Isomer 4) | A | A |
| 471 | B | B |
| 473 (Isomer 1) | A | A |
| 473 (Isomer 2) | A | A |
| 475 (Isomer 1 & Isomer 2) | C | B |
| 475 (Isomer 3) | B | A |
| 475 (Isomer 4) | A | A |
| 477 | A | B |
| 479 | B | A |
| 481 (Isomer 1) | A | A |
| 481 (Isomer 2) | A | A |
| 483 | A | A |
| 483 (Isomer 1) | A | A |
| 483 (Isomer 2) | A | A |
| 489 (Isomer 1) | A | A |
| 489 (Isomer 2) | A | A |
| 491 | D | D |
| 491 (Isomer 1) | D | D |
| 491 (Isomer 2) | A | B |
| 491A (Isomer 1) | A | A |
| 491A (Isomer 2) | D | D |
| 495 (Isomer 1) | A | A |
| 495 (Isomer 2) | A | A |
| 497 (Isomer 2) | D | D |
| 499 | D | D |
| 501 | A | A |
| 505 | A | B |
| 507 (Isomer 1.1) | D | D |
| 507 (Isomer 1.2) | D | D |
| 507 (Isomer 2.1) | D | D |
| 507 (Isomer 2.2) | D | D |
| 509 | D | D |
| 511 | D | D |
| 511 (Isomer 1) | D | D |
| 511 (Isomer 2) | D | D |
| 513 (Isomer 1) | C | C |
| 513 (Isomer 2) | C | D |
| 515 | D | D |
| 519 | D | D |
| 531 | D | D |
| 535 | A | C |
| 547 (Isomer 2) | D | B |
| 551 | D | D |
| 555 | B | B |
| 577 | D | D |
| 581 | A | B |
| 583 | A | B |
| 591 (Isomer 1) | A | A |
| 591 (Isomer 2) | A | C |
| 595 | D | D |
| 598 | C | D |
| 623 | A | A |
| 625 | D | D |
| 635 | D | D |
| 637 | D | D |
| 639 (Isomer 1) | D | D |
| 643 | D | D |
| 649 | C | C |
| 653 | D | D |
| 659 | A | A |
| 681 (Isomer 1) | D | D |
| 711 | D | D |
| 715 | D | D |

TABLE 2-continued

Activity data for compounds.

| Compound No. | 229E mPRO IC50 (μM) | Sars CoV2 mPRO IC50 (μM) |
|---|---|---|
| 717 | D | D |
| 719 (Isomer 2) | D | D |
| 721 | D | D |
| 723 (Isomer 2) | D | D |
| 725 | D | D |
| 729 (Isomer 1) | D | D |
| 731 (Isomer 1) | D | D |
| 733 (Isomer 1) | D | D |
| 735 | D | D |
| 737 | D | D |
| 739 | D | D |
| 743 (Isomer 2) | D | D |
| 745 | D | D |
| 747 | D | D |

A > 30 μM, B > 10 μM and ≤ 30 μM, C ≥ 2 μM and ≤ 10 μM, D < 2 μM.

TABLE 3

Activity data for compounds.

| Compound No. | 229E CPE EC$_{50}$ (μM) |
|---|---|
| 101 | D |
| 103 | D |
| 127 | C |
| 131 | C |
| 133 | D |
| 134 | D |
| 134 (Isomer 1) | D |
| 134 (Isomer 2) | D |
| 135 | D |
| 135 (Isomer 2) | D |
| 136 | A |
| 149 | C |
| 171 | D |
| 185 | D |
| 197 | D |
| 205 | D |
| 323 (Isomer 1) | D |
| 323 (Isomer 2) | D |
| 327 | C |
| 329 | D |
| 331 (Isomer 1) | D |
| 331 (Isomer 2) | D |
| 344D | D |
| 344C | D |
| 344A | D |
| 345 | D |
| 345 (Isomer 1) | D |
| 345 (Isomer 2) | D |
| 355 | A |
| 361 | D |
| 363 | D |
| 375A | D |
| 377 | D |
| 379 | D |
| 385 (Isomer 1) | D |
| 385 (Isomer 2) | D |
| 389A (Isomer 1) | D |
| 393 | D |
| 397 | D |
| 399 (Isomer 1) | D |
| 401 | D |
| 401 (Isomer 1) | D |
| 405 | D |
| 407 | D |
| 433 | C |
| 491 | D |
| 497 (Isomer 2) | D |
| 507 (Isomer 1.1) | D |
| 507 (Isomer 1.2) | D |
| 507 (Isomer 2.1) | D |
| 507 (Isomer 2.2) | D |
| 509 | D |
| 511 | D |
| 511 (Isomer 1) | D |
| 511 (Isomer 2) | D |
| 513 (Isomer 2) | C |
| 519 | D |
| 531 | D |
| 551 | C |
| 577 | D |
| 598 | D |
| 635 | D |
| 637 | D |
| 639 (Isomer 1) | D |
| 643 | D |
| 653 | D |
| 681 (Isomer 1) | D |
| 711 | D |
| 715 | D |
| 717 | D |
| 719 (Isomer 2) | D |
| 721 | D |
| 723 (Isomer 2) | D |
| 725 | D |
| 729 (Isomer 1) | D |
| 731 (Isomer 1) | D |
| 733 (Isomer 1) | D |
| 735 | D |
| 737 | D |
| 739 | D |
| 743 (Isomer 2) | D |
| 745 | D |
| 747 | D |

A > 30 μM, B > 10 μM and ≤ 30 μM, C ≥ 2 μM and ≤ 10 μM, D < 2 μM.

TABLE 4

Activity data for compounds.

| Compound No. | 229E CC$_{50}$ |
|---|---|
| 130 (Isomer 1) | A |
| 135 | A |
| 170 | A |

A > 30 μM, B > 10 μM and ≤ 30 μM, C ≥ 2 μM and ≤ 10 μM, D < 2 μM.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound represented by:

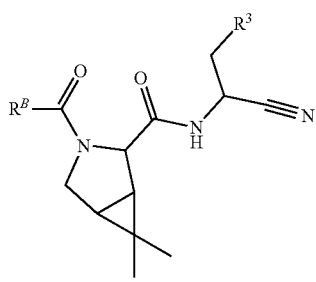

wherein:
$R^3$ is

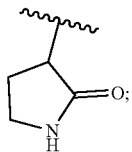

$R^B$ is $C_1$-$C_8$alkyl substituted by $R^x$;
$R^x$ is —N($R^y$)C(O)$R^y$, wherein $R^y$ is independently selected, for each occurrence, from H and $C_1$alkyl; and
$R^B$ is optionally substituted by one, two or three halogen substituents.

2. The compound of claim 1, wherein $R^x$ is NHC(O)$C_1$alkyl.

3. The compound of claim 1, wherein $R^B$ is substituted by three halogens.

4. The compound of claim 2, wherein $R^B$ is substituted by up to three halogens.

* * * * *